(12) United States Patent
Heard et al.

(10) Patent No.: US 7,598,429 B2
(45) Date of Patent: *Oct. 6, 2009

(54) TRANSCRIPTION FACTOR SEQUENCES FOR CONFERRING ADVANTAGEOUS PROPERTIES TO PLANTS

(75) Inventors: Jacqueline E. Heard, Stonington, CT (US); Jose Luis Riechmann, Pasadena, CA (US); Oliver Ratcliffe, Oakland, CA (US); Omaira Pineda, Vero Beach, FL (US)

(73) Assignee: Mendel Biotechnology, Inc., Hayward, CA (US)

( * ) Notice: Subject to any disclaimer, the term of this patent is extended or adjusted under 35 U.S.C. 154(b) by 170 days.

This patent is subject to a terminal disclaimer.

(21) Appl. No.: 11/375,241

(22) Filed: Mar. 13, 2006

(65) Prior Publication Data

US 2006/0195944 A1    Aug. 31, 2006

Related U.S. Application Data

(63) Continuation-in-part of application No. 10/225,067, filed on Aug. 9, 2002, now Pat. No. 7,135,616, which is a continuation-in-part of application No. 09/837,944, filed on Apr. 18, 2001, now abandoned, and a continuation-in-part of application No. 10/171,468, filed on Jun. 14, 2002, now abandoned, application No. 11/375,241, filed on Mar. 13, 2006, which is a continuation-in-part of application No. 10/714,887, filed on Nov. 13, 2003, and a continuation-in-part of application No. 10/666,642, filed on Sep. 18, 2003, now Pat. No. 7,196,245.

(60) Provisional application No. 60/713,952, filed on Aug. 31, 2005, provisional application No. 60/336,049, filed on Nov. 19, 2001, provisional application No. 60/310,847, filed on Aug. 9, 2001, provisional application No. 60/338,692, filed on Dec. 11, 2001, provisional application No. 60/465,809, filed on Apr. 24, 2003, provisional application No. 60/434,166, filed on Dec. 17, 2002, provisional application No. 60/411,837, filed on Sep. 18, 2002.

(51) Int. Cl.
*C12N 15/82* (2006.01)

(52) U.S. Cl. ........................ 800/290; 800/289

(58) Field of Classification Search ........................ None
See application file for complete search history.

(56) References Cited

U.S. PATENT DOCUMENTS

| | | | |
|---|---|---|---|
| 5,892,009 A | 4/1999 | Thomashow et al. |
| 5,981,729 A | 11/1999 | Chun et al. |
| 5,994,622 A | 11/1999 | Jofuku et al. |
| 6,093,874 A | 7/2000 | Jofuku et al. |
| 6,121,513 A | 9/2000 | Zhang et al. |
| 6,329,567 B1 | 12/2001 | Jofuku et al. |
| 6,417,428 B1 | 7/2002 | Thomashow et al. |
| 6,664,446 B2 | 12/2003 | Heard et al. |
| 6,706,866 B1 | 3/2004 | Thomashow et al. |
| 6,717,034 B2 | 4/2004 | Jiang |
| 6,833,446 B1 | 12/2004 | Wood et al. |
| 6,835,540 B2 | 12/2004 | Broun |
| 6,846,669 B1 | 1/2005 | Jofuku et al. |
| 6,946,586 B1 | 9/2005 | Fromm et al. |
| 7,109,393 B2 | 9/2006 | Gutterson et al. |
| 7,135,616 B2 * | 11/2006 | Heard et al. ............... 800/278 |
| 7,196,245 B2 | 3/2007 | Jiang et al. |
| 7,223,904 B2 | 5/2007 | Heard et al. |
| 7,238,860 B2 | 7/2007 | Ratcliffe et al. |
| 7,345,217 B2 | 3/2008 | Zhang et al. |
| 2002/0040490 A1 | 4/2002 | Gorlach et al. |
| 2003/0093837 A1 | 5/2003 | Keddie et al. |
| 2003/0121070 A1 | 6/2003 | Adam et al. |
| 2003/0135888 A1 | 7/2003 | Zhu et al. |
| 2003/0217383 A1 | 11/2003 | Reuber et al. |
| 2003/0226170 A1 | 12/2003 | Lammers et al. |
| 2003/0233680 A1 | 12/2003 | Thomashow et al. |
| 2004/0010815 A1 | 1/2004 | Kreps et al. |

(Continued)

FOREIGN PATENT DOCUMENTS

AU              735715         2/1998

(Continued)

OTHER PUBLICATIONS

Liu Q. et al. Two transcription factors, DREB1 and DREB2, with an EREBP/AP2 DNA binding domain separate two cellular signal transduction pathways in drought- and low-temperature-responsive gene expression, respectively, in Arabidopsis. Plant Cell. Aug. 1998;10(8):1391-406.*

(Continued)

*Primary Examiner*—Cynthia Collins
(74) *Attorney, Agent, or Firm*—Jeffrey M. Libby

(57) ABSTRACT

The invention relates to plant transcription factor polypeptides, polynucleotides that encode them, homologs from a variety of plant species, and methods of using the polynucleotides and polypeptides to produce transgenic plants having advantageous properties compared to a reference or control plant, including increased plant size, seed size, increased leaf size, lignification, water deprivation tolerance, cold tolerance, or altered flowering time. Sequence information related to these polynucleotides and polypeptides can also be used in bioinformatic search methods and is also disclosed.

21 Claims, 9 Drawing Sheets

U.S. PATENT DOCUMENTS

Figure 1:
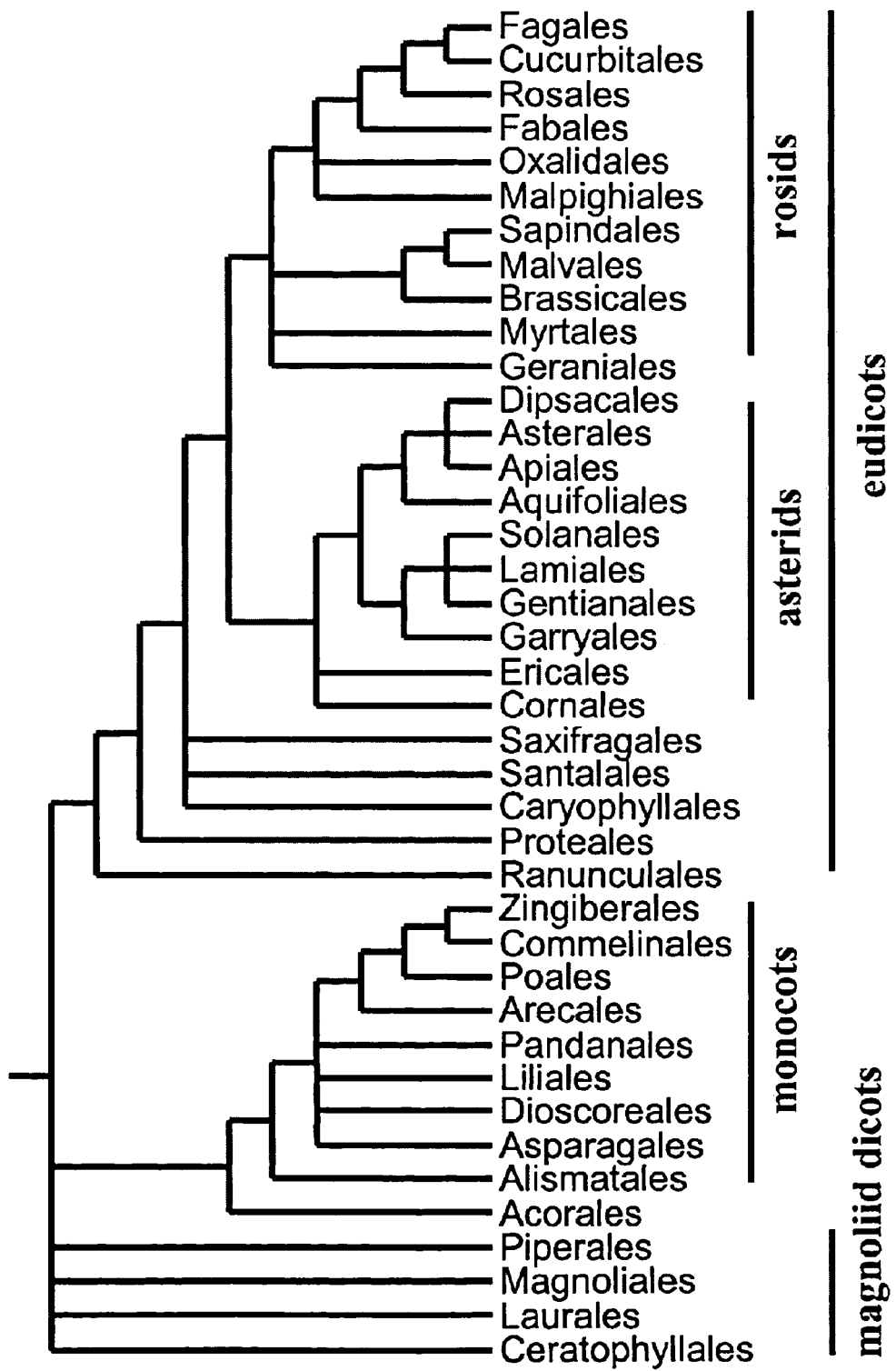

| | | |
|---|---|---|
| 2004/0016025 A1 | 1/2004 | Kreps et al. |
| 2004/0019927 A1 | 1/2004 | Sherman et al. |
| 2004/0031072 A1 | 2/2004 | La Rosa et al. |
| 2004/0034888 A1 | 2/2004 | Liu et al. |
| 2004/0123343 A1 | 6/2004 | La Rosa et al. |
| 2004/0128712 A1 | 7/2004 | Jiang et al. |
| 2004/0143098 A1 | 7/2004 | Pages et al. |
| 2004/0172684 A1 | 9/2004 | Kovalic et al. |
| 2004/0214272 A1 | 10/2004 | La Rosa et al. |
| 2004/0216190 A1 | 10/2004 | Kovalic et al. |
| 2004/0259145 A1 | 12/2004 | Wood et al. |
| 2005/0009187 A1 | 1/2005 | Shinozaki et al. |
| 2005/0086718 A1 | 4/2005 | Heard et al. |
| 2005/0097638 A1 | 5/2005 | Jiang et al. |
| 2005/0155117 A1 | 7/2005 | Century et al. |
| 2005/0172364 A1 | 8/2005 | Heard et al. |
| 2006/0008874 A1 | 1/2006 | Creelman et al. |
| 2006/0015972 A1 | 1/2006 | Heard et al. |
| 2006/0162018 A1 | 7/2006 | Gutterson et al. |
| 2006/0195944 A1 | 8/2006 | Heard et al. |
| 2006/0242738 A1 | 10/2006 | Sherman et al. |
| 2006/0272060 A1 | 11/2006 | Heard et al. |
| 2007/0022495 A1 | 1/2007 | Reuber |
| 2007/0101454 A1 | 5/2007 | Jiang et al. |
| 2007/0186308 A1 | 8/2007 | Reuber et al. |
| 2007/0199107 A1 | 8/2007 | Ratcliffe et al. |
| 2007/0209086 A1 | 9/2007 | Ratcliffe et al. |
| 2007/0226839 A1 | 9/2007 | Gutterson et al. |
| 2008/0010703 A1 | 1/2008 | Creelman et al. |
| 2008/0155706 A1 | 6/2008 | Riechmann et al. |
| 2008/0163397 A1 | 7/2008 | Ratcliffe et al. |
| 2008/0229448 A1 | 9/2008 | Libby et al. |

FOREIGN PATENT DOCUMENTS

| | | |
|---|---|---|
| AU | 759027 | 4/2003 |
| CN | 1475497 | 2/2004 |
| EP | 1033405 | 9/2000 |
| EP | 1054060 | 11/2000 |
| EP | 1055728 | 11/2000 |
| EP | 02757104 | 2/2003 |
| EP | 1402042 | 3/2004 |
| JP | 2003144175 | 5/2003 |
| JP | 2003219882 | 5/2003 |
| WO | WO98/07842 | 2/1998 |
| WO | WO 9941974 | 8/1999 |
| WO | WO99/55840 | 11/1999 |
| WO | WO0032761 | 6/2000 |
| WO | WO0053724 A2 | 9/2000 |
| WO | WO-0136598 A | 5/2001 |
| WO | WO0215675 A1 | 2/2002 |
| WO | WO 02079245 | 10/2002 |
| WO | WO 02081695 A2 | 10/2002 |
| WO | WO 03000898 | 1/2003 |
| WO | WO 03008540 | 1/2003 |
| WO | WO03013227 A2 | 2/2003 |
| WO | WO03013227 A3 | 2/2003 |
| WO | WO03013228 | 2/2003 |
| WO | WO03013228 A3 | 2/2003 |
| WO | WO-03014327 A | 2/2003 |
| WO | WO03014327 A2 | 2/2003 |
| WO | WO 2003044190 A1 | 5/2003 |
| WO | WO 03081978 | 10/2003 |
| WO | WO2004031349 | 4/2004 |
| WO | WO 2004035798 A2 | 4/2004 |
| WO | WO2004076638 | 9/2004 |
| WO | WO-2004076638 A | 9/2004 |
| WO | WO2005001050 A2 | 1/2005 |
| WO | WO2005047516 | 5/2005 |
| WO | WO2005047516 A2 | 5/2005 |
| WO | WO2005047516 A3 | 5/2005 |
| WO | WO2006033708 A2 | 3/2006 |
| WO | WO2006069201 A2 | 6/2006 |
| WO | WO2006130156 A2 | 12/2006 |
| WO | WO2007028165 A2 | 3/2007 |
| WO | WO2007028165 | 8/2007 |
| WO | WO2007028165 A3 | 8/2007 |
| WO | WO2007127186 A2 | 11/2007 |
| ZA | 2001007413 | 11/2002 |

OTHER PUBLICATIONS

U.S. Appl. No. 12/064,961, Gutterson et al.
U.S. Appl. No. 12/077,535, Repetti et al.
U.S. Appl. No. 11/981,576, Gutterson et al.
U.S. Appl. No. 11/632,390, Zhang et al.
U.S. Appl. No. 11/986,992, filed , Kumimoto et al.
U.S. Appl. No. 12/157,329, filed , Zhang et al.
U.S. Appl. No. 12/169,527, filed , Zhang et al.
U.S. Appl. No. 12/154,154, Century et al.
U.S. Appl. No. 11/981,733, Ratcliffe et al.
Winicov ILGA et al., (Jun. 1999) Transgenic overexpression of the transcription factor Alfin1enhances expression of the endogenous MsPRP2 gene in alfalfa and improves salinity tolerance of the plants. Plant Physiology vol. 120, No. 2, pp. 473-480.
Whisstock, et al. (Aug. 2003). Prediction of protein function from protein sequence and structure. Q Rev Biophys 36(3):307-340 Review.
Stern,M. And Ganetzky,B. (1992) Identification and characterization of inebriated, a gene affecting neuronal excitability in Drosophila. J. Neurogenet. 8 (3), 157-172.
Soehnge, H., et al. (1996). A neurotransmitter transporter encoded by the Drosophila inebriated gene. Proc. Natl. Acad. Sci. U.S.A. 93 (23), 13262-13267.
Bowie, et al. (1990). Deciphering the message in protein sequences: Tolerance to amino acid substitutions. Science 247: 1306-1310.
Yang, et al. (2001). Expression of the REB transcriptional activator in rice grains improves the yield. . . PNAS 98(20): 11438-11443.
McConnell, et al. (2001). Nature 411 (6838): 709-713.
Sasaki, T., et al. The genonme sequence and structure of rice chromosome 1. Nature 420 (6913), 312-316 (2002).
Mayer ,K., et al. Conservation of microstructure between a sequenced region of the genome of rice and multiple segments of the genome of Arabidopsis Thaliana. Genome Res. 11(7), 1167-1174 (2001).
Ayele ,M., et al. Whole genome shotgun sequencing of *Brassica oleracea* and its application to gene discovery and annotation in Arabidopsis. Genome Res. 15 (4), 487-495 (2005).
Demura,T., et al. "Visualization by comprehensive microarray analysis of gene expression programs during transdifferentiation of mesophyll cells into xylem cells" (Proc. Natl. Acad. Sci. U.S.A. 99 (24), 15794-15799 (2002)).
Liu Qiang et al. (Aug. 1998) "Two transcription factors, DREB1 and DREB2, with an EREBP/AP2 DNA binding domain separate two cellular signal transduction pathways in drought-and low-termperature-responsive gene expression, respectivley, in Arabidopsis" Plant Cell, vol. 10, No. 8, pp. 1391-1406.
Tamagnone et al., the AmMYB308 and AmMYB330 transcription factors from antirhinum regulate phenylpropanoid and lignin biosynthesis in transgenic tobacco. Plant Cell Feb. 1998; 10(2):135-154.
Park, J.M., et al. (2001). Overexpression of the tobacco Tsi1 gene encoding an EREBP/AP2-type transcription factor enhances resistance against pathogen attack and osmotic stress in tobacco. Plant Cell 13, 1035-1046.
Petersen,,S.G., et al. (1989). "Analysis of RNA2 of pea early browning virus strain SP5" (Plant Mol. Biol. 13 (6), 735-737.
Kim, et al. (Feb. 2001). A novel cold inducible zinc finger protein from soybean, SCOF-1, enhances cold tolerance in transgenic plants. The Plant Journal, vol. 25, No. 3: 247-259-.
Kasuga, Mie et al. (Mar. 1999), Improving plant drought, salt, and freezing tolerance by gene transfer of a single stress-inducible transcription factor, Nature Biotechnology vol. 17, No. 3, pp. 287-291.

Maes, Tamara et al: "The inflorescence architecture of *Petunia hybrida* is modified by the *Arabidopsis thaliana* Ap2 gene" Developmental Genetics, vol. 25, No. 3, 1999, pp. 199-208, XP008056283.

Riechmann, J. L., et al.: "The Ap2/Erebp Family of Plant Transcription Factors" Biological Chemistry, vol. 379, Jun. 1998, pp. 633-646, XP002937907.

Nole-Wilson Staci et al: "DNA binding properties of the Arabidopsis floral development protein Ainteguments" Nucleic Acids Research, Oxford University Press, Surrey, GB, vol. 28, No. 21, Nov. 1, 2000, pp. 4076-4082, XP002187932.

Kagaya, Yasuaki, et al.: "RAV1, a novel DNA-binding protein, binds to bipartite recognition sequence through two distinct DNA-binding domains uniquely found in higher plants" Nucleic Acids Research, Oxford University Press, Surrey, GB, vol. 27, No. 2, Jan. 15, 1999, pp. 470-478, XP002314310.

Sakurai , et al. RARGE: a large-scale database of RIKEN *Arabidopsis* resources ranging from transcriptome to phenome. Nucleic Acids Research (2005), 33(Database Iss), D647-D650.

Theologis , et al. Sequence and analysis of chromosome 1 of the plant *Arabidopsis thaliana*. Nature (London) (2000), 408(6814), 816-820.

Mayer, et al. (1999). Sequence and analysis of chromosome 4 of the plant *Arabidopsis thaliana*. Nature (London) (1999), 402(6763), 769-777.

Lin, et al. (1999). Sequence and analysis of chromosome 2 of the plant *Arabidopsis thaliana*. Nature (London) (1999), 402(6763), 760-768.

Terryn, et al. (1999). Evidence for an ancient chromosomal duplication in *Arabidopsis thaliana* by sequencing and analyzing a 400-kb contig at the APETALA2 locus on chromosome 4. FEBS Letters (1999), 445(2,3), 237-245.

Okamuro, et al. (1997). The AP2 domain of APETALA2 defines a large new family of DNA binding proteins in *Arabidopsis*. Proceedings of the National Academy of Sciences of the United States of America (1997), 94(13), 7076-7081.

NCBI acc. No. AL360314 (gi: 8953373) (Jul. 6, 2000); Bevan,M., et al. "*Arabidopsis thaliana* DNA chromosome 5, BAC clone F2I11 (ESSA project)"; source: *Arabidopsis thaliana* (thale cress); Title: "Direct Submission" (Unpublished).

NCBI acc. no. D13044 (gi: 285614) (Jun. 11, 1993); Yamaguchi-Shinozaki,K., et al. "*Arabidopsis thaliana* rd29A and rd29B genes"; source: Unknown.; Title: "*Arabidopsis* DNA encoding two desiccation-responsive rd29 genes" (Plant Physiol. 101, 1119-1120 (1993)).

Database EMBL [Online] Jan. 13, 1998, "*Arabidopsis thaliana* chromosome 1 BAC T22J18 sequence, complete sequence." XP002355968 retrieved from EBI accession No. EM_PRO:AC003979 Database accession No. AC003979.

NCBI acc. No. NP_173695 (gi: 15219954) (Aug. 21, 2001); Theologis,A., et al. "TINY-like transcription factor [*Arabidopsis thaliana*]"; source: *Arabidopsis thaliana* (thale cress); Title: "Sequence and analysis of chromosome 1 of the plant *Arabidopsis thaliana*" (Nature 408 (6814), 816-820 (2000)).

NCBI acc. No. AC007591 (gi: 4874280) (May 19, 1999); Vysotskaia,V.S., et al. "*Arabidopsis thaliana* chromosome 1 clone F9L1, * SEQUENCING IN PROGRESS *, 2 ordered pieces"; source: *Arabidopsis thaliana* (thale cress); Title: "*Arabidopsis thaliana* chromosome 1 BAC F9L1 sequence" (Unpublished (1999)).

NCBI acc. No. S55885 (gi: 235912) (May 7, 1993); Petersen,S.G., et al. "orf 212, orf 255 [pea early browning virus PEBV, strain 5P5, Genomic RNA, 2358 nt]"; source: Unknown.; Title: "Analysis of RNA2 of pea early browning virus strain 5P5" (Plant Mol. Biol. 13 (6), 735-737 (1989)).

Acc. No. AAC47292 Database Geneseq Derwent, EP Patent 1033405 Blast. (Oct. 2000) *Arabidopsis thaliana* DNA fragment SEQ ID No. 53281.

Acc. No. AAG42700 Database Geneseq, Derwent, EP Patent 1033405 Blast. (Oct. 2000) *Arabidopsis Thaliana* DNA fragment SEQ ID No. 53281.

*Arabidopsis thaliana* DNA fragment SEQ ID No: 54172 from Patent No. EP1033405A2 Blast (Sep. 6, 2000) Derwent Accession No. AAG43349.

NCBI acc. No. NP_177307 (gi: 15217518) (Aug. 21, 2001); Theologis,A., et al. "hypothetical protein [*Arabidopsis thaliana*]"; source: *Arabidopsis thaliana* (thale cress); Title: "Sequence and analysis of chromosome 1 of the plant *Arabidopsis thaliana*" (Nature 408 (6814), 816-820 (2000)).

NCBI acc. No. AC007067 (gi: 4406713) (Mar. 12, 1999); Shinn,P., et al. "*Arabidopsis thaliana* chromosome 1, * Sequencing in Progress *, 6 unordered pieces"; source: *Arabidopsis thaliana* (thale cress); Title: "Genomic sequence for *Arabidopsis thaliana* BAC T10O24" (Unpublished (1999)).

NCBI acc. No. BE320193 (gi: 11929308) (Jul. 14, 2000); Watson,B. S., et al. "NF024B04RT1F1029 Developing root *Medicago truncatula* cDNA clone NF024B04RT 5', mRNA sequence"; source: *Medicago truncatula* (barrel medic); Title: "Expressed Sequence Tags from the Samuel Roberts Noble Foundation *Medicago truncatula* root library" (Unpublished (2000)).

NCBI acc. No. AP003379 (gi: 13365596) (Mar. 16, 2001); Sasaki,T., et al. "*Oryza sativa* chromosome 1 clone P0408G07, * Sequencing in Progress *"; source: *Oryza sativa*; Title: "*Oryza sativa* nipponbare(GA3) genomic DNA, chromosome 1, PAC clone:P0408G07" (Published Only in DataBase (2001) in press).

NCBI acc. No. BE319522 (gi: 11929645) (Jul. 14, 2000); Watson,B S., et al. "NF019G12RT1F1088 Developing root *Medicago truncatula* cDNA clone NF019G12RT 5', mRNA sequence"; source: *Medicago truncatula* (barrel medic); Title: "Expressed Sequence Tags from the Samuel Roberts Noble Foundation *Medicago truncatula* root library" (Unpublished (2000)).

NCBI acc. No. AW685808 (gi: 7560544) (Apr. 14, 2000); Watson,B. S., et al. "NF035D03NR1F1000 Nodulated root *Medicago truncatula* cDNA clone NF035D03NR 5', mRNA sequence"; source: *Medicago truncatula* (barrel medic); Title: "Expressed Sequence Tags from the Samuel Roberts Noble Foundation *Medicago truncatula* nodulated root library" (Unpublished (2000)).

NCBI acc. No. BF644218 (gi: 11909347) (Dec. 20, 2000 Torres-Jerez,I., et al. "NF060H11EC1F1096 Elicited cell culture *Medicago truncatula* cDNA clone NF060H11EC 5', mRNA sequence"; source: *Medicago truncatula* (barrel medic); Title: "Expressed Sequence Tags from the Samuel Roberts Noble Foundation—Center for *Medicago* Genomics Research" (Unpublished (2000)).

NCBI acc. No. AW220454 (gi: 6531328) (Dec. 6, 1999); van der Hoeven,R.S., et al. "EST302937 tomato root during/after fruit set, Cornell University *Solanum lycopersicum* cDNA clone cLEX10P20, mRNA sequence"; source: *Solanum lycopersicum* (Lycopersicon esculentum); Title: "Generation of ESTs from tomato root tissue" (Unpublished (1999)).

NCBI acc. No. BI434553 (gi: 15259243) (Aug. 21, 2001); Restrepo,S., et al. "EST537314 P. infestans-challenged potato leaf, compatible reaction *Solanum tuberosum* cDNA clone PPCBR81 5' sequence, mRNA sequence"; source: *Solanum tuberosum* (potato); Title: "Generation of ESTs from Potato Leaves Challenged with *Phytophthora infestans*, Compatible Interaction" (Unpublished (2000)).

NCBI acc. No. CAC39072 (gi: 14140155) (May 17, 2001); Mayer,K., et al. "putative AP2 domain transcription factor [*Oryza sativa*]; source: *Oryza sativa*"; Title: "Conservation of microstructure bewtween a sequenced region of the genome of rice and multiple segments of the genome of *Arabidopsis thaliana*" (Unpublished).

NCBI acc. No. AF229199 (gi: 11244751) (Nov. 21, 2000); Yoon,U.-H., et al. "*Oryza sativa* chromosome 1 clone OSJNBa0048101, complete sequence"; source: *Oryza sativa* Japonica Group; Title: "*Oryza sativa* chromosome 1 OSJNBa0048101 genomic sequence" (Unpublished).

NCBI acc. No. BG832521 (gi: 14189163) (May 22, 2001); Sederoff,R., et al. "NXPV_073_H03_F NXPV (Nsf Xylem Planings wood Vertical) *Pinus taeda* cDNA clone NXPV_073_H03 5' similar to *Arabidopsis thaliana* sequence At1g19210 AP2 domain-containing unknown protein see http://mips.gsf.de/proj/thal/db/index.html, mRNA sequence"; source: *Pinus taeda* (loblolly pine); Title: "Molecular Basis of Wood Formation in the Pine Megagenome" (Unpublished (2000)).

NCBI acc. No. AF274033 (gi: 8571475) (Jun. 18, 2000); Shen,Y., et al. "*Atriplex hortensis* apetala2 domain-containing protein mRNA, complete cds"; source: *Atriplex hortensis*; Title: "Direct Submission" (Submitted (May 31, 2000) Plant Biotechnology Laboratory, Institute of Genetics, Chinese Academy of Sciences, Andingmenwai Datun Road, Beijing 100101, P.R. China).

NCBI acc. No. AAC25505 (gi: 3287677) (Jul. 3, 1998); Vysotskaia,V.S., et al. "Contains similarity to transcription factor (TINY) isolog T02O04.22 gb|2062174 from *A. thaliana* BAC gb|AC001645 [*Arabidopsis thaliana*]"; source: *Arabidopsis thaliana* (thale cress); Title: "*Arabidopsis thaliana* chromosome 1 BAC T22J18 sequence, complete sequence" (Unpublished (1998)).

NCBI acc. No. AAF23336 (gi: 6682615) (Jan. 8, 2000); Lin,X., et al. "hypothetical protein [*Arabidopsis thaliana*]"; source: *Arabidopsis thaliana* (thale cress); Title: "*Arabidopsis thaliana* chromosome I BAC F26A9 genomic sequence" (Unpublished).

NCBI acc. No. AC003979 (gi: 2754702) (Jan. 7, 1998); Vysotskaia,V.S., et al. "*Arabidopsis thaliana* chromosome 1 clone T22J18, * Sequencing in Progress *, 7 unordered pieces"; source: *Arabidopsis thaliana* (thale cress); Title: "Sequence of BAC T22J18 from *Arabidopsis thaliana* chromosome 1" (Unpublished (1997)).

NCBI acc. No. AC016162 (gi: 6466530) (Nov. 23, 1999); Lin,X., et al. "*Arabidopsis thaliana* chromosome I clone IGF-F26A9, * Sequencing in Progress *, 4 unordered pieces"; source: *Arabidopsis thaliana* (thale cress); Title: "*Arabidopsis thaliana* 'IGF' BAC 'F26A9' genomic sequence near marker 'PAB5'" (Unpublished).

NCBI. No. BG543936 (gi: 20374916) (May 1, 2002); Ryu,S.H., et al. "E1686 Chinese cabbage etiolated seedling library *Brassica rapa* subsp. pekinensis cDNA clone E1686, mRNA sequence"; source: *Brassica rapa* subsp. pekinensis (*Brassica campestris* (Pekinensis Group)); Title: "Expressed Sequence Tags of Chinese Cabbage Etiolated Seedling cDNA" (Unpublished (2001)).

NCBI acc. No. BH420519 (gi: 17606247) (Dec. 12, 2001); Ayele,M., et al. "BOGUH88TF BOGU *Brassica oleracea* genomic clone BOGUH88, genomic survey sequence"; source: *Brassica oleracea*; Title: "Whole genome shotgun sequencing of *Brassica oleracea* and its application to gene discovery and annotation in *Arabidopsis*" (Genome Res. 15 (4), 487-495 (2005)).

NCBI acc. No. AU292603 (gi: 24253111) (Oct. 22, 2002); Demura,T., et al. "AU292603 zinnia cultured mesophyll cell equalized cDNA *Zinnia violacea* cDNA clone Z7362, mRNA sequence"; source: *Zinnia violacea*; Title: "Visualization by comprehensive microarray analysis of gene expression programs during transdifferentiation of mesophyll cells into xylem cells" (Proc. Natl. Acad. Sci. U.S.A. 99 (24), 15794-15799 (2002)).

NCBI acc. No. AC137623 (gi: 25696494) (Nov. 27, 2002); Chow,T.-Y., et al. "*Oryza sativa* (japonica cultivar-group) chromosome 5 clone P0426G01, * Sequencing in Progress *, 8 ordered pieces"; source: *Oryza sativa* (japonica cultivar-group); Title: "*Oryza sativa* PAC P0426G01 genomic sequence" (Unpublished).

NCBI acc. No. Q9LFN7 (gi: 75263866) (Sep. 14, 2005); Bevan,M., et al. "Hypothetical protein F2I11_(Putative AP2/EREBP transcription factor)"; source: *Arabidopsis thaliana* (thale cress); Title: "Direct Submission" (Submitted (??-Jul. 2000)).

NCBI acc. No. G96768 (gi: 22747524) (Sep. 6, 2002); Wade,C., et al. "S208P6686RB8.T0 129S1/SvImJ Mus musculus STS genomic, sequence tagged site"; source: Mus musculus (house mouse); Title: "Polymorphism Structure in the Mouse" (Unpublished (2002)).

NCBI acc. No. AF371983 (gi: 14161426) (May 21, 2001); Werber,M., et al. "*Arabidopsis thaliana* putative transcription factor MYB122 (MYB122) mRNA, complete cds"; source: *Arabidopsis thaliana* (thale cress); Title: "R2R3-MYB transcription factor gene nomenclature in *Arabidopsis thaliana*" (Unpublished).

Sakuma et al. (2002). DNA-Binding Specificity of the ERF/AP2 Domain of *Arabidopsis* DREBs, Transcription Factors Involved in Dehydration- and Cold-Inducible Gene Expression Biochemical and Biophysical Research Communications, vol 290, Issue 3, Jan. 25, 2002, pp. 998-1009.

* cited by examiner

```
CBF4   (257)  IYRGVRQRN-SGKWVCEVREPNKKSRIWLGTFPTVEMAARAHDVAALALRGRS----------ACLNFA
G42    (258)  IYRGVRRRN-SGKWVCEVREPNKKSRIWLGTFPTVEMAARAHDVAALALRGRS----------ACLNFA
G41    (259)  IYRGVRQRN-SGKWVCELREPNKKTRIWLGTFQTAEMAARAHDVAAIALRGRS----------ACLNFA
G40    (260)  IYRGVRQRN-SGKWVSEVREPNKKTRIWLGTFQTAEMAARAHDVAALALRGRS----------ACLNFA
G867   (261)  KYKGVVPQP-NGRWGAQIY-EKHQRVWLGTFNEEDEAARAYDVAVHRFRRRD-----------AVTNFK
G3656  (262)  QYRGVRMRK-WGKWVAEIREPHKRTRPRLRSYATAVAAARAYDTAVFYLPGPS----------ARLNFP
G12    (263)  PYKGIRMRK-WGKWVAEIREPNKRSRIWLGSYSTPEAAARAYDTAVFYLRGPS----------ARLNFP
G1277  (264)  PFKGIRMRK-WGKWVAEIREPNKRSRLWLGSYSTPEAAARAYDTAVFYLRGPT----------ATLNFP
G872   (265)  KYKGVRKRK-WGKWVSEIRLPHSRERIWLGSYDTPEKAARAFDAAQFCLRGG---------DANFNFPN-
G2576  (266)  KYKGVRKRK-WGKWVSEIRLPNSRERIWLGSYDTPEKAARAFDAALYCLRGN---------NAKFNFPD-
G3655  (267)  KYKGVRLRQ-WGKWAAEIRLPSSCERIWLGSYDTPEKAARAFDAAFICLRGV---------QAIAGLNFP
G3653  (268)  KYRGVRLRQ-WGKWVAEIRLRLWLGSYDTPEKAARAFDAAFICLRGG----------EAIAGLNFP
G3652  (269)  RYKGVRLRQ-WGKWVAEIRLPNSRKRIWLGSYYTPEKAARAFDAAFICLRGG----------EAIAGLNFT
G3654  (270)  KYKGVRLRK-WGKWVSEIRLPNSRERIWLGSYDTPEEAARAFDAAFVCLRGGG---------EAAGNGINFP
G47    (271)  KYKGIRRRK-WGKWVSEIRVPGTRDRLWLGSFSTAEGAAVAHDVAFFCLHQPDSL--------ESLNFP
G3645  (272)  KYKGIRRRK-WGKWVSEIRVPGTRDRLWLGSFSTAEGAAVAHDVAFYCLHQPNSL--------ESLNFP
G3646  (273)  KYKGIRRRK-WGKWVSEIRVPATRERLWLGSFSTAEGAAVAHDVAFYCLHRPSSLD-------NEAFNFP
G2133  (274)  KYKGIRRRK-WGKWVSEIRVPGTRQRLWLGSFSTAEGAAVAHDVAFYCLHRPSSLD-------DESFNFP
G3648  (275)  KFKGVRRRK-WGKWVSEIRVPGTQERLWLGTYATPEAAAVAHDVAFYCLKRPSTL--------DKLNFP
G3643  (276)  KLKGVRRRK-WGKWVSEIRVPGTQERLWLGTYATPEAAAVAHDVAVYCLSRPSSL--------DKLNFP
G3647  (277)  TYKGVRCRR-WGKWVSEIRVPGSRERLWLGTYSTPEGAAVAHDVASYCLKGNTSF--------HKLNIP
G3651  (278)  RYRGVRRRR-WGKWVSEIRVPGTRERLWLGSYATPEAAAVAHDTAVYFLRGGAGD--GGGGATAQLP
G3644  (279)  RYRGVRRRR-WGKWVSEIRVPGTRERLWLGSYATPEAAAVAHDTAVYFLRGGAGD--GGGGATLNFP
G3650  (280)  RYRGVRRRA-WGKWVSEIRVPGTRQRLWLGSYAAPEAAAVAHDAAACLLRGCAGR--------RLNFP
G3649  (281)  RYRGVRRRR-WGKWVSEIRVPGTRERLWLGSYATAEAAAVAHDAAVCLLRLGGRRAAAGGGGLNFP
G3657  (282)  PYKGVRMRS-WGSWVSEIRAPHQKRRIWLGSYATPEAAARAYDAALLCLKGSDAV-----------LNFP
G2294  (283)  KYKGVRMRS-WGSWVSEIRAPNQKTRIWLGSYSTAEAAARAYDAALLCLKGSSANN-----------LNFP
```

FIG. 4

G47 (SEQ ID NO: 66) and G2133 (SEQ ID NO: 152) conserved domains

```
G47:    QSKYKGIRRRKWGKWVSEIRVPGTRDRLWLGSFSTAEGAAVAHDVA
        QSKYKGIRRRKWGKWVSEIRVPGTR RLWLGSFSTAEGAAVAHDVA
G2133:  QSKYKGIRRRKWGKWVSEIRVPGTRQRLWLGSFSTAEGAAVAHDVA

G47:    FFCLHQPDSL--ESLNFPHLLNPSLV
        F+CLH+P SL   ES NFPHLL  SL+
G2133:  FYCLHRPSSLDDESFNFPHLLTTSLA
```

G47 (SEQ ID NO: 66) and G3643 (SEQ ID NO: 158) conserved domains

```
G47:    SKYKGIRRRKWGKWVSEIRVPGTRDRLWLGSFSTAEGAAVAHDVAF
        +K KG+RRRKWGKWVSEIRVPGT++RLWLG+++T E AAVAHDVA
G3643:  NKLKGVRRRKWGKWVSEIRVPGTQERLWLGTYATPEAAAVAHDVAV

G47:    FCLHQPDSLESLNFPHLLN
        +CL +P SL+ LNFP  L+
G3643:  YCLSRPSSLDKLNFPETLS
```

G47 (SEQ ID NO: 66) and G3649 (SEQ ID NO: 154) conserved domains

```
G47:    KYKGIRRRKWGKWVSEIRVPGTRDRLWLGSFSTAEGAAVAHDVA
        +Y+G+RRR+WGKWVSEIRVPGTR+RLWLGS++TAE AAVAHD A
G3649:  RYRGVRRRWGKWVSEIRVPGTRERLWLGSYATAEAAAVAHDAA
```

G47 (SEQ ID NO: 6) and G3644 (SEQ ID NO: 156) conserved domains

```
G47:    KYKGIRRRKWGKWVSEIRVPGTRDRLWLGSFSTAEGAAVAHDVA
        +Y+G+RRR+WGKWVSEIRVPGTR+RLWLGS++T E AAVAHD A
G3644:  RYRGVRRRWGKWVSEIRVPGTRERLWLGSYATPEAAAVAHDTA

G47:    FFCL
        + L
G3644:  VYFL
```

FIG. 5

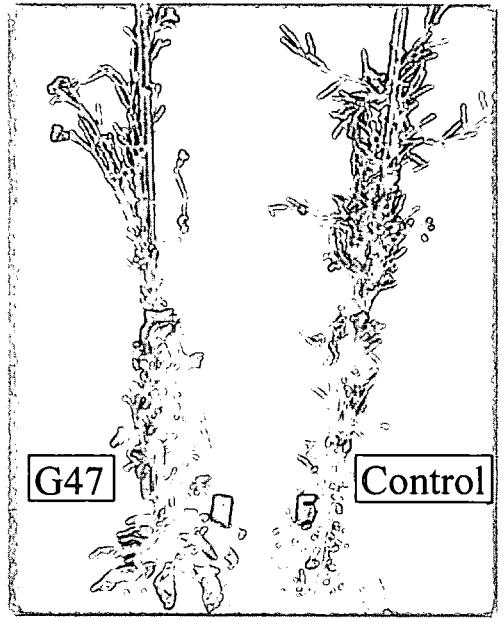
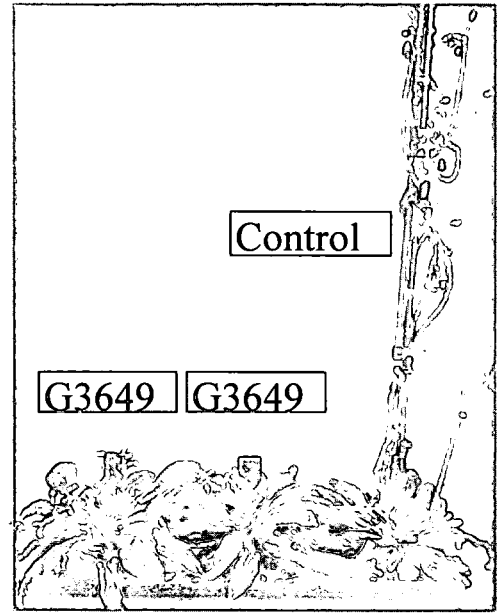
FIG. 6A
FIG. 6B
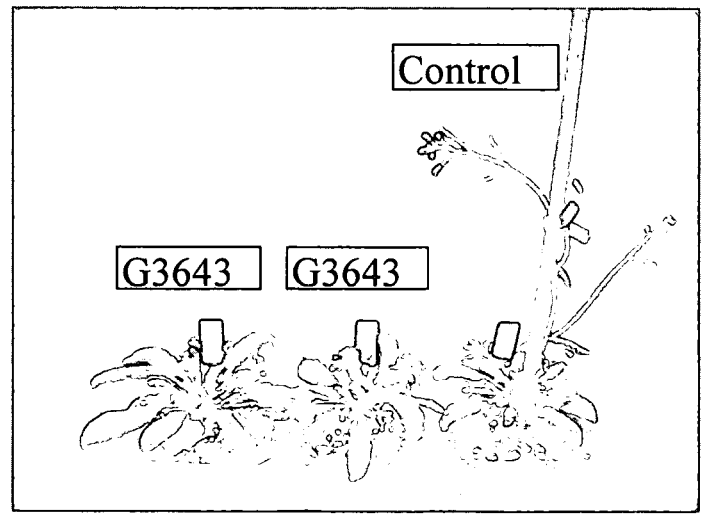
FIG. 6C

SEQUENCE LISTING

<160> NUMBER OF SEQ ID NOS: 256

<210> SEQ ID NO 1
<211> LENGTH: 2793
<212> TYPE: DNA
<213> ORGANISM: Arabidopsis thaliana
<220> FEATURE:
<223> OTHER INFORMATION: G1272

<400> SEQUENCE: 1

```
atggattcaa caaatggtaa cggagctgat cttgaatcag caaatggggc aaacgggagt      60
ggggttactg aggcattacc acctcctcca ccagttatac ctccaaatgt ggaaccagtt     120
cgtgttaaaa ctgaacttgc tgagaagaag gggccagttc gagttcctat ggctcgaaaa     180
ggatttggaa caagggggcca aaagatcccc ttgttaacaa atcatttcaa agtcgatgtg     240
gctaatcttc agggtcattt cttccactac agtgtggctc tattctatga tgatggtcgt     300
cctgttgaac aaaagggtgt tggaagaaaa atccttgaca aggtgcatca gacttaccat     360
tctgatctgg atggtaaaga gtttgcttat gacggtgaga agacgttgtt tacatatgga     420
gctttgccta gtaacaagat ggattttttct gtggtgcttg aggaagtatc tgctacaagt     480
aaggattttg tgagcagggc taatggaaac ggaagcccca atgggaatga agtccaagt     540
gatggtgata ggaaaagact gcgtaggcct aaccggtcca aaaactttag agtggagatc     600
agctatgcgg ccaaaattcc tcttcaagct cttgctaatg caatgcgggg acaagaatca     660
gagaattccc aggaggcaat acgggttctt gatatcatat tgaggcaaca tgctgctaga     720
caaggttgct tgcttgttcg acagtctttt ttccacaatg atccaaccaa ctgtgaacca     780
gttggtggta acatcttagg atgtagggga tttcactcca gtttcagaac aacgcagggt     840
ggcatgtcac ttaatatgga tgttacaacc accatgatca tcaagcctgg tccagtggtt     900
gatttcctaa ttgctaacca aatgctagg gaccctttatt cgattgactg gtctaaggct     960
aaacgaaccc ttaagaacct aagggtaaag gtcagcccct caggccaaga attcaagata    1020
accggattga gtgacaagcc ttgcagggaa caaacgtttg aattgaagaa aaggaaccca    1080
aatgaaaatg gagagttcga aactactgaa gttacagttg ctgactactt ccgcgataca    1140
aggcatattg atttgcaata ttctgcggat ttgccttgca tcaatgttgg gaagccaaag    1200
cgacccactt acattcctct cgagctctgc gcgttggttc cacttcagag gtacacaaaa    1260
gcacttacca cgttccaaag atctgccctt gttgagaaat ccagacagaa accccaagag    1320
aggatgactg ttctgtccaa agctctgaaa gttagcaact atgatgcgga accactcctg    1380
cgatcctgtg gcatttcgat cagctccaac tttactcagg tggagggtcg tgttctacca    1440
gctcccaagc tgaaaatggg atgtggatct gaaacctttc ccagaaatgg tcgctggaac    1500
ttcaacaaca aggaatttgt tgagcccacc aaaattcaac gatgggttgt tgtcaatttc    1560
tctgctcgct gtaatgtacg tcaagttgtt gatgatctga taaaaattgg aggatcaaaa    1620
ggaattgaaa ttgcttctcc ctttcaagtg tttgaggagg gtaatcaatt ccgccgtgct    1680
cctcctatga ttcgtgttga aacatgtttt aaggacatcc aatcgaaact ccctggtgtc    1740
ccacaattca tactatgtgt gctccctgac aaaaagaaca gtgatctcta tggtccatgg    1800
aagaaaaaaa acttaactga atttggcatt gttactcaat gcatggctcc aacgcgggcaa    1860
cctaatgatc agtatcttac taacttactt ctgaagatta atgcaaagct tggaggcctg    1920
aactcaatgt taagtgtaga gcgtacacct gcgttcactg tgatttctaa ggttccaacc    1980
```

```
attatccttg ggatggatgt ttcacatgga tctcctggac agtctgatgt cccgtccatc    2040
gctgctgtgg tgagttctag ggagtggcca ctgatatcca aatatagagc atctgttcgg    2100
acacagcctt ctaaggctga gatgattgag tcccttgtca agaaaaatgg aactgaagac    2160
gatggcatta tcaaggagtt gctggtagat ttctacacca gctcgaataa gagaaaacca    2220
gagcatatca taattttcag ggatggtgtg agtgaatctc aattcaatca ggttctgaat    2280
attgaacttg atcagatcat cgaggcttgc aagctcttag acgcaaattg gaacccaaag    2340
ttccttttgt tggtggctca aaagaatcat cataccaagt tcttccagcc aacgtctcct    2400
gaaaatgttc ctccagggac aatcattgac aacaaaatat gtcacccaaa gaacaatgat    2460
ttctacctct gtgctcacgc tggaatgatt ggaactaccc gcccaactca ctaccacgtc    2520
ctgtatgatg agattggttt ttcagctgac gaacttcagg aacttgtcca ctcgctctcc    2580
tatgtgtacc aaagaagcac cagtgccatt tctgttgttg cgccgatctg ctatgctcac    2640
ttggcagctg ctcagcttgg gacgttcatg aagtttgaag atcagtctga cacatcatca    2700
agccatggtg gtatcacagc tccaggacca atctctgttg cacagctccc aagactcaaa    2760
gacaacgtcg ccaactccat gttcttctgt taa                                 2793
```

<210> SEQ ID NO 2
<211> LENGTH: 930
<212> TYPE: PRT
<213> ORGANISM: Arabidopsis thaliana
<220> FEATURE:
<223> OTHER INFORMATION: G1272 polypeptide

<400> SEQUENCE: 2

```
Met Asp Ser Thr Asn Gly Asn Gly Ala Asp Leu Glu Ser Ala Asn Gly
1               5                   10                  15

Ala Asn Gly Ser Gly Val Thr Glu Ala Leu Pro Pro Pro Pro Pro Val
            20                  25                  30

Ile Pro Pro Asn Val Glu Pro Arg Val Lys Thr Glu Leu Ala Glu
        35                  40                  45

Lys Lys Gly Pro Val Arg Val Pro Met Ala Arg Lys Gly Phe Gly Thr
    50                  55                  60

Arg Gly Gln Lys Ile Pro Leu Leu Thr Asn His Phe Lys Val Asp Val
65                  70                  75                  80

Ala Asn Leu Gln Gly His Phe His Tyr Ser Val Ala Leu Phe Tyr
            85                  90                  95

Asp Asp Gly Arg Pro Val Glu Gln Lys Gly Val Gly Arg Lys Ile Leu
            100                 105                 110

Asp Lys Val His Gln Thr Tyr His Ser Asp Leu Asp Gly Lys Glu Phe
        115                 120                 125

Ala Tyr Asp Gly Glu Lys Thr Leu Phe Thr Tyr Gly Ala Leu Pro Ser
    130                 135                 140

Asn Lys Met Asp Phe Ser Val Val Leu Glu Glu Val Ser Ala Thr Ser
145                 150                 155                 160

Lys Asp Phe Val Ser Arg Ala Asn Gly Asn Gly Ser Pro Asn Gly Asn
            165                 170                 175

Glu Ser Pro Ser Asp Gly Asp Arg Lys Arg Leu Arg Arg Pro Asn Arg
        180                 185                 190

Ser Lys Asn Phe Arg Val Glu Ile Ser Tyr Ala Ala Lys Ile Pro Leu
    195                 200                 205

Gln Ala Leu Ala Asn Ala Met Arg Gly Gln Glu Ser Glu Asn Ser Gln
```

```
            210                 215                 220
Glu Ala Ile Arg Val Leu Asp Ile Ile Leu Arg Gln His Ala Ala Arg
225                 230                 235                 240

Gln Gly Cys Leu Leu Val Arg Gln Ser Phe Phe His Asn Asp Pro Thr
            245                 250                 255

Asn Cys Glu Pro Val Gly Gly Asn Ile Leu Gly Cys Arg Gly Phe His
            260                 265                 270

Ser Ser Phe Arg Thr Thr Gln Gly Gly Met Ser Leu Asn Met Asp Val
            275                 280                 285

Thr Thr Thr Met Ile Ile Lys Pro Gly Pro Val Val Asp Phe Leu Ile
            290                 295                 300

Ala Asn Gln Asn Ala Arg Asp Pro Tyr Ser Ile Asp Trp Ser Lys Ala
305                 310                 315                 320

Lys Arg Thr Leu Lys Asn Leu Arg Val Lys Val Ser Pro Ser Gly Gln
            325                 330                 335

Glu Phe Lys Ile Thr Gly Leu Ser Asp Lys Pro Cys Arg Glu Gln Thr
            340                 345                 350

Phe Glu Leu Lys Lys Arg Asn Pro Asn Glu Asn Gly Glu Phe Glu Thr
            355                 360                 365

Thr Glu Val Thr Val Ala Asp Tyr Phe Arg Asp Thr Arg His Ile Asp
            370                 375                 380

Leu Gln Tyr Ser Ala Asp Leu Pro Cys Ile Asn Val Gly Lys Pro Lys
385                 390                 395                 400

Arg Pro Thr Tyr Ile Pro Leu Glu Leu Cys Ala Leu Val Pro Leu Gln
            405                 410                 415

Arg Tyr Thr Lys Ala Leu Thr Thr Phe Gln Arg Ser Ala Leu Val Glu
            420                 425                 430

Lys Ser Arg Gln Lys Pro Gln Glu Arg Met Thr Val Leu Ser Lys Ala
            435                 440                 445

Leu Lys Val Ser Asn Tyr Asp Ala Glu Pro Leu Leu Arg Ser Cys Gly
            450                 455                 460

Ile Ser Ile Ser Ser Asn Phe Thr Gln Val Glu Gly Arg Val Leu Pro
465                 470                 475                 480

Ala Pro Lys Leu Lys Met Gly Cys Gly Ser Glu Thr Phe Pro Arg Asn
            485                 490                 495

Gly Arg Trp Asn Phe Asn Asn Lys Glu Phe Val Glu Pro Thr Lys Ile
            500                 505                 510

Gln Arg Trp Val Val Asn Phe Ser Ala Arg Cys Asn Val Arg Gln
            515                 520                 525

Val Val Asp Asp Leu Ile Lys Ile Gly Gly Ser Lys Gly Ile Glu Ile
            530                 535                 540

Ala Ser Pro Phe Gln Val Phe Glu Glu Gly Asn Gln Phe Arg Arg Ala
545                 550                 555                 560

Pro Pro Met Ile Arg Val Glu Asn Met Phe Lys Asp Ile Gln Ser Lys
            565                 570                 575

Leu Pro Gly Val Pro Gln Phe Ile Leu Cys Val Leu Pro Asp Lys Lys
            580                 585                 590

Asn Ser Asp Leu Tyr Gly Pro Trp Lys Lys Asn Leu Thr Glu Phe
            595                 600                 605

Gly Ile Val Thr Gln Cys Met Ala Pro Thr Arg Gln Pro Asn Asp Gln
            610                 615                 620

Tyr Leu Thr Asn Leu Leu Leu Lys Ile Asn Ala Lys Leu Gly Gly Leu
625                 630                 635                 640
```

Asn Ser Met Leu Ser Val Glu Arg Thr Pro Ala Phe Thr Val Ile Ser
            645                 650                 655

Lys Val Pro Thr Ile Ile Leu Gly Met Asp Val Ser His Gly Ser Pro
        660                 665                 670

Gly Gln Ser Asp Val Pro Ser Ile Ala Ala Val Val Ser Ser Arg Glu
    675                 680                 685

Trp Pro Leu Ile Ser Lys Tyr Arg Ala Ser Val Arg Thr Gln Pro Ser
690                 695                 700

Lys Ala Glu Met Ile Glu Ser Leu Val Lys Lys Asn Gly Thr Glu Asp
705                 710                 715                 720

Asp Gly Ile Ile Lys Glu Leu Leu Val Asp Phe Tyr Thr Ser Ser Asn
            725                 730                 735

Lys Arg Lys Pro Glu His Ile Ile Phe Arg Asp Gly Val Ser Glu
        740                 745                 750

Ser Gln Phe Asn Gln Val Leu Asn Ile Glu Leu Asp Gln Ile Ile Glu
    755                 760                 765

Ala Cys Lys Leu Leu Asp Ala Asn Trp Asn Pro Lys Phe Leu Leu Leu
770                 775                 780

Val Ala Gln Lys Asn His His Thr Lys Phe Phe Gln Pro Thr Ser Pro
785                 790                 795                 800

Glu Asn Val Pro Pro Gly Thr Ile Ile Asp Asn Lys Ile Cys His Pro
            805                 810                 815

Lys Asn Asn Asp Phe Tyr Leu Cys Ala His Ala Gly Met Ile Gly Thr
        820                 825                 830

Thr Arg Pro Thr His Tyr His Val Leu Tyr Asp Glu Ile Gly Phe Ser
    835                 840                 845

Ala Asp Glu Leu Gln Glu Leu Val His Ser Leu Ser Tyr Val Tyr Gln
850                 855                 860

Arg Ser Thr Ser Ala Ile Ser Val Val Ala Pro Ile Cys Tyr Ala His
865                 870                 875                 880

Leu Ala Ala Ala Gln Leu Gly Thr Phe Met Lys Phe Glu Asp Gln Ser
            885                 890                 895

Glu Thr Ser Ser Ser His Gly Gly Ile Thr Ala Pro Gly Pro Ile Ser
        900                 905                 910

Val Ala Gln Leu Pro Arg Leu Lys Asp Asn Val Ala Asn Ser Met Phe
    915                 920                 925

Phe Cys
    930

<210> SEQ ID NO 3
<211> LENGTH: 1413
<212> TYPE: DNA
<213> ORGANISM: Arabidopsis thaliana
<220> FEATURE:
<223> OTHER INFORMATION: G1506

<400> SEQUENCE: 3
atggggaagc aaggtccttg ctatcactgt ggagttacaa gtacacctct atggagaaac    60
gggccaccag agaagccggt gttgtgcaat gcgtgtggtt cgaggtggag aactaaagga   120
tcattagtaa actacacacc tcttcatgct cgtgctgaag tgatgagact gagattgag   180 gatcatagaa ctcaaacggt gatgattaag gaatgtctt tgaacaaaaa gattcccaag   240
aggaaaccat atcaagaaaa cttcacagtg aaaagagcta acttggaatt ccataccggt   300
ttcaagagga aggctctgga tgaagaagct agcaatagat cgagttcagg atcggttgta   360

-continued

```
tcaaactccg agagctgtgc acaatctaat gcgtgggact cgacttttcc ttgtaagaga      420
aggacatgtg tgggacgtcc aaaggcagct tcttctgttg aaaagctcac aaaggatctt      480
tatactattc tacaagaaca gcaatcttct tgtctctctg gtacttcaga ggaagatttg      540 cttttgaga atgaaacacc aatgctgtta ggacatggta gtgttcttat gagagatcct      600
cactcaggtg ctcgagaaga ggaatctgaa gctagctcac tcttagttga gagcagcaag      660
tcttcatcag ttcattctgt taaatttggt ggaaaagcaa tgaagcagga gcaagtgaag      720
aggagcaaat ctcaagtctt aggaagacat agttcactac tctgtagcat agatttgaag      780
gatgttttca actttgatga gttcatagaa aatttcacag aggaagaaca gcaaaaactg      840
atgaaattac ttcctcaagt tgactctgtt gatcgtcctg atagcctcag aagcatgttt      900
gagagttctc aattcaaaga gaacttatcc ttgtttcagc aacttgtggc agatggtgtt      960
tttgagacaa attcgtctta tgcaaaactt gaagacatta agacacttgc aaagcttgct     1020
ttatcagatc ctaacaaatc ccatttgttg gaaagctatt acatgctcaa gagaagagag     1080
attgaagact gtgttactac aacatcaagg gtctcaagct tgagtccatc gaataataat     1140
agtcttgtaa ccattgaaag accttgtgaa agcttaaacc aaaacttctc agagacaaga     1200
ggtgtgatga agcccgaa agaagtgatg aagattagat caaagcacac cgaagagaat     1260
ttagagaata gtgtatcttc ctttaaacct gtgagctgtg gtggacctct ggtgtttagc     1320
tatgaagata atgatatttc tgatcaggat cttcttcttg atgtgccgtc gaacggctca     1380
ttccctcaag cagagcttct aaacatgata tga                                 1413
```

<210> SEQ ID NO 4
<211> LENGTH: 470
<212> TYPE: PRT
<213> ORGANISM: Arabidopsis thaliana
<220> FEATURE:
<223> OTHER INFORMATION: G1506 polypeptide

<400> SEQUENCE: 4

Met Gly Lys Gln Gly Pro Cys Tyr His Cys Gly Val Thr Ser Thr Pro
1               5                   10                  15

Leu Trp Arg Asn Gly Pro Glu Lys Pro Val Leu Cys Asn Ala Cys
            20                  25                  30

Gly Ser Arg Trp Arg Thr Lys Gly Ser Leu Val Asn Tyr Thr Pro Leu
        35                  40                  45

His Ala Arg Ala Glu Gly Asp Glu Thr Glu Ile Glu Asp His Arg Thr
    50                  55                  60

Gln Thr Val Met Ile Lys Gly Met Ser Leu Asn Lys Lys Ile Pro Lys
65                  70                  75                  80

Arg Lys Pro Tyr Gln Glu Asn Phe Thr Val Lys Arg Ala Asn Leu Glu
                85                  90                  95

Phe His Thr Gly Phe Lys Arg Lys Ala Leu Asp Glu Glu Ala Ser Asn
            100                 105                 110

Arg Ser Ser Ser Gly Ser Val Val Ser Asn Ser Glu Ser Cys Ala Gln
        115                 120                 125

Ser Asn Ala Trp Asp Ser Thr Phe Pro Cys Lys Arg Thr Cys Val
    130                 135                 140

Gly Arg Pro Lys Ala Ala Ser Ser Val Glu Lys Leu Thr Lys Asp Leu
145                 150                 155                 160

Tyr Thr Ile Leu Gln Glu Gln Gln Ser Ser Cys Leu Ser Gly Thr Ser
                165                 170                 175

Glu Glu Asp Leu Leu Phe Glu Asn Glu Thr Pro Met Leu Leu Gly His
                180                 185                 190

Gly Ser Val Leu Met Arg Asp Pro His Ser Gly Ala Arg Glu Glu Glu
            195                 200                 205

Ser Glu Ala Ser Ser Leu Leu Val Glu Ser Ser Lys Ser Ser Ser Val
        210                 215                 220

His Ser Val Lys Phe Gly Gly Lys Ala Met Lys Gln Glu Gln Val Lys
225                 230                 235                 240

Arg Ser Lys Ser Gln Val Leu Gly Arg His Ser Ser Leu Leu Cys Ser
                245                 250                 255

Ile Asp Leu Lys Asp Val Phe Asn Phe Asp Glu Phe Ile Glu Asn Phe
            260                 265                 270

Thr Glu Glu Glu Gln Lys Leu Met Lys Leu Leu Pro Gln Val Asp
        275                 280                 285

Ser Val Asp Arg Pro Asp Ser Leu Arg Ser Met Phe Glu Ser Ser Gln
        290                 295                 300

Phe Lys Glu Asn Leu Ser Leu Phe Gln Gln Leu Val Ala Asp Gly Val
305                 310                 315                 320

Phe Glu Thr Asn Ser Ser Tyr Ala Lys Leu Glu Asp Ile Lys Thr Leu
                325                 330                 335

Ala Lys Leu Ala Leu Ser Asp Pro Asn Lys Ser His Leu Leu Glu Ser
            340                 345                 350

Tyr Tyr Met Leu Lys Arg Arg Glu Ile Glu Asp Cys Val Thr Thr Thr
        355                 360                 365

Ser Arg Val Ser Ser Leu Ser Pro Ser Asn Asn Asn Ser Leu Val Thr
        370                 375                 380

Ile Glu Arg Pro Cys Glu Ser Leu Asn Gln Asn Phe Ser Glu Thr Arg
385                 390                 395                 400

Gly Val Met Arg Ser Pro Lys Glu Val Met Lys Ile Arg Ser Lys His
                405                 410                 415

Thr Glu Glu Asn Leu Glu Asn Ser Val Ser Ser Phe Lys Pro Val Ser
            420                 425                 430

Cys Gly Gly Pro Leu Val Phe Ser Tyr Glu Asp Asn Asp Ile Ser Asp
        435                 440                 445

Gln Asp Leu Leu Leu Asp Val Pro Ser Asn Gly Ser Phe Pro Gln Ala
    450                 455                 460

Glu Leu Leu Asn Met Ile
465                 470

<210> SEQ ID NO 5
<211> LENGTH: 678
<212> TYPE: DNA
<213> ORGANISM: Arabidopsis thaliana
<220> FEATURE:
<223> OTHER INFORMATION: G1897

<400> SEQUENCE: 5
atgccttctg aattcagtga atctcgtcgg gttcctaaga ttccccacgg ccaaggagga      60
tctgttgcga ttccgacgga tcaacaagag cagctttctt gtcctcgctg tgaatcaacc     120
aacaccaagt tctgttacta caacaactac aacttctcac aacctcgtca tttctgcaag     180
tcttgtcgcc gttactggac tcatggaggt actctccgtg acattcccgt cggtggtgtt     240
tcccgtaaaa gctcaaaacg ttcccggact tattcctctg ccgctaccac ctccgttgtc     300
ggaagccgga actttccctt acaagctacg cctgttcttt tccctcagtc gtcttccaac     360

```
ggcggtatca cgacggcgaa gggaagtgct tcgtcgttct atggcggttt cagctctttg      420
atcaactaca acgccgccgt gagcagaaat gggcctggtg gcgggtttaa tgggccagat      480
gcttttggtc ttgggcttgg tcacgggtcg tattatgagg acgtcagata tgggcaagga      540
ataacggtct ggccgttttc aagtggcgct actgatgctg caactactac aagccacatt      600
gctcaaatac ccgccacgtg gcagtttgaa ggtcaagaga gcaaagtcgg gttcgtgtct      660
ggagactacg tagcgtga                                                    678
```

<210> SEQ ID NO 6
<211> LENGTH: 225
<212> TYPE: PRT
<213> ORGANISM: Arabidopsis thaliana
<220> FEATURE:
<223> OTHER INFORMATION: G1897 polypeptide

<400> SEQUENCE: 6

```
Met Pro Ser Glu Phe Ser Glu Ser Arg Arg Val Pro Lys Ile Pro His
1               5                   10                  15

Gly Gln Gly Gly Ser Val Ala Ile Pro Thr Asp Gln Gln Glu Gln Leu
            20                  25                  30

Ser Cys Pro Arg Cys Glu Ser Thr Asn Thr Lys Phe Cys Tyr Tyr Asn
        35                  40                  45

Asn Tyr Asn Phe Ser Gln Pro Arg His Phe Cys Lys Ser Cys Arg Arg
    50                  55                  60

Tyr Trp Thr His Gly Gly Thr Leu Arg Asp Ile Pro Val Gly Gly Val
65                  70                  75                  80

Ser Arg Lys Ser Ser Lys Arg Ser Arg Thr Tyr Ser Ser Ala Ala Thr
                85                  90                  95

Thr Ser Val Val Gly Ser Arg Asn Phe Pro Leu Gln Ala Thr Pro Val
            100                 105                 110

Leu Phe Pro Gln Ser Ser Ser Asn Gly Gly Ile Thr Thr Ala Lys Gly
        115                 120                 125

Ser Ala Ser Ser Phe Tyr Gly Gly Phe Ser Ser Leu Ile Asn Tyr Asn
    130                 135                 140

Ala Ala Val Ser Arg Asn Gly Pro Gly Gly Phe Asn Gly Pro Asp
145                 150                 155                 160

Ala Phe Gly Leu Gly Leu Gly His Gly Ser Tyr Tyr Glu Asp Val Arg
                165                 170                 175

Tyr Gly Gln Gly Ile Thr Val Trp Pro Phe Ser Ser Gly Ala Thr Asp
            180                 185                 190

Ala Ala Thr Thr Thr Ser His Ile Ala Gln Ile Pro Ala Thr Trp Gln
        195                 200                 205

Phe Glu Gly Gln Glu Ser Lys Val Gly Phe Val Ser Gly Asp Tyr Val
    210                 215                 220

Ala
225
```

<210> SEQ ID NO 7
<211> LENGTH: 1605
<212> TYPE: DNA
<213> ORGANISM: Arabidopsis thaliana
<220> FEATURE:
<223> OTHER INFORMATION: G1946

<400> SEQUENCE: 7

```
tctcacctat tgtaaaaatc accagtttcg tatataaaac cctaattttc tcaaaattcc       60
```

-continued

```
caaatattga cttggaatca aaaatccgaa tggatgtgag caaagtaacc acaagcgacg    120
gcggaggaga ttcaatggag actaagccat ctcctcaacc tcagcctgcg gcgattctaa    180
gttcaaacgc gcctcctccg tttctgagca agacctatga tatggttgat gatcacaata    240
cagattcgat tgtctcttgg agtgctaata caacagttt tatcgtttgg aaaccaccgg     300
agttcgctcg cgatcttctt cctaagaact ttaagcataa taatttctcc agcttcgtta    360
gacagcttaa tacctatggt ttcaggaagg ttgacccaga tagatgggaa tttgcgaatg    420 aaggttttt aagaggtcag aagcacttgc tacaatcaat aactaggcga aaacctgccc      480
atggacaggg acagggacat cagcgatctc agcactcgaa tggacagaac tcatctgtta    540
gcgcatgtgt tgaagttggc aaatttggtc tcgaagaaga agttgaaagg cttaaaagag    600
ataagaacgt ccttatgcaa gaactcgtca gattaagaca gcagcaacag tccactgata    660
accaacttca aacgatggtt cagcgtctcc agggcatgga gaatcggcaa caacaattaa    720
tgtcattcct tgcaaaggca gtacaaagcc ctcattttct atctcaattc ttacagcagc    780
agaatcagca aaacgagagt aataggcgca tcagtgatac cagtaagaag cggagattca    840
agcgagacgg cattgtccgt aataatgatt ctgctactcc tgatggacag atagtgaagt    900
atcaacctcc aatgcacgag caagccaaag caatgtttaa acagcttatg aagatggaac    960
cttacaaaac cggcgatgat ggtttccttc taggtaatgg tacgtctact accgagggaa   1020
cagagatgga gacttcatca aaccaagtat cgggtataac tcttaaggaa atgcctacag   1080
cttctgagat acagtcatca tcaccaattg aaacaactcc tgaaaatgtt tcggcagcat   1140
cagaagcaac cgagaactgt attccttcac ctgatgatct aactcttccc gacttcactc   1200
atatgctacc ggaaaataat tcagagaagc ctccagagag tttcatggaa ccaaacctgg   1260
gaggttctag tccattacta gatccagatc tgttgatcga tgattctttg tccttcgaca   1320
ttgacgactt tccaatggat tctgatatag accctgttga ttacggttta ctcgaacgct   1380
tactcatgtc aagcccggtt ccagataata tggattcaac accagtggac aatgaaacag   1440
agcaggaaca aaatggatgg acaaaaacta agcatatgga taatctgact caacagatgg   1500
gtctcctctc tcctgaaacc ttagatctct caaggcaaaa tccttgattt gggagttt     1560 taaagtctt tgaggtaaca cagtccctga gagcagcata ttcat                   1605
```

<210> SEQ ID NO 8
<211> LENGTH: 485
<212> TYPE: PRT
<213> ORGANISM: Arabidopsis thaliana
<220> FEATURE:
<223> OTHER INFORMATION: G1946 polypeptide

<400> SEQUENCE: 8

```
Met Asp Val Ser Lys Val Thr Thr Ser Asp Gly Gly Gly Asp Ser Met
1               5                   10                  15

Glu Thr Lys Pro Ser Pro Gln Pro Gln Pro Ala Ala Ile Leu Ser Ser
            20                  25                  30

Asn Ala Pro Pro Pro Phe Leu Ser Lys Thr Tyr Asp Met Val Asp Asp
        35                  40                  45

His Asn Thr Asp Ser Ile Val Ser Trp Ser Ala Asn Asn Ser Phe
    50                  55                  60

Ile Val Trp Lys Pro Pro Glu Phe Ala Arg Asp Leu Leu Pro Lys Asn
65                  70                  75                  80

Phe Lys His Asn Asn Phe Ser Ser Phe Val Arg Gln Leu Asn Thr Tyr
```

```
                    85                  90                  95
Gly Phe Arg Lys Val Asp Pro Asp Arg Trp Glu Phe Ala Asn Glu Gly
            100                 105                 110

Phe Leu Arg Gly Gln Lys His Leu Leu Gln Ser Ile Thr Arg Arg Lys
            115                 120                 125

Pro Ala His Gly Gln Gly Gly His Gln Arg Ser Gln His Ser Asn
            130                 135                 140

Gly Gln Asn Ser Ser Val Ser Ala Cys Val Glu Val Gly Lys Phe Gly
145                 150                 155                 160

Leu Glu Glu Glu Val Glu Arg Leu Lys Arg Asp Lys Asn Val Leu Met
                165                 170                 175

Gln Glu Leu Val Arg Leu Arg Gln Gln Gln Ser Thr Asp Asn Gln
            180                 185                 190

Leu Gln Thr Met Val Gln Arg Leu Gln Gly Met Glu Asn Arg Gln Gln
            195                 200                 205

Gln Leu Met Ser Phe Leu Ala Lys Ala Val Gln Ser Pro His Phe Leu
    210                 215                 220

Ser Gln Phe Leu Gln Gln Gln Asn Gln Gln Asn Glu Ser Asn Arg Arg
225                 230                 235                 240

Ile Ser Asp Thr Ser Lys Lys Arg Arg Phe Lys Arg Asp Gly Ile Val
            245                 250                 255

Arg Asn Asn Asp Ser Ala Thr Pro Asp Gly Gln Ile Val Lys Tyr Gln
            260                 265                 270

Pro Pro Met His Glu Gln Ala Lys Ala Met Phe Lys Gln Leu Met Lys
            275                 280                 285

Met Glu Pro Tyr Lys Thr Gly Asp Asp Gly Phe Leu Leu Gly Asn Gly
            290                 295                 300

Thr Ser Thr Thr Glu Gly Thr Glu Met Glu Thr Ser Ser Asn Gln Val
305                 310                 315                 320

Ser Gly Ile Thr Leu Lys Glu Met Pro Thr Ala Ser Glu Ile Gln Ser
                325                 330                 335

Ser Ser Pro Ile Glu Thr Thr Pro Glu Asn Val Ser Ala Ala Ser Glu
            340                 345                 350

Ala Thr Glu Asn Cys Ile Pro Ser Pro Asp Asp Leu Thr Leu Pro Asp
            355                 360                 365

Phe Thr His Met Leu Pro Glu Asn Asn Ser Glu Lys Pro Pro Glu Ser
            370                 375                 380

Phe Met Glu Pro Asn Leu Gly Gly Ser Ser Pro Leu Leu Asp Pro Asp
385                 390                 395                 400

Leu Leu Ile Asp Asp Ser Leu Ser Phe Asp Ile Asp Asp Phe Pro Met
                405                 410                 415

Asp Ser Asp Ile Asp Pro Val Asp Tyr Gly Leu Leu Glu Arg Leu Leu
            420                 425                 430

Met Ser Ser Pro Val Pro Asp Asn Met Asp Ser Thr Pro Val Asp Asn
            435                 440                 445

Glu Thr Glu Gln Glu Gln Asn Gly Trp Asp Lys Thr Lys His Met Asp
            450                 455                 460

Asn Leu Thr Gln Gln Met Gly Leu Leu Ser Pro Glu Thr Leu Asp Leu
465                 470                 475                 480

Ser Arg Gln Asn Pro
            485

<210> SEQ ID NO 9
```

```
<211> LENGTH: 640
<212> TYPE: DNA
<213> ORGANISM: Arabidopsis thaliana
<220> FEATURE:
<223> OTHER INFORMATION: G2113

<400> SEQUENCE: 9
ataacaaact catcaaactt cctcagcgtt tctttttctt acataaacaa tttttcttac      60
ataaacaaat cttgttgttt gttgttgtca tggcaccgac agttaaaacg gcggccgtca     120
aaaccaacga aggtaacgga gtccgttaca gaggagtgag gaagagacca tggggacgtt     180
acgcagccga gatcagagat cctttcaaga agtcacgtgt ctggctcggt actttcgaca     240
ctcctgaaga agccgctcgt gcctacgaca aacgtgctat tgagtttcgt ggagctaaag     300
ccaaaaccaa cttcccttgt tacaacatca acgcccactg cttgagtttg acacagagcc     360
tgagccagag cagcaccgtg gaatcatcgt ttcctaatct caacctcgga tctgactctg     420
ttagttcgag attcccttt cctaagattc aggttaaggc tgggatgatg gtgttcgatg     480
aaaggagtga atcggattct cgtcggtgg tgatggatgt cgttagatat gaaggacgac     540
gtgtggtttt ggacttggat cttaatttcc ctcctccacc tgagaactga ttaagattta     600
attatgatta ttagatataa ttaaatgttt ctgaattgag                            640

<210> SEQ ID NO 10
<211> LENGTH: 166
<212> TYPE: PRT
<213> ORGANISM: Arabidopsis thaliana
<220> FEATURE:
<223> OTHER INFORMATION: G2113 polypeptide

<400> SEQUENCE: 10

Met Ala Pro Thr Val Lys Thr Ala Ala Val Lys Thr Asn Glu Gly Asn
  1               5                  10                  15

Gly Val Arg Tyr Arg Gly Val Arg Lys Arg Pro Trp Gly Arg Tyr Ala
             20                  25                  30

Ala Glu Ile Arg Asp Pro Phe Lys Lys Ser Arg Val Trp Leu Gly Thr
         35                  40                  45

Phe Asp Thr Pro Glu Glu Ala Ala Arg Ala Tyr Asp Lys Arg Ala Ile
     50                  55                  60

Glu Phe Arg Gly Ala Lys Ala Lys Thr Asn Phe Pro Cys Tyr Asn Ile
 65                  70                  75                  80

Asn Ala His Cys Leu Ser Leu Thr Gln Ser Leu Ser Gln Ser Ser Thr
                 85                  90                  95

Val Glu Ser Ser Phe Pro Asn Leu Asn Leu Gly Ser Asp Ser Val Ser
            100                 105                 110

Ser Arg Phe Pro Phe Pro Lys Ile Gln Val Lys Ala Gly Met Met Val
        115                 120                 125

Phe Asp Glu Arg Ser Glu Ser Asp Ser Ser Val Val Met Asp Val
    130                 135                 140

Val Arg Tyr Glu Gly Arg Arg Val Val Leu Asp Leu Asp Leu Asn Phe
145                 150                 155                 160

Pro Pro Pro Pro Glu Asn
                165

<210> SEQ ID NO 11
<211> LENGTH: 506
<212> TYPE: DNA
<213> ORGANISM: Arabidopsis thaliana
<220> FEATURE:
```

<223> OTHER INFORMATION: G2117

<400> SEQUENCE: 11

```
atacttgtca acaaaaattt tcttaaagaa cgcataactg ttttttttcat ggctggttct      60
gtctataacc ttccaagtca aaaccctaat ccacagtctt tattccaaat ctttgttgat     120
cgagtaccac tttcaaactt gcctgccacg tcagacgact ctagccggac tgcagaagat     180
aatgagagga agcggagaag gaaggtatcg aaccgcgagt cagctcggag atcgcgtatg     240
cggaaacagc gtcacatgga agaactgtgg tccatgcttg ttcaactcat caataagaac     300
aaatctctag tcgatgagct aagccaagcc agggaatgtt acgagaaggt tatagaagag     360
aacatgaaac ttcgagagga aaactccaag tcgaggaaga tgattggtga gatcgggctt     420
aataggtttc ttagcgtaga ggccgatcag atctggacct ctaatcgtc tcgtaagctt      480
gttggttttt tgttgtttat ttaaag                                          506
```

<210> SEQ ID NO 12
<211> LENGTH: 138
<212> TYPE: PRT
<213> ORGANISM: Arabidopsis thaliana
<220> FEATURE:
<223> OTHER INFORMATION: G2117 polypeptide

<400> SEQUENCE: 12

```
Met Ala Gly Ser Val Tyr Asn Leu Pro Ser Gln Asn Pro Asn Pro Gln
1               5                   10                  15

Ser Leu Phe Gln Ile Phe Val Asp Arg Val Pro Leu Ser Asn Leu Pro
            20                  25                  30

Ala Thr Ser Asp Asp Ser Ser Arg Thr Ala Glu Asp Asn Glu Arg Lys
        35                  40                  45

Arg Arg Arg Lys Val Ser Asn Arg Glu Ser Ala Arg Arg Ser Arg Met
    50                  55                  60

Arg Lys Gln Arg His Met Glu Glu Leu Trp Ser Met Leu Val Gln Leu
65                  70                  75                  80

Ile Asn Lys Asn Lys Ser Leu Val Asp Glu Leu Ser Gln Ala Arg Glu
                85                  90                  95

Cys Tyr Glu Lys Val Ile Glu Glu Asn Met Lys Leu Arg Glu Glu Asn
            100                 105                 110

Ser Lys Ser Arg Lys Met Ile Gly Glu Ile Gly Leu Asn Arg Phe Leu
        115                 120                 125

Ser Val Glu Ala Asp Gln Ile Trp Thr Phe
    130                 135
```

<210> SEQ ID NO 13
<211> LENGTH: 1050
<212> TYPE: DNA
<213> ORGANISM: Arabidopsis thaliana
<220> FEATURE:
<223> OTHER INFORMATION: G2155

<400> SEQUENCE: 13

```
ctcatatata ccaaccaaac ctctctctgc atctttatta acacaaaatt ccaaaagatt      60
aaatgttgtc gaagctccct acacagcgac acttgcacct ctctccctcc tctccctcca     120
tggaaaccgt cgggcgtcca cgtggcagac ctcgaggttc aaaaacaaa cctaaagctc       180
caatctttgt caccattgac cctcctatga gtccttacat cctcgaagtg ccatccggaa     240
acgatgtcgt tgaagcccta aaccgttct gccgcggtaa agccatcggc ttttgcgtcc      300
```

```
tcagtggctc aggctccgtt gctgatgtca ctttgcgtca gccttctccg gcagctcctg    360
gctcaaccat tactttccac ggaaagttcg atcttctctc tgtctccgcc actttcctcc    420
ctcctctacc tcctacctcc ttgtcccctc ccgtctccaa tttcttcacc gtctctctcg    480
ccggacctca ggggaaagtc atcggtggat tcgtcgctgg tcctctcgtt gccgccggaa    540
ctgtttactt cgtcgccact agtttcaaga acccttccta tcaccggtta cctgctacgg    600
aggaagagca aagaaactcg gcggaagggg aagaggaggg acaatcgccg ccggtctctg    660
gaggtggtgg agagtcgatg tacgtgggtg gctctgatgt catttgggat cccaacgcca    720
aagctccatc gccgtactga ccacaaatcc atctcgttca aactagggtt tcttcttctt    780
tagatcatca agaatcaaca aaaagattgc atttttagat tctttgtaat atcataattg    840
actcactctt taatctctct atcacttctt ctttagcttt ttctgcagtg tcaaacttca    900
catatttgta gtttgatttg actatcccca agttttgtat tttatcatac aaattttttgc    960 ctgtctctaa tggttgtttt ttcgtttgta taatcttatg cattgtttat tggagctcca   1020
gagattgaat gtataatata atggtttaat                                    1050

<210> SEQ ID NO 14
<211> LENGTH: 225
<212> TYPE: PRT
<213> ORGANISM: Arabidopsis thaliana
<220> FEATURE:
<223> OTHER INFORMATION: G2155 polypeptide

<400> SEQUENCE: 14

Met Leu Ser Lys Leu Pro Thr Gln Arg His Leu His Leu Ser Pro Ser
1               5                   10                  15

Ser Pro Ser Met Glu Thr Val Gly Arg Pro Arg Gly Arg Pro Arg Gly
            20                  25                  30

Ser Lys Asn Lys Pro Lys Ala Pro Ile Phe Val Thr Ile Asp Pro Pro
        35                  40                  45

Met Ser Pro Tyr Ile Leu Glu Val Pro Ser Gly Asn Asp Val Val Glu
    50                  55                  60

Ala Leu Asn Arg Phe Cys Arg Gly Lys Ala Ile Gly Phe Cys Val Leu
65                  70                  75                  80

Ser Gly Ser Gly Ser Val Ala Asp Val Thr Leu Arg Gln Pro Ser Pro
                85                  90                  95

Ala Ala Pro Gly Ser Thr Ile Thr Phe His Gly Lys Phe Asp Leu Leu
            100                 105                 110

Ser Val Ser Ala Thr Phe Leu Pro Pro Leu Pro Pro Thr Ser Leu Ser
        115                 120                 125

Pro Pro Val Ser Asn Phe Phe Thr Val Ser Leu Ala Gly Pro Gln Gly
    130                 135                 140

Lys Val Ile Gly Gly Phe Val Ala Gly Pro Leu Val Ala Ala Gly Thr
145                 150                 155                 160

Val Tyr Phe Val Ala Thr Ser Phe Lys Asn Pro Ser Tyr His Arg Leu
                165                 170                 175

Pro Ala Thr Glu Glu Glu Gln Arg Asn Ser Ala Glu Gly Glu Glu
            180                 185                 190

Gly Gln Ser Pro Pro Val Ser Gly Gly Gly Glu Ser Met Tyr Val
        195                 200                 205

Gly Gly Ser Asp Val Ile Trp Asp Pro Asn Ala Lys Ala Pro Ser Pro
    210                 215                 220

Tyr
```

-continued

<210> SEQ ID NO 15
<211> LENGTH: 1312
<212> TYPE: DNA
<213> ORGANISM: Arabidopsis thaliana
<220> FEATURE:
<223> OTHER INFORMATION: G2290

<400> SEQUENCE: 15

```
ttctttcttt ctttctttct cttccaatca agaacaaacc ctagctcctc tcttttctc      60
tctctacctc tctttctcta tcttctctta tcactacttc tctcgccgat caatcatcat     120
gaacgatcct gataatcccg atctgagcaa cgacgactct gcttggagag aactcacact     180
cacagctcaa gattctgact tcttcgaccg agacacttcc aatatcctct ctgacttcgg     240
ttggaacctc caccactcct ccgatcatcc tcacagtctc agattcgact ccgatttaac     300
acaaaccacc ggagtcaaac ctaccaccgt cacttcttct tgttcctcat ccgccgccgt     360
ttccgttgcc gttacctcta ctaataataa tccctcagct acctcaagtt caagtgaaga     420
tccggccgag aactcaaccg cctccgccga gaaaacacca ccaccggaga caccagtgaa     480
ggagaagaag aaggctcaaa agcgaattcg gcaaccaaga ttcgcattca tgaccaagag     540
tgatgtggat aatcttgaag atggatatcg atggcgtaaa tatggacaaa agccgtcaa      600
gaatagccca ttcccaagga gctactatag atgcacaaac agcagatgca cggtgaagaa     660
gagagtagaa cgttcatcag atgatccatc gatagtgatc acaacatacg aaggacaaca     720
ttgccatcaa accattggat tccctcgtgg tggaatcctc actgcacacg acccacatag     780
cttcacttct catcatcatc tccctcctcc attaccaaat ccttattatt accaagaact     840
ccttcatcaa cttcacagag acaataatgc tccttcaccg cggttacccc gacctactac     900
tgaagataca cctgccgtgt ctactccatc agaggaaggc ttacttggtg atattgtacc     960
tcaaactatg cgcaacccctt gaggtaagct tggtacgtag caatagctaa ggaggtgcta    1020
actcattata tatagaagat attgcagacc agaatatgcg cagggagggt ataacaatat    1080
ggcgttgtaa caatggatct atatattacc tcattgttga tcaatagcac accaccggta    1140
cgtttgcaat tcttcatgt atatttcttg ttatatatgt agttatatat ccaggtataa      1200
ttttgatgta acacaacatt aatcttaatc gtggatccat cccacatttg atgcatgtat    1260
gtgcacttaa gaaaagaac atggaggaaa taacgttatt ttttattatt ct              1312
```

<210> SEQ ID NO 16
<211> LENGTH: 287
<212> TYPE: PRT
<213> ORGANISM: Arabidopsis thaliana
<220> FEATURE:
<223> OTHER INFORMATION: G2290 polypeptide

<400> SEQUENCE: 16

```
Met Asn Asp Pro Asp Asn Pro Asp Leu Ser Asn Asp Asp Ser Ala Trp
1               5                   10                  15

Arg Glu Leu Thr Leu Thr Ala Gln Asp Ser Asp Phe Phe Asp Arg Asp
            20                  25                  30

Thr Ser Asn Ile Leu Ser Asp Phe Gly Trp Asn Leu His His Ser Ser
        35                  40                  45

Asp His Pro His Ser Leu Arg Phe Asp Ser Asp Leu Thr Gln Thr Thr
    50                  55                  60

Gly Val Lys Pro Thr Thr Val Thr Ser Ser Cys Ser Ser Ser Ala Ala
```

```
                 65                  70                  75                  80
Val Ser Val Ala Val Thr Ser Thr Asn Asn Asn Pro Ser Ala Thr Ser
                     85                  90                  95

Ser Ser Ser Glu Asp Pro Ala Glu Asn Ser Thr Ala Ser Ala Glu Lys
            100                 105                 110

Thr Pro Pro Pro Glu Thr Pro Val Lys Glu Lys Lys Ala Gln Lys
        115                 120                 125

Arg Ile Arg Gln Pro Arg Phe Ala Phe Met Thr Lys Ser Asp Val Asp
        130                 135                 140

Asn Leu Glu Asp Gly Tyr Arg Trp Arg Lys Tyr Gly Gln Lys Ala Val
145                 150                 155                 160

Lys Asn Ser Pro Phe Pro Arg Ser Tyr Tyr Arg Cys Thr Asn Ser Arg
                165                 170                 175

Cys Thr Val Lys Lys Arg Val Glu Arg Ser Ser Asp Asp Pro Ser Ile
                180                 185                 190

Val Ile Thr Thr Tyr Glu Gly Gln His Cys His Gln Thr Ile Gly Phe
            195                 200                 205

Pro Arg Gly Gly Ile Leu Thr Ala His Asp Pro His Ser Phe Thr Ser
        210                 215                 220

His His His Leu Pro Pro Leu Pro Asn Pro Tyr Tyr Gln Glu
225                 230                 235                 240

Leu Leu His Gln Leu His Arg Asp Asn Asn Ala Pro Ser Pro Arg Leu
                245                 250                 255

Pro Arg Pro Thr Thr Glu Asp Thr Pro Ala Val Ser Thr Pro Ser Glu
            260                 265                 270

Glu Gly Leu Leu Gly Asp Ile Val Pro Gln Thr Met Arg Asn Pro
        275                 280                 285
```

<210> SEQ ID NO 17
<211> LENGTH: 1406
<212> TYPE: DNA
<213> ORGANISM: Arabidopsis thaliana
<220> FEATURE:
<223> OTHER INFORMATION: G2340

<400> SEQUENCE: 17

```
atacaaaact ccctcttctc tatcttcttc atcttaaaga aaaataaga gatattcgta      60 aagagagaac acaaaatttc agtttacgaa aagctagcaa agtcgagtat cgaggaataa     120
cagaataaga cgtatctatc cttgccttaa tgttcttacc aaaagatcta gtcctttctt     180
tgtatgatcg atccatcaca agcccacaac aacaacaact acatctcttt ctctatctct     240
agcttctatt tttaatacat tcaagaatca agaatggtac ggacgccgtg ttgtagagca     300
gaagggttga agaaggagc atggactcaa gaagaagacc aaaagcttat cgcctatgtt      360
caacgacatg gtgaaggcgg ttggcgaacc cttccggaca aagctggact caaaagatgt     420
ggcaaaagct gcagattgag atgggcgaat tacttaagac ctgacattaa acgtggagag     480
tttagccaag acgaggaaga ttccatcatc aacctccacg ccattcatgg caacaaatgg     540
tcggccatag ctcgtaaaat accaagaaga acagacaatg agatcaagaa ccattggaac     600
actcacatca gaaatgtct ggtcaagaaa ggtattgatc cgttgaccca caaatccctt      660
ctcgatggag ccggtaaatc atctgaccat tccgcgcatc ccgagaaaag cagcgttcat     720
gacgacaaag atgatcagaa ttcaaataac aaaaagttgt caggatcatc atcagctcgg    780
tttttgaaca gagtagcaaa cagattcggt catagaatca accacaatgt tctgtctgat    840
```

```
attattggaa gtaatggcct acttactagt cacactactc caactacaag tgtttcagaa    900
ggtgagaggt caacgagttc ttcctccaca catacctctt cgaatctccc catcaaccgt    960
agcataaccg ttgatgcaac atctctatcc tcatccacgt tctctgactc ccccgacccg   1020
tgtttatacg aggaaatagt cggtgacatt gaagatatga cgagattttc atcaagatgt   1080
ttgagtcatg ttttatctca tgaagattta ttgatgtccg ttgagtcttg tttggagaat   1140
acttcattca tgagggaaat tacaatgatc tttcaagagg ataaaatcga gacgacgtcg   1200
tttaatgata gctacgtgac gccgatcaat gaagttgatg actcctgtga agggattgac   1260
aattattttg gatgagttat attgatgatg atgaaaattt gcatttggca tgtaaatcaa   1320
ttagagtttg atttgctatg gtgtttttag tttgtgtgtg tagtgtgttt cgaccgtcaa   1380
aaaaaaaaaa aaaaaaaaaa aaaaaa                                        1406
```

<210> SEQ ID NO 18
<211> LENGTH: 333
<212> TYPE: PRT
<213> ORGANISM: Arabidopsis thaliana
<220> FEATURE:
<223> OTHER INFORMATION: G2340 polypeptide

<400> SEQUENCE: 18

```
Met Val Arg Thr Pro Cys Cys Arg Ala Glu Gly Leu Lys Lys Gly Ala
 1               5                  10                  15

Trp Thr Gln Glu Glu Asp Gln Lys Leu Ile Ala Tyr Val Gln Arg His
                20                  25                  30

Gly Glu Gly Gly Trp Arg Thr Leu Pro Asp Lys Ala Gly Leu Lys Arg
            35                  40                  45

Cys Gly Lys Ser Cys Arg Leu Arg Trp Ala Asn Tyr Leu Arg Pro Asp
        50                  55                  60

Ile Lys Arg Gly Glu Phe Ser Gln Asp Glu Asp Ser Ile Ile Asn
 65                  70                  75                  80

Leu His Ala Ile His Gly Asn Lys Trp Ser Ala Ile Ala Arg Lys Ile
                85                  90                  95

Pro Arg Arg Thr Asp Asn Glu Ile Lys Asn His Trp Asn Thr His Ile
               100                 105                 110

Lys Lys Cys Leu Val Lys Lys Gly Ile Asp Pro Leu Thr His Lys Ser
            115                 120                 125

Leu Leu Asp Gly Ala Gly Lys Ser Ser Asp His Ser Ala His Pro Glu
        130                 135                 140

Lys Ser Ser Val His Asp Lys Asp Asp Gln Asn Ser Asn Asn Lys
145                 150                 155                 160

Lys Leu Ser Gly Ser Ser Ala Arg Phe Leu Asn Arg Val Ala Asn
                165                 170                 175

Arg Phe Gly His Arg Ile Asn His Asn Val Leu Ser Asp Ile Ile Gly
            180                 185                 190

Ser Asn Gly Leu Leu Thr Ser His Thr Thr Pro Thr Ser Val Ser
        195                 200                 205

Glu Gly Glu Arg Ser Thr Ser Ser Ser Thr His Thr Ser Ser Asn
    210                 215                 220

Leu Pro Ile Asn Arg Ser Ile Thr Val Asp Ala Thr Ser Leu Ser Ser
225                 230                 235                 240

Ser Thr Phe Ser Asp Ser Pro Asp Pro Cys Leu Tyr Glu Glu Ile Val
                245                 250                 255

Gly Asp Ile Glu Asp Met Thr Arg Phe Ser Ser Arg Cys Leu Ser His
```

-continued

```
                260             265             270
    Val Leu Ser His Glu Asp Leu Leu Met Ser Val Glu Ser Cys Leu Glu
                275                 280                 285

Asn Thr Ser Phe Met Arg Glu Ile Thr Met Ile Phe Gln Glu Asp Lys
            290                 295                 300

Ile Glu Thr Thr Ser Phe Asn Asp Ser Tyr Val Thr Pro Ile Asn Glu
305                 310                 315                 320

Val Asp Asp Ser Cys Glu Gly Ile Asp Asn Tyr Phe Gly
                    325                 330
```

<210> SEQ ID NO 19
<211> LENGTH: 1384
<212> TYPE: DNA
<213> ORGANISM: Arabidopsis thaliana
<220> FEATURE:
<223> OTHER INFORMATION: G671

<400> SEQUENCE: 19

| | | | | | |
|---|---|---|---|---|---|
| ttcacttgag | aacaaccccc | tttgaactcg | atcaagaaag | ctaagtttga | agaatcaaga | 60 |
| atggtgcgga | caccgtgttg | caaagccgaa | ctagggttaa | agaaaggagc | ttggactccc | 120 |
| gaggaagatc | agaagcttct | ctcttacctt | aaccgccacg | gtgaaggtgg | atggcgaact | 180 |
| ctccccgaaa | aagctggact | caagagatgc | ggcaaaagct | gcagactgag | atgggccaat | 240 |
| tatcttagac | ctgacatcaa | aagaggagag | ttcactgaag | acgaagaacg | ttcaatcatc | 300 |
| tctcttcacg | cccttcacgg | caacaaatgg | tctgctatag | ctcgtggact | accaggaaga | 360 |
| accgataacg | agatcaagaa | ctactggaac | actcatatca | aaaacgtttt | gatcaagaaa | 420 |
| ggtattgatc | cagttacaca | aagggcata | acctccggta | ccgacaaatc | agaaaacctc | 480 |
| ccggagaaac | aaaatgttaa | tctgacaact | agtgaccatg | atcttgataa | tgacaaggcg | 540 |
| aagaagaaca | acaagaattt | tggattatca | tcggctagtt | tcttgaacaa | agtagctaat | 600 |
| aggttcggaa | agagaatcaa | tcagagtgtt | ctgtctgaga | ttatcggaag | tggaggccca | 660 |
| cttgcttcta | ctagtcacac | tactaatact | acaactacaa | gtgtttccgt | tgactctgaa | 720 |
| tcagttaagt | caacgagttc | ttccttcgca | ccaacctcga | atcttctctg | ccatgggacc | 780 |
| gttgcaacaa | caccagtttc | atcgaacttt | gacgttgatg | gtaacgttaa | tctgacgtgt | 840 |
| tcttcgtcca | cgttctctga | ttcctccgtt | aacaatcctc | taatgtactg | cgataatttc | 900 |
| gttggtaata | caacgttga | tgatgaggat | actatcgggt | tctccacatt | tctgaatgat | 960 |
| gaagatttca | tgatgttgga | ggagtcttgt | gttgaaaaca | ctgcgttcat | gaaagaactt | 1020 |
| acgaggtttc | ttcacgagga | tgaaaacgac | gtcgttgatg | tgacgccggt | ctatgaacgt | 1080 |
| caagacttgt | ttgacgaaat | tgataactat | tttggatgag | tgaaactcat | aatcgatgaa | 1140 |
| tcccacgtga | ccatgtcaat | atgatgtcta | tggatatgtt | accttgatga | tgttgatggt | 1200 |
| aataataata | aataatagat | ggtgatgatg | accatgcatg | aatcatgaat | gtagttcgtg | 1260 |
| ttgtcacata | tgcttgtgtt | tttgtgtttt | ttttttttgg | tctgaagtgt | gttgtttcgt | 1320 |
| tgtaaatgga | ttataaatgg | tgatgtaata | attataatgt | taaaaaaaaa | aaaaaaaaaa | 1380 |
| aaaa | | | | | | 1384 |

<210> SEQ ID NO 20
<211> LENGTH: 352
<212> TYPE: PRT
<213> ORGANISM: Arabidopsis thaliana
<220> FEATURE:
<223> OTHER INFORMATION: G671 polypeptide

<400> SEQUENCE: 20

| | | | | | | | | | | | | | | |
|---|---|---|---|---|---|---|---|---|---|---|---|---|---|---|
|Met|Val|Arg|Thr|Pro|Cys|Cys|Lys|Ala|Glu|Leu|Gly|Leu|Lys|Lys|Gly|
|1| | | |5| | | | |10| | | | |15| |
|Ala|Trp|Thr|Pro|Glu|Glu|Asp|Gln|Lys|Leu|Leu|Ser|Tyr|Leu|Asn|Arg|
| | | |20| | | | |25| | | | |30| | |
|His|Gly|Glu|Gly|Gly|Trp|Arg|Thr|Leu|Pro|Glu|Lys|Ala|Gly|Leu|Lys|
| | |35| | | | |40| | | | |45| | | |
|Arg|Cys|Gly|Lys|Ser|Cys|Arg|Leu|Arg|Trp|Ala|Asn|Tyr|Leu|Arg|Pro|
| |50| | | | |55| | | | |60| | | | |
|Asp|Ile|Lys|Arg|Gly|Glu|Phe|Thr|Glu|Asp|Glu|Arg|Ser|Ile|Ile|
|65| | | | |70| | | | |75| | | | |80|
|Ser|Leu|His|Ala|Leu|His|Gly|Asn|Lys|Trp|Ser|Ala|Ile|Ala|Arg|Gly|
| | | | |85| | | | |90| | | | |95| |
|Leu|Pro|Gly|Arg|Thr|Asp|Asn|Glu|Ile|Lys|Asn|Tyr|Trp|Asn|Thr|His|
| | | |100| | | | |105| | | | |110| | |
|Ile|Lys|Lys|Arg|Leu|Ile|Lys|Lys|Gly|Ile|Asp|Pro|Val|Thr|His|Lys|
| | |115| | | | |120| | | | |125| | | |
|Gly|Ile|Thr|Ser|Gly|Thr|Asp|Lys|Ser|Glu|Asn|Leu|Pro|Glu|Lys|Gln|
| |130| | | | |135| | | | |140| | | | |
|Asn|Val|Asn|Leu|Thr|Thr|Ser|Asp|His|Asp|Leu|Asp|Asn|Asp|Lys|Ala|
|145| | | | |150| | | | |155| | | | |160|
|Lys|Lys|Asn|Asn|Lys|Asn|Phe|Gly|Leu|Ser|Ser|Ala|Ser|Phe|Leu|Asn|
| | | | |165| | | | |170| | | | |175| |
|Lys|Val|Ala|Asn|Arg|Phe|Gly|Lys|Arg|Ile|Asn|Gln|Ser|Val|Leu|Ser|
| | | |180| | | | |185| | | | |190| | |
|Glu|Ile|Ile|Gly|Ser|Gly|Gly|Pro|Leu|Ala|Ser|Thr|Ser|His|Thr|Thr|
| | |195| | | | |200| | | | |205| | | |
|Asn|Thr|Thr|Thr|Thr|Ser|Val|Ser|Val|Asp|Ser|Glu|Ser|Val|Lys|Ser|
| |210| | | | |215| | | | |220| | | | |
|Thr|Ser|Ser|Ser|Phe|Ala|Pro|Thr|Ser|Asn|Leu|Leu|Cys|His|Gly|Thr|
|225| | | | |230| | | | |235| | | | |240|
|Val|Ala|Thr|Thr|Pro|Val|Ser|Ser|Asn|Phe|Asp|Val|Asp|Gly|Asn|Val|
| | | | |245| | | | |250| | | | |255| |
|Asn|Leu|Thr|Cys|Ser|Ser|Ser|Thr|Phe|Ser|Asp|Ser|Ser|Val|Asn|Asn|
| | | |260| | | | |265| | | | |270| | |
|Pro|Leu|Met|Tyr|Cys|Asp|Asn|Phe|Val|Gly|Asn|Asn|Asn|Val|Asp|Asp|
| | |275| | | | |280| | | | |285| | | |
|Glu|Asp|Thr|Ile|Gly|Phe|Ser|Thr|Phe|Leu|Asn|Asp|Glu|Asp|Phe|Met|
| |290| | | | |295| | | | |300| | | | |
|Met|Leu|Glu|Glu|Ser|Cys|Val|Glu|Asn|Thr|Ala|Phe|Met|Lys|Glu|Leu|
|305| | | | |310| | | | |315| | | | |320|
|Thr|Arg|Phe|Leu|His|Glu|Asp|Glu|Asn|Asp|Val|Val|Asp|Val|Thr|Pro|
| | | | |325| | | | |330| | | | |335| |
|Val|Tyr|Glu|Arg|Gln|Asp|Leu|Phe|Asp|Glu|Ile|Asp|Asn|Tyr|Phe|Gly|
| | | |340| | | | |345| | | | |350| | |

<210> SEQ ID NO 21
<211> LENGTH: 727
<212> TYPE: DNA
<213> ORGANISM: Arabidopsis thaliana
<220> FEATURE:
<223> OTHER INFORMATION: G353

<400> SEQUENCE: 21

```
accaaactca aaaaacacaa accacaagag gatcatttca ttttttattg tttcgtttta      60
atcatcatca tcagaagaaa aatggttgcg atatcggaga tcaagtcgac ggtggatgtc     120
acggcggcga attgtttgat gcttttatct agagttggac aagaaaacgt tgacggtggc     180
gatcaaaaac gcgttttcac atgtaaaacg tgtttgaagc agtttcattc gttccaagcc     240
ttaggaggtc accgtgcgag tcacaagaag cctaacaacg acgctttgtc gtctggattg     300
atgaagaagg tgaaaacgtc gtcgcatcct tgtcccatat gtggagtgga gtttccgatg     360
ggacaagctt tgggaggaca catgaggaga cacaggaacg agagtggggc tgctggtggc     420
gcgttggtta cacgcgcttt gttgccggag cccacggtga ctacgttgaa gaaatctagc     480
agtgggaaga gagtggcttg tttggatctg agtctaggga tggtggacaa tttgaatctc     540
aagttggagc ttggaagaac agtttattga ttttatttat tttccttaaa ttttctgaat     600
atatttgttt ctctcattct ttgaattttt cttaatattc tagattatac atacatccgc     660
agatttagga aactttcata gagtgtaatc ttttctttct gtaaaaatat attttacttg     720
tagcaaa                                                               727
```

<210> SEQ ID NO 22
<211> LENGTH: 162
<212> TYPE: PRT
<213> ORGANISM: Arabidopsis thaliana
<220> FEATURE:
<223> OTHER INFORMATION: G353 polypeptide

<400> SEQUENCE: 22

```
Met Val Ala Ile Ser Glu Ile Lys Ser Thr Val Asp Val Thr Ala Ala
1               5                   10                  15

Asn Cys Leu Met Leu Leu Ser Arg Val Gly Gln Glu Asn Val Asp Gly
            20                  25                  30

Gly Asp Gln Lys Arg Val Phe Thr Cys Lys Thr Cys Leu Lys Gln Phe
        35                  40                  45

His Ser Phe Gln Ala Leu Gly Gly His Arg Ala Ser His Lys Lys Pro
    50                  55                  60

Asn Asn Asp Ala Leu Ser Ser Gly Leu Met Lys Lys Val Lys Thr Ser
65                  70                  75                  80

Ser His Pro Cys Pro Ile Cys Gly Val Glu Phe Pro Met Gly Gln Ala
                85                  90                  95

Leu Gly Gly His Met Arg Arg His Arg Asn Glu Ser Gly Ala Ala Gly
            100                 105                 110

Gly Ala Leu Val Thr Arg Ala Leu Leu Pro Glu Pro Thr Val Thr Thr
        115                 120                 125

Leu Lys Lys Ser Ser Ser Gly Lys Arg Val Ala Cys Leu Asp Leu Ser
    130                 135                 140

Leu Gly Met Val Asp Asn Leu Asn Leu Lys Leu Glu Leu Gly Arg Thr
145                 150                 155                 160

Val Tyr
```

<210> SEQ ID NO 23
<211> LENGTH: 922
<212> TYPE: DNA
<213> ORGANISM: Arabidopsis thaliana
<220> FEATURE:
<223> OTHER INFORMATION: G484

<400> SEQUENCE: 23

```
attatattcc gtacaatccg atcgatttcc cggcgccaga tctcaccgcg actcgtctac      60
```

-continued

```
tttccgattt ggttcgtgtt gactcagtta cgattaaact atggatccaa tggatatagt    120
cggcaaatcc aaggaagacg cttctcttcc aaaagctacg atgactaaaa ttataaagga    180
gatgttacca ccagatgttc gtgttgcaag agatgctcaa gatcttctca ttgaatgttg    240
tgtagagttt ataaatcttg tatcttcaga atctaatgat gtttgtaaca agaggataa     300 acggacgatt gctcctgagc atgttctcaa ggcattacag gttcttggtt ttggagaata    360
cattgaagaa gtctatgctg cgtatgagca acataagtat gaaacaatgc aggacacaca    420
gaggagcgtg aaatggaacc ctggagctca aatgactgag gaggaagcag cagctgagca    480
acaacgtatg tttgcagaag cacgtgcaag aatgaatgga ggtgtttcgg ttcctcaacc    540
tgaacatcca gaaactgacc agagaagtcc gcaaagctaa ctgaaaccgt aagggtaagt    600
gttaggcaag aaaaaacaac atccttttaa cattcccttg taagttgcaa atgcgtatgt    660
tctctgttta tatgctctta gtatgatata tgttagttag tgtttcacga tctaaaaaca    720
cttgtgattc agatgtaatt agtaagcatt ccttgttttg tgtttacttt gtgtcttgac    780
taagcatggt gggtcaggtc tacacaaagc atctgattcg atgacttaca ggaatcttaa    840
tgtttgtaga ttggataaat ttggtgattg gtgtaattgt ttttccataa acacaatgca    900
atcattgttt agtgttgtta ac                                             922
```

<210> SEQ ID NO 24
<211> LENGTH: 159
<212> TYPE: PRT
<213> ORGANISM: Arabidopsis thaliana
<220> FEATURE:
<223> OTHER INFORMATION: G484 polypeptide

<400> SEQUENCE: 24

Met Asp Pro Met Asp Ile Val Gly Lys Ser Lys Glu Asp Ala Ser Leu
1               5                   10                  15

Pro Lys Ala Thr Met Thr Lys Ile Ile Lys Glu Met Leu Pro Pro Asp
            20                  25                  30

Val Arg Val Ala Arg Asp Ala Gln Asp Leu Leu Ile Glu Cys Cys Val
        35                  40                  45

Glu Phe Ile Asn Leu Val Ser Ser Glu Ser Asn Asp Val Cys Asn Lys
    50                  55                  60

Glu Asp Lys Arg Thr Ile Ala Pro Glu His Val Leu Lys Ala Leu Gln
65                  70                  75                  80

Val Leu Gly Phe Gly Glu Tyr Ile Glu Glu Val Tyr Ala Ala Tyr Glu
                85                  90                  95

Gln His Lys Tyr Glu Thr Met Gln Asp Thr Gln Arg Ser Val Lys Trp
            100                 105                 110

Asn Pro Gly Ala Gln Met Thr Glu Glu Glu Ala Ala Ala Glu Gln Gln
        115                 120                 125

Arg Met Phe Ala Glu Ala Arg Ala Arg Met Asn Gly Gly Val Ser Val
    130                 135                 140

Pro Gln Pro Glu His Pro Glu Thr Asp Gln Arg Ser Pro Gln Ser
145                 150                 155

<210> SEQ ID NO 25
<211> LENGTH: 786
<212> TYPE: DNA
<213> ORGANISM: Arabidopsis thaliana
<220> FEATURE:
<223> OTHER INFORMATION: G674

-continued

```
<400> SEQUENCE: 25
atggtgttta aatcagaaaa atcaaaccgg gaaatgaaat caaaggagaa gcaaaggaag      60
ggattatggt cacccgagga agatgagaag cttaggagtc atgtcctcaa atatggccat     120
ggatgctgga gtactattcc tcttcaagct ggattgcaga ggaatgggaa gagttgtaga     180
ttaaggtggg ttaattattt aagacctgga cttaagaagt ctttattcac taaacaagag     240
gaaactatac ttctttcact tcattccatg ttgggtaaca aatggtctca gatatcgaaa     300
ttcttaccag gaagaaccga caacgagatc aaaaactatt ggcattctaa tctaaagaag     360
ggtgtaactt tgaaacaaca tgaaaccaca aaaaaacatc aaacaccttt aatcacaaac     420
tcacttgagg ccttgcagag ttcaactgaa agatcttctt catctatcaa tgtcggagaa     480
acgtctaatg ctcaaacctc aagcttttcg ccaaatctcg tgttctcgga atggttagat     540
catagtttgc ttatggatca gtcacctcaa aagtctagct atgttcaaaa tcttgtttta     600
ccggaagaga gaggattcat tggaccatgt ggccctcgtt atttgggaaa cgactctttg     660
cctgatttcg tgccaaattc agaattttg ttggatgatg agatatcatc tgagatcgag      720
ttctgtactt cattttcaga caactttttg ttcgatggtc tcatcaacga gctacgacca     780
atgtaa                                                                 786

<210> SEQ ID NO 26
<211> LENGTH: 261
<212> TYPE: PRT
<213> ORGANISM: Arabidopsis thaliana
<220> FEATURE:
<223> OTHER INFORMATION: G674 polypeptide

<400> SEQUENCE: 26

Met Val Phe Lys Ser Glu Lys Ser Asn Arg Glu Met Lys Ser Lys Glu
1               5                   10                  15

Lys Gln Arg Lys Gly Leu Trp Ser Pro Glu Glu Asp Glu Lys Leu Arg
            20                  25                  30

Ser His Val Leu Lys Tyr Gly His Gly Cys Trp Ser Thr Ile Pro Leu
        35                  40                  45

Gln Ala Gly Leu Gln Arg Asn Gly Lys Ser Cys Arg Leu Arg Trp Val
    50                  55                  60

Asn Tyr Leu Arg Pro Gly Leu Lys Lys Ser Leu Phe Thr Lys Gln Glu
65                  70                  75                  80

Glu Thr Ile Leu Leu Ser Leu His Ser Met Leu Gly Asn Lys Trp Ser
                85                  90                  95

Gln Ile Ser Lys Phe Leu Pro Gly Arg Thr Asp Asn Glu Ile Lys Asn
            100                 105                 110

Tyr Trp His Ser Asn Leu Lys Lys Gly Val Thr Leu Lys Gln His Glu
        115                 120                 125

Thr Thr Lys Lys His Gln Thr Pro Leu Ile Thr Asn Ser Leu Glu Ala
    130                 135                 140

Leu Gln Ser Ser Thr Glu Arg Ser Ser Ser Ile Asn Val Gly Glu
145                 150                 155                 160

Thr Ser Asn Ala Gln Thr Ser Ser Phe Ser Pro Asn Leu Val Phe Ser
                165                 170                 175

Glu Trp Leu Asp His Ser Leu Leu Met Asp Gln Ser Pro Gln Lys Ser
            180                 185                 190

Ser Tyr Val Gln Asn Leu Val Leu Pro Glu Glu Arg Gly Phe Ile Gly
        195                 200                 205
```

```
Pro Cys Gly Pro Arg Tyr Leu Gly Asn Asp Ser Leu Pro Asp Phe Val
        210                 215                 220

Pro Asn Ser Glu Phe Leu Leu Asp Asp Glu Ile Ser Ser Glu Ile Glu
225                 230                 235                 240

Phe Cys Thr Ser Phe Ser Asp Asn Phe Leu Phe Asp Gly Leu Ile Asn
                245                 250                 255

Glu Leu Arg Pro Met
                260

<210> SEQ ID NO 27
<211> LENGTH: 1304
<212> TYPE: DNA
<213> ORGANISM: Arabidopsis thaliana
<220> FEATURE:
<223> OTHER INFORMATION: G1052

<400> SEQUENCE: 27
tgatcatcta aaactttcaa tttctctctt gatcctcact tgaatttttt gttgtttctc        60
tcaaatcttt gatcctttcc tttgtttttc atttgacctc ttacaaaaaa atctggtgtg       120
ccattaaatc tttattaatg cacaacttc ctccgaaaat cccaaccatg acgacgccaa        180
attggcctga cttctcctcc cagaaactcc cttccatagc cgcaacggcg cagccgcag        240 caaccgctgg acctcaacaa caaaacccctt catggatgga tgagtttctc gacttctcag      300
cgactcgccg tgggactcac cgtcgttcta aagcgactc cattgctttc cttgaaccac        360
cttcctccgg cgtcggaaac caccacttcg ataggtttga cgacgagcaa ttcatgtcca       420
tgttcaacga cgacgtacac aacaataacc acaatcatca tcatcatcac agcatcaacg      480
gcaatgtggg tcccacgcgt tcatcctcca cacctccac gccgtccgat cataatagcc        540
ttagcgacga cgacaacaac aaagaagcac caccgtccga tcatgatcat cacatggaca       600
ataatgtagc caatcaaaac aacgccgccg gtaacaatta caacgaatca gacgaggtcc       660
aaagccagtg caagacggag ccacaagatg gtccgtcggc gaatcaaaac tccggtggaa       720
gctccggtaa tcgtattcac gaccctaaaa gggtaaaaag aattttagca aataggcaat       780
cagcacagag atcaagggtg aggaaattgc aatacatatc agagcttgaa aggagcgtta      840
cttcattgca gactgaagtg tcagtgttat cgccaagagt tgcgttttg gatcatcagc       900 gattgcttct caacgtcgac aatagtgcta tcaagcaacg aatcgcagct ttagcacaag       960
ataagatttt caaagacgct catcaagaag cattgaagag agaaatagag agacttcgac      1020
aagtatatca tcaacaaagc ctcaagaaga tggagaataa tgtctccgat caatctccgg      1080
ccgatatcaa accgtccgtt gagaaggaac agctcctcaa tgtctaaagc tgttcgttca      1140
ctaagatctt tcttttcatg gcgaaaagat tcttgactat aaaacctctt tgtgtcaaga     1200
aattaattta tcaaagaaga tggcctttt tatttgatct aatcacattt ttttaagttg     1260
tgatgaattt gcttttgatg tatctgtttt tttttttttt tttt                      1304

<210> SEQ ID NO 28
<211> LENGTH: 329
<212> TYPE: PRT
<213> ORGANISM: Arabidopsis thaliana
<220> FEATURE:
<223> OTHER INFORMATION: G1052 polypeptide

<400> SEQUENCE: 28

Met Ala Gln Leu Pro Pro Lys Ile Pro Thr Met Thr Thr Pro Asn Trp
1               5                   10                  15
```

```
Pro Asp Phe Ser Ser Gln Lys Leu Pro Ser Ile Ala Ala Thr Ala Ala
        20                  25                  30

Ala Ala Ala Thr Ala Gly Pro Gln Gln Gln Asn Pro Ser Trp Met Asp
            35                  40                  45

Glu Phe Leu Asp Phe Ser Ala Thr Arg Arg Gly Thr His Arg Arg Ser
50                  55                  60

Ile Ser Asp Ser Ile Ala Phe Leu Glu Pro Ser Ser Gly Val Gly
65                  70                  75                  80

Asn His His Phe Asp Arg Phe Asp Glu Gln Phe Met Ser Met Phe
                85                  90                  95

Asn Asp Asp Val His Asn Asn His Asn His His His His His Ser
                100                 105                 110

Ile Asn Gly Asn Val Gly Pro Thr Arg Ser Ser Ser Asn Thr Ser Thr
            115                 120                 125

Pro Ser Asp His Asn Ser Leu Ser Asp Asp Asn Asn Lys Glu Ala
    130                 135                 140

Pro Pro Ser Asp His Asp His His Met Asp Asn Asn Val Ala Asn Gln
145                 150                 155                 160

Asn Asn Ala Ala Gly Asn Asn Tyr Asn Glu Ser Asp Glu Val Gln Ser
                165                 170                 175

Gln Cys Lys Thr Glu Pro Gln Asp Gly Pro Ser Ala Asn Gln Asn Ser
                180                 185                 190

Gly Gly Ser Ser Gly Asn Arg Ile His Asp Pro Lys Arg Val Lys Arg
            195                 200                 205

Ile Leu Ala Asn Arg Gln Ser Ala Gln Arg Ser Arg Val Arg Lys Leu
        210                 215                 220

Gln Tyr Ile Ser Glu Leu Glu Arg Ser Val Thr Ser Leu Gln Thr Glu
225                 230                 235                 240

Val Ser Val Leu Ser Pro Arg Val Ala Phe Leu Asp His Gln Arg Leu
                245                 250                 255

Leu Leu Asn Val Asp Asn Ser Ala Ile Lys Gln Arg Ile Ala Ala Leu
                260                 265                 270

Ala Gln Asp Lys Ile Phe Lys Asp Ala His Gln Glu Ala Leu Lys Arg
            275                 280                 285

Glu Ile Glu Arg Leu Arg Gln Val Tyr His Gln Ser Leu Lys Lys
290                 295                 300

Met Glu Asn Asn Val Ser Asp Gln Ser Pro Ala Asp Ile Lys Pro Ser
305                 310                 315                 320

Val Glu Lys Glu Gln Leu Leu Asn Val
                325

<210> SEQ ID NO 29
<211> LENGTH: 1161
<212> TYPE: DNA
<213> ORGANISM: Arabidopsis thaliana
<220> FEATURE:
<223> OTHER INFORMATION: G1328

<400> SEQUENCE: 29
aattcaatca ctatattttt ttaaaaacat ttgacttcat cgatcggtta acaattaatc      60
aaaaagatgg gacgatcacc atgttgtgag aagaagaatg gtctcaagaa aggaccatgg     120
actcctgagg aggatcaaaa gctcattgat tatatcaata tacatggtta tggaaattgg     180
agaactcttc ccaagaatgc tgggttacaa agatgtggta agagttgtcg tctccggtgg     240
accaactatc tccgaccaga tattaagcgt ggaagattct cttttgaaga agaagaaacc     300
```

-continued

```
attattcaac ttcacagcat catgggaaac aagtggtctg cgattgcggc tcgtttgcct      360
ggaagaacag acaacgagat caaaaactat tggaacactc acatcagaaa aagacttcta      420
aagatgggaa tcgacccggt tacacacact ccacgtcttg atcttctcga tatctcctcc      480
attctcagct catctatcta caactcttcg catcatcatc atcatcatca tcaacaacat      540
atgaacatgt cgaggctcat gatgagtgat ggtaatcatc aaccattggt taaccccgag      600
atactcaaac tcgcaacctc tctcttttca aaccaaaacc accccaacaa cacacacgag      660
aacaacacgg ttaaccaaac cgaagtaaac caataccaaa ccggttacaa catgcctggt      720
aatgaagaat tacaatcttg gttccctatc atggatcaat tcacgaattt ccaagacctc      780
atgccaatga agacgacggt ccaaaattca ttgtcatacg atgatgattg ttcgaagtcc      840
aattttgtat tagaacctta ttactccgac tttgcttcag tcttgaccac accttcttca      900
agcccgactc cgttaaactc aagttcctca acttacatca atagtagcac ttgcagcacc      960
gaggatgaaa agagagtta ttacagtgat aatatcacta attattcgtt tgatgttaat     1020
ggttttctcc aattccaata acaaaacgc cattggaata gagttatgta acatgcaat     1080 cattgtattt gttatataga ttttgttaca tatccaaaat ccaaaatact atagttttaa     1140
aataaaaaaa aaaaaaaaa a                                               1161
```

```
<210> SEQ ID NO 30
<211> LENGTH: 324
<212> TYPE: PRT
<213> ORGANISM: Arabidopsis thaliana
<220> FEATURE:
<223> OTHER INFORMATION: G1328 polypeptide

<400> SEQUENCE: 30
```

| Met | Gly | Arg | Ser | Pro | Cys | Cys | Glu | Lys | Lys | Asn | Gly | Leu | Lys | Lys | Gly |
|---|---|---|---|---|---|---|---|---|---|---|---|---|---|---|---|
| 1 | | | | 5 | | | | | 10 | | | | | 15 | |

| Pro | Trp | Thr | Pro | Glu | Glu | Asp | Gln | Lys | Leu | Ile | Asp | Tyr | Ile | Asn | Ile |
|---|---|---|---|---|---|---|---|---|---|---|---|---|---|---|---|
| | | | 20 | | | | | 25 | | | | | 30 | | |

| His | Gly | Tyr | Gly | Asn | Trp | Arg | Thr | Leu | Pro | Lys | Asn | Ala | Gly | Leu | Gln |
|---|---|---|---|---|---|---|---|---|---|---|---|---|---|---|---|
| | | 35 | | | | | 40 | | | | | 45 | | | |

| Arg | Cys | Gly | Lys | Ser | Cys | Arg | Leu | Arg | Trp | Thr | Asn | Tyr | Leu | Arg | Pro |
|---|---|---|---|---|---|---|---|---|---|---|---|---|---|---|---|
| | 50 | | | | | 55 | | | | | 60 | | | | |

| Asp | Ile | Lys | Arg | Gly | Arg | Phe | Ser | Phe | Glu | Glu | Glu | Thr | Ile | Ile |
|---|---|---|---|---|---|---|---|---|---|---|---|---|---|---|
| 65 | | | | | 70 | | | | | 75 | | | | 80 |

| Gln | Leu | His | Ser | Ile | Met | Gly | Asn | Lys | Trp | Ser | Ala | Ile | Ala | Ala | Arg |
|---|---|---|---|---|---|---|---|---|---|---|---|---|---|---|---|
| | | | | 85 | | | | | 90 | | | | | 95 | |

| Leu | Pro | Gly | Arg | Thr | Asp | Asn | Glu | Ile | Lys | Asn | Tyr | Trp | Asn | Thr | His |
|---|---|---|---|---|---|---|---|---|---|---|---|---|---|---|---|
| | | | | 100 | | | | | 105 | | | | | 110 | |

| Ile | Arg | Lys | Arg | Leu | Leu | Lys | Met | Gly | Ile | Asp | Pro | Val | Thr | His | Thr |
|---|---|---|---|---|---|---|---|---|---|---|---|---|---|---|---|
| | | | 115 | | | | | 120 | | | | | 125 | | |

| Pro | Arg | Leu | Asp | Leu | Leu | Asp | Ile | Ser | Ser | Ile | Leu | Ser | Ser | Ser | Ile |
|---|---|---|---|---|---|---|---|---|---|---|---|---|---|---|---|
| | 130 | | | | | 135 | | | | | 140 | | | | |

| Tyr | Asn | Ser | Ser | His | His | His | His | His | His | Gln | Gln | His | Met | Asn |
|---|---|---|---|---|---|---|---|---|---|---|---|---|---|---|
| 145 | | | | | 150 | | | | | 155 | | | | 160 |

| Met | Ser | Arg | Leu | Met | Met | Ser | Asp | Gly | Asn | His | Gln | Pro | Leu | Val | Asn |
|---|---|---|---|---|---|---|---|---|---|---|---|---|---|---|---|
| | | | | 165 | | | | | 170 | | | | | 175 | |

| Pro | Glu | Ile | Leu | Lys | Leu | Ala | Thr | Ser | Leu | Phe | Ser | Asn | Gln | Asn | His |
|---|---|---|---|---|---|---|---|---|---|---|---|---|---|---|---|
| | | | 180 | | | | | 185 | | | | | 190 | | |

| Pro | Asn | Asn | Thr | His | Glu | Asn | Asn | Thr | Val | Asn | Gln | Thr | Glu | Val | Asn |
|---|---|---|---|---|---|---|---|---|---|---|---|---|---|---|---|
| | | | 195 | | | | | 200 | | | | | 205 | | |

-continued

Gln Tyr Gln Thr Gly Tyr Asn Met Pro Gly Asn Glu Glu Leu Gln Ser
    210                 215                 220

Trp Phe Pro Ile Met Asp Gln Phe Thr Asn Phe Gln Asp Leu Met Pro
225                 230                 235                 240

Met Lys Thr Thr Val Gln Asn Ser Leu Ser Tyr Asp Asp Asp Cys Ser
                245                 250                 255

Lys Ser Asn Phe Val Leu Glu Pro Tyr Tyr Ser Asp Phe Ala Ser Val
            260                 265                 270

Leu Thr Thr Pro Ser Ser Ser Pro Thr Pro Leu Asn Ser Ser Ser Ser
        275                 280                 285

Thr Tyr Ile Asn Ser Ser Thr Cys Ser Thr Glu Asp Glu Lys Glu Ser
    290                 295                 300

Tyr Tyr Ser Asp Asn Ile Thr Asn Tyr Ser Phe Asp Val Asn Gly Phe
305                 310                 315                 320

Leu Gln Phe Gln

<210> SEQ ID NO 31
<211> LENGTH: 1155
<212> TYPE: DNA
<213> ORGANISM: Arabidopsis thaliana
<220> FEATURE:
<223> OTHER INFORMATION: G1930

<400> SEQUENCE: 31
attcacatta ctaatctctc aagatttcac aattttcttg tgattttctc tcagtttctt      60
atttcgtttc ataacatgga tgccatgagt agcgtagacg agagctctac aactacagat     120
tccattccgg cgagaaagtc atcgtctccg gcgagtttac tatatagaat gggaagcgga     180
acaagcgtgg tacttgattc agagaacggt gtcgaagtcg aagtcgaagc cgaatcaaga     240
aagcttcctt cttcaagatt caaaggtgtt gttcctcaac caaatggaag atggggagct     300
cagatttacg agaaacatca acgcgtgtgg cttggtactt tcaacgagga agacgaagca     360
gctcgtgctt acgacgtcgc ggctcaccgt ttccgtggcc gcgatgccgt tactaatttc     420
aaagacacga cgttcgaaga agaggttgag ttcttaaacg cgcattcgaa atcagagatc     480
gtagatatgt tgagaaaaca cacttacaaa gaagagttag accaaaggaa acgtaaccgt     540
gacggtaacg gaaagagac gacggcgttt gctttggctt cgatggtggt tatgacgggg     600
tttaaaacgg cggagttact gtttgagaaa acgtaacgc caagtgacgt cgggaaacta     660
aaccgtttag ttataccaaa acaccaagcg gagaaacatt ttccgttacc gttaggtaat     720
aataacgtct ccgttaaagg tatgctgttg aatttcgaag acgttaacgg gaaagtgtgg     780
aggttccgtt actcttattg gaatagtagt caaagttatg tgttgaccaa aggttggagt     840
agattcgtta agagaagag actttgtgct ggtgatttga tcagttttaa aagatccaac     900
gatcaagatc aaaaattctt tatcgggtgg aaatcgaaat ccgggttgga tctagagacg     960
ggtcgggtta tgagattgtt tggggttgat atttctttaa acgccgtcgt tgtagtgaag    1020
gaaacaacgg aggtgttaat gtcgtcgtta aggtgtaaga agcaacgagt tttgtaataa    1080
caatttaaca acttgggaaa gaaaaaaaag cttttttgatt ttaatttctc ttcaacgtta    1140
atcttgctga gatta                                                    1155

<210> SEQ ID NO 32
<211> LENGTH: 333
<212> TYPE: PRT
<213> ORGANISM: Arabidopsis thaliana
<220> FEATURE:
<223> OTHER INFORMATION: G1930 polypeptide

<400> SEQUENCE: 32

```
Met Asp Ala Met Ser Ser Val Asp Glu Ser Thr Thr Thr Asp Ser
1               5                   10                  15

Ile Pro Ala Arg Lys Ser Ser Pro Ala Ser Leu Leu Tyr Arg Met
            20                  25                  30

Gly Ser Gly Thr Ser Val Val Leu Asp Ser Glu Asn Gly Val Glu Val
            35                  40                  45

Glu Val Glu Ala Glu Ser Arg Lys Leu Pro Ser Arg Phe Lys Gly
    50                  55                  60

Val Val Pro Gln Pro Asn Gly Arg Trp Gly Ala Gln Ile Tyr Glu Lys
65                  70                  75                  80

His Gln Arg Val Trp Leu Gly Thr Phe Asn Glu Glu Asp Glu Ala Ala
                85                  90                  95

Arg Ala Tyr Asp Val Ala Ala His Arg Phe Arg Gly Arg Asp Ala Val
                100                 105                 110

Thr Asn Phe Lys Asp Thr Thr Phe Glu Glu Glu Val Glu Phe Leu Asn
            115                 120                 125

Ala His Ser Lys Ser Glu Ile Val Asp Met Leu Arg Lys His Thr Tyr
    130                 135                 140

Lys Glu Glu Leu Asp Gln Arg Lys Arg Asn Arg Asp Gly Asn Gly Lys
145                 150                 155                 160

Glu Thr Thr Ala Phe Ala Leu Ala Ser Met Val Val Met Thr Gly Phe
                165                 170                 175

Lys Thr Ala Glu Leu Leu Phe Glu Lys Thr Val Thr Pro Ser Asp Val
            180                 185                 190

Gly Lys Leu Asn Arg Leu Val Ile Pro Lys His Gln Ala Glu Lys His
    195                 200                 205

Phe Pro Leu Pro Leu Gly Asn Asn Val Ser Val Lys Gly Met Leu
210                 215                 220

Leu Asn Phe Glu Asp Val Asn Gly Lys Val Trp Arg Phe Arg Tyr Ser
225                 230                 235                 240

Tyr Trp Asn Ser Ser Gln Ser Tyr Val Leu Thr Lys Gly Trp Ser Arg
                245                 250                 255

Phe Val Lys Glu Lys Arg Leu Cys Ala Gly Asp Leu Ile Ser Phe Lys
            260                 265                 270

Arg Ser Asn Asp Gln Asp Gln Lys Phe Phe Ile Gly Trp Lys Ser Lys
    275                 280                 285

Ser Gly Leu Asp Leu Glu Thr Gly Arg Val Met Arg Leu Phe Gly Val
    290                 295                 300

Asp Ile Ser Leu Asn Ala Val Val Val Lys Glu Thr Thr Glu Val
305                 310                 315                 320

Leu Met Ser Ser Leu Arg Cys Lys Lys Gln Arg Val Leu
                325                 330
```

<210> SEQ ID NO 33
<211> LENGTH: 2240
<212> TYPE: DNA
<213> ORGANISM: Arabidopsis thaliana
<220> FEATURE:
<223> OTHER INFORMATION: G214

<400> SEQUENCE: 33
tgagatttct ccatttccgt agcttctggt ctctttttct tgtttcattg atcaaaagca      60

```
aatcacttct tcttcttctt cttctcgatt tcttactgtt ttcttatcca acgaaatctg      120
gaattaaaaa tggaatcttt atcgaatcca agctgatttt gtttctttca ttgaatcatc      180
tctctaaagt ggaattttgt aaagagaaga tctgaagttg tgtagaggag cttagtgatg      240
gagacaaatt cgtctggaga agatctggtt attaagactc ggaagccata tacgataaca      300
aagcaacgtg aaaggtggac tgaggaagaa cataatagat tcattgaagc tttgaggctt      360
tatggtagag catggcagaa gattgaagaa catgtagcaa caaaaactgc tgtccagata      420
agaagtcacg ctcagaaatt tttctccaag gtagagaaag aggctgaagc taaaggtgta      480
gctatgggtc aagcgctaga catagctatt cctcctccac ggcctaagcg taaaccaaac      540
aatccttatc ctcgaaagac gggaagtgga acgatcctta tgtcaaaaac gggtgtgaat      600
gatggaaaag agtcccttgg atcagaaaaa gtgtcgcatc ctgagatggc caatgaagat      660
cgacaacaat caaagcctga agagaaaact ctgcaggaag acaactgttc agattgtttc      720
actcatcagt atctctctgc tgcatcctcc atgaataaaa gttgtataga acatcaaac      780 gcaagcactt ccgcgagtt cttgccttca cgggaagagg gaagtcagaa taacagggta      840
agaaaggagt caaactcaga tttgaatgca aaatctctgg aaaacggtaa tgagcaagga      900
cctcagactt atccgatgca tatccctgtg ctagtgccat tggggagctc aataacaagt      960
tctctatcac atcctccttc agagccagat agtcatcccc acacagttgc aggagattat     1020
cagtcgtttc ctaatcatat aatgtcaacc cttttacaaa caccggctct ttatactgcc     1080
gcaactttcg cctcatcatt ttggcctccc gattctagtg gtggctcacc tgttccaggg     1140
aactcacctc cgaatctggc tgccatggcc gcagccactg ttgcagctgc tagtgcttgg     1200
tgggctgcca atgattatt accttttatgt gctcctctta gttcaggtgg tttcactagt     1260
catcctccat ctacttttgg accatcatgt gatgtagagt acacaaaagc aagcacttta     1320
caacatggtt ctgtgcagag ccgagagcaa gaacactccg aggcatcaaa ggctcgatct     1380
tcactggact cagaggatgt tgaaaataag agtaaaccag tttgtcatga gcagccttct     1440
gcaacacctg agagtgatgc aaagggttca gatggagcag gagacagaaa caagttgac      1500 cggtcctcgt gtggctcaaa cactccgtcg agtagtgatg atgttgaggc ggatgcatca     1560
gaaaggcaag aggatggcac caatggtgag gtgaaagaaa cgaatgaaga cactaataaa     1620
cctcaaactt cagagtccaa tgcacgccgc agtagaatca gctccaatat aaccgatcca     1680
tggaagtctg tgtctgacga gggtcgaatt gccttccaag ctctcttctc cagagaggta     1740
ttgccgcaaa gttttacata tcgagaagaa cacagagagg aagaacaaca caacaagaa      1800 caaagatatc caatggcact tgatcttaac ttcacagctc agttaacacc agttgatgat     1860
caagaggaga agagaaacac aggatttctt ggaatcggat tagatgcttc aaagctaatg     1920
agtagaggaa gaacaggttt taaaccatac aaaagatgtt ccatggaagc caaagaaagt     1980
agaatcctca caacaatcc tatcattcat gtggaacaga aagatcccaa acggatgcgg     2040
ttggaaactc aagcttccac atgagactct attttcatct gatctgttgt ttgtactctg     2100
tttttaagtt ttcaagacca ctgctacatt ttcttttttct tttgaggcct ttgtatttgt     2160
ttccttgtcc atagtcttcc tgtaacattt gactctgtat tattcaacaa atcataaact     2220
gtttaatctt ttttttttcca                                                 2240
```

<210> SEQ ID NO 34
<211> LENGTH: 608
<212> TYPE: PRT

<213> ORGANISM: Arabidopsis thaliana
<220> FEATURE:
<223> OTHER INFORMATION: G214 polypeptide

<400> SEQUENCE: 34

```
Met Glu Thr Asn Ser Ser Gly Glu Asp Leu Val Ile Lys Thr Arg Lys
1               5                   10                  15

Pro Tyr Thr Ile Thr Lys Gln Arg Glu Arg Trp Thr Glu Glu Glu His
            20                  25                  30

Asn Arg Phe Ile Glu Ala Leu Arg Leu Tyr Gly Arg Ala Trp Gln Lys
        35                  40                  45

Ile Glu Glu His Val Ala Thr Lys Thr Ala Val Gln Ile Arg Ser His
    50                  55                  60

Ala Gln Lys Phe Phe Ser Lys Val Glu Lys Glu Ala Glu Ala Lys Gly
65                  70                  75                  80

Val Ala Met Gly Gln Ala Leu Asp Ile Ala Ile Pro Pro Pro Arg Pro
                85                  90                  95

Lys Arg Lys Pro Asn Asn Pro Tyr Pro Arg Lys Thr Gly Ser Gly Thr
            100                 105                 110

Ile Leu Met Ser Lys Thr Gly Val Asn Asp Gly Lys Glu Ser Leu Gly
        115                 120                 125

Ser Glu Lys Val Ser His Pro Glu Met Ala Asn Glu Asp Arg Gln Gln
130                 135                 140

Ser Lys Pro Glu Glu Lys Thr Leu Gln Glu Asp Asn Cys Ser Asp Cys
145                 150                 155                 160

Phe Thr His Gln Tyr Leu Ser Ala Ala Ser Met Asn Lys Ser Cys
                165                 170                 175

Ile Glu Thr Ser Asn Ala Ser Thr Phe Arg Glu Phe Leu Pro Ser Arg
            180                 185                 190

Glu Glu Gly Ser Gln Asn Asn Arg Val Arg Lys Glu Ser Asn Ser Asp
        195                 200                 205

Leu Asn Ala Lys Ser Leu Glu Asn Gly Asn Glu Gln Gly Pro Gln Thr
    210                 215                 220

Tyr Pro Met His Ile Pro Val Leu Val Pro Leu Gly Ser Ser Ile Thr
225                 230                 235                 240

Ser Ser Leu Ser His Pro Pro Ser Glu Pro Asp Ser His Pro His Thr
                245                 250                 255

Val Ala Gly Asp Tyr Gln Ser Phe Pro Asn His Ile Met Ser Thr Leu
            260                 265                 270

Leu Gln Thr Pro Ala Leu Tyr Thr Ala Ala Thr Phe Ala Ser Ser Phe
        275                 280                 285

Trp Pro Pro Asp Ser Ser Gly Gly Ser Pro Val Pro Gly Asn Ser Pro
    290                 295                 300

Pro Asn Leu Ala Ala Met Ala Ala Thr Val Ala Ala Ser Ala
305                 310                 315                 320

Trp Trp Ala Ala Asn Gly Leu Leu Pro Leu Cys Ala Pro Leu Ser Ser
                325                 330                 335

Gly Gly Phe Thr Ser His Pro Pro Ser Thr Phe Gly Pro Ser Cys Asp
            340                 345                 350

Val Glu Tyr Thr Lys Ala Ser Thr Leu Gln His Gly Ser Val Gln Ser
        355                 360                 365

Arg Glu Gln Glu His Ser Glu Ala Ser Lys Ala Arg Ser Ser Leu Asp
    370                 375                 380

Ser Glu Asp Val Glu Asn Lys Ser Lys Pro Val Cys His Glu Gln Pro
```

-continued

```
            385                 390                 395                 400
Ser Ala Thr Pro Glu Ser Asp Ala Lys Gly Ser Asp Gly Ala Gly Asp
                405                 410                 415

Arg Lys Gln Val Asp Arg Ser Ser Cys Gly Ser Asn Thr Pro Ser Ser
            420                 425                 430

Ser Asp Val Glu Ala Asp Ala Ser Glu Arg Gln Glu Asp Gly Thr
            435                 440                 445

Asn Gly Glu Val Lys Glu Thr Asn Glu Asp Thr Asn Lys Pro Gln Thr
        450                 455                 460

Ser Glu Ser Asn Ala Arg Arg Ser Arg Ile Ser Ser Asn Ile Thr Asp
465                 470                 475                 480

Pro Trp Lys Ser Val Ser Asp Glu Gly Arg Ile Ala Phe Gln Ala Leu
                485                 490                 495

Phe Ser Arg Glu Val Leu Pro Gln Ser Phe Thr Tyr Arg Glu Glu His
            500                 505                 510

Arg Glu Glu Gln Gln Gln Gln Glu Gln Arg Tyr Pro Met Ala Leu
            515                 520                 525

Asp Leu Asn Phe Thr Ala Gln Leu Thr Pro Val Asp Asp Gln Glu Glu
        530                 535                 540

Lys Arg Asn Thr Gly Phe Leu Gly Ile Gly Leu Asp Ala Ser Lys Leu
545                 550                 555                 560

Met Ser Arg Gly Arg Thr Gly Phe Lys Pro Tyr Lys Arg Cys Ser Met
                565                 570                 575

Glu Ala Lys Glu Ser Arg Ile Leu Asn Asn Asn Pro Ile Ile His Val
            580                 585                 590

Glu Gln Lys Asp Pro Lys Arg Met Arg Leu Glu Thr Gln Ala Ser Thr
            595                 600                 605
```

<210> SEQ ID NO 35
<211> LENGTH: 1000
<212> TYPE: DNA
<213> ORGANISM: Arabidopsis thaliana
<220> FEATURE:
<223> OTHER INFORMATION: G2509

<400> SEQUENCE: 35

```
atatattccc tctttcattc tccttcttcg tcttttcttt gtttctcata ttcaagacat    60
cctcaattcc aaatcttaaa ccctaaattt acagacacaa tcgagatcac ctgaaaaaag   120
aggtttaaag attttagcaa agatggcgaa ttcaggaaat tatggaaaga ggcccttttcg  180
aggcgatgaa tcggatgaaa agaaagaagc cgatgatgat gagaacatat tccctttctt   240
ctctgcccga tcccaatatg acatgcgtgc catggtctca gccttgactc aagtcattgg   300
aaaccaaagc agctctcatg ataataacca acatcaacct gttgtgtata atcaacaaga   360
tcctaaccca ccggctcctc caactcaaga tcaagggcta ttgaggaaga ggcactatag   420
aggggtaaga caacgaccat ggggaaagtg ggcagctgaa attcgggatc cgcaaaaggc   480
agcacgggtg tggctcggga catttgagac tgctgaagct gcggctttag cttatgataa   540
cgcagctctt aagttcaaag gaagcaaagc caaactcaat ttccctgaga gagctcaact   600
agcaagtaac actagtacaa ctaccggtcc accaaactat tattcttcta ataatcaaat   660
ttactactca aatccgcaga ctaatccgca aaccatacct tattttaacc aatactacta   720
taaccaatat cttcatcaag gggggaatag taacgatgca ttaagttata gcttggccgg   780
tggagaaacc ggaggctcaa tgtataatca tcagacgtta tctactacaa attcttcatc   840
```

```
ttctggtgga tcttcaaggc aacaagatga tgaacaagat tacgccagat atttgcgttt      900
tggggattct tcacctccta attctggttt ttgagatctc caataaactg ataataaagg      960
atttgggtca cttgttatga ggggatcata tgttttctaa                           1000
```

<210> SEQ ID NO 36
<211> LENGTH: 263
<212> TYPE: PRT
<213> ORGANISM: Arabidopsis thaliana
<220> FEATURE:
<223> OTHER INFORMATION: G2509 polypeptide

<400> SEQUENCE: 36

```
Met Ala Asn Ser Gly Asn Tyr Gly Lys Arg Pro Phe Arg Gly Asp Glu
1               5                   10                  15

Ser Asp Glu Lys Lys Glu Ala Asp Asp Glu Asn Ile Phe Pro Phe
            20                  25                  30

Phe Ser Ala Arg Ser Gln Tyr Asp Met Arg Ala Met Val Ser Ala Leu
        35                  40                  45

Thr Gln Val Ile Gly Asn Gln Ser Ser Ser His Asp Asn Asn Gln His
    50                  55                  60

Gln Pro Val Val Tyr Asn Gln Asp Pro Asn Pro Ala Pro Pro
65                  70                  75                  80

Thr Gln Asp Gln Gly Leu Leu Arg Lys Arg His Tyr Arg Gly Val Arg
                85                  90                  95

Gln Arg Pro Trp Gly Lys Trp Ala Ala Glu Ile Arg Asp Pro Gln Lys
            100                 105                 110

Ala Ala Arg Val Trp Leu Gly Thr Phe Glu Thr Ala Glu Ala Ala Ala
        115                 120                 125

Leu Ala Tyr Asp Asn Ala Ala Leu Lys Phe Lys Gly Ser Lys Ala Lys
    130                 135                 140

Leu Asn Phe Pro Glu Arg Ala Gln Leu Ala Ser Asn Thr Ser Thr Thr
145                 150                 155                 160

Thr Gly Pro Pro Asn Tyr Tyr Ser Ser Asn Asn Gln Ile Tyr Tyr Ser
                165                 170                 175

Asn Pro Gln Thr Asn Pro Gln Thr Ile Pro Tyr Phe Asn Gln Tyr Tyr
            180                 185                 190

Tyr Asn Gln Tyr Leu His Gln Gly Gly Asn Ser Asn Asp Ala Leu Ser
        195                 200                 205

Tyr Ser Leu Ala Gly Gly Glu Thr Gly Gly Ser Met Tyr Asn His Gln
    210                 215                 220

Thr Leu Ser Thr Thr Asn Ser Ser Ser Ser Gly Gly Ser Ser Arg Gln
225                 230                 235                 240

Gln Asp Asp Glu Gln Asp Tyr Ala Arg Tyr Leu Arg Phe Gly Asp Ser
                245                 250                 255

Ser Pro Pro Asn Ser Gly Phe
            260
```

<210> SEQ ID NO 37
<211> LENGTH: 1197
<212> TYPE: DNA
<213> ORGANISM: Arabidopsis thaliana
<220> FEATURE:
<223> OTHER INFORMATION: G2520

<400> SEQUENCE: 37

```
aaggagtttt gcatactcac caagccacaa tcatttctct cttctctatc tctctggttt       60
```

```
tgaatcggcg acgactgagt caactcggtg ttgttactgg tttcgtcgta tgtgttgtaa      120
ctgattaagt tgatggatcc gagtgggatg atgaacgaag gaggaccgtt taatctagcg      180
gagatctggc agtttccgtt gaacggagtt tcaaccgccg gagattcttc tagaagaagc      240
ttcgttggac cgaatcagtt cggtgatgct gatctaacca cagctgctaa cggtgatcca      300
gcgcgtatga gtcacgcgtt gtctcaggcg gttattgaag gtatctccgg cgcttggaaa      360
cggagggaag atgagtctaa gtcggcgaag atcgtctcca ccattggcgc tagtgaaggt      420
gagaacaaaa gacagaagat agatgaagtg tgtgatggga aagcagaagc agaatcgcta      480
ggaacagaga cggaacaaaa gaagcaacag atggaaccaa cgaaagatta tattcatgtt      540
cgagctagaa gaggtcaagc tactgatagt cacagtttag ctgaaagagc gagaagagag      600
aaaataagtg agcggatgaa aatcttgcaa gatcttgttc cgggatgtaa caaggttatt      660
ggaaaagcac ttgttctaga tgagataatt aactatatac aatcattgca acgtcaagtt      720
gagttcttat cgatgaagct tgaagcagtc aactcaagaa tgaaccctgg tatcgaggtt      780
tttccaccca agaggtgat gattctcatg atcatcaact caatcttctc cattttttc      840 acaaaacaat acatgtttct atcgaggtat tctcggggta ggagtctcga tgtttatgcg      900
gttcggtcat ttaagcattg caataaacgg agtgacctct gttttgctc ctgctcccca      960 aaaacagaac ttaagacaac tatattttca caaacatga catgtttctg tcgatattct     1020
cgagtaggag tcgctattag ttcatctaag cattgcaatg aaccgtttgg tcagcaagcg     1080
tttgagaatc cggagataca gttcgggtcg cagtctacga gggaatacag tagaggagca     1140
tcaccagagt ggttgcacat gcagatagga tcaggtggtt tcgaaagaac gtcttga        1197
```

<210> SEQ ID NO 38
<211> LENGTH: 354
<212> TYPE: PRT
<213> ORGANISM: Arabidopsis thaliana
<220> FEATURE:
<223> OTHER INFORMATION: G2520 polypeptide

<400> SEQUENCE: 38

```
Met Asp Pro Ser Gly Met Met Asn Glu Gly Gly Pro Phe Asn Leu Ala
1               5                   10                  15

Glu Ile Trp Gln Phe Pro Leu Asn Gly Val Ser Thr Ala Gly Asp Ser
            20                  25                  30

Ser Arg Arg Ser Phe Val Gly Pro Asn Gln Phe Gly Asp Ala Asp Leu
        35                  40                  45

Thr Thr Ala Ala Asn Gly Asp Pro Ala Arg Met Ser His Ala Leu Ser
    50                  55                  60

Gln Ala Val Ile Glu Gly Ile Ser Gly Ala Trp Lys Arg Arg Glu Asp
65                  70                  75                  80

Glu Ser Lys Ser Ala Lys Ile Val Ser Thr Ile Gly Ala Ser Glu Gly
                85                  90                  95

Glu Asn Lys Arg Gln Lys Ile Asp Glu Val Cys Asp Gly Lys Ala Glu
            100                 105                 110

Ala Glu Ser Leu Gly Thr Glu Thr Glu Gln Lys Lys Gln Gln Met Glu
        115                 120                 125

Pro Thr Lys Asp Tyr Ile His Val Arg Ala Arg Gly Gln Ala Thr
    130                 135                 140

Asp Ser His Ser Leu Ala Glu Arg Ala Arg Arg Glu Lys Ile Ser Glu
145                 150                 155                 160

Arg Met Lys Ile Leu Gln Asp Leu Val Pro Gly Cys Asn Lys Val Ile
```

```
                   165                 170                 175
Gly Lys Ala Leu Val Leu Asp Glu Ile Ile Asn Tyr Ile Gln Ser Leu
                180                 185                 190

Gln Arg Gln Val Glu Phe Leu Ser Met Lys Leu Glu Ala Val Asn Ser
            195                 200                 205

Arg Met Asn Pro Gly Ile Glu Val Phe Pro Lys Glu Val Met Ile
    210                 215                 220

Leu Met Ile Ile Asn Ser Ile Phe Ser Ile Phe Thr Lys Gln Tyr
225                 230                 235                 240

Met Phe Leu Ser Arg Tyr Ser Arg Gly Arg Ser Leu Asp Val Tyr Ala
                245                 250                 255

Val Arg Ser Phe Lys His Cys Asn Lys Arg Ser Asp Leu Cys Phe Cys
            260                 265                 270

Ser Cys Ser Pro Lys Thr Glu Leu Lys Thr Thr Ile Phe Ser Gln Asn
        275                 280                 285

Met Thr Cys Phe Cys Arg Tyr Ser Arg Val Gly Val Ala Ile Ser Ser
    290                 295                 300

Ser Lys His Cys Asn Glu Pro Phe Gly Gln Gln Ala Phe Glu Asn Pro
305                 310                 315                 320

Glu Ile Gln Phe Gly Ser Gln Ser Thr Arg Glu Tyr Ser Arg Gly Ala
                325                 330                 335

Ser Pro Glu Trp Leu His Met Gln Ile Gly Ser Gly Phe Glu Arg
            340                 345                 350

Thr Ser
```

<210> SEQ ID NO 39
<211> LENGTH: 896
<212> TYPE: DNA
<213> ORGANISM: Arabidopsis thaliana
<220> FEATURE:
<223> OTHER INFORMATION: G259

<400> SEQUENCE: 39

```
gagatcttct actacttgtt ttcttcaaga ataataattt tcgttttata tatggaagat      60
gctggtgaac atttacggtg taacgataac gttaacgacg aggagcgttt gccattggag     120
tttatgatcg gaaactcaac atccacggcg gagctacagc cgcctccacc gttcttggta     180
aagacataca aagtggtgga ggatccgacg acggacgggg ttatatcttg aacgaatac      240
ggaactggtt tcgtcgtgtg gcagccggca gaattcgcta gagatctgtt accaacactt     300
ttcaagcatt gcaacttctc tagcttcgtt cgccagctca atacttacgg ttttcgaaaa     360
gtaacgacga taagatggga atttagtaat gagatgtttc gaaagggca aagagagctt      420
atgagcaata tccgaagaag gaagagccaa cattggtcac acaacaagtc taatcaccag     480
gttgtaccaa caacaacgat ggtgaatcaa gaaggtcatc aacggattgg gattgatcat     540
caccatgagg atcaacagtc ttccgccact tcatcctctt tcgtatacac tgcattactc     600
gacgaaaaca aatgcttgaa gaatgaaaac gagttattaa gctgcgaact tgggaaaacc     660
aagaagaaat gcaagcagct tatggagttg gtggagagat acagaggaga agacgaagat     720
gcaactgatg aaagtgatga tgaagaagat gaagggctta agttgttcgg agtaaaactt     780
gaatgaaact agattgctag attgatattc gtaatatacc agtttcttca tattcttaga     840
agttttgcat aactatatat agtactcttt taagacatgc aagatcagaa catatg         896
```

<210> SEQ ID NO 40

```
<211> LENGTH: 244
<212> TYPE: PRT
<213> ORGANISM: Arabidopsis thaliana
<220> FEATURE:
<223> OTHER INFORMATION: G259 polypeptide

<400> SEQUENCE: 40

Met Glu Asp Ala Gly Glu His Leu Arg Cys Asn Asp Asn Val Asn Asp
1               5                   10                  15
Glu Glu Arg Leu Pro Leu Glu Phe Met Ile Gly Asn Ser Thr Ser Thr
                20                  25                  30
Ala Glu Leu Gln Pro Pro Pro Phe Leu Val Lys Thr Tyr Lys Val
            35                  40                  45
Val Glu Asp Pro Thr Thr Asp Gly Val Ile Ser Trp Asn Glu Tyr Gly
        50                  55                  60
Thr Gly Phe Val Val Trp Gln Pro Ala Glu Phe Ala Arg Asp Leu Leu
65                  70                  75                  80
Pro Thr Leu Phe Lys His Cys Asn Phe Ser Ser Phe Val Arg Gln Leu
                85                  90                  95
Asn Thr Tyr Gly Phe Arg Lys Val Thr Thr Ile Arg Trp Glu Phe Ser
            100                 105                 110
Asn Glu Met Phe Arg Lys Gly Gln Arg Glu Leu Met Ser Asn Ile Arg
        115                 120                 125
Arg Arg Lys Ser Gln His Trp Ser His Asn Lys Ser Asn His Gln Val
130                 135                 140
Val Pro Thr Thr Thr Met Val Asn Gln Glu Gly His Gln Arg Ile Gly
145                 150                 155                 160
Ile Asp His His His Glu Asp Gln Gln Ser Ser Ala Thr Ser Ser Ser
                165                 170                 175
Phe Val Tyr Thr Ala Leu Leu Asp Glu Asn Lys Cys Leu Lys Asn Glu
            180                 185                 190
Asn Glu Leu Leu Ser Cys Glu Leu Gly Lys Thr Lys Lys Cys Lys
        195                 200                 205
Gln Leu Met Glu Leu Val Glu Arg Tyr Arg Gly Glu Asp Glu Asp Ala
    210                 215                 220
Thr Asp Glu Ser Asp Asp Glu Glu Asp Glu Gly Leu Lys Leu Phe Gly
225                 230                 235                 240
Val Lys Leu Glu

<210> SEQ ID NO 41
<211> LENGTH: 588
<212> TYPE: DNA
<213> ORGANISM: Arabidopsis thaliana
<220> FEATURE:
<223> OTHER INFORMATION: G490

<400> SEQUENCE: 41
atgaggaggc caaagtcatc tcacgtcagg atggaacctg ttgcgcctcg ttcacataac      60
acgatgccaa tgcttgatca atttcgatct aatcatcctg aaacaagcaa gatcgagggg     120
gtctcttcgt tggacacagc tctgaaggtg ttttggaata tcaaagggaa gcagctagga     180
aactttgcag ccaaactca tttgccgcta tctagggtca gaaagatttt gaaatctgat      240
cctgaagtca agaagataag ctgtgatgtt cctgctttgt tttcgaaagc tgtgaatac      300 ttcattctag aggtaacatt acgagcttgg atgcatactc aatcatgcac tcgtgagacc     360
atccggcgtt gtgatatctt ccaggccgta agaactcag gaacttatga tttcctgatt      420
```

```
gatcgtgtcc cttttggacc gcactgtgtc acccatcagg gtgtgcaacc tcctgctgaa    480
atgattttgc cggatatgaa tgttccaatc gatatggacc agattgagga ggagaatatg    540
atggaagagc gctctgtcgg gtttgacctc aactgtgatc tccagtga                588
```

<210> SEQ ID NO 42
<211> LENGTH: 195
<212> TYPE: PRT
<213> ORGANISM: Arabidopsis thaliana
<220> FEATURE:
<223> OTHER INFORMATION: G490 polypeptide

<400> SEQUENCE: 42

```
Met Arg Arg Pro Lys Ser Ser His Val Arg Met Glu Pro Val Ala Pro
1               5                   10                  15

Arg Ser His Asn Thr Met Pro Met Leu Asp Gln Phe Arg Ser Asn His
            20                  25                  30

Pro Glu Thr Ser Lys Ile Glu Gly Val Ser Ser Leu Asp Thr Ala Leu
        35                  40                  45

Lys Val Phe Trp Asn Asn Gln Arg Glu Gln Leu Gly Asn Phe Ala Gly
    50                  55                  60

Gln Thr His Leu Pro Leu Ser Arg Val Arg Lys Ile Leu Lys Ser Asp
65                  70                  75                  80

Pro Glu Val Lys Lys Ile Ser Cys Asp Val Pro Ala Leu Phe Ser Lys
                85                  90                  95

Ala Cys Glu Tyr Phe Ile Leu Glu Val Thr Leu Arg Ala Trp Met His
            100                 105                 110

Thr Gln Ser Cys Thr Arg Glu Thr Ile Arg Arg Cys Asp Ile Phe Gln
        115                 120                 125

Ala Val Lys Asn Ser Gly Thr Tyr Asp Phe Leu Ile Asp Arg Val Pro
    130                 135                 140

Phe Gly Pro His Cys Val Thr His Gln Gly Val Gln Pro Pro Ala Glu
145                 150                 155                 160

Met Ile Leu Pro Asp Met Asn Val Pro Ile Asp Met Asp Gln Ile Glu
                165                 170                 175

Glu Glu Asn Met Met Glu Glu Arg Ser Val Gly Phe Asp Leu Asn Cys
            180                 185                 190

Asp Leu Gln
        195
```

<210> SEQ ID NO 43
<211> LENGTH: 606
<212> TYPE: DNA
<213> ORGANISM: Arabidopsis thaliana
<220> FEATURE:
<223> OTHER INFORMATION: G652

<400> SEQUENCE: 43

```
atgagcggag gaggagacgt gaacatgagt ggtggagaca acgcaaggg aacggtgaag    60 tggtttgata cacagaaggg gtttggtttc atcacaccta cgacggtgg tgacgatctc   120 ttcgttcacc agtcttccat cagatctgaa ggatttcgta gcctcgcagc tgaggaatct   180
gttgagttcg acgttgaggt tgacaactcc ggccgtccca aggctattga agtgtctgga   240
cccgacggtg ctcccgttca gggtaacagc ggtggtggtg gttcatctgg tggacgcggt   300
ggttttggcg gcggtggtgg aagaggaggg ggacgtggtg gaggaagcta cggaggaggt   360
tatggtggaa gaggaagcgg tggccgtgga ggaggtggtg gtgataattc ttgctttaag   420
```

-continued

```
tgcggtgaac caggtcacat ggcgagagaa tgctctcaag gtggtggagg atacagcgga      480
ggcgggggtg gtggaaggta cgggtctggc ggcggcggag gaggaggtgg tggtggctta      540
agctgctaca gctgtggaga gtctgggcac tttgcaaggg attgcactag cggtggtgct      600
cgttga                                                                 606
```

<210> SEQ ID NO 44
<211> LENGTH: 201
<212> TYPE: PRT
<213> ORGANISM: Arabidopsis thaliana
<220> FEATURE:
<223> OTHER INFORMATION: G652 polypeptide

<400> SEQUENCE: 44

Met Ser Gly Gly Gly Asp Val Asn Met Ser Gly Gly Asp Arg Arg Lys
1               5                   10                  15

Gly Thr Val Lys Trp Phe Asp Thr Gln Lys Gly Phe Gly Phe Ile Thr
            20                  25                  30

Pro Ser Asp Gly Gly Asp Asp Leu Phe Val His Gln Ser Ser Ile Arg
        35                  40                  45

Ser Glu Gly Phe Arg Ser Leu Ala Ala Glu Ser Val Glu Phe Asp
    50                  55                  60

Val Glu Val Asp Asn Ser Gly Arg Pro Lys Ala Ile Glu Val Ser Gly
65                  70                  75                  80

Pro Asp Gly Ala Pro Val Gln Gly Asn Ser Gly Gly Gly Ser Ser
            85                  90                  95

Gly Gly Arg Gly Gly Phe Gly Gly Gly Gly Arg Gly Gly Gly Arg
            100                 105                 110

Gly Gly Gly Ser Tyr Gly Gly Gly Tyr Gly Gly Arg Gly Ser Gly Gly
            115                 120                 125

Arg Gly Gly Gly Gly Asp Asn Ser Cys Phe Lys Cys Gly Glu Pro
            130                 135                 140

Gly His Met Ala Arg Glu Cys Ser Gln Gly Gly Gly Tyr Ser Gly
145                 150                 155                 160

Gly Gly Gly Gly Gly Arg Tyr Gly Ser Gly Gly Gly Gly Gly Gly
            165                 170                 175

Gly Gly Gly Leu Ser Cys Tyr Ser Cys Gly Glu Ser Gly His Phe Ala
            180                 185                 190

Arg Asp Cys Thr Ser Gly Gly Ala Arg
            195                 200

<210> SEQ ID NO 45
<211> LENGTH: 1707
<212> TYPE: DNA
<213> ORGANISM: Arabidopsis thaliana
<220> FEATURE:
<223> OTHER INFORMATION: G748

<400> SEQUENCE: 45

```
ccacgcgtcc gcactctccc aaatctctct tctttaacaa caaaaaaaaa atcacagaga       60
catagagaga agaagacgga acagaggctc caaaaaaatg atgatggaga ctagagatcc      120
agctattaag cttttcggta tgaaaatccc ttttccgtcg gtttttgaat cggcagttac      180
ggtggaggat gacgaagaag atgactggag cggcggagat gacaaatcac cagagaaggt      240
aactccagag ttatcagata agaacaacaa caactgtaac gacaacagtt ttaacaattc      300
gaaacccgaa accttggaca agaggaagc gacatcaact gatcagatag agagtagtga      360
```

```
cacgcctgag gataatcagc agacgacacc tgatggtaaa accctaaaga aaccgactaa    420
gattctaccg tgtccgagat gcaaaagcat ggagaccaag ttctgttatt acaacaacta    480
caacataaac cagcctcgtc atttctgcaa ggcttgtcag agatattgga ctgctggagg    540
gactatgagg aatgttcctg tgggggcagg acgtcgtaag aacaaaagct catcttctca    600
ttaccgtcac atcactattt ccgaggctct tgaggctgcg aggcttgacc cgggcttaca    660
ggcaaacaca agggtcttga gttttggtct cgaagctcag cagcagcacg ttgctgctcc    720
catgacacct gttatgaagc tacaagaaga tcaaaaggtc tcaaacggtg ctaggaacag    780
gtttcacggg ttagcggatc aacggcttgt agctcgggta gagaatggag atgattgctc    840
aagcggatcc tctgtgacca cctctaacaa tcactcagtg gatgaatcaa gagcacaaag    900
cggcagtgtt gttgaagcac aaatgaacaa caacaacaac aataacatga atggttatgc    960
ttgcatccca ggtgttccat ggccttacac gtggaatcca gcgatgcctc caccaggttt   1020
ttacccgcct ccagggtatc caatgccgtt ttacccttac tggaccatcc caatgctacc   1080
accgcatcaa tcctcatcgc ctataagcca aaagtgttca aatacaaact ctccgactct   1140
cggaaagcat ccgagagatg aaggatcatc gaaaaaggac aatgagacag agcgaaaaca   1200
gaaggccggg tgcgttctgg tcccgaaaac gttgagaata gatgatccta acgaagcagc   1260
aaagagctcg atatggacaa cattgggaat caagaacgag gcgatgtgca aagccggtgg   1320
tatgttcaaa gggtttgatc ataagacaaa gatgtataac aacgacaaag ctgagaactc   1380
ccctgttctt tctgctaacc ctgctgctct atcaagatca cacaatttcc atgaacagat   1440
ttagagttac atatgtatat gtatatatgt atgattgatt gtatgtatag atgatactgg   1500
agaatgatga gttttttgaga atcaaactct tttcttcttt ctagtgattg cctttattcc   1560
tttacatgtt ttggttctct gtacactatt tgatttacct tttttacttt ctttcttcat   1620
ttgtcaggaa atgttggaag ataacattaa tggtaaaaag ttggtgtgga ccgttgttgc   1680
gttggcattt caaaaaaaaa aaaaaaa                                      1707
```

<210> SEQ ID NO 46
<211> LENGTH: 448
<212> TYPE: PRT
<213> ORGANISM: Arabidopsis thaliana
<220> FEATURE:
<223> OTHER INFORMATION: G748 polypeptide

<400> SEQUENCE: 46

```
Met Met Met Glu Thr Arg Asp Pro Ala Ile Lys Leu Phe Gly Met Lys
1               5                   10                  15

Ile Pro Phe Pro Ser Val Phe Glu Ser Ala Val Thr Val Glu Asp Asp
            20                  25                  30

Glu Glu Asp Asp Trp Ser Gly Gly Asp Asp Lys Ser Pro Glu Lys Val
        35                  40                  45

Thr Pro Glu Leu Ser Asp Lys Asn Asn Asn Cys Asn Asp Asn Ser
    50                  55                  60

Phe Asn Asn Ser Lys Pro Glu Thr Leu Asp Lys Glu Glu Ala Thr Ser
65                  70                  75                  80

Thr Asp Gln Ile Glu Ser Ser Asp Thr Pro Glu Asp Asn Gln Gln Thr
                85                  90                  95

Thr Pro Asp Gly Lys Thr Leu Lys Lys Pro Thr Lys Ile Leu Pro Cys
            100                 105                 110

Pro Arg Cys Lys Ser Met Glu Thr Lys Phe Cys Tyr Tyr Asn Asn Tyr
        115                 120                 125
```

```
Asn Ile Asn Gln Pro Arg His Phe Cys Lys Ala Cys Gln Arg Tyr Trp
        130                 135                 140
Thr Ala Gly Gly Thr Met Arg Asn Val Pro Val Gly Ala Gly Arg Arg
145                 150                 155                 160
Lys Asn Lys Ser Ser Ser His Tyr Arg His Ile Thr Ile Ser Glu
            165                 170                 175
Ala Leu Glu Ala Ala Arg Leu Asp Pro Gly Leu Gln Ala Asn Thr Arg
                180                 185                 190
Val Leu Ser Phe Gly Leu Glu Ala Gln Gln His Val Ala Ala Pro
            195                 200                 205
Met Thr Pro Val Met Lys Leu Gln Glu Asp Gln Lys Val Ser Asn Gly
        210                 215                 220
Ala Arg Asn Arg Phe His Gly Leu Ala Asp Gln Arg Leu Val Ala Arg
225                 230                 235                 240
Val Glu Asn Gly Asp Asp Cys Ser Ser Gly Ser Ser Val Thr Thr Ser
                245                 250                 255
Asn Asn His Ser Val Asp Glu Ser Arg Ala Gln Ser Gly Ser Val Val
            260                 265                 270
Glu Ala Gln Met Asn Asn Asn Asn Asn Asn Met Asn Gly Tyr Ala
            275                 280                 285
Cys Ile Pro Gly Val Pro Trp Pro Tyr Thr Trp Asn Pro Ala Met Pro
        290                 295                 300
Pro Pro Gly Phe Tyr Pro Pro Pro Gly Tyr Pro Met Pro Phe Tyr Pro
305                 310                 315                 320
Tyr Trp Thr Ile Pro Met Leu Pro Pro His Gln Ser Ser Pro Ile
            325                 330                 335
Ser Gln Lys Cys Ser Asn Thr Asn Ser Pro Thr Leu Gly Lys His Pro
                340                 345                 350
Arg Asp Glu Gly Ser Ser Lys Lys Asp Asn Glu Thr Glu Arg Lys Gln
            355                 360                 365
Lys Ala Gly Cys Val Leu Val Pro Lys Thr Leu Arg Ile Asp Asp Pro
        370                 375                 380
Asn Glu Ala Ala Lys Ser Ser Ile Trp Thr Thr Leu Gly Ile Lys Asn
385                 390                 395                 400
Glu Ala Met Cys Lys Ala Gly Gly Met Phe Lys Gly Phe Asp His Lys
                405                 410                 415
Thr Lys Met Tyr Asn Asn Asp Lys Ala Glu Asn Ser Pro Val Leu Ser
            420                 425                 430
Ala Asn Pro Ala Ala Leu Ser Arg Ser His Asn Phe His Glu Gln Ile
        435                 440                 445

<210> SEQ ID NO 47
<211> LENGTH: 1195
<212> TYPE: DNA
<213> ORGANISM: Arabidopsis thaliana
<220> FEATURE:
<223> OTHER INFORMATION: G883

<400> SEQUENCE: 47
ctctctcgtc ttcgtcttct tcttcttcaa cgttcctctc caaaatcctc agaccaagaa      60
atcatcatgg ccgtcgatct aatgcgtttc cctaagatag atgatcaaac ggctattcag     120
gaagctgcat cgcaaggttt acaaagtatg aacatctga tccgtgtcct ctctaaccgt      180
cccgaacaac aacacaacgt tgactgctcc gagatcactg acttcaccgt ttctaaattc     240
```

```
aaaaccgtca tttctctcct taaccgtact ggtcacgctc ggttcagacg cggaccggtt      300
cactccactt cctctgccgc atctcagaaa ctacagagtc agatcgttaa aaatactcaa      360
cctgaggctc cgatagtgag aacaactacg aatcaccctc aaatcgttcc tccaccgtct      420
agtgtaacac tcgatttctc taaaccaagc atcttcggca ccaaagctaa gagcgccgag      480
ctggaattct ccaaagaaaa cttcagtgtt tctttaaact cctcattcat gtcgtcggcg      540
ataaccggag acggcagcgt ctccaatgga aaaatcttcc ttgcttctgc tccgtcgcag      600
cctgttaact cttccggaaa accaccgttg gctggtcatc cttacagaaa gagatgtctc      660
gagcatgagc actcagagag tttctccgga aaagtctccg gctccgccta cggaaagtgc      720
cattgcaaga aaggaaaaa tcggatgaag agaaccgtga gagtaccggc ataagtgca       780 aagatcgccg atattccacc ggacgaatat tcgtggagga agtacggaca aaaccgatc      840 aagggctcac cacacccacg tggttactac aagtgcagta cattcagagg atgtccagcg      900
aggaaacacg tggaacgagc attagatgat ccagcgatgc ttattgtgac atacgaagga      960
gagcaccgtc ataaccaatc cgcgatgcag gagaatattt cttcttcagg cattaatgat     1020
ttagtgtttg cctcggcttg actttttttt gtactatttg tttttttgatt ttttgagtac     1080 tttagatgga ttgaaatttg taaatttttt tattaagaaa tcaatttaaa tagagaaaaa     1140
ttagtggtgg tgcaaaaaaa aaaaaaaaaa aaaaaaaaaa aaaaaaaaaa aaaaa          1195
```

<210> SEQ ID NO 48
<211> LENGTH: 324
<212> TYPE: PRT
<213> ORGANISM: Arabidopsis thaliana
<220> FEATURE:
<223> OTHER INFORMATION: G883 polypeptide

<400> SEQUENCE: 48

```
Met Ala Val Asp Leu Met Arg Phe Pro Lys Ile Asp Asp Gln Thr Ala
1               5                   10                  15

Ile Gln Glu Ala Ala Ser Gln Gly Leu Gln Ser Met Glu His Leu Ile
            20                  25                  30

Arg Val Leu Ser Asn Arg Pro Glu Gln Gln His Asn Val Asp Cys Ser
        35                  40                  45

Glu Ile Thr Asp Phe Thr Val Ser Lys Phe Lys Thr Val Ile Ser Leu
    50                  55                  60

Leu Asn Arg Thr Gly His Ala Arg Phe Arg Arg Gly Pro Val His Ser
65                  70                  75                  80

Thr Ser Ser Ala Ala Ser Gln Lys Leu Gln Ser Gln Ile Val Lys Asn
                85                  90                  95

Thr Gln Pro Glu Ala Pro Ile Val Arg Thr Thr Thr Asn His Pro Gln
            100                 105                 110

Ile Val Pro Pro Ser Ser Val Thr Leu Asp Phe Ser Lys Pro Ser
        115                 120                 125

Ile Phe Gly Thr Lys Ala Lys Ser Ala Glu Leu Glu Phe Ser Lys Glu
    130                 135                 140

Asn Phe Ser Val Ser Leu Asn Ser Ser Phe Met Ser Ser Ala Ile Thr
145                 150                 155                 160

Gly Asp Gly Ser Val Ser Asn Gly Lys Ile Phe Leu Ala Ser Ala Pro
                165                 170                 175

Ser Gln Pro Val Asn Ser Ser Gly Lys Pro Pro Leu Ala Gly His Pro
            180                 185                 190

Tyr Arg Lys Arg Cys Leu Glu His Glu His Ser Glu Ser Phe Ser Gly
```

```
                195                 200                 205
Lys Val Ser Gly Ser Ala Tyr Gly Lys Cys His Cys Lys Lys Arg Lys
    210                 215                 220

Asn Arg Met Lys Arg Thr Val Arg Val Pro Ala Ile Ser Ala Lys Ile
225                 230                 235                 240

Ala Asp Ile Pro Pro Asp Glu Tyr Ser Trp Arg Lys Tyr Gly Gln Lys
                245                 250                 255

Pro Ile Lys Gly Ser Pro His Pro Arg Gly Tyr Tyr Lys Cys Ser Thr
            260                 265                 270

Phe Arg Gly Cys Pro Ala Arg Lys His Val Glu Arg Ala Leu Asp Asp
        275                 280                 285

Pro Ala Met Leu Ile Val Thr Tyr Glu Gly Glu His Arg His Asn Gln
    290                 295                 300

Ser Ala Met Gln Glu Asn Ile Ser Ser Ser Gly Ile Asn Asp Leu Val
305                 310                 315                 320

Phe Ala Ser Ala

<210> SEQ ID NO 49
<211> LENGTH: 1650
<212> TYPE: DNA
<213> ORGANISM: Arabidopsis thaliana
<220> FEATURE:
<223> OTHER INFORMATION: G20

<400> SEQUENCE: 49
ctctcactct ctttttctct ctctttactt ctactgtatc aagaagctcc gttttgctta      60
gccatagtgc gtctagggtt tggttggtgg aagaaggtt ccgatcatgg cgtcggtgtc     120
gtcgtcggat caaggaccta agacagaagc aggatgtagc ggcggaggag gaggagagag     180
ctcggagaca gtggcggcga gtgatcagat gttgttgtat agaggtttta agaaggcgaa     240
gaaggagaga ggttgtacag ctaaggagcg tattagtaaa atgcctccgt gcactgctgg     300
gaaaaggagt tccatatacc ggggagtcac cagacataga tggacaggtc gttatgaagc     360
tcacctttgg gataagagta cctggaacca aaccagaac aagaagggaa acaagttta      420 tctaggagca tatgatgatg aagaggctgc tgctagagct tacgaccttg ctgccttaaa     480
atattggggt cctgggacac ttataaattt tccggtgact gattatacca gggatttaga     540
agaaatgcaa aatctctcaa gggaagaata ccttgcatct ttacgtagat atcccttttgg    600 cagaaaaagc agcggtttct ctaggggaat agcgaaatat cgtggacttc aaagccgatg     660
ggacgcatca gccagtcgta tgcctggacc tgaatacttc agtaacattc attacggggc     720
aggtgatgat cgtggaacag aaggtgactt tctaggtagc ttttgtctgg aaagaaagat     780
tgatctaaca ggatacataa agtggtgggg agccaacaag aaccgtcaac cagaatcttc     840
atcaaaagca tcagaggatg caaacgtcga agatgctggt actgagctta aaacactgga     900
acacacatcc catgcaacag aaccatacaa ggcgccaaac cttggcgtcc tttgtggaac     960
tcagagaaaa gaaaagaaa tatcatcacc atcaagctct tctgctttaa gcatcttgtc    1020
tcagtcgcct gccttcaaga gcctagagga gaaagtgttg aagatccaag aaagctgcaa    1080
taatgaaaac gatgagaatg caaaccgtaa catcatcaat atggagaaga ataacggcaa    1140
ggcaatagag aaaccagttg tgagtcatgg agttgcttta ggcggtgctg ctgctttgtc    1200
tcttcagaaa agcatgtacc cacttacctc tcttaacg gctccattgc tcaccaacta     1260
caatacattg gatcctcttg cagaccctat tctctggaca ccattcttc cttcaggatc     1320
```

```
ctctcttact tcagaggtga caaagacaga gaccagctgt tccacgtaca gctacctccc    1380
acaagagaaa tgagccgttc cctttagact ttatgtatgt cagattctcc ttttttgaga    1440
tgaattcgtc gacttgacat ctctttgtct cttttatgga gaaaaagttg ggaaaagtgt    1500
gacaatggtc tgaagcagga atgtacaggt tttgttagtg gttgtgtttt tttttttcca    1560
gtgtggaata tagaatcatg atattttgtg taaaacagaa aaaagttatc attatagtat    1620
agaagtttgc tcttaaaaaa aaaaaaaaaa                                     1650
```

<210> SEQ ID NO 50
<211> LENGTH: 428
<212> TYPE: PRT
<213> ORGANISM: Arabidopsis thaliana
<220> FEATURE:
<223> OTHER INFORMATION: G20 polypeptide

<400> SEQUENCE: 50

```
Met Ala Ser Val Ser Ser Asp Gln Gly Pro Lys Thr Glu Ala Gly
 1               5                  10                  15

Cys Ser Gly Gly Gly Gly Glu Ser Ser Glu Thr Val Ala Ala Ser
                20                  25                  30

Asp Gln Met Leu Leu Tyr Arg Gly Phe Lys Ala Lys Lys Glu Arg
            35                  40                  45

Gly Cys Thr Ala Lys Glu Arg Ile Ser Lys Met Pro Pro Cys Thr Ala
 50                  55                  60

Gly Lys Arg Ser Ser Ile Tyr Arg Gly Val Thr Arg His Arg Trp Thr
 65                  70                  75                  80

Gly Arg Tyr Glu Ala His Leu Trp Asp Lys Ser Thr Trp Asn Gln Asn
                85                  90                  95

Gln Asn Lys Lys Gly Lys Gln Val Tyr Leu Gly Ala Tyr Asp Asp Glu
            100                 105                 110

Glu Ala Ala Ala Arg Ala Tyr Asp Leu Ala Ala Leu Lys Tyr Trp Gly
        115                 120                 125

Pro Gly Thr Leu Ile Asn Phe Pro Val Thr Asp Tyr Thr Arg Asp Leu
    130                 135                 140

Glu Glu Met Gln Asn Leu Ser Arg Glu Glu Tyr Leu Ala Ser Leu Arg
145                 150                 155                 160

Arg Tyr Pro Phe Gly Arg Lys Ser Ser Gly Phe Ser Arg Gly Ile Ala
                165                 170                 175

Lys Tyr Arg Gly Leu Gln Ser Arg Trp Asp Ala Ser Ala Ser Arg Met
            180                 185                 190

Pro Gly Pro Glu Tyr Phe Ser Asn Ile His Tyr Gly Ala Gly Asp Asp
        195                 200                 205

Arg Gly Thr Glu Gly Asp Phe Leu Gly Ser Phe Cys Leu Glu Arg Lys
    210                 215                 220

Ile Asp Leu Thr Gly Tyr Ile Lys Trp Trp Gly Ala Asn Lys Asn Arg
225                 230                 235                 240

Gln Pro Glu Ser Ser Lys Ala Ser Glu Asp Ala Asn Val Glu Asp
                245                 250                 255

Ala Gly Thr Glu Leu Lys Thr Leu Glu His Thr Ser His Ala Thr Glu
            260                 265                 270

Pro Tyr Lys Ala Pro Asn Leu Gly Val Leu Cys Gly Thr Gln Arg Lys
        275                 280                 285

Glu Lys Glu Ile Ser Ser Pro Ser Ser Ser Ala Leu Ser Ile Leu
    290                 295                 300
```

```
Ser Gln Ser Pro Ala Phe Lys Ser Leu Glu Glu Lys Val Leu Lys Ile
305                 310                 315                 320

Gln Glu Ser Cys Asn Asn Glu Asn Asp Glu Asn Ala Asn Arg Asn Ile
            325                 330                 335

Ile Asn Met Glu Lys Asn Asn Gly Lys Ala Ile Glu Lys Pro Val Val
        340                 345                 350

Ser His Gly Val Ala Leu Gly Gly Ala Ala Leu Ser Leu Gln Lys
    355                 360                 365

Ser Met Tyr Pro Leu Thr Ser Leu Leu Thr Ala Pro Leu Leu Thr Asn
370                 375                 380

Tyr Asn Thr Leu Asp Pro Leu Ala Asp Pro Ile Leu Trp Thr Pro Phe
385                 390                 395                 400

Leu Pro Ser Gly Ser Ser Leu Thr Ser Glu Val Thr Lys Thr Glu Thr
                405                 410                 415

Ser Cys Ser Thr Tyr Ser Tyr Leu Pro Gln Glu Lys
            420                 425

<210> SEQ ID NO 51
<211> LENGTH: 1430
<212> TYPE: DNA
<213> ORGANISM: Arabidopsis thaliana
<220> FEATURE:
<223> OTHER INFORMATION: G974

<400> SEQUENCE: 51
aaaaaaaaag ttgatatact ttctggtttt ctccttaact tttattcttt acaaatccat      60
cccccttaga tctgtttatt tcccgctact ttgattcatt tctgttagta atctgtcttt     120
cgtatagaag aaaactgatt tcttggtttg tattttctta aagagatcaa tcttttttta     180
tttttgatct tcttgtgttt tttttctttt gtagaattaa tcgtttgtga gggtattttt     240
ttaattccct cctctcagaa atctacacag aggttttta ttttataaac ctcttttcg     300
attttcttga aaacaaaaaa tcctgttctt tacttttttt acaagaacaa gggaaaaaaa     360
tttcttttta ttagaaatga caacttctat ggattttac agtaacaaaa cgtttcaaca     420
atctgatcca ttcggtggtg aattaatgga agcgcttta cctttatca aaagcccttc     480
caacgattca tccgcgtttg cgttctctct acccgctcca atttcatacg ggtcggatct     540
ccactcattt tctcaccatc ttagtcctaa accggtctca atgaaacaaa ccggtacttc     600
cgcggctaaa ccgacgaagc tatacagagg agtgagacaa cgtcactggg gaaaatgggt     660
ggctgagatt cgtttaccga ggaatcgaac tcgactttgg ctcggaacat tcgacacggc     720
ggaggaagct gctttagctt atgacaaggc ggcgtataag ctccgaggag attttgcgcg     780
gcttaatttc cctgatctcc gtcataacga cgagtatcaa cctcttcaat catcagtcga     840
cgctaagctt gaagctattt gtcaaaactt agctgagacg acgcagaaac aggtgagatc     900
aacgaagaag tcttcttctc ggaaacgttc atcaaccgtc gcagtgaaac taccggagga     960
ggactactct agcgccggat cttcgccgct gttaacggag agttatggat ctggtggatc    1020
ttcttcgccg ttgtcggagc tgacgtttgg tgatacggag gaggagattc agccgccgtg    1080
gaacgagaac gcgttggaga agtatccgtc gtacgagatc gattgggatt cgattcttca    1140
gtgttcgagt cttgtaaatt agatgttgcc ataggggtat tttagggact ttagagctct    1200
ctgcgatgga gttttggtc attgcagaga ttttattatt attaagggg tttgttatgt    1260
taatatcaaa taagtttatc tactttgatg ttaattagtg ttaatctctg cgtcggtcca    1320
agctgttttt ttttggcatg cttcgaccgt gtgagatttc ttatgtaatt tttgtagttc    1380
```

```
cttgattttc ttagttcaag ttaaattggc acaaaaaaaa aaaaaaaaa        1430
```

<210> SEQ ID NO 52
<211> LENGTH: 261
<212> TYPE: PRT
<213> ORGANISM: Arabidopsis thaliana
<220> FEATURE:
<223> OTHER INFORMATION: G974 polypeptide

<400> SEQUENCE: 52

```
Met Thr Thr Ser Met Asp Phe Tyr Ser Asn Lys Thr Phe Gln Gln Ser
  1               5                  10                  15

Asp Pro Phe Gly Gly Glu Leu Met Glu Ala Leu Leu Pro Phe Ile Lys
             20                  25                  30

Ser Pro Ser Asn Asp Ser Ser Ala Phe Ala Phe Ser Leu Pro Ala Pro
         35                  40                  45

Ile Ser Tyr Gly Ser Asp Leu His Ser Phe Ser His His Leu Ser Pro
     50                  55                  60

Lys Pro Val Ser Met Lys Gln Thr Gly Thr Ser Ala Ala Lys Pro Thr
 65                  70                  75                  80

Lys Leu Tyr Arg Gly Val Arg Gln Arg His Trp Gly Lys Trp Val Ala
                 85                  90                  95

Glu Ile Arg Leu Pro Arg Asn Arg Thr Arg Leu Trp Leu Gly Thr Phe
            100                 105                 110

Asp Thr Ala Glu Glu Ala Ala Leu Ala Tyr Asp Lys Ala Ala Tyr Lys
        115                 120                 125

Leu Arg Gly Asp Phe Ala Arg Leu Asn Phe Pro Asp Leu Arg His Asn
    130                 135                 140

Asp Glu Tyr Gln Pro Leu Gln Ser Ser Val Asp Ala Lys Leu Glu Ala
145                 150                 155                 160

Ile Cys Gln Asn Leu Ala Glu Thr Thr Gln Lys Gln Val Arg Ser Thr
                165                 170                 175

Lys Lys Ser Ser Ser Arg Lys Arg Ser Ser Thr Val Ala Val Lys Leu
            180                 185                 190

Pro Glu Glu Asp Tyr Ser Ser Ala Gly Ser Ser Pro Leu Leu Thr Glu
        195                 200                 205

Ser Tyr Gly Ser Gly Gly Ser Ser Ser Pro Leu Ser Glu Leu Thr Phe
    210                 215                 220

Gly Asp Thr Glu Glu Glu Ile Gln Pro Pro Trp Asn Glu Asn Ala Leu
225                 230                 235                 240

Glu Lys Tyr Pro Ser Tyr Glu Ile Asp Trp Asp Ser Ile Leu Gln Cys
                245                 250                 255

Ser Ser Leu Val Asn
            260
```

<210> SEQ ID NO 53
<211> LENGTH: 1113
<212> TYPE: DNA
<213> ORGANISM: Arabidopsis thaliana
<220> FEATURE:
<223> OTHER INFORMATION: G2343

<400> SEQUENCE: 53

```
atgggtcatc actcatgctg caaccagcaa aaggtgaaga gagggctttg gtcaccggaa      60
gaagatgaga agcttattag atatatcaca actcatggct atggatgttg gagtgaagtc     120
cctgaaaaag cagggcttca agatgtggaa aaagttgta gattgcgatg dataaactat      180
```

-continued

```
cttcgacctg atatcaggag aggaaggttc tctccagaag aagagaaatt gatcataagc    240
cttcatggag ttgtgggaaa caggtgggct catatagcta gtcatttacc gggaagaaca    300
gataacgaga ttaaaaacta ttggaattca tggattaaga aaaagatacg aaaaccgcac    360
catcattaca gtcgtcatca accgtcagta actactgtga cattgaatgc ggacactaca    420
tcgattgcca ctaccatcga ggcctctacc accacaacat cgactatcga taacttacat    480
tttgacggtt tcactgattc tcctaaccaa ttaaatttca ccaatgatca agaaactaat    540
ataaagattc aagaaacttt tttctcccat aaacctcctc tcttcatggt agacacaaca    600
cttcctatcc tagaaggaat gttctctgaa acatcatca caaacaataa caagaacaat    660
gatcatgatg acacgcaaag aggaggaaga gaaaatgttt gtgaacaagc atttctaaca    720
actaacacgg aagaatggga tatgaatctt cgtcagcaag agccgtttca agttcctaca    780
ctggcgtcac atgtgttcaa caactcttcc aattcaaata ttgacacggt tataagttat    840
aatctaccgg cgctaataga gggaaatgtc gataacatcg tccataatga aaacagcaat    900
gtccaagatg gagaaatggc gtccacattc gaatgtttaa agaggcaaga actaagctat    960
gatcaatggg acgattcaca acaatgctct aactttttct tttgggacaa ccttaatata   1020
aacgtggaag gttcatctct tgttggaaac caagacccat caatgaattt gggatcatct   1080
gccttatctt cttcttccc ttcttcgttt taa                                 1113
```

<210> SEQ ID NO 54
<211> LENGTH: 370
<212> TYPE: PRT
<213> ORGANISM: Arabidopsis thaliana
<220> FEATURE:
<223> OTHER INFORMATION: G2343 polypeptide

<400> SEQUENCE: 54

```
Met Gly His His Ser Cys Cys Asn Gln Gln Lys Val Lys Arg Gly Leu
1               5                   10                  15

Trp Ser Pro Glu Glu Asp Glu Lys Leu Ile Arg Tyr Ile Thr Thr His
            20                  25                  30

Gly Tyr Gly Cys Trp Ser Glu Val Pro Glu Lys Ala Gly Leu Gln Arg
        35                  40                  45

Cys Gly Lys Ser Cys Arg Leu Arg Trp Ile Asn Tyr Leu Arg Pro Asp
    50                  55                  60

Ile Arg Arg Gly Arg Phe Ser Pro Glu Glu Glu Lys Leu Ile Ile Ser
65                  70                  75                  80

Leu His Gly Val Val Gly Asn Arg Trp Ala His Ile Ala Ser His Leu
                85                  90                  95

Pro Gly Arg Thr Asp Asn Glu Ile Lys Asn Tyr Trp Asn Ser Trp Ile
            100                 105                 110

Lys Lys Lys Ile Arg Lys Pro His His His Tyr Ser Arg His Gln Pro
        115                 120                 125

Ser Val Thr Thr Val Thr Leu Asn Ala Asp Thr Thr Ser Ile Ala Thr
    130                 135                 140

Thr Ile Glu Ala Ser Thr Thr Thr Ser Thr Ile Asp Asn Leu His
145                 150                 155                 160

Phe Asp Gly Phe Thr Asp Ser Pro Asn Gln Leu Asn Phe Thr Asn Asp
                165                 170                 175

Gln Glu Thr Asn Ile Lys Ile Gln Glu Thr Phe Phe Ser His Lys Pro
            180                 185                 190
```

```
Pro Leu Phe Met Val Asp Thr Thr Leu Pro Ile Leu Glu Gly Met Phe
        195                 200                 205

Ser Glu Asn Ile Ile Thr Asn Asn Lys Asn Asn Asp His Asp Asp
    210                 215                 220

Thr Gln Arg Gly Gly Arg Glu Asn Val Cys Glu Gln Ala Phe Leu Thr
225                 230                 235                 240

Thr Asn Thr Glu Glu Trp Asp Met Asn Leu Arg Gln Gln Pro Phe
            245                 250                 255

Gln Val Pro Thr Leu Ala Ser His Val Phe Asn Asn Ser Asn Ser
        260                 265                 270

Asn Ile Asp Thr Val Ile Ser Tyr Asn Leu Pro Ala Leu Ile Glu Gly
        275                 280                 285

Asn Val Asp Asn Ile Val His Asn Glu Asn Ser Asn Val Gln Asp Gly
290                 295                 300

Glu Met Ala Ser Thr Phe Glu Cys Leu Lys Arg Gln Glu Leu Ser Tyr
305                 310                 315                 320

Asp Gln Trp Asp Asp Ser Gln Gln Cys Ser Asn Phe Phe Phe Trp Asp
                325                 330                 335

Asn Leu Asn Ile Asn Val Glu Gly Ser Ser Leu Val Gly Asn Gln Asp
            340                 345                 350

Pro Ser Met Asn Leu Gly Ser Ser Ala Leu Ser Ser Ser Phe Pro Ser
        355                 360                 365

Ser Phe
    370

<210> SEQ ID NO 55
<211> LENGTH: 2006
<212> TYPE: DNA
<213> ORGANISM: Arabidopsis thaliana
<220> FEATURE:
<223> OTHER INFORMATION: G1777

<400> SEQUENCE: 55
ctcgtacttt atcacctccg tcgttctata atactctctt ccgtcaatca tatcatttgt      60
cgacaatttc attctgatca gtttaaaaat tgatccatgg atgataattt aagcggcgag     120
gaagaagatt actattactc ctccgatcag gaatctctca acgggattga taatgatgaa     180
tccgtttcga tacctgtttc ttcccgatca aatactgtca aggttattac gaaggaatca     240
cttttggctg cacagaggga ggatttgcgg agagtgatgg aattgttatc ggttaaggag     300
caccatgctc ggactcttct tatacattac cgatgggatg tggagaagtt gtttgctgtt     360
cttgttgaga aagggaaaga tagcttgttt tctggtgctg gtgttacact tcttgaaaac     420
caaagttgtg attcttccgt ttctggttct tcttcgatga tgagttgtga tatctgcgta     480
gaggatgtac cgggttatca gctgacaagg atggactgtg ccatagctt ttgcaataac     540
tgttggactg gcatttttac tgtaaagata atgaaggtc agagcaaaag gattatatgc     600
atggctcata gtgtaatgc tatttgtgat gaagatgttg tcagggctct agttagtaaa     660
agccaaccag atttagctga aagtttgat cgttttcttc ttgagtcgta tatcgaagat     720
aacaaaatgg tgaagtggtg tccgagtact cctcattgtg ggaatgccat acgtgttgag     780
gatgacgagc tctgtgaggt tgaatgctct tgtggtttgc agttctgttt cagttgttca     840
tctcaagctc actccccttg ctcttgtgtg atgtgggaac tatggagaaa gaagtgcttt     900
gatgagtccg agactgttaa ttggataact gttcacacaa agccgtgtcc caaatgtcac     960
aagcctgttg aaaagaatgg tggatgcaat ctcgtgactt gtctttgtcg acaatctttt    1020
```

-continued

```
tgttggttgt gtggtgaagc tactggaagg gaccacactt gggctagaat ctcgggtcat    1080
agttgtggtc ggttccaaga agataaagag aaacaaatgg agagagcgaa aagggatctc    1140
aagcggtata tgcattatca taaccgatac aaagcacata tcgactcctc caagctagag    1200
gctaagctta gtaataatat tagtaaaaag gtgtctattt cagaaaagag ggagttacaa    1260
cttaaagact tcagctgggc taccaatgga ctccatcggt tatttagatc aagacgagtt    1320
ctttcatatt catacccttt cgcattttac atgtttggag atgagctgtt taaagatgag    1380
atgagctctg aggaaagaga aataaaacaa aatctgtttg aggatcagca gcagcagctt    1440
gaggctaatg ttgagaaact ttctaagttc ttggaggaac cttttgatca atttgctgat    1500
gataaggtca tgcagataag gattcaagtc atcaatttgt cagttgcggt cgatacactc    1560
tgcgaaaata tgtatgaatg cattgagaat gacttgttgg gttctctgca acttggcatc    1620
cacaacatta ctccatacag atcaaacggc atagaacgag catctgattt ttatagttcc    1680
cagaattcca aggaagctgt tggtcagtct tcggattgtg gatggacgtc caggctcgat    1740
caagctttgg agtcagggaa gtcggaagac acaagttgct cttccgggaa gcgtgctaga    1800
atagacgaaa gttacagaaa cagccaaacc accttactag atttaaactt gccagcggaa    1860
gccattgagc ggaaatgaac acttatcctt cttcacctcc caataacacc ctttttgtcc    1920
aaataaagtg tgttacccgg atatttatag ctctaaaccc aatcccctct gcttaatttg    1980
tcagtgacct tacctaaccc tcttca                                        2006
```

<210> SEQ ID NO 56
<211> LENGTH: 593
<212> TYPE: PRT
<213> ORGANISM: Arabidopsis thaliana
<220> FEATURE:
<223> OTHER INFORMATION: G1777 polypeptide

<400> SEQUENCE: 56

```
Met Asp Asp Asn Leu Ser Gly Glu Glu Glu Asp Tyr Tyr Tyr Ser Ser
1               5                   10                  15

Asp Gln Glu Ser Leu Asn Gly Ile Asp Asn Asp Glu Ser Val Ser Ile
            20                  25                  30

Pro Val Ser Ser Arg Ser Asn Thr Val Lys Val Ile Thr Lys Glu Ser
        35                  40                  45

Leu Leu Ala Ala Gln Arg Glu Asp Leu Arg Arg Val Met Glu Leu Leu
    50                  55                  60

Ser Val Lys Glu His His Ala Arg Thr Leu Leu Ile His Tyr Arg Trp
65                  70                  75                  80

Asp Val Glu Lys Leu Phe Ala Val Leu Val Glu Lys Gly Lys Asp Ser
                85                  90                  95

Leu Phe Ser Gly Ala Gly Val Thr Leu Leu Glu Asn Gln Ser Cys Asp
            100                 105                 110

Ser Ser Val Ser Gly Ser Ser Ser Met Met Ser Cys Asp Ile Cys Val
        115                 120                 125

Glu Asp Val Pro Gly Tyr Gln Leu Thr Arg Met Asp Cys Gly His Ser
    130                 135                 140

Phe Cys Asn Asn Cys Trp Thr Gly His Phe Thr Val Lys Ile Asn Glu
145                 150                 155                 160

Gly Gln Ser Lys Arg Ile Ile Cys Met Ala His Lys Cys Asn Ala Ile
                165                 170                 175

Cys Asp Glu Asp Val Val Arg Ala Leu Val Ser Lys Ser Gln Pro Asp
```

-continued

```
                 180                 185                 190
Leu Ala Glu Lys Phe Asp Arg Phe Leu Glu Ser Tyr Ile Glu Asp
            195                 200                 205
Asn Lys Met Val Lys Trp Cys Pro Ser Thr Pro His Cys Gly Asn Ala
    210                 215                 220
Ile Arg Val Glu Asp Glu Leu Cys Glu Val Glu Cys Ser Cys Gly
225                 230                 235                 240
Leu Gln Phe Cys Phe Ser Cys Ser Ser Gln Ala His Ser Pro Cys Ser
            245                 250                 255
Cys Val Met Trp Glu Leu Trp Arg Lys Lys Cys Phe Asp Glu Ser Glu
        260                 265                 270
Thr Val Asn Trp Ile Thr Val His Thr Lys Pro Cys Pro Lys Cys His
        275                 280                 285
Lys Pro Val Glu Lys Asn Gly Gly Cys Asn Leu Val Thr Cys Leu Cys
        290                 295                 300
Arg Gln Ser Phe Cys Trp Leu Cys Gly Glu Ala Thr Gly Arg Asp His
305                 310                 315                 320
Thr Trp Ala Arg Ile Ser Gly His Ser Cys Gly Arg Phe Gln Glu Asp
                325                 330                 335
Lys Glu Lys Gln Met Glu Arg Ala Lys Arg Asp Leu Lys Arg Tyr Met
            340                 345                 350
His Tyr His Asn Arg Tyr Lys Ala His Ile Asp Ser Ser Lys Leu Glu
        355                 360                 365
Ala Lys Leu Ser Asn Asn Ile Ser Lys Lys Val Ser Ile Ser Glu Lys
370                 375                 380
Arg Glu Leu Gln Leu Lys Asp Phe Ser Trp Ala Thr Asn Gly Leu His
385                 390                 395                 400
Arg Leu Phe Arg Ser Arg Arg Val Leu Ser Tyr Ser Tyr Pro Phe Ala
                405                 410                 415
Phe Tyr Met Phe Gly Asp Glu Leu Phe Lys Asp Glu Met Ser Ser Glu
                420                 425                 430
Glu Arg Glu Ile Lys Gln Asn Leu Phe Glu Asp Gln Gln Gln Gln Leu
        435                 440                 445
Glu Ala Asn Val Glu Lys Leu Ser Lys Phe Leu Glu Glu Pro Phe Asp
450                 455                 460
Gln Phe Ala Asp Asp Lys Val Met Gln Ile Arg Ile Gln Val Ile Asn
465                 470                 475                 480
Leu Ser Val Ala Val Asp Thr Leu Cys Glu Asn Met Tyr Glu Cys Ile
                485                 490                 495
Glu Asn Asp Leu Leu Gly Ser Leu Gln Leu Gly Ile His Asn Ile Thr
                500                 505                 510
Pro Tyr Arg Ser Asn Gly Ile Glu Arg Ala Ser Asp Phe Tyr Ser Ser
        515                 520                 525
Gln Asn Ser Lys Glu Ala Val Gly Gln Ser Ser Asp Cys Gly Trp Thr
        530                 535                 540
Ser Arg Leu Asp Gln Ala Leu Glu Ser Gly Lys Ser Glu Asp Thr Ser
545                 550                 555                 560
Cys Ser Ser Gly Lys Arg Ala Arg Ile Asp Glu Ser Tyr Arg Asn Ser
                565                 570                 575
Gln Thr Thr Leu Leu Asp Leu Asn Leu Pro Ala Glu Ala Ile Glu Arg
            580                 585                 590
Lys
```

<210> SEQ ID NO 57
<211> LENGTH: 1209
<212> TYPE: DNA
<213> ORGANISM: Arabidopsis thaliana
<220> FEATURE:
<223> OTHER INFORMATION: G229

<400> SEQUENCE: 57

```
ttgtggtcag tggaataaac acatataacc gccggagaaa atgggaagag cgccatgttg      60
cgagaaggtc ggtatcaaga gagggcggtg gacggcggag gaggaccaga ttctctccaa     120
ctacattcaa tccaatggtg aaggttcttg gagatctctc cccaaaaatg ccggattaaa     180
aaggtgtgga agagctgta gattgagatg gataaactat ctaagatcag acctcaagcg     240
tggaaacata actccagaag aagaagaact cgttgttaaa ttgcattcca ctttgggaaa     300
caggtggtca ctaatcgcgg gtcatctacc agggagaaca gacaacgaaa taaaaaatta     360
ttggaactct catctcagcc gtaaactcca caacttcatt aggaagccat ccatctctca     420
agacgtctcc gccgtaatca tggcgaacgc ttcttcagcg ccaccgccgc cgcaggcaaa     480
acgcagactt gggagaacga gtaggtccgc tatgaaacca aaaatccgca gaacaaaaac     540
tcgtaaaacg aagaaaacgt ctgcaccacc ggagcctaac gccgatgtag ctggggctga     600
taaagaagca ttaatggtgg agtcaagtgg agccgaggct gagctaggac gaccatgtga     660
ctactatgga gatgattgta acaaaaatct catgagcatt aatggcgata atggagtttt     720
aacgtttgat gatgatatca tcgatctttt gttggacgag tcagatcctg cccacttgta     780
cacaaacaca acgtgcggtg gtggtgggga gttgcataac ataagagact ctgaaggagc     840
cagagggttc tcggatactt ggaaccaagg gaatctcgac tgtcttcttc agtcttgtcc     900
atctgtggag tcgtttctca actacgacca ccaagttaac gacgcgtcga cggatgagtt     960
tatcgattgg gattgtgttt ggcaagaagg tagtgataat aatctttggc atgagaaaga    1020
gaatcccgac tcaatggtct cgtggctttt agacggtgat gatgaggcca cgatcgggaa    1080
tagtaattgt gagaactttg gagaaccgtt agatcatgac gacgaaagcg ctttggtcgc    1140
ttggcttctg tcatgatgat attgattgat ccgttatgta atcttttttg tgcattcaca    1200
gtttgaatc                                                            1209
```

<210> SEQ ID NO 58
<211> LENGTH: 371
<212> TYPE: PRT
<213> ORGANISM: Arabidopsis thaliana
<220> FEATURE:
<223> OTHER INFORMATION: G229 polypeptide

<400> SEQUENCE: 58

```
Met Gly Arg Ala Pro Cys Cys Glu Lys Val Gly Ile Lys Arg Gly
1               5                   10                  15

Trp Thr Ala Glu Glu Asp Gln Ile Leu Ser Asn Tyr Ile Gln Ser Asn
            20                  25                  30

Gly Glu Gly Ser Trp Arg Ser Leu Pro Lys Asn Ala Gly Leu Lys Arg
        35                  40                  45

Cys Gly Lys Ser Cys Arg Leu Arg Trp Ile Asn Tyr Leu Arg Ser Asp
    50                  55                  60

Leu Lys Arg Gly Asn Ile Thr Pro Glu Glu Glu Leu Val Val Lys
65                  70                  75                  80

Leu His Ser Thr Leu Gly Asn Arg Trp Ser Leu Ile Ala Gly His Leu
                85                  90                  95
```

```
Pro Gly Arg Thr Asp Asn Glu Ile Lys Asn Tyr Trp Asn Ser His Leu
            100                 105                 110
Ser Arg Lys Leu His Asn Phe Ile Arg Lys Pro Ser Ile Ser Gln Asp
        115                 120                 125
Val Ser Ala Val Ile Met Ala Asn Ala Ser Ser Ala Pro Pro Pro
    130                 135                 140
Gln Ala Lys Arg Arg Leu Gly Arg Thr Ser Arg Ser Ala Met Lys Pro
145                 150                 155                 160
Lys Ile Arg Arg Thr Lys Thr Arg Lys Thr Lys Lys Thr Ser Ala Pro
                165                 170                 175
Pro Glu Pro Asn Ala Asp Val Ala Gly Ala Asp Lys Glu Ala Leu Met
            180                 185                 190
Val Glu Ser Ser Gly Ala Glu Ala Glu Leu Gly Arg Pro Cys Asp Tyr
        195                 200                 205
Tyr Gly Asp Asp Cys Asn Lys Asn Leu Met Ser Ile Asn Gly Asp Asn
    210                 215                 220
Gly Val Leu Thr Phe Asp Asp Ile Ile Asp Leu Leu Leu Asp Glu
225                 230                 235                 240
Ser Asp Pro Gly His Leu Tyr Thr Asn Thr Thr Cys Gly Gly Gly
                245                 250                 255
Glu Leu His Asn Ile Arg Asp Ser Glu Gly Ala Arg Gly Phe Ser Asp
            260                 265                 270
Thr Trp Asn Gln Gly Asn Leu Asp Cys Leu Leu Gln Ser Cys Pro Ser
        275                 280                 285
Val Glu Ser Phe Leu Asn Tyr Asp His Gln Val Asn Asp Ala Ser Thr
    290                 295                 300
Asp Glu Phe Ile Asp Trp Asp Cys Val Trp Gln Glu Gly Ser Asp Asn
305                 310                 315                 320
Asn Leu Trp His Glu Lys Glu Asn Pro Asp Ser Met Val Ser Trp Leu
                325                 330                 335
Leu Asp Gly Asp Asp Glu Ala Thr Ile Gly Asn Ser Asn Cys Glu Asn
            340                 345                 350
Phe Gly Glu Pro Leu Asp His Asp Asp Glu Ser Ala Leu Val Ala Trp
        355                 360                 365
Leu Leu Ser
    370

<210> SEQ ID NO 59
<211> LENGTH: 1033
<212> TYPE: DNA
<213> ORGANISM: Arabidopsis thaliana
<220> FEATURE:
<223> OTHER INFORMATION: G663

<400> SEQUENCE: 59
gtcgacccac gcgtccgtgg gaagccacaa taaccccta  ttcctcggcc tttttaaaa      60 aagttttaga ataatccgat aaaatacttt tatattaatt tttctttggt ccatggaggg    120
ttcgtccaaa gggttgagga aggtgcatg  gactgctgaa gaagatagtc tcttgaggct    180
atgtattgat aagtatggag aaggcaaatg gcatcaagtt cctttgagag ctgggctaaa    240
tcgatgcaga aagagttgta gactaagatg gttgaactat ttgaagccaa gtatcaagag    300
aggaagactt agcaatgatg aagttgatct tcttcttcgc cttcataagc ttctaggaaa    360
taggtggtcc ttgattgctg gtcgattgcc tggtcggacc gctaatgatg tcaaaaatta    420
```

-continued

```
ctggaacacc catctgagta aaaaacatga gtcttcgtgt tgtaagtcta aatgaaaaa      480 gaaaaacatt atttcccctc ctacaacacc ggtccaaaaa atcggtgttt ttaagcctcg      540
acctcgatcc ttctctgtta caatggttg cagccatctc aatggtctgc cagaagttga      600
tttaattcct tcatgccttg gactcaagaa aaataatgtt tgtgaaaata gtatcacatg      660
taacaaagat gatgagaaag atgattttgt gaataatcta atgaatggag ataatatgtg      720
gttggagaat ttactggggg aaaaccaaga agctgatgcg attgttcctg aagcgacgac      780
agctgaacat ggggccactt tggcgtttga cgttgagcaa ctttggagtc tgtttgatgg      840
agagactgtt gaacttgatt agtgtttctc accgtttgtt taagattgtg ggtggctttt      900
ctttcgtatt ttagtaatgt atttttctgt atgaagtaaa gaatttcagc attttaagaa      960
aaatggttat gtttctacgt aataaaaaaa aacgttattt ataaaaaaaa aaaaaaaaaa     1020
aaaaaaaaaa aaa                                                       1033
```

<210> SEQ ID NO 60
<211> LENGTH: 249
<212> TYPE: PRT
<213> ORGANISM: Arabidopsis thaliana
<220> FEATURE:
<223> OTHER INFORMATION: G663 polypeptide

<400> SEQUENCE: 60

```
Met Glu Gly Ser Ser Lys Gly Leu Arg Lys Gly Ala Trp Thr Ala Glu
1               5                   10                  15

Glu Asp Ser Leu Leu Arg Leu Cys Ile Asp Lys Tyr Gly Glu Gly Lys
            20                  25                  30

Trp His Gln Val Pro Leu Arg Ala Gly Leu Asn Arg Cys Arg Lys Ser
        35                  40                  45

Cys Arg Leu Arg Trp Leu Asn Tyr Leu Lys Pro Ser Ile Lys Arg Gly
    50                  55                  60

Arg Leu Ser Asn Asp Glu Val Asp Leu Leu Leu Arg Leu His Lys Leu
65                  70                  75                  80

Leu Gly Asn Arg Trp Ser Leu Ile Ala Gly Arg Leu Pro Gly Arg Thr
                85                  90                  95

Ala Asn Asp Val Lys Asn Tyr Trp Asn Thr His Leu Ser Lys Lys His
            100                 105                 110

Glu Ser Ser Cys Cys Lys Ser Lys Met Lys Lys Asn Ile Ile Ser
        115                 120                 125

Pro Pro Thr Thr Pro Val Gln Lys Ile Gly Val Phe Lys Pro Arg Pro
    130                 135                 140

Arg Ser Phe Ser Val Asn Asn Gly Cys Ser His Leu Asn Gly Leu Pro
145                 150                 155                 160

Glu Val Asp Leu Ile Pro Ser Cys Leu Gly Leu Lys Lys Asn Asn Val
                165                 170                 175

Cys Glu Asn Ser Ile Thr Cys Asn Lys Asp Asp Glu Lys Asp Asp Phe
            180                 185                 190

Val Asn Asn Leu Met Asn Gly Asp Asn Met Trp Leu Glu Asn Leu Leu
        195                 200                 205

Gly Glu Asn Gln Glu Ala Asp Ala Ile Val Pro Glu Ala Thr Thr Ala
    210                 215                 220

Glu His Gly Ala Thr Leu Ala Phe Asp Val Glu Gln Leu Trp Ser Leu
225                 230                 235                 240

Phe Asp Gly Glu Thr Val Glu Leu Asp
                245
```

<210> SEQ ID NO 61
<211> LENGTH: 977
<212> TYPE: DNA
<213> ORGANISM: Arabidopsis thaliana
<220> FEATURE:
<223> OTHER INFORMATION: G362

<400> SEQUENCE: 61

```
ataaaaaacc cttcatacaa tataaaattt ctttagacat acaatatatt atactattac      60
agatgcaatg catcattagt tacaaactat taaactaaat atcccccgtc tctctcttgc     120
tatataaaga agatcattta cacatctcct taagcaaatt aaacccatcg ataaacacat     180
acgttcacac atatatgtct ataaatccga caatgtctcg tactggcgaa agttcttcag     240
gttcgtcctc cgacaagacg ataaagctat tcggcttcga actcatcagc ggcagtcgta     300
cgccggaaat cacgcggcg gaaagcgtga gctcgtccac aaacacgacg tcgttaacag     360
tgatgaaaag acacgagtgc caatactgcg gtaaagagtt tgcaaattct caagccttag     420
gaggtcacca aaacgctcac aagaaggaga ggttgaagaa gaagaggctt cagcttcaag     480
ctcggcgagc cagcatcggc tattatctca ccaaccacca acaacccata acgacgtcat     540
ttcagagaca atacaaaacg ccgtcgtatt gtgcattctc ctccatgcac gtgaataatg     600
atcagatggg tgtgtacaac gaagattggt cgtcgaggtc gtcgcagatt aacttcggta     660
ataatgacac gtgccaagat cttaatgaac aaagcggtga gatgggtaag ctgtacggtg     720
ttcgaccgaa catgattcag ttccagagag atctgagttc tcgttctgat cagatgagaa     780
gtattaactc gctggatctt catctaggtt ttgccggaga tgcggcataa caaattaaag     840
agagatatat gattaagatt atatgtacta tagtggcgta tttcattggg atcatgaagg     900
ggaaaaaacg agacatatag tattcttgat gcaatttgag ttttgtaatt tatttaggtt     960
tatgtatgtt ttcgaag                                                    977
```

<210> SEQ ID NO 62
<211> LENGTH: 211
<212> TYPE: PRT
<213> ORGANISM: Arabidopsis thaliana
<220> FEATURE:
<223> OTHER INFORMATION: G362 polypeptide

<400> SEQUENCE: 62

```
Met Ser Ile Asn Pro Thr Met Ser Arg Thr Gly Glu Ser Ser Ser Gly
1               5                   10                  15

Ser Ser Ser Asp Lys Thr Ile Lys Leu Phe Gly Phe Glu Leu Ile Ser
            20                  25                  30

Gly Ser Arg Thr Pro Glu Ile Thr Thr Ala Glu Ser Val Ser Ser Ser
        35                  40                  45

Thr Asn Thr Thr Ser Leu Thr Val Met Lys Arg His Glu Cys Gln Tyr
    50                  55                  60

Cys Gly Lys Glu Phe Ala Asn Ser Gln Ala Leu Gly Gly His Gln Asn
65                  70                  75                  80

Ala His Lys Lys Glu Arg Leu Lys Lys Arg Leu Gln Leu Gln Ala
                85                  90                  95

Arg Arg Ala Ser Ile Gly Tyr Tyr Leu Thr Asn His Gln Gln Pro Ile
                100                 105                 110

Thr Thr Ser Phe Gln Arg Gln Tyr Lys Thr Pro Ser Tyr Cys Ala Phe
            115                 120                 125
```

```
Ser Ser Met His Val Asn Asn Asp Gln Met Gly Val Tyr Asn Glu Asp
    130                 135                 140

Trp Ser Ser Arg Ser Ser Gln Ile Asn Phe Gly Asn Asn Asp Thr Cys
145                 150                 155                 160

Gln Asp Leu Asn Glu Gln Ser Gly Glu Met Gly Lys Leu Tyr Gly Val
                165                 170                 175

Arg Pro Asn Met Ile Gln Phe Gln Arg Asp Leu Ser Ser Arg Ser Asp
            180                 185                 190

Gln Met Arg Ser Ile Asn Ser Leu Asp Leu His Leu Gly Phe Ala Gly
        195                 200                 205

Asp Ala Ala
    210

<210> SEQ ID NO 63
<211> LENGTH: 1536
<212> TYPE: DNA
<213> ORGANISM: Arabidopsis thaliana
<220> FEATURE:
<223> OTHER INFORMATION: G2105

<400> SEQUENCE: 63
ctctctgact tgaactcttc tcttctaccg aatcaaacca aatggaggat catcaaaacc      60
atccacagta cggtatagaa caaccatctt ctcaattctc ctctgatctc ttcggcttca     120
acctcgtttc agcgccggac cagcaccatc gtcttcattt caccgaccat gagataagtt     180
tattgccacg tggaatacaa gggcttacgg tggctggaaa caacagtaac actattacaa     240
cgatccagag tggtggctgt gttggtgggt ttagtggctt tacggacggc ggaggaacag     300
ggaggtggcc gaggcaagag acgttgatgt tgttggaggt cagatctcgt cttgatcaca     360
agttcaaaga agctaatcaa aagggtcctc tctgggatga agtttctagg attatgtcgg     420
aggaacatgg atacactagg agtggcaaga agtgtagaga gaagttcgag aatctctaca     480
agtactataa aaaaacaaaa gaaggcaaat ccggtcggcg acaagatggt aaaaactata     540
gatttttccg gcagcttgaa gcgatatacg gcgaatccaa agactcggtt tcttgctata     600
acaacacgca gttcataatg accaatgctc ttcatagtaa tttccgcgct tctaacattc     660
ataacatcgt ccctcatcat cagaatccct tgatgaccaa taccaatact caaagtcaaa     720
gccttagcat ttctaacaat ttcaactcct cctccgattt ggatctaact tcttcctctg     780
aaggaaacga aactactaaa agagagggga tgcattggaa ggaaaagatc aaggaattca     840
ttggtgttca tatggagagg ttgatagaga agcaagattt ttggcttgag aagttgatga     900
agattgtgga agacaaagaa catcaaagga tgctgagaga gaggaatgg agaaggattg      960
aagcggaaag gatcgataag gaacgttcgt tttggacaaa agagagggag aggattgaag    1020
ctcgggatgt tgcggtgatt aatgccttgc agtacttgac gggaagggca ttgataaggc    1080
cggattcttc gtctcctaca gagaggatta atgggaatgg aagcgataaa atgatggctg    1140
ataatgaatt tgctgatgaa ggaaataagg gcaagatgga taaaaaacaa atgaataaga    1200
aaaggaagga gaaatggtca agccacggag ggaatcatcc aagaaccaaa gagaatatga    1260
tgatatacaa caatcaagaa actaagatta atgattttg tcgagatgat gaccaatgcc    1320
atcatgaagg ttactcacct tcaaactcca agaacgcagg aactccgagc tgcagcaatg    1380
ccatggcagc tagtacaaag tgcttttcca tgcttgaagg agaaggagat cagaacttgt    1440
gggaggggtta tggtttgaag caaaggaaag aaaataatca tcagtaagct acatttttca    1500
ttctcaaaat gaagaataag agaacttaga aacgat                             1536
```

<210> SEQ ID NO 64
<211> LENGTH: 481
<212> TYPE: PRT
<213> ORGANISM: Arabidopsis thaliana
<220> FEATURE:
<223> OTHER INFORMATION: G2105 polypeptide

<400> SEQUENCE: 64

```
Met Glu Asp His Gln Asn His Pro Gln Tyr Gly Ile Glu Gln Pro Ser
1               5                   10                  15

Ser Gln Phe Ser Ser Asp Leu Phe Gly Phe Asn Leu Val Ser Ala Pro
            20                  25                  30

Asp Gln His His Arg Leu His Phe Thr Asp His Glu Ile Ser Leu Leu
        35                  40                  45

Pro Arg Gly Ile Gln Gly Leu Thr Val Ala Gly Asn Asn Ser Asn Thr
    50                  55                  60

Ile Thr Thr Ile Gln Ser Gly Gly Cys Val Gly Phe Ser Gly Phe
65                  70                  75                  80

Thr Asp Gly Gly Gly Thr Gly Arg Trp Pro Arg Gln Glu Thr Leu Met
                85                  90                  95

Leu Leu Glu Val Arg Ser Arg Leu Asp His Lys Phe Lys Glu Ala Asn
            100                 105                 110

Gln Lys Gly Pro Leu Trp Asp Glu Val Ser Arg Ile Met Ser Glu Glu
        115                 120                 125

His Gly Tyr Thr Arg Ser Gly Lys Lys Cys Arg Glu Lys Phe Glu Asn
    130                 135                 140

Leu Tyr Lys Tyr Tyr Lys Lys Thr Lys Glu Gly Lys Ser Gly Arg Arg
145                 150                 155                 160

Gln Asp Gly Lys Asn Tyr Arg Phe Phe Arg Gln Leu Glu Ala Ile Tyr
                165                 170                 175

Gly Glu Ser Lys Asp Ser Val Ser Cys Tyr Asn Asn Thr Gln Phe Ile
            180                 185                 190

Met Thr Asn Ala Leu His Ser Asn Phe Arg Ala Ser Asn Ile His Asn
        195                 200                 205

Ile Val Pro His His Gln Asn Pro Leu Met Thr Asn Thr Asn Thr Gln
    210                 215                 220

Ser Gln Ser Leu Ser Ile Ser Asn Asn Phe Asn Ser Ser Ser Asp Leu
225                 230                 235                 240

Asp Leu Thr Ser Ser Ser Glu Gly Asn Glu Thr Thr Lys Arg Glu Gly
                245                 250                 255

Met His Trp Lys Glu Lys Ile Lys Glu Phe Ile Gly Val His Met Glu
            260                 265                 270

Arg Leu Ile Glu Lys Gln Asp Phe Trp Leu Glu Lys Leu Met Lys Ile
        275                 280                 285

Val Glu Asp Lys Glu His Gln Arg Met Leu Arg Glu Glu Trp Arg
    290                 295                 300

Arg Ile Glu Ala Glu Arg Ile Asp Lys Glu Arg Ser Phe Trp Thr Lys
305                 310                 315                 320

Glu Arg Glu Arg Ile Glu Ala Arg Asp Val Ala Val Ile Asn Ala Leu
                325                 330                 335

Gln Tyr Leu Thr Gly Arg Ala Leu Ile Arg Pro Asp Ser Ser Ser Pro
            340                 345                 350

Thr Glu Arg Ile Asn Gly Asn Gly Ser Asp Lys Met Met Ala Asp Asn
        355                 360                 365
```

```
Glu Phe Ala Asp Glu Gly Asn Lys Gly Lys Met Asp Lys Lys Gln Met
            370                 375                 380
Asn Lys Lys Arg Lys Glu Lys Trp Ser Ser His Gly Gly Asn His Pro
385                 390                 395                 400
Arg Thr Lys Glu Asn Met Met Ile Tyr Asn Asn Gln Glu Thr Lys Ile
            405                 410                 415
Asn Asp Phe Cys Arg Asp Asp Gln Cys His His Glu Gly Tyr Ser
            420                 425                 430
Pro Ser Asn Ser Lys Asn Ala Gly Thr Pro Ser Cys Ser Asn Ala Met
            435                 440                 445
Ala Ala Ser Thr Lys Cys Phe Pro Leu Leu Glu Gly Glu Gly Asp Gln
            450                 455                 460
Asn Leu Trp Glu Gly Tyr Gly Leu Lys Gln Arg Lys Glu Asn Asn His
465                 470                 475                 480
Gln

<210> SEQ ID NO 65
<211> LENGTH: 785
<212> TYPE: DNA
<213> ORGANISM: Arabidopsis thaliana
<220> FEATURE:
<223> OTHER INFORMATION: G47

<400> SEQUENCE: 65
cttcttcttc acatcgatca tcatacaaca acaaaaaatg gattacagag aatccaccgg      60
tgaaagtcag tcaaagtaca aggaatccg tcgtcggaaa tggggcaaat gggtatcaga    120
gattagagtt ccgggaactc gtgaccgtct ctggttaggt tcattctcaa cagcagaagg    180
tgccgccgta gcacacgacg ttgctttctt ctgtttacac caacctgatt ctttagaatc    240
tctcaatttc cctcatttgc ttaatccttc actcgtttcc agaacttctc cgagatctat    300
ccagcaagct gcttctaacg ccggcatggc cattgacgcc ggaatcgtcc acagtaccag    360
cgtgaactct ggatgcggag atacgacgac gtattacgag aatggagctg atcaagtgga    420
gccgttgaat atttcagtgt atgattatct gggcggccac gatcacgttt gatttatctc    480
gacggtcatg atcacgtttg atcttctttt gagtaagatt ttgtaccata atcaaaacag    540
gtgtggtgct aaaatcttac tcaaaacaag attaggtacc acagagaaac aatcaaatgg    600
ttgtgaatat acattataag gttttgatta atgtttgttt cactgattta gtgaagtttg    660
gtccattgta tacaaatcta ttcaagaaac ctagcgcgag atcatgtttc gtgattgaag    720
attgagattt ttaagtattc gtaatatttt tgtaaaatac aaataaaaaa aaaaaaaaa    780 aaaaa                                                              785

<210> SEQ ID NO 66
<211> LENGTH: 144
<212> TYPE: PRT
<213> ORGANISM: Arabidopsis thaliana
<220> FEATURE:
<223> OTHER INFORMATION: G47 polypeptide

<400> SEQUENCE: 66

Met Asp Tyr Arg Glu Ser Thr Gly Glu Ser Gln Ser Lys Tyr Lys Gly
1               5                   10                  15
Ile Arg Arg Arg Lys Trp Gly Lys Trp Val Ser Glu Ile Arg Val Pro
            20                  25                  30
Gly Thr Arg Asp Arg Leu Trp Leu Gly Ser Phe Ser Thr Ala Glu Gly
```

```
                35                  40                  45
Ala Ala Val Ala His Asp Val Ala Phe Phe Cys Leu His Gln Pro Asp
         50                  55                  60

Ser Leu Glu Ser Leu Asn Phe Pro His Leu Leu Asn Pro Ser Leu Val
 65                  70                  75                  80

Ser Arg Thr Ser Pro Arg Ser Ile Gln Gln Ala Ala Ser Asn Ala Gly
                 85                  90                  95

Met Ala Ile Asp Ala Gly Ile Val His Ser Thr Ser Val Asn Ser Gly
            100                 105                 110

Cys Gly Asp Thr Thr Thr Tyr Tyr Glu Asn Gly Ala Asp Gln Val Glu
        115                 120                 125

Pro Leu Asn Ile Ser Val Tyr Asp Tyr Leu Gly Gly His Asp His Val
    130                 135                 140

<210> SEQ ID NO 67
<211> LENGTH: 657
<212> TYPE: DNA
<213> ORGANISM: Arabidopsis thaliana
<220> FEATURE:
<223> OTHER INFORMATION: G2123

<400> SEQUENCE: 67
atgagaaaag tatgtgagct tgatatagag ctaagtgaag aggaaagaga cctactaaca      60
actggataca agaatgtcat ggaggctaag agagtttcat tgagagtaat atcatccatt    120
gaaaaaatgg aagactcgaa aggaaacgac caaaatgtga aactgataaa aggacaacaa    180
gaaatggtta aatatgagtt tttcaatgtt tgtaatgaca ttttgtctct cattgattct    240
catctcatac catcaactac tactaatgtc gaatcaattg tcctttttaa cagagtgaaa    300
ggagattatt ttcgatatat ggcagagttt ggttctgatg ctgaacgtaa agaaaatgca    360
gataattctc tagatgcata taaggttgca atggaaatgg cagagaatag ttttagcaccc    420 accaatatgg ttagacttgg attggcttta aatttctcga tattcaatta tgagatccat    480
aaatctattg aaagcgcatg taaattggtt aagaaagctt acgatgaagc aatcactgaa    540
ctcgatggcc ttgacaagaa tatatgcgaa gagagcatgt atatcataga gatgcttaaa    600
tacaatcttt ctacgtggac ttcaggcgat ggtaatggta ataagacaga cggttag      657

<210> SEQ ID NO 68
<211> LENGTH: 218
<212> TYPE: PRT
<213> ORGANISM: Arabidopsis thaliana
<220> FEATURE:
<223> OTHER INFORMATION: G2123 polypeptide

<400> SEQUENCE: 68

Met Arg Lys Val Cys Glu Leu Asp Ile Glu Leu Ser Glu Glu Glu Arg
 1               5                  10                  15

Asp Leu Leu Thr Thr Gly Tyr Lys Asn Val Met Glu Ala Lys Arg Val
             20                  25                  30

Ser Leu Arg Val Ile Ser Ser Ile Glu Lys Met Glu Asp Ser Lys Gly
         35                  40                  45

Asn Asp Gln Asn Val Lys Leu Ile Lys Gly Gln Gln Glu Met Val Lys
     50                  55                  60

Tyr Glu Phe Phe Asn Val Cys Asn Asp Ile Leu Ser Leu Ile Asp Ser
 65                  70                  75                  80

His Leu Ile Pro Ser Thr Thr Asn Val Glu Ser Ile Val Leu Phe
             85                  90                  95
```

Asn Arg Val Lys Gly Asp Tyr Phe Arg Tyr Met Ala Glu Phe Gly Ser
                100                 105                 110

Asp Ala Glu Arg Lys Glu Asn Ala Asp Asn Ser Leu Asp Ala Tyr Lys
            115                 120                 125

Val Ala Met Glu Met Ala Glu Asn Ser Leu Ala Pro Thr Asn Met Val
        130                 135                 140

Arg Leu Gly Leu Ala Leu Asn Phe Ser Ile Phe Asn Tyr Glu Ile His
145                 150                 155                 160

Lys Ser Ile Glu Ser Ala Cys Lys Leu Val Lys Ala Tyr Asp Glu
                165                 170                 175

Ala Ile Thr Glu Leu Asp Gly Leu Asp Lys Asn Ile Cys Glu Glu Ser
            180                 185                 190

Met Tyr Ile Ile Glu Met Leu Lys Tyr Asn Leu Ser Thr Trp Thr Ser
        195                 200                 205

Gly Asp Gly Asn Gly Asn Lys Thr Asp Gly
    210                 215

<210> SEQ ID NO 69
<211> LENGTH: 859
<212> TYPE: DNA
<213> ORGANISM: Arabidopsis thaliana
<220> FEATURE:
<223> OTHER INFORMATION: G1266

<400> SEQUENCE: 69
caatccacta acgatccota accgaaaaca gagtagtcaa gaaacagagt attttttcta      60
catggatcca tttttaattc agtccccatt ctccggcttc tcaccggaat attctatcgg     120
atcttctcca gattctttct catcctcttc ttctaacaat tactctcttc ccttcaacga     180
gaacgactca gaggaaatgt ttctctacgg tctaatcgag cagtccacgc aacaaaccta     240
tattgactcg gatagtcaag accttccgat caaatccgta agctcaagaa agtcagagaa     300
gtcttacaga ggcgtaagac gacggccatg ggggaaattc gcggcggaga taagagattc     360
gactagaaac ggtattaggg tttggctcgg acgttcgaa agcgcggaag aggcggcttt      420
agcctacgat caagctgctt tctcgatgag agggtcctcg gcgattctca ttttttcggc     480
ggagagagtt caagagtcgc tttcggagat taaatatacc tacgaggatg ttgttctcc      540 ggttgtggcg ttgaagagga acactcgat gagacggaga atgaccaata agaagacgaa      600
agatagtgac tttgatcacc gctccgtgaa gttagataat gtagttgtct ttgaggattt     660
gggagaacag taccttgagg agcttttggg gtcttctgaa aatagtggga cttggtgaaa     720
gattaggatt tgtattaggg accttaagtt tgaagtggtt gattaatttt aaccctaata     780
tgttttttgt ttgcttaaat atttgattct attgagaaac atcgaaaaca gtttgtatgt     840
acttttgtga tacttggcg                                                 859

<210> SEQ ID NO 70
<211> LENGTH: 218
<212> TYPE: PRT
<213> ORGANISM: Arabidopsis thaliana
<220> FEATURE:
<223> OTHER INFORMATION: G1266 polypeptide

<400> SEQUENCE: 70

Met Asp Pro Phe Leu Ile Gln Ser Pro Phe Ser Gly Phe Ser Pro Glu
1               5                   10                  15

Tyr Ser Ile Gly Ser Ser Pro Asp Ser Phe Ser Ser Ser Ser Ser Asn

```
                    20                  25                  30
Asn Tyr Ser Leu Pro Phe Asn Glu Asn Asp Ser Glu Glu Met Phe Leu
         35                  40                  45

Tyr Gly Leu Ile Glu Gln Ser Thr Gln Thr Tyr Ile Asp Ser Asp
 50                  55                  60

Ser Gln Asp Leu Pro Ile Lys Ser Val Ser Arg Lys Ser Glu Lys
 65                  70                  75                  80

Ser Tyr Arg Gly Val Arg Arg Pro Trp Gly Lys Phe Ala Ala Glu
                 85                  90                  95

Ile Arg Asp Ser Thr Arg Asn Gly Ile Arg Val Trp Leu Gly Thr Phe
             100                 105                 110

Glu Ser Ala Glu Glu Ala Ala Leu Ala Tyr Asp Gln Ala Ala Phe Ser
         115                 120                 125

Met Arg Gly Ser Ser Ala Ile Leu Asn Phe Ser Ala Glu Arg Val Gln
         130                 135                 140

Glu Ser Leu Ser Glu Ile Lys Tyr Thr Tyr Glu Asp Gly Cys Ser Pro
145                 150                 155                 160

Val Val Ala Leu Lys Arg Lys His Ser Met Arg Arg Met Thr Asn
                 165                 170                 175

Lys Lys Thr Lys Asp Ser Asp Phe Asp His Arg Ser Val Lys Leu Asp
             180                 185                 190

Asn Val Val Phe Glu Asp Leu Gly Glu Gln Tyr Leu Glu Glu Leu
                 195                 200                 205

Leu Gly Ser Ser Glu Asn Ser Gly Thr Trp
    210                 215

<210> SEQ ID NO 71
<211> LENGTH: 1630
<212> TYPE: DNA
<213> ORGANISM: Arabidopsis thaliana
<220> FEATURE:
<223> OTHER INFORMATION: G1337

<400> SEQUENCE: 71
aatggatttg tcatcattct tctcaccgtc cttagtctct gaaataaat  tctgattttg      60
atttcgaatt ttagggattt tgagagagag tcagttatga gtagttcgga gagagtaccg     120
tgcgatttct gcggcgagcg tacggcggtt ttgttttgta gagccgatac ggcgaagctg     180
tgtttgcctt gtgatcagca agttcacacg gcgaatctgt tgtcgaggaa gcacgtgcga     240
tctcagatct gcgataattg cggtaacgag ccagtctctg ttcggtgttt caccgataat     300
ctgattttgt gtcaggagtg tgattgggat gttcacggaa gttgttcagt ttccgatgct     360
catgttcgat ccgccgtgga aggttttcc ggttgtccat cggcgttgga gcttgctgct      420
ttatggggac ttgatttgga gcaagggagg aaagatgaag agaatcaagt tccgatgatg     480
gcgatgatga tggataattt cgggatgcag ttggattctt gggttttggg atctaatgaa     540
ttgattgttc ccagcgatac gacgtttaag aagcgtggat cttgtggatc tagttgtggg     600
aggtataagc aggtattgtg taagcagctt gaggagttgc ttaagagtgg tgttgtcggt     660
ggtgatggcg atgatggtga tcgtgaccgt gattgtgacc gtgagggtgc ttgtgatgga     720
gatggagatg gagaagcagg agagggctt  atggttccgg agatgtcaga gagattgaaa     780
tggtcaagag atgttgagga gatcaatggt ggcggaggag gaggagttaa ccagcagtgg     840
aatgctacta ctactaatcc tagtggtggc cagagttctc agatatggga ttttaacttg     900
ggacagtcac ggggacctga ggatacgagt cgagtggaag ctgcatatgt agggaaaggt     960
```

-continued

```
gctgcttctt cattcacaat caacaatttt gttgaccata tgaatgaaac ttgttccact    1020
aatgtgaaag gtgtcaaaga gattaaaaag gatgactaca agcgatcaac ttcaggccag    1080
gtacaaccaa caaatctgaa gcaacaat cgtccaatta cctttggctc tgagaaggt     1140 tcgaactcct ccagtgactt gcatttcaca gagcatattg ctggaactag ttgtaagacc    1200
acaagactag ttgcaactaa ggctgatctg gagcggctgg ctcagaacag aggagatgca    1260
atgcagcgtt acaaggaaaa gaggaagaca cggagatatg ataagaccat aaggtatgaa    1320
tcgaggaagg caagagctga cactaggttg cgtgtcagag gcagatttgt gaaagctagt    1380
gaagctcctt acccttaacc ttaagttttt tcacataggc ttccttttag ctacaaactt    1440
agttactttt tttactccac tgcctcataa atgtacagac cggtctcgtt tcatctggcc    1500
gcccttcttg ttttattgcc ttatctggcc cttttatgta ccttggaatc ttatctagtt    1560 taaaaagat tgtaaccttc tagaaaacca tattctgttg acagtatata catgtctatc    1620
caagcaaaaa                                                          1630
```

<210> SEQ ID NO 72
<211> LENGTH: 433
<212> TYPE: PRT
<213> ORGANISM: Arabidopsis thaliana
<220> FEATURE:
<223> OTHER INFORMATION: G1337 polypeptide

<400> SEQUENCE: 72

```
Met Ser Ser Ser Glu Arg Val Pro Cys Asp Phe Cys Gly Glu Arg Thr
1               5                   10                  15

Ala Val Leu Phe Cys Arg Ala Asp Thr Ala Lys Leu Cys Leu Pro Cys
            20                  25                  30

Asp Gln Gln Val His Thr Ala Asn Leu Leu Ser Arg Lys His Val Arg
        35                  40                  45

Ser Gln Ile Cys Asp Asn Cys Gly Asn Glu Pro Val Ser Val Arg Cys
    50                  55                  60

Phe Thr Asp Asn Leu Ile Leu Cys Gln Glu Cys Asp Trp Asp Val His
65                  70                  75                  80

Gly Ser Cys Ser Val Ser Asp Ala His Val Arg Ser Ala Val Glu Gly
                85                  90                  95

Phe Ser Gly Cys Pro Ser Ala Leu Glu Leu Ala Ala Leu Trp Gly Leu
            100                 105                 110

Asp Leu Glu Gln Gly Arg Lys Asp Glu Glu Asn Gln Val Pro Met Met
        115                 120                 125

Ala Met Met Met Asp Asn Phe Gly Met Gln Leu Asp Ser Trp Val Leu
    130                 135                 140

Gly Ser Asn Glu Leu Ile Val Pro Ser Asp Thr Thr Phe Lys Lys Arg
145                 150                 155                 160

Gly Ser Cys Gly Ser Cys Gly Arg Tyr Lys Gln Val Leu Cys Lys
                165                 170                 175

Gln Leu Glu Glu Leu Leu Lys Ser Gly Val Val Gly Gly Asp Gly Asp
            180                 185                 190

Asp Gly Asp Arg Asp Arg Asp Cys Asp Arg Glu Gly Ala Cys Asp Gly
        195                 200                 205

Asp Gly Asp Gly Glu Ala Gly Glu Gly Leu Met Val Pro Glu Met Ser
    210                 215                 220

Glu Arg Leu Lys Trp Ser Arg Asp Val Glu Glu Ile Asn Gly Gly Gly
225                 230                 235                 240
```

Gly Gly Gly Val Asn Gln Gln Trp Asn Ala Thr Thr Asn Pro Ser
            245                 250                 255

Gly Gly Gln Ser Ser Gln Ile Trp Asp Phe Asn Leu Gly Gln Ser Arg
        260                 265                 270

Gly Pro Glu Asp Thr Ser Arg Val Glu Ala Ala Tyr Val Gly Lys Gly
    275                 280                 285

Ala Ala Ser Ser Phe Thr Ile Asn Asn Phe Val Asp His Met Asn Glu
    290                 295                 300

Thr Cys Ser Thr Asn Val Lys Gly Val Lys Glu Ile Lys Lys Asp Asp
305                 310                 315                 320

Tyr Lys Arg Ser Thr Ser Gly Gln Val Gln Pro Thr Lys Ser Glu Ser
                325                 330                 335

Asn Asn Arg Pro Ile Thr Phe Gly Ser Glu Lys Gly Ser Asn Ser Ser
            340                 345                 350

Ser Asp Leu His Phe Thr Glu His Ile Ala Gly Thr Ser Cys Lys Thr
        355                 360                 365

Thr Arg Leu Val Ala Thr Lys Ala Asp Leu Glu Arg Leu Ala Gln Asn
    370                 375                 380

Arg Gly Asp Ala Met Gln Arg Tyr Lys Glu Lys Arg Lys Thr Arg Arg
385                 390                 395                 400

Tyr Asp Lys Thr Ile Arg Tyr Glu Ser Arg Lys Ala Arg Ala Asp Thr
                405                 410                 415

Arg Leu Arg Val Arg Gly Arg Phe Val Lys Ala Ser Glu Ala Pro Tyr
            420                 425                 430

Pro

<210> SEQ ID NO 73
<211> LENGTH: 1674
<212> TYPE: DNA
<213> ORGANISM: Arabidopsis thaliana
<220> FEATURE:
<223> OTHER INFORMATION: G1399

<400> SEQUENCE: 73
aggtcgaatt ttctgaaatt aagattcatt cctccatgga agaagctctg ttttattct      60
ctttagctta gcttagcttc tactgatctg tttttgctac aaaatcccat cttttcttt    120
aaaactcttt atctctgaat cttgagtttc ttgtagaaga agaagcaatt ttgaatcttt    180
cgtaatcata aagattcgtg gaggatctct actgatttgt cggaatctct cactacagaa    240
tcacttgatc ttatgtccgg atggaggaga gagaaggaac caacatcaac aacaacatca    300
ctagcagttt cggcttgaag cagcaacatg aagctgctgc ttctgatggt ggttactcaa    360
tggacccacc accaagaccc gaaaaccta cccgttttt agtcccaccc actactgtcc      420
ccgcggccgc caccgtagca gcagctgtta ctgagaatgc ggctactccg tttagcttaa    480
caatgccgac ggagaacact tcagctgagc agctgaaaaa gagagaggt aggccgagaa     540
agtataatcc cgatgggact cttgtcgtga ctttatcgcc gatgccaatc tcgtcctctg    600
ttccgttgac gtcggagttt cctccaagga acgaggaag aggacgtggc aagtctaatc      660
gatggctcaa gaagtctcaa atgttccaat tcgatagaag tcctgttgat accaatttgg    720
caggtgtagg aactgctgat tttgttggtg ccaactttac acctcatgta ctgatcgtca    780
acgccggaga ggatgtgacg atgaagataa tgacattctc tcaacaagga gtctcgtgcta   840
tctgcatcct ttcagctaat ggtcccatct ccaatgttac gcttcgtcaa tctatgacat    900

-continued

```
ccggtggtac tctaacttat gagggtcgtt ttgagattct ctctttgacg ggttcgttta      960
tgcaaaatga ctctggagga actcgaagta gagctggtgg tatgagtgtt tgccttgcag     1020
gaccagatgg tcgtgtcttt ggtggaggac tcgctggtct ctttcttgct gctggtcctg     1080
tccaggtaat ggtagggact tttatagctg gtcaagagca gtcacagctg gagctagcaa     1140
aagaaagacg gctaagattt ggggctcaac catcttctat ctcctttaac atatccgcag     1200
aagaacggaa ggcgagattc gagaggctta acaagtctgt tgctattcct gcaccaacca     1260
cttcatacac gcatgtaaac acaacaaatg cggttcacag ttactataca aactcggtta     1320
accatgtcaa ggatcccttc tcgtctatcc cagtaggagg aggaggaggt ggagaggtag     1380
gagaagaaga gggtgaagaa gatgatgatg aattagaagg tgaagacgaa gaattcggag     1440
gcgatagcca atctgacaac gagattccga gctgatgatg atcataccggt ttcttttcgc     1500 ggatttgtta ggtttgatgg atttcagatt ttggttgatt gttttttatta acacagaatg     1560 tttagaagct gctatcttta ggttcccatc ctcttgtgat tgttgagtat ccttgttaga     1620
aacaaactta ctgttgcaaa actctcttca aaaagtttc actttgcttt ccca            1674
```

<210> SEQ ID NO 74
<211> LENGTH: 404
<212> TYPE: PRT
<213> ORGANISM: Arabidopsis thaliana
<220> FEATURE:
<223> OTHER INFORMATION: G1399 polypeptide

<400> SEQUENCE: 74

```
Met Glu Glu Arg Glu Gly Thr Asn Ile Asn Asn Ile Thr Ser Ser
1               5                   10                  15

Phe Gly Leu Lys Gln Gln His Glu Ala Ala Ser Asp Gly Gly Tyr
            20                  25                  30

Ser Met Asp Pro Pro Arg Pro Glu Asn Pro Asn Pro Phe Leu Val
        35                  40                  45

Pro Pro Thr Thr Val Pro Ala Ala Thr Val Ala Ala Ala Val Thr
    50                  55                  60

Glu Asn Ala Ala Thr Pro Phe Ser Leu Thr Met Pro Thr Glu Asn Thr
65                  70                  75                  80

Ser Ala Glu Gln Leu Lys Lys Lys Arg Gly Arg Pro Arg Lys Tyr Asn
                85                  90                  95

Pro Asp Gly Thr Leu Val Val Thr Leu Ser Pro Met Pro Ile Ser Ser
            100                 105                 110

Ser Val Pro Leu Thr Ser Glu Phe Pro Pro Arg Lys Arg Gly Arg Gly
        115                 120                 125

Arg Gly Lys Ser Asn Arg Trp Leu Lys Lys Ser Gln Met Phe Gln Phe
    130                 135                 140

Asp Arg Ser Pro Val Asp Thr Asn Leu Ala Gly Val Gly Thr Ala Asp
145                 150                 155                 160

Phe Val Gly Ala Asn Phe Thr Pro His Val Leu Ile Val Asn Ala Gly
                165                 170                 175

Glu Asp Val Thr Met Lys Ile Met Thr Phe Ser Gln Gln Gly Ser Arg
            180                 185                 190

Ala Ile Cys Ile Leu Ser Ala Asn Gly Pro Ile Ser Asn Val Thr Leu
        195                 200                 205

Arg Gln Ser Met Thr Ser Gly Gly Thr Leu Thr Tyr Glu Gly Arg Phe
    210                 215                 220

Glu Ile Leu Ser Leu Thr Gly Ser Phe Met Gln Asn Asp Ser Gly Gly
```

```
              225                 230                 235                 240
Thr Arg Ser Arg Ala Gly Gly Met Ser Val Cys Leu Ala Gly Pro Asp
                    245                 250                 255
Gly Arg Val Phe Gly Gly Gly Leu Ala Gly Leu Phe Leu Ala Ala Gly
                260                 265                 270
Pro Val Gln Val Met Val Gly Thr Phe Ile Ala Gly Gln Glu Gln Ser
            275                 280                 285
Gln Leu Glu Leu Ala Lys Glu Arg Arg Leu Arg Phe Gly Ala Gln Pro
        290                 295                 300
Ser Ser Ile Ser Phe Asn Ile Ser Ala Glu Glu Arg Lys Ala Arg Phe
305                 310                 315                 320
Glu Arg Leu Asn Lys Ser Val Ala Ile Pro Ala Pro Thr Thr Ser Tyr
                325                 330                 335
Thr His Val Asn Thr Thr Asn Ala Val His Ser Tyr Tyr Thr Asn Ser
                340                 345                 350
Val Asn His Val Lys Asp Pro Phe Ser Ser Ile Pro Val Gly Gly Gly
                355                 360                 365
Gly Gly Gly Glu Val Gly Glu Glu Gly Glu Glu Asp Asp Asp Glu
370                 375                 380
Leu Glu Gly Glu Asp Glu Glu Phe Gly Gly Asp Ser Gln Ser Asp Asn
385                 390                 395                 400
Glu Ile Pro Ser

<210> SEQ ID NO 75
<211> LENGTH: 1066
<212> TYPE: DNA
<213> ORGANISM: Arabidopsis thaliana
<220> FEATURE:
<223> OTHER INFORMATION: G1465

<400> SEQUENCE: 75
ctcattcttg cgtttgatct ttctttctct agatcccata tttttcttga tcaatttagt      60
ttcattatgg aggaagatgc agcttttgat ctactcaaag ccgaactctt aaacgcagaa     120
gacgatgcaa taatctcacg ttatctgaag cgtatggtcg tcaacggaga ctcatggcct     180
gatcacttca tcgaagacgc agacgtgttc aacaagaatc aaatgtggag gttcgatgct     240
gagagcccta gcttcgtgat agttaaacct cgaacagagg cttgtggtaa aaccgatgga     300
tgtgaaactg gttgctggag gatcatgggt cgtgataaac cgataaaatc gacggagact     360
gtgaagattc aagggttcaa gaagattctc aagttctgcc taaagaggaa acctagagga     420
tacaagagaa gttgggtaat ggaagagtat aggcttacca ataacttgaa ctggaagcaa     480
gatcatgtga tttgcaagat tcggtttatg tttgaagctg aaatcagttt cttgctagcc     540
aagcatttct acactacatc agaatcactt cctcgaaatg agctgttgcc agcttacgga     600
ttcctttcat cagataagca attggaggat gtatcttatc cggtgacgat aatgacttct     660
gaaggaaacg attggcctag ctacgttacc aacaatgtgt attgtctgca tccattggag     720
ctcgttgatc ttcaagatcg gatgtttaat gattacggaa cctgcatctt cgctaacaag     780
acttgtggta aaaccgatag atgcattaat ggtggttact ggaaaatttt gcaccgtgat     840
aggctgatca gtcaaagtc cgggatagtt attggtttca agaaggtgtt taagtttcat     900
gaaacggaga agaaagata cttctgtggt ggagaagatg tgaaggtaac ttggactcta     960
gaagagtata ggcttagcgt gaagcagaat aaattcttgt gcgttatcaa gtttacttat    1020
gataactaag aatctttttct ttggatttta tgatcatctt agtatc                  1066
```

<210> SEQ ID NO 76
<211> LENGTH: 320
<212> TYPE: PRT
<213> ORGANISM: Arabidopsis thaliana
<220> FEATURE:
<223> OTHER INFORMATION: G1465 polypeptide

<400> SEQUENCE: 76

```
Met Glu Glu Asp Ala Ala Phe Asp Leu Leu Lys Ala Glu Leu Leu Asn
1               5                   10                  15
Ala Glu Asp Asp Ala Ile Ile Ser Arg Tyr Leu Lys Arg Met Val Val
            20                  25                  30
Asn Gly Asp Ser Trp Pro Asp His Phe Ile Glu Asp Ala Asp Val Phe
        35                  40                  45
Asn Lys Asn Pro Asn Val Glu Phe Asp Ala Glu Ser Pro Ser Phe Val
    50                  55                  60
Ile Val Lys Pro Arg Thr Glu Ala Cys Gly Lys Thr Asp Gly Cys Glu
65                  70                  75                  80
Thr Gly Cys Trp Arg Ile Met Gly Arg Asp Lys Pro Ile Lys Ser Thr
                85                  90                  95
Glu Thr Val Lys Ile Gln Gly Phe Lys Lys Ile Leu Lys Phe Cys Leu
            100                 105                 110
Lys Arg Lys Pro Arg Gly Tyr Lys Arg Ser Trp Val Met Glu Glu Tyr
        115                 120                 125
Arg Leu Thr Asn Asn Leu Asn Trp Lys Gln Asp His Val Ile Cys Lys
    130                 135                 140
Ile Arg Phe Met Phe Glu Ala Glu Ile Ser Phe Leu Leu Ala Lys His
145                 150                 155                 160
Phe Tyr Thr Thr Ser Glu Ser Leu Pro Arg Asn Glu Leu Leu Pro Ala
                165                 170                 175
Tyr Gly Phe Leu Ser Ser Asp Lys Gln Leu Glu Asp Val Ser Tyr Pro
            180                 185                 190
Val Thr Ile Met Thr Ser Glu Gly Asn Asp Trp Pro Ser Tyr Val Thr
        195                 200                 205
Asn Asn Val Tyr Cys Leu His Pro Leu Glu Leu Val Asp Leu Gln Asp
    210                 215                 220
Arg Met Phe Asn Asp Tyr Gly Thr Cys Ile Phe Ala Asn Lys Thr Cys
225                 230                 235                 240
Gly Lys Thr Asp Arg Cys Ile Asn Gly Gly Tyr Trp Lys Ile Leu His
                245                 250                 255
Arg Asp Arg Leu Ile Lys Ser Lys Ser Gly Ile Val Ile Gly Phe Lys
            260                 265                 270
Lys Val Phe Lys Phe His Glu Thr Glu Lys Glu Arg Tyr Phe Cys Gly
        275                 280                 285
Gly Glu Asp Val Lys Val Thr Trp Thr Leu Glu Glu Tyr Arg Leu Ser
    290                 295                 300
Val Lys Gln Asn Lys Phe Leu Cys Val Ile Lys Phe Thr Tyr Asp Asn
305                 310                 315                 320
```

<210> SEQ ID NO 77
<211> LENGTH: 732
<212> TYPE: DNA
<213> ORGANISM: Arabidopsis thaliana
<220> FEATURE:
<223> OTHER INFORMATION: G1512

-continued

<400> SEQUENCE: 77

```
atggaaggga acttcttcat caggtctgat gctcaacgag cacatgacaa tggcttcata      60
gccaaacaaa aacctaatct caccacggct ccaacagcag gtcaagctaa tgaaagtggc     120
tgttttgact gcaacatctg tttagacaca gcccatgatc cggtggtcac tctctgcggg     180
cacctttct gctggccttg catttacaag tggttacatg ttcagttatc ttctgtctcc      240
gttgatcagc accagaacaa ttgccctgtt tgtaaatcca acattactat cacctctttg     300
gttcctctct atggaagagg catgtcttcg ccttcttcca cgtttggctc aagaaacaa      360
gacgcactgt ccactgacat ccccgcagaa cctgctccat cagccttacg caatccgatt     420
acctcagcat catctctgaa cccaagcttg caacatcaaa ctctgtctcc ttcatttcat     480
aatcatcagt attcccctcg tggcttcacc acaaccgaat caaccgacct tgccaatgct     540
gtaatgatga gtttcctcta ccctgtgatt ggaatgtttg gagacctggt ctacaccagg     600
atattcggga ccttcacaaa cacaatagct cagccttacc aaagccagag gatgatgcag     660
cgtgagaagt ctcttaatcg ggtatcgata ttcttccttt gttgcatcat cctttgcctc     720
cttctcttct ag                                                         732
```

<210> SEQ ID NO 78
<211> LENGTH: 243
<212> TYPE: PRT
<213> ORGANISM: Arabidopsis thaliana
<220> FEATURE:
<223> OTHER INFORMATION: G1512 polypeptide

<400> SEQUENCE: 78

```
Met Glu Gly Asn Phe Phe Ile Arg Ser Asp Ala Gln Arg Ala His Asp
  1               5                  10                  15

Asn Gly Phe Ile Ala Lys Gln Lys Pro Asn Leu Thr Thr Ala Pro Thr
                 20                  25                  30

Ala Gly Gln Ala Asn Glu Ser Gly Cys Phe Asp Cys Asn Ile Cys Leu
             35                  40                  45

Asp Thr Ala His Asp Pro Val Val Thr Leu Cys Gly His Leu Phe Cys
         50                  55                  60

Trp Pro Cys Ile Tyr Lys Trp Leu His Val Gln Leu Ser Ser Val Ser
 65                  70                  75                  80

Val Asp Gln His Gln Asn Asn Cys Pro Val Cys Lys Ser Asn Ile Thr
                 85                  90                  95

Ile Thr Ser Leu Val Pro Leu Tyr Gly Arg Gly Met Ser Ser Pro Ser
            100                 105                 110

Ser Thr Phe Gly Ser Lys Lys Gln Asp Ala Leu Ser Thr Asp Ile Pro
        115                 120                 125

Arg Arg Pro Ala Pro Ser Ala Leu Arg Asn Pro Ile Thr Ser Ala Ser
    130                 135                 140

Ser Leu Asn Pro Ser Leu Gln His Gln Thr Leu Ser Pro Ser Phe His
145                 150                 155                 160

Asn His Gln Tyr Ser Pro Arg Gly Phe Thr Thr Thr Glu Ser Thr Asp
                165                 170                 175

Leu Ala Asn Ala Val Met Met Ser Phe Leu Tyr Pro Val Ile Gly Met
            180                 185                 190

Phe Gly Asp Leu Val Tyr Thr Arg Ile Phe Gly Thr Phe Thr Asn Thr
        195                 200                 205

Ile Ala Gln Pro Tyr Gln Ser Gln Arg Met Met Gln Arg Glu Lys Ser
    210                 215                 220
```

Leu Asn Arg Val Ser Ile Phe Phe Leu Cys Cys Ile Ile Leu Cys Leu
225                 230                 235                 240

Leu Leu Phe

<210> SEQ ID NO 79
<211> LENGTH: 783
<212> TYPE: DNA
<213> ORGANISM: Arabidopsis thaliana
<220> FEATURE:
<223> OTHER INFORMATION: G1537

<400> SEQUENCE: 79

| | | |
|---|---|---|
| atggaaaacg aagtaaacgc aggaacagca agcagttcaa gatggaaccc aacgaaagat | 60 |
| cagatcacgc tactggaaaa tctttacaag gaaggaatac gaactccgag cgccgatcag | 120 |
| attcagcaga tcaccggtag gcttcgtgcg tacggccata tcgaaggtaa aaacgtcttt | 180 |
| tactggttcc agaaccataa ggctaggcaa cgccaaaagc agaaacagga gcgcatggct | 240 |
| tacttcaatc gcctcctcca caaaacctcc cgtttcttct accccccctcc ttgctcaaac | 300 |
| gtgggttgtg tcagtccgta ctatttacag caagcaagtg atcatcatat gaatcaacat | 360 |
| ggaagtgtat acacaaacga tcttcttcac agaaacaatg tgatgattcc aagtggtggc | 420 |
| tacgagaaac ggacagtcac acaacatcag aaacaacttt cagacataag aacaacagca | 480 |
| gccacaagaa tgccaatttc tccgagttca ctcagatttg acagatttgc cctccgtgat | 540 |
| aactgttatg ccggtgagga cattaacgtc aattccagtg gacggaaaac actccctctt | 600 |
| tttcctcttc agcctttgaa tgcaagtaat gctgatggta tgggaagttc cagttttgcc | 660 |
| cttggtagtg attctccggt ggattgttct agcgatggag ccggccgaga gcagccgttt | 720 |
| attgatttct tttctggtgg ttctacttct actcgtttcg atagtaatgg taatgggttg | 780 |
| taa | 783 |

<210> SEQ ID NO 80
<211> LENGTH: 260
<212> TYPE: PRT
<213> ORGANISM: Arabidopsis thaliana
<220> FEATURE:
<223> OTHER INFORMATION: G1537 polypeptide

<400> SEQUENCE: 80

Met Glu Asn Glu Val Asn Ala Gly Thr Ala Ser Ser Ser Arg Trp Asn
1               5                   10                  15

Pro Thr Lys Asp Gln Ile Thr Leu Leu Glu Asn Leu Tyr Lys Glu Gly
                20                  25                  30

Ile Arg Thr Pro Ser Ala Asp Gln Ile Gln Gln Ile Thr Gly Arg Leu
            35                  40                  45

Arg Ala Tyr Gly His Ile Glu Gly Lys Asn Val Phe Tyr Trp Phe Gln
        50                  55                  60

Asn His Lys Ala Arg Gln Arg Gln Lys Gln Lys Gln Glu Arg Met Ala
65                  70                  75                  80

Tyr Phe Asn Arg Leu Leu His Lys Thr Ser Arg Phe Phe Tyr Pro Pro
                85                  90                  95

Pro Cys Ser Asn Val Gly Cys Val Ser Pro Tyr Tyr Leu Gln Gln Ala
            100                 105                 110

Ser Asp His His Met Asn Gln His Gly Ser Val Tyr Thr Asn Asp Leu
        115                 120                 125

Leu His Arg Asn Asn Val Met Ile Pro Ser Gly Gly Tyr Glu Lys Arg

```
                 130                 135                 140
Thr Val Thr Gln His Gln Lys Gln Leu Ser Asp Ile Arg Thr Thr Ala
145                 150                 155                 160

Ala Thr Arg Met Pro Ile Ser Pro Ser Ser Leu Arg Phe Asp Arg Phe
                165                 170                 175

Ala Leu Arg Asp Asn Cys Tyr Ala Gly Glu Asp Ile Asn Val Asn Ser
            180                 185                 190

Ser Gly Arg Lys Thr Leu Pro Leu Phe Pro Leu Gln Pro Leu Asn Ala
        195                 200                 205

Ser Asn Ala Asp Gly Met Gly Ser Ser Ser Phe Ala Leu Gly Ser Asp
    210                 215                 220

Ser Pro Val Asp Cys Ser Ser Asp Gly Ala Gly Arg Glu Gln Pro Phe
225                 230                 235                 240

Ile Asp Phe Phe Ser Gly Gly Ser Thr Ser Thr Arg Phe Asp Ser Asn
                245                 250                 255

Gly Asn Gly Leu
            260

<210> SEQ ID NO 81
<211> LENGTH: 739
<212> TYPE: DNA
<213> ORGANISM: Arabidopsis thaliana
<220> FEATURE:
<223> OTHER INFORMATION: G2136

<400> SEQUENCE: 81
acaaaaatct cttgttcttc ttgtcttcaa tatggaggat ggggaagctt caacaatcac    60
tttcttacca accacggaac caaaacccct acaaaaccct aacttgctgg ccaaaccaaa   120
aaaagagact aaacaaaaaa aacctaaaac caccaaaggt cgacagaaga tagagatcaa   180
ggagatcatg ctggagaccc gaaggcaagt gacgttttcc aaacgacgat ccgggctttt   240
caaaaaagcg gcagaattaa gcgttctctg cggcgcacag attggtatca aacgttttc    300
acgttgcgat aggatctact cgtttggtaa cgtgaactca ctcatcgata aatacttgcg   360
taaggctccg gtgatgctga ggtcacatcc cggtggtaac gtggcaaacg agagggaaga   420
taacgacggt ttgatgtggt gggagagagc ggtggagagt gtgccggagg agcatatgga   480
agagtacaag aatgccttga gtgtgttaag ggagaatttg ttgacgagga tctaccagat   540
gagtggtgat cggacggttg agaatcttcc ggcatttcca aatgagatgg ctatggctga   600
ctggaaatta acgaatgaaa atctgatggc taggaacgat cgaggttatg gaggtaacaa   660
tggtgatttg gagtttgcgt ttatgcctca aaacggtaga cagtgaggtg ttttttcttt   720
aatttattat tacagtttg                                                739

<210> SEQ ID NO 82
<211> LENGTH: 224
<212> TYPE: PRT
<213> ORGANISM: Arabidopsis thaliana
<220> FEATURE:
<223> OTHER INFORMATION: G2136 polypeptide

<400> SEQUENCE: 82

Met Glu Asp Gly Glu Ala Ser Thr Ile Thr Phe Leu Pro Thr Thr Glu
1               5                   10                  15

Pro Lys Pro Leu Gln Asn Pro Asn Leu Leu Ala Lys Pro Lys Lys Glu
            20                  25                  30

Thr Lys Gln Lys Lys Pro Lys Thr Thr Lys Gly Arg Gln Lys Ile Glu
```

-continued

```
                35                  40                  45
Ile Lys Glu Ile Met Leu Glu Thr Arg Arg Gln Val Thr Phe Ser Lys
         50                  55                  60
Arg Arg Ser Gly Leu Phe Lys Lys Ala Ala Glu Leu Ser Val Leu Cys
 65                  70                  75                  80
Gly Ala Gln Ile Gly Ile Ile Thr Phe Ser Arg Cys Asp Arg Ile Tyr
                 85                  90                  95
Ser Phe Gly Asn Val Asn Ser Leu Ile Asp Lys Tyr Leu Arg Lys Ala
                100                 105                 110
Pro Val Met Leu Arg Ser His Pro Gly Gly Asn Val Ala Asn Gly Glu
            115                 120                 125
Glu Asp Asn Asp Gly Leu Met Trp Trp Glu Arg Ala Val Glu Ser Val
130                 135                 140
Pro Glu Glu His Met Glu Glu Tyr Lys Asn Ala Leu Ser Val Leu Arg
145                 150                 155                 160
Glu Asn Leu Leu Thr Arg Ile Tyr Gln Met Ser Gly Asp Arg Thr Val
                165                 170                 175
Glu Asn Leu Pro Ala Phe Pro Asn Glu Met Ala Met Ala Asp Trp Lys
            180                 185                 190
Leu Thr Asn Glu Asn Leu Met Ala Arg Asn Asp Arg Gly Tyr Gly Gly
        195                 200                 205
Asn Asn Gly Asp Leu Glu Phe Ala Phe Met Pro Gln Asn Gly Arg Gln
        210                 215                 220

<210> SEQ ID NO 83
<211> LENGTH: 1366
<212> TYPE: DNA
<213> ORGANISM: Arabidopsis thaliana
<220> FEATURE:
<223> OTHER INFORMATION: G2147

<400> SEQUENCE: 83
ctgtgattgt caagagtttg aacacacaaa gaagaaagaa gaactcaaca tttcaagcaa      60
gaagaaagag agaagagaga aggtccaata atagagagaa caaaaaaaaa gagagcttaa     120
ttgtcagttt attctctgca acgtgcggc  ctaagtaaca catgtcgaat tatggagtta     180
aagagctcac atgggaaaat gggcaactaa ccgttcatgg tctaggcgac gaagtagaac     240
caaccacctc gaataaccct atttggactc aaagtctcaa cggttgtgag actttggagt     300
ctgtggttca tcaagcggct ctacagcagc caagcaagtt tcagctgcag agtccgaatg     360
gtccaaacca caattatgag agcaaggatg gatcttgttc aagaaaacgc ggttatcctc     420
aagaaatgga ccgatggttc gctgttcaag aggagagcca tagagttggc cacagcgtca     480
ctgcaagtgc gagtggtacc aatatgtctt gggcgtcttt tgaatccggt cggagcttga     540
agacagctag aaccggagac agagactatt tccgctctgg atcggaaact caagatactg     600
aaggagatga acaagagaca agaggagaag caggtagatc taatggacga cggggacgag     660
cagcagcgat tcacaacgag tccgaaagga gacggcgtga taggataaac cagaggatga     720
gaacacttca gaagctgctt cctactgcaa gtaaggcgga taaagtctca atcttggatg     780
atgttatcga cacttgaaa  cagctacaag cacaagtaca gttcatgagc ctaagagcca     840
acttgccaca acaaatgatg attccgcaac tacctccacc acagtcagtt ctcagcatcc     900
aacaccaaca acaacaacaa caacagcagc agcagcagca acaacagcag caacagtttc     960
agatgtcgtt gcttgcaaca atggcaagaa tgggaatggg aggtggtgga aatggttatg    1020
```

```
gaggtttagt tcctcctcct cctcctccac caatgatggt ccctcctatg ggtaacagag   1080
actgcaccaa cggttcttca gccacattat ctgatccata cagcgccttt ttcgcacaga   1140
caatgaatat ggatctctac aataaaatgg cagcagctat ctatagacaa cagtctgatc   1200
aaacaacaaa ggtaaatatc ggcatgcctt caagttcttc gaatcatgag aaaagagatt   1260
agtctagcga cctagtatta ttgatccata tatatagttc ttgaaagatt gttgtatcat   1320
gattgtaaaa actgttttga gtatggaaaa agacttgcag ataaaa                 1366
```

<210> SEQ ID NO 84
<211> LENGTH: 366
<212> TYPE: PRT
<213> ORGANISM: Arabidopsis thaliana
<220> FEATURE:
<223> OTHER INFORMATION: G2147 polypeptide

<400> SEQUENCE: 84

```
Met Ser Asn Tyr Gly Val Lys Glu Leu Thr Trp Glu Asn Gly Gln Leu
1               5                   10                  15

Thr Val His Gly Leu Gly Asp Glu Val Glu Pro Thr Thr Ser Asn Asn
            20                  25                  30

Pro Ile Trp Thr Gln Ser Leu Asn Gly Cys Glu Thr Leu Glu Ser Val
        35                  40                  45

Val His Gln Ala Ala Leu Gln Gln Pro Ser Lys Phe Gln Leu Gln Ser
    50                  55                  60

Pro Asn Gly Pro Asn His Asn Tyr Glu Ser Lys Asp Gly Ser Cys Ser
65                  70                  75                  80

Arg Lys Arg Gly Tyr Pro Gln Glu Met Asp Arg Trp Phe Ala Val Gln
                85                  90                  95

Glu Glu Ser His Arg Val Gly His Ser Val Thr Ala Ser Ala Ser Gly
            100                 105                 110

Thr Asn Met Ser Trp Ala Ser Phe Glu Ser Gly Arg Ser Leu Lys Thr
        115                 120                 125

Ala Arg Thr Gly Asp Arg Asp Tyr Phe Arg Ser Gly Ser Glu Thr Gln
    130                 135                 140

Asp Thr Glu Gly Asp Glu Gln Glu Thr Arg Gly Glu Ala Gly Arg Ser
145                 150                 155                 160

Asn Gly Arg Arg Gly Arg Ala Ala Ala Ile His Asn Glu Ser Glu Arg
                165                 170                 175

Arg Arg Arg Asp Arg Ile Asn Gln Arg Met Arg Thr Leu Gln Lys Leu
            180                 185                 190

Leu Pro Thr Ala Ser Lys Ala Asp Lys Val Ser Ile Leu Asp Asp Val
        195                 200                 205

Ile Glu His Leu Lys Gln Leu Gln Ala Gln Val Gln Phe Met Ser Leu
    210                 215                 220

Arg Ala Asn Leu Pro Gln Gln Met Met Ile Pro Gln Leu Pro Pro Pro
225                 230                 235                 240

Gln Ser Val Leu Ser Ile Gln His Gln Gln Gln Gln Gln Gln Gln Gln
                245                 250                 255

Gln Gln Gln Gln Gln Gln Gln Gln Phe Gln Met Ser Leu Leu Ala
            260                 265                 270

Thr Met Ala Arg Met Gly Met Gly Gly Gly Gly Asn Gly Tyr Gly Gly
        275                 280                 285

Leu Val Pro Pro Pro Pro Pro Pro Met Met Val Pro Pro Met Gly
    290                 295                 300
```

Asn Arg Asp Cys Thr Asn Gly Ser Ser Ala Thr Leu Ser Asp Pro Tyr
305                 310                 315                 320

Ser Ala Phe Phe Ala Gln Thr Met Asn Met Asp Leu Tyr Asn Lys Met
            325                 330                 335

Ala Ala Ala Ile Tyr Arg Gln Gln Ser Asp Gln Thr Thr Lys Val Asn
        340                 345                 350

Ile Gly Met Pro Ser Ser Ser Asn His Glu Lys Arg Asp
        355                 360                 365

<210> SEQ ID NO 85
<211> LENGTH: 396
<212> TYPE: DNA
<213> ORGANISM: Arabidopsis thaliana
<220> FEATURE:
<223> OTHER INFORMATION: G377

<400> SEQUENCE: 85
atgggtctct cgcattttcc aacagcgtca gaaggagtac taccacttct ggtgatgaac     60
acggttgttt caatcactct gttgaagaac atggtgaggt ctgttttca aattgttgca    120 tccgagactg aatcttccat ggagatagac gacgagcctg aagatgattt tgttactaga   180
agaatctcga taacacagtt caagtctcta tgtgagaaca tagaagagga agaagaagag   240
aaaggtgtgg agtgttgtgt gtgcctttgt gggtttaaag aggaagagga agtgagtgag   300
ttggtttctt gcaagcattt cttccacaga gcttgtctag acaactggtt tggtaataac   360
cacaccacat gccctctttg caggtccatt ctctag                              396

<210> SEQ ID NO 86
<211> LENGTH: 131
<212> TYPE: PRT
<213> ORGANISM: Arabidopsis thaliana
<220> FEATURE:
<223> OTHER INFORMATION: G377 polypeptide

<400> SEQUENCE: 86

Met Gly Leu Ser His Phe Pro Thr Ala Ser Glu Gly Val Leu Pro Leu
1               5                   10                  15

Leu Val Met Asn Thr Val Val Ser Ile Thr Leu Leu Lys Asn Met Val
            20                  25                  30

Arg Ser Val Phe Gln Ile Val Ala Ser Glu Thr Glu Ser Ser Met Glu
        35                  40                  45

Ile Asp Asp Glu Pro Glu Asp Asp Phe Val Thr Arg Arg Ile Ser Ile
50                  55                  60

Thr Gln Phe Lys Ser Leu Cys Glu Asn Ile Glu Glu Glu Glu Glu Glu
65                  70                  75                  80

Lys Gly Val Glu Cys Cys Val Cys Leu Cys Gly Phe Lys Glu Glu Glu
                85                  90                  95

Glu Val Ser Glu Leu Val Ser Cys Lys His Phe Phe His Arg Ala Cys
            100                 105                 110

Leu Asp Asn Trp Phe Gly Asn Asn His Thr Thr Cys Pro Leu Cys Arg
        115                 120                 125

Ser Ile Leu
    130

<210> SEQ ID NO 87
<211> LENGTH: 1444
<212> TYPE: DNA
<213> ORGANISM: Arabidopsis thaliana
<220> FEATURE:

<223> OTHER INFORMATION: G962

<400> SEQUENCE: 87

```
cgtcgactct ctactcaaca ccactcaatt tcatctctct ttttcccttc cattgttagt      60
ataaaaacca agcaaaccct taatcacttt tcatcatcat atatcacctt aatccacatg     120
catacacata tctagtcttt ttgatatatg gcaattgtat cctccacaac aagcatcatt     180
cccatgagta accaagtcaa caataacgaa aaaggtatag aagacaatga tcatagaggc     240
ggccaagaga gtcatgtcca aaatgaagat gaagctgatg atcatgatca tgacatggtc     300
atgcccggat ttagattcca tcctaccgaa gaagaactca tagagtttta ccttcgccga     360
aaagttgaag gcaaacgctt taatgtagaa ctcatcactt tcctcgatct ttatcgctat     420
gatccttggg aacttcctgc tatggcggcg ataggagaga aagagtggta cttctatgtg     480
ccaagagatc ggaaatatag aaatggagat agaccgaacc gagtaacgac ttcaggatat     540
tggaaagcca ccggagctga taggatgatc agatcggaga cttctcggcc tatcggatta     600
aagaaaaccc tagttttcta ctctggtaaa gcccctaaag gcactcgtac tagttggatc     660
atgaacgagt atcgtcttcc gcaccatgaa accgagaagt accaaaaggc tgaaatatca     720
ttgtgccgag tgtacaaaag gccaggagta gaagatcatc catcggtacc acgttctctc     780
tccacaagac atcataacca taactcatcg acatcatccc gtttagcctt aagcaacaa      840
caacaccatt catcctcctc taatcattcc gacaacaacc ttaacaacaa caacaacatc     900
aacaatctcg agaagctctc caccgaatat tccggcgacg gcagcacaac aacaacgacc     960
acaaacagta actctgacgt taccattgct ctagccaatc aaaacatata tcgtccaatg    1020
ccttacgaca caagcaacaa cacattgata gtctctacga aaatcatca agacgatgat     1080
gaaactgcca ttgttgacga tcttcaaaga ctagttaact accaaatatc agatggaggt    1140
aacatcaatc accaatactt tcaaattgct caacagtttc atcatactca acaacaaaat    1200
gctaacgcaa acgcattaca attggtggct gcggcgacta cagcgacaac gctaatgcct    1260
caaactcaag cggcgttagc tatgaacatg attcctgcag aacgattcc aaacaatgct    1320
ttgtgggata tgtggaatcc aatagtacca gatggaaaca gagatcacta tactaatatt    1380
ccttttaagt aatttaatta gatcatgatt attatccatg acaataatta atgctgcttt    1440
gcgc                                                                 1444
```

<210> SEQ ID NO 88
<211> LENGTH: 414
<212> TYPE: PRT
<213> ORGANISM: Arabidopsis thaliana
<220> FEATURE:
<223> OTHER INFORMATION: G962 polypeptide

<400> SEQUENCE: 88

```
Met Ala Ile Val Ser Ser Thr Thr Ser Ile Ile Pro Met Ser Asn Gln
1               5                   10                  15

Val Asn Asn Asn Glu Lys Gly Ile Glu Asp Asn Asp His Arg Gly Gly
            20                  25                  30

Gln Glu Ser His Val Gln Asn Glu Asp Glu Ala Asp Asp His Asp His
        35                  40                  45

Asp Met Val Met Pro Gly Phe Arg Phe His Pro Thr Glu Glu Glu Leu
    50                  55                  60

Ile Glu Phe Tyr Leu Arg Arg Lys Val Glu Gly Lys Arg Phe Asn Val
65                  70                  75                  80
```

```
Glu Leu Ile Thr Phe Leu Asp Leu Tyr Arg Tyr Asp Pro Trp Glu Leu
                85                  90                  95
Pro Ala Met Ala Ala Ile Gly Glu Lys Glu Trp Tyr Phe Tyr Val Pro
            100                 105                 110
Arg Asp Arg Lys Tyr Arg Asn Gly Asp Arg Pro Asn Arg Val Thr Thr
        115                 120                 125
Ser Gly Tyr Trp Lys Ala Thr Gly Ala Asp Arg Met Ile Arg Ser Glu
    130                 135                 140
Thr Ser Arg Pro Ile Gly Leu Lys Lys Thr Leu Val Phe Tyr Ser Gly
145                 150                 155                 160
Lys Ala Pro Lys Gly Thr Arg Thr Ser Trp Ile Met Asn Glu Tyr Arg
                165                 170                 175
Leu Pro His His Glu Thr Glu Lys Tyr Gln Lys Ala Glu Ile Ser Leu
            180                 185                 190
Cys Arg Val Tyr Lys Arg Pro Gly Val Glu Asp His Pro Ser Val Pro
        195                 200                 205
Arg Ser Leu Ser Thr Arg His His Asn His Asn Ser Ser Thr Ser Ser
    210                 215                 220
Arg Leu Ala Leu Arg Gln Gln His His Ser Ser Ser Ser Asn His
225                 230                 235                 240
Ser Asp Asn Asn Leu Asn Asn Asn Asn Ile Asn Asn Leu Glu Lys
                245                 250                 255
Leu Ser Thr Glu Tyr Ser Gly Asp Gly Ser Thr Thr Thr Thr Thr
            260                 265                 270
Asn Ser Asn Ser Asp Val Thr Ile Ala Leu Ala Asn Gln Asn Ile Tyr
        275                 280                 285
Arg Pro Met Pro Tyr Asp Thr Ser Asn Asn Thr Leu Ile Val Ser Thr
290                 295                 300
Arg Asn His Gln Asp Asp Asp Glu Thr Ala Ile Val Asp Asp Leu Gln
305                 310                 315                 320
Arg Leu Val Asn Tyr Gln Ile Ser Asp Gly Gly Asn Ile Asn His Gln
                325                 330                 335
Tyr Phe Gln Ile Ala Gln Gln Phe His His Thr Gln Gln Gln Asn Ala
            340                 345                 350
Asn Ala Asn Ala Leu Gln Leu Val Ala Ala Thr Thr Ala Thr Thr
        355                 360                 365
Leu Met Pro Gln Thr Gln Ala Ala Leu Ala Met Asn Met Ile Pro Ala
370                 375                 380
Gly Thr Ile Pro Asn Asn Ala Leu Trp Asp Met Trp Asn Pro Ile Val
385                 390                 395                 400
Pro Asp Gly Asn Arg Asp His Tyr Thr Asn Ile Pro Phe Lys
                405                 410
```

<210> SEQ ID NO 89
<211> LENGTH: 768
<212> TYPE: DNA
<213> ORGANISM: Arabidopsis thaliana
<220> FEATURE:
<223> OTHER INFORMATION: G975

<400> SEQUENCE: 89

```
attactcatc atcaagttcc tactttctct ctgacaaaca tcacagagta agtaagaatg      60
gtacagacga agaagttcag aggtgtcagg caacgccatt ggggttcttg ggtcgctgag     120
attcgtcatc ctctcttgaa acggaggatt tggctaggga cgttcgagac cgcagaggag     180
```

```
gcagcaagag catacgacga ggccgccgtt ttaatgagcg gccgcaacgc caaaaccaac    240
tttcccctca acaacaacaa caccggagaa acttccgagg gcaaaaccga tatttcagct    300
tcgtccacaa tgtcatcctc aacatcatct tcatcgctct cttccatcct cagcgccaaa    360
ctgaggaaat gctgcaagtc tccttcccca tccctcacct gcctccgtct tgacacagcc    420
agctcccata tcggcgtctg gcagaaacgg gccggttcaa agtctgactc cagctgggtc    480
atgacggtgg agctaggtcc cgcaagctcc tcccaagaga ctactagtaa agcttcacaa    540
gacgctattc ttgctccgac cactgaagtt gaaattggtg gcagcagaga agaagtattg    600
gatgaggaag aaaaggttgc tttgcaaatg atagaggagc ttctcaatac aaactaaatc    660
ttatttgctt atatatatgt acctattttc attgctgatt tacagccaaa ataatcaatt    720
ataccgtgta ttttatagat gttttatatt aaaaggttgt tagatata                768
```

<210> SEQ ID NO 90
<211> LENGTH: 199
<212> TYPE: PRT
<213> ORGANISM: Arabidopsis thaliana
<220> FEATURE:
<223> OTHER INFORMATION: G975 polypeptide

<400> SEQUENCE: 90

```
Met Val Gln Thr Lys Lys Phe Arg Gly Val Arg Gln Arg His Trp Gly
  1               5                  10                  15

Ser Trp Val Ala Glu Ile Arg His Pro Leu Leu Lys Arg Arg Ile Trp
             20                  25                  30

Leu Gly Thr Phe Glu Thr Ala Glu Glu Ala Ala Arg Ala Tyr Asp Glu
         35                  40                  45

Ala Ala Val Leu Met Ser Gly Arg Asn Ala Lys Thr Asn Phe Pro Leu
     50                  55                  60

Asn Asn Asn Thr Gly Glu Thr Ser Glu Gly Lys Thr Asp Ile Ser
 65                  70                  75                  80

Ala Ser Ser Thr Met Ser Ser Ser Thr Ser Ser Ser Leu Ser Ser
                 85                  90                  95

Ile Leu Ser Ala Lys Leu Arg Lys Cys Cys Lys Ser Pro Ser Pro Ser
            100                 105                 110

Leu Thr Cys Leu Arg Leu Asp Thr Ala Ser Ser His Ile Gly Val Trp
        115                 120                 125

Gln Lys Arg Ala Gly Ser Lys Ser Asp Ser Ser Trp Val Met Thr Val
    130                 135                 140

Glu Leu Gly Pro Ala Ser Ser Ser Gln Glu Thr Thr Ser Lys Ala Ser
145                 150                 155                 160

Gln Asp Ala Ile Leu Ala Pro Thr Thr Glu Val Glu Ile Gly Gly Ser
                165                 170                 175

Arg Glu Glu Val Leu Asp Glu Glu Lys Val Ala Leu Gln Met Ile
            180                 185                 190

Glu Glu Leu Leu Asn Thr Asn
        195
```

<210> SEQ ID NO 91
<211> LENGTH: 4011
<212> TYPE: DNA
<213> ORGANISM: Arabidopsis thaliana
<220> FEATURE:
<223> OTHER INFORMATION: G987

<400> SEQUENCE: 91

```
atgggttctt actcagctgg cttccctgga tccttggact ggtttgattt tcccggttta      60
ggaaacggat cctatctaaa tgatcaacct ttgttagata ttggatctgt tcctcctcct     120
ctagacccat atcctcaaca gaatcttgct tctgcggatg ctgatttctc tgattctgtt     180
ttgaagtaca taagccaagt tcttatggaa gaggacatgg aagataagcc ttgtatgttt     240
catgatgctt tatctcttca agcagctgag aagtctctct atgaagctct cggcgagaag     300
tacccggttg atgattctga tcagcctctg actactacta ctagccttgc tcaattggtt     360
agtagtcctg gtggttcttc ttatgcttca agcaccacaa ccacttcctc tgattcacaa     420
tggagttttg attgttgga gaataatagg ccttcttctt ggttgcagac accgatcccg     480
agtaacttca ttttcagtc tacatctact agagccagta gcggtaacgc ggttttcggg     540
tcaagtttta gcggtgattt ggtttctaat atgtttaatg atactgactt ggcgttacaa     600
ttcaagaaag ggatggagga agctagtaaa ttccttccta agagctctca gttggttata     660
gataactctg ttcctaacag attaaccgga aagaagagcc attggcgcga agaagaacat     720
ttgactgaag aaagaagtaa gaaacaatct gctatttatg ttgatgaaac tgatgagctt     780
actgatatgt ttgacaatat tctgatattt ggcgaggcta aggaacaacc tgtatgcatt     840
cttaacgaga gtttccctaa ggaacctgcg aaagcttcaa cgtttagtaa gagtcctaaa     900
ggcgaaaaac cggaagctag tggtaacagt tatacaaaag agacacctga tttgaggaca     960
atgctggttt cttgtgctca agctgtttcg attaacgatc gtagaactgc tgacgagctg    1020
ttaagtcgga taaggcaaca ttcttcatct tacggcgatg aacagagag attggctcat    1080
tattttgcta acagtcttga agcacgtttg gctgggatag gtacacaggt ttatactgcc    1140
ttgtcttcca agaaaacatc tacttctgac atgttgaaag cttatcagac atatatatca    1200
gtctgtccgt tcaagaaaat cgcaatcata ttcgccaacc atagtattat gcggttggct    1260
tcaagtgcta atgccaaaac catccacatc atagattttg gaatatctga tggtttccag    1320
tggccttctc tgattcatcg acttgcttgg agacgtggtt catcttgtaa gcttcggata    1380
accggtatag agttgcctca acgtggtttt agaccagccg agggagttat tgagactggt    1440
cgtcgcttgg ctaagtattg tcagaagttc aatattccgt ttgagtacaa tgcgattgcg    1500
cagaaatggg aatcaatcaa gttggaggac ttgaagctaa aagaaggcga gtttgttgcg    1560
gtaaactctt tatttcggtt taggaatctt ctagatgaga cggtggcagt gcatagcccg    1620
agagatacgg ttttgaagct gataaggaag ataaagccag acgtgttcat ccccgggatc    1680
ctcagcggat cctacaacgc gccttttctt gtcacgaggt ttagagaagt tctgtttcat    1740
tactcatctc tgtttgacat gtgtgacacg aatctaacac gggaagatcc aatgagggtt    1800
atgtttgaga aagagttcta tgggcggag atcatgaacg tggtggcgtg tgagggacg    1860
gagagagtgg agaggccaga gagttataag cagtggcagg cgagggcgat gagagccggg    1920
tttagacaga ttccgctgga gaaggaacta gttcagaaac tgaagttgat ggtggaaagt    1980
ggatacaaac ccaaagagtt tgatgttgat caagattgtc actggttgct tcagggctgg    2040
aaaggtagaa ttgtatacgg ttcatctatt tgggttcctt tctttttcta tgtgggcaga    2100
gcaactaggg ttttgatcat ggatccaaac ttctctgaat ctctaaacgg ctttgagtat    2160
tttgatggta accctaattt gcttactgat ccaatggaag atcagtatcc accaccatct    2220
gatactctgt tgaaatacgt gagtgagatt cttatggaag agagtaatgg agattataag    2280
caatctatgt tctatgattc attggcttta cgaaaaactg aagaaatgtt gcagcaagtc    2340
attactgatt ctcaaaatca gtcctttagt cctgctgatt cattgattac taattcttgg    2400
```

```
gatgcaagcg gaagcatcga tgaatcggct tattcggctg atccgcaacc tgtgaatgaa      2460
attatggtta agagtatgtt tagtgatgca gaatcagctt tacagtttaa gaaaggggtt      2520
gaagaagcta gtaaattcct tcccaatagt gatcaatggg ttatcaatct ggatatcgag      2580
agatccgaaa ggcgcgattc ggttaaagaa gagatgggat tggatcagtt gagagttaag      2640
aagaatcatg aaagggattt tgaggaagtt aggagtagta agcaatttgc tagtaatgta      2700
gaagatagta aggttacaga tatgtttgat aaggttttgc ttcttgacgg tgaatgcgat      2760
ccgcaaacat tgttagacag cgagattcaa gcgattcgga gtagtaagaa cataggagag      2820
aaagggaaga agaagaagaa gaagaagagt caagtggttg attttcgtac acttctcact      2880
cattgtgcac aagccatttc cacaggagat aaaaccacgg ctcttgagtt tctgttacag      2940
ataaggcaac agtcttcgcc tctcggtgac gcggggcaaa gactagctca ttgtttcgct      3000
aacgcgcttg aagctcgtct acagggaagt accggtccta tgatccagac ttattacaat      3060
gctttaacct cgtcgttgaa ggatactgct gcggatacaa ttagagcgta tcgagtttat      3120
ctttcttcgt ctccgtttgt taccttgatg tatttcttct ccatctggat gattcttgat      3180
gtggctaaag atgctcctgt tcttcatata gttgattttg ggattctata cgggtttcaa      3240
tggccgatgt ttattcagtc tatatcagat cgaaaagatg taccgcggaa gctgcggatt      3300
actggtatcg agcttcctca gtgcgggttt cggcccgcgg agcgaataga ggagacagga      3360
cggagattgg ctgagtattg taaacggttt aatgttccgt ttgagtacaa agccattgcg      3420
tctcagaact gggaaacaat ccggatagaa gatctcgata tacgaccaaa cgaagtctta      3480
gcggttaatg ctggacttag actcaagaac cttcaagatg aaacaggaag cgaagagaat      3540
tgcccgagag atgctgtctt gaagctaata agaaacatga acccggacgt tttcatccac      3600
gcgattgtca acggttcatt caacgcaccc ttctttatct cgcggtttaa agaagcggtt      3660
taccattact ccgctctctt cgacatgttt gattcgacgt tgcctcggga taacaaagag      3720
aggattaggt tcgagaggga gttttacggg agagaggcta tgaacgtgat agcgtgcgag      3780
gaagctgatc gagtggagag gcctgagact tacaggcaat ggcaggttag aatggttaga      3840
gccgggttta agcagaaaac gattaagcct gagctggtag agttgtttag aggaaagctg      3900
aagaaatggc gttaccataa agactttgtg ttgatgaaa atagtaaatg gttgttacaa      3960
ggctggaaag gtcgaactct ctatgcttct tcttgttggg ttcctgccta g              4011
```

<210> SEQ ID NO 92
<211> LENGTH: 1336
<212> TYPE: PRT
<213> ORGANISM: Arabidopsis thaliana
<220> FEATURE:
<223> OTHER INFORMATION: G987 polypeptide

<400> SEQUENCE: 92

```
Met Gly Ser Tyr Ser Ala Gly Phe Pro Gly Ser Leu Asp Trp Phe Asp
1               5                   10                  15

Phe Pro Gly Leu Gly Asn Gly Ser Tyr Leu Asn Asp Gln Pro Leu Leu
            20                  25                  30

Asp Ile Gly Ser Val Pro Pro Leu Asp Pro Tyr Pro Gln Gln Asn
        35                  40                  45

Leu Ala Ser Ala Asp Ala Asp Phe Ser Asp Ser Val Leu Lys Tyr Ile
    50                  55                  60

Ser Gln Val Leu Met Glu Glu Asp Met Glu Asp Lys Pro Cys Met Phe
65                  70                  75                  80
```

-continued

```
His Asp Ala Leu Ser Leu Gln Ala Ala Glu Lys Ser Leu Tyr Glu Ala
                85                  90                  95

Leu Gly Glu Lys Tyr Pro Val Asp Asp Ser Asp Gln Pro Leu Thr Thr
            100                 105                 110

Thr Thr Ser Leu Ala Gln Leu Val Ser Ser Pro Gly Ser Ser Ser Tyr
        115                 120                 125

Ala Ser Ser Thr Thr Thr Thr Ser Ser Asp Ser Gln Trp Ser Phe Asp
    130                 135                 140

Cys Leu Glu Asn Asn Arg Pro Ser Ser Trp Leu Gln Thr Pro Ile Pro
145                 150                 155                 160

Ser Asn Phe Ile Phe Gln Ser Thr Ser Thr Arg Ala Ser Ser Gly Asn
                165                 170                 175

Ala Val Phe Gly Ser Ser Phe Ser Gly Asp Leu Val Ser Asn Met Phe
            180                 185                 190

Asn Asp Thr Asp Leu Ala Leu Gln Phe Lys Lys Gly Met Glu Glu Ala
        195                 200                 205

Ser Lys Phe Leu Pro Lys Ser Ser Gln Leu Val Ile Asp Asn Ser Val
    210                 215                 220

Pro Asn Arg Leu Thr Gly Lys Lys Ser His Trp Arg Glu Glu His
225                 230                 235                 240

Leu Thr Glu Glu Arg Ser Lys Lys Gln Ser Ala Ile Tyr Val Asp Glu
                245                 250                 255

Thr Asp Glu Leu Thr Asp Met Phe Asp Asn Ile Leu Ile Phe Gly Glu
            260                 265                 270

Ala Lys Glu Gln Pro Val Cys Ile Leu Asn Glu Ser Phe Pro Lys Glu
        275                 280                 285

Pro Ala Lys Ala Ser Thr Phe Ser Lys Ser Pro Lys Gly Glu Lys Pro
    290                 295                 300

Glu Ala Ser Gly Asn Ser Tyr Thr Lys Glu Thr Pro Asp Leu Arg Thr
305                 310                 315                 320

Met Leu Val Ser Cys Ala Gln Ala Val Ser Ile Asn Asp Arg Arg Thr
                325                 330                 335

Ala Asp Glu Leu Leu Ser Arg Ile Arg Gln His Ser Ser Tyr Gly
            340                 345                 350

Asp Gly Thr Glu Arg Leu Ala His Tyr Phe Ala Asn Ser Leu Glu Ala
        355                 360                 365

Arg Leu Ala Gly Ile Gly Thr Gln Val Tyr Thr Ala Leu Ser Ser Lys
    370                 375                 380

Lys Thr Ser Thr Ser Asp Met Leu Lys Ala Tyr Gln Thr Tyr Ile Ser
385                 390                 395                 400

Val Cys Pro Phe Lys Lys Ile Ala Ile Ile Phe Ala Asn His Ser Ile
                405                 410                 415

Met Arg Leu Ala Ser Ser Ala Asn Ala Lys Thr Ile His Ile Ile Asp
            420                 425                 430

Phe Gly Ile Ser Asp Gly Phe Gln Trp Pro Ser Leu Ile His Arg Leu
        435                 440                 445

Ala Trp Arg Arg Gly Ser Ser Cys Lys Leu Arg Ile Thr Gly Ile Glu
    450                 455                 460

Leu Pro Gln Arg Gly Phe Arg Pro Ala Glu Val Ile Glu Thr Gly
465                 470                 475                 480

Arg Arg Leu Ala Lys Tyr Cys Gln Lys Phe Asn Ile Pro Phe Glu Tyr
                485                 490                 495
```

-continued

```
Asn Ala Ile Ala Gln Lys Trp Glu Ser Ile Lys Leu Glu Asp Leu Lys
            500                 505                 510

Leu Lys Glu Gly Glu Phe Val Ala Val Asn Ser Leu Phe Arg Phe Arg
        515                 520                 525

Asn Leu Leu Asp Glu Thr Val Ala Val His Ser Pro Arg Asp Thr Val
            530                 535                 540

Leu Lys Leu Ile Arg Lys Ile Lys Pro Asp Val Phe Ile Pro Gly Ile
545                 550                 555                 560

Leu Ser Gly Ser Tyr Asn Ala Pro Phe Phe Val Thr Arg Phe Arg Glu
                565                 570                 575

Val Leu Phe His Tyr Ser Ser Leu Phe Asp Met Cys Asp Thr Asn Leu
            580                 585                 590

Thr Arg Glu Asp Pro Met Arg Val Met Phe Glu Lys Glu Phe Tyr Gly
        595                 600                 605

Arg Glu Ile Met Asn Val Val Ala Cys Glu Gly Thr Glu Arg Val Glu
            610                 615                 620

Arg Pro Glu Ser Tyr Lys Gln Trp Gln Ala Arg Ala Met Arg Ala Gly
625                 630                 635                 640

Phe Arg Gln Ile Pro Leu Glu Lys Glu Leu Val Gln Lys Leu Lys Leu
                645                 650                 655

Met Val Glu Ser Gly Tyr Lys Pro Lys Glu Phe Asp Val Asp Gln Asp
            660                 665                 670

Cys His Trp Leu Leu Gln Gly Trp Lys Gly Arg Ile Val Tyr Gly Ser
        675                 680                 685

Ser Ile Trp Val Pro Phe Phe Tyr Val Gly Arg Ala Thr Arg Val
            690                 695                 700

Leu Ile Met Asp Pro Asn Phe Ser Glu Ser Leu Asn Gly Phe Glu Tyr
705                 710                 715                 720

Phe Asp Gly Asn Pro Asn Leu Leu Thr Asp Pro Met Glu Asp Gln Tyr
                725                 730                 735

Pro Pro Pro Ser Asp Thr Leu Leu Lys Tyr Val Ser Glu Ile Leu Met
            740                 745                 750

Glu Glu Ser Asn Gly Asp Tyr Lys Gln Ser Met Phe Tyr Asp Ser Leu
        755                 760                 765

Ala Leu Arg Lys Thr Glu Glu Met Leu Gln Gln Val Ile Thr Asp Ser
        770                 775                 780

Gln Asn Gln Ser Phe Ser Pro Ala Asp Ser Leu Ile Thr Asn Ser Trp
785                 790                 795                 800

Asp Ala Ser Gly Ser Ile Asp Glu Ser Ala Tyr Ser Ala Asp Pro Gln
                805                 810                 815

Pro Val Asn Glu Ile Met Val Lys Ser Met Phe Ser Asp Ala Glu Ser
            820                 825                 830

Ala Leu Gln Phe Lys Lys Gly Val Glu Glu Ala Ser Lys Phe Leu Pro
        835                 840                 845

Asn Ser Asp Gln Trp Val Ile Asn Leu Asp Ile Glu Arg Ser Glu Arg
        850                 855                 860

Arg Asp Ser Val Lys Glu Met Gly Leu Asp Gln Leu Arg Val Lys
865                 870                 875                 880

Lys Asn His Glu Arg Asp Phe Glu Glu Val Arg Ser Ser Lys Gln Phe
                885                 890                 895

Ala Ser Asn Val Glu Asp Ser Lys Val Thr Asp Met Phe Asp Lys Val
            900                 905                 910

Leu Leu Leu Asp Gly Glu Cys Asp Pro Gln Thr Leu Leu Asp Ser Glu
```

```
                915                 920                 925
Ile Gln Ala Ile Arg Ser Ser Lys Asn Ile Gly Glu Lys Gly Lys Lys
    930                 935                 940

Lys Lys Lys Lys Lys Ser Gln Val Val Asp Phe Arg Thr Leu Leu Thr
945                 950                 955                 960

His Cys Ala Gln Ala Ile Ser Thr Gly Asp Lys Thr Thr Ala Leu Glu
                965                 970                 975

Phe Leu Leu Gln Ile Arg Gln Gln Ser Ser Pro Leu Gly Asp Ala Gly
            980                 985                 990

Gln Arg Leu Ala His Cys Phe Ala Asn Ala Leu Glu Ala Arg Leu Gln
        995                 1000                1005

Gly Ser Thr Gly Pro Met Ile Gln Thr Tyr Tyr Asn Ala Leu Thr
    1010                1015                1020

Ser Ser Leu Lys Asp Thr Ala Asp Thr Ile Arg Ala Tyr Arg
    1025                1030                1035

Val Tyr Leu Ser Ser Ser Pro Phe Val Thr Leu Met Tyr Phe Phe
    1040                1045                1050

Ser Ile Trp Met Ile Leu Asp Val Ala Lys Asp Ala Pro Val Leu
    1055                1060                1065

His Ile Val Asp Phe Gly Ile Leu Tyr Gly Phe Gln Trp Pro Met
    1070                1075                1080

Phe Ile Gln Ser Ile Ser Asp Arg Lys Asp Val Pro Arg Lys Leu
    1085                1090                1095

Arg Ile Thr Gly Ile Glu Leu Pro Gln Cys Gly Phe Arg Pro Ala
    1100                1105                1110

Glu Arg Ile Glu Glu Thr Gly Arg Arg Leu Ala Glu Tyr Cys Lys
    1115                1120                1125

Arg Phe Asn Val Pro Phe Glu Tyr Lys Ala Ile Ala Ser Gln Asn
    1130                1135                1140

Trp Glu Thr Ile Arg Ile Glu Asp Leu Asp Ile Arg Pro Asn Glu
    1145                1150                1155

Val Leu Ala Val Asn Ala Gly Leu Arg Leu Lys Asn Leu Gln Asp
    1160                1165                1170

Glu Thr Gly Ser Glu Glu Asn Cys Pro Arg Asp Ala Val Leu Lys
    1175                1180                1185

Leu Ile Arg Asn Met Asn Pro Asp Val Phe Ile His Ala Ile Val
    1190                1195                1200

Asn Gly Ser Phe Asn Ala Pro Phe Phe Ile Ser Arg Phe Lys Glu
    1205                1210                1215

Ala Val Tyr His Tyr Ser Ala Leu Phe Asp Met Phe Asp Ser Thr
    1220                1225                1230

Leu Pro Arg Asp Asn Lys Glu Arg Ile Arg Phe Glu Arg Glu Phe
    1235                1240                1245

Tyr Gly Arg Glu Ala Met Asn Val Ile Ala Cys Glu Gly Ala Asp
    1250                1255                1260

Arg Val Glu Arg Pro Glu Thr Tyr Arg Gln Trp Gln Val Arg Met
    1265                1270                1275

Val Arg Ala Gly Phe Lys Gln Lys Thr Ile Lys Pro Glu Leu Val
    1280                1285                1290

Glu Leu Phe Arg Gly Lys Leu Lys Lys Trp Arg Tyr His Lys Asp
    1295                1300                1305

Phe Val Val Asp Glu Asn Ser Lys Trp Leu Leu Gln Gly Trp Lys
    1310                1315                1320
```

Gly Arg Thr Leu Tyr Ala Ser Ser Cys Trp Val Pro Ala
     1325              1330             1335

<210> SEQ ID NO 93
<211> LENGTH: 1116
<212> TYPE: DNA
<213> ORGANISM: Arabidopsis thaliana
<220> FEATURE:
<223> OTHER INFORMATION: G1069

<400> SEQUENCE: 93

```
ttggaaccct agaggccttt caagcaaatc atcagggtaa caatttcttg atctttcttt     60
ttagcgaatt tccagttttt ggtcaatcat ggcaaaccct tggtggacga accagagtgg    120
tttagcgggc atggtggacc attcggtctc ctcaggccat caccaaaacc atcaccacca    180
aagtcttctt accaaaggag atcttggaat agccatgaat cagagccaag acaacgacca    240
agacgaagaa gatgatccta gaaggagc cgttgaggtg gtcaaccgta gaccaagagg       300
tagaccacca ggatccaaaa acaaacccaa agctccaatc tttgtgacaa gagacagccc    360
caacgcactc cgtagccatg tcttggagat ctccgacggc agtgacgtcg ccgacacaat    420
cgctcacttc tcaagacgca ggcaacgcgg cgtttgcgtt ctcagcggga caggctcagt    480
cgctaacgtc accctccgcc aagccgccgc accaggaggt gtggtctctc tccaaggcag    540
gtttgaaatc ttatctttaa ccggtgcttt cctccctgga ccttccccac ccgggtcaac    600
cggtttaacg gtttacttag ccggggtcca gggtcaggtc gttggaggta gcgttgtagg    660
cccactctta gccatagggt cggtcatggt gattgctgct actttctcta acgctactta    720
tgagagattg cccatggaag aagaggaaga cggtggcggc tcaagacaga ttcacggagg    780
cggtgactca ccgcccagaa tcggtagtaa cctgcctgat ctatcaggga tggccgggcc    840
aggctacaat atgccgccgc atctgattcc aaatgggggct ggtcagctag gcacgaacc    900
atatacatgg gtccacgcaa gaccaccta ctgactcagt gagccatttc tatatataat    960
ggtctatata aataaatata tagatgaata taagcaagca atttgaggta gtctattaca   1020
aagcttttgc tctggttgga aaaataaata agtatcaaag ctttgtttgt tcttaatgga   1080
aatatagagc ttgggaaggt agaaagagac gacatt                              1116
```

<210> SEQ ID NO 94
<211> LENGTH: 281
<212> TYPE: PRT
<213> ORGANISM: Arabidopsis thaliana
<220> FEATURE:
<223> OTHER INFORMATION: G1069 polypeptide

<400> SEQUENCE: 94

Met Ala Asn Pro Trp Trp Thr Asn Gln Ser Gly Leu Ala Gly Met Val
1               5                   10                  15

Asp His Ser Val Ser Ser Gly His His Gln Asn His His Gln Ser
            20                  25                  30

Leu Leu Thr Lys Gly Asp Leu Gly Ile Ala Met Asn Gln Ser Gln Asp
        35                  40                  45

Asn Asp Gln Asp Glu Glu Asp Asp Pro Arg Glu Gly Ala Val Glu Val
    50                  55                  60

Val Asn Arg Arg Pro Arg Gly Arg Pro Gly Ser Lys Asn Lys Pro
65                  70                  75                  80

Lys Ala Pro Ile Phe Val Thr Arg Asp Ser Pro Asn Ala Leu Arg Ser
                85                  90                  95

His Val Leu Glu Ile Ser Asp Gly Ser Asp Val Ala Asp Thr Ile Ala
            100                 105                 110

His Phe Ser Arg Arg Arg Gln Arg Gly Val Cys Val Leu Ser Gly Thr
        115                 120                 125

Gly Ser Val Ala Asn Val Thr Leu Arg Gln Ala Ala Ala Pro Gly Gly
    130                 135                 140

Val Val Ser Leu Gln Gly Arg Phe Glu Ile Leu Ser Leu Thr Gly Ala
145                 150                 155                 160

Phe Leu Pro Gly Pro Ser Pro Gly Ser Thr Gly Leu Thr Val Tyr
            165                 170                 175

Leu Ala Gly Val Gln Gly Gln Val Val Gly Gly Ser Val Val Gly Pro
            180                 185                 190

Leu Leu Ala Ile Gly Ser Val Met Val Ile Ala Ala Thr Phe Ser Asn
            195                 200                 205

Ala Thr Tyr Glu Arg Leu Pro Met Glu Glu Glu Asp Gly Gly Gly
            210                 215                 220

Ser Arg Gln Ile His Gly Gly Gly Asp Ser Pro Pro Arg Ile Gly Ser
225                 230                 235                 240

Asn Leu Pro Asp Leu Ser Gly Met Ala Gly Pro Gly Tyr Asn Met Pro
                245                 250                 255

Pro His Leu Ile Pro Asn Gly Ala Gly Gln Leu Gly His Glu Pro Tyr
            260                 265                 270

Thr Trp Val His Ala Arg Pro Pro Tyr
            275                 280

<210> SEQ ID NO 95
<211> LENGTH: 1780
<212> TYPE: DNA
<213> ORGANISM: Arabidopsis thaliana
<220> FEATURE:
<223> OTHER INFORMATION: G1198

<400> SEQUENCE: 95
tcttttcaaa ttccaatcat tgatcaact aatcaagaat taattataag actttgcaat      60
ctctctccct ctccctctcc ctagctagtt ctctcttgtg tttcttaact cgagcttctc    120
tcaatagtga ttatcatctt tttcatcatt tcaagattta atgtgttttg cagaaaagag    180
actaatcaag aagagatatc atcaattgaa gctgttttct tgagtagaga tggcgaacca    240
tagaatgagc gaagctacaa accataacca caatcatcat cttccttatt cacttattca    300
tggtctcaac aacaatcatc catcttctgg tttcattaac caagatggat cgtccagttt    360
cgattttgga gagctagaag aagcaattgt tctgcaaggt gtcaagtata ggaacgagga    420
agccaagcca cctttattag gaggaggagg aggagctacg actctggaga tgttcccttc    480
gtggccaatc agaactcacc aaactcttcc tactgagagt tccaagtcag gaggagagag    540
cagcgattca ggatcggcta atttctccgg caaagctgaa agtcaacaac cggagtctcc    600
tatgagtagc aaacatcatc tcatgcttca acctcatcat aataacatgg caaactcaag    660
ttcaacatct ggacttcctt ccacttctcg aactttagct cctcctaaac cttcggaaga    720
taagaggaag gctacaactt caggcaaaca gcttgatgct aagacgttga cgtttggc     780 ccaaaataga gaagctgctc gcaaaagccg tcttaggaaa aaggcgtatg tgcaacagct    840
agaatcaagt aggataaagc tttcccaatt ggagcaagaa cttcagcgag ctcgttctca    900
ggggctgttc atgggtggtt gtggaccacc aggacctaac atcacttccg gagctgcaat    960

-continued

```
atttgacatg gaatatggga gatggctaga ggatgataac cggcatatgt cggagattcg    1020
aaccggtctt caggctcatt tatctgacaa tgatttaagg ttgatcgttg acggttacat    1080
tgctcatttt gatgagatat tccgattaaa agccgtggca gcgaaagccg atgtttttca    1140
cctcatcatt gggacatgga tgtccccagc cgaacgttgt tttatttgga tggctggttt    1200
ccgtccatcc gacctaatca agatattggt gtcgcaaatg gatctattga cggagcaaca    1260
actgatggga atatatagcc tacaacactc gtcgcaacaa gcagaggagg ctctctcgca    1320
aggcctcgaa caacttcagc aatctctcat cgatactctc gccgcatctc cagtcattga    1380
cggaatgcaa caaatggctg tcgctctcgg aaagatctct aatctcgaag ctttatccg     1440 ccaggctgat aacttgaggc agcagaccgt tcaccagctg aggcggatct tgaccgtccg    1500
acaagctgca cggtgtttcc tagtcatcgg agagtactat ggacggctca gagctcttag    1560 ctcccttttgg ttgtcacgcc cacgagagac actgatgagt gatgaaacct cttgtcaaac   1620
gacgacggat ttgcagattg ttcagtcatc tcggaaccac ttctccaatt tctgaatgga    1680
atgaaacttt gtataactaa aaggccaagt ttcattgtct gtcgtaattt cacctatttc    1740
ctttaaagtt gtactagaga aaagatagga tcttccttcg                          1780
```

<210> SEQ ID NO 96
<211> LENGTH: 481
<212> TYPE: PRT
<213> ORGANISM: Arabidopsis thaliana
<220> FEATURE:
<223> OTHER INFORMATION: G1198 polypeptide

<400> SEQUENCE: 96

```
Met Ala Asn His Arg Met Ser Glu Ala Thr Asn His Asn His Asn His
1               5                   10                  15

His Leu Pro Tyr Ser Leu Ile His Gly Leu Asn Asn Asn His Pro Ser
            20                  25                  30

Ser Gly Phe Ile Asn Gln Asp Gly Ser Ser Phe Asp Phe Gly Glu
        35                  40                  45

Leu Glu Glu Ala Ile Val Leu Gln Gly Val Lys Tyr Arg Asn Glu Glu
    50                  55                  60

Ala Lys Pro Pro Leu Leu Gly Gly Gly Gly Ala Thr Thr Leu Glu
65                  70                  75                  80

Met Phe Pro Ser Trp Pro Ile Arg Thr His Gln Thr Leu Pro Thr Glu
                85                  90                  95

Ser Ser Lys Ser Gly Gly Glu Ser Asp Ser Gly Ser Ala Asn Phe
            100                 105                 110

Ser Gly Lys Ala Glu Ser Gln Gln Pro Glu Ser Pro Met Ser Ser Lys
        115                 120                 125

His His Leu Met Leu Gln Pro His His Asn Asn Met Ala Asn Ser Ser
    130                 135                 140

Ser Thr Ser Gly Leu Pro Ser Thr Ser Arg Thr Leu Ala Pro Pro Lys
145                 150                 155                 160

Pro Ser Glu Asp Lys Arg Lys Ala Thr Thr Ser Gly Lys Gln Leu Asp
                165                 170                 175

Ala Lys Thr Leu Arg Arg Leu Ala Gln Asn Arg Glu Ala Ala Arg Lys
            180                 185                 190

Ser Arg Leu Arg Lys Lys Ala Tyr Val Gln Gln Leu Glu Ser Ser Arg
        195                 200                 205

Ile Lys Leu Ser Gln Leu Glu Gln Glu Leu Gln Arg Ala Arg Ser Gln
    210                 215                 220
```

-continued

```
Gly Leu Phe Met Gly Gly Cys Gly Pro Pro Gly Pro Asn Ile Thr Ser
225                 230                 235                 240

Gly Ala Ala Ile Phe Asp Met Glu Tyr Gly Arg Trp Leu Glu Asp Asp
            245                 250                 255

Asn Arg His Met Ser Glu Ile Arg Thr Gly Leu Gln Ala His Leu Ser
        260                 265                 270

Asp Asn Asp Leu Arg Leu Ile Val Asp Gly Tyr Ile Ala His Phe Asp
    275                 280                 285

Glu Ile Phe Arg Leu Lys Ala Val Ala Ala Lys Ala Asp Val Phe His
290                 295                 300

Leu Ile Ile Gly Thr Trp Met Ser Pro Ala Glu Arg Cys Phe Ile Trp
305                 310                 315                 320

Met Ala Gly Phe Arg Pro Ser Asp Leu Ile Lys Ile Leu Val Ser Gln
            325                 330                 335

Met Asp Leu Leu Thr Glu Gln Gln Leu Met Gly Ile Tyr Ser Leu Gln
        340                 345                 350

His Ser Ser Gln Gln Ala Glu Ala Leu Ser Gln Gly Leu Glu Gln
    355                 360                 365

Leu Gln Gln Ser Leu Ile Asp Thr Leu Ala Ala Ser Pro Val Ile Asp
370                 375                 380

Gly Met Gln Gln Met Ala Val Ala Leu Gly Lys Ile Ser Asn Leu Glu
385                 390                 395                 400

Gly Phe Ile Arg Gln Ala Asp Asn Leu Arg Gln Gln Thr Val His Gln
            405                 410                 415

Leu Arg Arg Ile Leu Thr Val Arg Gln Ala Ala Arg Cys Phe Leu Val
        420                 425                 430

Ile Gly Glu Tyr Tyr Gly Arg Leu Arg Ala Leu Ser Ser Leu Trp Leu
    435                 440                 445

Ser Arg Pro Arg Glu Thr Leu Met Ser Asp Glu Thr Ser Cys Gln Thr
450                 455                 460

Thr Thr Asp Leu Gln Ile Val Gln Ser Ser Arg Asn His Phe Ser Asn
465                 470                 475                 480

Phe

<210> SEQ ID NO 97
<211> LENGTH: 1011
<212> TYPE: DNA
<213> ORGANISM: Arabidopsis thaliana
<220> FEATURE:
<223> OTHER INFORMATION: G1322

<400> SEQUENCE: 97
aaagttattg atagtttctg ttacttatta attttttaagg ttatgtgtat tattaccaat    60
tggaggacta tatagtcgca agtctcaacc ctataaaaga aaacattcgt cgatcatctt   120
cccgcctcga gtatctctct ctctctctct cttctctgtt ttctttattg attgcataga   180
caaaaataca cacatacaca acagaaagaa agatggagac gacgatgaag aagaaaggga   240
gagtgaaagc gacaataacg tcacagaaag aagaagaagg aacagtgaga aaaggacctt   300
ggactatgga agaagatttc atcctctttt a attacatcct taatcatggt gaaggtcttt   360
ggaactctgt cgccaaagcc tctggtctaa acgtactgg aaaaagttgt cggctccggt    420
ggctgaacta tctccgacca gatgtgcggc gagggaacat aaccgaagaa gaacagcttt   480
tgatcattca gcttcatgct aagcttggaa acaggtggtc gaagattgcg aagcatcttc   540
```

```
cgggaagaac ggacaacgag ataaagaact tctggaggac aaagattcag agacacatga      600
aagtgtcatc ggaaaatatg atgaatcatc aacatcattg ttcgggaaac tcacagagct      660
cggggatgac gacgcaaggc agctccggca aagccataga cacggctgag agcttctctc      720
aggcgaagac gacgacgttt aatgtggtgg aacaacagtc aaacgagaat tactggaacg      780
ttgaagatct gtggcccgtc cacttgctta atggtgacca ccatgtgatt taagatatat      840
atatagacct cctatacatt tatatgcccc agctgggttt ttttgtatgg tacgttattt      900 ggttttcta ttgctgaaat gtcgttgcat ttaatttaca tacgaaagt gcattaaatc       960 attaaatctt caatacatat ggaggtggtg tttgagtaaa aaaaaaaaa a              1011
```

<210> SEQ ID NO 98
<211> LENGTH: 206
<212> TYPE: PRT
<213> ORGANISM: Arabidopsis thaliana
<220> FEATURE:
<223> OTHER INFORMATION: G1322 polypeptide

<400> SEQUENCE: 98

```
Met Glu Thr Thr Met Lys Lys Lys Gly Arg Val Lys Ala Thr Ile Thr
1               5                   10                  15

Ser Gln Lys Glu Glu Glu Gly Thr Val Arg Lys Gly Pro Trp Thr Met
            20                  25                  30

Glu Glu Asp Phe Ile Leu Phe Asn Tyr Ile Leu Asn His Gly Glu Gly
        35                  40                  45

Leu Trp Asn Ser Val Ala Lys Ala Ser Gly Leu Lys Arg Thr Gly Lys
    50                  55                  60

Ser Cys Arg Leu Arg Trp Leu Asn Tyr Leu Arg Pro Asp Val Arg Arg
65                  70                  75                  80

Gly Asn Ile Thr Glu Glu Glu Gln Leu Leu Ile Ile Gln Leu His Ala
                85                  90                  95

Lys Leu Gly Asn Arg Trp Ser Lys Ile Ala Lys His Leu Pro Gly Arg
            100                 105                 110

Thr Asp Asn Glu Ile Lys Asn Phe Trp Arg Thr Lys Ile Gln Arg His
        115                 120                 125

Met Lys Val Ser Ser Glu Asn Met Met Asn His Gln His His Cys Ser
    130                 135                 140

Gly Asn Ser Gln Ser Ser Gly Met Thr Thr Gln Gly Ser Ser Gly Lys
145                 150                 155                 160

Ala Ile Asp Thr Ala Glu Ser Phe Ser Gln Ala Lys Thr Thr Thr Phe
                165                 170                 175

Asn Val Val Glu Gln Gln Ser Asn Glu Asn Tyr Trp Asn Val Glu Asp
            180                 185                 190

Leu Trp Pro Val His Leu Leu Asn Gly Asp His His Val Ile
        195                 200                 205
```

<210> SEQ ID NO 99
<211> LENGTH: 1260
<212> TYPE: DNA
<213> ORGANISM: Arabidopsis thaliana
<220> FEATURE:
<223> OTHER INFORMATION: G1421

<400> SEQUENCE: 99

```
gaaatttcat ccctaaataa gaaaaaagca tctccttctt tagtgtcctc cttcaccaaa       60
ctcttgattc cataagcata tattaaaaaa gctctctgct ttcttcaact ttcccgggaa      120
```

```
aatcttcttg ttacaaagca tcaatctctt gttttaccaa ttttctctct ttattccttt       180
tttgcccttt acttttccta actttggtct ttatatataa acacacgaca caaagaagaa       240
cacacataag ttaaaactat tacaacagtt ttaaagagag agatttaaaa aatggagaca       300
gagaagaaag tttctctccc aagaatctta cgaatctctg ttactgatcc ttacgcaaca       360
gattcgtcaa gcgacgaaga agaagaagtt gattttgatg cattatctac aaaacgacgt       420
cgtgttaaga agtacgtgaa ggaagtggtg cttgattcgg tggtttctga taaagagaag       480
ccgatgaaga agaagagaaa gaagcgcgtt gttactgttc cagtggttgt tacgacggcg       540
acgaggaagt ttcgtggagt gaggcaaaga ccgtggggaa aatgggcggc ggagattaga       600
gatccgagta gacgtgttag ggtttggtta ggtacttttg acacggcgga ggaagctgcc       660
attgtttacg ataacgcagc tattcagcta cgtggtccta acgcagagct taacttccct       720
cctcctccgg tgacggagaa tgttgaagaa gcttcgacgg aggtgaaagg agtttcggat       780
tttatcattg gcggtggaga atgtcttcgt tcgccggttt ctgttctcga atctccgttc       840
tccggcgagt ctactgcggt taaagaggag tttgtcggtg tatcgacggc ggagattgtg       900
gttaaaaagg agccgtcttt taacggttca gatttctcgg cgccgttgtt ctcggacgac       960 gacgttttg gtttctcgac gtcgatgagt gaaagtttcg gcggcgattt atttggagat      1020 aatcttttg cggatatgag ttttggatcc gggtttggat tcgggtctgg gtctggattc      1080
tccagctggc acgttgagga ccattttcaa gatattgggg atttattcgg gtcggatcct      1140
gtcttaactg tttaagaaat aactggccgt ttaacggcgt ttagtgaagt tttgttaccg      1200
gcgacggcga ggattaaaaa aaaacggcga tttatttttt gaatgaagat ttgttaaata      1260
```

<210> SEQ ID NO 100
<211> LENGTH: 287
<212> TYPE: PRT
<213> ORGANISM: Arabidopsis thaliana
<220> FEATURE:
<223> OTHER INFORMATION: G1421 polypeptide

<400> SEQUENCE: 100

Met Glu Thr Glu Lys Lys Val Ser Leu Pro Arg Ile Leu Arg Ile Ser
1               5                   10                  15

Val Thr Asp Pro Tyr Ala Thr Asp Ser Ser Ser Asp Glu Glu Glu Glu
            20                  25                  30

Val Asp Phe Asp Ala Leu Ser Thr Lys Arg Arg Val Lys Lys Tyr
        35                  40                  45

Val Lys Glu Val Val Leu Asp Ser Val Val Ser Asp Lys Glu Lys Pro
    50                  55                  60

Met Lys Lys Lys Arg Lys Lys Arg Val Val Thr Val Pro Val Val
65                  70                  75                  80

Thr Thr Ala Thr Arg Lys Phe Arg Gly Val Arg Gln Arg Pro Trp Gly
            85                  90                  95

Lys Trp Ala Ala Glu Ile Arg Asp Pro Ser Arg Val Arg Val Trp
        100                 105                 110

Leu Gly Thr Phe Asp Thr Ala Glu Glu Ala Ala Ile Val Tyr Asp Asn
    115                 120                 125

Ala Ala Ile Gln Leu Arg Gly Pro Asn Ala Glu Leu Asn Phe Pro
130                 135                 140

Pro Pro Val Thr Glu Asn Val Glu Glu Ala Ser Thr Glu Val Lys Gly
145                 150                 155                 160

Val Ser Asp Phe Ile Ile Gly Gly Gly Glu Cys Leu Arg Ser Pro Val

```
                     165                 170                 175
Ser Val Leu Glu Ser Pro Phe Ser Gly Glu Ser Thr Ala Val Lys Glu
                180                 185                 190
Glu Phe Val Gly Val Ser Thr Ala Glu Ile Val Lys Lys Glu Pro
            195                 200                 205
Ser Phe Asn Gly Ser Asp Phe Ser Ala Pro Leu Phe Ser Asp Asp Asp
        210                 215                 220
Val Phe Gly Phe Ser Thr Ser Met Ser Glu Ser Phe Gly Gly Asp Leu
225                 230                 235                 240
Phe Gly Asp Asn Leu Phe Ala Asp Met Ser Phe Gly Ser Gly Phe Gly
                245                 250                 255
Phe Gly Ser Gly Ser Gly Phe Ser Ser Trp His Val Glu Asp His Phe
            260                 265                 270
Gln Asp Ile Gly Asp Leu Phe Gly Ser Asp Pro Val Leu Thr Val
        275                 280                 285
```

<210> SEQ ID NO 101
<211> LENGTH: 1562
<212> TYPE: DNA
<213> ORGANISM: Arabidopsis thaliana
<220> FEATURE:
<223> OTHER INFORMATION: G1794

<400> SEQUENCE: 101

| | | | | | |
|---|---|---|---|---|---|
| tctttctttc | ttcctctttg | tctctgtttc | ttgtttctct | ctctctctct | ctacagagtt | 60 |
| ttctttccct | cgaagaaaaa | gaatattttt | aaatttaatt | ttctctgcgt | ttataagctt | 120 |
| taagtttcag | aggaggagga | tttagaagga | gggttttgta | tgtgtgtctt | aaaagtggca | 180 |
| aatcaggaag | ataacgttgg | caaaaaagcc | gagtctatta | gagacgatga | tcatcggacg | 240 |
| ttatctgaaa | tcgatcaatg | gctttactta | ttcgcagccg | aagacgacca | ccaccgtcat | 300 |
| agcttcccta | cgcagcagcc | gcctccatcg | tcgtcgtcct | catctcttat | ctcaggtttc | 360 |
| agtagagaga | tggagatgtc | tgctattgtc | tctgctttga | ctcacgttgt | tgctggaaat | 420 |
| gttcctcagc | atcaacaagg | aggcggtgaa | ggtagcggag | aagggacttc | gaattcgtct | 480 |
| tcttcctcgg | ggcagaaaag | gaggagagag | gtggaggaag | gtggcgccaa | agcggttaag | 540 |
| gcagctaata | ctttgacggt | tgatcaatat | ttctccggtg | gtagctctac | ttctaaagtg | 600 |
| agagaagctt | cgagtaacat | gtcaggtccg | ggcccaacat | acgagtatac | aactacggca | 660 |
| actgctagta | gcgaaacgtc | gtcgtttagt | ggggaccaac | ctcggcgaag | atacagagga | 720 |
| gttagacaaa | gaccatgggg | aaagtgggcg | gctgagattc | gagatccatt | taaagcagct | 780 |
| agagtttggc | tcggtacgtt | cgacaatgct | gaatcagcag | caagagctta | cgacgaagct | 840 |
| gcacttcggt | ttagaggcaa | caaagccaaa | ctcaacttcc | ctgaaaacgt | caaactcgtt | 900 |
| agacctgctt | caaccgaagc | acaacctgtg | caccaaaccg | ctgctcaaag | accgacccag | 960 |
| tcaaggaact | cgggttcaac | gactacccct | ttgcccataa | gacctgcttc | gaatcaaagc | 1020 |
| gttcattcgc | agccgttgat | gcaatcatac | aacttgagtt | actctgaaat | ggctcgtcaa | 1080 |
| caacaacagt | ttcagcaaca | tcatcaacaa | tctttggatt | tatacgatca | aatgtcgttt | 1140 |
| ccgttgcgtt | tcggtcacac | tggaggttca | atgatgcaat | ctacgtcgtc | atcatcatct | 1200 |
| cattctcgtc | ctctgttttc | cccggctgct | gttcagccgc | caccagaatc | agctagcgaa | 1260 |
| accggttatc | tccaggatat | acaatggcca | tcagacaaga | ctagtaataa | ctacaataat | 1320 |
| agtccatcct | cctgatgact | tgcttcattt | tatttgtttc | actatagagt | aatagaaaac | 1380 |

```
aggaaaatga ttatatgtta tagagttatt tttccaaata ttatagggtt taggttgttt    1440
gtattgttct gctttcatcc tctcatgctt ttttcttaa tttattatat ttttgcatta    1500
taatttcgtt tcattgtaac aaacattaaa aagaccacat ggagaaagga aaaaaagag    1560 ag                                                                  1562
```

<210> SEQ ID NO 102
<211> LENGTH: 391
<212> TYPE: PRT
<213> ORGANISM: Arabidopsis thaliana
<220> FEATURE:
<223> OTHER INFORMATION: G1794 polypeptide

<400> SEQUENCE: 102

Met Cys Val Leu Lys Val Ala Asn Gln Glu Asp Asn Val Gly Lys Lys
1               5                   10                  15

Ala Glu Ser Ile Arg Asp Asp His Arg Thr Leu Ser Glu Ile Asp
            20                  25                  30

Gln Trp Leu Tyr Leu Phe Ala Ala Glu Asp Asp His His Arg His Ser
        35                  40                  45

Phe Pro Thr Gln Gln Pro Pro Ser Ser Ser Ser Ser Ser Leu Ile
    50                  55                  60

Ser Gly Phe Ser Arg Glu Met Glu Met Ser Ala Ile Val Ser Ala Leu
65                  70                  75                  80

Thr His Val Val Ala Gly Asn Val Pro Gln His Gln Gln Gly Gly
                85                  90                  95

Glu Gly Ser Gly Glu Gly Thr Ser Asn Ser Ser Ser Ser Gly Gln
            100                 105                 110

Lys Arg Arg Arg Glu Val Glu Glu Gly Gly Ala Lys Ala Val Lys Ala
        115                 120                 125

Ala Asn Thr Leu Thr Val Asp Gln Tyr Phe Ser Gly Gly Ser Ser Thr
    130                 135                 140

Ser Lys Val Arg Glu Ala Ser Ser Asn Met Ser Gly Pro Gly Pro Thr
145                 150                 155                 160

Tyr Glu Tyr Thr Thr Thr Ala Thr Ala Ser Ser Glu Thr Ser Ser Phe
                165                 170                 175

Ser Gly Asp Gln Pro Arg Arg Arg Tyr Arg Gly Val Arg Gln Arg Pro
            180                 185                 190

Trp Gly Lys Trp Ala Ala Glu Ile Arg Asp Pro Phe Lys Ala Ala Arg
        195                 200                 205

Val Trp Leu Gly Thr Phe Asp Asn Ala Glu Ser Ala Ala Arg Ala Tyr
    210                 215                 220

Asp Glu Ala Ala Leu Arg Phe Arg Gly Asn Lys Ala Lys Leu Asn Phe
225                 230                 235                 240

Pro Glu Asn Val Lys Leu Val Arg Pro Ala Ser Thr Glu Ala Gln Pro
                245                 250                 255

Val His Gln Thr Ala Ala Gln Arg Pro Thr Gln Ser Arg Asn Ser Gly
            260                 265                 270

Ser Thr Thr Thr Leu Leu Pro Ile Arg Pro Ala Ser Asn Gln Ser Val
        275                 280                 285

His Ser Gln Pro Leu Met Gln Ser Tyr Asn Leu Ser Tyr Ser Glu Met
    290                 295                 300

Ala Arg Gln Gln Gln Gln Phe Gln Gln His Gln Gln Ser Leu Asp
305                 310                 315                 320

Leu Tyr Asp Gln Met Ser Phe Pro Leu Arg Phe Gly His Thr Gly Gly

|  |  |  | 325 |  |  |  | 330 |  |  |  | 335 |
|--|--|--|--|--|--|--|--|--|--|--|--|

Ser Met Met Gln Ser Thr Ser Ser Ser Ser His Ser Arg Pro Leu
          340                    345                    350

Phe Ser Pro Ala Ala Val Gln Pro Pro Pro Glu Ser Ala Ser Glu Thr
          355                    360                    365

Gly Tyr Leu Gln Asp Ile Gln Trp Pro Ser Asp Lys Thr Ser Asn Asn
          370                    375                    380

Tyr Asn Asn Ser Pro Ser Ser
385                      390

```
<210> SEQ ID NO 103
<211> LENGTH: 1456
<212> TYPE: DNA
<213> ORGANISM: Arabidopsis thaliana
<220> FEATURE:
<223> OTHER INFORMATION: G2144

<400> SEQUENCE: 103
```

| | | | | |
|---|---|---|---|---|
| attagggttt | tgttgtcgtg | agatttgatt | acacaaattg ctgaatttgg tttcgattat | 60 |
| tggtgttatt | gttttcgaag | atttccagtg | agtttccgtt tatggatctg actgaggat | 120 |
| ttggagctag | atccggcggt | gttggaccgt | gccgggaacc aataggcctt gaatcgctac | 180 |
| atctcggtga | cgaatttcgg | caactagtga | cgactttacc tcccgagaac cccggcggtt | 240 |
| cgttcacggc | tttgcttgag | cttccaccta | cacaagcagt ggagcttctc catttcactg | 300 |
| attcttcgtc | ttctcaacaa | gcggcagtga | cagggatcgg tggagagatt cctccgccgc | 360 |
| ttcactcttt | cggtgggaca | ttggcttttc | cttctaactc agttctcatg gagcgagcag | 420 |
| ctcgtttctc | ggtgattgcc | actgagcaac | aaaacggaaa tatctccggg gagactccga | 480 |
| cgagctctgt | accttccaat | tcaagtgcta | atctcgacag agtcaagacg gagcctgctg | 540 |
| agaccgattc | atctcagcgg | ttgatttctg | attcagcgat tgagaatcaa atcccttgcc | 600 |
| ctaaccagaa | caatcgaaat | gggaagagga | agatttcga aagaagggt aaaagctcga | 660 |
| cgaagaagaa | caaagctct | gaagagaacg | agaagctgcc atatgttcac gttagagctc | 720 |
| gtcgtggtca | agcaaccgat | agccatagct | agcagaacg agcaagaaga gagaagataa | 780 |
| atgcacgaat | gaagctgtta | caggaactgg | tcccaggctg tgataagatt caaggtaccg | 840 |
| cgctggtgct | ggatgaaatc | attaaccatg | tccagtcatt acaacgtcaa gtggagatgc | 900 |
| tatcaatgag | acttgctgcg | gtaaaccca | gaatcgactt caatctcgac accatattgg | 960 |
| cttcagaaaa | cggttcttta | atggatggga | gcttcaatgc cgcaccaatg cagcttgctt | 1020 |
| ggcctcagca | agccattgag | accgaacagt | cctttcatca ccggcaactg caacaaccac | 1080 |
| caacacaaca | atggcctttt | gacggcttga | accagccggt atggggaaga gaagaggatc | 1140 |
| aagctcatgg | caatgataac | agcaatttga | tggcagtttc tgaaaatgta atggtggctt | 1200 |
| ctgctaattt | gcacccaaat | caggtcaaaa | tggagctgta agttgggaaa acggtagaga | 1260 |
| tcatgaatgt | gtatatacat | cgtataagct | cgtttctctc tatataaata taatcataaa | 1320 |
| tatagatatc | tgttaagaag | gtatcagtca | tttgattcag agagacaaca ctggtatgat | 1380 |
| tgtttcttat | tcttgtacca | gatttcgaca | atgtagaatt tagtaggata tgatcatttt | 1440 |
| gatctcgtta | tatata | | | 1456 |

```
<210> SEQ ID NO 104
<211> LENGTH: 379
<212> TYPE: PRT
<213> ORGANISM: Arabidopsis thaliana
```

<220> FEATURE:
<223> OTHER INFORMATION: G2144 polypeptide

<400> SEQUENCE: 104

| | | | | | | | | | | | | | | |
|---|---|---|---|---|---|---|---|---|---|---|---|---|---|---|
| Met | Asp | Leu | Thr | Gly | Gly | Phe | Gly | Ala | Arg | Ser | Gly | Val | Gly | Pro |
| 1 | | | | 5 | | | | | 10 | | | | | 15 |
| Cys | Arg | Glu | Pro | Ile | Gly | Leu | Glu | Ser | Leu | His | Leu | Gly | Asp | Glu | Phe |
| | | | 20 | | | | | 25 | | | | | 30 | |
| Arg | Gln | Leu | Val | Thr | Thr | Leu | Pro | Glu | Asn | Pro | Gly | Ser | Phe |
| | | 35 | | | | | 40 | | | | | 45 | |
| Thr | Ala | Leu | Leu | Glu | Leu | Pro | Pro | Thr | Gln | Ala | Val | Glu | Leu | Leu | His |
| 50 | | | | | 55 | | | | | 60 | | | | | |
| Phe | Thr | Asp | Ser | Ser | Ser | Gln | Gln | Ala | Ala | Val | Thr | Gly | Ile | Gly |
| 65 | | | | | 70 | | | | | 75 | | | | | 80 |
| Gly | Glu | Ile | Pro | Pro | Pro | Leu | His | Ser | Phe | Gly | Gly | Thr | Leu | Ala | Phe |
| | | | | 85 | | | | | 90 | | | | | 95 | |
| Pro | Ser | Asn | Ser | Val | Leu | Met | Glu | Arg | Ala | Ala | Arg | Phe | Ser | Val | Ile |
| | | | 100 | | | | | 105 | | | | | 110 | |
| Ala | Thr | Glu | Gln | Gln | Asn | Gly | Asn | Ile | Ser | Gly | Glu | Thr | Pro | Thr | Ser |
| | | 115 | | | | | 120 | | | | | 125 | |
| Ser | Val | Pro | Ser | Asn | Ser | Ser | Ala | Asn | Leu | Asp | Arg | Val | Lys | Thr | Glu |
| 130 | | | | | 135 | | | | | 140 | | | | | |
| Pro | Ala | Glu | Thr | Asp | Ser | Ser | Gln | Arg | Leu | Ile | Ser | Asp | Ser | Ala | Ile |
| 145 | | | | | 150 | | | | | 155 | | | | | 160 |
| Glu | Asn | Gln | Ile | Pro | Cys | Pro | Asn | Gln | Asn | Arg | Asn | Gly | Lys | Arg |
| | | | | 165 | | | | | 170 | | | | | 175 |
| Lys | Asp | Phe | Glu | Lys | Lys | Gly | Lys | Ser | Ser | Thr | Lys | Lys | Asn | Lys | Ser |
| | | | 180 | | | | | 185 | | | | | 190 | |
| Ser | Glu | Glu | Asn | Glu | Lys | Leu | Pro | Tyr | Val | His | Val | Arg | Ala | Arg | Arg |
| | | 195 | | | | | 200 | | | | | 205 | |
| Gly | Gln | Ala | Thr | Asp | Ser | His | Ser | Leu | Ala | Glu | Arg | Ala | Arg | Arg | Glu |
| | | 210 | | | | | 215 | | | | | 220 | |
| Lys | Ile | Asn | Ala | Arg | Met | Lys | Leu | Leu | Gln | Glu | Leu | Val | Pro | Gly | Cys |
| 225 | | | | | 230 | | | | | 235 | | | | | 240 |
| Asp | Lys | Ile | Gln | Gly | Thr | Ala | Leu | Val | Leu | Asp | Glu | Ile | Ile | Asn | His |
| | | | | 245 | | | | | 250 | | | | | 255 |
| Val | Gln | Ser | Leu | Gln | Arg | Gln | Val | Glu | Met | Leu | Ser | Met | Arg | Leu | Ala |
| | | | 260 | | | | | 265 | | | | | 270 | |
| Ala | Val | Asn | Pro | Arg | Ile | Asp | Phe | Asn | Leu | Asp | Thr | Ile | Leu | Ala | Ser |
| | | 275 | | | | | 280 | | | | | 285 | |
| Glu | Asn | Gly | Ser | Leu | Met | Asp | Gly | Ser | Phe | Asn | Ala | Ala | Pro | Met | Gln |
| | 290 | | | | | 295 | | | | | 300 | |
| Leu | Ala | Trp | Pro | Gln | Gln | Ala | Ile | Glu | Thr | Glu | Gln | Ser | Phe | His | His |
| 305 | | | | | 310 | | | | | 315 | | | | | 320 |
| Arg | Gln | Leu | Gln | Gln | Pro | Pro | Thr | Gln | Gln | Trp | Pro | Phe | Asp | Gly | Leu |
| | | | 325 | | | | | 330 | | | | | 335 | |
| Asn | Gln | Pro | Val | Trp | Gly | Arg | Glu | Glu | Asp | Gln | Ala | His | Gly | Asn | Asp |
| | | | 340 | | | | | 345 | | | | | 350 | |
| Asn | Ser | Asn | Leu | Met | Ala | Val | Ser | Glu | Asn | Val | Met | Val | Ala | Ser | Ala |
| | | | 355 | | | | | 360 | | | | | 365 | |
| Asn | Leu | His | Pro | Asn | Gln | Val | Lys | Met | Glu | Leu |
| | | 370 | | | | | 375 | | | |

<210> SEQ ID NO 105

<211> LENGTH: 832
<212> TYPE: DNA
<213> ORGANISM: Arabidopsis thaliana
<220> FEATURE:
<223> OTHER INFORMATION: G2512

<400> SEQUENCE: 105

```
aacttagtgc cacttagaca caataagaaa accgttaaca agaagaaaaa aaaaagatcg    60
aaaatggaat atcaaactaa cttcttaagt ggagagtttt ccccggagaa ctcttcttca   120
agctcatgga gctcacaaga atcattcttg tgggaagaga gtttcttaca tcaatcattt   180
gaccaatcct tcctttatc tagccctact gataactact gtgatgactt ctttgcattt    240
gaatcatcaa tcataaaaga agaaggaaaa gaagccaccg tggcggccga ggaggaggag   300
aagtcataca gaggagtgag gaaacggccg tggggggaaat tcgcggccga gataagagac   360
tcaacgagga aagggataag agtgtggctt gggacattcg acaccgcgga ggcggcggct   420
ctcgcttatg atcaggcggc tttcgctttg aaaggcagcc tcgcagtact caatttcccc   480
gcggatgtcg ttgaagaatc tctccggaag atggagaatg tgaatctcaa tgatggagag   540
tctccggtga tagccttgaa gagaaaacac tccatgagaa accgtcctag aggaaagaag   600
aaatcttctt cttcttcgac gttgacatct tctccttctt cctcctcctc ctattcatct   660
tcttcgtctt cttcttcttt gtcgtcaaga agtagaaaac agagtgttgt tatgacgcaa   720
gaaagtaata caacacttgt ggttcttgag gatttaggtg ctgaatactt agaagagctt   780
atgagatcat gttcttgata atctctgctt ctacaatttt tatgtaattt ga            832
```

<210> SEQ ID NO 106
<211> LENGTH: 244
<212> TYPE: PRT
<213> ORGANISM: Arabidopsis thaliana
<220> FEATURE:
<223> OTHER INFORMATION: G2512 polypeptide

<400> SEQUENCE: 106

```
Met Glu Tyr Gln Thr Asn Phe Leu Ser Gly Glu Phe Ser Pro Glu Asn
1               5                   10                  15

Ser Ser Ser Ser Ser Trp Ser Ser Gln Glu Ser Phe Leu Trp Glu Glu
                20                  25                  30

Ser Phe Leu His Gln Ser Phe Asp Gln Ser Phe Leu Leu Ser Ser Pro
            35                  40                  45

Thr Asp Asn Tyr Cys Asp Asp Phe Phe Ala Phe Glu Ser Ser Ile Ile
        50                  55                  60

Lys Glu Glu Gly Lys Glu Ala Thr Val Ala Ala Glu Glu Glu Glu Lys
65                  70                  75                  80

Ser Tyr Arg Gly Val Arg Lys Arg Pro Trp Gly Lys Phe Ala Ala Glu
                85                  90                  95

Ile Arg Asp Ser Thr Arg Lys Gly Ile Arg Val Trp Leu Gly Thr Phe
            100                 105                 110

Asp Thr Ala Glu Ala Ala Ala Leu Ala Tyr Asp Gln Ala Ala Phe Ala
        115                 120                 125

Leu Lys Gly Ser Leu Ala Val Leu Asn Phe Pro Ala Asp Val Val Glu
    130                 135                 140

Glu Ser Leu Arg Lys Met Glu Asn Val Asn Leu Asn Asp Gly Glu Ser
145                 150                 155                 160

Pro Val Ile Ala Leu Lys Arg Lys His Ser Met Arg Asn Arg Pro Arg
                165                 170                 175
```

```
Gly Lys Lys Lys Ser Ser Ser Ser Thr Leu Thr Ser Ser Pro Ser
            180                 185                 190

Ser Ser Ser Tyr Ser Ser Ser Ser Ser Ser Ser Leu Ser Ser
            195                 200                 205

Arg Ser Arg Lys Gln Ser Val Val Met Thr Gln Glu Ser Asn Thr Thr
        210                 215                 220

Leu Val Val Leu Glu Asp Leu Gly Ala Glu Tyr Leu Glu Glu Leu Met
225                 230                 235                 240

Arg Ser Cys Ser

<210> SEQ ID NO 107
<211> LENGTH: 1182
<212> TYPE: DNA
<213> ORGANISM: Arabidopsis thaliana
<220> FEATURE:
<223> OTHER INFORMATION: G2552

<400> SEQUENCE: 107
```

| | | | | | |
|---|---|---|---|---|---|
| cacaaatgga | aggaagagtc | aacgctctgt | caaacataaa | cgatctcgaa | cttcacaatt | 60 |
| tcttggtcga | tccaaacttc | gatcagttca | taaacctcat | aagaggagat | catcaaacca | 120 |
| ttgacgaaaa | cccagttctt | gatttcgatc | ttggtccatt | acaaaacagc | ccctgtttca | 180 |
| tagacgagaa | ccagttcatc | ccaacacctg | tcgatgacct | cttcgacgaa | ttgcctgact | 240 |
| tagactccaa | cgttgctgaa | tcattccgta | gcttcgacgg | tgatagtgtt | agagccggtg | 300 |
| gtgaagaaga | tgaagaagat | acaacgacg | gtgatgattc | ttcagccact | actacgaata | 360 |
| atgatgggac | ccgtaagacg | aagactgatc | ggtctaggac | tttgatctct | gagagaagaa | 420 |
| ggagagggcg | tatgaaggat | aagctttatg | cattgagatc | tcttgttccc | aatattacta | 480 |
| agatggataa | agcatccatt | gttggagatg | cagtgttgta | tgttcaagaa | cttcagtcac | 540 |
| aagcgaagaa | actcaaatcc | gatatcgcgg | gtcttgaagc | ttctttaaac | tctactggag | 600 |
| ggtaccaaga | acatgctcct | gatgctcaaa | agactcaacc | ttttcgcggt | atcaatcctc | 660 |
| ctgcttccaa | aaaaatcatt | cagatggatg | ttatacaagt | ggaggagaaa | gggttttatg | 720 |
| tgagattggt | gtgtaacaaa | ggagaaggtg | ttgctccatc | tctttacaag | tctttggagt | 780 |
| ctcttacaag | tttccaagtg | cagaactcta | acctaagctc | tccttctccg | gacacatacc | 840 |
| tcttaacata | taccttagat | gggacatgct | tcgaacagag | cttaaacttg | cctaacctga | 900 |
| agctgtggat | cactggatca | ctttaaatc | aaggttttga | attcatcaag | tcatttactt | 960 |
| gattctataa | cgcttgctct | aacgtgagtc | aaatccggtt | ctgcactata | ttgattgtgt | 1020 |
| accttctta | catgtttcat | aacttccagg | gctctaattt | ctattctagt | gatgatgtaa | 1080 |
| ccgagattgt | tgattctcta | ttgaataaac | accatgttat | atagtaattt | agcgacaaat | 1140 |
| tgtatggtta | aatgaagtaa | tatttatgtt | ttgtttataa | aa | | 1182 |

```
<210> SEQ ID NO 108
<211> LENGTH: 318
<212> TYPE: PRT
<213> ORGANISM: Arabidopsis thaliana
<220> FEATURE:
<223> OTHER INFORMATION: G2552 polypeptide

<400> SEQUENCE: 108

Met Glu Gly Arg Val Asn Ala Leu Ser Asn Ile Asn Asp Leu Glu Leu
1               5                   10                  15

His Asn Phe Leu Val Asp Pro Asn Phe Asp Gln Phe Ile Asn Leu Ile
            20                  25                  30
```

```
Arg Gly Asp His Gln Thr Ile Asp Glu Asn Pro Val Leu Asp Phe Asp
         35                  40                  45
Leu Gly Pro Leu Gln Asn Ser Pro Cys Phe Ile Asp Glu Asn Gln Phe
     50                  55                  60
Ile Pro Thr Pro Val Asp Asp Leu Phe Asp Glu Leu Pro Asp Leu Asp
 65                  70                  75                  80
Ser Asn Val Ala Glu Ser Phe Arg Ser Phe Asp Gly Asp Ser Val Arg
                 85                  90                  95
Ala Gly Glu Glu Asp Glu Glu Asp Tyr Asn Asp Gly Asp Asp Ser
            100                 105                 110
Ser Ala Thr Thr Thr Asn Asn Asp Gly Thr Arg Lys Thr Lys Thr Asp
        115                 120                 125
Arg Ser Arg Thr Leu Ile Ser Glu Arg Arg Arg Gly Arg Met Lys
    130                 135                 140
Asp Lys Leu Tyr Ala Leu Arg Ser Leu Val Pro Asn Ile Thr Lys Met
145                 150                 155                 160
Asp Lys Ala Ser Ile Val Gly Asp Ala Val Leu Tyr Val Gln Glu Leu
                165                 170                 175
Gln Ser Gln Ala Lys Lys Leu Lys Ser Asp Ile Ala Gly Leu Glu Ala
            180                 185                 190
Ser Leu Asn Ser Thr Gly Gly Tyr Gln Glu His Ala Pro Asp Ala Gln
        195                 200                 205
Lys Thr Gln Pro Phe Arg Gly Ile Asn Pro Pro Ala Ser Lys Lys Ile
    210                 215                 220
Ile Gln Met Asp Val Ile Gln Val Glu Glu Lys Gly Phe Tyr Val Arg
225                 230                 235                 240
Leu Val Cys Asn Lys Gly Glu Gly Val Ala Pro Ser Leu Tyr Lys Ser
                245                 250                 255
Leu Glu Ser Leu Thr Ser Phe Gln Val Gln Asn Ser Asn Leu Ser Ser
            260                 265                 270
Pro Ser Pro Asp Thr Tyr Leu Leu Thr Tyr Thr Leu Asp Gly Thr Cys
        275                 280                 285
Phe Glu Gln Ser Leu Asn Leu Pro Asn Leu Lys Leu Trp Ile Thr Gly
    290                 295                 300
Ser Leu Leu Asn Gln Gly Phe Glu Phe Ile Lys Ser Phe Thr
305                 310                 315

<210> SEQ ID NO 109
<211> LENGTH: 1613
<212> TYPE: DNA
<213> ORGANISM: Arabidopsis thaliana
<220> FEATURE:
<223> OTHER INFORMATION: G264

<400> SEQUENCE: 109
cttgtaccag tttctgatta gattcaacaa tgaacggcgc attaggtaac tcctccgcct      60
ccgttagcgg cggagaagga gccggaggac cagcgccttt cttggtgaaa acctacgaga     120
tggtcgacga ttcatcaacg gaccagatcg tatcgtggag cgctaacaac aacagcttca     180
tcgtttggaa tcatgccgaa ttttcacgcc tccttcttcc aacctacttc aaacacaata     240
acttctcttc cttcattcgt cagctcaata cctatgggtt taggaagatt gatccagaga     300
ggtgggagtt tttgaatgat gattttatta aggatcagaa gcatcttctc aagaatatac     360
atagaaggaa acctatacac agccacagtc atccacctgc ttcgtcgact gatcaagaaa     420
```

-continued

```
gagcagtgtt gcaagagcaa atggacaagc tttcacgtga gaaagctgca attgaagcta      480
agcttttaaa gttcaaacaa cagaaggttg tagcaaagca tcagtttgaa gaaatgactg      540
agcatgttga tgatatggag aataggcaga agaagctgct gaattttttg gaaactgcga      600
ttcggaatcc tacttttgtt aagaattttg gtaagaaagt cgagcagttg gatatttcag      660
cttacaacaa aaagcgaagg ctccctgaag ttgagcaatc aaagccacct tcagaagatt      720
ctcatctgga taatagtagt ggtagctcga cgcgagtc tggaaacatt ttcatcaaa        780 atttctctaa taaattgcga ctagagcttt ctccagctga ttcagatatg aacatggttt      840
cacacagtat acaaagttcc aatgaagaag gtgcgagtcc caagggata ctgtcaggag       900 gtgatccaaa tactacacta acaaaaagag aaggcctacc atttgcacct gaagctctag      960
agcttgcgga taccgggaca tgcccgagga gattactgtt aaatgataat acaagggtgg     1020
agaccttgca gcagaggcta acttcttcag aggagactga tggtagcttt tcatgtcatt     1080
taaatctaac cctggcttct gctccgttac cggacaaaac agcttcacag atagctaaga     1140
cgactcttaa aagtcaggag ttaaacttta actcaataga aacaagtgca agtgagaaaa     1200
atcggggtag acaagagatt gcagttggag gtagccaagc aaatgcagct cctccagcaa     1260
gagtgaatga tgtattctgg gaacagttcc taacagaaag gccagggtct tcagataatg     1320
aggaggcaag ttcgacttat agaggtaacc catacgaaga gcaagaggag aaaagaaacg     1380
ggagtatgat gttacgtaat acaaagaata tcgagcagct gaccttataa actatttgga     1440
cggttacatc aacgagagta cgaactgagg ttttggtaag aagtatgggt gagtaagtaa     1500
tgaaacattg gactgaaaaa gcgtaagtag ctttgttgta aacacttgcg tctctgtcta     1560
cacaagtaat tgactgtaa atgtaagtgt acaggattta aattgaataa gca             1613
```

<210> SEQ ID NO 110
<211> LENGTH: 466
<212> TYPE: PRT
<213> ORGANISM: Arabidopsis thaliana
<220> FEATURE:
<223> OTHER INFORMATION: G264 polypeptide

<400> SEQUENCE: 110

```
Met Asn Gly Ala Leu Gly Asn Ser Ser Ala Ser Val Ser Gly Gly Glu
1               5                   10                  15

Gly Ala Gly Gly Pro Ala Pro Phe Leu Val Lys Thr Tyr Glu Met Val
                20                  25                  30

Asp Asp Ser Ser Thr Asp Gln Ile Val Ser Trp Ser Ala Asn Asn Asn
            35                  40                  45

Ser Phe Ile Val Trp Asn His Ala Glu Phe Ser Arg Leu Leu Leu Pro
        50                  55                  60

Thr Tyr Phe Lys His Asn Asn Phe Ser Phe Ile Arg Gln Leu Asn
65                  70                  75                  80

Thr Tyr Gly Phe Arg Lys Ile Asp Pro Glu Arg Trp Glu Phe Leu Asn
                85                  90                  95

Asp Asp Phe Ile Lys Asp Gln Lys His Leu Leu Lys Asn Ile His Arg
            100                 105                 110

Arg Lys Pro Ile His Ser His Ser His Pro Ala Ser Ser Thr Asp
        115                 120                 125

Gln Glu Arg Ala Val Leu Gln Glu Gln Met Asp Lys Leu Ser Arg Glu
    130                 135                 140

Lys Ala Ala Ile Glu Ala Lys Leu Leu Lys Phe Lys Gln Gln Lys Val
145                 150                 155                 160
```

```
Val Ala Lys His Gln Phe Glu Glu Met Thr Glu His Val Asp Asp Met
            165                 170                 175

Glu Asn Arg Gln Lys Lys Leu Leu Asn Phe Leu Glu Thr Ala Ile Arg
            180                 185                 190

Asn Pro Thr Phe Val Lys Asn Phe Gly Lys Val Glu Gln Leu Asp
            195                 200                 205

Ile Ser Ala Tyr Asn Lys Lys Arg Arg Leu Pro Glu Val Glu Gln Ser
            210                 215                 220

Lys Pro Pro Ser Glu Asp Ser His Leu Asp Asn Ser Ser Gly Ser Ser
225                 230                 235                 240

Arg Arg Glu Ser Gly Asn Ile Phe His Gln Asn Phe Ser Asn Lys Leu
            245                 250                 255

Arg Leu Glu Leu Ser Pro Ala Asp Ser Asp Met Asn Met Val Ser His
            260                 265                 270

Ser Ile Gln Ser Ser Asn Glu Glu Gly Ala Ser Pro Lys Gly Ile Leu
            275                 280                 285

Ser Gly Gly Asp Pro Asn Thr Thr Leu Thr Lys Arg Glu Gly Leu Pro
            290                 295                 300

Phe Ala Pro Glu Ala Leu Glu Leu Ala Asp Thr Gly Thr Cys Pro Arg
305                 310                 315                 320

Arg Leu Leu Leu Asn Asp Asn Thr Arg Val Glu Thr Leu Gln Gln Arg
            325                 330                 335

Leu Thr Ser Ser Glu Glu Thr Asp Gly Ser Phe Ser Cys His Leu Asn
            340                 345                 350

Leu Thr Leu Ala Ser Ala Pro Leu Pro Asp Lys Thr Ala Ser Gln Ile
            355                 360                 365

Ala Lys Thr Thr Leu Lys Ser Gln Glu Leu Asn Phe Asn Ser Ile Glu
            370                 375                 380

Thr Ser Ala Ser Glu Lys Asn Arg Gly Arg Gln Glu Ile Ala Val Gly
385                 390                 395                 400

Gly Ser Gln Ala Asn Ala Ala Pro Pro Ala Arg Val Asn Asp Val Phe
            405                 410                 415

Trp Glu Gln Phe Leu Thr Glu Arg Pro Gly Ser Ser Asp Asn Glu Glu
            420                 425                 430

Ala Ser Ser Thr Tyr Arg Gly Asn Pro Tyr Glu Glu Gln Glu Glu Lys
            435                 440                 445

Arg Asn Gly Ser Met Met Leu Arg Asn Thr Lys Asn Ile Glu Gln Leu
450                 455                 460

Thr Leu
465

<210> SEQ ID NO 111
<211> LENGTH: 840
<212> TYPE: DNA
<213> ORGANISM: Arabidopsis thaliana
<220> FEATURE:
<223> OTHER INFORMATION: G681

<400> SEQUENCE: 111
atggggagga cgacatggtt cgacgtcgac gggatgaaga aaggagagtg gacggcagag      60
gaagaccaga agctcggcgc ttacatcaac gagcatggcg tttgtgattg gcgttccctc     120
cccaaaagag ctggttttgca gagatgtgga aagagctgca gattaaggtg gcttaactat     180
ctaaagcctg ggattagaag aggcaaattc actcctcaag aagaagaaga aatcatccaa     240
```

```
cttcatgctg ttctcggaaa caggtgggca gccatggcga agaagatgca gaatcgaaca    300
gacaatgata tcaagaacca ttggaactct tgtctcaaga aaagactttc gagaaaggga    360
atcgaccctg tgaccacga gcccatcatc aaacacctca ccgtcaatac cactaacgca    420
gattgtggta actcttccac cacgacgtcc ccgtcgacga cggaaagctc tccttcctcc    480
ggctcgtctc gtcttcttaa caaactcgcc gcaggtatct catctagaca acatagtctc    540
gataggatca agtacatctt gtcgaattca ataatcgaaa gcagtgatca agcaaaagag    600
gaagaagaaa aagaagaaga agaagaagaa agagattcaa tgatgggtca agagattgac    660
ggtagtgaag gagaagatat tcagatttgg ggcgaggagg aagttaggcg tttaatggag    720
attgatgcaa tggatatgta cgagatgact tcgtacgacg ctgtcatgta cgagagtagt    780
cacatacttg atcatctctt ttgacttaat atagtgtgac tgtgtgagtg catgcatgtt    840
```

```
<210> SEQ ID NO 112
<211> LENGTH: 267
<212> TYPE: PRT
<213> ORGANISM: Arabidopsis thaliana
<220> FEATURE:
<223> OTHER INFORMATION: G681 polypeptide

<400> SEQUENCE: 112

Met Gly Arg Thr Thr Trp Phe Asp Val Asp Gly Met Lys Lys Gly Glu
1               5                   10                  15

Trp Thr Ala Glu Glu Asp Gln Lys Leu Gly Ala Tyr Ile Asn Glu His
            20                  25                  30

Gly Val Cys Asp Trp Arg Ser Leu Pro Lys Arg Ala Gly Leu Gln Arg
        35                  40                  45

Cys Gly Lys Ser Cys Arg Leu Arg Trp Leu Asn Tyr Leu Lys Pro Gly
    50                  55                  60

Ile Arg Arg Gly Lys Phe Thr Pro Gln Glu Glu Glu Ile Ile Gln
65                  70                  75                  80

Leu His Ala Val Leu Gly Asn Arg Trp Ala Ala Met Ala Lys Lys Met
                85                  90                  95

Gln Asn Arg Thr Asp Asn Asp Ile Lys Asn His Trp Asn Ser Cys Leu
            100                 105                 110

Lys Lys Arg Leu Ser Arg Lys Gly Ile Asp Pro Met Thr His Glu Pro
        115                 120                 125

Ile Ile Lys His Leu Thr Val Asn Thr Thr Asn Ala Asp Cys Gly Asn
    130                 135                 140

Ser Ser Thr Thr Thr Ser Pro Ser Thr Thr Glu Ser Ser Pro Ser Ser
145                 150                 155                 160

Gly Ser Ser Arg Leu Leu Asn Lys Leu Ala Ala Gly Ile Ser Ser Arg
                165                 170                 175

Gln His Ser Leu Asp Arg Ile Lys Tyr Ile Leu Ser Asn Ser Ile Ile
            180                 185                 190

Glu Ser Ser Asp Gln Ala Lys Glu Glu Glu Lys Glu Glu Glu Glu
        195                 200                 205

Glu Glu Arg Asp Ser Met Met Gly Gln Lys Ile Asp Gly Ser Glu Gly
    210                 215                 220

Glu Asp Ile Gln Ile Trp Gly Glu Glu Val Arg Arg Leu Met Glu
225                 230                 235                 240

Ile Asp Ala Met Asp Met Tyr Glu Met Thr Ser Tyr Asp Ala Val Met
                245                 250                 255

Tyr Glu Ser Ser His Ile Leu Asp His Leu Phe
```

<210> SEQ ID NO 113
<211> LENGTH: 476
<212> TYPE: DNA
<213> ORGANISM: Arabidopsis thaliana
<220> FEATURE:
<223> OTHER INFORMATION: G1012

<400> SEQUENCE: 113

```
aacacacaat tcgttgattc atcatatctc ctcttcatta atgaatggcc tcgtcgactc      60
ttctcgagat aagaagatga aaatccgcg attttcgttt cgcacaaaga gtgatgcaga     120
tattctcgat gatggttatc gatggagaaa gtacggtcag aaatccgtca agaacagctt    180
gtatcccagg agctattata gatgcacaca acacatgtgt aacgtgaaga agcaagttca    240
gaggctgtcg aaggagacga gcattgtgga gacaacttat gaaggaatcc ataaccatcc    300
ttgtgaggag ctcatgcaaa ccctaactcc tcttcttcat caattgcagt tcctctctaa    360
gttcacctaa ttatgtttgt atatatatta acgttctaag agcatctcca atggaagtat    420
ctcaatgaga tacctaacaa aagaaaaaaa atttaaaaaa aaaaaaaaaa aaaaaa         476
```

<210> SEQ ID NO 114
<211> LENGTH: 109
<212> TYPE: PRT
<213> ORGANISM: Arabidopsis thaliana
<220> FEATURE:
<223> OTHER INFORMATION: G1012 polypeptide

<400> SEQUENCE: 114

Met Asn Gly Leu Val Asp Ser Ser Arg Asp Lys Lys Met Lys Asn Pro
1               5                   10                  15

Arg Phe Ser Phe Arg Thr Lys Ser Asp Ala Asp Ile Leu Asp Asp Gly
            20                  25                  30

Tyr Arg Trp Arg Lys Tyr Gly Gln Lys Ser Val Lys Asn Ser Leu Tyr
        35                  40                  45

Pro Arg Ser Tyr Tyr Arg Cys Thr Gln His Met Cys Asn Val Lys Lys
    50                  55                  60

Gln Val Gln Arg Leu Ser Lys Glu Thr Ser Ile Val Glu Thr Thr Tyr
65                  70                  75                  80

Glu Gly Ile His Asn His Pro Cys Glu Glu Leu Met Gln Thr Leu Thr
                85                  90                  95

Pro Leu Leu His Gln Leu Gln Phe Leu Ser Lys Phe Thr
            100                 105

<210> SEQ ID NO 115
<211> LENGTH: 912
<212> TYPE: DNA
<213> ORGANISM: Arabidopsis thaliana
<220> FEATURE:
<223> OTHER INFORMATION: G1309

<400> SEQUENCE: 115

```
cgtcgacctc ttaattaaga cgacttgaga gagaaagaaa gatacgtgga agatgaccaa      60
atctggagag agaccaaaac agagacagag gaaagggtta tggtcacctg aagaagacca    120
gaagctcaag agtttcatcc tctctcgtgg ccatgcttgc tggaccactg ttcccatcct    180
agctggattg caaaggaatg ggaaaagctg cagattaagg tggattaatt acctaagacc    240
aggactaaag aggggggtcgt ttagtgaaga agaagaagag accatcttga ctttacattc    300
```

```
ttccttgggt aacaagtggt ctcggattgc aaaatattta ccgggaagaa cagacaacga    360
gattaagaac tattggcatt cctatctgaa gaagagatgg ctcaaatctc aaccacaact    420
caaaagccaa atatcagacc tcacagaatc tccttcttca ctactttctt gcgggaaaag    480
aaatctggaa accgaaaccc tagatcacgt gatctccttc agaaattttt cagagaatcc    540
aacttcatca ccatccaaag aaagcaacaa caacatgatc atgaacaaca gtaataactt    600
gcctaaactg ttcttctctg agtggatcag ttcttcaaat ccacacatcg attactcctc    660
tgcttttaca gattccaagc acattaatga aactcaagat caaatcaatg aagaggaagt    720
gatgatgatc aataacaaca actactcttc acttgaggat gtcatgctcc gtacagattt    780
tttgcagcct gatcatgaat atgcaaatta ttattcttct ggagatttct tcatcaacag    840
tgaccaaaat tatgtctaag aagagtgaat atgatcgtaa gaggaacata agctagttac    900
ttgtgttaca gc                                                        912
```

<210> SEQ ID NO 116
<211> LENGTH: 268
<212> TYPE: PRT
<213> ORGANISM: Arabidopsis thaliana
<220> FEATURE:
<223> OTHER INFORMATION: G1309 polypeptide

<400> SEQUENCE: 116

```
Met Thr Lys Ser Gly Glu Arg Pro Lys Gln Arg Gln Arg Lys Gly Leu
1               5                   10                  15

Trp Ser Pro Glu Glu Asp Gln Lys Leu Lys Ser Phe Ile Leu Ser Arg
            20                  25                  30

Gly His Ala Cys Trp Thr Thr Val Pro Ile Leu Ala Gly Leu Gln Arg
        35                  40                  45

Asn Gly Lys Ser Cys Arg Leu Arg Trp Ile Asn Tyr Leu Arg Pro Gly
    50                  55                  60

Leu Lys Arg Gly Ser Phe Ser Glu Glu Glu Glu Thr Ile Leu Thr
65                  70                  75                  80

Leu His Ser Ser Leu Gly Asn Lys Trp Ser Arg Ile Ala Lys Tyr Leu
                85                  90                  95

Pro Gly Arg Thr Asp Asn Glu Ile Lys Asn Tyr Trp His Ser Tyr Leu
            100                 105                 110

Lys Lys Arg Trp Leu Lys Ser Gln Pro Gln Leu Lys Ser Gln Ile Ser
        115                 120                 125

Asp Leu Thr Glu Ser Pro Ser Ser Leu Leu Ser Cys Gly Lys Arg Asn
    130                 135                 140

Leu Glu Thr Glu Thr Leu Asp His Val Ile Ser Phe Gln Lys Phe Ser
145                 150                 155                 160

Glu Asn Pro Thr Ser Ser Pro Ser Lys Glu Ser Asn Asn Met Ile
                165                 170                 175

Met Asn Asn Ser Asn Asn Leu Pro Lys Leu Phe Ser Glu Trp Ile
            180                 185                 190

Ser Ser Ser Asn Pro His Ile Asp Tyr Ser Ser Ala Phe Thr Asp Ser
        195                 200                 205

Lys His Ile Asn Glu Thr Gln Asp Gln Ile Asn Glu Glu Val Met
    210                 215                 220

Met Ile Asn Asn Asn Asn Tyr Ser Ser Leu Glu Asp Val Met Leu Arg
225                 230                 235                 240

Thr Asp Phe Leu Gln Pro Asp His Glu Tyr Ala Asn Tyr Tyr Ser Ser
                245                 250                 255
```

Gly Asp Phe Phe Ile Asn Ser Asp Gln Asn Tyr Val
             260                 265

<210> SEQ ID NO 117
<211> LENGTH: 1414
<212> TYPE: DNA
<213> ORGANISM: Arabidopsis thaliana
<220> FEATURE:
<223> OTHER INFORMATION: G158

<400> SEQUENCE: 117

| | | | | | |
|---|---|---|---|---|---|
| gatctgggta | ttatagattg | cagattctgg | aaacgtatta | tgttaatgat | tcatttcaag | 60 |
| ttttgatttt | ttgtgttgga | ttgaagagaa | gaatagttta | ttgatgtttt | gtgaagaaga | 120 |
| agaagaagag | attttgattt | tggtttaata | tatagttggg | gattaacagg | atgggaaggg | 180 |
| taaaattgaa | gataaagaag | ttagagaaca | caaatggacg | ccaatctaca | tttgctaaaa | 240 |
| ggaaaaatgg | gatcttgaaa | aaggctaatg | agctatctat | tctttgtgac | attgatattg | 300 |
| ttcttcttat | gttctctcct | actggcaagg | ctgcaatatg | ttgcggtaca | cgaagatgtt | 360 |
| tctctttcga | aagctcagaa | cttgaagaaa | actttccaaa | agttggatca | cgatgtaaat | 420 |
| atacgcgaat | ttatagcctc | aaggacttga | gtactcaagc | aaggattctg | caggctcgga | 480 |
| tttctgagat | acatggaaga | ttaagttatt | ggacggaacc | agataagatt | aacaatgttg | 540 |
| aacacttggg | acagctcgaa | atttcgatta | ggcaatccct | tgatcaattg | cgtgcacaca | 600 |
| agatgcaaga | tgggattcag | attccttag | aacaacagct | tcaatctatg | tcatggattc | 660 |
| ttaatagcaa | caccaccaac | attgtcaccg | aggaacacaa | ttcaatcccg | cagagggaag | 720 |
| tcgagtgctc | agcgagttct | tcattcggga | gctatccagg | ctactttgga | acagggaaat | 780 |
| ctcctgaaat | gacaattccg | ggtcaagaaa | caagctttct | tgatgaacta | aacaccggac | 840 |
| agctgaaaca | ggacacaagc | tcgcagcagc | agttcactaa | taataataat | atcacagcat | 900 |
| acaatcccaa | tcttcacaat | gatatgaatc | atcaccaaac | gttgcctcct | cctcctcttc | 960 |
| ctcttactct | tccgcatgct | caggtgtata | ttccaatgaa | tcagagagag | tatcatatga | 1020 |
| atggattctt | tgaagcacca | ccacctgatt | cttctgctta | caacgacaac | accaaccaaa | 1080 |
| ccaggtttgg | ttctagcagc | agctccttgc | cttgctcaat | ctcaatgttc | gacgaatact | 1140 |
| tgttttccca | gatgcagcag | ccgaactgag | agagatttga | tgaatgatga | taaaacatct | 1200 |
| cactgaagaa | actcaaacca | atatttttt | tcagaaacag | caagaaagct | aaaactctgc | 1260 |
| cgatttctga | attggttcca | agaagaaaaa | aaccagtggt | aatccctggt | agattgtgca | 1320 |
| accaaaccac | acacaatacg | tgttcattta | ttttttctat | atcttcaata | gatgtcactt | 1380 |
| aattcttttc | tatacataat | ttctcagtca | gaat | | | 1414 |

<210> SEQ ID NO 118
<211> LENGTH: 332
<212> TYPE: PRT
<213> ORGANISM: Arabidopsis thaliana
<220> FEATURE:
<223> OTHER INFORMATION: G158 polypeptide

<400> SEQUENCE: 118

Met Gly Arg Val Lys Leu Lys Ile Lys Lys Leu Glu Asn Thr Asn Gly
1               5                   10                  15

Arg Gln Ser Thr Phe Ala Lys Arg Lys Asn Gly Ile Leu Lys Lys Ala
            20                  25                  30

Asn Glu Leu Ser Ile Leu Cys Asp Ile Asp Ile Val Leu Leu Met Phe

```
                35                  40                  45
Ser Pro Thr Gly Lys Ala Ala Ile Cys Cys Gly Thr Arg Arg Cys Phe
 50                  55                  60

Ser Phe Glu Ser Ser Glu Leu Glu Asn Phe Pro Lys Val Gly Ser
 65                  70                  75                  80

Arg Cys Lys Tyr Thr Arg Ile Tyr Ser Leu Lys Asp Leu Ser Thr Gln
                 85                  90                  95

Ala Arg Ile Leu Gln Ala Arg Ile Ser Glu Ile His Gly Arg Leu Ser
                100                 105                 110

Tyr Trp Thr Glu Pro Asp Lys Ile Asn Asn Val Glu His Leu Gly Gln
                115                 120                 125

Leu Glu Ile Ser Ile Arg Gln Ser Leu Asp Gln Leu Arg Ala His Lys
130                 135                 140

Met Gln Asp Gly Ile Gln Ile Pro Leu Glu Gln Gln Leu Gln Ser Met
145                 150                 155                 160

Ser Trp Ile Leu Asn Ser Asn Thr Thr Asn Ile Val Thr Glu Glu His
                165                 170                 175

Asn Ser Ile Pro Gln Arg Glu Val Glu Cys Ser Ala Ser Ser Ser Phe
                180                 185                 190

Gly Ser Tyr Pro Gly Tyr Phe Gly Thr Gly Lys Ser Pro Glu Met Thr
                195                 200                 205

Ile Pro Gly Gln Glu Thr Ser Phe Leu Asp Glu Leu Asn Thr Gly Gln
                210                 215                 220

Leu Lys Gln Asp Thr Ser Ser Gln Gln Gln Phe Thr Asn Asn Asn Asn
225                 230                 235                 240

Ile Thr Ala Tyr Asn Pro Asn Leu His Asn Asp Met Asn His His Gln
                245                 250                 255

Thr Leu Pro Pro Pro Pro Leu Pro Leu Thr Leu Pro His Ala Gln Val
                260                 265                 270

Tyr Ile Pro Met Asn Gln Arg Glu Tyr His Met Asn Gly Phe Phe Glu
                275                 280                 285

Ala Pro Pro Pro Asp Ser Ser Ala Tyr Asn Asp Asn Thr Asn Gln Thr
                290                 295                 300

Arg Phe Gly Ser Ser Ser Ser Ser Leu Pro Cys Ser Ile Ser Met Phe
305                 310                 315                 320

Asp Glu Tyr Leu Phe Ser Gln Met Gln Gln Pro Asn
                325                 330

<210> SEQ ID NO 119
<211> LENGTH: 867
<212> TYPE: DNA
<213> ORGANISM: Arabidopsis thaliana
<220> FEATURE:
<223> OTHER INFORMATION: G1641

<400> SEQUENCE: 119
atggaggtta tgagaccgtc gacgtcacac gtgtcaggtg ggaactggct catggaggaa    60
actaagagcg gcgtcgcagc ttctggtgaa ggtgccacgt ggacggcggc agagaacaag   120
gcattcgaga atgctttggc ggtttacgac gacaacactc ctgatcggtg cagaaggtg    180 gctgcggtga ttccgggaa gacagtgagt gacgtaatta gacagtataa cgatttggaa    240
gctgatgtca gcagcatcga ggccggttta atcccggtcc ccggttacat cacctcgccg   300
cctttcactc tagattgggc cggcggcggt ggcggatgta acgggtttaa accgggtcat   360 caggttttgta ataaacggtc gcaggccggt agatcgccgg agctggagcg gaagaaaggc   420
```

```
gttccttgga cggaggaaga acacaagcta tttctaatgg gtttgaagaa atatgggaaa      480
ggagattgga gaaacatatc tcggaacttt gtgataacgc gaacgccaac acaagtagct      540
agccacgccc aaaagtactt catccggcaa ctttccggcg gcaaggacaa agacgagca       600 agcattcacg acataaccac cgtaaatctc gaagaggagg cttctttgga gaccaataag      660
agctccattg ttgttggaga tcagcgttca aggctaaccg cgtttccttg gaaccaaacg      720
gacaacaatg aacacaggc agacgctttc aatataacga ttggaaacgc tattagtggc       780
gttcattcat acggccaggt tatgattgga gggtataaca atgcagattc ttgctatgac      840
gcccaaaaca caatgtttca actatag                                          867
```

<210> SEQ ID NO 120
<211> LENGTH: 288
<212> TYPE: PRT
<213> ORGANISM: Arabidopsis thaliana
<220> FEATURE:
<223> OTHER INFORMATION: G1641 polypeptide

<400> SEQUENCE: 120

```
Met Glu Val Met Arg Pro Ser Thr Ser His Val Ser Gly Gly Asn Trp
1               5                   10                  15

Leu Met Glu Glu Thr Lys Ser Gly Val Ala Ala Ser Gly Glu Gly Ala
            20                  25                  30

Thr Trp Thr Ala Ala Glu Asn Lys Ala Phe Glu Asn Ala Leu Ala Val
        35                  40                  45

Tyr Asp Asp Asn Thr Pro Asp Arg Trp Gln Lys Val Ala Ala Val Ile
    50                  55                  60

Pro Gly Lys Thr Val Ser Asp Val Ile Arg Gln Tyr Asn Asp Leu Glu
65                  70                  75                  80

Ala Asp Val Ser Ser Ile Glu Ala Gly Leu Ile Pro Val Pro Gly Tyr
                85                  90                  95

Ile Thr Ser Pro Pro Phe Thr Leu Asp Trp Ala Gly Gly Gly Gly
            100                 105                 110

Cys Asn Gly Phe Lys Pro Gly His Gln Val Cys Asn Lys Arg Ser Gln
        115                 120                 125

Ala Gly Arg Ser Pro Glu Leu Glu Arg Lys Gly Val Pro Trp Thr
    130                 135                 140

Glu Glu Glu His Lys Leu Phe Leu Met Gly Leu Lys Lys Tyr Gly Lys
145                 150                 155                 160

Gly Asp Trp Arg Asn Ile Ser Arg Asn Phe Val Ile Thr Arg Thr Pro
                165                 170                 175

Thr Gln Val Ala Ser His Ala Gln Lys Tyr Phe Ile Arg Gln Leu Ser
            180                 185                 190

Gly Gly Lys Asp Lys Arg Arg Ala Ser Ile His Asp Ile Thr Thr Val
        195                 200                 205

Asn Leu Glu Glu Glu Ala Ser Leu Glu Thr Asn Lys Ser Ser Ile Val
    210                 215                 220

Val Gly Asp Gln Arg Ser Arg Leu Thr Ala Phe Pro Trp Asn Gln Thr
225                 230                 235                 240

Asp Asn Asn Gly Thr Gln Ala Asp Ala Phe Asn Ile Thr Ile Gly Asn
                245                 250                 255

Ala Ile Ser Gly Val His Ser Tyr Gly Gln Val Met Ile Gly Gly Tyr
            260                 265                 270

Asn Asn Ala Asp Ser Cys Tyr Asp Ala Gln Asn Thr Met Phe Gln Leu
```

<210> SEQ ID NO 121
<211> LENGTH: 952
<212> TYPE: DNA
<213> ORGANISM: Arabidopsis thaliana
<220> FEATURE:
<223> OTHER INFORMATION: G1865

<400> SEQUENCE: 121

| | | | | | |
|---|---|---|---|---|---|
| aagaagagga | catgaagcac | agagattctg | cagactgcag | gtgaccaatg | gacactttat | 60 |
| caataaaaac | atacctacta | ctctcttaca | ctttcaattt | tccaatacaa | atcccaatct | 120 |
| ttaatctctc | tttcttcttc | atctctcttt | ctctttctct | cttcatggct | acaaggattc | 180 |
| cattcacaga | atcacaatgg | gaagaacttg | aaaaccaagc | tcttgtgttc | aagtacttag | 240 |
| ctgcaaatat | gcctgttcca | cctcatcttc | tcttcctcat | caaaagaccc | tttctcttct | 300 |
| cttcttcttc | ttcttcatct | tcttcttcaa | gcttcttctc | tcccactctt | tctccacact | 360 |
| ttgggtggaa | tgtgtatgag | atgggaatgg | gaagaaagat | agatgcagag | ccaggaagat | 420 |
| gtagaagaac | tgatggcaag | aaatggagat | gctctaaaga | agcttaccct | gactctaagt | 480 |
| actgtgagag | acatatgcat | agaggcaaga | accgttcttc | ctcaagaaag | cctcctccta | 540 |
| ctcaattcac | tccaaatctc | tttctcgact | cttcttccag | aagaagaaga | agtggataca | 600 |
| tggatgattt | cttctccata | gaaccttccg | ggtcaatcaa | aagctgctct | ggctcagcaa | 660 |
| tggaagataa | tgatgatggc | tcatgtgagg | gcatcaacaa | cgaggagaag | cagccggatc | 720 |
| gacattgctt | catccttggt | actgacttga | ggacacgtga | gaggccattg | atgttagagg | 780 |
| agaagctgaa | acaaagagat | catgataatg | aagaagagca | aggaagcaag | aggtttata | 840 |
| ggtttcttga | tgaatggcct | tcttctaaat | cttctgtttc | tacttcactc | ttcatttgat | 900 |
| catcttttgt | tcttataacc | ttgtatttct | tgttaagatg | gtaatgcaaa | tt | 952 |

<210> SEQ ID NO 122
<211> LENGTH: 283
<212> TYPE: PRT
<213> ORGANISM: Arabidopsis thaliana
<220> FEATURE:
<223> OTHER INFORMATION: G1865 polypeptide

<400> SEQUENCE: 122

Met Asp Thr Leu Ser Ile Lys Thr Tyr Leu Leu Ser Tyr Thr Phe
1               5                   10                  15

Asn Phe Pro Ile Gln Ile Pro Ile Phe Asn Leu Ser Phe Phe Ile
                20                  25                  30

Ser Leu Ser Leu Ser Leu Phe Met Ala Thr Arg Ile Pro Phe Thr Glu
        35                  40                  45

Ser Gln Trp Glu Glu Leu Glu Asn Gln Ala Leu Val Phe Lys Tyr Leu
    50                  55                  60

Ala Ala Asn Met Pro Val Pro Pro His Leu Leu Phe Leu Ile Lys Arg
65                  70                  75                  80

Pro Phe Leu Phe Ser Ser Ser Ser Ser Ser Ser Ser Ser Ser Phe
                85                  90                  95

Phe Ser Pro Thr Leu Ser Pro His Phe Gly Trp Asn Val Tyr Glu Met
            100                 105                 110

Gly Met Gly Arg Lys Ile Asp Ala Glu Pro Gly Arg Cys Arg Arg Thr
        115                 120                 125

Asp Gly Lys Lys Trp Arg Cys Ser Lys Glu Ala Tyr Pro Asp Ser Lys

-continued

```
            130                 135                 140
Tyr Cys Glu Arg His Met His Arg Gly Lys Asn Arg Ser Ser Ser Arg
145                 150                 155                 160

Lys Pro Pro Thr Gln Phe Thr Pro Asn Leu Phe Leu Asp Ser Ser
            165                 170                 175

Ser Arg Arg Arg Arg Ser Gly Tyr Met Asp Asp Phe Phe Ser Ile Glu
            180                 185                 190

Pro Ser Gly Ser Ile Lys Ser Cys Ser Gly Ser Ala Met Glu Asp Asn
            195                 200                 205

Asp Asp Gly Ser Cys Arg Gly Ile Asn Asn Glu Glu Lys Gln Pro Asp
210                 215                 220

Arg His Cys Phe Ile Leu Gly Thr Asp Leu Arg Thr Arg Glu Arg Pro
225                 230                 235                 240

Leu Met Leu Glu Glu Lys Leu Lys Gln Arg Asp His Asp Asn Glu Glu
            245                 250                 255

Glu Gln Gly Ser Lys Arg Phe Tyr Arg Phe Leu Asp Glu Trp Pro Ser
            260                 265                 270

Ser Lys Ser Ser Val Ser Thr Ser Leu Phe Ile
            275                 280
```

<210> SEQ ID NO 123
<211> LENGTH: 450
<212> TYPE: DNA
<213> ORGANISM: Arabidopsis thaliana
<220> FEATURE:
<223> OTHER INFORMATION: G2094

<400> SEQUENCE: 123

```
atgctagatc ccaccgagaa agtaatcgat tcagaatcaa tggaaagcaa actcacatca      60
gtagatgcga tcgaagaaca cagcagcagt agcagtaatg aagctatcag caacgagaag     120
aagagttgtg ccatttgtgg taccagcaaa accoctcttt ggcgaggcgg tcctgccggt     180
cccaagtcgc tttgtaacgc atgcgggatc agaaacagaa agaaaagaag aacactgatc     240
tcaaatagat cagaagataa gaagaagaag agtcataaca gaaacccgaa gtttggtgac     300
tcgttgaagc agcgattaat ggaattgggg agagaagtga tgatgcagcg atcaacggct     360
gagaatcaac ggcggaataa gcttggcgaa gaagagcaag ccgccgtgtt actcatggct     420
ctctcttatg cttcttccgt ttatgcttaa                                      450
```

<210> SEQ ID NO 124
<211> LENGTH: 149
<212> TYPE: PRT
<213> ORGANISM: Arabidopsis thaliana
<220> FEATURE:
<223> OTHER INFORMATION: G2094 polypeptide

<400> SEQUENCE: 124

```
Met Leu Asp Pro Thr Glu Lys Val Ile Asp Ser Glu Ser Met Glu Ser
1               5                   10                  15

Lys Leu Thr Ser Val Asp Ala Ile Glu Glu His Ser Ser Ser Ser Ser
            20                  25                  30

Asn Glu Ala Ile Ser Asn Glu Lys Lys Ser Cys Ala Ile Cys Gly Thr
        35                  40                  45

Ser Lys Thr Pro Leu Trp Arg Gly Gly Pro Ala Gly Pro Lys Ser Leu
    50                  55                  60

Cys Asn Ala Cys Gly Ile Arg Asn Arg Lys Lys Arg Arg Thr Leu Ile
65                  70                  75                  80
```

Ser Asn Arg Ser Glu Asp Lys Lys Lys Ser His Asn Arg Asn Pro
                85                  90                  95

Lys Phe Gly Asp Ser Leu Lys Gln Arg Leu Met Glu Leu Gly Arg Glu
            100                 105                 110

Val Met Met Gln Arg Ser Thr Ala Glu Asn Gln Arg Asn Lys Leu
        115                 120                 125

Gly Glu Glu Gln Ala Ala Val Leu Leu Met Ala Leu Ser Tyr Ala
    130                 135                 140

Ser Ser Val Tyr Ala
145

<210> SEQ ID NO 125
<211> LENGTH: 750
<212> TYPE: DNA
<213> ORGANISM: Arabidopsis thaliana
<220> FEATURE:
<223> OTHER INFORMATION: G211

<400> SEQUENCE: 125
atgatgtcat gtggtgggaa gaagccagtg tctaagaaaa caacgccgtg ttgcacgaag     60
atggggatga agagaggacc atggacggtg gaggaagacg agattcttgt gagcttcatt    120
aagaaagaag gtgaaggacg gtggcgatcg cttcctaaga gagctggttt actcagatgt    180
ggaaagagct gtcgtctacg gtggatgaac tatctccgac cctcggttaa acgtggagga    240
attacgtcgg acgaggaaga tctcatcctc cgtcttcacc gcctcctcgg caacaggtgg    300
tcattgatcg cgggaaggat accgggaagg actgataatg aaattaagaa ctattggaac    360
actcatcttc gtaagaaact tttaaggcaa ggaattgatc ctcaaaccca caagcctctt    420
gatgcaaaca acatccataa accagaagaa gaagtttccg gtggacaaaa gtaccctcta    480
gagcctattt ctagttctca tactgatgat accactgtta atggcgggga tggagatagc    540
aagaacagta tcaatgtctt tggtggtgaa cacggctacg aagactttgg tttctgctac    600
gacgacaagt tctcatcgtt tcttaattcg ctcatcaacg atgttggtga tccttttggt    660
aatattatcc caatatctca acctttgcag atggatgatt gtaaggatgg gattgttgga    720
gcgtcgtctt ctagcttagg acatgactag                                     750

<210> SEQ ID NO 126
<211> LENGTH: 249
<212> TYPE: PRT
<213> ORGANISM: Arabidopsis thaliana
<220> FEATURE:
<223> OTHER INFORMATION: G211 polypeptide

<400> SEQUENCE: 126

Met Met Ser Cys Gly Gly Lys Lys Pro Val Ser Lys Lys Thr Thr Pro
1               5                   10                  15

Cys Cys Thr Lys Met Gly Met Lys Arg Gly Pro Trp Thr Val Glu Glu
            20                  25                  30

Asp Glu Ile Leu Val Ser Phe Ile Lys Lys Glu Gly Glu Gly Arg Trp
        35                  40                  45

Arg Ser Leu Pro Lys Arg Ala Gly Leu Leu Arg Cys Gly Lys Ser Cys
    50                  55                  60

Arg Leu Arg Trp Met Asn Tyr Leu Arg Pro Ser Val Lys Arg Gly Gly
65                  70                  75                  80

Ile Thr Ser Asp Glu Glu Asp Leu Ile Leu Arg Leu His Arg Leu Leu
                85                  90                  95

```
Gly Asn Arg Trp Ser Leu Ile Ala Gly Arg Ile Pro Gly Arg Thr Asp
            100                 105                 110

Asn Glu Ile Lys Asn Tyr Trp Asn Thr His Leu Arg Lys Lys Leu Leu
    115                 120                 125

Arg Gln Gly Ile Asp Pro Gln Thr His Lys Pro Leu Asp Ala Asn Asn
130                 135                 140

Ile His Lys Pro Glu Glu Val Ser Gly Gln Lys Tyr Pro Leu
145                 150                 155                 160

Glu Pro Ile Ser Ser Ser His Thr Asp Thr Thr Val Asn Gly Gly
                165                 170                 175

Asp Gly Asp Ser Lys Asn Ser Ile Asn Val Phe Gly Gly Glu His Gly
                180                 185                 190

Tyr Glu Asp Phe Gly Phe Cys Tyr Asp Asp Lys Phe Ser Ser Phe Leu
                195                 200                 205

Asn Ser Leu Ile Asn Asp Val Gly Asp Pro Phe Gly Asn Ile Ile Pro
210                 215                 220

Ile Ser Gln Pro Leu Gln Met Asp Asp Cys Lys Asp Gly Ile Val Gly
225                 230                 235                 240

Ala Ser Ser Ser Ser Leu Gly His Asp
                245

<210> SEQ ID NO 127
<211> LENGTH: 1195
<212> TYPE: DNA
<213> ORGANISM: Arabidopsis thaliana
<220> FEATURE:
<223> OTHER INFORMATION: G242

<400> SEQUENCE: 127
ctctcaaaac caaaatcact aaagaggaga agattgctaa agtttgataa aacattccaa      60
aatcaatggc tgataggatc aaaggtccat ggagtcctga gaagacgag cagcttcgta     120
ggcttgttgt taaatacggt ccaagaaact ggacagtgat tagcaaatct attcccggta     180
gatcggggaa atcgtgtcgt ttacggtggt gcaaccagct ttcgccgcaa gttgagcatc     240
ggccgttttc ggctgaggaa gacgagacga tcgcacgtgc tcacgctcag ttcgggaata     300
aatgggcgac gattgctcgt cttctcaacg tcgtacgga caacgccgtg aagaatcact     360
ggaactcgac gctcaagagg aaatgcggcg ttacgaccat cggggttac gatggttcgg     420
aggatcatcg gccggttaag agatcggtga gtgcggatc tccacctgtt gttactgggc     480
tttacatgag cccaggaagc ccaactggat ctgatgtcag tgattcaagt actatcccga     540
tattccttc cgttgagctt ttcaagcctg tgcctagacc tggtgctgtt gtgctaccgc     600
ttcctatcga aacgtcgtct ttttccgatg atccaccgac ttcgttaagc ttgtcacttc     660
ctggtgccga cgtaagcgag gagtcaaacc gtagccacga gtcaacgaat atcaacaaca     720
ccacttcgag ccgccacaac cacaacaata cggtgtcgtt tatgccgttt agtggtgggt     780
ttagaggtgc gattgaggaa atggggaagt ctttccccgg taacggaggc gagtttatgg     840
cggtggtgca agagatgatt aaggcggaag tgaggagtta catgacggag atgcaacgga     900
acaatggtgg cggattcgtc ggaggattca ttgataatgg catgattccg atgagtcaaa     960
ttggagttgg gagaatcgag tagacaaagt gagattatta ggaaactgtt taaattggag    1020
aagaagaaaa atgctctgtt tttttctcct ttggattagg cttaagaatt ttgggtttta    1080
aggaaatgta tagaggaaat cgagtgaaca aagctcgaga gctggggacg tagtgacgaa    1140
```
gacgaagatc aaatttctct taagctattc aggaaaataa aataaatttt tattt    1195

<210> SEQ ID NO 128
<211> LENGTH: 305
<212> TYPE: PRT
<213> ORGANISM: Arabidopsis thaliana
<220> FEATURE:
<223> OTHER INFORMATION: G242 polypeptide

<400> SEQUENCE: 128

Met Ala Asp Arg Ile Lys Gly Pro Trp Ser Pro Glu Glu Asp Glu Gln
1               5                   10                  15

Leu Arg Arg Leu Val Val Lys Tyr Gly Pro Arg Asn Trp Thr Val Ile
            20                  25                  30

Ser Lys Ser Ile Pro Gly Arg Ser Gly Lys Ser Cys Arg Leu Arg Trp
        35                  40                  45

Cys Asn Gln Leu Ser Pro Gln Val Glu His Arg Pro Phe Ser Ala Glu
    50                  55                  60

Glu Asp Glu Thr Ile Ala Arg Ala His Ala Gln Phe Gly Asn Lys Trp
65                  70                  75                  80

Ala Thr Ile Ala Arg Leu Leu Asn Gly Arg Thr Asp Asn Ala Val Lys
                85                  90                  95

Asn His Trp Asn Ser Thr Leu Lys Arg Lys Cys Gly Gly Tyr Asp His
            100                 105                 110

Arg Gly Tyr Asp Gly Ser Glu Asp His Arg Pro Val Lys Arg Ser Val
        115                 120                 125

Ser Ala Gly Ser Pro Pro Val Val Thr Gly Leu Tyr Met Ser Pro Gly
    130                 135                 140

Ser Pro Thr Gly Ser Asp Val Ser Asp Ser Ser Thr Ile Pro Ile Leu
145                 150                 155                 160

Pro Ser Val Glu Leu Phe Lys Pro Val Pro Arg Pro Gly Ala Val Val
                165                 170                 175

Leu Pro Leu Pro Ile Glu Thr Ser Ser Phe Ser Asp Asp Pro Pro Thr
            180                 185                 190

Ser Leu Ser Leu Ser Leu Pro Gly Ala Asp Val Ser Glu Glu Ser Asn
        195                 200                 205

Arg Ser His Glu Ser Thr Asn Ile Asn Asn Thr Thr Ser Ser Arg His
    210                 215                 220

Asn His Asn Asn Thr Val Ser Phe Met Pro Phe Ser Gly Gly Phe Arg
225                 230                 235                 240

Gly Ala Ile Glu Glu Met Gly Lys Ser Phe Pro Gly Asn Gly Glu
                245                 250                 255

Phe Met Ala Val Val Gln Glu Met Ile Lys Ala Glu Val Arg Ser Tyr
            260                 265                 270

Met Thr Glu Met Gln Arg Asn Asn Gly Gly Phe Val Gly Phe
        275                 280                 285

Ile Asp Asn Gly Met Ile Pro Met Ser Gln Ile Gly Val Gly Arg Ile
    290                 295                 300

Glu
305

<210> SEQ ID NO 129
<211> LENGTH: 1379
<212> TYPE: DNA
<213> ORGANISM: Arabidopsis thaliana
<220> FEATURE:
<223> OTHER INFORMATION: G2589

-continued

```
<400> SEQUENCE: 129
aaagaaaaga aaaataaaga taatgaggac gaagactaag ttagtactca tacctgatag      60
acactttcgg agagccacat tcaggaagag gaatgcaggg ataaggaaga aactccacga     120
gctgacaact ctctgtgaca tcaaagcatg tgcggtaatc tacagtccgt tcgagaatcc     180
aacggtgtgg ccgtcaaccg aaggtgttca agaggtgatt tcggagttca tggagaagcc     240
ggcgacagaa cggtccaaga cgatgatgag tcatgagact ttcttgcggg accaaatcac     300
caaagaacaa aacaaactag agagtctacg tcgtgaaaac cgagaaactc agcttaagca     360
ttttatgttt gattgcgttg gaggcaagat gagtgagcaa cagtatggtg caagggacct     420
tcaagattta agtcttttta ctgatcaata tcttaatcag cttaatgcca ggaagaagtt     480
ccttacagaa tatggtgagt cttcttcttc tgttcctcct ctgtttgatg ttgcgggtgc     540
caatcctcct gttgttgcag atcaagctgc ggtaactgtt cctcctttgt ttgctgttgc     600
gggtgccaat cttcctgttg ttgctgatca agctgcggta actgttcctc ctctgtttgc     660
tgttgcgggt gccaatcttc ctgttgttgc agatcaagct gcggttaatg ttcctactgg     720
atttcataac atgaatgtga accagaatca gtatgagccg ttcagccct atgtccctac     780
tggttttagt gatcatattc aatatcagaa tatgaacttc aatcaaaacc aacaagagcc     840
ggttcattac caggctcttg ctgttgcggg tgccggtctt cctatgactc agaatcagta     900
tgagcccgtt cactaccaga gtcttgctgt cgcgggtggc ggtcttccta tgagtcagtt     960
gcagtatgag ccggttcagc cttatatccc tactgttttt agtgataatg ttcaatatca    1020
gcatatgaat ttgtatcaaa atcaacaaga gccggttcac taccaagctc ttggtgttgc    1080
aggtgccggt cttcctatga atcagaatca gtatgagccg ttcagccct atgtccctac    1140
tggttttagt gatcatttc agtttgagaa tatgaatttg aatcaaaatc aacaggagcc    1200
ggttcaatac caagctcctg ttgattttaa tcatcagatt caacaaggaa actatgatat    1260
gaatttgaac cagaatatga gtttggatcc aaatcagtat ccgtttcaaa atgatccatt    1320
catgaatatg ttgacagaat atccttatga ataagcgggt tatgttggag agcatgcac    1379
```

```
<210> SEQ ID NO 130
<211> LENGTH: 443
<212> TYPE: PRT
<213> ORGANISM: Arabidopsis thaliana
<220> FEATURE:
<223> OTHER INFORMATION: G2589 polypeptide

<400> SEQUENCE: 130
```

Met Arg Thr Lys Thr Lys Leu Val Leu Ile Pro Asp Arg His Phe Arg
1               5                   10                  15

Arg Ala Thr Phe Arg Lys Arg Asn Ala Gly Ile Arg Lys Lys Leu His
            20                  25                  30

Glu Leu Thr Thr Leu Cys Asp Ile Lys Ala Cys Ala Val Ile Tyr Ser
        35                  40                  45

Pro Phe Glu Asn Pro Thr Val Trp Pro Ser Thr Glu Gly Val Gln Glu
    50                  55                  60

Val Ile Ser Glu Phe Met Glu Lys Pro Ala Thr Glu Arg Ser Lys Thr
65                  70                  75                  80

Met Met Ser His Glu Thr Phe Leu Arg Asp Gln Ile Thr Lys Glu Gln
                85                  90                  95

Asn Lys Leu Glu Ser Leu Arg Arg Glu Asn Arg Glu Thr Gln Leu Lys
            100                 105                 110

His Phe Met Phe Asp Cys Val Gly Gly Lys Met Ser Glu Gln Gln Tyr
            115                 120                 125

Gly Ala Arg Asp Leu Gln Asp Leu Ser Leu Phe Thr Asp Gln Tyr Leu
        130                 135                 140

Asn Gln Leu Asn Ala Arg Lys Lys Phe Leu Thr Glu Tyr Gly Glu Ser
145                 150                 155                 160

Ser Ser Ser Val Pro Pro Leu Phe Asp Val Ala Gly Ala Asn Pro Pro
                165                 170                 175

Val Val Ala Asp Gln Ala Ala Val Thr Val Pro Pro Leu Phe Ala Val
            180                 185                 190

Ala Gly Ala Asn Leu Pro Val Val Ala Asp Gln Ala Ala Val Thr Val
        195                 200                 205

Pro Pro Leu Phe Ala Val Ala Gly Ala Asn Leu Pro Val Val Ala Asp
    210                 215                 220

Gln Ala Ala Val Asn Val Pro Thr Gly Phe His Asn Met Asn Val Asn
225                 230                 235                 240

Gln Asn Gln Tyr Glu Pro Val Gln Pro Tyr Val Pro Thr Gly Phe Ser
                245                 250                 255

Asp His Ile Gln Tyr Gln Asn Met Asn Phe Asn Gln Asn Gln Gln Glu
            260                 265                 270

Pro Val His Tyr Gln Ala Leu Ala Val Ala Gly Ala Gly Leu Pro Met
        275                 280                 285

Thr Gln Asn Gln Tyr Glu Pro Val His Tyr Gln Ser Leu Ala Val Ala
    290                 295                 300

Gly Gly Gly Leu Pro Met Ser Gln Leu Gln Tyr Glu Pro Val Gln Pro
305                 310                 315                 320

Tyr Ile Pro Thr Val Phe Ser Asp Asn Val Gln Tyr Gln His Met Asn
                325                 330                 335

Leu Tyr Gln Asn Gln Gln Glu Pro Val His Tyr Gln Ala Leu Gly Val
            340                 345                 350

Ala Gly Ala Gly Leu Pro Met Asn Gln Asn Gln Tyr Glu Pro Val Gln
        355                 360                 365

Pro Tyr Val Pro Thr Gly Phe Ser Asp His Phe Gln Phe Glu Asn Met
    370                 375                 380

Asn Leu Asn Gln Asn Gln Gln Glu Pro Val Gln Tyr Gln Ala Pro Val
385                 390                 395                 400

Asp Phe Asn His Gln Ile Gln Gln Gly Asn Tyr Asp Met Asn Leu Asn
                405                 410                 415

Gln Asn Met Ser Leu Asp Pro Asn Gln Tyr Pro Phe Gln Asn Asp Pro
            420                 425                 430

Phe Met Asn Met Leu Thr Glu Tyr Pro Tyr Glu
        435                 440

<210> SEQ ID NO 131
<211> LENGTH: 2330
<212> TYPE: DNA
<213> ORGANISM: Arabidopsis thaliana
<220> FEATURE:
<223> OTHER INFORMATION: G274

<400> SEQUENCE: 131
agctttatac tttctggcta ctgcaagctc atcagtgaaa agagcttaaa ccagagagat      60
ctgataagag aaattttaga gtctctctgc ttcaacaaga tctacatcga ccaggagatt     120
agaaagaatc atgggttcta agcataaccc accagggaat aacagatcga gaagtacact     180

```
atctctactc gttgtggttg gtttatgttg tttcttctat cttcttggag catggcaaaa      240
gagtgggttt ggtaaaggag atagcatagc tatggagatt acaaagcaag cgcagtgtac      300
tgacattgtc actgatcttg attttgaacc tcatcacaac acagtgaaga tcccacataa      360
agctgatccc aaacctgttt ctttcaaacc gtgtgatgtg aagctcaagg attacacgcc      420
ttgtcaagag caagaccgag ctatgaagtt cccgagagag aacatgattt acagagagag      480
acattgtcct cctgataatg agaagctgcg ttgtcttgtt ccagctccta agggtatat       540 gactcctttc ccttggccta aaagcagaga ttatgttcac tatgctaatg ctccttcaa       600 gagcttgact gtcgaaaaag ctggacagaa ttgggttcag tttcaaggga atgtgtttaa      660
attccctggt ggaggaacta tgtttcctca aggtgctgat gcgtatattg aagagctagc      720
ttctgttatc cctatcaaag atggctctgt tagaaccgca ttggacactg atgtggggt       780 tgctagttgg ggtgcttata tgcttaagag gaatgttttg actatgtcgt ttgcgccaag      840
ggataaccac gaagcacaag tccagtttgc gcttgagaga ggtgttccag cgattatcgc      900
tgttcttgga tcaatccttc ttccttaccc tgcaagagcc tttgacatgg ctcaatgctc      960
tcgatgcttg ataccatgga ccgcaaacga gggaacatac ttaatggaag tagatagagt     1020
cttgagacct ggaggttact gggtcttatc gggtcctcca atcaactgga agacatggca     1080
caagacgtgg aaccgaacta agcagagct aaatgccgag caaaagagaa tagagggaat      1140
cgcagagtcc ttatgctggg agaagaagta tgagaaggga gacattgcaa ttttcagaaa     1200
gaaaataaac gatagatcat gcgatagatc aacaccggtt gacacctgca aaagaaggaa     1260
cactgacgat gtctggtaca aggagataga acgtgtgta acaccattcc ctaaagtatc      1320
aaacgaagaa gaagttgctg gaggaaagct aagaagttc cccgagaggc tattcgcagt      1380
gcctccaagt atctctaaag gtttgattaa tggcgtcgac gaggaatcat accaagaaga     1440
catcaatcta tggaagaagc gagtgaccgg atacaagaga attaacagac tgataggttc     1500
caccagatac cgtaatgtga tggatatgaa cgccggtctt ggtggattcg ctgctgcgct     1560
tgaatcgcct aaatcgtggg ttatgaatgt gattccaacc attaacaaga acacattgag     1620
tgttgtttat gagagaggtc tcattggtat ctatcatgac tggtgtgaag cttttcaac      1680 ttatccaaga acatacgatt tcattcacgc tagtggtgtc ttcagcttgt atcagcacag     1740
ctgcaaactt gaggatattc ttcttgaaac tgatcggatt ttacgaccgg aagggattgt     1800
gattttccgg gatgaggttg atgttttgaa tgatgtgagg aagatcgttg atggaatgag     1860
atgggatact aagttaatgg atcatgaaga cggtcctctc gtgccggaga agattcttgt     1920
cgccacgaag cagtattggg tagccggcga cgatggaaac aattctccgt cgtcttctaa     1980
tagtgaagaa gaataaaaca aaaacaaaaa actcctcagg ttactaagct tgaagtgtag     2040
atctatttta caacatctgg aaaattctta tcaaaaaagg aaggaatcag aatttccatt     2100
aaagaaaggt gtcaaaaaaa agttgtaaaa ctatatagta gtgatcaaga cgaatatgtg     2160
catttatgtt ttattttgt tccctagttt ttaattttat ttttttgaag gaagaaaaaa      2220
ttagttccat gtgttttgc aagatagttg aaaccttgga cgcttgttat gtatgatgcg      2280
atcttgacat ttttaataa cagttatttt aaataaattt atgatataaa                 2330
```

<210> SEQ ID NO 132
<211> LENGTH: 621
<212> TYPE: PRT
<213> ORGANISM: Arabidopsis thaliana
<220> FEATURE:

<223> OTHER INFORMATION: G274 polypeptide

<400> SEQUENCE: 132

Met Gly Ser Lys His Asn Pro Pro Gly Asn Arg Ser Arg Ser Thr
1               5                   10                  15

Leu Ser Leu Leu Val Val Gly Leu Cys Cys Phe Phe Tyr Leu Leu
            20                  25                  30

Gly Ala Trp Gln Lys Ser Gly Phe Gly Lys Gly Asp Ser Ile Ala Met
        35                  40                  45

Glu Ile Thr Lys Gln Ala Gln Cys Thr Asp Ile Val Thr Asp Leu Asp
50                  55                  60

Phe Glu Pro His His Asn Thr Val Lys Ile Pro His Lys Ala Asp Pro
65                  70                  75                  80

Lys Pro Val Ser Phe Lys Pro Cys Asp Val Lys Leu Lys Asp Tyr Thr
                85                  90                  95

Pro Cys Gln Glu Gln Asp Arg Ala Met Lys Phe Pro Arg Glu Asn Met
            100                 105                 110

Ile Tyr Arg Glu Arg His Cys Pro Pro Asp Asn Glu Lys Leu Arg Cys
        115                 120                 125

Leu Val Pro Ala Pro Lys Gly Tyr Met Thr Pro Phe Pro Trp Pro Lys
130                 135                 140

Ser Arg Asp Tyr Val His Tyr Ala Asn Ala Pro Phe Lys Ser Leu Thr
145                 150                 155                 160

Val Glu Lys Ala Gly Gln Asn Trp Val Gln Phe Gln Gly Asn Val Phe
                165                 170                 175

Lys Phe Pro Gly Gly Gly Thr Met Phe Pro Gln Gly Ala Asp Ala Tyr
            180                 185                 190

Ile Glu Glu Leu Ala Ser Val Ile Pro Ile Lys Asp Gly Ser Val Arg
        195                 200                 205

Thr Ala Leu Asp Thr Gly Cys Gly Val Ala Ser Trp Gly Ala Tyr Met
210                 215                 220

Leu Lys Arg Asn Val Leu Thr Met Ser Phe Ala Pro Arg Asp Asn His
225                 230                 235                 240

Glu Ala Gln Val Gln Phe Ala Leu Glu Arg Gly Val Pro Ala Ile Ile
                245                 250                 255

Ala Val Leu Gly Ser Ile Leu Leu Pro Tyr Pro Ala Arg Ala Phe Asp
            260                 265                 270

Met Ala Gln Cys Ser Arg Cys Leu Ile Pro Trp Thr Ala Asn Glu Gly
        275                 280                 285

Thr Tyr Leu Met Glu Val Asp Arg Val Leu Arg Pro Gly Gly Tyr Trp
290                 295                 300

Val Leu Ser Gly Pro Pro Ile Asn Trp Lys Thr Trp His Lys Thr Trp
305                 310                 315                 320

Asn Arg Thr Lys Ala Glu Leu Asn Ala Glu Gln Lys Arg Ile Glu Gly
                325                 330                 335

Ile Ala Glu Ser Leu Cys Trp Glu Lys Lys Tyr Glu Lys Gly Asp Ile
            340                 345                 350

Ala Ile Phe Arg Lys Lys Ile Asn Asp Arg Ser Cys Asp Arg Ser Thr
        355                 360                 365

Pro Val Asp Thr Cys Lys Arg Lys Asp Thr Asp Val Trp Tyr Lys
370                 375                 380

Glu Ile Glu Thr Cys Val Thr Pro Phe Pro Lys Val Ser Asn Glu Glu
385                 390                 395                 400

-continued

```
Glu Val Ala Gly Gly Lys Leu Lys Lys Phe Pro Glu Arg Leu Phe Ala
            405                 410                 415
Val Pro Pro Ser Ile Ser Lys Gly Leu Ile Asn Gly Val Asp Glu Glu
        420                 425                 430
Ser Tyr Gln Glu Asp Ile Asn Leu Trp Lys Lys Arg Val Thr Gly Tyr
    435                 440                 445
Lys Arg Ile Asn Arg Leu Ile Gly Ser Thr Arg Tyr Arg Asn Val Met
450                 455                 460
Asp Met Asn Ala Gly Leu Gly Gly Phe Ala Ala Leu Glu Ser Pro
465                 470                 475                 480
Lys Ser Trp Val Met Asn Val Ile Pro Thr Ile Asn Lys Asn Thr Leu
                485                 490                 495
Ser Val Val Tyr Glu Arg Gly Leu Ile Gly Ile Tyr His Asp Trp Cys
            500                 505                 510
Glu Gly Phe Ser Thr Tyr Pro Arg Thr Tyr Asp Phe Ile His Ala Ser
        515                 520                 525
Gly Val Phe Ser Leu Tyr Gln His Ser Cys Lys Leu Glu Asp Ile Leu
    530                 535                 540
Leu Glu Thr Asp Arg Ile Leu Arg Pro Glu Gly Ile Val Ile Phe Arg
545                 550                 555                 560
Asp Glu Val Asp Val Leu Asn Asp Val Arg Lys Ile Val Asp Gly Met
                565                 570                 575
Arg Trp Asp Thr Lys Leu Met Asp His Glu Asp Gly Pro Leu Val Pro
            580                 585                 590
Glu Lys Ile Leu Val Ala Thr Lys Gln Tyr Trp Val Ala Gly Asp Asp
        595                 600                 605
Gly Asn Asn Ser Pro Ser Ser Ser Asn Ser Glu Glu Glu
    610                 615                 620

<210> SEQ ID NO 133
<211> LENGTH: 1226
<212> TYPE: DNA
<213> ORGANISM: Arabidopsis thaliana
<220> FEATURE:
<223> OTHER INFORMATION: G598

<400> SEQUENCE: 133
gtccgttgtc atattttaaa tttatcacct tcttgagaat tccacatttt tatccttttt      60
gtcatgtagt gtatatttt tcctctaacc taattaaaat caaaacaaaa tcctttgacc     120
caattagctt cgcgatatat cagaagagat caaactactt tgatcagacc atgatcttct     180
tcttcttctt cttcttcttc ttcttctttt tagacgatca caattcctaa accctatttc     240
tcagattatg ctgactcttt accatcaaga aggtcaccg gacgccacaa gtaatgatcg      300
cgatgagacg ccagagactg tggttagaga agtccacgcg ctaactccag cgccggagga     360
taattcccgg acgatgacgg cgacgctacc tccaccgcct gctttccgag ctatttttc      420 tcctccaagg tcagcgacga cgatgagcga aggagagaac ttcacaacta taagcagaga     480
gttcaacgct ctagtcatcg ccggatcctc catggagaac aacgaactaa tgactcgtga     540
cgtcacgcag cgtgaagatg agagacaaga cgagttgatg agaatccacg aggacacgga     600
tcatgaagag gaaacgaatc ctttagcaat cgtgccggat cagtatcctg gttcgggttt     660
ggatcctgga agtgataatg ggccgggtca gagtcgggtt gggtcgacgg tgcaaagagt     720
taagagggaa gaggtggaag cgaagataac ggcgtggcag acggcaaaac tggctaagat     780
taataacagg tttaagaggg aagacgccgt tattaacggt tggtttaatg aacaagttaa     840
```

```
caaggccaac tcttggatga agaaaattga gtataatgta ggttcattca acaatcgtct      900
aaatgaggaa gctagaggag agaaaagcaa agcgatgga gaaaacgcaa acaatgtgg       960 cgaaagcgca gaggaaagcg gaggagagaa gagcgacggc agaggcaaag agagggacag    1020
aggttgcaaa agtagttgaa gttgctaatc tcatgagagc ccttggacgt cctcctgcca    1080
aacgctcctt cttctctttc tcctaatttt tagttatatc aaaccattaa attaaacagt    1140
actcgttata tatctagtta gtaaacaaag gggcagtttt atagctcatg tacacataat    1200
tgagagtgta gtactgttgt gtcaaa                                          1226
```

<210> SEQ ID NO 134  
<211> LENGTH: 263  
<212> TYPE: PRT  
<213> ORGANISM: Arabidopsis thaliana  
<220> FEATURE:  
<223> OTHER INFORMATION: G598 polypeptide

<400> SEQUENCE: 134

```
Met Leu Thr Leu Tyr His Gln Glu Arg Ser Pro Asp Ala Thr Ser Asn
1               5                   10                  15

Asp Arg Asp Glu Thr Pro Glu Thr Val Val Arg Glu Val His Ala Leu
                20                  25                  30

Thr Pro Ala Pro Glu Asp Asn Ser Arg Thr Met Thr Ala Thr Leu Pro
            35                  40                  45

Pro Pro Pro Ala Phe Arg Gly Tyr Phe Ser Pro Arg Ser Ala Thr
        50                  55                  60

Thr Met Ser Glu Gly Glu Asn Phe Thr Thr Ile Ser Arg Glu Phe Asn
65                  70                  75                  80

Ala Leu Val Ile Ala Gly Ser Ser Met Glu Asn Asn Glu Leu Met Thr
                85                  90                  95

Arg Asp Val Thr Gln Arg Glu Asp Glu Arg Gln Asp Glu Leu Met Arg
                100                 105                 110

Ile His Glu Asp Thr Asp His Glu Glu Glu Thr Asn Pro Leu Ala Ile
            115                 120                 125

Val Pro Asp Gln Tyr Pro Gly Ser Gly Leu Asp Pro Gly Ser Asp Asn
        130                 135                 140

Gly Pro Gly Gln Ser Arg Val Gly Ser Thr Val Gln Arg Val Lys Arg
145                 150                 155                 160

Glu Glu Val Glu Ala Lys Ile Thr Ala Trp Gln Thr Ala Lys Leu Ala
                165                 170                 175

Lys Ile Asn Asn Arg Phe Lys Arg Glu Asp Ala Val Ile Asn Gly Trp
                180                 185                 190

Phe Asn Glu Gln Val Asn Lys Ala Asn Ser Trp Met Lys Lys Ile Glu
            195                 200                 205

Tyr Asn Val Gly Ser Phe Asn Asn Arg Leu Asn Glu Glu Ala Arg Gly
        210                 215                 220

Glu Lys Ser Lys Ser Asp Gly Glu Asn Ala Lys Gln Cys Gly Glu Ser
225                 230                 235                 240

Ala Glu Glu Ser Gly Gly Glu Lys Ser Asp Gly Arg Gly Lys Glu Arg
                245                 250                 255

Asp Arg Gly Cys Lys Ser Ser
            260
```

<210> SEQ ID NO 135  
<211> LENGTH: 828

```
<212> TYPE: DNA
<213> ORGANISM: Arabidopsis thaliana
<220> FEATURE:
<223> OTHER INFORMATION: G1543

<400> SEQUENCE: 135
atgataaaac tactatttac gtacatatgc acatacacat ataaactata tgctctatat    60
catatggatt acgcatgcgt gtgtatgtat aaatataaag gcatcgtcac gcttcaagtt   120
tgtctctttt atattaaact gagagttttc ctctcaaact ttaccttttc ttcttcgatc   180
ctagctctta agaaccctaa taattcattg atcaaaataa tggcgatttt gccggaaaac   240
tcttcaaact tggatcttac tatctccgtt ccaggcttct cttcatcccc tctctccgat   300
gaaggaagtg gcggaggaag agaccagcta aggctagaca tgaatcggtt accgtcgtct   360
gaagacggag acgatgaaga attcagtcac gatgatggct ctgctcctcc gcgaaagaaa   420
ctccgtctaa ccagagaaca gtcacgtctt cttgaagata gtttcagaca gaatcatacc   480
cttaatccca acaaaagga agtacttgcc aagcatttga tgctacggcc aagacaaatt   540
gaagtttggt ttcaaaaccg tagagcaagg agcaaattga agcaaaccga gatggaatgc   600
gagtatctca aaaggtggtt tggttcatta acggaagaaa accacaggct ccatagagaa   660
gtagaagagc ttagagccat aaaggttggc ccaacaacgg tgaactctgc ctcgagcctt   720
actatgtgtc ctcgctgcga gcgagttacc cctgccgcga gcccttcgag ggcggtggtg   780
ccggttccgg ctaagaaaac gtttccgccg caagagcgtg atcgttga                828

<210> SEQ ID NO 136
<211> LENGTH: 275
<212> TYPE: PRT
<213> ORGANISM: Arabidopsis thaliana
<220> FEATURE:
<223> OTHER INFORMATION: G1543 polypeptide

<400> SEQUENCE: 136

Met Ile Lys Leu Leu Phe Thr Tyr Ile Cys Thr Tyr Thr Tyr Lys Leu
1               5                   10                  15

Tyr Ala Leu Tyr His Met Asp Tyr Ala Cys Val Cys Met Tyr Lys Tyr
            20                  25                  30

Lys Gly Ile Val Thr Leu Gln Val Cys Leu Phe Tyr Ile Lys Leu Arg
        35                  40                  45

Val Phe Leu Ser Asn Phe Thr Phe Ser Ser Ser Ile Leu Ala Leu Lys
    50                  55                  60

Asn Pro Asn Asn Ser Leu Ile Lys Ile Met Ala Ile Leu Pro Glu Asn
65                  70                  75                  80

Ser Ser Asn Leu Asp Leu Thr Ile Ser Val Pro Gly Phe Ser Ser Ser
                85                  90                  95

Pro Leu Ser Asp Glu Gly Ser Gly Gly Gly Arg Asp Gln Leu Arg Leu
            100                 105                 110

Asp Met Asn Arg Leu Pro Ser Ser Glu Asp Gly Asp Asp Glu Glu Phe
        115                 120                 125

Ser His Asp Asp Gly Ser Ala Pro Pro Arg Lys Lys Leu Arg Leu Thr
    130                 135                 140

Arg Glu Gln Ser Arg Leu Leu Glu Asp Ser Phe Arg Gln Asn His Thr
145                 150                 155                 160

Leu Asn Pro Lys Gln Lys Glu Val Leu Ala Lys His Leu Met Leu Arg
                165                 170                 175

Pro Arg Gln Ile Glu Val Trp Phe Gln Asn Arg Arg Ala Arg Ser Lys
```

```
                    180                 185                 190
Leu Lys Gln Thr Glu Met Glu Cys Glu Tyr Leu Lys Arg Trp Phe Gly
            195                 200                 205

Ser Leu Thr Glu Glu Asn His Arg Leu His Arg Glu Val Glu Glu Leu
        210                 215                 220

Arg Ala Ile Lys Val Gly Pro Thr Thr Val Asn Ser Ala Ser Ser Leu
225                 230                 235                 240

Thr Met Cys Pro Arg Cys Glu Arg Val Thr Pro Ala Ala Ser Pro Ser
                245                 250                 255

Arg Ala Val Val Pro Val Pro Ala Lys Lys Thr Phe Pro Pro Gln Glu
            260                 265                 270

Arg Asp Arg
        275

<210> SEQ ID NO 137
<211> LENGTH: 983
<212> TYPE: DNA
<213> ORGANISM: Arabidopsis thaliana
<220> FEATURE:
<223> OTHER INFORMATION: G280

<400> SEQUENCE: 137
aagttaatat gagaataatg agaaaaccac tttcccaaat tgctttttaa aatccctcct      60
cacacagatt ccttccttca tcacctcaca cactctctac gcttgacatg gccttcgatc     120
tccaccatgg ctcagcttca gatacgcatt catcagaact ccgtcgtttt ctctccccac     180
cttatcctca gatgataatg gaagcgattg agtccttgaa cgataagaac ggctgcaaca     240
aaacgacgat tgctaagcac atcgagtcga ctcaacaaac tctaccgccg tcacacatga     300
cgctgctcag ctaccatctc aaccagatga agaaaaccgg tcagctaatc atggtgaaga     360
acaattatat gaaaccagat ccagatgctc tcctaagcg tggtcgtggc cgtcctccga      420
agcagaagac tcaggccgaa tctgacgccg ctgctgctgc tgttgttgct gccaccgtcg     480
tctctacaga tccgcctaga tctcgtggcc gtccaccgaa gccgaaagat ccatcggagc     540
ctccccagga gaaggtcatt accggatctg gaaggccacg aggacgacca ccgaagagac     600
cgagaacaga ttcggagacg gttgctgcgc cggaaccggc agctcaggcg acaggtgagc     660
gtaggggacg tgggagacct ccgaaggtga agccgacggt ggttgctccg gttgggtgct     720
gaattaatcg gtacttatgc aatttcggaa tctttagtta ctgaaaaatg gaatctctta     780
gagagtaaga gagtgcttta atttagctta attagatttta tttggatttc tttcagtatt     840
tggattgtaa actttagaat ttgtgtgtgt gttgttgctt agtcctgaga taagatataa     900
cattagcgac tgtgtattat tattattact gcattgtgtt atgtgaaact ttgttctctt     960
gttgaaaaaa aaaaaaaaaa aaa                                            983

<210> SEQ ID NO 138
<211> LENGTH: 204
<212> TYPE: PRT
<213> ORGANISM: Arabidopsis thaliana
<220> FEATURE:
<223> OTHER INFORMATION: G280 polypeptide

<400> SEQUENCE: 138

Met Ala Phe Asp Leu His His Gly Ser Ala Ser Asp Thr His Ser Ser
1               5                   10                  15

Glu Leu Pro Ser Phe Ser Leu Pro Pro Tyr Pro Gln Met Ile Met Glu
            20                  25                  30
```

-continued

```
Ala Ile Glu Ser Leu Asn Asp Lys Asn Gly Cys Asn Lys Thr Thr Ile
        35                  40                  45

Ala Lys His Ile Glu Ser Thr Gln Gln Thr Leu Pro Pro Ser His Met
    50                  55                  60

Thr Leu Leu Ser Tyr His Leu Asn Gln Met Lys Lys Thr Gly Gln Leu
65                  70                  75                  80

Ile Met Val Lys Asn Asn Tyr Met Lys Pro Asp Pro Asp Ala Pro Pro
                85                  90                  95

Lys Arg Gly Arg Gly Arg Pro Pro Lys Gln Lys Thr Gln Ala Glu Ser
            100                 105                 110

Asp Ala Ala Ala Ala Val Val Ala Ala Thr Val Val Ser Thr Asp
            115                 120                 125

Pro Pro Arg Ser Arg Gly Arg Pro Pro Lys Pro Lys Asp Pro Ser Glu
        130                 135                 140

Pro Pro Gln Glu Lys Val Ile Thr Gly Ser Gly Arg Pro Arg Gly Arg
145                 150                 155                 160

Pro Pro Lys Arg Pro Arg Thr Asp Ser Glu Thr Val Ala Ala Pro Glu
                165                 170                 175

Pro Ala Ala Gln Ala Thr Gly Glu Arg Arg Gly Arg Gly Arg Pro Pro
            180                 185                 190

Lys Val Lys Pro Thr Val Val Ala Pro Val Gly Cys
        195                 200
```

<210> SEQ ID NO 139
<211> LENGTH: 1065
<212> TYPE: DNA
<213> ORGANISM: Arabidopsis thaliana
<220> FEATURE:
<223> OTHER INFORMATION: G2131

<400> SEQUENCE: 139

```
gtctctcatt ttcataattc cattttcagg attgtctctc aatcttttat tcttctcatt     60
caccggtaat ggcaaaagtc tctgggagga gcaagaaaac aatcgttgac gatgaaatca    120
gcgataaaac agcgtctgcg tctgagtctg cgtccattgc cttaacatcc aaacgcaaac    180
gtaagtcgcc gcctcgaaac gctcctcttc aacgcagctc cccttacaga ggcgtcacaa    240
ggcatagatg gactgggaga tacgaagcgc atttgtggga taagaacagc tggaacgata    300
cacagaccaa gaaaggacgt caagtttatc tagggcttac gacgaagaa gaagcagcag    360
cacgtgccta cgacttagca gcattgaagt actggggacg agacacactc ttgaacttcc    420
ctttgccgag ttatgacgaa gacgtcaaag aaatggaagg ccaatccaag gaagagtata    480
ttggatcatt gagaagaaaa agtagtggat tttctcgcgg tgtatcaaaa tacagaggcg    540
ttgcaaggca tcaccataat gggagatggg aagctagaat tggaagggtg tttggtaata    600
aatatctata tcttggaaca tacgccacgc aagaagaagc agcaatcgcc tacgacatcg    660
cggcaataga gtaccgtgga cttaacgccg ttaccaattt cgacgtcagc cgttatctaa    720
accctaacgc cgccgcggat aaagccgatt ccgattctaa gcccattcga agccctagtc    780
gcgagcccga atcgtcggat gataacaaat ctccgaaatc agaggaagta atcgaaccat    840
ctacatcgcc ggaagtgatt ccaactcgcc ggagcttccc cgacgatatc cagacgtatt    900
ttgggtgtca agattccggc aagttagcga ctgaggaaga cgtaatattc gattgtttca    960
attcttatat aaatcctggc ttctataacg agtttgatta tggaccttaa tcgtatttc    1020
tacaagtttt gttttgatta tctacacaat acatcaatat attct                   1065
```

<210> SEQ ID NO 140
<211> LENGTH: 313
<212> TYPE: PRT
<213> ORGANISM: Arabidopsis thaliana
<220> FEATURE:
<223> OTHER INFORMATION: G2131 polypeptide

<400> SEQUENCE: 140

```
Met Ala Lys Val Ser Gly Arg Ser Lys Thr Ile Val Asp Asp Glu
1               5                   10                  15

Ile Ser Asp Lys Thr Ala Ser Ser Glu Ser Ala Ser Ile Ala Leu
            20                  25                  30

Thr Ser Lys Arg Lys Arg Lys Ser Pro Pro Arg Asn Ala Pro Leu Gln
        35                  40                  45

Arg Ser Pro Tyr Arg Gly Val Thr Arg His Arg Trp Thr Gly Arg
    50                  55                  60

Tyr Glu Ala His Leu Trp Asp Lys Asn Ser Trp Asn Asp Thr Gln Thr
65                  70                  75                  80

Lys Lys Gly Arg Gln Val Tyr Leu Gly Ala Tyr Asp Glu Glu Ala
                85                  90                  95

Ala Ala Arg Ala Tyr Asp Leu Ala Ala Leu Lys Tyr Trp Gly Arg Asp
            100                 105                 110

Thr Leu Leu Asn Phe Pro Leu Pro Ser Tyr Asp Glu Asp Val Lys Glu
        115                 120                 125

Met Glu Gly Gln Ser Lys Glu Glu Tyr Ile Gly Ser Leu Arg Arg Lys
130                 135                 140

Ser Ser Gly Phe Ser Arg Gly Val Ser Lys Tyr Arg Gly Val Ala Arg
145                 150                 155                 160

His His His Asn Gly Arg Trp Glu Ala Arg Ile Gly Arg Val Phe Gly
                165                 170                 175

Asn Lys Tyr Leu Tyr Leu Gly Thr Tyr Ala Thr Gln Glu Glu Ala Ala
            180                 185                 190

Ile Ala Tyr Asp Ile Ala Ala Ile Glu Tyr Arg Gly Leu Asn Ala Val
        195                 200                 205

Thr Asn Phe Asp Val Ser Arg Tyr Leu Asn Pro Asn Ala Ala Ala Asp
    210                 215                 220

Lys Ala Asp Ser Asp Ser Lys Pro Ile Arg Ser Pro Ser Arg Glu Pro
225                 230                 235                 240

Glu Ser Ser Asp Asp Asn Lys Ser Pro Lys Ser Glu Glu Val Ile Glu
                245                 250                 255

Pro Ser Thr Ser Pro Glu Val Ile Pro Thr Arg Arg Ser Phe Pro Asp
            260                 265                 270

Asp Ile Gln Thr Tyr Phe Gly Cys Gln Asp Ser Gly Lys Leu Ala Thr
        275                 280                 285

Glu Glu Asp Val Ile Phe Asp Cys Phe Asn Ser Tyr Ile Asn Pro Gly
    290                 295                 300

Phe Tyr Asn Glu Phe Asp Tyr Gly Pro
305                 310
```

<210> SEQ ID NO 141
<211> LENGTH: 999
<212> TYPE: DNA
<213> ORGANISM: Arabidopsis thaliana
<220> FEATURE:
<223> OTHER INFORMATION: G2424

<400> SEQUENCE: 141

```
atgaggatgg agatggtgca tgctgacgtg gcgtctctct ccataacacc ttgcttcccg        60
tcttctttgt cttcgtcctc acatcatcac tataaccaac aacaacattg tatcatgtcg       120
gaagatcaac accattcgat ggatcagacc acttcatcgg actacttctc tttaaatatc       180
gacaatgctc aacatctccg tagctactac acaagtcata gagaagaaga catgaaccct       240
aatctaagtg attacagtaa ttgcaacaag aaagacacaa cagtctatag aagctgtgga       300
cactcgtcaa aagcttcggt gtctagagga cattggagac agctgaaga tactaagctc        360
aaagaactag tcgccgtcta cggtccacaa aactggaacc tcatagctga aagctccaa        420
ggaagatccg ggaaaagctg taggcttcga tggtttaacc aactagaccc aaggataaat       480
agaagagcct tcactgagga agaagaagag aggctaatgc aagctcatag gctttatggt       540
aacaaatggg cgatgatagc gaggcttttc cctggtagga ctgataattc tgtgaagaac       600
cattggcatg ttataatggc tcgcaagttt agggaacaat cttcttctta ccgtaggagg       660
aagacgatgg tttctcttaa gccactcatt aaccctaatc ctcacatttt caatgatttt       720
gaccctaccc ggttagcttt gacccacctt gctagtagtg accataagca gcttatgtta       780
ccagttcctt gcttcccagg ttatgatcat gaaaatgaga gtccattaat ggtggatatg       840
ttcgaaaccc aaatgatggt tggcgattac attgcatgga cacaagaggc aactacattc       900
gatttcttaa accaaaccgg gaagagtgag atatttgaaa gaatcaatga ggagaagaaa       960
ccaccatttt tcgatttctt tggggttgggg acggtgtga                             999
```

<210> SEQ ID NO 142
<211> LENGTH: 332
<212> TYPE: PRT
<213> ORGANISM: Arabidopsis thaliana
<220> FEATURE:
<223> OTHER INFORMATION: G2424 polypeptide

<400> SEQUENCE: 142

```
Met Arg Met Glu Met Val His Ala Asp Val Ala Ser Leu Ser Ile Thr
1               5                  10                  15

Pro Cys Phe Pro Ser Ser Leu Ser Ser Ser His His Tyr Asn
            20                  25                  30

Gln Gln Gln His Cys Ile Met Ser Glu Asp Gln His His Ser Met Asp
        35                  40                  45

Gln Thr Thr Ser Ser Asp Tyr Phe Ser Leu Asn Ile Asp Asn Ala Gln
    50                  55                  60

His Leu Arg Ser Tyr Tyr Thr Ser His Arg Glu Glu Asp Met Asn Pro
65                  70                  75                  80

Asn Leu Ser Asp Tyr Ser Asn Cys Asn Lys Lys Asp Thr Thr Val Tyr
                85                  90                  95

Arg Ser Cys Gly His Ser Ser Lys Ala Ser Val Ser Arg Gly His Trp
            100                 105                 110

Arg Pro Ala Glu Asp Thr Lys Leu Lys Glu Leu Val Ala Val Tyr Gly
        115                 120                 125

Pro Gln Asn Trp Asn Leu Ile Ala Glu Lys Leu Gln Gly Arg Ser Gly
    130                 135                 140

Lys Ser Cys Arg Leu Arg Trp Phe Asn Gln Leu Asp Pro Arg Ile Asn
145                 150                 155                 160

Arg Arg Ala Phe Thr Glu Glu Glu Glu Glu Arg Leu Met Gln Ala His
                165                 170                 175
```

```
Arg Leu Tyr Gly Asn Lys Trp Ala Met Ile Ala Arg Leu Phe Pro Gly
                180                 185                 190

Arg Thr Asp Asn Ser Val Lys Asn His Trp His Val Ile Met Ala Arg
            195                 200                 205

Lys Phe Arg Glu Gln Ser Ser Tyr Arg Arg Lys Thr Met Val
        210                 215                 220

Ser Leu Lys Pro Leu Ile Asn Pro Asn Pro His Ile Phe Asn Asp Phe
225                 230                 235                 240

Asp Pro Thr Arg Leu Ala Leu Thr His Leu Ala Ser Ser Asp His Lys
                245                 250                 255

Gln Leu Met Leu Pro Val Pro Cys Phe Pro Gly Tyr Asp His Glu Asn
            260                 265                 270

Glu Ser Pro Leu Met Val Asp Met Phe Glu Thr Gln Met Met Val Gly
        275                 280                 285

Asp Tyr Ile Ala Trp Thr Gln Glu Ala Thr Thr Phe Asp Phe Leu Asn
            290                 295                 300

Gln Thr Gly Lys Ser Glu Ile Phe Glu Arg Ile Asn Glu Glu Lys Lys
305                 310                 315                 320

Pro Pro Phe Phe Asp Phe Leu Gly Leu Gly Thr Val
                325                 330
```

<210> SEQ ID NO 143
<211> LENGTH: 653
<212> TYPE: DNA
<213> ORGANISM: Arabidopsis thaliana
<220> FEATURE:
<223> OTHER INFORMATION: G2583

<400> SEQUENCE: 143

```
caaatcagaa aatatagagt ttgaaggaaa ctaaaagatg gtacattcga ggaagttccg      60
aggtgtccgc cagcgacaat ggggttcttg ggtctctgag attcgccatc ctctattgaa     120
gagaagagtg tggcttggaa ctttcgaaac ggcagaagcg gctgcaagag catacgacca     180
agcggctctt ctaatgaacg gccaaaacgc taagaccaat ttccctgtcg taaaatcaga     240
ggaaggctcc gatcacgtta agatgttaa ctctccgttg atgtcaccaa agtcattatc     300
tgagcttttg aacgctaagc taaggaagag ctgcaaagac ctaacgcctt ctttgacgtg     360
tctccgtctt gatactgaca gttcccacat tggagtttgg cagaaacggg ccgggtcgaa     420
aacaagtccg acttgggtca tgcgcctcga acttgggaac gtagtcaacg aaagtgcggt     480
tgacttaggg ttgactacga tgaacaaaca aaacgttgag aaagaagaag aagaagaaga     540
agctattatt agtgatgagg atcagttagc tatggagatg atcgaggagt tgctgaattg     600
gagttgactt ttgactttaa cttgttgcaa gtccacaagg ggtaagggtt ttc            653
```

<210> SEQ ID NO 144
<211> LENGTH: 189
<212> TYPE: PRT
<213> ORGANISM: Arabidopsis thaliana
<220> FEATURE:
<223> OTHER INFORMATION: G2583 polypeptide

<400> SEQUENCE: 144

```
Met Val His Ser Arg Lys Phe Arg Gly Val Arg Gln Arg Gln Trp Gly
1               5                  10                  15

Ser Trp Val Ser Glu Ile Arg His Pro Leu Leu Lys Arg Arg Val Trp
            20                  25                  30

Leu Gly Thr Phe Glu Thr Ala Glu Ala Ala Ala Arg Ala Tyr Asp Gln
```

```
            35                  40                  45
Ala Ala Leu Leu Met Asn Gly Gln Asn Ala Lys Thr Asn Phe Pro Val
         50                  55                  60

Val Lys Ser Glu Glu Gly Ser Asp His Val Lys Asp Val Asn Ser Pro
 65                  70                  75                  80

Leu Met Ser Pro Lys Ser Leu Ser Glu Leu Leu Asn Ala Lys Leu Arg
                 85                  90                  95

Lys Ser Cys Lys Asp Leu Thr Pro Ser Leu Thr Cys Leu Arg Leu Asp
             100                 105                 110

Thr Asp Ser Ser His Ile Gly Val Trp Gln Lys Arg Ala Gly Ser Lys
         115                 120                 125

Thr Ser Pro Thr Trp Val Met Arg Leu Glu Leu Gly Asn Val Val Asn
     130                 135                 140

Glu Ser Ala Val Asp Leu Gly Leu Thr Thr Met Asn Lys Gln Asn Val
145                 150                 155                 160

Glu Lys Glu Glu Glu Glu Glu Ala Ile Ile Ser Asp Glu Asp Gln
                 165                 170                 175

Leu Ala Met Glu Met Ile Glu Glu Leu Leu Asn Trp Ser
             180                 185
```

<210> SEQ ID NO 145
<211> LENGTH: 844
<212> TYPE: DNA
<213> ORGANISM: Arabidopsis thaliana
<220> FEATURE:
<223> OTHER INFORMATION: G1387

<400> SEQUENCE: 145

```
tctctctccc actctcactt tctctcctat tcttagttcg tgtcagaaac acacagagaa      60
attaagaacc ctaatttaaa acagaagaat ggtacattcg aagaagttcc gaggtgtccg     120
ccagcgtcag tggggttctt gggtttctga gattcgtcat cctctcttga agagaagagt     180
gtggctagga acattcgaca cggcggaaac agcggctaga gcctacgacc aagccgcggt     240
tctaatgaac ggccagagcg cgaagactaa cttccccgtc atcaaatcga acggttcaaa     300
ttccttggag attaactctg cgttaaggtc tcccaaatca ttatcggaac tattgaacgc     360
taagctaagg aagaactgta aagaccagac accgtatctg acgtgtctcc gcctcgacaa     420
cgacagctca cacatcggcg tctggcagaa acgcgccggg tcaaaaacga gtccaaactg     480
ggtcaagctt gttgaactag gtgacaaagt taacgcacgt cccggtggtg atattgagac     540
taataagatg aaggtacgaa acgaagacgt tcaggaagat gatcaaatgg cgatgcagat     600
gatcgaggag ttgcttaact ggacctgtcc tggatctgga tccattgcac aggtctaaag     660
gagaatcatt gaattatatg atcaagataa taatatagtt gagggttaat aataatcgag     720
ggtaagtaat ttacgtgtag ctaataatta atataatttt cgaacatata tatgaatata     780
tgatagctct agaaatgagt acgtatatat acgtaaacat ttttcctcaa atatagtata     840
tgtg                                                                  844
```

<210> SEQ ID NO 146
<211> LENGTH: 189
<212> TYPE: PRT
<213> ORGANISM: Arabidopsis thaliana
<220> FEATURE:
<223> OTHER INFORMATION: G1387 polypeptide

<400> SEQUENCE: 146

```
Met Val His Ser Lys Lys Phe Arg Gly Val Arg Gln Arg Gln Trp Gly
1               5                   10                  15

Ser Trp Val Ser Glu Ile Arg His Pro Leu Leu Lys Arg Arg Val Trp
            20                  25                  30

Leu Gly Thr Phe Asp Thr Ala Glu Thr Ala Ala Arg Ala Tyr Asp Gln
        35                  40                  45

Ala Ala Val Leu Met Asn Gly Gln Ser Ala Lys Thr Asn Phe Pro Val
    50                  55                  60

Ile Lys Ser Asn Gly Ser Asn Ser Leu Glu Ile Asn Ser Ala Leu Arg
65                  70                  75                  80

Ser Pro Lys Ser Leu Ser Glu Leu Leu Asn Ala Lys Leu Arg Lys Asn
                85                  90                  95

Cys Lys Asp Gln Thr Pro Tyr Leu Thr Cys Leu Arg Leu Asp Asn Asp
            100                 105                 110

Ser Ser His Ile Gly Val Trp Gln Lys Arg Ala Gly Ser Lys Thr Ser
        115                 120                 125

Pro Asn Trp Val Lys Leu Val Glu Leu Gly Asp Lys Val Asn Ala Arg
130                 135                 140

Pro Gly Gly Asp Ile Glu Thr Asn Lys Met Lys Val Arg Asn Glu Asp
145                 150                 155                 160

Val Gln Glu Asp Asp Gln Met Ala Met Gln Met Ile Glu Glu Leu Leu
                165                 170                 175

Asn Trp Thr Cys Pro Gly Ser Gly Ser Ile Ala Gln Val
            180                 185

<210> SEQ ID NO 147
<211> LENGTH: 833
<212> TYPE: DNA
<213> ORGANISM: Arabidopsis thaliana
<220> FEATURE:
<221> NAME/KEY: misc_feature
<222> LOCATION: (810)..(810)
<223> OTHER INFORMATION: n is a, c, g, or t
<220> FEATURE:
<223> OTHER INFORMATION: G977

<400> SEQUENCE: 147
caccaaactc acctgaaacc ctatttccat ttaccattca cactaatggc acgaccacaa      60
caacgctttc gaggcgttag acagaggcat tggggctctt gggtctccga aattcgtcac     120
cctctcttga aaacaagaat ctggctaggg acgtttgaga cagcggagga tgcagcaagg     180
gcctacgacg aggcggctag gctaatgtgt ggcccgagag ctcgtactaa tttcccatac     240
aaccctaatg ccattcctac ttcctcttcc aagcttctat cagcaactct taccgctaaa     300
ctccacaaat gctacatggc ttctcttcaa atgaccaagc aaacgcaaac acaaacgcaa     360
acgcagaccg caagatcaca atccgcggac agtgacggtg tgacggctaa cgaaagtcat     420
ttgaacagag gagtaacgga gacgacagag atcaagtggg aagatggaaa tgcgaatatg     480
caacagaatt ttaggccatt ggaggaagat catatcgagc aaatgattga ggagctgctt     540
cactacggtt ccattgagct tgctctgtt ttaccaactc agacgctgtg agaaatggcc     600
ttgtcgtttt agcgtattct tttcattttt atttttgttt ccacaaaaac ggcgtcgtaa     660
gtgatgagag tagtagtgag agaaggctaa tttcaagaca ttttgatctg aattggcctc     720
ttttgaaaca ctgattctag tttctataag agcaatcgat catatgctat gttatgtata     780
gtattataaa aaatgttat tttctgattn aaaaaaaaaa aaaaaaaaa aaa              833
```

```
<210> SEQ ID NO 148
<211> LENGTH: 181
<212> TYPE: PRT
<213> ORGANISM: Arabidopsis thaliana
<220> FEATURE:
<223> OTHER INFORMATION: G977 polypeptide

<400> SEQUENCE: 148

Met Ala Arg Pro Gln Gln Arg Phe Arg Gly Val Arg Gln Arg His Trp
  1               5                  10                  15

Gly Ser Trp Val Ser Glu Ile Arg His Pro Leu Leu Lys Thr Arg Ile
             20                  25                  30

Trp Leu Gly Thr Phe Glu Thr Ala Glu Asp Ala Ala Arg Ala Tyr Asp
         35                  40                  45

Glu Ala Ala Arg Leu Met Cys Gly Pro Arg Ala Arg Thr Asn Phe Pro
 50                  55                  60

Tyr Asn Pro Asn Ala Ile Pro Thr Ser Ser Lys Leu Leu Ser Ala
 65                  70                  75                  80

Thr Leu Thr Ala Lys Leu His Lys Cys Tyr Met Ala Ser Leu Gln Met
                 85                  90                  95

Thr Lys Gln Thr Gln Thr Gln Thr Gln Thr Gln Thr Ala Arg Ser Gln
            100                 105                 110

Ser Ala Asp Ser Asp Gly Val Thr Ala Asn Glu Ser His Leu Asn Arg
        115                 120                 125

Gly Val Thr Glu Thr Thr Glu Ile Lys Trp Glu Asp Gly Asn Ala Asn
    130                 135                 140

Met Gln Gln Asn Phe Arg Pro Leu Glu Glu Asp His Ile Glu Gln Met
145                 150                 155                 160

Ile Glu Glu Leu Leu His Tyr Gly Ser Ile Glu Leu Cys Ser Val Leu
                165                 170                 175

Pro Thr Gln Thr Leu
            180

<210> SEQ ID NO 149
<211> LENGTH: 732
<212> TYPE: DNA
<213> ORGANISM: Arabidopsis thaliana
<220> FEATURE:
<223> OTHER INFORMATION: G4294

<400> SEQUENCE: 149
atgggacagt cgaagaagaa gttccgcgga gtcaggcagc gccactgggg ctcctgggtc     60
tccgagatca ggcaccctct ccttaagagg agggtgtggc tgggtacctt tgagacggcg    120
gaggaggcgg cgcgggcgta cgacgaggcc gccatcctga tgagcggccg caacgccaag    180
accaacttcc cagtcgcgag gaacgccacg ggggagctca ccggcggc tgcggtggca    240 gggcgggatg ccgtgtcgg cggcggcagc ggcagctcgt cctcaatgac ggccaacggc    300
ggcgggaaca gcctgtctca gatcctcagc gccaagctcc gcaagtgctg caagacgccg    360
tcgccgtcgc tcacctgcct ccgccttgac ccggagaagt cccacattgg cgtctggcag    420
aagcgcgccg gcgcacgcgc tgactccagc tgggtcatga ccgtcgagct caacaaggac    480
acggccgtgt cgtcggctgc gacggtggca gcagcaacag cagtgtcgtc cagcgaccag    540
ccgactccga gtgacagcac agtcacaacg acgtccacgt ccaccacggg ctcgccgtcg    600
ccaccacctc cggcaatgga cgacgaggag aggatcgcgc tgcagatgat cgaggagctg    660
ctgggcagga gcggcccggg ctcgccgtca catgggctgc tgcacggtgg tgaaggtagc    720
```

```
ctcgtcatct ga                                                        732

<210> SEQ ID NO 150
<211> LENGTH: 243
<212> TYPE: PRT
<213> ORGANISM: Oryza sativa
<220> FEATURE:
<223> OTHER INFORMATION: G4294 polypeptide

<400> SEQUENCE: 150

Met Gly Gln Ser Lys Lys Phe Arg Gly Val Arg Gln His Trp
1               5                   10                  15

Gly Ser Trp Val Ser Glu Ile Arg His Pro Leu Leu Lys Arg Arg Val
            20                  25                  30

Trp Leu Gly Thr Phe Glu Thr Ala Glu Glu Ala Ala Arg Ala Tyr Asp
        35                  40                  45

Glu Ala Ala Ile Leu Met Ser Gly Arg Asn Ala Lys Thr Asn Phe Pro
    50                  55                  60

Val Ala Arg Asn Ala Thr Gly Glu Leu Thr Pro Ala Ala Val Ala
65                  70                  75                  80

Gly Arg Asp Gly Arg Val Gly Gly Gly Ser Gly Ser Ser Ser Ser Met
                85                  90                  95

Thr Ala Asn Gly Gly Asn Ser Leu Ser Gln Ile Leu Ser Ala Lys
            100                 105                 110

Leu Arg Lys Cys Cys Lys Thr Pro Ser Pro Ser Leu Thr Cys Leu Arg
        115                 120                 125

Leu Asp Pro Glu Lys Ser His Ile Gly Val Trp Gln Lys Arg Ala Gly
    130                 135                 140

Ala Arg Ala Asp Ser Ser Trp Val Met Thr Val Glu Leu Asn Lys Asp
145                 150                 155                 160

Thr Ala Val Ser Ser Ala Ala Thr Val Ala Ala Thr Ala Val Ser
                165                 170                 175

Ser Ser Asp Gln Pro Thr Pro Ser Asp Ser Thr Val Thr Thr Thr Ser
            180                 185                 190

Thr Ser Thr Thr Gly Ser Pro Ser Pro Pro Pro Ala Met Asp Asp
        195                 200                 205

Glu Glu Arg Ile Ala Leu Gln Met Ile Glu Glu Leu Leu Gly Arg Ser
    210                 215                 220

Gly Pro Gly Ser Pro Ser His Gly Leu Leu His Gly Gly Glu Gly Ser
225                 230                 235                 240

Leu Val Ile

<210> SEQ ID NO 151
<211> LENGTH: 485
<212> TYPE: DNA
<213> ORGANISM: Arabidopsis thaliana
<220> FEATURE:
<223> OTHER INFORMATION: G2133

<400> SEQUENCE: 151
atctcatctt catccaccca aaaacatgga ttcaagagac accggagaaa ctgaccagag    60
caagtacaaa ggtatccgtc gtcggaaatg gggaaaatgg gtatcagaga ttcgtgtccc   120
gggaactcgt caacgtctct ggttaggctc tttctccacc gcagaaggcg ctgccgtagc   180
ccacgacgtc gcttttttact gcttgcaccg accatcttcc ctcgacgacg aatcttttaa   240
cttccctcac ttacttacaa cctccctcgc ctccaatata tctcctaagt ccatccaaaa   300
```

```
agctgcttcc gacgccggca tggccgtgga cgccggattc catggtgctg tgtctgggag    360
tggtggttgt gaagagagat cttccatggc gaatatggag gaggaggaca aacttagtat    420
ctccgtgtat gattatcttg aagacgatct cgtttgatct atacgagtac gtttttagca    480
gttaa                                                                 485
```

<210> SEQ ID NO 152
<211> LENGTH: 143
<212> TYPE: PRT
<213> ORGANISM: Arabidopsis thaliana
<220> FEATURE:
<223> OTHER INFORMATION: G2133 polypeptide

<400> SEQUENCE: 152

```
Met Asp Ser Arg Asp Thr Gly Glu Thr Asp Gln Ser Lys Tyr Lys Gly
1               5                   10                  15

Ile Arg Arg Arg Lys Trp Gly Lys Trp Val Ser Glu Ile Arg Val Pro
            20                  25                  30

Gly Thr Arg Gln Arg Leu Trp Leu Gly Ser Phe Ser Thr Ala Glu Gly
        35                  40                  45

Ala Ala Val Ala His Asp Val Ala Phe Tyr Cys Leu His Arg Pro Ser
    50                  55                  60

Ser Leu Asp Asp Glu Ser Phe Asn Phe Pro His Leu Leu Thr Thr Ser
65                  70                  75                  80

Leu Ala Ser Asn Ile Ser Pro Lys Ser Ile Gln Lys Ala Ala Ser Asp
                85                  90                  95

Ala Gly Met Ala Val Asp Ala Gly Phe His Gly Ala Val Ser Gly Ser
            100                 105                 110

Gly Gly Cys Glu Glu Arg Ser Ser Met Ala Asn Met Glu Glu Glu Asp
        115                 120                 125

Lys Leu Ser Ile Ser Val Tyr Asp Tyr Leu Glu Asp Asp Leu Val
    130                 135                 140
```

<210> SEQ ID NO 153
<211> LENGTH: 594
<212> TYPE: DNA
<213> ORGANISM: Oryza sativa
<220> FEATURE:
<223> OTHER INFORMATION: G3649

<400> SEQUENCE: 153

```
atgggccggg tggcggcgag cggcggcggc ggcggcggag gggagatgat gaggtacagg    60
ggcgtgcggc ggcggcggtg ggggaagtgg gtgtcggaga tccgggtgcc cgggacgcgg    120
gagcgcctgt ggctcggctc ctacgccacc gccgaggccg ccgccgtcgc gcacgacgcc    180
gccgtctgcc tcctccggct cggcggcggc cgccgcgccg ccgcaggcgg aggcggcggg    240
ctcaacttcc ccgcccgcgc gctcgccgcg cggcggcgcc cctcctccta cggcggcgcc    300
ggcggtctcc tgtccccgcg ctccgtgcag cgcgtggcgt ccgacgccgg catggccgcc    360
gacgcgcagc tcgtggacct cgccgcgac cacccgcccg ccgccgccgc cgcctcatcc    420
tccggcagcg gcgtggcggg agacggtgca agaaagcaag ggacacgtgg cgaggttagc    480
gacacgtatt ggtgtaggaa tgagaggat gggagcagaa gccggagctc cgggagtgag    540
gagctcattg tttacgaggg cttaagtgta gatgacatgg aaattttgat gtaa          594
```

<210> SEQ ID NO 154
<211> LENGTH: 197
<212> TYPE: PRT

<213> ORGANISM: Oryza sativa
<220> FEATURE:
<223> OTHER INFORMATION: G3649 polypeptide

<400> SEQUENCE: 154

```
Met Gly Arg Val Ala Ala Ser Gly Gly Gly Gly Gly Gly Gly Glu Met
1               5                   10                  15
Met Arg Tyr Arg Gly Val Arg Arg Arg Trp Gly Lys Trp Val Ser
            20                  25                  30
Glu Ile Arg Val Pro Gly Thr Arg Glu Arg Leu Trp Leu Gly Ser Tyr
        35                  40                  45
Ala Thr Ala Glu Ala Ala Ala Val Ala His Asp Ala Ala Val Cys Leu
    50                  55                  60
Leu Arg Leu Gly Gly Arg Ala Ala Ala Gly Gly Gly Gly
65                  70                  75                  80
Leu Asn Phe Pro Ala Arg Ala Leu Ala Ala Ala Ala Ala Ser Ser
                85                  90                  95
Tyr Gly Gly Ala Gly Gly Leu Leu Ser Pro Arg Ser Val Gln Arg Val
            100                 105                 110
Ala Ser Asp Ala Gly Met Ala Ala Asp Ala Gln Leu Val Asp Leu Arg
        115                 120                 125
Arg Asp His Pro Pro Ala Ala Ala Ala Ser Ser Ser Gly Ser Gly
    130                 135                 140
Val Ala Gly Asp Gly Ala Arg Lys Gln Gly Thr Arg Gly Glu Val Ser
145                 150                 155                 160
Asp Thr Tyr Trp Cys Arg Asn Gly Glu Asp Gly Ser Arg Ser Arg Ser
                165                 170                 175
Ser Gly Ser Glu Glu Leu Ile Val Tyr Glu Gly Leu Ser Val Asp Asp
            180                 185                 190
Met Glu Ile Leu Met
        195
```

<210> SEQ ID NO 155
<211> LENGTH: 687
<212> TYPE: DNA
<213> ORGANISM: Oryza sativa
<220> FEATURE:
<223> OTHER INFORMATION: G3644

<400> SEQUENCE: 155

```
atgccttttg tacgtacact tgctttccca acgctcgcga atcaaatcga gggtgaaatt      60
aagtcaagaa cggagagaga tcacggtgag gttgatctca gctcgccgga ggaggcaatg     120
agccgggcgg agtgcggcgg cggcgaggag gaggagcggt gcaggtacag ggcgtgcgg      180
cggcggcggt gggggaagtg ggtgtcggag atccgggtgc ccggcacgcg ggagcggctg     240
tggctgggt cctacgccac gccggaggcc gccgccgtcg cgcacgacac ggccgtctac     300
ttcctccgcg gaggcgcggg cgacggcggt ggcggcggcg cgacgctcaa cttcccggag     360
cgcgcggcgg ccacgtacgg cggcggcgcc gccgtggcgc gcctgtcgcc gcggtccgtg     420
cagcgcgtgg cgtccgacgc cggcatggcc gccgacgcgc agctcgtggc ggcgcgggac     480
gccgcgcccg cgcccgcgcc ggcgacggcc tacgcgcgcc cggatcactg cgccggcgcg     540
acgacggcgc ggcacgacga gctggcgcgc cgcgggatgt acggcgctca cgcgcatgcc     600
gccggcgcga acgccaggac gagcggcgag cggcagctcg tctgtgccga ggagattagc     660
gtggatgaca tggagatcct gatgtaa                                        687
```

```
<210> SEQ ID NO 156
<211> LENGTH: 228
<212> TYPE: PRT
<213> ORGANISM: Oryza sativa
<220> FEATURE:
<223> OTHER INFORMATION: G3644 polypeptide

<400> SEQUENCE: 156

Met Pro Phe Val Arg Thr Leu Ala Phe Pro Thr Leu Ala Asn Gln Ile
1               5                   10                  15

Glu Gly Glu Ile Lys Ser Arg Thr Glu Arg Asp His Gly Glu Val Asp
            20                  25                  30

Leu Ser Ser Pro Glu Glu Ala Met Ser Arg Ala Glu Cys Gly Gly Gly
        35                  40                  45

Glu Glu Glu Arg Cys Arg Tyr Arg Gly Val Arg Arg Arg Arg Trp
    50                  55                  60

Gly Lys Trp Val Ser Glu Ile Arg Val Pro Gly Thr Arg Glu Arg Leu
65              70                  75                  80

Trp Leu Gly Ser Tyr Ala Thr Pro Glu Ala Ala Val Ala His Asp
                85                  90                  95

Thr Ala Val Tyr Phe Leu Arg Gly Gly Ala Gly Asp Gly Gly Gly
            100                 105                 110

Gly Ala Thr Leu Asn Phe Pro Glu Arg Ala Ala Thr Tyr Gly Gly
            115                 120                 125

Gly Ala Ala Val Ala Arg Leu Ser Pro Arg Ser Val Gln Arg Val Ala
    130                 135                 140

Ser Asp Ala Gly Met Ala Ala Asp Ala Gln Leu Val Ala Ala Arg Asp
145                 150                 155                 160

Ala Ala Pro Ala Pro Ala Pro Ala Thr Ala Tyr Ala Arg Pro Asp His
                165                 170                 175

Cys Ala Gly Ala Thr Thr Ala Arg His Asp Glu Leu Ala Arg Arg Gly
            180                 185                 190

Met Tyr Gly Ala His Ala His Ala Ala Gly Ala Asn Ala Arg Thr Ser
        195                 200                 205

Gly Glu Arg Gln Leu Val Cys Ala Glu Glu Ile Ser Val Asp Asp Met
    210                 215                 220

Glu Ile Leu Met
225

<210> SEQ ID NO 157
<211> LENGTH: 1082
<212> TYPE: DNA
<213> ORGANISM: Glycine max
<220> FEATURE:
<223> OTHER INFORMATION: G3643

<400> SEQUENCE: 157
ccacgcgtcc gcttcttctc tcagaataca caacacaaag tcaatataat tatagtatat    60
ccctatgagt aggagttcgg cgatgcatgg aattacaagc acaaacaaca agttgaaggg   120
agttcggcgt cgaaaatggg gcaaatgggt gtcggagatt cgtgttccgg gcacgcaaga   180
gcgtttgtgg ttgggaacct acgccacgcc ggaggctgcc gcggtggctc acgacgttgc   240
cgtctactgt ctaagtaggc cttcttcgtt ggacaaactt aacttccccg aaaccttgtc   300
ttcgtacagt gttcagctca gggacatgtc tccgaggtct gtgcagaagg tggcttccga   360
tgttggcatg gatgttgatg caagaaacat tgttgcgggc aaaacttcaa cggtggggc    420
```

-continued

```
agaaactaat tgcgagagtg atgagaggac tagtactgcg tctgtgtgta atgttgttgg    480
agaaggtggt gctgatcatt cggatgtgtt ttggtgggat gatgatggtg ggtcttggca    540
tggaagtggt ggagattcta cggaaaggga tgccttgagc atttccattg aagattatct    600
ttagctgttc taggtttcaa ctttagttat cttttttttt tttttttttga gttatgatcg    660 atgcgcatag ttagtagtta cagataatta ctgctagtgt tgggtgttta acggtcaga    720 gatgatgata tataaatttg atgtgcgcta gctgcctttt tgaagaaact aaaaaaaggt    780
aaaacaagaa agattgtacc cccaaaatga acttggtcaa tttcacactt tcacgccatt    840
tgcattttgt gcacgttgtt agttttcaaa ttgttaattc ccttgctaaa cccactcaaa    900
cttgagtgcg ttcacctttt attaccacgt agtaactgag agttaacgaa atatttctt    960 tataaaaatt atttaccatt tagtgtctttt cgtttacttg taattattca acttgtcaat   1020
aagatgaaag ttctaatttt agatataata aaattcagct agtatttgtg aattactcac   1080
tt                                                                  1082
```

<210> SEQ ID NO 158
<211> LENGTH: 179
<212> TYPE: PRT
<213> ORGANISM: Glycine max
<220> FEATURE:
<223> OTHER INFORMATION: G3643 polypeptide

<400> SEQUENCE: 158

```
Met Ser Arg Ser Ser Ala Met His Gly Ile Thr Ser Thr Asn Asn Lys
1               5                   10                  15

Leu Lys Gly Val Arg Arg Lys Trp Gly Lys Trp Val Ser Glu Ile
            20                  25                  30

Arg Val Pro Gly Thr Gln Glu Arg Leu Trp Leu Gly Thr Tyr Ala Thr
        35                  40                  45

Pro Glu Ala Ala Val Ala His Asp Val Ala Val Tyr Cys Leu Ser
    50                  55                  60

Arg Pro Ser Ser Leu Asp Lys Leu Asn Phe Pro Glu Thr Leu Ser Ser
65                  70                  75                  80

Tyr Ser Val Gln Leu Arg Asp Met Ser Pro Arg Ser Val Gln Lys Val
                85                  90                  95

Ala Ser Asp Val Gly Met Asp Val Asp Ala Arg Asn Ile Val Ala Gly
            100                 105                 110

Lys Thr Ser Thr Val Gly Ala Glu Thr Asn Cys Glu Ser Asp Glu Arg
        115                 120                 125

Thr Ser Thr Ala Ser Val Cys Asn Val Val Gly Glu Gly Gly Ala Asp
    130                 135                 140

His Ser Asp Val Phe Trp Trp Asp Asp Gly Ser Trp His Gly
145                 150                 155                 160

Ser Gly Asp Ser Thr Glu Arg Asp Ala Leu Ser Ile Ser Ile Glu
                165                 170                 175

Asp Tyr Leu
```

<210> SEQ ID NO 159
<211> LENGTH: 813
<212> TYPE: DNA
<213> ORGANISM: Zea mays
<220> FEATURE:
<223> OTHER INFORMATION: G3650

<400> SEQUENCE: 159

```
ccacccgtgc tcgatcgatc atgccatgtc aacgccccccg ccgcgctga ccttgatcct      60
tctcgtctca ccgcaccta taaatacgcc cacgtcgctc gtgtcgtcgt gtgctccatc     120
gcaaacggcc aaaaaccacc agcacaagtg cacaagccat tgcccatcgg acgcccagcc     180
ggccagcccc tgtcccgacg gtcggccgac gacgatgagc cgcgcagcga ccaacagcgg     240
cgcggagcgg cggtgccggt acaggggcgt gcggcggcgg gcctggggga agtgggtgtc     300
ggagatccgg gtgccgggca cgcggagcg gctgtggctg ggatcctacg cggcgcccga     360
ggccgccgcc gtcgcgcacg acgccgccgc gtgcctcctc cgcggctgcg cgggccgccg     420
cctcaacttc ccgggccgcg ccgcctgcta ctacgcctgc ggcgggcagc agccgctgtc     480
gccgcgctcc gtgcagcgcg tcgcgtccga cgccggcatg gccgccgacg cgcagatcgt     540
cgacgcgcgg gcgcccctcg cctcgccgcc gcccgttgtc cagcccgccg ctctcgctgg     600
cattattggc ggcgccgcgc gagaaggcgg cggaggcgtg cgaggccccg cgtgcgcgcc     660
ggcgccgcca agcaacggcg ctggcagcag cagtacgtat tggtccacgc cgagcagtga     720
gccgccgctt gtttacgggg acattagcgt agacgacata gagatcttga tttgactatt     780
aggcactagt tagtagcata gtcatggcag ttc                                  813
```

<210> SEQ ID NO 160
<211> LENGTH: 249
<212> TYPE: PRT
<213> ORGANISM: Zea mays
<220> FEATURE:
<223> OTHER INFORMATION: G3650 polypeptide

<400> SEQUENCE: 160

```
Met Ser Thr Pro Pro Ala Ala Leu Thr Leu Ile Leu Leu Val Ser Pro
1               5                   10                  15

His Leu Ile Asn Thr Pro Thr Ser Leu Val Ser Cys Ala Pro Ser
            20                  25                  30

Gln Thr Ala Lys Asn His Gln His Lys Cys Thr Ser His Cys Pro Ser
        35                  40                  45

Asp Ala Gln Pro Ala Ser Pro Cys Pro Asp Gly Arg Pro Thr Thr Met
    50                  55                  60

Ser Arg Ala Ala Thr Asn Ser Gly Ala Glu Arg Cys Arg Tyr Arg
65                  70                  75                  80

Gly Val Arg Arg Arg Ala Trp Gly Lys Trp Val Ser Glu Ile Arg Val
                85                  90                  95

Pro Gly Thr Arg Glu Arg Leu Trp Leu Gly Ser Tyr Ala Ala Pro Glu
            100                 105                 110

Ala Ala Ala Val Ala His Asp Ala Ala Ala Cys Leu Leu Arg Gly Cys
        115                 120                 125

Ala Gly Arg Arg Leu Asn Phe Pro Gly Arg Ala Ala Cys Tyr Tyr Ala
    130                 135                 140

Cys Gly Gly Gln Gln Pro Leu Ser Pro Arg Ser Val Gln Arg Val Ala
145                 150                 155                 160

Ser Asp Ala Gly Met Ala Ala Asp Ala Gln Ile Val Asp Ala Arg Ala
                165                 170                 175

Ala Leu Ala Ser Pro Pro Val Val Gln Pro Ala Ala Leu Ala Gly
            180                 185                 190

Ile Ile Gly Gly Ala Ala Arg Glu Gly Gly Gly Val Arg Gly Pro
        195                 200                 205

Ala Cys Ala Pro Ala Pro Pro Ser Asn Gly Ala Gly Ser Ser Ser Thr
    210                 215                 220
```

Tyr Trp Ser Thr Pro Ser Ser Glu Pro Pro Leu Val Tyr Gly Asp Ile
225                 230                 235                 240

Ser Val Asp Asp Ile Glu Ile Leu Ile
                245

<210> SEQ ID NO 161
<211> LENGTH: 702
<212> TYPE: DNA
<213> ORGANISM: Oryza sativa
<220> FEATURE:
<223> OTHER INFORMATION: G3651

<400> SEQUENCE: 161

| | | |
|---|---|---|
| atggctgacc tcccatgcat atatatacgc gtagtacgta cacttgcttt cccaacgctc | 60 |
| gcgaatcaaa tcgagggtga aattaagtca agaacggaga gagatcacgg tgaggttgat | 120 |
| ctcagctcgc cggaggaggc aatgagccgg gcggagtgcg gcggcggcga ggaggaggag | 180 |
| cggtgcaggt acagggcgt gcggcggcgg cggtggggga agtgggtgtc ggagatccgg | 240 |
| gtgcccggca cgcgggagcg gctgtggctg gggtcctacg ccacgccgga ggccgccgcc | 300 |
| gtcgcgcacg acacggccgt ctacttcctc cgcgaggcg cgggcgacgg cggtggcggc | 360 |
| ggcgcgaccg ctcaacttcc cggagcgcgc ggcggccacc gtacggcggc cgccgtggcg | 420 |
| cgcctgtcgc cgcggtccgt gcagcgcgtg gcgtccgacg cggcatggcc gccgacgcgc | 480 |
| agctcggcgt gccgggaccc ggcccggccc gcgccggcga cggcgtacgc gcgcccggat | 540 |
| cactgcgccg gcgcgacgac ggcgcggcac gacgagctgg cgccgccgcgg gatgtacggc | 600 |
| gctcacgcgc atgccgccgg cgcgaacgcc aggacgagcg gcgagcggca gctcgtctgt | 660 |
| gccgaggaga ttagcgtgga tgacatggag atcctgatgt aa | 702 |

<210> SEQ ID NO 162
<211> LENGTH: 233
<212> TYPE: PRT
<213> ORGANISM: Oryza sativa
<220> FEATURE:
<223> OTHER INFORMATION: G3651 polypeptide

<400> SEQUENCE: 162

Met Ala Asp Leu Pro Cys Ile Tyr Ile Arg Val Val Arg Thr Leu Ala
1               5                   10                  15

Phe Pro Thr Leu Ala Asn Gln Ile Glu Gly Glu Ile Lys Ser Arg Thr
                20                  25                  30

Glu Arg Asp His Gly Glu Val Asp Leu Ser Ser Pro Glu Glu Ala Met
            35                  40                  45

Ser Arg Ala Glu Cys Gly Gly Gly Glu Glu Glu Arg Cys Arg Tyr
        50                  55                  60

Arg Gly Val Arg Arg Arg Arg Trp Gly Lys Trp Val Ser Glu Ile Arg
65                  70                  75                  80

Val Pro Gly Thr Arg Glu Arg Leu Trp Leu Gly Ser Tyr Ala Thr Pro
                85                  90                  95

Glu Ala Ala Ala Val Ala His Asp Thr Ala Val Tyr Phe Leu Arg Gly
            100                 105                 110

Gly Ala Gly Asp Gly Gly Gly Gly Ala Thr Ala Gln Leu Pro Gly
        115                 120                 125

Ala Arg Gly Gly His Arg Thr Ala Ala Ala Val Ala Arg Leu Ser Pro
    130                 135                 140

Arg Ser Val Gln Arg Val Ala Ser Asp Ala Ala Trp Pro Pro Thr Arg

```
                145                 150                 155                 160
Ser Ser Ala Cys Arg Asp Pro Ala Arg Pro Ala Pro Ala Thr Ala Tyr
            165                 170                 175

Ala Arg Pro Asp His Cys Ala Gly Ala Thr Thr Ala Arg His Asp Glu
            180                 185                 190

Leu Ala Arg Arg Gly Met Tyr Gly Ala His Ala His Ala Ala Gly Ala
            195                 200                 205

Asn Ala Arg Thr Ser Gly Glu Arg Gln Leu Val Cys Ala Glu Glu Ile
            210                 215                 220

Ser Val Asp Asp Met Glu Ile Leu Met
225                 230

<210> SEQ ID NO 163
<211> LENGTH: 495
<212> TYPE: DNA
<213> ORGANISM: Zinnia elegans
<220> FEATURE:
<223> OTHER INFORMATION: G3647

<400> SEQUENCE: 163
attcgcggcc gcgaatatga gtaccagctc agatgaaggt aacaactgtt taagccaaaa      60
gacttacaaa ggcgttaggt gccgacgatg gggcaaatgg gtgtcagaga ttcgagttcc     120
aggaagtcga gaacggctct ggctaggcac gtactctacg cctgagggtg cagctgtggc     180
tcatgatgta gcctcgtact gtttaaaagg gaatacgtct tttcataaac ttaatattcc     240
gtctatgtta cctccgacag cacggacaga cctatctcct aggtccatcc aaaaggctgc     300
gtctgatgct ggtatggcca tagacgcacg gtttatcgcg tctagagata ccacaccgac     360
taatgaggcg ttgaacattt ctgtagatga ttatctttaa attttgagaa ctaatattgt     420
gtcaccaata ttgtaagtcg atctacattg gcaaacacaa tgtacgtgtt ggtggcact     480 tccagattat tgttt                                                      495

<210> SEQ ID NO 164
<211> LENGTH: 127
<212> TYPE: PRT
<213> ORGANISM: Zinnia elegans
<220> FEATURE:
<223> OTHER INFORMATION: G3647 polypeptide

<400> SEQUENCE: 164

Met Ser Thr Ser Ser Asp Glu Gly Asn Asn Cys Leu Ser Gln Lys Thr
1               5                   10                  15

Tyr Lys Gly Val Arg Cys Arg Arg Trp Gly Lys Trp Val Ser Glu Ile
            20                  25                  30

Arg Val Pro Gly Ser Arg Glu Arg Leu Trp Leu Gly Thr Tyr Ser Thr
        35                  40                  45

Pro Glu Gly Ala Ala Val Ala His Asp Val Ala Ser Tyr Cys Leu Lys
    50                  55                  60

Gly Asn Thr Ser Phe His Lys Leu Asn Ile Pro Ser Met Leu Pro Pro
65                  70                  75                  80

Thr Ala Arg Thr Asp Leu Ser Pro Arg Ser Ile Gln Lys Ala Ser
            85                  90                  95

Asp Ala Gly Met Ala Ile Asp Ala Arg Phe Ile Ala Ser Arg Asp Thr
            100                 105                 110

Thr Pro Thr Asn Glu Ala Leu Asn Ile Ser Val Asp Asp Tyr Leu
            115                 120                 125
```

```
<210> SEQ ID NO 165
<211> LENGTH: 649
<212> TYPE: DNA
<213> ORGANISM: Brassica oleracea
<220> FEATURE:
<223> OTHER INFORMATION: G3646

<400> SEQUENCE: 165
cagccgcata acatattact attcccctg gtcatatctt tgactttat ttttatttgc      60 tctaacctaa aagtattata taagtattgc acaattcata caatcggaat tgactttctt    120
ctcctccaat cgtattttta ttcaacagtt cctctcaaga tcatcaactc aaaaaatgga    180
tcctagagac ggcggagaaa cccatcaggc caagtacaaa ggcatccgtc gccggaaatg    240
gggaaaatgg gtatcggaga ttagggttcc agcaactcgt gaacgactct ggttaggctc    300
tttctccacc gccgaaggag ctgcggtagc ccacgacgtc gcttttact gcttgcaccg     360 accatcttct ctcgacaacg aagcttttaa cttccctcac ttgctgcaac cttcccttgc    420
ctccaacaca tctcctaagt ccatacaaaa agctgcttcg gacgcaggca tgggcgtaga    480
cgcaggattc gccctaaaca acgacagcgc gagtggtggc gtggaggaag caccgaacg     540 ggaaacgttg aacatctccg tgtacgatta tctagacgac ggtcgcattt gatatattgg    600
tttatatcta cgagcacctt atattagtaa ttaatatagg atgtgaata               649

<210> SEQ ID NO 166
<211> LENGTH: 137
<212> TYPE: PRT
<213> ORGANISM: Brassica oleracea
<220> FEATURE:
<223> OTHER INFORMATION: G3646 polypeptide

<400> SEQUENCE: 166

Asp Pro Arg Asp Gly Gly Glu Thr His Gln Ala Lys Tyr Lys Gly Ile
1               5                   10                  15

Arg Arg Arg Lys Trp Gly Lys Trp Val Ser Glu Ile Arg Val Pro Ala
            20                  25                  30

Thr Arg Glu Arg Leu Trp Leu Gly Ser Phe Ser Thr Ala Glu Gly Ala
        35                  40                  45

Ala Val Ala His Asp Val Ala Phe Tyr Cys Leu His Arg Pro Ser Ser
    50                  55                  60

Leu Asp Asn Glu Ala Phe Asn Phe Pro His Leu Leu Gln Pro Ser Leu
65                  70                  75                  80

Ala Ser Asn Thr Ser Pro Lys Ser Ile Gln Lys Ala Ala Ser Asp Ala
                85                  90                  95

Gly Met Gly Val Asp Ala Gly Phe Ala Leu Asn Asn Asp Ser Ala Ser
            100                 105                 110

Gly Gly Val Glu Glu Gly Thr Glu Arg Glu Thr Leu Asn Ile Ser Val
        115                 120                 125

Tyr Asp Tyr Leu Asp Asp Gly Arg Ile
    130                 135

<210> SEQ ID NO 167
<211> LENGTH: 656
<212> TYPE: DNA
<213> ORGANISM: Brassica rapa
<220> FEATURE:
<223> OTHER INFORMATION: G3645

<400> SEQUENCE: 167
```

```
cccacgcgtc cgatggatta catcgacaac accgtcgaaa ctcaatcaaa gtacaaaggc      60
atccgtcgcc ggaaatgggg gaaatgggta tcggagattc gagttccggg aactcgcgac     120
cgtctctggt taggctcatt ctccacggcg gaaggcgcag ccgtggcgca cgacgtggct     180
ttctactgtt tacaccaacc aaactcgctc gaatctctca acttccctca cttgcttcct     240
ccttccattg tttccaagac ttcgccgagg tctatccagc aagctgcttc taatgccgga     300
atggccgttg acgccggaat cgttaacagc tgtgatcacg cgtcagggaa ctctgggaat     360
ggagatacaa cgacggcgta ttgtgagaat ggaggtgcgt tgaatatatc agtgtatgat     420
tatttggacg gtcacgatca cgtttgaact tcatcttctt gttttttcgt ttaaagatac     480
agctactcaa aagaagcagt gatggagcct ggtgtgtaag caagcaaaac gttgtgaata     540 tataccgg tatgtttcgc tgttggccca atgcaagaaa cttttgtagt acgaatatat       600
atattttatt ttgaatgcct tcaagaggat tataatgcga gtgaagcttt gtttca         656
```

<210> SEQ ID NO 168
<211> LENGTH: 144
<212> TYPE: PRT
<213> ORGANISM: Brassica rapa
<220> FEATURE:
<223> OTHER INFORMATION: G3645 polypeptide

<400> SEQUENCE: 168

Met Asp Tyr Ile Asp Asn Thr Val Glu Thr Gln Ser Lys Tyr Lys Gly
1               5                   10                  15

Ile Arg Arg Arg Lys Trp Gly Lys Trp Val Ser Glu Ile Arg Val Pro
            20                  25                  30

Gly Thr Arg Asp Arg Leu Trp Leu Gly Ser Phe Ser Thr Ala Glu Gly
        35                  40                  45

Ala Ala Val Ala His Asp Val Ala Phe Tyr Cys Leu His Gln Pro Asn
    50                  55                  60

Ser Leu Glu Ser Leu Asn Phe Pro His Leu Leu Pro Pro Ser Ile Val
65                  70                  75                  80

Ser Lys Thr Ser Pro Arg Ser Ile Gln Gln Ala Ala Ser Asn Ala Gly
                85                  90                  95

Met Ala Val Asp Ala Gly Ile Val Asn Ser Cys Asp His Ala Ser Gly
            100                 105                 110

Asn Ser Gly Asn Gly Asp Thr Thr Thr Ala Tyr Cys Glu Asn Gly Gly
        115                 120                 125

Ala Leu Asn Ile Ser Val Tyr Asp Tyr Leu Asp Gly His Asp His Val
    130                 135                 140

<210> SEQ ID NO 169
<211> LENGTH: 576
<212> TYPE: DNA
<213> ORGANISM: Oryza sativa
<220> FEATURE:
<223> OTHER INFORMATION: G3652

<400> SEQUENCE: 169

```
atgcaggcca acacgacgca gccggcgccg gagaaggaga cgaggtataa gggcgtgcgg      60
ctacggcagt gggggaaatg gtggcggag atccgactgc ccaacagccg caagaggata     120
tggctgggat cctactacac accggagaag gcggcgcggg cgttcgacgc cgcgttcata     180
tgtctccgcg gcggtgaggc cattgccggg ctcaacttca ccgagtcacc gccggccgtc     240
gtcgcccgca ccaccgaccc gcgggaggtg ctcgccttcg cgacgtcgca tgccaacctg     300
```

```
ctgtcgttgt tggatgccgc cattgcgcaa gaagaagaag ctcattcttt caaaaaagaa    360
gaagaagctc aggtggagga gaagacggct gaggagtcct cagacgtggt cagggcaaat    420
gcggcgccac caccgccggt gcaggtggca ggtgggagct ttgactggtc acagctgccg    480
ctctactcgc caacgacaac cccagctgca gagcattggg aggaagataa cgtcgaaggt    540
actacaagtg ataacctttg gagcttcgat ttctga                              576
```

<210> SEQ ID NO 170
<211> LENGTH: 191
<212> TYPE: PRT
<213> ORGANISM: Oryza sativa
<220> FEATURE:
<223> OTHER INFORMATION: G3652 polypeptide

<400> SEQUENCE: 170

```
Met Gln Ala Asn Thr Thr Gln Pro Ala Pro Glu Lys Glu Thr Arg Tyr
1               5                   10                  15

Lys Gly Val Arg Leu Arg Gln Trp Gly Lys Trp Val Ala Glu Ile Arg
            20                  25                  30

Leu Pro Asn Ser Arg Lys Arg Ile Trp Leu Gly Ser Tyr Tyr Thr Pro
        35                  40                  45

Glu Lys Ala Ala Arg Ala Phe Asp Ala Ala Phe Ile Cys Leu Arg Gly
    50                  55                  60

Gly Glu Ala Ile Ala Gly Leu Asn Phe Thr Glu Ser Pro Pro Ala Val
65                  70                  75                  80

Val Ala Arg Thr Thr Asp Pro Arg Glu Val Leu Ala Phe Ala Thr Ser
                85                  90                  95

His Ala Asn Leu Leu Ser Leu Leu Asp Ala Ala Ile Ala Gln Glu Glu
            100                 105                 110

Glu Ala His Ser Phe Lys Lys Glu Glu Ala Gln Val Glu Glu Lys
        115                 120                 125

Thr Ala Glu Glu Ser Ser Asp Val Val Arg Ala Asn Ala Ala Pro Pro
    130                 135                 140

Pro Pro Val Gln Val Ala Gly Gly Ser Phe Asp Trp Ser Gln Leu Pro
145                 150                 155                 160

Leu Tyr Ser Pro Thr Thr Thr Pro Ala Ala Glu His Trp Glu Asp
                165                 170                 175

Asn Val Glu Gly Thr Thr Ser Asp Asn Leu Trp Ser Phe Asp Phe
            180                 185                 190
```

<210> SEQ ID NO 171
<211> LENGTH: 441
<212> TYPE: DNA
<213> ORGANISM: Oryza sativa
<220> FEATURE:
<223> OTHER INFORMATION: G3653

<400> SEQUENCE: 171

```
atgcaacctc cggctacttc ccgccaaaag ctggagttgt ttgaattctg ccgacataat     60
agttttctgg atctctctct ccatttcatg caggccaacg gtacgtcgcc ggcgccagtg    120
gagaggaagt acaggggcgt gcggctgcgg cagtggggga gtgggtggc ggagattcgg     180 ctgcccaaca gcctcaagag gatatggctg gatcctacg actcgccgga gaaggcggcg     240
cgggcgttcg acgccgcctt catctgtctc cgcggcggcg aggccatcgc cggcctcaac    300
ttccccgagt cgccgcccac cgtcgttgcc gcactagcg acccgcggga ggtgctcgcc     360
tacgcgacgt cgcatgctaa ccggctggga tgccaccatt gcacaggaag aagcagctct    420
```

```
ggtggaggag gagacggcta a                                              441
```

<210> SEQ ID NO 172
<211> LENGTH: 146
<212> TYPE: PRT
<213> ORGANISM: Oryza sativa
<220> FEATURE:
<223> OTHER INFORMATION: G3653 polypeptide

<400> SEQUENCE: 172

```
Met Gln Pro Pro Ala Thr Ser Arg Gln Lys Leu Glu Leu Phe Glu Phe
1               5                   10                  15

Cys Arg His Asn Ser Phe Leu Asp Leu Ser Leu His Phe Met Gln Ala
            20                  25                  30

Asn Gly Thr Ser Pro Ala Pro Val Glu Arg Lys Tyr Arg Gly Val Arg
        35                  40                  45

Leu Arg Gln Trp Gly Lys Trp Val Ala Glu Ile Arg Leu Pro Asn Ser
    50                  55                  60

Leu Lys Arg Ile Trp Leu Gly Ser Tyr Asp Ser Pro Glu Lys Ala Ala
65                  70                  75                  80

Arg Ala Phe Asp Ala Ala Phe Ile Cys Leu Arg Gly Gly Glu Ala Ile
                85                  90                  95

Ala Gly Leu Asn Phe Pro Glu Ser Pro Pro Thr Val Val Ala Arg Thr
            100                 105                 110

Ser Asp Pro Arg Glu Val Leu Ala Tyr Ala Thr Ser His Ala Asn Arg
        115                 120                 125

Leu Gly Cys His His Cys Thr Gly Arg Ser Ser Gly Gly Gly Gly
    130                 135                 140

Asp Gly
145
```

<210> SEQ ID NO 173
<211> LENGTH: 636
<212> TYPE: DNA
<213> ORGANISM: Oryza sativa
<220> FEATURE:
<223> OTHER INFORMATION: G3655

<400> SEQUENCE: 173

```
atgagctcac cgatggagcc agtgtctttc atgcagaaga gcgcggcggc ggcggcggac      60
ggcggcagcg cggcgcaggc ggcggcggag aggaggaaat acaagggcgt gcggctgcgt     120
cagtggggga agtgggcggc ggagatccgt ctgcccagca gctgcgagag gatatggctg     180
ggatcctacg acacgccgga gaaggcggcg cgggcgttcg acgccgcgtt catctgcctc     240
cgcggcgtcc aagccattgc cgggctcaac ttccccgagt ccccgccgcc gcctaccgcc     300
gcccgcaccg cgatctgcg tgaggtgtat gccttcgctg tgtcgcatgc caacggccg      360 tcggccgaag cggcgccggc cgacattgtt gttccagctc aggtcgcgac cgaggagtcc     420
gacggcgtgg tgaggggaaa tgcggcgccg ccgccggtgc aggtggcggc tgggagcttg     480
gactggtcgc agttcatggc aaacccacca cctatgtact caccgacggc gacagccgga     540
agccaggcga gtgtggccggt gacagcaccg gcagcagaag ccgacggtga ggatgacgaa     600
ttagctacta catgtcgttg gagcttcgat gcctag                                636
```

<210> SEQ ID NO 174
<211> LENGTH: 211
<212> TYPE: PRT

<213> ORGANISM: Oryza sativa
<220> FEATURE:
<223> OTHER INFORMATION: G3655 polypeptide

<400> SEQUENCE: 174

```
Met Ser Ser Pro Met Glu Pro Val Ser Phe Met Gln Lys Ser Ala Ala
1               5                   10                  15
Ala Ala Ala Asp Gly Gly Ser Ala Ala Gln Ala Ala Glu Arg Arg
            20                  25                  30
Lys Tyr Lys Gly Val Arg Leu Arg Gln Trp Gly Lys Trp Ala Ala Glu
        35                  40                  45
Ile Arg Leu Pro Ser Ser Cys Glu Arg Ile Trp Leu Gly Ser Tyr Asp
    50                  55                  60
Thr Pro Glu Lys Ala Ala Arg Ala Phe Asp Ala Ala Phe Ile Cys Leu
65                  70                  75                  80
Arg Gly Val Gln Ala Ile Ala Gly Leu Asn Phe Pro Glu Ser Pro Pro
                85                  90                  95
Pro Pro Thr Ala Ala Arg Thr Gly Asp Leu Arg Glu Val Tyr Ala Phe
            100                 105                 110
Ala Val Ser His Ala Asn Arg Pro Ser Ala Glu Ala Ala Pro Ala Asp
        115                 120                 125
Ile Val Val Pro Ala Gln Val Ala Thr Glu Glu Ser Asp Gly Val Val
    130                 135                 140
Arg Gly Asn Ala Ala Pro Pro Pro Val Gln Val Ala Ala Gly Ser Leu
145                 150                 155                 160
Asp Trp Ser Gln Phe Met Ala Asn Pro Pro Met Tyr Ser Pro Thr
                165                 170                 175
Ala Thr Ala Gly Ser Gln Ala Met Trp Pro Val Thr Ala Pro Ala Ala
            180                 185                 190
Glu Ala Asp Gly Glu Asp Asp Glu Leu Ala Thr Thr Cys Arg Trp Ser
        195                 200                 205
Phe Asp Ala
    210
```

<210> SEQ ID NO 175
<211> LENGTH: 624
<212> TYPE: DNA
<213> ORGANISM: Oryza sativa
<220> FEATURE:
<223> OTHER INFORMATION: G3654

<400> SEQUENCE: 175

```
atgtcgtcgt cgtcttcggc gacgacgacg aagtataggg gagtgcggct gcgcaagtgg      60
gggaagtggg tgtcggagat ccggctgccc aacagccgcg agaggatatg gctgggatcc     120
tacgacacgc ccgaggaggc ggcgcgggcg ttcgacgccg cgttcgtctg cctccgcggc     180
ggcggcgagg ccgccgggaa cgggatcaac ttccccggct cgcccccgtg cgtggcgcgc     240
accagcgacc gcaggaggt gtacgcggcc gcggtgtcgc atgccaacaa ccggccgccg     300
ccgccgccgt cggcccgagc aacgtcgtct gcacttccat gggaggaagc tccggtggtg     360
gcggctcagg aggcggcggc ggacatggcg cccgacgtgg tggtgctgcc atcgtcgccg     420
gtgaatgtgc tggcagcagc tgggagcttc gaatattggt cgcaacaacc actctactcg     480
ccgacggcag caagcctcga tttgcagagg tggatgacgg cggcggcggc ggccgaggaa     540
tcaataatgg aggatgacga cgacgaagga acaagtgatg gtctttggag tttccactac     600
tcaccgactc gttccaagtg gtaa                                            624
```

<210> SEQ ID NO 176
<211> LENGTH: 207
<212> TYPE: PRT
<213> ORGANISM: Oryza sativa
<220> FEATURE:
<223> OTHER INFORMATION: G3654 polypeptide

<400> SEQUENCE: 176

```
Met Ser Ser Ser Ser Ala Thr Thr Thr Lys Tyr Arg Gly Val Arg
1               5                   10                  15

Leu Arg Lys Trp Gly Lys Trp Val Ser Glu Ile Arg Leu Pro Asn Ser
            20                  25                  30

Arg Glu Arg Ile Trp Leu Gly Ser Tyr Asp Thr Pro Glu Glu Ala Ala
        35                  40                  45

Arg Ala Phe Asp Ala Ala Phe Val Cys Leu Arg Gly Gly Gly Glu Ala
    50                  55                  60

Ala Gly Asn Gly Ile Asn Phe Pro Gly Ser Pro Ala Val Ala Arg
65              70                  75                  80

Thr Ser Asp Pro Gln Glu Val Tyr Ala Ala Val Ser His Ala Asn
                85                  90                  95

Asn Arg Pro Pro Pro Pro Ser Ala Arg Ala Thr Ser Ser Ala Leu
            100                 105                 110

Pro Trp Glu Glu Ala Pro Val Val Ala Ala Gln Glu Ala Ala Ala Asp
        115                 120                 125

Met Ala Pro Asp Val Val Val Leu Pro Ser Ser Pro Val Asn Val Leu
    130                 135                 140

Ala Ala Ala Gly Ser Phe Glu Tyr Trp Ser Gln Gln Pro Leu Tyr Ser
145                 150                 155                 160

Pro Thr Ala Ala Ser Leu Asp Leu Gln Arg Trp Met Thr Ala Ala Ala
                165                 170                 175

Ala Ala Glu Glu Ser Ile Met Glu Asp Asp Asp Glu Gly Thr Ser
            180                 185                 190

Asp Gly Leu Trp Ser Phe His Tyr Ser Pro Thr Arg Ser Lys Trp
        195                 200                 205
```

<210> SEQ ID NO 177
<211> LENGTH: 719
<212> TYPE: DNA
<213> ORGANISM: Arabidopsis thaliana
<220> FEATURE:
<223> OTHER INFORMATION: G2576

<400> SEQUENCE: 177

```
caatcgcgtc tttgtttggt ttaatcgtga tggaagggtc gtcttcttcg atgcagtcaa      60
agtacaaagg agtgaggaag aggaaatggg gaaatgggt ttcagagatc agacttccca     120
acagcagaga acgtatttgg ttgggctctt acgatactcc tgagaaggcg gcgcgtgctt     180
tcgacgcggc tctttattgt ctccgtggca acaacgcaaa gttcaatttc cctgataatc     240
ctccggtgat ctccggcgga cgtaacttgt cgcgatctga gaagagaaa gctgctgcga     300 ggttcgctaa ttcggcgag atgattcaa gtggcggagc aggatacgag atacggcaag     360
aatctgcttc aacatcgatg gacgttgatt cggagttttt gagtatgctt ccgacggttg     420
gttcgggtaa cttcgcttcg gagtttgggt tattccctgg gtttgatgat ttctccgatg     480
aatactccgg tgatcgtttc agagagcagc tttcgcctac acaagattat tatcagcttg     540
gagaagagac ttacgccgat ggttccatgt ttctttggaa tttttgaatt ccattattca     600
```

```
caatctgaaa attttgactt gggttttta ttttttttg tagttcttta cccaattttt      660
ttttgatcat tgggataaag agttattcat tcactatttt tttcccacgt gttagattt      719
```

<210> SEQ ID NO 178
<211> LENGTH: 185
<212> TYPE: PRT
<213> ORGANISM: Arabidopsis thaliana
<220> FEATURE:
<223> OTHER INFORMATION: G2576 polypeptide

<400> SEQUENCE: 178

```
Met Glu Gly Ser Ser Ser Ser Met Gln Ser Lys Tyr Lys Gly Val Arg
1               5                   10                  15

Lys Arg Lys Trp Gly Lys Trp Val Ser Glu Ile Arg Leu Pro Asn Ser
            20                  25                  30

Arg Glu Arg Ile Trp Leu Gly Ser Tyr Asp Thr Pro Glu Lys Ala Ala
        35                  40                  45

Arg Ala Phe Asp Ala Ala Leu Tyr Cys Leu Arg Gly Asn Asn Ala Lys
    50                  55                  60

Phe Asn Phe Pro Asp Asn Pro Val Ile Ser Gly Gly Arg Asn Leu
65                  70                  75                  80

Ser Arg Ser Glu Ile Arg Glu Ala Ala Ala Arg Phe Ala Asn Ser Ala
                85                  90                  95

Glu Asp Ser Ser Gly Gly Ala Gly Tyr Glu Ile Arg Gln Glu Ser
            100                 105                 110

Ala Ser Thr Ser Met Asp Val Asp Ser Glu Phe Leu Ser Met Leu Pro
        115                 120                 125

Thr Val Gly Ser Gly Asn Phe Ala Ser Glu Phe Gly Leu Phe Pro Gly
    130                 135                 140

Phe Asp Asp Phe Ser Asp Glu Tyr Ser Gly Asp Arg Phe Arg Glu Gln
145                 150                 155                 160

Leu Ser Pro Thr Gln Asp Tyr Tyr Gln Leu Gly Glu Glu Thr Tyr Ala
                165                 170                 175

Asp Gly Ser Met Phe Leu Trp Asn Phe
            180                 185
```

<210> SEQ ID NO 179
<211> LENGTH: 891
<212> TYPE: DNA
<213> ORGANISM: Arabidopsis thaliana
<220> FEATURE:
<223> OTHER INFORMATION: G872

<400> SEQUENCE: 179

```
ccggaaacag aatccaattc aaccaaaccg aatcgaaccg aaccggagtt tttatccaat      60
ggtgaagcaa gcgatgaagg aagaggagaa gaagagaaac acggcgatgc agtcaaagta     120
caaaggagtg aggaagagga atggggaaa atgggtatcg gagatcagac ttccacacag     180
cagagaacga atttggttag gctcttacga cactcccgag aaggcggcgc gtgctttcga     240
cgccgctcaa ttttgtctcc gcggcggcga tgctaatttc aatttcccta ataatccacc     300
gtcgatctcc gtagaaaagt cgttgacgcc tccggagatt caggaagctg ctgctagatt     360
cgctaacaca ttccaagaca ttgtcaaggg agaagaagaa tcgggtttag tacccggatc     420
cgagatccga ccagagtctc cttctacatc tgcatctgtt gctacatcga cggtggatta     480 tgattttcg ttttggatt tgcttccgat gaatttcggg tttgattcct tctccgacga     540
```

```
cttctctggc ttctccggtg gtgatcgatt tacagagatt ttacccatcg aagattacgg    600
aggagagagt ttattagatg aatctttgat tctttgggat ttttgaattc ccaaacataa    660 tatttttta gagcgaactg tgagattttc cttggagtca tggagaaatc tggagatttt    720
ttgtaacacg gagctccaat gacccgggaa tttctttcgt ttcggatccg aatttgatgt    780
ggatcatatt cacacctata tttttcatt tttttgttgt aaagaaaaat cggataagat    840
tctagtaata aatgttaaaa gtccatttca ttaaaaaaaa aaaaaaaaa a              891
```

<210> SEQ ID NO 180
<211> LENGTH: 195
<212> TYPE: PRT
<213> ORGANISM: Arabidopsis thaliana
<220> FEATURE:
<223> OTHER INFORMATION: G872 polypeptide

<400> SEQUENCE: 180

```
Met Val Lys Gln Ala Met Lys Glu Glu Lys Lys Arg Asn Thr Ala
1               5                   10                  15

Met Gln Ser Lys Tyr Lys Gly Val Arg Lys Arg Lys Trp Gly Lys Trp
                20                  25                  30

Val Ser Glu Ile Arg Leu Pro His Ser Arg Glu Arg Ile Trp Leu Gly
            35                  40                  45

Ser Tyr Asp Thr Pro Glu Lys Ala Ala Arg Ala Phe Asp Ala Ala Gln
        50                  55                  60

Phe Cys Leu Arg Gly Gly Asp Ala Asn Phe Asn Phe Pro Asn Asn Pro
65                  70                  75                  80

Pro Ser Ile Ser Val Glu Lys Ser Leu Thr Pro Pro Glu Ile Gln Glu
                85                  90                  95

Ala Ala Ala Arg Phe Ala Asn Thr Phe Gln Asp Ile Val Lys Gly Glu
            100                 105                 110

Glu Glu Ser Gly Leu Val Pro Gly Ser Glu Ile Arg Pro Glu Ser Pro
        115                 120                 125

Ser Thr Ser Ala Ser Val Ala Thr Ser Thr Val Asp Tyr Asp Phe Ser
    130                 135                 140

Phe Leu Asp Leu Leu Pro Met Asn Phe Gly Phe Asp Ser Phe Ser Asp
145                 150                 155                 160

Asp Phe Ser Gly Phe Ser Gly Gly Asp Arg Phe Thr Glu Ile Leu Pro
                165                 170                 175

Ile Glu Asp Tyr Gly Gly Glu Ser Leu Leu Asp Glu Ser Leu Ile Leu
            180                 185                 190

Trp Asp Phe
        195
```

<210> SEQ ID NO 181
<211> LENGTH: 861
<212> TYPE: DNA
<213> ORGANISM: Oryza sativa
<220> FEATURE:
<223> OTHER INFORMATION: G3657

<400> SEQUENCE: 181

```
ccgagcactg cgcactgagc acctcgacac ggcgcgcgcg cggccatggt gaagaacacg    60
agcaacaagt gcattgctgc tgccggcgcg acggcggcgg ccggcttagg cggtggcgcg    120
gcgtcgtgca gcggcggcgg aggtgatggg aaggtgacga cggcggcggc agcggcgttg    180
gcggtgaggc cgtacaaggg ggtgaggatg cggagctggg ggtcgtgggt gtcggagatc    240
```

-continued

```
agggcgccgc accagaagcg gcggatctgg ctgggctcct acgccacgcc ggaggccgcg      300
gcgcgcgcct acgacgccgc gctgctctgc ctcaagggct ccgacgccgt cctcaacttc      360
ccctcctccg cctcgtctcg ccgccgcctc gacatccacc ggggggggcac ggactcggcg      420 gcgggcgaca tgtcgccgag gtccatccag cgcgtcgcgg ccgccgcggc ggcggcattc      480
gacgccgccg ccgccgccgt cgtcgtcgac gaaagctgct cgtgcagcgc cgaggcgatg      540
tcgtcgacgc cgacgtcggg agcgacctcg ctgtccacgc tgggaagctc cggcggcggt      600
gacgtgctgg accacgcgac gacgccgtcg tcgtcgtcgt ctgccgcggc caacgtttgc      660
tcgccgccgc tggaggggga ccatgagctg tggacggagc tggacgcgtt cgcgtcgccg      720
aagttcatgg atctaatggc cgccggcggc acggcgttct cgtcgccgtg gaggagccc       780 gaggaggacg gcgagctgat gaggctgtgg agcttctgct agcttagcta ggagcctagg      840
aaacgatcgt gaatccattc t                                                 861
```

<210> SEQ ID NO 182
<211> LENGTH: 258
<212> TYPE: PRT
<213> ORGANISM: Oryza sativa
<220> FEATURE:
<223> OTHER INFORMATION: G3657 polypeptide

<400> SEQUENCE: 182

```
Met Val Lys Asn Thr Ser Asn Lys Cys Ile Ala Ala Gly Ala Thr
1               5                   10                  15

Ala Ala Ala Gly Leu Gly Gly Gly Ala Ala Ser Cys Ser Gly Gly Gly
            20                  25                  30

Gly Asp Gly Lys Val Thr Thr Ala Ala Ala Ala Leu Ala Val Arg
        35                  40                  45

Pro Tyr Lys Gly Val Arg Met Arg Ser Trp Gly Ser Trp Val Ser Glu
    50                  55                  60

Ile Arg Ala Pro His Gln Lys Arg Arg Ile Trp Leu Gly Ser Tyr Ala
65                  70                  75                  80

Thr Pro Glu Ala Ala Ala Arg Ala Tyr Asp Ala Ala Leu Leu Cys Leu
                85                  90                  95

Lys Gly Ser Asp Ala Val Leu Asn Phe Pro Ser Ser Ala Ser Ser Arg
            100                 105                 110

Arg Arg Leu Asp Ile His Arg Gly Gly Thr Asp Ser Ala Ala Gly Asp
        115                 120                 125

Met Ser Pro Arg Ser Ile Gln Arg Val Ala Ala Ala Ala Ala Ala
    130                 135                 140

Phe Asp Ala Ala Ala Ala Val Val Val Asp Glu Ser Cys Ser Cys
145                 150                 155                 160

Ser Ala Glu Ala Met Ser Ser Thr Pro Thr Ser Gly Ala Thr Ser Leu
                165                 170                 175

Ser Thr Leu Gly Ser Ser Gly Gly Gly Asp Val Leu Asp His Ala Thr
            180                 185                 190

Thr Pro Ser Ser Ser Ser Ala Ala Ala Asn Val Cys Ser Pro Pro
        195                 200                 205

Leu Glu Gly Asp His Glu Leu Trp Thr Glu Leu Asp Ala Phe Ala Ser
    210                 215                 220

Pro Lys Phe Met Asp Leu Met Ala Ala Gly Gly Thr Ala Phe Ser Ser
225                 230                 235                 240

Pro Trp Glu Glu Pro Glu Glu Asp Gly Glu Leu Met Arg Leu Trp Ser
                245                 250                 255
```

Phe Cys

<210> SEQ ID NO 183
<211> LENGTH: 765
<212> TYPE: DNA
<213> ORGANISM: Arabidopsis thaliana
<220> FEATURE:
<223> OTHER INFORMATION: G2115

<400> SEQUENCE: 183

```
aatcactcta caaagcctgt acgtacacaa caacattacc atggtgaaac aagaacgcaa      60
gatccaaacc agcagcacaa aaaggaaat gcctttgtca tcatcaccat cttcttcttc     120
ttcttcatct tcttcctcgt cttcgtcttc gtgtaagaac aagaacaaga agagtaagat     180
taagaagtac aaaggagtga ggatgagaag ttggggatca tgggtctctg agattagggc     240
accaaatcaa aagacaagga tttggttagg ttcttactca acagctgaag cagctgctag     300
agcttacgat gttgcactct tatgtctcaa aggccctcaa gccaatctca acttccctac     360
ttcttcttct tctcatcatc ttcttgataa tctcttagat gaaaataccc ttttgtcccc     420
caaatccatc caaagagtag ctgctcaagc tgccaactca tttaaccatt ttgccctac      480
ttcatcagcc gtctcgtcac cgtccgatca tgatcatcac catgatgatg ggatgcaatc     540
tttgatggga tcttttgtgg acaatcatgt gtctttgatg gattcaacat cttcatggta     600
tgatgatcat aatgggatgt tcttgtttga taatggagct ccattcaatt actctcctca     660
actaaactcg acgacgatgc tcgatgaata cttctacgaa gatgctgaca ttccgctttg     720
gagtttcaat taatccgacg gtccataata catactttaa ttagt                     765
```

<210> SEQ ID NO 184
<211> LENGTH: 230
<212> TYPE: PRT
<213> ORGANISM: Arabidopsis thaliana
<220> FEATURE:
<223> OTHER INFORMATION: G2115 polypeptide

<400> SEQUENCE: 184

```
Met Val Lys Gln Glu Arg Lys Ile Gln Thr Ser Ser Thr Lys Lys Glu
1               5                   10                  15

Met Pro Leu Ser Ser Ser Pro Ser Ser Ser Ser Ser Ser Ser Ser Ser
            20                  25                  30

Ser Ser Ser Ser Ser Cys Lys Asn Lys Asn Lys Lys Ser Lys Ile Lys
        35                  40                  45

Lys Tyr Lys Gly Val Arg Met Arg Ser Trp Gly Ser Trp Val Ser Glu
    50                  55                  60

Ile Arg Ala Pro Asn Gln Lys Thr Arg Ile Trp Leu Gly Ser Tyr Ser
65                  70                  75                  80

Thr Ala Glu Ala Ala Arg Ala Tyr Asp Val Ala Leu Leu Cys Leu
                85                  90                  95

Lys Gly Pro Gln Ala Asn Leu Asn Phe Pro Thr Ser Ser Ser Ser His
            100                 105                 110

His Leu Leu Asp Asn Leu Leu Asp Glu Asn Thr Leu Leu Ser Pro Lys
        115                 120                 125

Ser Ile Gln Arg Val Ala Ala Gln Ala Ala Asn Ser Phe Asn His Phe
    130                 135                 140

Ala Pro Thr Ser Ser Ala Val Ser Ser Pro Ser Asp His Asp His His
145                 150                 155                 160
```

```
His Asp Asp Gly Met Gln Ser Leu Met Gly Ser Phe Val Asp Asn His
            165                 170                 175

Val Ser Leu Met Asp Ser Thr Ser Ser Trp Tyr Asp His Asn Gly
        180                 185                 190

Met Phe Leu Phe Asp Asn Gly Ala Pro Phe Asn Tyr Ser Pro Gln Leu
            195                 200                 205

Asn Ser Thr Thr Met Leu Asp Glu Tyr Phe Tyr Glu Asp Ala Asp Ile
        210                 215                 220

Pro Leu Trp Ser Phe Asn
225             230

<210> SEQ ID NO 185
<211> LENGTH: 687
<212> TYPE: DNA
<213> ORGANISM: Arabidopsis thaliana
<220> FEATURE:
<223> OTHER INFORMATION: G2294

<400> SEQUENCE: 185
tcctccctta attagtatca aaaatggtga aaacacttca aaagacacca aagagaatgt      60
catctccatc atcatcatct tcatcatcct catcaacatc atcatcatcc ataaggatga     120
agaagtacaa gggagtgaga atgagaagtt ggggttcatg ggtttcagag atcagagctc     180
ctaatcaaaa gacaaggatc tggcttggtt cttactcaac tgctgaagcc gcggctagag     240
cctacgacgc agcactccta tgtcttaaag gatcctcagc taataatctc aacttcccag     300
agatctcaac ttctctctac catattatca acaatggtga taacaacaat gacatgtccc     360
ctaagtctat acaaagagta gcagctgcag ctgctgctgc caacacagat ccttcctcat     420
catcagtctc tacttcatct ccattgcttt cctctccatc tgaagatctc tatgatgttg     480
tctccatgtc acagtatgac caacaagtct ccttgtctga atcatcatca tggtacaact     540
gctttgatgg tgatgatcag ttcatgttca ttaatggagt ctccgcgccg tatttgacaa     600
catcactttc tgatgatttc tttgaggaag agatatcag attatggaac ttctgctgat      660
tctactttca ttatacctta ttctttg                                         687

<210> SEQ ID NO 186
<211> LENGTH: 211
<212> TYPE: PRT
<213> ORGANISM: Arabidopsis thaliana
<220> FEATURE:
<223> OTHER INFORMATION: G2294 polypeptide

<400> SEQUENCE: 186

Met Val Lys Thr Leu Gln Lys Thr Pro Lys Arg Met Ser Ser Pro Ser
1               5                   10                  15

Ser Ser Ser Ser Ser Ser Ser Thr Ser Ser Ser Ser Ile Arg Met
            20                  25                  30

Lys Lys Tyr Lys Gly Val Arg Met Arg Ser Trp Gly Ser Trp Val Ser
        35                  40                  45

Glu Ile Arg Ala Pro Asn Gln Lys Thr Arg Ile Trp Leu Gly Ser Tyr
    50                  55                  60

Ser Thr Ala Glu Ala Ala Ala Arg Ala Tyr Asp Ala Ala Leu Leu Cys
65                  70                  75                  80

Leu Lys Gly Ser Ser Ala Asn Asn Leu Asn Phe Pro Glu Ile Ser Thr
                85                  90                  95

Ser Leu Tyr His Ile Ile Asn Asn Gly Asp Asn Asn Asn Asp Met Ser
            100                 105                 110
```

```
Pro Lys Ser Ile Gln Arg Val Ala Ala Ala Ala Ala Asn Thr
    115                 120                 125

Asp Pro Ser Ser Ser Val Ser Thr Ser Ser Pro Leu Leu Ser Ser
    130                 135                 140

Pro Ser Glu Asp Leu Tyr Asp Val Val Ser Met Ser Gln Tyr Asp Gln
145                 150                 155                 160

Gln Val Ser Leu Ser Glu Ser Ser Trp Tyr Asn Cys Phe Asp Gly
                165                 170                 175

Asp Asp Gln Phe Met Phe Ile Asn Gly Val Ser Ala Pro Tyr Leu Thr
                180                 185                 190

Thr Ser Leu Ser Asp Asp Phe Phe Glu Glu Gly Asp Ile Arg Leu Trp
                195                 200                 205

Asn Phe Cys
        210

<210> SEQ ID NO 187
<211> LENGTH: 838
<212> TYPE: DNA
<213> ORGANISM: Arabidopsis thaliana
<220> FEATURE:
<223> OTHER INFORMATION: G1090

<400> SEQUENCE: 187
aaactaattc gcacagttct atatacactc acaaacacac acacacacaa tatagtgcta      60
ctaaaataac cttgtattaa ttatggaaaa cacttacgtt ggccaacgag attaccgctt     120
caacgttaac cagttgtcct acagaggcat tcgtcggagg aaatggggca atgggtatc     180 ggagatccga gaacccggta agaaaacaag gatttggctt ggaagctacg agacggccga     240
gatggctgca gcggcctacg atgctgcggc tcttcacctc cgaggacgtg ggaccaatct     300
caactttccg gaactcgtcg acagttttcc tcggccggaa agctctagtt cggagcacat     360
tcaagcggct gcacaagatg cagcacttat gtttaaacca ggtaggttga gtgaaccagc     420
tctcgagtct ggtcaaggac tttctcgagt aggattgtct ccggatcaga ttcaagcgat     480
taatgagtct ccattagact cgccgaggat ggggtggatg caggatttgg aagttgctga     540
ctacgaagaa ttatacggac aattttttgg tcagcacgat agggatgagt ttttgaaat     600 gcagcaattt cagtccatat ggaattctaa taattgatat acgttcgctt aattgcttaa     660
ccatttgatt ttttttttaa taatgtcata tcatcaacca aggttttcg attatattca     720 gtaaagtata ataaattttc gacccttact gttttcttg ggttcaattt gtaatctctt     780
aacaatgatg atgtcataaa taccaatatg attaattcaa atttcaaaa aaaaaaaa     838

<210> SEQ ID NO 188
<211> LENGTH: 184
<212> TYPE: PRT
<213> ORGANISM: Arabidopsis thaliana
<220> FEATURE:
<223> OTHER INFORMATION: G1090 polypeptide

<400> SEQUENCE: 188

Met Glu Asn Thr Tyr Val Gly Gln Arg Asp Tyr Arg Phe Asn Val Asn
1                5                  10                  15

Gln Leu Ser Tyr Arg Gly Ile Arg Arg Lys Trp Gly Lys Trp Val
            20                  25                  30

Ser Glu Ile Arg Glu Pro Gly Lys Lys Thr Arg Ile Trp Leu Gly Ser
        35                  40                  45
```

Tyr Glu Thr Ala Glu Met Ala Ala Ala Tyr Asp Ala Ala Leu
    50              55                  60

His Leu Arg Gly Arg Gly Thr Asn Leu Asn Phe Pro Glu Leu Val Asp
65              70                  75                  80

Ser Phe Pro Arg Pro Glu Ser Ser Ser Glu His Ile Gln Ala Ala
                85                  90                  95

Ala Gln Asp Ala Ala Leu Met Phe Lys Pro Gly Arg Leu Ser Glu Pro
            100                 105                 110

Ala Leu Glu Ser Gly Gln Gly Leu Ser Arg Val Gly Leu Ser Pro Asp
            115                 120                 125

Gln Ile Gln Ala Ile Asn Glu Ser Pro Leu Asp Ser Pro Arg Met Gly
    130                 135                 140

Trp Met Gln Asp Leu Glu Val Ala Asp Tyr Glu Glu Leu Tyr Gly Gln
145                 150                 155                 160

Phe Phe Gly Gln His Asp Arg Asp Glu Phe Phe Glu Met Gln Gln Phe
                165                 170                 175

Gln Ser Ile Trp Asn Ser Asn Asn
            180

<210> SEQ ID NO 189
<211> LENGTH: 724
<212> TYPE: DNA
<213> ORGANISM: Arabidopsis thaliana
<220> FEATURE:
<223> OTHER INFORMATION: CBF4

<400> SEQUENCE: 189
catcttatcc aaagaaaaaa tgaatccatt ttactctaca ttcccagact cgtttctctc    60
aatctccgat catagatctc cggtttcaga cagtagtgag tgttcaccaa agttagcttc   120
aagttgtcca agaaacgag ctgggaggaa gaagtttcgt gagacacgtc atccgattta   180
cagaggagtt cgtcagagga attctggtaa atgggtttgt gaagttagag agcctaataa   240
gaaatctagg atttggttag gtacttttcc gacggttgaa atggctgctc gtgctcatga   300
tgttgctgct ttagctcttc gtggtcgctc tgcttgtctc aatttcgctg attctgcttg   360
gcggcttcgt attcctgaga ctacttgtcc taaggagatt cagaaagctg cgtctgaagc   420
tgcaatggcg tttcagaatg agactacgac ggagggatct aaaactgcgg cggaggcaga   480
ggaggcggca ggggaggggg tgagggaggg ggagaggagg gcggaggagc agaatggtgg   540
tgtgttttat atggatgatg aggcgctttt ggggatgccc aacttttttg agaatatggc   600
ggagggatg cttttgccgc cgccggaagt tggctggaat cataacgact ttgacggagt   660
gggtgacgtg tcactctgga gttttgacga gtaatttttt ggctcttttt ctggataata   720
agtt                                                              724

<210> SEQ ID NO 190
<211> LENGTH: 224
<212> TYPE: PRT
<213> ORGANISM: Arabidopsis thaliana
<220> FEATURE:
<223> OTHER INFORMATION: CBF4 polypeptide

<400> SEQUENCE: 190

Met Asn Pro Phe Tyr Ser Thr Phe Pro Asp Ser Phe Leu Ser Ile Ser
1               5                   10                  15

Asp His Arg Ser Pro Val Ser Asp Ser Ser Glu Cys Ser Pro Lys Leu
            20                  25                  30

```
Ala Ser Ser Cys Pro Lys Lys Arg Ala Gly Arg Lys Lys Phe Arg Glu
         35                  40                  45

Thr Arg His Pro Ile Tyr Arg Gly Val Arg Gln Arg Asn Ser Gly Lys
     50                  55                  60

Trp Val Cys Glu Val Arg Glu Pro Asn Lys Lys Ser Arg Ile Trp Leu
 65                  70                  75                  80

Gly Thr Phe Pro Thr Val Glu Met Ala Ala Arg Ala His Asp Val Ala
                 85                  90                  95

Ala Leu Ala Leu Arg Gly Arg Ser Ala Cys Leu Asn Phe Ala Asp Ser
                100                 105                 110

Ala Trp Arg Leu Arg Ile Pro Glu Thr Thr Cys Pro Lys Glu Ile Gln
                115                 120                 125

Lys Ala Ala Ser Glu Ala Ala Met Ala Phe Gln Asn Glu Thr Thr Thr
130                 135                 140

Glu Gly Ser Lys Thr Ala Ala Glu Ala Glu Ala Ala Gly Glu Gly
145                 150                 155                 160

Val Arg Glu Gly Glu Arg Arg Ala Glu Glu Gln Asn Gly Val Phe
                165                 170                 175

Tyr Met Asp Asp Glu Ala Leu Leu Gly Met Pro Asn Phe Phe Glu Asn
                180                 185                 190

Met Ala Glu Gly Met Leu Leu Pro Pro Pro Glu Val Gly Trp Asn His
                195                 200                 205

Asn Asp Phe Asp Gly Val Gly Asp Val Ser Leu Trp Ser Phe Asp Glu
                210                 215                 220

<210> SEQ ID NO 191
<211> LENGTH: 803
<212> TYPE: DNA
<213> ORGANISM: Arabidopsis thaliana
<220> FEATURE:
<223> OTHER INFORMATION: CBF2

<400> SEQUENCE: 191
ctgatcaatg aactcatttt ctgccttttc tgaaatgttt ggctccgatt acgagtctcc     60
ggtttcctca ggcggtgatt acagtccgaa gcttgccacg agctgcccca agaaaccagc    120
gggaaggaag aagtttcgtg agactcgtca cccaatttac agaggagttc gtcaaagaaa    180
ctccggtaag tgggtgtgtg agttgagaga gccaaacaag aaaacgagga tttggctcgg    240
gactttccaa accgctgaga tggcagctcg tgctcacgac gtcgccgcca tagctctccg    300
tggcagatct gcctgtctca atttcgctga ctcggcttgg cggctacgaa tcccggaatc    360
aacctgtgcc aaggaaatcc aaaggcggc ggctgaagcc gcgttgaatt tcaagatga    420 gatgtgtcat atgacgacgg atgctcatgg tcttgacatg gaggagacct tggtggaggc    480 tattatacg ccggaacaga gccaagatgc gttttatatg gatgaagagg cgatgttggg    540
gatgtctagt tgttggata acatggccga agggatgctt taccgtcgc cgtcggttca    600 atggaactat aattttgatg tcgagggaga tgatgacgtg tccttatgga gctattaaaa    660 ttcgatttt atttccattt ttggtattat agctttttat acatttgatc cttttttaga    720
atggatcttc ttcttttttt ggttgtgaga aacgaatgta aatggtaaaa gttgttgtca    780
aatgcaaatg ttttgagtg cag                                              803

<210> SEQ ID NO 192
<211> LENGTH: 207
<212> TYPE: PRT
<213> ORGANISM: Arabidopsis thaliana
```

```
<220> FEATURE:
<223> OTHER INFORMATION: CBF2 polypeptide

<400> SEQUENCE: 192

Met Phe Gly Ser Asp Tyr Glu Ser Pro Val Ser Ser Gly Gly Asp Tyr
1               5                   10                  15

Ser Pro Lys Leu Ala Thr Ser Cys Pro Lys Lys Pro Ala Gly Arg Lys
            20                  25                  30

Lys Phe Arg Glu Thr Arg His Pro Ile Tyr Arg Gly Val Arg Gln Arg
        35                  40                  45

Asn Ser Gly Lys Trp Val Cys Glu Leu Arg Glu Pro Asn Lys Lys Thr
    50                  55                  60

Arg Ile Trp Leu Gly Thr Phe Gln Thr Ala Glu Met Ala Ala Arg Ala
65                  70                  75                  80

His Asp Val Ala Ala Ile Ala Leu Arg Gly Arg Ser Ala Cys Leu Asn
                85                  90                  95

Phe Ala Asp Ser Ala Trp Arg Leu Arg Ile Pro Glu Ser Thr Cys Ala
            100                 105                 110

Lys Glu Ile Gln Lys Ala Ala Ala Glu Ala Ala Leu Asn Phe Gln Asp
        115                 120                 125

Glu Met Cys His Met Thr Thr Asp Ala His Gly Leu Asp Met Glu Glu
    130                 135                 140

Thr Leu Val Glu Ala Ile Tyr Thr Pro Glu Gln Ser Gln Asp Ala Phe
145                 150                 155                 160

Tyr Met Asp Glu Glu Ala Met Leu Gly Met Ser Ser Leu Leu Asp Asn
                165                 170                 175

Met Ala Glu Gly Met Leu Leu Pro Ser Pro Ser Val Gln Trp Asn Tyr
            180                 185                 190

Asn Phe Asp Val Glu Gly Asp Asp Val Ser Leu Trp Ser Tyr
        195                 200                 205

<210> SEQ ID NO 193
<211> LENGTH: 850
<212> TYPE: DNA
<213> ORGANISM: Arabidopsis thaliana
<220> FEATURE:
<223> OTHER INFORMATION: CBF3

<400> SEQUENCE: 193
cctgaactag aacagaaaga gagagaaact attatttcag caaaccatac caacaaaaaa     60
gacagagatc ttttagttac cttatccagt ttcttgaaac agagtactct tctgatcaat    120
gaactcattt tctgcttttt ctgaaatgtt tggctccgat tacgagtctt cggtttcctc    180
aggcggtgat tatattccga cgcttgcgag cagctgcccc aagaaaccgg cgggtcgtaa    240
gaagtttcgt gagactcgtc acccaatata cagaggagtt cgtcggagaa actccggtaa    300
gtgggtttgt gaggttagag aaccaaacaa gaaaacaagg atttggctcg gaacatttca    360
aaccgctgag atggcagctc gagctcacga cgttgccgct ttagcccttc gtggccgatc    420
agcctgtctc aatttcgctg actcggcttg gagactccga atcccggaat caacttgcgc    480
taaggacatc caaaaggcgg cggctgaagc tgcgttggcg tttcaggatg agatgtgtga    540
tgcgacgacg gatcatggct tcgacatgga ggagacgttg gtggaggcta tttacacggc    600
ggaacagagc gaaaatgcgt tttatatgca cgatgaggcg atgtttgaga tgccgagttt    660
gttggctaat atggcagaag ggatgctttt gccgcttccg tccgtacagt ggaatcataa    720
tcatgaagtc gacggcgatg atgacgacgt atcgttatgg agttattaaa actcagatta    780
```

```
ttatttccat ttttagtacg atacttttta tttattatt attttttagat cctttttttag    840 aatggaatct                                                              850
```

<210> SEQ ID NO 194
<211> LENGTH: 216
<212> TYPE: PRT
<213> ORGANISM: Arabidopsis thaliana
<220> FEATURE:
<223> OTHER INFORMATION: CBF3 polypeptide

<400> SEQUENCE: 194

```
Met Asn Ser Phe Ser Ala Phe Ser Glu Met Phe Gly Ser Asp Tyr Glu
1               5                   10                  15

Ser Ser Val Ser Ser Gly Gly Asp Tyr Ile Pro Thr Leu Ala Ser Ser
            20                  25                  30

Cys Pro Lys Lys Pro Ala Gly Arg Lys Lys Phe Arg Glu Thr Arg His
        35                  40                  45

Pro Ile Tyr Arg Gly Val Arg Arg Asn Ser Gly Lys Trp Val Cys
    50                  55                  60

Glu Val Arg Glu Pro Asn Lys Lys Thr Arg Ile Trp Leu Gly Thr Phe
65                  70                  75                  80

Gln Thr Ala Glu Met Ala Ala Arg Ala His Asp Val Ala Ala Leu Ala
                85                  90                  95

Leu Arg Gly Arg Ser Ala Cys Leu Asn Phe Ala Asp Ser Ala Trp Arg
            100                 105                 110

Leu Arg Ile Pro Glu Ser Thr Cys Ala Lys Asp Ile Gln Lys Ala Ala
        115                 120                 125

Ala Glu Ala Ala Leu Ala Phe Gln Asp Glu Met Cys Asp Ala Thr Thr
    130                 135                 140

Asp His Gly Phe Asp Met Glu Glu Thr Leu Val Glu Ala Ile Tyr Thr
145                 150                 155                 160

Ala Glu Gln Ser Glu Asn Ala Phe Tyr Met His Asp Glu Ala Met Phe
                165                 170                 175

Glu Met Pro Ser Leu Leu Ala Asn Met Ala Glu Gly Met Leu Leu Pro
            180                 185                 190

Leu Pro Ser Val Gln Trp Asn His Asn His Glu Val Asp Gly Asp Asp
        195                 200                 205

Asp Asp Val Ser Leu Trp Ser Tyr
    210                 215
```

<210> SEQ ID NO 195
<211> LENGTH: 929
<212> TYPE: DNA
<213> ORGANISM: Arabidopsis thaliana
<220> FEATURE:
<223> OTHER INFORMATION: CBF1

<400> SEQUENCE: 195

```
cttgaaaaag aatctacctg aaagaaaaaa aagagagag agatataaat agctttacca      60
agacagatat actatctttt attaatccaa aaagactgag aactctagta actacgtact    120 acttaaaacct tatccagttt cttgaaacag agtactctga tcaatgaact cattttcagc   180
tttttctgaa atgtttggct ccgattacga gcctcaaggc ggagattatt gtccgacgtt   240
ggccacgagt tgtccgaaga aaccggcggg ccgtaagaag tttcgtgaga ctcgtcaccc   300
aatttacaga ggagttcgtc aaagaaactc cggtaagtgg gtttctgaag tgagagagcc   360
```

```
aaacaagaaa accaggattt ggctcgggac tttccaaacc gctgagatgg cagctcgtgc      420
tcacgacgtc gctgcattag ccctccgtgg ccgatcagca tgtctcaact tcgctgactc      480
ggcttggcgg ctacgaatcc cggagtcaac atgcgccaag gatatccaaa agcggctgc       540 tgaagcggcg ttggcttttc aagatgagac gtgtgatacg acgaccacga atcatggcct      600
ggacatggag gagacgatgg tggaagctat ttatacaccg gaacagagcg aaggtgcgtt      660
ttatatggat gaggagacaa tgtttgggat gccgactttg ttggataata tggctgaagg      720 catgcttta ccgccgccgt ctgttcaatg gaatcataat tatgacggcg aaggagatgg      780
tgacgtgtcg ctttggagtt actaatattc gatagtcgtt tccattttg tactatagtt       840 tgaaaatatt ctagttcctt tttttagaat ggttccttca tttattttta tttttattgtt      900 gtagaaacga gtggaaaata attcaatac                                         929
```

<210> SEQ ID NO 196
<211> LENGTH: 213
<212> TYPE: PRT
<213> ORGANISM: Arabidopsis thaliana
<220> FEATURE:
<223> OTHER INFORMATION: CBF1 polypeptide

<400> SEQUENCE: 196

```
Met Asn Ser Phe Ser Ala Phe Ser Glu Met Phe Gly Ser Asp Tyr Glu
1               5                   10                  15

Pro Gln Gly Gly Asp Tyr Cys Pro Thr Leu Ala Thr Ser Cys Pro Lys
            20                  25                  30

Lys Pro Ala Gly Arg Lys Lys Phe Arg Glu Thr Arg His Pro Ile Tyr
        35                  40                  45

Arg Gly Val Arg Gln Arg Asn Ser Gly Lys Trp Val Ser Glu Val Arg
    50                  55                  60

Glu Pro Asn Lys Lys Thr Arg Ile Trp Leu Gly Thr Phe Gln Thr Ala
65                  70                  75                  80

Glu Met Ala Ala Arg Ala His Asp Val Ala Ala Leu Ala Leu Arg Gly
                85                  90                  95

Arg Ser Ala Cys Leu Asn Phe Ala Asp Ser Ala Trp Arg Leu Arg Ile
            100                 105                 110

Pro Glu Ser Thr Cys Ala Lys Asp Ile Gln Lys Ala Ala Ala Glu Ala
        115                 120                 125

Ala Leu Ala Phe Gln Asp Glu Thr Cys Asp Thr Thr Thr Asn His
    130                 135                 140

Gly Leu Asp Met Glu Glu Thr Met Val Glu Ala Ile Tyr Thr Pro Glu
145                 150                 155                 160

Gln Ser Glu Gly Ala Phe Tyr Met Asp Glu Thr Met Phe Gly Met
                165                 170                 175

Pro Thr Leu Leu Asp Asn Met Ala Glu Gly Met Leu Leu Pro Pro Pro
            180                 185                 190

Ser Val Gln Trp Asn His Asn Tyr Asp Gly Glu Gly Asp Gly Asp Val
        195                 200                 205

Ser Leu Trp Ser Tyr
    210
```

<210> SEQ ID NO 197
<211> LENGTH: 1146
<212> TYPE: DNA
<213> ORGANISM: Zea mays
<220> FEATURE:
<223> OTHER INFORMATION: G3656

-continued

```
<400> SEQUENCE: 197
ggcggtgaag atggaggcgg agcaagcggc gatggcggcg ccgcagctgg gggcggcgca      60
ccagcagacg cagccgcggc ggcagtaccg cggcgtgcgc atgcgcaagt ggggcaagtg     120
ggtggcggag atccgggagc cgcacaagcg cacgcgcccc cgcctccggt cctacgccac     180
ggccgtggcg gcggcgcgcg cctacgacac ggccgtgttc tacctgcccg gcccgtcggc     240
gcggctcaac ttccccgagg agatcccctc gttcgggctg gcggatggcg tggacgtggg     300
ggagcacgcg cgcgacccgg ccgccgccgc cgccggcggc ggcggcggct gcacgctgtc     360
cgcggcgtcc atacggaaga aggccatcga ggtggggtcc cgcgtggacg cgctccagac     420
cggcatggtg gtcccgccgc cgcaccaccg cgagcgccat aggcaccaca accacctgcc     480
gcagctgcgg gtgcacgcgg aggagcagca ggaggaagag gagcagaagc cgcagcggcc     540
tgcgtggagc gggcgcgtca agaacccgga tctgaaccgt cgccgagcc ccgagagctc     600
cgacgccgag tgacaagcga gcgagagcgc agcagcagcc accgcaaggc gaggttcaac     660
gacgacgtcc gttatcggtt attcccaatc ccacgacgca gcatgccgtt gtcgtctccg     720
tccgaccgtc cccacgtacg tacgtacgta cgtacacgac gatccagctg accctgccgc     780
ctgcctatcc tatccgtcct cgacgacgac cggatggtcg gcgggcggga gggagggcgg     840
tgcggcgagg gttttgggta cgttgtggat aagcacgagg gcagcagcag caggggcggc     900
gtgcgcgggc aggcaggcga agacggaggg aggcggccac aagcggcggt ctttccaaac     960
gtcaaaaagg acagctgtaa cagcgataag aaaaaacaag tcatcatcac cctcgtctca    1020
ctactagttc tactactgtt cccgagagta gtagtaacga ttagcactcc actagcagta    1080
tgattattcg aatcggcctt gcttgacagc gattaaaaaa aaaaaaaaaa aaaaaaaaaa    1140
aaaaaa                                                              1146

<210> SEQ ID NO 198
<211> LENGTH: 200
<212> TYPE: PRT
<213> ORGANISM: Zea mays
<220> FEATURE:
<223> OTHER INFORMATION: G3656 polypeptide

<400> SEQUENCE: 198

Met Glu Ala Glu Gln Ala Ala Met Ala Ala Pro Gln Leu Gly Ala Ala
 1               5                  10                  15

His Gln Gln Thr Gln Pro Arg Arg Gln Tyr Arg Gly Val Arg Met Arg
            20                  25                  30

Lys Trp Gly Lys Trp Val Ala Glu Ile Arg Glu Pro His Lys Arg Thr
        35                  40                  45

Arg Pro Arg Leu Arg Ser Tyr Ala Thr Ala Val Ala Ala Ala Arg Ala
    50                  55                  60

Tyr Asp Thr Ala Val Phe Tyr Leu Pro Gly Pro Ser Ala Arg Leu Asn
65                  70                  75                  80

Phe Pro Glu Glu Ile Pro Ser Phe Gly Leu Ala Asp Gly Val Asp Val
                85                  90                  95

Gly Glu His Ala Arg Asp Pro Ala Ala Ala Ala Gly Gly Gly Gly
            100                 105                 110

Gly Cys Thr Leu Ser Ala Ala Ser Ile Arg Lys Lys Ala Ile Glu Val
        115                 120                 125

Gly Ser Arg Val Asp Ala Leu Gln Thr Gly Met Val Val Pro Pro Pro
    130                 135                 140
```

His His Arg Glu Arg His Arg His Asn His Leu Pro Gln Leu Arg
145                 150                 155                 160

Val His Ala Glu Glu Gln Gln Glu Glu Glu Gln Lys Pro Gln Arg
                165                 170                 175

Pro Ala Trp Ser Gly Arg Val Lys Asn Pro Asp Leu Asn Arg Ala Pro
            180                 185                 190

Ser Pro Glu Ser Ser Asp Ala Glu
        195                 200

<210> SEQ ID NO 199
<211> LENGTH: 831
<212> TYPE: DNA
<213> ORGANISM: Arabidopsis thaliana
<220> FEATURE:
<223> OTHER INFORMATION: G12

<400> SEQUENCE: 199
gtgtcggtga atttttgaa acttcttctc ttttgcggtt tcgtgttcca ctcctctctt      60
cttggcccac gtgttcatca atctctccct ccgcatgtaa tcgcttcgcc gtcaatatca     120
catctttctt cttctttatc tttaaaatct ctttagatcg attcttttgt ggattcttga    180
aatctccgga gaaaaccact atggagacgg cgactgaagt ggccacggtg gtgtcaactc    240
cggcggttac ggttgcggcg gtggcgacga ggaagagaga taagccgtat aaagggataa    300
ggatgaggaa gtggggggaag tgggtggcgg agataagaga gcctaataaa aggtcaagga    360
tctggcttgg ctcttactct actcctgaag cggcggcgcg tgcttacgac acggcggtgt    420
tttatctccg aggtccttct gctcggctta acttcccgga gcttttagcc ggagtgacgg    480 tgacgggag aggcggagga ggagtgaacg gtggtgaga tatgtcggcg gcgtatataa     540
ggagaaaagc ggcggaggtt ggagcacaag tggatgcgtt agaagcggcg ggggcgggag    600
ggaatcgtca tcatcatcat catcaacatc aacgtggtaa tcatgattac gtagataatc    660
atagtgatta tcgtattaat gatgatctta tggagtgtag tagtaaagaa gggtttaaga    720
ggtgtaatgg atcgttggaa cgggttgatt taaacaaatt acccgatccg gaaacttcag    780
atgacgatta ggaaagcaaa aatagaaaac aaaaaaaaaa aaaaaaaaa a              831

<210> SEQ ID NO 200
<211> LENGTH: 196
<212> TYPE: PRT
<213> ORGANISM: Arabidopsis thaliana
<220> FEATURE:
<223> OTHER INFORMATION: G12 polypeptide

<400> SEQUENCE: 200

Met Glu Thr Ala Thr Glu Val Ala Thr Val Val Ser Thr Pro Ala Val
1               5                   10                  15

Thr Val Ala Ala Val Ala Thr Arg Lys Arg Asp Lys Pro Tyr Lys Gly
            20                  25                  30

Ile Arg Met Arg Lys Trp Gly Lys Trp Val Ala Glu Ile Arg Glu Pro
        35                  40                  45

Asn Lys Arg Ser Arg Ile Trp Leu Gly Ser Tyr Ser Thr Pro Glu Ala
    50                  55                  60

Ala Ala Arg Ala Tyr Asp Thr Ala Val Phe Tyr Leu Arg Gly Pro Ser
65                  70                  75                  80

Ala Arg Leu Asn Phe Pro Glu Leu Leu Ala Gly Val Thr Val Thr Gly
                85                  90                  95

Gly Gly Gly Gly Gly Val Asn Gly Gly Gly Asp Met Ser Ala Ala Tyr
            100                 105                 110

Ile Arg Arg Lys Ala Ala Glu Val Gly Ala Gln Val Asp Ala Leu Glu
            115                 120                 125

Ala Ala Gly Ala Gly Gly Asn Arg His His His His Gln His Gln
            130                 135                 140

Arg Gly Asn His Asp Tyr Val Asp Asn His Ser Asp Tyr Arg Ile Asn
145                 150                 155                 160

Asp Asp Leu Met Glu Cys Ser Ser Lys Glu Gly Phe Lys Arg Cys Asn
            165                 170                 175

Gly Ser Leu Glu Arg Val Asp Leu Asn Lys Leu Pro Asp Pro Glu Thr
            180                 185                 190

Ser Asp Asp Asp
        195

<210> SEQ ID NO 201
<211> LENGTH: 957
<212> TYPE: DNA
<213> ORGANISM: Arabidopsis thaliana
<220> FEATURE:
<223> OTHER INFORMATION: G24

<400> SEQUENCE: 201

```
cggacgcgtg ggcaaatatt aaaataaaaa gtgtcggtga attctcaatc tttgtcttct      60
ttcgtcgtct cttaaaaact cctccgtccc tccttattat gtaaccgtct cgccgtcaaa     120
ttttcaaaat ctctccctcc gttcataaac ccagatcgaa atttatggtt ttgtaatttt     180
tttaccggcg gttatggaga cggaagcggc ggtgacagcg acggttacgg cggcgacgat     240
ggggattggg acgaggaaga gagatctgaa accgtataaa ggaatacgaa tgaggaaatg     300
ggggaaatgg gtggcggaga tacgggaacc gaataagaga tcaaggatct ggttaggttc     360
ttatgcgacg cctgaagcgg cggcgagagc ttacgacact gctgtttttt acctccgtgg     420
tccttcagcg aggcttaatt ttccggagct tttggctgga cttactgttt ctaacggcgg     480
aggaagaggt ggtgatttat cggcggcgta tattaggaga aaagcggcgg aggttggtgc     540
tcaggttgat gcgcttggag cgacggtggt tgtgaatacc ggcggcgaga atcgcggtga     600
ttacgagaag attgagaatt gtcgtaagag cggtaacggg tcattggaac gggtcgattt     660
gaataaatta cccgacccgg aaaattcgga tggtgatgat gacgaatgtg tgaaaagaag     720
atagaaaaaa taaaaagtag ttgtagaagg agagacgaga atgtttgtct ttaagatgcg     780
ctgttgccgc taacatgcgc tttcgatttt agtgttaaac atgcgcctcc attgtttttg     840
ggttttgttt tcgtcgtcga taatcaaaga ttttaaaaca caattctcaa attttttcact     900
tgttacaaac tagatttgca tgatctttgt attaacgaat aacgattaag tcctaaa        957
```

<210> SEQ ID NO 202
<211> LENGTH: 176
<212> TYPE: PRT
<213> ORGANISM: Arabidopsis thaliana
<220> FEATURE:
<223> OTHER INFORMATION: G24 polypeptide

<400> SEQUENCE: 202

Met Glu Thr Glu Ala Ala Val Thr Ala Thr Val Thr Ala Ala Thr Met
1               5                   10                  15

Gly Ile Gly Thr Arg Lys Arg Asp Leu Lys Pro Tyr Lys Gly Ile Arg
            20                  25                  30

```
Met Arg Lys Trp Gly Lys Trp Val Ala Glu Ile Arg Glu Pro Asn Lys
         35                  40                  45

Arg Ser Arg Ile Trp Leu Gly Ser Tyr Ala Thr Pro Glu Ala Ala Ala
 50                  55                  60

Arg Ala Tyr Asp Thr Ala Val Phe Tyr Leu Arg Gly Pro Ser Ala Arg
 65                  70                  75                  80

Leu Asn Phe Pro Glu Leu Leu Ala Gly Leu Thr Val Ser Asn Gly Gly
                 85                  90                  95

Gly Arg Gly Gly Asp Leu Ser Ala Ala Tyr Ile Arg Arg Lys Ala Ala
                100                 105                 110

Glu Val Gly Ala Gln Val Asp Ala Leu Gly Ala Thr Val Val Asn
         115                 120                 125

Thr Gly Gly Glu Asn Arg Gly Asp Tyr Glu Lys Ile Glu Asn Cys Arg
130                 135                 140

Lys Ser Gly Asn Gly Ser Leu Glu Arg Val Asp Leu Asn Lys Leu Pro
145                 150                 155                 160

Asp Pro Glu Asn Ser Asp Gly Asp Asp Glu Cys Val Lys Arg Arg
                165                 170                 175

<210> SEQ ID NO 203
<211> LENGTH: 911
<212> TYPE: DNA
<213> ORGANISM: Arabidopsis thaliana
<220> FEATURE:
<223> OTHER INFORMATION: G1277

<400> SEQUENCE: 203
attctaaagt cctcctctcg gaaagtaaga gactcaactt ccgagccgcc atggacgccg     60
gagtagcagt aaaagctgac gtggcagtca aatgaagag agaaagacca ttcaaaggga    120
tcagaatgag aaaatggggg aaatggggttg cggagattcg agaacccaac aagcgttcaa    180
gactttggct cggctcttac tctactcccg aagcggcggc gcgtgcatac gacacggctg    240
tcttttacct cagaggacca actgctacgc tcaacttccc ggagcttctg ccgtgtacct    300
ccgccgagga tatgtcagcg gcaacgatca ggaaaaaggc gacggaggtg ggagctcaag    360
tagatgcgat aggggcgacg gtggtgcaga caacaaacg ccgccgcgtt tttagtcaaa    420
agcgtgactt tggcggcggg ttattagagc ttgttgactt gaacaagtta cctgacccgg    480
aaaatctcga tgatgatttg gtgggaaaat agactgaaaa ataataataa aatatcttac    540
aatggtggct gtagctatcg tacgcggaat gcttgggctt gtgttatatg actacgtggt    600
tacggaaaga ttcctctgtt tcgtcattgt attaaaattt aatcccacaa gtcaaacata    660
ctgtacatta ttcttaattt agtattttct tattaatatc tatcatttgt ttggtgaaca    720
ccagaatatt agactattaa tgtaacgagt ttttaatatt tcgatcataa taacaccaag    780
ctagttaaag gttaatatct tgttacgaag tcttgagtaa gttcaattgt catatatatg    840
taacggaaga ggttcgttcg ggtcccaagt gaagtggatc aaaggtgact tcacataaaa    900
aataaaaaaa a                                                         911

<210> SEQ ID NO 204
<211> LENGTH: 153
<212> TYPE: PRT
<213> ORGANISM: Arabidopsis thaliana
<220> FEATURE:
<223> OTHER INFORMATION: G1277 polypeptide

<400> SEQUENCE: 204
```

```
Met Asp Ala Gly Val Ala Val Lys Ala Asp Val Ala Val Lys Met Lys
1               5                   10                  15

Arg Glu Arg Pro Phe Lys Gly Ile Arg Met Arg Lys Trp Gly Lys Trp
            20                  25                  30

Val Ala Glu Ile Arg Glu Pro Asn Lys Arg Ser Arg Leu Trp Leu Gly
        35                  40                  45

Ser Tyr Ser Thr Pro Glu Ala Ala Arg Ala Tyr Asp Thr Ala Val
    50                  55                  60

Phe Tyr Leu Arg Gly Pro Thr Ala Thr Leu Asn Phe Pro Glu Leu Leu
65              70                  75                  80

Pro Cys Thr Ser Ala Glu Asp Met Ser Ala Thr Ile Arg Lys Lys
                85                  90                  95

Ala Thr Glu Val Gly Ala Gln Val Asp Ala Ile Gly Ala Thr Val Val
                100                 105                 110

Gln Asn Asn Lys Arg Arg Val Phe Ser Gln Lys Arg Asp Phe Gly
            115                 120                 125

Gly Gly Leu Leu Glu Leu Val Asp Leu Asn Lys Leu Pro Asp Pro Glu
        130                 135                 140

Asn Leu Asp Asp Asp Leu Val Gly Lys
145                 150
```

<210> SEQ ID NO 205
<211> LENGTH: 839
<212> TYPE: DNA
<213> ORGANISM: Arabidopsis thaliana
<220> FEATURE:
<223> OTHER INFORMATION: G1379

<400> SEQUENCE: 205

```
ctctgcctct ctctctctct caaaacccat ctcgaaagtc tttctctttc gagggtttag      60
atcctccatg gaaggcggcg gagttgctga cgtggctgtc cccggtacga ggaagagaga     120
cagaccttac aaaggaatta ggatgaggaa gtggggaaag tgggtggcgg agattcgtga     180
gcctaacaag cgctctaggt tatggcttgg ctcttactct actcccgagg cggcggcgcg     240
agcttacgac acggcggttt tctatcttag aggacctacg gcgaggctta acttccctga     300
gcttcttcct ggggagaaat tctccgacga ggatatgtcg gctgcgacca tcaggaagaa     360
agccacggag gtcggtgctc aggttgatgc tttgggcacg gcggtgcaaa ataaccgcca     420
ccgtgttttt ggtcagaatc gagatagtga tgtggataat aagaattttc atcggaatta     480
tcaaaacggt gaacgagaag aagaagaaga agatgaggat gacaagagat tgaggagtgg     540
cggccggtta ttggatcggg ttgacttgaa taaattaccc gacccggaaa gctccgatga     600
agaatgggaa agcaaacatt aaaaatatat agtttggagc ggtggctgtt gctaacgtac     660
gccaacggct tgcttctacg aatcattagc gccgtttatg attttttttt ttttttttt     720
cattatctga aaatttaggg cttttagtt attaattttt gttttgtttt tttccttct      780
tgcgagtttt gcggtttatg gaattttagg ctattgctta acgaaaaaaa aaaaaaaaa     839
```

<210> SEQ ID NO 206
<211> LENGTH: 184
<212> TYPE: PRT
<213> ORGANISM: Arabidopsis thaliana
<220> FEATURE:
<223> OTHER INFORMATION: G1379 polypeptide

<400> SEQUENCE: 206

Met Glu Gly Gly Gly Val Ala Asp Val Ala Val Pro Gly Thr Arg Lys

```
                 1               5                  10                 15
Arg Asp Arg Pro Tyr Lys Gly Ile Arg Met Arg Lys Trp Gly Lys Trp
             20                  25                 30

Val Ala Glu Ile Arg Glu Pro Asn Lys Arg Ser Arg Leu Trp Leu Gly
             35                  40                 45

Ser Tyr Ser Thr Pro Glu Ala Ala Arg Ala Tyr Asp Thr Ala Val
             50                  55                 60

Phe Tyr Leu Arg Gly Pro Thr Ala Arg Leu Asn Phe Pro Glu Leu Leu
65                  70                  75                 80

Pro Gly Glu Lys Phe Ser Asp Glu Asp Met Ser Ala Ala Thr Ile Arg
                85                  90                 95

Lys Lys Ala Thr Glu Val Gly Ala Gln Val Asp Ala Leu Gly Thr Ala
                100                 105                110

Val Gln Asn Asn Arg His Arg Val Phe Gly Gln Asn Arg Asp Ser Asp
                115                 120                125

Val Asp Asn Lys Asn Phe His Arg Asn Tyr Gln Asn Gly Glu Arg Glu
                130                 135                140

Glu Glu Glu Glu Asp Glu Asp Lys Arg Leu Arg Ser Gly Gly Arg
145                 150                 155                160

Leu Leu Asp Arg Val Asp Leu Asn Lys Leu Pro Asp Pro Glu Ser Ser
                165                 170                175

Asp Glu Glu Trp Glu Ser Lys His
                180
```

<210> SEQ ID NO 207
<211> LENGTH: 1281
<212> TYPE: DNA
<213> ORGANISM: Arabidopsis thaliana
<220> FEATURE:
<223> OTHER INFORMATION: G867

<400> SEQUENCE: 207

```
cacaacacaa acacatttct gttttctcca ttgtttcaaa ccataaaaaa aaacacagat     60
taaatggaat cgagtagcgt tgatgagagt actacaagta caggttccat ctgtgaaacc    120
ccggcgataa ctccggcgaa aaagtcgtcg gtaggtaact tatacaggat gggaagcgga    180
tcaagcgttg tgttagattc agagaacggc gtagaagctg aatctaggaa gcttccgtcg    240
tcaaaataca aaggtgtggt gccacaacca aacggaagat ggggagctca gatttacgag    300
aaacaccagc gcgtgtggct cgggacattc aacgaagaag acgaagccgc tcgtgcctac    360
gacgtcgcgg ttcacaggtt ccgtcgccgt gacgccgtca caatttcaa agacgtgaag     420
atggacgaag acgaggtcga tttcttgaat tctcattcga aatctgagat cgttgatatg    480
ttgaggaaac atacttataa cgaagagtta gagcagagta acggcgtcg taatggtaac     540
ggaaacatga ctaggacgtt gttaacgtcg gggttagta atgatggtgt ttctacgacg     600
gggtttagat cggcggaggc actgtttgag aaagcggtaa cgccaagcga cgttgggaag    660
ctaaaccgtt tggttatacc gaaacatcac gcagagaaac attttccgtt accgtcaagt    720
aacgtttccg tgaaaggagt gttgttgaac tttgaggacg ttaacgggaa agtgtggagg    780
ttccgttact cgtattggaa cagtagtcag agttatgttt tgactaaagg ttggagcagg    840
ttcgttaagg agaagaatct acgtgctggt gacgtggtta gtttcagtag atctaacggt    900
caggatcaac agttgtacat tgggtggaag tcgagatccg ggtcagattt agatgcgggt    960
cgggttttga gattgttcgg agttaacatt tcaccggaga gttcaagaaa cgacgtcgta   1020
```

-continued

```
ggaaacaaaa gagtgaacga tactgagatg ttatcgttgg tgtgtagcaa gaagcaacgc    1080
atctttcacg cctcgtaaca actcttcttc ttttttttc ttttgttgtt ttaataattt     1140
ttaaaaactc catttcgtt ttctttattt gcatcggttt ctttcttctt gtttaccaaa     1200
ggttcatgag ttgttttgt tgtattgatg aactgtaaat tttatttata ggataaattt     1260
taaaaaaaaa aaaaaaaaaa a                                              1281
```

<210> SEQ ID NO 208
<211> LENGTH: 344
<212> TYPE: PRT
<213> ORGANISM: Arabidopsis thaliana
<220> FEATURE:
<223> OTHER INFORMATION: G867 polypeptide

<400> SEQUENCE: 208

| | | | | | | | | | | | | | | |
|---|---|---|---|---|---|---|---|---|---|---|---|---|---|---|
| Met | Glu | Ser | Ser | Ser | Val | Asp | Glu | Ser | Thr | Thr | Ser | Thr | Gly | Ser | Ile |
| 1 | | | | 5 | | | | | 10 | | | | | 15 | |
| Cys | Glu | Thr | Pro | Ala | Ile | Thr | Pro | Ala | Lys | Lys | Ser | Ser | Val | Gly | Asn |
| | | | 20 | | | | | 25 | | | | | 30 | | |
| Leu | Tyr | Arg | Met | Gly | Ser | Gly | Ser | Ser | Val | Val | Leu | Asp | Ser | Glu | Asn |
| | | 35 | | | | | 40 | | | | | 45 | | | |
| Gly | Val | Glu | Ala | Glu | Ser | Arg | Lys | Leu | Pro | Ser | Ser | Lys | Tyr | Lys | Gly |
| | 50 | | | | | 55 | | | | | 60 | | | | |
| Val | Val | Pro | Gln | Pro | Asn | Gly | Arg | Trp | Gly | Ala | Gln | Ile | Tyr | Glu | Lys |
| 65 | | | | | 70 | | | | | 75 | | | | | 80 |
| His | Gln | Arg | Val | Trp | Leu | Gly | Thr | Phe | Asn | Glu | Glu | Asp | Glu | Ala | Ala |
| | | | | 85 | | | | | 90 | | | | | 95 | |
| Arg | Ala | Tyr | Asp | Val | Ala | Val | His | Arg | Phe | Arg | Arg | Arg | Asp | Ala | Val |
| | | | 100 | | | | | 105 | | | | | 110 | | |
| Thr | Asn | Phe | Lys | Asp | Val | Lys | Met | Asp | Glu | Asp | Glu | Val | Asp | Phe | Leu |
| | | 115 | | | | | 120 | | | | | 125 | | | |
| Asn | Ser | His | Ser | Lys | Ser | Glu | Ile | Val | Asp | Met | Leu | Arg | Lys | His | Thr |
| | 130 | | | | | 135 | | | | | 140 | | | | |
| Tyr | Asn | Glu | Glu | Leu | Glu | Gln | Ser | Lys | Arg | Arg | Arg | Asn | Gly | Asn | Gly |
| 145 | | | | | 150 | | | | | 155 | | | | | 160 |
| Asn | Met | Thr | Arg | Thr | Leu | Leu | Thr | Ser | Gly | Leu | Ser | Asn | Asp | Gly | Val |
| | | | | 165 | | | | | 170 | | | | | 175 | |
| Ser | Thr | Thr | Gly | Phe | Arg | Ser | Ala | Glu | Ala | Leu | Phe | Glu | Lys | Ala | Val |
| | | | 180 | | | | | 185 | | | | | 190 | | |
| Thr | Pro | Ser | Asp | Val | Gly | Lys | Leu | Asn | Arg | Leu | Val | Ile | Pro | Lys | His |
| | | 195 | | | | | 200 | | | | | 205 | | | |
| His | Ala | Glu | Lys | His | Phe | Pro | Leu | Pro | Ser | Ser | Asn | Val | Ser | Val | Lys |
| | 210 | | | | | 215 | | | | | 220 | | | | |
| Gly | Val | Leu | Leu | Asn | Phe | Glu | Asp | Val | Asn | Gly | Lys | Val | Trp | Arg | Phe |
| 225 | | | | | 230 | | | | | 235 | | | | | 240 |
| Arg | Tyr | Ser | Tyr | Trp | Asn | Ser | Ser | Gln | Ser | Tyr | Val | Leu | Thr | Lys | Gly |
| | | | | 245 | | | | | 250 | | | | | 255 | |
| Trp | Ser | Arg | Phe | Val | Lys | Glu | Lys | Asn | Leu | Arg | Ala | Gly | Asp | Val | Val |
| | | | 260 | | | | | 265 | | | | | 270 | | |
| Ser | Phe | Ser | Arg | Ser | Asn | Gly | Gln | Asp | Gln | Gln | Leu | Tyr | Ile | Gly | Trp |
| | | 275 | | | | | 280 | | | | | 285 | | | |
| Lys | Ser | Arg | Ser | Gly | Ser | Asp | Leu | Asp | Ala | Gly | Arg | Val | Leu | Arg | Leu |
| | 290 | | | | | 295 | | | | | 300 | | | | |
| Phe | Gly | Val | Asn | Ile | Ser | Pro | Glu | Ser | Ser | Arg | Asn | Asp | Val | Val | Gly |
| 305 | | | | | 310 | | | | | 315 | | | | | 320 |

Asn Lys Arg Val Asn Asp Thr Glu Met Leu Ser Leu Val Cys Ser Lys
                325                 330                 335

Lys Gln Arg Ile Phe His Ala Ser
            340

<210> SEQ ID NO 209
<211> LENGTH: 574
<212> TYPE: DNA
<213> ORGANISM: Cauliflower mosaic virus
<220> FEATURE:
<223> OTHER INFORMATION: CaMV 35S constitutive promoter

<400> SEQUENCE: 209

| | | | | | |
|---|---|---|---|---|---|
| gcggattcca | ttgcccagct | atctgtcact | ttattgtgaa | gatagtgaaa | aagaaggtgg | 60 |
| ctcctacaaa | tgccatcatt | gcgataaagg | aaaggccatc | gttgaagatg | cctctgccga | 120 |
| cagtggtccc | aaagatggac | ccccacccac | gaggagcatc | gtggaaaaag | aagacgttcc | 180 |
| aaccacgtct | tcaaagcaag | tggattgatg | tgatggtccg | attgagactt | tcaacaaag | 240 |
| ggtaatatcc | ggaaacctcc | tcggattcca | ttgcccagct | atctgtcact | ttattgtgaa | 300 |
| gatagtggaa | aaggaaggtg | gctcctacaa | atgccatcat | tgcgataaag | gaaaggccat | 360 |
| cgttgaagat | gcctctgccg | acagtggtcc | caaagatgga | cccccaccca | cgaggagcat | 420 |
| cgtggaaaaa | gaagacgttc | caaccacgtc | ttcaaagcaa | gtggattgat | gtgatatctc | 480 |
| cactgacgta | aggatgacg | cacaatccca | ctatccttcg | caagacccct | tcctctatata | 540 |
| aggaagttca | tttcatttgg | agaggacacg | ctga | | | 574 |

<210> SEQ ID NO 210
<211> LENGTH: 4361
<212> TYPE: DNA
<213> ORGANISM: Arabidopsis thaliana
<220> FEATURE:
<223> OTHER INFORMATION: STM (Shoot Meristemless) shoot apical
      meristem-specific promoter

<400> SEQUENCE: 210

| | | | | | |
|---|---|---|---|---|---|
| agaatgtagc | aatacaaata | tatgacggta | ccgttatcca | tcaccattat | atgtatatat | 60 |
| gtataatttg | ataaatattc | actttgtgtt | tcgtcgtttg | cttaataaac | agctcatttc | 120 |
| catggtattg | agtcttctat | atgcgagaga | atcagattcc | cgctgggata | acaaaagaac | 180 |
| aaggtactga | aaaaaataga | caaaactttt | ttttaaatta | tataagctat | aaaagaaaag | 240 |
| agtatagaga | gagattagcc | ctactgttta | agagggagag | agtagggtca | ttagggcttt | 300 |
| agagagagaa | gacattcgga | ctgtccccac | ttgcttttct | gtagaataac | attatttaaa | 360 |
| tcttattttt | aattaaatat | tacaactaaa | agaagaaacc | aacttttaaa | ataaatgcag | 420 |
| attatatgct | ctgacttgga | ctaaataaaa | cttgcaagta | acagtttcaa | gtccttttgt | 480 |
| tttagaactt | tttctttcgt | agaagtgata | aatgattgcc | ctagacctga | tagattctct | 540 |
| aaaattctac | gtattacagc | ataagttacc | tcctttattt | gactattaga | ccatccatat | 600 |
| tggtgggctt | ttagcaaatg | ttcttaacaa | taatttata | atttatttta | atgttaagag | 660 |
| gtttgataat | tttttttttt | taagagtgta | ttttgtttat | taaatgtgt | tttgtttctt | 720 |
| atataagaac | caaatcttaa | ctattttacc | aattaaacat | taaatttaaa | ttttaatatc | 780 |
| tctaagaatt | atattaagag | ccaatataga | tgcttttaaa | accattggtt | gaataaataa | 840 |
| atctaacctt | cttaattatt | tctgtgtgaa | tattttctaa | attttcattt | taatttagca | 900 |
| caatataatc | catgttctaa | aaagaacaat | taacataata | tttacaaacc | taaaaagatt | 960 |

```
ataaaacaca attttattttt ttacagctta taatgtttta aagttcaggt ttatttttta    1020
aaagttcagg tttattacat taggtttgac ttgtaatcat catttatcac aacgatcaaa    1080
ctattattac aatcacaata gtagacaaaa tttaggatat atatatatat atataattat    1140
gtataaacta tgaacattta aagtgagatt tttcaaaata atatataaat tcaaatagaa    1200
atagactatt tggttcttaa atgagagacc cccgaaaaaa tcttttttttt tttctcatca    1260 agctgtttac attttttagat ataaaatcat attctttata gtttagaata tgaattaaat    1320
agttttatat gttattaact tatcataaga tatgcgtgag gttggccaaa aactcatcaa    1380
ttaaccaaat aagaaaagta aaattgtatt ttgctttgct aaaaatgtaa atatttcatt    1440
gaaaaatgaa aaaggtttag gtaatacaat taagtaaatc ctacaatttt ggttccatgg    1500
caaaagaata aaattgtatt gctttggtaa aagttgatcc aactaatata ttcagtagaa    1560
actgcaaaac tgaagaaata agtttgttta gtagaattgc tttcggttat gtaatgaata    1620
tacatccaaa atggcttttt agtaatgatg tcttttcata ctctttccaa tccctactac    1680
tttcagatta tttgtcctac tattatagag atatacgttc gttttcaata atatgaaaag    1740
tgatatatat ttaaatagtg tgatatatat ataagttttg caagtgcatc acttcccaaa    1800
atcgcataaa tcattaatca tattgtcgaa aacagtataa taacttctta aacgaaaacg    1860
cagcgcaatt aaaaataaca actagagata attgacaaaa cattgattaa tatttaccta    1920
taagttaatt attgtattta aaatttattt aaagttcata aggaaaacat atgcaaaaat    1980
atttatatct aatattttgc tatgttatcc tttttttttt ttacgttatc ctaatttttgt    2040 ttatcctaat ttgttgtggt taaaatctta ttattgataa aaagagaact ttttttttttg    2100 tcatcataaa aaagagaact tattacttcg attttaaaat tctatgagcg taggagacaa    2160
agaaaaaaaa aataaaaaaa aaagaagag aaaaatcact tcttttcttc tttttagtcc    2220
agatccaaca tattttggat aactaaatga agatttttta aaaaaatata ttttagggta    2280
tatataaatc ataatttgaa gcaaatgaaa taaaatccag tttggtaata tataaatatg    2340
atttgatggg ttccttgtaa tctctctcta tctattagtt tctcagttat cttttctttg    2400
ccagaaatgg cagtgaaggc agtggctgag gagagagttt ttttttcttct ttcatgggga    2460 aagtaaaact ttgccttgaa gatttctctc ttcaatattt ttctaagact tttgatttca    2520
acgaatcact gtccttaacc taaaagcaag aaaaattagc tttatactgg tctttacttt    2580
tttttaacat atttattttt atatagttta cttataaaca tagacatacg agtatgggaa    2640
tatatagtat atccaacttc taaataatat ttcgaatagt gataacaaaa ttagcaatac    2700
atacggctag tgaaatgttg atcgaataaa cggcactgat gtaatgtact tatcaatttt    2760
gataatttta attgtattgt ttttctttttt ttcccacagt attgaactag acaattaaat    2820
ttaaagtaaa attatacatt tcttttcgttg tgtattaaag taacatgcat aatatcatttt    2880 tccttcgtac aatcctccaa attgacaatt gatgaattac tttgtcaatc gtaaatgaat    2940
ttttctcaag tctgtatact atttttcaggg ataaacaggt acaggtgtcc catgcttatt    3000
ctcttgatag taacatgtgt cctatgttga gtcaattcta cgttcgaaga agtgctaaca    3060
attgttaata gcctcgtata ttattctaat taaaatgcct cgatagattt ggttagtggt    3120
ctgaatgtga ttggttatttt tttcaagtgg caagaggtct accatctaat attacaatca    3180
atcgaccaaa aaggtcgaga acatgataat ggtggcaaat acaaatggtt cattgttgtc    3240
taatataaca agccatcagt tgtcactttt taaaaacaat acagaataca agatactttt    3300
```

-continued

```
ttttaaggt aaaatgtgtg tttaatatttt tcgtttatat aacaaataaa cagttacatg    3360
ttttactcta tgattatatt tatgacatttt ttcttcttct taacaacatt tttttcccat    3420
aagaacattt acaatagtat taaaactttg attgcaatca aatgttagat cacttattat    3480
aaaattacta agactgctat cttttcctat tgacaaaagc gaatccaata tatgttactg    3540
aaacaaatgc gtaaattata ctatatggag atctatcggt taattattga gagaatctaa    3600
gaaagttttt gagtacaaca gtcctaataa tatcttcaca taccatataa tatacatata    3660
tacatataca caaatgtact ttttaaacca acatcagcat acgtatatcc catcaggaaa    3720
cttagacttt tgggaattca tggtatgaaa accaaaacca aatgacaaca ttcgatttga    3780
tactcccgac ccatggtaaa gaaataacaa attccaatat atctttcact ggactttccg    3840
aggcacattc cggttttctc catttcaaga aattgtcaaa aataaattga gatccggttt    3900
attacctcaa aaagaagaa gagaaattac aacattaatt tccgaaaagg cataaatgag    3960
aaatcatatt tcagcagaag aacacaaaag agttaagaac ccacagatca cacaacctct    4020
gtccatgtct gctttttaca ctttttttaaa ataagtttct cctaaaaagt tatttcctat    4080
ttataataat ttccttagat ttatcttcct ggtctctctt ctgctgcttc cctctcccc    4140 ataactatca ctatttagaa ttttcaatgt ggaaaaggaa gctgattgtt gaagcataaa    4200
tcccgggaga ccacttttgc attttcaaat aattaaatta aaccatagat acacacacac    4260
agttacttac tcttttaggg tttcccaata aatttatagt actttaatgt gtttcatgat    4320
attgatgata aatgctagct gtatttacaa tgggggctcc t                       4361
```

<210> SEQ ID NO 211
<211> LENGTH: 1176
<212> TYPE: DNA
<213> ORGANISM: Arabidopsis thaliana
<220> FEATURE:
<223> OTHER INFORMATION: CUT1 (Cuticular Wax Condensing Enzyme1) epidermal-specific promoter promoter

<400> SEQUENCE: 211

```
tgtgaattat attttactct tcgatatcgg ttgttgacga ttaaccatgc aaaaaagaaa      60
cattaattgc gaatgtaaat aacaaaacat gtaactcttg tagatataca tgtatcgaca     120
tttaaacccg aatatatatg tatacctata atttctctga ttttcacgct acctgccacg     180
tacatgggtg ataggtccaa actcacaagt aaaagtttac gtacagtgaa ttcgtctttt     240
tgggtataaa cgtacattta atttacacgt aagaaaggat taccaattct ttcatttatg     300
gtaccagaca gagttaaggc aaacaagaga acatatagaa gttttgatat gttttcttgg     360
ataaatatta aattgatgca atatttaggg atggacacaa ggtaatatat gccttttaag     420
gtatatgtgc tatatgaatc gtttcgcatg ggtactaaaa ttatttgtcc ttactttata     480
taaacaaatt ccaacaaaat caagtttttg ctaaaactag tttatttgcg ggttatttaa     540
ttacctatca tattacttgt aatatcattc gtatgttaac gggtaaacca aaccaaaccg     600
gatattgaac tattaaaaat cttgtaaatt tgacacaaac taatgaatat ctaaattatg     660
ttactgctat gataacgacc atttttgttt ttgagaacca taatataaat tacaggtacg     720
tgacaagtac taagtatttta tatccacctt tagtcacagt accaatattg cgcctaccgg     780
gcaacgtgaa cgtgatcatc aaatcaaagt agttaccaaa cgctttgatc tcgataaaac     840
taaaagctga cacgtcttgc tgtttcttaa tttatttctc ttacaacgac aattttgaga     900
aatatgaaat ttttatatcg aaagggaaca gtccttatca tttgctccca tcacttgctt     960
```

```
ttgtctagtt acaactggaa atcgaagaga agtattacaa aaacattttt ctcgtcattt    1020
ataaaaaaat gacaaaaaat taaatagaga gcaaagcaag agcgttgggt gacgttggtc    1080
tcttcattaa ctcctctcat ctaccccttc ctctgttcgc ctttatatcc ttcaccttcc    1140
ctctctcatc ttcattaact catcttcaaa aatacc                              1176

<210> SEQ ID NO 212
<211> LENGTH: 1183
<212> TYPE: DNA
<213> ORGANISM: Arabidopsis thaliana
<220> FEATURE:
<223> OTHER INFORMATION: LTP1 (Lipid Transfer Protein 1)
      epidermal-specific promoter

<400> SEQUENCE: 212
gatatgacca aaatgattaa cttgcattac agttgggaag tatcaagtaa acaacatttt      60 gttttttgttt gatatcggga atctcaaaac caaagtccac actagttttt ggactatata   120
atgataaaag tcagatatct actaatacta gttgatcagt atattcgaaa acatgacttt    180
ccaaatgtaa gttatttact tttttttttgc tattataatt aagatcaata aaaatgtcta   240
agttttaaat ctttatcatt atatccaaac aatcataatc ttattgttaa tctctcatca    300
acacacagtt tttaaaataa attaattacc ctttgcatga taccgaagag aaacgaattc    360
gttcaaataa ttttataaca ggaaataaaa tagataaccg aaataaacga tagaatgatt    420
tcttagtact aactcttaac aacagttttta tttaaatgac ttttgtaaaa aaacaaagt    480 taacttatac acgtacacgt gtcgaaaata ttattgacaa tggatagcat gattcttatt    540
agagtcatgt aaaagataaa cacatgcaaa tatatatatg aataatatgt tgttaagata    600
aactagacga ttagaatata tagcacatct atagtttgta aaataactat ttctcaacta    660
gacttaagtc ttcgaaatac ataaataaac aaaactataa aaattcgaaa aaaacatga     720 gagtacgtta gtaaaatgta ttttttttggt aaaataatca cttttcatca ggtcttttgt   780
aaagcagttt tcatgttaga taaacgagat tttaattttt tttaaaaaaa gaagtaaact    840
aactatgttc ctatctacac acctataatt ttgaacaatt acaaaacaac aatgaaatgc    900
aaagaagacg tagggcactg tcacactaca atacgattaa taaatgtatt ttggtcgaat    960
taataacttt ccatacgata aagttgaatt aacatgtcaa acaaaagaga tgagtggtcc   1020
tatacatagt taggaattag gaacctctaa attaaatgag tacaaccacc aactactcct   1080
tccctctata atctatcgca ttcacaccac ataacatata cgtacctact ctatataaca   1140
ctcactcccc aaactctctt catcatccat cactacacac atc                     1183

<210> SEQ ID NO 213
<211> LENGTH: 2244
<212> TYPE: DNA
<213> ORGANISM: Arabidopsis thaliana
<220> FEATURE:
<223> OTHER INFORMATION: SUC2 (Sucrose-proton Symporter)
      vascular-specific promoter

<400> SEQUENCE: 213
aactaggggt gcataatgat ggaacaaagc acaaatcttt taacgcaaac taactacaac      60
cttcttttgg ggtccccatc cccgacccta atgttttgga attaataaaa ctacaatcac    120
ttaccaaaaa ataaaagttc aaggccacta taatttctca tatgaaccta catttataaa    180
taaaatctgg tttcatatta atttcacaca ccaagttact ttctattatt aactgttata    240
atggaccatg aaatcatttg catatgaact gcaatgatac ataatccact ttgttttgtg    300
```

-continued

```
ggagacattt accagatttc ggtaaattgg tattccccct tttatgtgat tggtcattga    360
tcattgttag tggccagaca tttgaactcc cgttttttg tctataagaa ttcggaaaca     420
tatagtatcc tttgaaaacg gagaaacaaa taacaatgtg gacaaactag atataatttc   480
aacacaagac tatgggaatg attttacccca ctaattataa tccgatcaca aggtttcaac  540
gaactagttt tccagatatc aaccaaattt actttggaat taaactaact taaaactaat  600
tggttgttcg taaatggtgc ttttttttt tgcggatgtt agtaaagggt tttatgtatt    660
ttatattatt agttatctgt tttcagtgtt atgttgtctc atccataaag tttatatgtt  720
ttttctttgc tctataactt atatatatat atgagtttac agttatattt atacatttca  780
gatacttgat cggcattttt tttggtaaaa aatatatgca tgaaaaactc aagtgtttct  840 ttttttaagga attttaaat ggtgattata tgaatataat catatgtata tccgtatata   900
tatgtagcca gatagttaat tatttgggg atatttgaat tattaatgtt ataatattct  960
ttcttttgac tcgtctggtt aaattaaaga acaaaaaaaa cacatacttt tactgtttta  1020
aaaggttaaa ttaacataat ttattgatta caagtgtcaa gtccatgaca ttgcatgtag  1080
gttcgagact tcagagataa cggaagagat cgataattgt gatcgtaaca tccagatatg  1140
tatgtttaat tttcatttag atgtggatca gagaagataa gtcaaactgt cttcataatt  1200
taagacaacc tcttttaata ttttcccaaa acatgtttta tgtaactact ttgcttatgt  1260
gattgcctga ggatactatt attctctgtc tttattctct tcacaccaca tttaaatagt  1320
ttaagagcat agaaattaat tattttcaaa aaggtgatta tatgcatgca aaatagcaca  1380
ccatttatgt ttatattttc aaattattta atacatttca atatttcata agtgtgattt  1440
tttttttttt tgtcaatttc ataagtgtga tttgtcattt gtattaaaca attgtatcgc  1500
gcagtacaaa taacagtgg gagaggtgaa aatgcagtta taaaactgtc caataattta  1560
ctaacacatt taaatatcta aaagagtgt ttcaaaaaaa attcttttga aataagaaaa   1620
gtgatagata tttttacgct ttcgtctgaa aataaaacaa taatagttta ttagaaaaat  1680
gttatcaccg aaaattattc tagtgccact cgctcggatc gaaattcgaa agttatattc  1740
tttctcttta cctaatataa aaatcacaag aaaaatcaat ccgaatatat ctatcaacat  1800
agtatatgcc cttacatatt gtttctgact tttctctatc cgaatttctc gcttcatggt  1860
ttttttttaa catattctca tttaattttc attactatta tataactaaa agatggaaat  1920
aaaataaagt gtctttgaga atcgaacgtc catatcagta agatagtttg tgtgaaggta  1980
aaatctaaaa gatttaagtt ccaaaaacag aaaataatat attacgctaa aaaagaagaa  2040
aataattaaa tacaaaacag aaaaaaataa tatacgacag acacgtgtca cgaagatacc  2100
ctacgctata gacacagctc tgttttctct tttctatgcc tcaaggctct cttaacttca  2160
ctgtctcctc ttcggataat cctatccttc tcttcctata aatacctctc cactcttcct  2220
cttcctccac cactacaacc acca                                         2244
```

<210> SEQ ID NO 214
<211> LENGTH: 1009
<212> TYPE: DNA
<213> ORGANISM: Lycopersicon esculentum
<220> FEATURE:
<223> OTHER INFORMATION: RBCS3 (Ribulose 1,5-bisphosphate carboxylase, small subunit 3) leaf-specific promoter

<400> SEQUENCE: 214

```
aaatggagta atatggataa tcaacgcaac tatatagaga aaaaataata gcgctaccat    60
```

```
atacgaaaaa tagtaaaaaa ttataataat gattcagaat aaattattaa taactaaaaa      120
gcgtaaagaa ataaattaga gaataagtga tacaaaattg gatgttaatg gatacttctt      180
ataattgctt aaaaggaata caagatggga aataatgtgt tattattatt gatgtataaa      240
gaatttgtac aattttttgta tcaataaagt tccaaaaata atctttaaaa aataaaagta     300
cccttttatg aactttttat caaataaatg aaatccaata ttagcaaaac attgatatta     360
ttactaaata tttgttaaat taaaaaatat gtcattttat ttttttaacag atattttta     420 aagtaaatgt tataaattac gaaaaaggga ttaatgagta tcaaaacagc ctaaatggga     480
ggagacaata acagaaattt gctgtagtaa ggtggcttaa gtcatcattt aatttgatat     540
tataaaaatt ctaattagtt tatagtcttt ctttcctct tttgtttgtc ttgtatgcta     600
aaaaaggtat attatatcta taaattatgt agcataatga ccacatctgg catcatcttt     660
acacaattca cctaaatatc tcaagcgaag ttttgccaaa actgaagaaa agattgaac     720 aacctatcaa gtaacaaaaa tcccaaacaa tatagtcatc tatattaaat cttttcaatt    780
gaagaaattg tcaaagacac ataccctat gagtttttc atcaatttt tttcctttt       840 taaactgtat ttttaaaaaa atattgaata aaacatgtcc tattcattag tttgggaact   900
ttaagataag gagtgtgtaa tttcagaggc tattaatttt gaaatgtcaa gagccacata   960
atccaatggt tatggttgct cttagatgag gttattgctt taggtgaaa              1009

<210> SEQ ID NO 215
<211> LENGTH: 2365
<212> TYPE: DNA
<213> ORGANISM: Arabidopsis thaliana
<220> FEATURE:
<223> OTHER INFORMATION: ARSK1 (Root-specific Kinase 1) root-specific
      promoter

<400> SEQUENCE: 215
ggcgagtgat ggtatattta ttggttgggc ttaaatatat ttcagatgca aaaccatatt     60
gaatcaataa attataaata catagcttcc ctaaccactt aaaccaccag ctacaaaacc   120 aataaaccg atcaatcatt atgttttcat aggatttcct gaacatacat taaattattt    180
ttcattttct tggtgctctt ttctgtctta ttcacgtttt aatggacata atcggtttca   240
tattgtaaat ctcttttaacc taacgaacaa tttaatgacc ctagtaatag gataagaagg   300
tcgtgaaaaa tgaacgagaa aaacccacc aaaacactat ataagaaga ccgaaaaagt    360 aaaagggtg agccataaac caaaaacctt accagatgtt gtcaaagaac aaaatcatc    420 atccatgatt aacctacgct tcactactaa gacaaggcga ttgtgtcccg gttgaaaagg   480
ttgtaaaaca gtttgaggat gctacaaaag tggatgttaa gtatgaagcg ctaaggttt    540 tggatttggt ctaggagcac attggttaag caatatcttc ggtggagatt gagtttttag   600
agatagtaga tactaattca tctatggaga catgcaaatt catcaaaatg cttggatgaa   660
ttagaaaaac taggtggaga atacagtaaa aaaattcaaa aagtgcatat tgtttggaca   720
acattaatat gtacaaatag tttacattta aatgtattat tttactaatt aagtacatat   780
aaagttgcta aactaaacta atataatttt tgcataagta aatttatcgt taaaagtttt   840 cttctagcc actaaacaac aatacaaaat cgcccaagtc acccattaat taatttagaa    900
gtgaaaaaca aaatcttaat tatatggacg atcttgtcta ccatatttca agggctacag    960
gcctacagcc gccgaataaa tcttaccagc cttaaaccag aacaacggca aataagttca    1020
tgtggcggct ggtgatgatt cacaatttcc ccgacagttc tatgataatg aaactatata    1080
```

```
attattgtac gtacatacat gcatgcgacg aacaacactt caatttaatt gttagtatta    1140
aattacattt atagtgaagt atgttgggac gattagacgg atacaatgca cttatgttct    1200
ccggaaaatg aatcatttgt gttcagagca tgactccaag agtcaaaaaa gttattaaat    1260
ttatttgaat ttaaaactta aaaatagtgt aattttttaac cacccgctgc cgcaaacgtt    1320
ggcggaagaa tacgcggtgt taaacaattt ttgtgatcgt tgtcaaacat ttgtaaccgc    1380
aatctctact gcacaatctg ttacgtttac aatttacaag ttagtataga agaacgttcg    1440
tacctgaaga ccaaccgacc tttagttatt gaataaatga ttatttagtt aagagtaaca    1500
aaatcaatgg ttcaaatttg tttctcttcc ttacttctta aattttaatc atggaagaaa    1560
caaagtcaac ggacatccaa ttatggccta atcatctcat tctcctttca acaaggcgaa    1620
tcaaatcttc tttatacgta atatttattt gccagcctga aatgtatacc aaatcatttt    1680
taaattaatt gcctaaatta ttagaacaaa aactattagt aaataactaa ttagtcttat    1740
gaaactagaa atcgagatag tggaatatag agagacacca ttaaattcac aaaatcattt    1800
ttaaattacc taattatta caacaaaaac tattagacag aactaagtct ataatgaaac    1860
gagagatcgt atttggaatg tagagcgaga gacaattttc aattcattga atatataagc    1920
aaaattatat agcccgtaga cttggtgag atgaagtcta agtacaaaca actgaatgaa     1980
tttataatca ataatattga ttatattgtg attagaaaaa gaaacaact tgcgttattt     2040 ttcaatatta ttgtgaggat taatgtgaac atggaatcgt gtttctcctg aaaaaaatat    2100
cagcatagag cttagaacaa tataaatata tccaccaaaa ataacttcaa cattttata    2160 caactaatac aaaaaaaaa aagcaaactt tttgtatata taaataaatt tgaaaactca   2220
aaggtcggtc agtacgaata agacacaaca actactataa attagaggac tttgaagaca    2280
agtaggttaa ctagaacatc cttaattcct aaacctacgc actctacaaa agattcatca    2340
aaaggagtaa aagactaact ttctc                                          2365
```

<210> SEQ ID NO 216
<211> LENGTH: 1510
<212> TYPE: DNA
<213> ORGANISM: Arabidopsis thaliana
<220> FEATURE:
<223> OTHER INFORMATION: RD29A (Desiccation-responsive 29a) stress inducible promoter

<400> SEQUENCE: 216

```
ggttgctatg gtagggacta tggggttttc ggattccggt ggaagtgagt ggggaggcag      60
tggcggaggt aagggagttc aagattctgg aactgaagat ttggggtttt gcttttgaat    120
gtttgcgttt ttgtatgatg cctctgtttg tgaactttga tgtatttat ctttgtgtga     180 aaaagagatt gggttaataa aatatttgct ttttggata agaaactctt ttagcggccc      240
attaataaag gttacaaatg caaaatcatg ttagcgtcag atatttaatt attcgaagat    300
gattgtgata gatttaaaat tatcctagtc aaaagaaag agtaggttga gcagaaacag     360
tgacatctgt tgtttgtacc atacaaatta gtttagatta ttggttaaca tgttaaatgg    420
ctatgcatgt gacatttaga ccttatcgga attaatttgt agaattatta attaagatgt    480
tgattagttc aaacaaaaat tttatattaa aaaatgtaaa cgaatatttt gtatgttcag    540
tgaaagtaaa acaaattaaa ttaacaagaa acttatagaa gaaattttt actatttaag     600 agaaagaaaa aaatctatca tttaatctga gtccctaaaaa ctgttatact taacagttaa    660
cgcatgattt gatggaggag ccatagatgc aattcaatca aactgaaatt tctgcaagaa    720
```

| | |
|---|---|
| tctcaaacac ggagatctca aagtttgaaa gaaaatttat ttcttcgact caaaacaaac | 780 |
| ttacgaaatt taggtagaac ttatatacat tatattgtaa ttttttgtaa caaaatgttt | 840 |
| ttattattat tatagaattt tactggttaa attaaaaatg aatagaaaag gtgaattaag | 900 |
| aggagagagg aggtaaacat tttcttctat tttttcatat tttcaggata aattattgta | 960 |
| aaagtttaca agatttccat ttgactagtg taaatgagga atattctcta gtaagatcat | 1020 |
| tatttcatct acttctttta tcttctacca gtagaggaat aaacaatatt tagctccttt | 1080 |
| gtaaatacaa attaattttc cttcttgaca tcattcaatt ttaattttac gtataaaata | 1140 |
| aaagatcata cctattagaa cgattaagga gaaatacaat tcgaatgaga aggatgtgcc | 1200 |
| gtttgttata ataaacagcc acacgacgta aacgtaaaat gaccacatga tgggccaata | 1260 |
| gacatggacc gactactaat aatagtaagt tacattttag gatggaataa atatcatacc | 1320 |
| gacatcagtt ttgaaagaaa agggaaaaaa agaaaaaata aataaaagat atactaccga | 1380 |
| catgagttcc aaaaagcaaa aaaaaagatc aagccgacac agacacgcgt agagagcaaa | 1440 |
| atgactttga cgtcacacca cgaaaacaga cgcttcatac gtgtcccttt atctctctca | 1500 |
| gtctctctat | 1510 |

<210> SEQ ID NO 217
<211> LENGTH: 3446
<212> TYPE: DNA
<213> ORGANISM: Arabidopsis thaliana
<220> FEATURE:
<223> OTHER INFORMATION: AP1 (floral meristem-specific) promoter) floral
      meristem-specific promoter
<400> SEQUENCE: 217

| | |
|---|---|
| cacggacctt ggatctgaag ttatgaacaa taacatattt ggcaaaacaa agaaaaaaga | 60 |
| aacaacaata ctaacatatt ttggtaaaag aacattgaga agtctcaaaa attaacttct | 120 |
| tcttattttg tttcctaata agaccgtttg cttcatttca agttcttagg aaataaattttc | 180 |
| atgtaacgtg tatgtagata tgtttatgta cagataaaga gagatctgaa aatgatatat | 240 |
| agagcttttg tggtgataag tgcaacaagc aggatatata tatcgaacgt ggtggttaga | 300 |
| agatagcgtc aaaatagatg ctagctgctg cgtatacatc atattcatat catatgtact | 360 |
| tctcttttgt gatttctcat gtgattgaac atactacata aatcttgata gatttataaa | 420 |
| aatgcaacaa attgttgttt atataagaaa aataaaacac tgatatgata tttcattagt | 480 |
| tattatcaaa tttgcaatat aatgtttaac atccaagatt tgttttacat aatcgttacg | 540 |
| gttactaaag tttaatttat gatgttttaa aacaaattga gactaaattt ctaaaagaaa | 600 |
| catatacgta catgtgtgta gctgcgtata tatatagaat ggtggggcta aaagctaatg | 660 |
| atgtgtacat taattggaca tttgatgtgg ctggattgga cccaacttgc tctttgatag | 720 |
| agacctaact aagacaattt tgctcttcat tcatttctcc cgtatacata attgaattaa | 780 |
| ctgtacataa tgtttcacaa caagcgatct agctatatat ttcaaaataa cagagactga | 840 |
| tattttaatc tggtcttcta agctctaacg tcaaattaaa aaaaaaatcc gatcttctaa | 900 |
| ttaattagaa gaaatcaatt atagaacctc tctctttaat ttcatttatt taaaactgct | 960 |
| tggaaattta attattcact aaaagactca ctattctcctt aatttatgat aatttgtaga | 1020 |
| tcatatgttc agttttattt tatttgccat tcgaatgttg agttttaatt aaaccaatat | 1080 |
| gttaatattc gaattaaaaa aacttaccta taattcactt atttaaaaac ataaaataat | 1140 |
| aataattgca tcaccgtgat acaaagcaac ctcacaagtc acaactctcg tgactacaaa | 1200 |

-continued

```
gatcactcat taaacaaacc ttcctgcctt cttttttttct acttgggcac ctcgaccgat    1260
cgaagactat tcttgggatc tgcttcaaaa acgactatat gttctaaatc cacttcgtat    1320
gatgacgaac atttggttta ctactgaaga tagagattac gtccttctaa ttagaagtaa    1380
ttaattattt tagtatttgg aagctaatgg tggagatgta accgtatctt agtggatcga    1440
gatattgtat ataaaatatg tatgctacat cgaataataa actgaaagag agtaaaaagg    1500
gatatttaat gggaagaaaa gaagggtgga gatgtaacaa aggcgaagat aatggatatt    1560
cttgggatgt tgtcttcaag gccacgagct tagattcttt tagttttgct caatttgtta    1620
agtttctact tttcctttg ttgcttacta cttttgctca tgatctccat atacatatca    1680
tacatatata tagtatacta tctttagact gatttctcta tacactatct tttaacttat    1740
gtatcgtttc aaaactcagg acgtacatgt ttaaatttgg ttatataacc acgaccattt    1800
caagtatata tgtcatacca taccagattt aatataactt ctatgaagaa aatacataaa    1860
gttggattaa aatgcaagtg acatcttttt agcataggtt catttggcat agaagaaata    1920
tataactaaa aatgaacttt aacttaaata gattttacta tattacaatt ttttctttt    1980 acatggtcta atttattttt ctaaaattag tataattgtt gttttgatga aacaataata    2040
ccgtaagcaa tagttgctaa aagatgtcca aatatttata aattacaaag taaatcaaat    2100
aaggaagaag acacgtggaa aacaccaaat aagagaagaa atggaaaaaa cagaaagaaa    2160 tttttttaaca agaaaaatca attagtcctc aaacctgaga tatttaaagt aatcaactaa    2220
aacaggaaca cttgactaac aaagaaattt gaaacgtggt ccaactttca cttaattata    2280
ttgttttctc taaggcttat gcaatatatg ccttaagcaa atgccgaatc tgtttttttt    2340 tttttttgtta ttggatattg actgaaaata aggggttttt tcacacttga agatctcaaa    2400
agagaaaact attacaacgg aaattcattg taaaagaagt gattaagcaa attgagcaaa    2460 ggttttatg tggtttattt cattatatga ttgacatcaa attgtatata tatggttgtt    2520
ttatttaaca atatatatgg ataaacgta caaactaaat atgtttgatt gacgaaaaaa    2580
aatatatgta tgtttgatta acaacatagc acatattcaa ctgattttg tcctgatcat    2640 ctacaactta ataagaacac acaacattga acaaatcttt gacaaaatac tattttttggg    2700 tttgaaattt tgaatactta caattattct tctcgatctt cctctctttc cttaaatcct    2760
gcgtacaaat ccgtcgacgc aatacattac acagttgtca attggttctc agctctacca    2820
aaaacatcta ttgccaaaag aaaggtctat ttgtacttca ctgttacagc tgagaacatt    2880
aaatataata agcaaatttg ataaaacaaa gggttctcac cttattccaa aagaatagtg    2940
taaaataggg taatagagaa atgttaataa aaggaaatta aaaatagata ttttggttgg    3000
ttcagatttt gtttcgtaga tctacaggga aatctccgcc gtcaatgcaa agcgaaggtg    3060
acacttgggg aaggaccagt ggtccgtaca atgttactta cccatttctc ttcacgagac    3120
gtcgataatc aaattgttta ttttcatatt tttaagtccg cagttttatt aaaaaatcat    3180
ggacccgaca ttagtacgag atataccaat gagaagtcga cacgcaaatc ctaaagaaac    3240
cactgtggtt tttgcaaaca agagaaacca gctttagctt ttccctaaaa ccactcttac    3300
ccaaatctct ccataaataa agatcccgag actcaaacac aagtcttttt ataaggaaa    3360 gaaagaaaaa ctttcctaat tggttcatac caaagtctga gctcttcttt atatctctct    3420
tgtagtttct tattgggggt ctttgt                                         3446
```

<210> SEQ ID NO 218  
<211> LENGTH: 505

```
<212> TYPE: DNA
<213> ORGANISM: artificial sequence
<220> FEATURE:
<223> OTHER INFORMATION: artificial sequence
<220> FEATURE:
<223> OTHER INFORMATION: P894 (35S::G47)

<400> SEQUENCE: 218
cttcttcttc acatcgatca tcatacaaca acaaaaaatg gattacagag aatccaccgg      60
tgaaagtcag tcaaagtaca aaggaatccg tcgtcggaaa tggggcaaat gggtatcaga    120
gattagagtt ccgggaactc gtgaccgtct ctggttaggt tcattctcaa cagcagaagg    180
tgccgccgta gcacacgacg ttgctttctt ctgtttacac caacctgatt ctttagaatc    240
tctcaatttc cctcatttgc ttaatccttc actcgtttcc agaacttctc cgagatctat    300
ccagcaagct gcttctaacg ccggcatggc cattgacgcc ggaatcgtcc acagtaccag    360
cgtgaactct ggatgcggag atacgacgac gtattacgag aatggagctg atcaagtgga    420
gccgttgaat atttcagtgt atgattatct gggcggccac gatcacgttt gatttatctc    480
gacggtcatg atcacgtttg atctt                                          505

<210> SEQ ID NO 219
<211> LENGTH: 485
<212> TYPE: DNA
<213> ORGANISM: artificial sequence
<220> FEATURE:
<223> OTHER INFORMATION: artificial sequence
<220> FEATURE:
<223> OTHER INFORMATION: P1572 (35S::G2133)

<400> SEQUENCE: 219
atctcatctt catccaccca aaaacatgga ttcaagagac accggagaaa ctgaccagag      60
caagtacaaa ggtatccgtc gtcggaaatg gggaaaatgg gtatcagaga ttcgtgtccc    120
gggaactcgt caacgtctct ggttaggctc tttctccacc gcagaaggcg ctgccgtagc    180
ccacgacgtc gcttttttact gcttgcaccg accatcttcc ctcgacgacg aatctttaa    240
cttccctcac ttacttacaa cctccctcgc ctccaatata tctcctaagt ccatccaaaa    300
agctgcttcc gacgccggca tggccgtgga cgccggattc catggtgctg tgtctgggag    360
tggtggttgt gaagagagat cttccatggc gaatatggag gaggaggaca aacttagtat    420
ctccgtgtat gattatcttg aagacgatct cgtttgatct atacgagtac gtttttagca    480
gttaa                                                                485

<210> SEQ ID NO 220
<211> LENGTH: 707
<212> TYPE: DNA
<213> ORGANISM: artificial sequence
<220> FEATURE:
<223> OTHER INFORMATION: artificial sequence
<220> FEATURE:
<223> OTHER INFORMATION: P23456 (35S::G3649)

<400> SEQUENCE: 220
acgagctcga gctcagagtg atctcagatc gtcgtcgcgg tcagcgccga cgacgagcaa      60
gcttcgccgg aggggaaga cggtacgtac atgggccggg tggcggcgag cggcggcggc    120
ggcggcggag gggagatgat gaggtacagg ggcgtgcggg gcggcggtg ggggaagtgg    180
gtgtcggaga tccgggtgcc cgggacgcg gagcgcctgt ggctcggctc ctacgccacc    240
gccgaggccg ccgccgtcgc gcacgacgcc gccgtctgcc tcctccggct cggcggcggc    300
```

```
cgccgcgccg ccgcaggcgg aggcggcggg ctcaacttcc ccgcccgcgc gctcgccgcg      360
gcggcggccg cctcctccta cggcggcgcc ggcggtctcc tgtccccgcg ctccgtgcag      420
cgcgtggcgt ccgacgccgg catggccgcc gacgcgcagc tcgtggacct cgccgcgac      480 cacccgcccg ccgccgccgc cgcctcatcc tccggcagcg cgtggcggg  agacggtgca     540 agaaagcaag ggacacgtgg cgaggttagc gacacgtatt ggtgtaggaa tggagaggat      600
gggagcagaa gccggagctc cgggagtgag gagctcattg tttacgaggg cttaagtgta      660
gatgacatgg aaattttgat gtaaacagtg attattttat taatatg                   707

<210> SEQ ID NO 221
<211> LENGTH: 869
<212> TYPE: DNA
<213> ORGANISM: artificial sequence
<220> FEATURE:
<223> OTHER INFORMATION: artificial sequence
<220> FEATURE:
<223> OTHER INFORMATION: P23455 (35S::G3644)

<400> SEQUENCE: 221
tcgacctcac gtaccggcca gaaatatcac agcacacaca cacgttaac tttttccg        60 cgcgaaatct ctcgaagtga acatcccaa gcaaaaatcc gatcgattcg gcgagctagc      120
aggtcaactc gccatggctg acctcccatg catatatata cgcgtagtac gtacacttgc     180
tttcccaacg ctcgcgaatc aaatcgaggg tgaaattaag tcaagaacgg agagagatca     240
cggtgaggtt gatctcagct cgccggagga ggcaatgagc cgggcggagt gcggcggcgg     300
cgaggaggag gagcggtgca ggtacagggg cgtgcggcgg cggcggtggg ggaagtgggt     360
gtcggagatc cgggtgcccg gcacgcggga gcggctgtgg ctggggtcct acgccacgcc     420
ggaggccgcc gccgtcgcgc acgacacggc cgtctacttc ctccgcggag gcgcgggcga     480
cggcggtggc ggcggcgcga cgctcaactt cccggagcgc gcggcggcca cgtacgcgg     540 cggcgccgcc gtggcgcgcc tgtcgccgcg gtccgtgcag cgcgtggcgt ccgacgccgg     600
catggccgcc gacgcgcagc tcgtggcggc gcggacgcc gcgcccgcgc ccgcgccggc     660
gacggcgtac gcgcgcccgg atcactgcgc cggcgcgacg acggcgcggc acgacgagct     720
ggcgcgccgc gggatgtacg gcgctcacgc gcatgccgcc ggcgcgaacg ccaggacgag     780
cggcgagcgg cagctcgtct gtgccgagga gattagcgtg gatgacatgg agatcctgat     840
gtaatcacgc agtgacaaaa tagcaaagc                                       869

<210> SEQ ID NO 222
<211> LENGTH: 631
<212> TYPE: DNA
<213> ORGANISM: artificial sequence
<220> FEATURE:
<223> OTHER INFORMATION: artificial sequence
<220> FEATURE:
<223> OTHER INFORMATION: P23465 (35S::G3643)

<400> SEQUENCE: 222
tcgacgcgtc cgcttcttct ctcagaatac acaacacaaa gtcaatataa ttatagtata      60
tccctatgag taggagttcg gcgatgcatg gaattacaag cacaaacaac aagttgaagg     120
gagttcggcg tcgaaaatgg ggcaaatggg tgtcggagat tcgtgttccg ggcacgcaag     180
agcgtttgtg gttgggaacc tacgccacgc cggaggctgc cgcggtggct cacgacgttg     240
ccgtctactg tctaagtagg ccttcttcgt tggacaaact taacttcccc gaaaccttgt     300
cttcgtacag tgttcagctc agggacatgt ctccgaggtc tgtgcagaag gtggcttccg     360
```

```
atgttggcat ggatgttgat gcaagaaaca ttgttgcggg caaaacttca acggtggggg    420
cagaaactaa ttgcgagagt gatgagagga ctagtactgc gtctgtgtgt aatgttgttg    480
gagaaggtgg tgctgatcat tcggatgtgt tttggtggga tgatgatggt gggtcttggc    540
atggaagtgg tggagattct acggaaaggg atgccttgag catttccatt gaagattatc    600
tttagctgtt ctaggtttca actttagttg c    631

<210> SEQ ID NO 223
<211> LENGTH: 813
<212> TYPE: DNA
<213> ORGANISM: artificial sequence
<220> FEATURE:
<223> OTHER INFORMATION: artificial sequence
<220> FEATURE:
<223> OTHER INFORMATION: P25402 (35S::G3650)

<400> SEQUENCE: 223
ccacccgtgc tcgatcgatc atgccatgtc aacgcccccg gccgcgctga ccttgatcct     60
tctcgtctca ccgcacctta taaatacgcc cacgtcgctc gtgtcgtcgt gtgctccatc    120
gcaaacggcc aaaaccacc agcacaagtg cacaagccat tgcccatcgg acgcccagcc    180
ggccagcccc tgtcccgacg gtcggccgac gacgatgagc cgcgcagcga ccaacagcgg    240
cgcggagcgg cggtgccggt acaggggcgt gcggcggcgg gcctggggga agtgggtgtc    300
ggagatccgg gtgccgggca cgcgggagcg gctgtggctg gatcctacg cggcgcccga    360 ggccgccgcc gtcgcgcacg acgccgcgc gtgcctcctc cgcggctgcg cgggccgccg    420
cctcaacttc ccgggccgcg ccgcctgcta ctacgcctgc ggcgggcagc agccgctgtc    480
gccgcgctcc gtgcagcgcg tcgcgtccga cgccggcatg gccgccgacg cgcagatcgt    540
cgacgcgcgg gcggccctcg cctcgccgcc gcccgttgtc cagcccgccg ctctcgctgg    600
cattattggc ggcgccgcgc gagaaggcgg cggaggcgtg cgaggccccg cgtgcgcgcc    660
ggcgccgcca agcaacggcg ctggcagcag cagtacgtat tggtccacgc cgagcagtga    720
gccgccgctt gtttacgggg acattagcgt agacgacata gagatcttga tttgactatt    780
aggcactagt tagtagcata gtcatggcag ttc    813

<210> SEQ ID NO 224
<211> LENGTH: 505
<212> TYPE: DNA
<213> ORGANISM: artificial sequence
<220> FEATURE:
<223> OTHER INFORMATION: artificial sequence
<220> FEATURE:
<223> OTHER INFORMATION: P3853 (opLexA::G47)

<400> SEQUENCE: 224
cttcttcttc acatcgatca tcatacaaca acaaaaaatg gattacagag aatccaccgg     60
tgaaagtcag tcaaagtaca aaggaatccg tcgtcggaaa tggggcaaat gggtatcaga    120
gattagagtt ccgggaactc gtgaccgtct ctggttaggt tcattctcaa cagcagaagg    180
tgccgccgta gcacacgacg ttgctttctt ctgtttacac caacctgatt ctttagaatc    240
tctcaatttc cctcatttgc ttaatccttc actcgtttcc agaacttctc cgagatctat    300
ccagcaagct gcttctaacg ccggcatggc cattgacgcc ggaatcgtcc acagtaccag    360
cgtgaactct ggatgcggag atacgacgac gtattacgag aatggagctg atcaagtgga    420
gccgttgaat atttcagtgt atgattatct gggcggccac gatcacgttt gatttatctc    480
```
gacggtcatg atcacgtttg atctt 505

<210> SEQ ID NO 225
<211> LENGTH: 4361
<212> TYPE: DNA
<213> ORGANISM: artificial sequence
<220> FEATURE:
<223> OTHER INFORMATION: artificial sequence
<220> FEATURE:
<223> OTHER INFORMATION: P5318 (prSTM::m35S::oEnh::LexAGal4(GFP))

<400> SEQUENCE: 225

| | | | | | |
|---|---|---|---|---|---|
| agaatgtagc | aatacaaata | tatgacggta | ccgttatcca | tcaccattat | atgtatatat | 60 |
| gtaatttg | ataaatattc | actttgtgtt | tcgtcgtttg | cttaataaac | agctcatttc | 120 |
| catggtattg | agtcttctat | atgcgagaga | atcagattcc | cgctgggata | acaaagaac | 180 |
| aaggtactga | aaaaaataga | caaaactttt | ttttaaatta | tataagctat | aaaagaaaag | 240 |
| agtatagaga | gagattagcc | ctactgttta | agagggagag | agtagggtca | ttagggcttt | 300 |
| agagagagaa | gacattcgga | ctgtccccac | ttgctttcct | gtagaataac | attatttaaa | 360 |
| tcttattttt | aattaaatat | tacaactaaa | agaagaaacc | aacttttaaa | ataaatgcag | 420 |
| attatatgct | ctgacttgga | ctaaataaaa | cttgcaagta | acagtttcaa | gtcctttgt | 480 |
| tttagaactt | tttctttcgt | agaagtgata | aatgattgcc | ctagacctga | tagattctct | 540 |
| aaaattctac | gtattacagc | ataagttacc | tcctttattt | gactattaga | ccatccatat | 600 |
| tggtgggctt | ttagcaaatg | ttcttaacaa | taatttatat | atttattttta | atgttaagag | 660 |
| gtttgataat | ttttttttt | taagagtgta | ttttgtttat | taaaatgtgt | tttgtttctt | 720 |
| atataagaac | caaatcttaa | ctattttacc | aattaaacat | taaatttaaa | ttttaatatc | 780 |
| tctaagaatt | atattaagag | ccaatataga | tgcttttaaa | accattggtt | gaataaataa | 840 |
| atctaacctt | cttaattatt | tctgtgtgaa | tattttctaa | attttcattt | taatttagca | 900 |
| caatataatc | catgttctaa | aaagaacaat | taacataata | tttacaaacc | taaaaagatt | 960 |
| ataaaacaca | atttttattt | ttacagctta | taatgtttta | aagttcaggt | ttatttttta | 1020 |
| aaagttcagg | tttattacat | taggtttgac | ttgtaatcat | catttatcac | aacgatcaaa | 1080 |
| ctattattac | aatcacaata | gtagacaaaa | tttaggatat | atatatatat | atataattat | 1140 |
| gtataaacta | tgaacattta | aagtgagatt | tttcaaaata | atatataaat | tcaaatagaa | 1200 |
| atagactatt | tggttcttaa | atgagagacc | cccgaaaaaa | tcttttttttt | tttctcatca | 1260 |
| agctgtttac | atttttagat | ataaaatcat | attcttata | gtttagaata | tgaattaaat | 1320 |
| agttttatat | gttattaact | tatcataaga | tatgcgtgag | gttggccaaa | aactcatcaa | 1380 |
| ttaaccaaat | aagaaaagta | aaattgtatt | ttgctttgct | aaaaatgtaa | atatttcatt | 1440 |
| gaaaatgaa | aaaggtttag | gtaatacaat | taagtaaatc | ctacaatttt | ggttccatgg | 1500 |
| caaaagaata | aaattgtatt | gctttggtaa | aagttgatcc | aactaatata | ttcagtagaa | 1560 |
| actgcaaaac | tgaagaaata | agtttgttta | gtagaattgc | tttcggttat | gtaatgaata | 1620 |
| tacatccaaa | atggcttttt | agtaatgatg | tctttttcata | ctctttccaa | tccctactac | 1680 |
| tttcagatta | tttgtcctac | tattatagag | atatacgttc | gttttcaata | atatgaaaag | 1740 |
| tgatatatat | ttaaatagtg | tgatatatat | ataagttttg | caagtgcatc | acttcccaaa | 1800 |
| atcgcataaa | tcattaatca | tattgtcgaa | aacagtataa | taacttctta | aacgaaaacg | 1860 |
| cagcgcaatt | aaaaataaca | actagagata | attgacaaaa | cattgattaa | tatttaccta | 1920 |
| taagttaatt | attgtattta | aaatttattt | aaagttcata | aggaaaacat | atgcaaaaat | 1980 |

-continued

```
atttatatct aatattttgc tatgttatcc tttttttttt ttacgttatc ctaattttgt    2040
ttatcctaat ttgttgtggt taaaatctta ttattgataa aaagagaact tttttttttg    2100
tcatcataaa aaagagaact tattacttcg attttaaaat tctatgagcg taggagacaa    2160
agaaaaaaaa aataaaaaaa aaaagaagag aaaaatcact tcttttcttc tttttagtcc    2220
agatccaaca tattttggat aactaaatga agatttttta aaaaaatata ttttagggta    2280
tatataaatc ataatttgaa gcaaatgaaa taaaatccag tttggtaata tataaatatg    2340
atttgatggg ttccttgtaa tctctctcta tctattagtt tctcagttat cttttctttg    2400
ccagaaatgg cagtgaaggc agtggctgag gagagagttt tttttcttct ttcatgggga    2460
aagtaaaact ttgccttgaa gatttctctc ttcaatattt ttctaagact tttgatttca    2520
acgaatcact gtccttaacc taaaagcaag aaaaattagc tttatactgg tctttacttt    2580
tttttaacat atttatttttt atatagttta cttataaaca tagacatacg agtatgggaa    2640
tatatagtat atccaacttc taaataatat ttcgaatagt gataacaaaa ttagcaatac    2700
atacggctag tgaaatgttg atcgaataaa cggcactgat gtaatgtact tatcaatttt    2760 gataattta attgtattgt ttttctttttt ttcccacagt attgaactag acaattaaat    2820
ttaaagtaaa attatacatt tcttttcgttg tgtattaaag taacatgcat aatatcattt    2880
tccttcgtac aatcctccaa attgacaatt gatgaattac tttgtcaatc gtaaatgaat    2940
ttttctcaag tctgtatact attttcaggg ataaacaggt acaggtgtcc catgcttatt    3000
ctcttgatag taacatgtgt cctatgttga gtcaattcta cgttcgaaga agtgctaaca    3060
attgttaata gcctcgtata ttattctaat taaaatgcct cgatagattt ggttagtggt    3120
ctgaatgtga ttggttattt tttcaagtgg caagaggtct accatctaat attacaatca    3180
atcgaccaaa aaggtcgaga acatgataat ggtggcaaat acaaatggtt cattgttgtc    3240
taatataaca agccatcagt tgtcactttt taaaaacaat acagaataca agatactttt    3300
tttttaaggt aaaatgtgtg tttaatattt tcgtttatat aacaaataaa cagttacatg    3360
ttttactcta tgattatatt tatgacattt ttcttcttct taacaacatt ttttttcccat   3420 aagaacattt acaatagtat taaaactttg attgcaatca aatgttagat cacttattat    3480
aaaattacta agactgctat cttttcctat tgacaaaagc gaatccaata tatgttactg    3540
aaacaaatgc gtaaattata ctatatggag atctatcggt taattattga gagaatctaa    3600
gaaagttttt gagtacaaca gtcctaataa tatcttcaca taccatataa tatacatata    3660
tacatataca caaatgtact ttttaaacca acatcagcat acgtatatcc catcaggaaa    3720 cttagactttt tgggaattca tggtatgaaa accaaaacca aatgacaaca ttcgatttga    3780
tactcccgac ccatggtaaa gaaataacaa attccaatat atctttcact ggactttccg    3840
aggcacattc cggttttctc catttcaaga aattgtcaaa aataaattga gatccggttt    3900
attacctcaa aaaagaagaa gagaaattac aacattaatt tccgaaaagg cataaatgag    3960
aaatcatatt tcagcagaag aacacaaaag agttaagaac ccacagatca cacaacctct    4020
gtccatgtct gcttttttaca cttttttaaa ataagtttct cctaaaaagt tatttcctat    4080
ttataataat ttccttagat ttatcttcct ggtctctctt ctgctgcttc cctctcccc    4140 ataactatca ctatttagaa ttttcaatgt ggaaaaggaa gctgattgtt gaagcataaa    4200
tcccgggaga ccacttttgc attttcaaat aattaaatta aaccatagat acacacacac    4260
agttacttac tcttttaggg tttcccaata aatttatagt actttaatgt gtttcatgat    4320
```

| attgatgata aatgctagct gtatttacaa tgggggctcc t | 4361 |
|---|---|

<210> SEQ ID NO 226
<211> LENGTH: 1176
<212> TYPE: DNA
<213> ORGANISM: artificial sequence
<220> FEATURE:
<223> OTHER INFORMATION: artificial sequence
<220> FEATURE:
<223> OTHER INFORMATION: P5288 (prCUT1::m35S::oEnh::LexAGal4(GFP))

<400> SEQUENCE: 226

| tgtgaattat attttactct tcgatatcgg ttgttgacga ttaaccatgc aaaaaagaaa | 60 |
|---|---|
| cattaattgc gaatgtaaat aacaaaacat gtaactcttg tagatataca tgtatcgaca | 120 |
| tttaaacccg aatatatatg tatacctata atttctctga ttttcacgct acctgccacg | 180 |
| tacatgggtg ataggtccaa actcacaagt aaaagtttac gtacagtgaa ttcgtctttt | 240 |
| tgggtataaa cgtacattta atttacacgt aagaaaggat taccaattct ttcatttatg | 300 |
| gtaccagaca gagttaaggc aaacaagaga acatataga gttttgatat gttttcttgg | 360 |
| ataaatatta aattgatgca atatttaggg atggacacaa ggtaatatat gccttttaag | 420 |
| gtatatgtgc tatatgaatc gtttcgcatg ggtactaaaa ttatttgtcc ttactttata | 480 |
| taaacaaatt ccaacaaaat caagtttttg ctaaaactag tttatttgcg ggttatttaa | 540 |
| ttacctatca tattacttgt aatatcattc gtatgttaac gggtaaacca aaccaaaccg | 600 |
| gatattgaac tattaaaaat cttgtaaatt tgacacaaac taatgaatat ctaaattatg | 660 |
| ttactgctat gataacgacc attttgttt tgagaacca taatataaat tacaggtacg | 720 |
| tgacaagtac taagtattta tatccaccctt tagtcacagt accaatattg cgcctaccgg | 780 |
| gcaacgtgaa cgtgatcatc aaatcaaagt agttaccaaa cgctttgatc tcgataaaac | 840 |
| taaaagctga cacgtcttgc tgtttcttaa tttatttctc ttacaacgac aattttgaga | 900 |
| aatatgaaat ttttatatcg aaagggaaca gtccttatca tttgctccca tcacttgctt | 960 |
| ttgtctagtt acaactggaa atcgaagaga agtattacaa aaacattttt ctcgtcattt | 1020 |
| ataaaaaaat gacaaaaaat taaatagaga gcaaagcaag agcgttgggt gacgttggtc | 1080 |
| tcttcattaa ctcctctcat ctaccccttc ctctgttcgc ctttatatcc ttcaccttcc | 1140 |
| ctctctcatc ttcattaact catcttcaaa aatacc | 1176 |

<210> SEQ ID NO 227
<211> LENGTH: 485
<212> TYPE: DNA
<213> ORGANISM: artificial sequence
<220> FEATURE:
<223> OTHER INFORMATION: artificial sequence
<220> FEATURE:
<223> OTHER INFORMATION: P4361 (opLexA::G2133)

<400> SEQUENCE: 227

| atctcatctt catccaccca aaaacatgga ttcaagagac accggagaaa ctgaccagag | 60 |
|---|---|
| caagtacaaa ggtatccgtc gtcggaaatg gggaaaatgg gtatcagaga ttcgtgtccc | 120 |
| gggaactcgt caacgtctct ggttaggctc tttctccacc gcagaaggcg ctgccgtagc | 180 |
| ccacgacgtc gcttttact gcttgcaccg accatcttcc ctcgacgacg aatcttttaa | 240 |
| cttccctcac ttacttacaa cctccctcgc ctccaatata tctcctaagt ccatccaaaa | 300 |
| agctgcttcc gacgccggca tggccgtgga cgccggattc catggtgctg tgtctgggag | 360 |
| tggtggttgt gaagagagat cttccatggc gaatatggag gaggaggaca aacttagtat | 420 |

```
ctccgtgtat gattatcttg aagacgatct cgtttgatct atacgagtac gttttagca    480 gttaa                                                              485
```

<210> SEQ ID NO 228
<211> LENGTH: 1183
<212> TYPE: DNA
<213> ORGANISM: artificial sequence
<220> FEATURE:
<223> OTHER INFORMATION: artificial sequence
<220> FEATURE:
<223> OTHER INFORMATION: P5287 (prLTP1::m35S::oEnh::LexAGal4(GFP))

<400> SEQUENCE: 228

```
gatatgacca aaatgattaa cttgcattac agttgggaag tatcaagtaa acaacatttt     60 gttttttgttt gatatcggga atctcaaaac caaagtccac actagttttt ggactatata   120
atgataaaag tcagatatct actaatacta gttgatcagt atattcgaaa acatgacttt   180
ccaaatgtaa gttatttact ttttttttgc tattataatt aagatcaata aaaatgtcta   240
agttttaaat ctttatcatt atatccaaac aatcataatc ttattgttaa tctctcatca   300
acacacagtt tttaaaataa attaattacc ctttgcatga taccgaagag aaacgaattc   360
gttcaaataa ttttataaca ggaaataaaa tagataaccg aaataaacga tagaatgatt   420
tcttagtact aactcttaac aacagtttta tttaaatgac ttttgtaaaa aaaacaaagt   480
taacttatac acgtacacgt gtcgaaaata ttattgacaa tggatagcat gattcttatt   540
agagtcatgt aaaagataaa cacatgcaaa tatatatatg aataatatgt tgttaagata   600
aactagacga ttagaatata tagcacatct atagtttgta aaataactat ttctcaacta   660
gacttaagtc ttcgaaatac ataaataaac aaaactataa aaattcagaa aaaaacatga   720
gagtacgtta gtaaaatgta ttttttttggt aaaataatca cttttcatca ggtcttttgt   780 aaaagcagttt tcatgttaga taaacgagat tttaatttttt tttaaaaaaa gaagtaaact   840
aactatgttc ctatctacac acctataatt ttgaacaatt acaaaacaac aatgaaatgc   900
aaagaagacg tagggcactg tcacactaca atacgattaa taaatgtatt ttggtcgaat   960
taataacttt ccatacgata aagttgaatt aacatgtcaa acaaaagaga tgagtggtcc   1020
tatacatagt taggaattag gaacctctaa attaaatgag tacaaccacc aactactcct   1080
tccctctata atctatcgca ttcacaccac ataacatata cgtacctact ctatataaca   1140
ctcactcccc aaactctctt catcatccat cactacacac atc                    1183
```

<210> SEQ ID NO 229
<211> LENGTH: 686
<212> TYPE: DNA
<213> ORGANISM: artificial sequence
<220> FEATURE:
<223> OTHER INFORMATION: artificial sequence
<220> FEATURE:
<223> OTHER INFORMATION: P3367 (opLexA::G975)

<400> SEQUENCE: 229

```
attactcatc atcaagttcc tactttctct ctgacaaaca tcacagagta agtaagaatg     60
gtacagacga agaagttcag aggtgtcagg caacgccatt ggggttcttg ggtcgctgag   120
attcgtcatc ctctcttgaa acggaggatt tggctaggga cgttcgagac cgcagaggag   180
gcagcaagag catacgacga ggccgccgtt ttaatgagcg gccgcaacgc caaaaccaac   240
tttcccctca acaacaacaa caccggagaa acttccgagg gcaaaaccga tatttcagct   300
```

```
tcgtccacaa tgtcatcctc aacatcatct tcatcgctct cttccatcct cagcgccaaa    360
ctgaggaaat gctgcaagtc tccttcccca tccctcacct gcctccgtct tgacacagcc    420
agctcccata tcggcgtctg gcagaaacgg gccggttcaa agtctgactc cagctgggtc    480
atgacggtgg agctaggtcc cgcaagctcc tcccaagaga ctactagtaa agcttcacaa    540
gacgctattc ttgctccgac cactgaagtt gaaattggtg gcagcagaga agaagtattg    600
gatgaggaag aaaaggttgc tttgcaaatg atagaggagc ttctcaatac aaaactaaatc   660 ttatttgctt atatatatgt acctat                                         686
```

<210> SEQ ID NO 230
<211> LENGTH: 686
<212> TYPE: DNA
<213> ORGANISM: artificial sequence
<220> FEATURE:
<223> OTHER INFORMATION: artificial sequence
<220> FEATURE:
<223> OTHER INFORMATION: P408 (35S::G975)

<400> SEQUENCE: 230

```
attactcatc atcaagttcc tactttctct ctgacaaaca tcacagagta agtaagaatg     60
gtacagacga agaagttcag aggtgtcagg caacgccatt ggggttcttg ggtcgctgag    120
attcgtcatc ctctcttgaa acggaggatt tggctaggga cgttcgagac cgcagaggag    180
gcagcaagag catacgacga ggccgccgtt taatgagcg gccgcaacgc caaaaccaac     240
tttcccctca acaacaacaa caccggagaa acttccgagg gcaaaaccga tatttcagct    300
tcgtccacaa tgtcatcctc aacatcatct tcatcgctct cttccatcct cagcgccaaa    360
ctgaggaaat gctgcaagtc tccttcccca tccctcacct gcctccgtct tgacacagcc    420
agctcccata tcggcgtctg gcagaaacgg gccggttcaa agtctgactc cagctgggtc    480
atgacggtgg agctaggtcc cgcaagctcc tcccaagaga ctactagtaa agcttcacaa    540
gacgctattc ttgctccgac cactgaagtt gaaattggtg gcagcagaga agaagtattg    600
gatgaggaag aaaaggttgc tttgcaaatg atagaggagc ttctcaatac aaaactaaatc   660 ttatttgctt atatatatgt acctat                                         686
```

<210> SEQ ID NO 231
<211> LENGTH: 666
<212> TYPE: DNA
<213> ORGANISM: artificial sequence
<220> FEATURE:
<223> OTHER INFORMATION: artificial sequence
<220> FEATURE:
<223> OTHER INFORMATION: P954 (35S::G1387)

<400> SEQUENCE: 231

```
ctctcctatt cttagttcgt gtcagaaaca cacagagaaa ttaagaaccc taatttaaaa     60
cagaagaatg gtacattcga agaagttccg aggtgtccgc cagcgtcagt ggggttcttg    120
ggtttctgag attcgtcatc ctctcttgaa gagaagagtg tggctaggaa cattcgacac    180
ggcggaaaca gcggctagag cctacgacca agccgcggtt ctaatgaacg gccagagcgc    240
gaagactaac ttccccgtca tcaaatcgaa cggttcaaat tccttggaga ttaactctgc    300
gttaaggtct cccaaatcat tatcggaact attgaacgct aagctaagga agaactgtaa    360
agaccagaca ccgtatctga cgtgtctccg cctcgacaac gacagctcac acatcggcgt    420
ctggcagaaa cgcgccgggt caaaaacgag tccaaactgg gtcaagcttg ttgaactagg    480
tgacaaagtt aacgcacgtc ccggtggtga tattgagact aataagatga aggtacgaaa    540
```

```
cgaagacgtt caggaagatg atcaaatggc gatgcagatg atcgaggagt tgcttaactg      600
gacctgtcct ggatctggat ccattgcaca ggtctaaagg agaatcattg aattatatga      660
tcaaga                                                                 666
```

<210> SEQ ID NO 232
<211> LENGTH: 653
<212> TYPE: DNA
<213> ORGANISM: artificial sequence
<220> FEATURE:
<223> OTHER INFORMATION: artificial sequence
<220> FEATURE:
<223> OTHER INFORMATION: P2002 (35S::G2583)

<400> SEQUENCE: 232

```
caaatcagaa aatatagagt ttgaaggaaa ctaaagatg gtacattcga ggaagttccg        60
aggtgtccgc cagcgacaat ggggttcttg ggtctctgag attcgccatc ctctattgaa      120
gagaagagtg tggcttggaa ctttcgaaac ggcagaagcg gctgcaagag catacgacca      180
agcggctctt ctaatgaacg gccaaaacgc taagaccaat ttccctgtcg taaaatcaga      240
ggaaggctcc gatcacgtta agatgttaa ctctccgttg atgtcaccaa agtcattatc      300
tgagcttttg aacgctaagc taaggaagag ctgcaaagac ctaacgcctt ctttgacgtg      360
tctccgtctt gatactgaca gttcccacat tggagtttgg cagaaacggg ccgggtcgaa      420
aacaagtccg acttgggtca tgcgcctcga acttgggaac gtagtcaacg aaagtgcggt      480
tgacttaggg ttgactacga tgaacaaaca aaacgttgag aaagaagaag aagaagaaga      540
agctattatt agtgatgagg atcagttagc tatggagatg atcgaggagt tgctgaattg      600
gagttgactt ttgactttaa cttgttgcaa gtccacaagg ggtaagggtt ttc             653
```

<210> SEQ ID NO 233
<211> LENGTH: 4276
<212> TYPE: DNA
<213> ORGANISM: artificial sequence
<220> FEATURE:
<223> OTHER INFORMATION: artificial sequence
<220> FEATURE:
<223> OTHER INFORMATION: P6506 (35S::LexA-GAL4TA)

<400> SEQUENCE: 233

```
catgcctgca ggtccccaga ttagcctttt caatttcaga agaatgcta acccacagat        60 ggttagagag gcttacgcag caggtctcat caagacgatc tacccgagca ataatctcca      120
ggaaatcaaa taccttccca agaaggttaa agatgcagtc aaaagattca ggactaactg      180
catcaagaac acagagaaag atatatttct caagatcaga agtactattc agtatggac       240 gattcaaggc ttgcttcaca aaccaaggca agtaatagag attggagtct ctaaaaaggt      300
agttcccact gaatcaaagg ccatggagtc aaagattcaa atagaggacc taacagaact      360
cgccgtaaag actggcgaac agttcataca gagtctctta cgactcaatg acaagaagaa      420
aatcttcgtc aacatggtgg agcacgcac acttgtctac tccaaaaata tcaaagatac      480
agtctcagaa gaccaaaggg caattgagac ttttcaacaa agggtaatat ccggaaacct      540
cctcggattc cattgcccag ctatctgtca ctttattgtg aagatagtgg aaaaggaagg      600
tggctcctac aaatgccatc attgcgataa aggaaaggcc atcgttgaag atgcctctgc      660
cgacagtggt cccaaagatg gacccccacc cacgaggagc atcgtggaaa agaagacgt      720 tccaaccacg tcttcaaagc aagtggattg atgtgatatc tccactgacg taagggatga      780
```

```
cgcacaatcc cactatcctt cggcggccgc aagacccttc ctctatataa ggaagttcat    840
ttcatttgga gaggacacgc tcgagtataa gagctcattt ttacaacaat taccaacaac    900
aacaaacaac aaacaacatt acaattacat ttacaattac catggaagcg ttaacggcca    960
ggcaacaaga ggtgtttgat ctcatccgtg atcacatcag ccagacaggt atgccgccga   1020
cgcgtgcgga aatcgcgcag cgtttgggt tccgttcccc aaacgcggct gaagaacatc    1080
tgaaggcgct ggcacgcaaa ggcgttattg aaattgtttc cggcgcatca cgcgggattc   1140
gtctgttgca ggaagaggaa gaagggttgc cgctggtagg tcgtgtggct gccggtgaac   1200
cacttctggc gcaacagcat attgaaggtc attatcaggt cgatccttcc ttattcaagc   1260
cgaatgctga tttcctgctg cgcgtcagcg ggatgtcgat gaaagatatc ggcattatgg   1320
atggtgactt gctggcagtg cataaaactc aggatgtacg taacggtcag gtcgttgtcg   1380
cacgtattga tgacgaagtt accgttaagc gcctgaaaaa acagggcaat aaagtcgaac   1440
tgttgccaga aaatagcgag tttaaaccaa ttgtcgtaga tcttcgtcag cagagcttca   1500
ccattgaagg gctggcggtt ggggttattc gcaacggcga ctggctggaa ttccccaatt   1560
ttaatcaaag tgggaatatt gctgatagct cattgtcctt cactttcact aacagtagca   1620
acggtccgaa cctcataaca actcaaacaa attctcaagc gctttcacaa ccaattgcct   1680
cctctaacgt tcatgataac ttcatgaata atgaaatcac ggctagtaaa attgatgatg   1740
gtaataattc aaaaccactg tcacctggtt ggacggacca aactgcgtat aacgcgtttg   1800
gaatcactac agggatgttt aataccacta caatggatga tgtatataac tatctattcg   1860
atgatgaaga tacccacca aacccaaaaa aagagtagct agagctttcg ttcgtatcat    1920
cggtttcgac aacgttcgtc aagttcaatg catcagtttc attgcgcaca caccagaatc   1980
ctactgagtt tgagtattat ggcattggga aaactgtttt tcttgtacca tttgttgtgc   2040
ttgtaattta ctgtgttttt tattcggttt tcgctatcga actgtgaaat ggaaatggat   2100
ggagaagagt taatgaatga tatggtcctt ttgttcattc tcaaattaat attatttgtt   2160
ttttctctta tttgttgtgt gttgaatttg aaattataag agatatgcaa acattttgtt   2220
ttgagtaaaa atgtgtcaaa tcgtggcctc taatgaccga agttaatatg aggagtaaaa   2280
cacttgtagt tgtaccatta tgcttattca ctaggcaaca aatatatttt cagacctaga   2340
aaagctgcaa atgttactga atacaagtat gtcctcttgt gttttagaca tttatgaact   2400
ttcctttatg taattttcca gaatccttgt cagattctaa tcattgcttt ataattatag   2460
ttatactcat ggatttgtag ttgagtatga aaatattttt taatgcattt tatgacttgc   2520
caattgattg acaacatgca tcaatctaga acatatccat atctaatctt acctcgactg   2580
ctgtatataa accagtggt tatatgtcca gtactgctgt atataaaacc agtggttata    2640
tgtacagtac gtcgatcgat cgacgactgc tgtatataaa accagtggtt atatgtacag   2700
tactgctgta tataaaacca gtggttatat gtacagtacg tcgagggat gatcaagacc    2760 cttcctctat ataaggaagt tcatttcatt tggagaggac acgctcgagt ataagagctc   2820
atttttacaa caattaccaa caacaacaaa caacaaacaa cattcaaatt acatttacaa   2880
ttaccatggt gagcaagggc gaggagctgt tcaccggggt ggtgcccatc ctggtcgagc   2940
tggacgcgca cgtaaacggc cacaagttca gcgtgtccgg cgagggcgag ggcgatgcca   3000
cctacggcaa gctgaccctg aagttcatct gcaccaccgg caagctgccc gtgccctggc   3060
ccaccctcgt gaccaccctg acctacggcg tgcagtgctt cagccgctac cccgaccaca   3120
tgaagcagca cgacttcttc aagtccgcca tgcccgaagg ctacgtccag gagcgcacca   3180
```

| | |
|---|---|
| tcttcttcaa ggacgacggc aactacaaga cccgcgccga ggtgaagttc gagggcgaca | 3240 |
| ccctggtgaa ccgcatcgag ctgaagggca tcgacttcaa ggaggacggc aacatcctgg | 3300 |
| ggcacaagct ggagtacaac tacaacagcc acaacgtcta tatcatggcc gacaagcaga | 3360 |
| agaacggcat caaggtgaac ttcaagatcc gccacaacat cgaggacggc agcgtgcagc | 3420 |
| tcgccgacca ctaccagcag aacaccccca tcggcgacgg ccccgtgctg ctgcccgaca | 3480 |
| accactacct gagcacccag tccgccctga gcaaagaccc caacgagaag cgcgatcaca | 3540 |
| tggtcctgct ggagttcgtg accgccgccg ggatcactct cggcatggac gagctgtaca | 3600 |
| agtccggagg gatcctctag ctagagcttt cgttcgtatc atcggtttcg acaacgttcg | 3660 |
| tcaagttcaa tgcatcagtt tcattgcgca cacaccagaa tcctactgag tttgagtatt | 3720 |
| atggcattgg gaaaactgtt tttcttgtac catttgttgt gcttgtaatt tactgtgttt | 3780 |
| tttattcggt tttcgctatc gaactgtgaa atggaaatgg atggagaaga gttaatgaat | 3840 |
| gatatggtcc ttttgttcat tctcaaatta atattatttg ttttttctct tatttgttgt | 3900 |
| gtgttgaatt tgaaattata agagatatgc aaacattttg ttttgagtaa aaatgtgtca | 3960 |
| aatcgtggcc tctaatgacc gaagttaata tgaggagtaa aacacttgta gttgtaccat | 4020 |
| tatgcttatt cactaggcaa caaatatatt ttcagaccta gaaaagctgc aaatgttact | 4080 |
| gaatacaagt atgtcctctt gtgttttaga catttatgaa ctttcccttta tgtaattttc | 4140 |
| cagaatcctt gtcagattct aatcattgct ttataattat agttatactc atggatttgt | 4200 |
| agttgagtat gaaaatattt tttaatgcat tttatgactt gccaattgat tgacaacatg | 4260 |
| catcaatcga cctgca | 4276 |

<210> SEQ ID NO 234
<211> LENGTH: 2244
<212> TYPE: DNA
<213> ORGANISM: artificial sequence
<220> FEATURE:
<223> OTHER INFORMATION: artificial sequence
<220> FEATURE:
<223> OTHER INFORMATION: P5290 (SUC2::LexA-GAL4TA)

<400> SEQUENCE: 234

| | |
|---|---|
| aactagggt gcataatgat ggaacaaagc acaaatcttt taacgcaaac taactacaac | 60 |
| cttcttttgg ggtccccatc cccgacccta atgttttgga attaataaaa ctacaatcac | 120 |
| ttaccaaaaa ataaaagttc aaggccacta taatttctca tatgaaccta catttataaa | 180 |
| taaaatctgg tttcatatta atttcacaca ccaagttact ttctattatt aactgttata | 240 |
| atggaccatg aaatcatttg catatgaact gcaatgatac ataatccact ttgttttgtg | 300 |
| ggagacattt accagatttc ggtaaattgg tattccccct tttatgtgat tggtcattga | 360 |
| tcattgttag tggccagaca tttgaactcc cgtttttttg tctataagaa ttcggaaaca | 420 |
| tatagtatcc tttgaaaacg gagaaacaaa taacaatgtg gacaaactag atataatttc | 480 |
| aacacaagac tatgggaatg attttaccca ctaattataa tccgatcaca aggtttcaac | 540 |
| gaactagttt tccagatatc aaccaaattt actttggaat taaactaact taaaactaat | 600 |
| tggttgttcg taaatggtgc tttttttttt tgcggatgtt agtaaagggt tttatgtatt | 660 |
| ttatattatt agttatctgt tttcagtgtt atgttgtctc atccataaag tttatatgtt | 720 |
| ttttctttgc tctataactt atatatatat atgagtttac agttatattt atacatttca | 780 |
| gatacttgat cggcattttt tttggtaaaa aatatatgca tgaaaaactc aagtgtttct | 840 |

```
ttttttaagga  atttttaaat  ggtgattata  tgaatataat  catatgtata  tccgtatata    900
tatgtagcca  gatagttaat  tatttggggg  atatttgaat  tattaatgtt  ataatattct    960
ttcttttgac  tcgtctggtt  aaattaaaga  acaaaaaaaa  cacatacttt  tactgtttta   1020
aaaggttaaa  ttaacataat  ttattgatta  caagtgtcaa  gtccatgaca  ttgcatgtag   1080
gttcgagact  tcagagataa  cggaagagat  cgataattgt  gatcgtaaca  tccagatatg   1140
tatgtttaat  tttcatttag  atgtggatca  gagaagataa  gtcaaactgt  cttcataatt   1200
taagacaacc  tcttttaata  tttttcccaaa  acatgtttta  tgtaactact  ttgcttatgt   1260
gattgcctga  ggatactatt  attctctgtc  tttattctct  tcacaccaca  tttaaatagt   1320
ttaagagcat  agaaattaat  tattttcaaa  aggtgatta  tatgcatgca  aaatagcaca   1380
ccatttatgt  ttatattttc  aaattattta  atacatttca  atatttcata  agtgtgattt   1440
tttttttttt  tgtcaatttc  ataagtgtga  tttgtcattt  gtattaaaca  attgtatcgc   1500
gcagtacaaa  taacagtgg   gagaggtgaa  aatgcagtta  taaaactgtc  caataattta   1560
ctaacacatt  taaatatcta  aaagagtgt   ttcaaaaaaa  attcttttga  aataagaaaa   1620
gtgatagata  tttttacgct  ttcgtctgaa  aataaaacaa  taatagttta  ttagaaaaat   1680
gttatcaccg  aaaattattc  tagtgccact  cgctcggatc  gaaattcgaa  agttatattc   1740
tttctctttta  cctaatataa  aaatcacaag  aaaaatcaat  ccgaatatat  ctatcaacat   1800
agtatatgcc  cttacatatt  gtttctgact  tttctctatc  cgaatttctc  gcttcatggt   1860
tttttttaa   catattctca  tttaattttc  attactatta  tataactaaa  agatggaaat   1920
aaaataaagt  gtctttgaga  atcgaacgtc  catatcagta  agatagtttg  tgtgaaggta   1980
aaatctaaaa  gatttaagtt  ccaaaaacag  aaaataatat  attacgctaa  aaagaagaa    2040
aataattaaa  tacaaaacag  aaaaaaataa  tatacgacag  acacgtgtca  cgaagatacc   2100
ctacgctata  gacacagctc  tgttttctct  tttctatgcc  tcaaggctct  cttaacttca   2160
ctgtctcctc  ttcggataat  cctatccttc  tcttcctata  aatacctctc  cactcttcct   2220
cttcctccac  cactacaacc  acca                                              2244
```

<210> SEQ ID NO 235  
<211> LENGTH: 1010  
<212> TYPE: DNA  
<213> ORGANISM: artificial sequence  
<220> FEATURE:  
<223> OTHER INFORMATION: artificial sequence  
<220> FEATURE:  
<223> OTHER INFORMATION: P5284 (RBCS3::LexA-GAL4TA)

<400> SEQUENCE: 235

```
aaatggagta  atatggataa  tcaacgcaac  tatatagaga  aaaaataata  gcgctaccat     60
atacgaaaaa  tagtaaaaaa  ttataataat  gattcagaat  aaattattaa  taactaaaaa   120
gcgtaaagaa  ataaattaga  gaataagtga  tacaaaattg  gatgttaatg  gatacttctt   180
ataattgctt  aaaaggaata  caagatggga  aataatgtgt  tattattatt  gatgtataaa   240
gaatttgtac  aattttttgta  tcaataaagt  tccaaaaata  atctttaaaa  aataaaagta   300
cccttttatg  aactttttat  caaataaatg  aaatccaata  ttagcaaaac  attgatatta   360
ttactaaata  tttgttaaat  taaaaaatat  gtcattttat  tttttaacag  atatttttta   420
aagtaaatgt  tataaattac  gaaaagggga  ttaatgagta  tcaaaacagc  taaatgggaa   480
ggagacaata  acagaaattt  gctgtagtaa  ggtggcttaa  gtcatcattt  aatttgatat   540
tataaaaatt  ctaattagtt  tatagtcttt  cttttcctct  tttgtttgtc  ttgtatgcta   600
```

| | |
|---|---|
| aaaaaggtat attatatcta taaattatgt agcataatga ccacatctgg catcatcttt | 660 |
| acacaattca cctaaatatc tcaagcgaag ttttgccaaa actgaagaaa agatttgaac | 720 |
| aacctatcaa gtaacaaaaa tcccaaacaa tatagtcatc tatattaaat cttttcaatt | 780 |
| gaagaaattg tcaaagacac atacctctat gagttttttc atcaattttt ttttcttttt | 840 |
| taaactgtat ttttaaaaaa atattgaata aaacatgtcc tattcattag tttgggaact | 900 |
| ttaagataag gagtgtgtaa tttcagaggc tattaatttt gaaatgtcaa gagccacata | 960 |
| atccaatggt tatggttgct cttagatgag gttattgctt taggtgaaag | 1010 |

<210> SEQ ID NO 236
<211> LENGTH: 2365
<212> TYPE: DNA
<213> ORGANISM: artificial sequence
<220> FEATURE:
<223> OTHER INFORMATION: artificial sequence
<220> FEATURE:
<223> OTHER INFORMATION: P5311 (ARSK1::LexA-GAL4TA)

<400> SEQUENCE: 236

| | |
|---|---|
| ggcgagtgat ggtatattta ttggttgggc ttaaatatat ttcagatgca aaaccatatt | 60 |
| gaatcaataa attataaata catagcttcc ctaaccactt aaaccaccag ctacaaaacc | 120 |
| aataaacccg atcaatcatt atgttttcat aggatttcct gaacatacat taaattattt | 180 |
| ttcattttct tggtgctctt ttctgtctta ttcacgtttt aatggacata atcggtttca | 240 |
| tattgtaaat ctctttaacc taacgaacaa tttaatgacc ctagtaatag gataagaagg | 300 |
| tcgtgaaaaa tgaacgagaa aaacccacc aaaaacactat ataagaaaga ccgaaaaagt | 360 |
| aaaaagggtg agccataaac caaaaacctt accagatgtt gtcaaagaac aaaaatcatc | 420 |
| atccatgatt aacctacgct tcactactaa gacaaggcga ttgtgtcccg gttgaaaagg | 480 |
| ttgtaaaaca gtttgaggat gctacaaaag tggatgttaa gtatgaagcg gctaaggttt | 540 |
| tggatttggt ctaggagcac attggttaag caatatcttc ggtggagatt gagtttttag | 600 |
| agatagtaga tactaattca tctatggaga catgcaaatt catcaaaatg cttggatgaa | 660 |
| ttagaaaaac taggtggaga atacagtaaa aaaattcaaa aagtgcatat tgtttggaca | 720 |
| acattaatat gtacaaatag tttacattta aatgtattat tttactaatt aagtacatat | 780 |
| aaagttgcta aactaaacta atataatttt tgcataagta aatttatcgt taaaagtttt | 840 |
| ctttctagcc actaaacaac aatacaaaat cgcccaagtc acccattaat taatttagaa | 900 |
| gtgaaaaaca aaatcttaat tatatggacg atcttgtcta ccatatttca agggctacag | 960 |
| gcctacagcc gccgaataaa tcttaccagc cttaaaccag aacaacggca ataagttca | 1020 |
| tgtggcggct ggtgatgatt cacaatttcc ccgacagttc tatgataatg aaactatata | 1080 |
| attattgtac gtacatacat gcatgcgacg aacaacactt caatttaatt gttagtatta | 1140 |
| aattacattt atagtgaagt atgttgggac gattagacgg atacaatgca cttatgttct | 1200 |
| ccggaaaatg aatcatttgt gttcagagca tgactccaag agtcaaaaaa gttattaaat | 1260 |
| ttatttgaat ttaaaactta aaaatagtgt aatttttaac cacccgctgc cgcaaacgtt | 1320 |
| ggcggaagaa tacgcggtgt taaacaattt ttgtgatcgt tgtcaaacat ttgtaaccgc | 1380 |
| aatctctact gcacaatctg ttacgtttac aatttacaag ttagtataga agaacgttcg | 1440 |
| tacctgaaga ccaaccgacc tttagttatt gaataaatga ttatttagtt aagagtaaca | 1500 |
| aaatcaatgg ttcaaatttg tttctcttcc ttacttctta aattttaatc atggaagaaa | 1560 |

-continued

```
caaagtcaac ggacatccaa ttatggccta atcatctcat tctcctttca acaaggcgaa    1620
tcaaatcttc tttatacgta atatttattt gccagcctga aatgtatacc aaatcatttt    1680
taaattaatt gcctaaatta ttagaacaaa aactattagt aaataactaa ttagtcttat    1740
gaaactagaa atcgagatag tggaatatag agagacacca ttaaattcac aaaatcattt    1800
ttaaattacc taaattatta caacaaaaac tattagacag aactaagtct ataatgaaac    1860
gagagatcgt atttggaatg tagagcgaga gacaattttc aattcattga atatataagc    1920
aaaattatat agcccgtaga ctttggtgag atgaagtcta agtacaaaca actgaatgaa    1980
tttataatca ataatattga ttatattgtg attagaaaaa gaaaacaact tgcgttattt    2040
ttcaatatta ttgtgaggat taatgtgaac atggaatcgt gtttctcctg aaaaaaatat    2100
cagcatagag cttagaacaa tataaatata tccaccaaaa ataacttcaa cattttata     2160 caactaatac aaaaaaaaaa aagcaaactt tttgtatata taaataaatt tgaaaactca    2220
aaggtcggtc agtacgaata agacacaaca actactataa attagaggac tttgaagaca    2280
agtaggttaa ctagaacatc cttaattttct aaacctacgc actctacaaa agattcatca   2340
aaaggagtaa aagactaact ttctc                                          2365
```

<210> SEQ ID NO 237
<211> LENGTH: 1510
<212> TYPE: DNA
<213> ORGANISM: artificial sequence
<220> FEATURE:
<223> OTHER INFORMATION: artificial sequence
<220> FEATURE:
<223> OTHER INFORMATION: P9002 (RD29A::LexA-GAL4TA)

<400> SEQUENCE: 237

```
ggttgctatg gtagggacta tggggttttc ggattccggt ggaagtgagt ggggaggcag      60
tggcggaggt aagggagttc aagattctgg aactgaagat ttggggtttt gcttttgaat    120
gtttgcgttt ttgtatgatg cctctgtttg tgaactttga tgtatttat ctttgtgtga     180 aaaagagatt gggttaataa aatatttgct tttttggata agaaactctt ttagcggccc    240
attaataaag gttacaaatg caaaatcatg ttagcgtcag atatttaatt attcgaagat    300
gattgtgata gatttaaaat tatcctagtc aaaagaaag agtaggttga gcagaaacag     360
tgacatctgt tgtttgtacc atacaaatta gtttagatta ttggttaaca tgttaaatgg    420
ctatgcatgt gacatttaga ccttatcgga attaatttgt agaattatta attaagatgt    480
tgattagttc aaacaaaaat tttatattaa aaatgtaaa cgaatatttt gtatgttcag     540
tgaaagtaaa acaaattaaa ttaacaagaa acttatagaa gaaattttt actatttaag    600 agaagaaaa aaatctatca tttaatctga gtcctaaaaa ctgttatact taacagttaa     660
cgcatgattt gatggaggag ccatagatgc aattcaatca aactgaaatt tctgcaagaa    720
tctcaaacac ggagatctca aagtttgaaa gaaaatttat ttcttcgact caaacaaac    780 ttacgaaatt taggtagaac ttatatacat tatattgtaa ttttttgtaa caaatgttt     840 ttattattat tatagaattt tactggttaa attaaaaatg aatagaaaag gtgaattaag    900
aggagagagg aggtaaacat tttcttctat tttttcatat tttcaggata aattattgta    960
aaagtttaca agatttccat ttgactagtg taaatgagga atattctcta gtaagatcat   1020
tatttcatct acttctttta tcttctacca gtagaggaat aaacaatatt tagctccttt   1080
gtaaatacaa attaattttc cttccttgaca tcattcaatt ttaatttttac gtataaaata   1140 aaagatcata cctattagaa cgattaagga gaaatacaat tcgaatgaga aggatgtgcc    1200
```

```
gtttgttata ataaacagcc acacgacgta aacgtaaaat gaccacatga tgggccaata    1260
gacatggacc gactactaat aatagtaagt tacattttag gatggaataa atatcatacc    1320
gacatcagtt ttgaaagaaa agggaaaaaa agaaaaaata aataaaagat atactaccga    1380
catgagttcc aaaaagcaaa aaaaaagatc aagccgacac agacacgcgt agagagcaaa    1440
atgactttga cgtcacacca cgaaaacaga cgcttcatac gtgtcccttt atctctctca    1500
gtctctctat                                                          1510
```

<210> SEQ ID NO 238
<211> LENGTH: 3446
<212> TYPE: DNA
<213> ORGANISM: artificial sequence
<220> FEATURE:
<223> OTHER INFORMATION: artificial sequence
<220> FEATURE:
<223> OTHER INFORMATION: P5326 (AP1::LexA-GAL4TA)

<400> SEQUENCE: 238

```
cacggacctt ggatctgaag ttatgaacaa taacatatatt ggcaaaacaa agaaaaaaga     60
aacaacaata ctaacatatt ttggtaaaag aacattgaga agtctcaaaa attaacttct    120
tcttattttg tttcctaata agaccgtttg cttcatttca agttcttagg aaataaatttc   180 atgtaacgtg tatgtagata tgtttatgta cagataaaga gagatctgaa aatgatatat    240
agagcttttg tggtgataag tgcaacaagc aggatatata tatcgaacgt ggtggttaga    300
agatagcgtc aaaatagatg ctagctgctg cgtatacatc atattcatat catatgtact    360
tctcttttgt gatttctcat gtgattgaac atactacata aatcttgata gatttataaa    420
aatgcaacaa attgttgttt ataagaaaa ataaaaacac tgatatgata tttcattagt     480
tattatcaaa tttgcaatat aatgtttaac atccaagatt tgttttacat aatcgttacg    540
gttactaaag tttaatttat gatgttttaa aacaaattga gactaaattt ctaaaagaaa    600
catatacgta catgtgtgta gctgcgtata tatatagaat ggtggggcta aaagctaatg    660
atgtgtacat taattggaca tttgatgtgg ctggattgga cccaacttgc tctttgatag    720
agacctaact aagacaattt tgctcttcat tcatttctcc cgtatacata attgaattaa    780
ctgtacataa tgtttcacaa caagcgatct agctatatat ttcaaaataa cagagactga    840
tattttaatc tggtcttcta agctctaacg tcaaattaaa aaaaaaatcc gatcttctaa    900
ttaattagaa gaaatcaatt atagaacctc tctctttaat ttcatttatt taaaactgct    960
tggaaattta attattcact aaagactcac tattctcctt aatttatgat aatttgtaga   1020
tcatatgttc agttttttatt tatttgccat tcgaatgttg agttttaatt aaaccaatat   1080
gttaatattc gaattaaaaa aacttaccta taattcactt atttaaaaac ataaataat    1140 aataattgca tcaccgtgat acaaagcaac ctcacaagtc acaactctcg tgactacaaa   1200
gatcactcat taaacaaacc ttcctgcctt cttttttctct acttgggcac ctcgaccgat   1260
cgaagactat tcttgggatc tgcttcaaaa acgactatat gttctaaatc cacttcgtat   1320
gatgacgaac atttggttta ctactgaaga tagagattac gtccttctaa ttagaagtaa   1380
ttaattattt tagtatttgg aagctaatgg tgggagatgta accgtatctt agtggatcga   1440
gatattgtat ataaaatatg tatgctacat cgaataataa actgaaagag agtaaaaagg   1500 gatattaat gggaagaaaa gaagggtgga gatgtaacaa aggcgaagat aatggatatt   1560
cttgggatgt tgtcttcaag gccacgagct tagattcttt tagttttgct caatttgtta   1620
```

-continued

```
agtttctact tttccttttg ttgcttacta cttttgctca tgatctccat atacatatca      1680
tacatatata tagtatacta tctttagact gatttctcta tacactatct tttaacttat      1740
gtatcgtttc aaaactcagg acgtacatgt ttaaatttgg ttatataacc acgaccattt      1800
caagtatata tgtcatacca taccagattt aatataactt ctatgaagaa aatacataaa      1860
gttggattaa aatgcaagtg acatcttttt agcataggtt catttggcat agaagaaata      1920
tataactaaa aatgaacttt aacttaaata gattttacta tattacaatt ttttcttttt      1980
acatggtcta atttattttt ctaaaattag tataattgtt gttttgatga aacaataata      2040
ccgtaagcaa tagttgctaa aagatgtcca aatatttata aattacaaag taaatcaaat      2100
aaggaagaag acacgtggaa acaccaaat aagagaagaa atggaaaaaa cagaaagaaa       2160
tttttaaca agaaaaatca attagtcctc aaacctgaga tatttaaagt aatcaactaa       2220
aacaggaaca cttgactaac aaagaaattt gaaacgtggt ccaactttca cttaattata     2280
ttgttttctc taaggcttat gcaatatatg ccttaagcaa atgccgaatc tgtttttttt     2340
tttttgtta ttggatattg actgaaaata aggggttttt tcacacttga agatctcaaa      2400
agagaaaact attacaacgg aaattcattg taaaagaagt gattaagcaa attgagcaaa     2460
ggttttatg tggtttattt cattatatga ttgacatcaa attgtatata tatggttgtt      2520
ttatttaaca atatatatgg atataacgta caaactaaat atgtttgatt gacgaaaaaa     2580
aatatatgta tgtttgatta acaacatagc acatattcaa ctgattttg tcctgatcat      2640
ctacaactta ataagaacac acaacattga acaaatcttt gacaaaatac tattttggg     2700
tttgaaattt tgaatactta caattattct tctcgatctt cctctctttc cttaaatcct     2760
gcgtacaaat ccgtcgacgc aatacattac acagttgtca attggttctc agctctacca    2820
aaaacatcta ttgccaaaag aaaggtctat ttgtacttca ctgttacagc tgagaacatt    2880
aaatataata agcaaatttg ataaaacaaa gggttctcac cttattccaa aagaatagtg    2940
taaaataggg taatagagaa atgttaataa aaggaaatta aaaatagata ttttggttgg    3000
ttcagatttt gtttcgtaga tctacaggga atctccgcc gtcaatgcaa agcgaaggtg      3060
acacttgggg aaggaccagt ggtccgtaca atgttactta cccatttctc ttcacgagac    3120
gtcgataatc aaattgttta ttttcatatt tttaagtccg cagttttatt aaaaaatcat    3180
ggacccgaca ttagtacgag atataccaat gagaagtcga cacgcaaatc ctaaagaaac    3240
cactgtggtt tttgcaaaca agagaaacca gctttagctt ttccctaaaa ccactcttac    3300
ccaaatctct ccataaataa agatcccgag actcaaacac aagtcttttt ataaggaaa    3360
gaaagaaaaa ctttcctaat tggttcatac caaagtctga gctcttcttt atatctctct    3420
tgtagttcct tattggggt ctttgt                                          3446
```

<210> SEQ ID NO 239
<211> LENGTH: 825
<212> TYPE: DNA
<213> ORGANISM: artificial sequence
<220> FEATURE:
<223> OTHER INFORMATION: artificial sequence
<220> FEATURE:
<223> OTHER INFORMATION: P25186 (35S::GAL4-G47 fusion)

<400> SEQUENCE: 239

```
atgcccaatt ttaatcaaag tgggaatatt gctgatagct cattgtcctt cactttcact       60
aacagtagca acgtccgaa cctcataaca actcaaacaa attctcaagc gctttcacaa      120
ccaattgcct cctctaacgt tcatgataac ttcatgaata atgaaatcac ggctagtaaa     180
```

```
attgatgatg gtaataattc aaaaccactg tcacctggtt ggacggacca aactgcgtat   240
aacgcgtttg gaatcactac agggatgttt aataccacta caatggatga tgtatataac   300
tatctattcg atgatgaaga tacccccacca aacccaaaaa aagagggtac cgtcgacatg   360
gattacagag aatccaccgg tgaaagtcag tcaaagtaca aaggaatccg tcgtcggaaa   420
tggggcaaat gggtatcaga gattagagtt ccgggaactc gtgaccgtct ctggttaggt   480
tcattctcaa cagcagaagg tgccgccgta gcacacgacg ttgctttctt ctgtttacac   540
caacctgatt ctttagaatc tctcaatttc cctcatttgc ttaatccttc actcgtttcc   600
agaacttctc cgagatctat ccagcaagct gcttctaacg ccggcatggc cattgacgcc   660
ggaatcgtcc acagtaccag cgtgaactct ggatgcggag atacgacgac gtattacgag   720
aatggagctg atcaagtgga gccgttgaat atttcagtgt atgattatct gggcggccac   780
gatcacgttt gatttatctc gacggtcatg atcacgtttg atctt                  825
```

<210> SEQ ID NO 240
<211> LENGTH: 263
<212> TYPE: PRT
<213> ORGANISM: artificial sequence
<220> FEATURE:
<223> OTHER INFORMATION: artificial sequence
<220> FEATURE:
<223> OTHER INFORMATION: 35S::GAL4-G47 predicted protein

<400> SEQUENCE: 240

```
Met Pro Asn Phe Asn Gln Ser Gly Asn Ile Ala Asp Ser Ser Leu Ser
 1               5                  10                  15

Phe Thr Phe Thr Asn Ser Ser Asn Gly Pro Asn Leu Ile Thr Thr Gln
                20                  25                  30

Thr Asn Ser Gln Ala Leu Ser Gln Pro Ile Ala Ser Ser Asn Val His
            35                  40                  45

Asp Asn Phe Met Asn Asn Glu Ile Thr Ala Ser Lys Ile Asp Asp Gly
        50                  55                  60

Asn Asn Ser Lys Pro Leu Ser Pro Gly Trp Thr Asp Gln Thr Ala Tyr
65                  70                  75                  80

Asn Ala Phe Gly Ile Thr Thr Gly Met Phe Asn Thr Thr Thr Met Asp
                85                  90                  95

Asp Val Tyr Asn Tyr Leu Phe Asp Asp Glu Asp Thr Pro Pro Asn Pro
               100                 105                 110

Lys Lys Glu Gly Thr Val Asp Met Asp Tyr Arg Glu Ser Thr Gly Glu
           115                 120                 125

Ser Gln Ser Lys Tyr Lys Gly Ile Arg Arg Arg Lys Trp Gly Lys Trp
       130                 135                 140

Val Ser Glu Ile Arg Val Pro Gly Thr Arg Asp Arg Leu Trp Leu Gly
145                 150                 155                 160

Ser Phe Ser Thr Ala Glu Gly Ala Ala Val Ala His Asp Val Ala Phe
               165                 170                 175

Phe Cys Leu His Gln Pro Asp Ser Leu Glu Ser Leu Asn Phe Pro His
           180                 185                 190

Leu Leu Asn Pro Ser Leu Val Ser Arg Thr Ser Pro Arg Ser Ile Gln
       195                 200                 205

Gln Ala Ala Ser Asn Ala Gly Met Ala Ile Asp Ala Gly Ile Val His
   210                 215                 220

Ser Thr Ser Val Asn Ser Gly Cys Gly Asp Thr Thr Thr Tyr Tyr Glu
225                 230                 235                 240
```

-continued

Asn Gly Ala Asp Gln Val Glu Pro Leu Asn Ile Ser Val Tyr Asp Tyr
            245                 250                 255

Leu Gly Gly His Asp His Val
        260

<210> SEQ ID NO 241
<211> LENGTH: 1176
<212> TYPE: DNA
<213> ORGANISM: artificial sequence
<220> FEATURE:
<223> OTHER INFORMATION: artificial sequence
<220> FEATURE:
<223> OTHER INFORMATION: P25279 (35S::G47-GFP fusion)

<400> SEQUENCE: 241

```
atggattaca gagaatccac cggtgaaagt cagtcaaagt acaaggaat ccgtcgtcgg      60
aaatggggca atgggtatc agagattaga gttccgggaa ctcgtgaccg tctctggtta    120
ggttcattct caacagcaga aggtgccgcc gtagcacacg acgttgcttt cttctgttta    180
caccaacctg attctttaga atctctcaat ttccctcatt tgcttaatcc ttcactcgtt    240
tccagaactt ctccgagatc tatccagcaa gctgcttcta acgccggcat ggccattgac    300
gccggaatcg tccacagtac cagcgtgaac tctggatgcg agatacgac gacgtattac     360
gagaatggag ctgatcaagt ggagccgttg aatatttcag tgtatgatta tctgggcggc    420
cacgatcacg tttgcggccg catggtgagc aagggcgagg agctgttcac cggggtggtg    480
cccatcctgg tcgagctgga cggcgacgta acggccaca agttcagcgt gtccggcgag    540
ggcgagggcg atgccaccta cggcaagctg accctgaagt tcatctgcac caccggcaag    600
ctgcccgtgc cctggcccac cctcgtgacc accctgacct acggcgtgca gtgcttcagc    660
cgctaccccg accacatgaa gcagcacgac ttcttcaagt ccgccatgcc cgaaggctac    720
gtccaggagc gcaccatctt cttcaaggac gacggcaact acaagacccg cgccgaggtg    780
aagttcgagg gcgacaccct ggtgaaccgc atcgagctga agggcatcga cttcaaggag    840
gacggcaaca tcctggggca caagctggag tacaactaca acagccacaa cgtctatatc    900
atggccgaca agcagaagaa cggcatcaag gtgaacttca agatccgcca caacatcgag    960
gacggcagcg tgcagctcgc cgaccactac cagcagaaca cccccatcgg cgacggcccc   1020
gtgctgctgc ccgacaacca ctacctgagc acccagtccg ccctgagcaa agaccccaac   1080
gagaagcgcg atcacatggt cctgctggag ttcgtgaccg ccgccgggat cactctcggc   1140
atggacgagc tgtacaagtc cggagggatc ctctag                             1176
```

<210> SEQ ID NO 242
<211> LENGTH: 391
<212> TYPE: PRT
<213> ORGANISM: artificial sequence
<220> FEATURE:
<223> OTHER INFORMATION: artificial sequence
<220> FEATURE:
<223> OTHER INFORMATION: 35S::G47-GFP fusion predicted protein

<400> SEQUENCE: 242

Met Asp Tyr Arg Glu Ser Thr Gly Glu Ser Gln Ser Lys Tyr Lys Gly
1               5                   10                  15

Ile Arg Arg Arg Lys Trp Gly Lys Trp Val Ser Glu Ile Arg Val Pro
            20                  25                  30

Gly Thr Arg Asp Arg Leu Trp Leu Gly Ser Phe Ser Thr Ala Glu Gly
        35                  40                  45

```
Ala Ala Val Ala His Asp Val Ala Phe Phe Cys Leu His Gln Pro Asp
         50                  55                  60

Ser Leu Glu Ser Leu Asn Phe Pro His Leu Leu Asn Pro Ser Leu Val
65                  70                  75                  80

Ser Arg Thr Ser Pro Arg Ser Ile Gln Gln Ala Ala Ser Asn Ala Gly
                85                  90                  95

Met Ala Ile Asp Ala Gly Ile Val His Ser Thr Ser Val Asn Ser Gly
            100                 105                 110

Cys Gly Asp Thr Thr Tyr Tyr Glu Asn Gly Ala Asp Gln Val Glu
            115                 120                 125

Pro Leu Asn Ile Ser Val Tyr Asp Tyr Leu Gly Gly His Asp His Val
            130                 135                 140

Cys Gly Arg Met Val Ser Lys Gly Glu Glu Leu Phe Thr Gly Val Val
145                 150                 155                 160

Pro Ile Leu Val Glu Leu Asp Gly Asp Val Asn Gly His Lys Phe Ser
                165                 170                 175

Val Ser Gly Glu Gly Glu Gly Asp Ala Thr Tyr Gly Lys Leu Thr Leu
            180                 185                 190

Lys Phe Ile Cys Thr Thr Gly Lys Leu Pro Val Pro Trp Pro Thr Leu
            195                 200                 205

Val Thr Thr Leu Thr Tyr Gly Val Gln Cys Phe Ser Arg Tyr Pro Asp
            210                 215                 220

His Met Lys Gln His Asp Phe Phe Lys Ser Ala Met Pro Glu Gly Tyr
225                 230                 235                 240

Val Gln Glu Arg Thr Ile Phe Phe Lys Asp Asp Gly Asn Tyr Lys Thr
                245                 250                 255

Arg Ala Glu Val Lys Phe Glu Gly Asp Thr Leu Val Asn Arg Ile Glu
                260                 265                 270

Leu Lys Gly Ile Asp Phe Lys Glu Asp Gly Asn Ile Leu Gly His Lys
            275                 280                 285

Leu Glu Tyr Asn Tyr Asn Ser His Asn Val Tyr Ile Met Ala Asp Lys
290                 295                 300

Gln Lys Asn Gly Ile Lys Val Asn Phe Lys Ile Arg His Asn Ile Glu
305                 310                 315                 320

Asp Gly Ser Val Gln Leu Ala Asp His Tyr Gln Gln Asn Thr Pro Ile
                325                 330                 335

Gly Asp Gly Pro Val Leu Leu Pro Asp Asn His Tyr Leu Ser Thr Gln
            340                 345                 350

Ser Ala Leu Ser Lys Asp Pro Asn Glu Lys Arg Asp His Met Val Leu
            355                 360                 365

Leu Glu Phe Val Thr Ala Ala Gly Ile Thr Leu Gly Met Asp Glu Leu
            370                 375                 380

Tyr Lys Ser Gly Gly Ile Leu
385                 390
```

<210> SEQ ID NO 243
<211> LENGTH: 922
<212> TYPE: DNA
<213> ORGANISM: Arabidopsis thaliana
<220> FEATURE:
<223> OTHER INFORMATION: G361

<400> SEQUENCE: 243
tctgtctctc tctctctctt tgtaaatata catatataga taagctcaca tatatggcga     60

```
ctgaaacatc ttctttgaag ctcttcggta taaacctact tgaaacgacg tcggttcaaa        120
accagtcatc ggaaccaaga cccggatccg gatcaggatc cgagtcacgt aagtacgagt        180
gtcaatactg ttgtagagag tttgctaact ctcaagctct tggtggtcac caaaacgctc        240
acaagaaaga gcgtcagctt cttaaacgtg cacagatgtt agctactcgt ggtttgccac        300
gtcatcataa ttttcaccct cataccaatc cgcttctctc cgccttcgcg ccgctgcctc        360
acctcctctc tcagccgcat cctccgccgc atatgatgct ctctccttct tcttcgagtt        420
ctaagtggct ttacggtgaa cacatgtcgt cacaaaacgc cgttgggtac tttcatggtg        480 gaagggggact ttacggaggt ggcatggagt ctatggccgg agaagtaaag actcatggtg        540
gttctttgcc ggagatgagg aggttcgccg agatagtga tcggagtagc ggaattaagt        600
tagagaatgg tattgggctg gacctccatt taagccttgg gccatgaatg attataattt        660
tggcccagta aagatctgta aaatactact aggatttcat ttttatagag tatgtttttt        720
tccttaattt cggttgaaat tggtgaatat ttttatctct tacttaccaa atctcatatt        780
tctatgtatg cgtttgcttt cacttttttt ttttatataa ttcttcttgt aaaaaatgca        840
atgtgagttt tcttccctat cattctgtca agctttggtt caattattta gtaatcgaat        900
aatataggaa tagtgttgaa ag                                                  922
```

<210> SEQ ID NO 244
<211> LENGTH: 197
<212> TYPE: PRT
<213> ORGANISM: Arabidopsis thaliana
<220> FEATURE:
<223> OTHER INFORMATION: G361 polypeptide
<400> SEQUENCE: 244

```
Met Ala Thr Glu Thr Ser Ser Leu Lys Leu Phe Gly Ile Asn Leu Leu
1               5                   10                  15

Glu Thr Thr Ser Val Gln Asn Gln Ser Ser Glu Pro Arg Pro Gly Ser
            20                  25                  30

Gly Ser Gly Ser Glu Ser Arg Lys Tyr Glu Cys Gln Tyr Cys Cys Arg
        35                  40                  45

Glu Phe Ala Asn Ser Gln Ala Leu Gly Gly His Gln Asn Ala His Lys
    50                  55                  60

Lys Glu Arg Gln Leu Leu Lys Arg Ala Gln Met Leu Ala Thr Arg Gly
65                  70                  75                  80

Leu Pro Arg His His Asn Phe His Pro His Thr Asn Pro Leu Leu Ser
                85                  90                  95

Ala Phe Ala Pro Leu Pro His Leu Leu Ser Gln Pro His Pro Pro Pro
            100                 105                 110

His Met Met Leu Ser Pro Ser Ser Ser Ser Lys Trp Leu Tyr Gly
        115                 120                 125

Glu His Met Ser Ser Gln Asn Ala Val Gly Tyr Phe His Gly Gly Arg
    130                 135                 140

Gly Leu Tyr Gly Gly Gly Met Glu Ser Met Ala Gly Glu Val Lys Thr
145                 150                 155                 160

His Gly Gly Ser Leu Pro Glu Met Arg Arg Phe Ala Gly Asp Ser Asp
                165                 170                 175

Arg Ser Ser Gly Ile Lys Leu Glu Asn Gly Ile Gly Leu Asp Leu His
            180                 185                 190

Leu Ser Leu Gly Pro
        195
```

-continued

<210> SEQ ID NO 245
<211> LENGTH: 735
<212> TYPE: DNA
<213> ORGANISM: Arabidopsis thaliana
<220> FEATURE:
<223> OTHER INFORMATION: G2826

<400> SEQUENCE: 245

```
atggaggagc tggattttag ttcaaaaaca acaacttctc gtctaaagct atttggattt      60
agtgttgatg agaagaaga tttctccgat caatcagtca aaactaacct atcttctgta     120
tcaccggaac gtggcgagtt ccggcagga tcttccggaa gagtggcgg tggtgtacga      180
agccgaggcg aggaggagg aggaggagaa cgtaagtatg agtgtcagta ttgttgtaga      240
gagtttggta actcacaagc cttaggtggt caccaaaacg ctcacaagaa agagcgtcaa     300
cagcttaaac gtgctcagct tcaagctaca cgaaacgcag ccgcaaattt ctcaaacgct     360
ggatcagcgt ctcagttttt aaggaatcct atagtctctg cttttgctcc tccgcctcat     420
cttttatcat catccgccgt gcctcagcct atgggaggtc cttggatgta tcttccacgt     480
gtttctccat ctcaacttca cgtgtctcat ggctgcgtca tccaagatgg ttcgggtggt     540
gcgggtgctg gtgggttctc gtacgagtat ggggctcgtg attcagggtt tggagtagtt     600
ggggctcaga tgagacatgt tcaggcccat gggccgagac catcggttaa tgggttttca     660
agagaagtag gaactacttt tgatgatggt ttagggttgg atttgcatct cagtcttgca     720
cctgctggtc attga                                                      735
```

<210> SEQ ID NO 246
<211> LENGTH: 244
<212> TYPE: PRT
<213> ORGANISM: Arabidopsis thaliana
<220> FEATURE:
<223> OTHER INFORMATION: G2826 polypeptide

<400> SEQUENCE: 246

```
Met Glu Glu Leu Asp Phe Ser Ser Lys Thr Thr Thr Ser Arg Leu Lys
 1               5                  10                  15

Leu Phe Gly Phe Ser Val Asp Gly Glu Glu Asp Phe Ser Asp Gln Ser
             20                  25                  30

Val Lys Thr Asn Leu Ser Ser Val Ser Pro Glu Arg Gly Glu Phe Pro
         35                  40                  45

Ala Gly Ser Ser Gly Arg Ser Gly Gly Val Arg Ser Arg Gly Gly
     50                  55                  60

Gly Gly Gly Gly Glu Arg Lys Tyr Glu Cys Gln Tyr Cys Cys Arg
65                  70                  75                  80

Glu Phe Gly Asn Ser Gln Ala Leu Gly Gly His Gln Asn Ala His Lys
                 85                  90                  95

Lys Glu Arg Gln Gln Leu Lys Arg Ala Gln Leu Gln Ala Thr Arg Asn
            100                 105                 110

Ala Ala Ala Asn Phe Ser Asn Ala Gly Ser Ala Ser Gln Phe Leu Arg
        115                 120                 125

Asn Pro Ile Val Ser Ala Phe Ala Pro Pro His Leu Leu Ser Ser
    130                 135                 140

Ser Ala Val Pro Gln Pro Met Gly Gly Pro Trp Met Tyr Leu Pro Arg
145                 150                 155                 160

Val Ser Pro Ser Gln Leu His Val Ser His Gly Cys Val Ile Gln Asp
                165                 170                 175
```

-continued

```
Gly Ser Gly Gly Ala Gly Ala Gly Phe Ser Tyr Glu Tyr Gly Ala
            180                 185                 190

Arg Asp Ser Gly Phe Gly Val Val Gly Ala Gln Met Arg His Val Gln
        195                 200                 205

Ala His Gly Pro Arg Pro Ser Val Asn Gly Phe Ser Arg Glu Val Gly
    210                 215                 220

Thr Thr Phe Asp Asp Gly Leu Gly Leu Asp Leu His Leu Ser Leu Ala
225                 230                 235                 240

Pro Ala Gly His
```

<210> SEQ ID NO 247
<211> LENGTH: 998
<212> TYPE: DNA
<213> ORGANISM: Arabidopsis thaliana
<220> FEATURE:
<223> OTHER INFORMATION: G2838

<400> SEQUENCE: 247

```
cgggaattaa atgcaagaaa catagaggag accgtacttc gaagttgcaa atttaacact      60
aagttgaaga atctagaaat agaaagccaa aatcttcctt tacttcaact ctacaatttc     120
aatcttttct ctgtacttag ccatccagag tcataaccac cactatatta aaatgaagac     180
ttatgatttc atgaacgtca actctttctc tcctaaggaa agaccccattc gcctctttgg    240
cttcgagttt ggagcttctc atgaagaatc tgagtccaaa gacaattaca cgagaacaa     300
tgaaagcatc aaagacgata caaagaaaa aagattcaag tgccactatt gtttccggaa     360
cttccctact tcacaagccc taggcggcca tcaaaacgct cacaagagag aacgtcaaca     420
aactaaacgc ttcaacctcc attcaaacgc agccgctttc ttccaccgcc aacaaaacca     480
cattgctgct tctaggctct acgaggatcg ctatagcctt gaagctgttc aaatcaacga     540
cgcgagatta gggttatgtc gtatgtataa ctcatctgcg agttttaatc gtgaccgttc     600
atcttattat aatagatata ttccttggtt catcggtgat caccagacta gaccaacgta     660
tgtcggtggt ggtagcagca gccatggtct gttttacgag tccaagaaga atgtaccgga     720
ccacgtgagt ttggatctac gcctctagtt ccattctttt agtatctctc tctagctagt     780
tcttaaaaaa aaaaaaagag agactagttt tttttccttc tttcaaatac ttttttatttt     840
attttagtct acttgattaa ttatgaattt atgatagtgt atccccgtag atatcatgtt     900
atattaacag ttaaacaatt ttatggagat gaactttaac ttcagatagt ttctttctga     960
gatttaaagt cttaaatatt atcgacgcat tccaatct                              998
```

<210> SEQ ID NO 248
<211> LENGTH: 191
<212> TYPE: PRT
<213> ORGANISM: Arabidopsis thaliana
<220> FEATURE:
<223> OTHER INFORMATION: G2838 polypeptide

<400> SEQUENCE: 248

```
Met Lys Thr Tyr Asp Phe Met Asn Val Asn Ser Phe Ser Pro Lys Glu
1               5                   10                  15

Arg Pro Ile Arg Leu Phe Gly Phe Glu Phe Gly Ala Ser His Glu Glu
            20                  25                  30

Ser Glu Ser Lys Asp Asn Tyr Asn Glu Asn Asn Glu Ser Ile Lys Asp
        35                  40                  45

Asp Asn Lys Glu Lys Arg Phe Lys Cys His Tyr Cys Phe Arg Asn Phe
    50                  55                  60
```

```
Pro Thr Ser Gln Ala Leu Gly Gly His Gln Asn Ala His Lys Arg Glu
 65                  70                  75                  80

Arg Gln Gln Thr Lys Arg Phe Asn Leu His Ser Asn Ala Ala Ala Phe
             85                  90                  95

Phe His Arg Gln Gln Asn His Ile Ala Ala Ser Arg Leu Tyr Glu Asp
         100                 105                 110

Arg Tyr Ser Leu Glu Ala Val Gln Ile Asn Asp Ala Arg Leu Gly Leu
     115                 120                 125

Cys Arg Met Tyr Asn Ser Ser Ala Ser Phe Asn Arg Asp Arg Ser Ser
 130                 135                 140

Tyr Tyr Asn Arg Tyr Ile Pro Trp Phe Ile Gly Asp His Gln Thr Arg
145                 150                 155                 160

Pro Thr Tyr Val Gly Gly Gly Ser Ser Ser His Gly Leu Phe Tyr Glu
                165                 170                 175

Ser Lys Lys Asn Val Pro Asp His Val Ser Leu Asp Leu Arg Leu
            180                 185                 190
```

<210> SEQ ID NO 249
<211> LENGTH: 762
<212> TYPE: DNA
<213> ORGANISM: Arabidopsis thaliana
<220> FEATURE:
<223> OTHER INFORMATION: G1995

<400> SEQUENCE: 249

```
atggacgagg ctaccggaga acagaaaact caagatttca tgaacgtcga atccttctct      60
cagcttcctt tcattcgccg tcctaaagat aagaaccccta aacccattcg tgtcttcgga    120
aaagatttca ccggcagaga tttctctatt actaccggtc aagaagacta caccgatcct    180
taccagacca aaacaaaga agaagaagag gaagaagacc aaaccggaga caacagtacg     240
gacaataata gcatcagcca acaggagga ttcgagtgtc actattgctt tagaaatttt    300
cctacttcac aagccctagg tggacaccaa aacgctcaca acgcgaacg tcagcttgcc    360 aaacgcggtg tttcctctta cttttatcat cctgacaata accctacag ttaccgtcat    420 tacccgtcgt ggaccaatgg tccgttaacc gcggctaggt cctatggagg attttcttct    480
ggtcctaagc cgtcgggta ttattcacga cccagctatg ggagtcagtt aggactatgg    540
cgtctaccgc ctcgcgttca aggcgtttat aactcaaacg cagcgtttac tagtaatggc    600
tcttcttctt cttctaattc gactttaccg ttgttgaccc gttctcaaac tcaactatca    660
tcgcaagtgg gtggctccgc tgctcagaac agaatgtcat cgtacggtta cggattgagc    720
cctaacgtgc aagatcatgt gagtctcgat cttcatcttt aa                       762
```

<210> SEQ ID NO 250
<211> LENGTH: 253
<212> TYPE: PRT
<213> ORGANISM: Arabidopsis thaliana
<220> FEATURE:
<223> OTHER INFORMATION: G1995 polypeptide

<400> SEQUENCE: 250

```
Met Asp Glu Ala Thr Gly Glu Thr Glu Thr Gln Asp Phe Met Asn Val
  1               5                  10                  15

Glu Ser Phe Ser Gln Leu Pro Phe Ile Arg Arg Pro Lys Asp Lys Asn
             20                  25                  30

Pro Lys Pro Ile Arg Val Phe Gly Lys Asp Phe Thr Gly Arg Asp Phe
         35                  40                  45
```

```
Ser Ile Thr Thr Gly Gln Glu Asp Tyr Thr Asp Pro Tyr Gln Thr Lys
 50                  55                  60

Asn Lys Glu Glu Glu Glu Glu Asp Gln Thr Gly Asp Asn Ser Thr
 65                  70                  75                  80

Asp Asn Asn Ser Ile Ser His Asn Arg Arg Phe Glu Cys His Tyr Cys
                 85                  90                  95

Phe Arg Asn Phe Pro Thr Ser Gln Ala Leu Gly Gly His Gln Asn Ala
             100                 105                 110

His Lys Arg Glu Arg Gln Leu Ala Lys Arg Gly Val Ser Ser Tyr Phe
         115                 120                 125

Tyr His Pro Asp Asn Asn Pro Tyr Ser Tyr Arg His Tyr Pro Ser Trp
     130                 135                 140

Thr Asn Gly Pro Leu Thr Ala Ala Arg Ser Tyr Gly Gly Phe Ser Ser
145                 150                 155                 160

Gly Pro Lys Pro Ser Gly Tyr Tyr Ser Arg Pro Ser Tyr Gly Ser Gln
                165                 170                 175

Leu Gly Leu Trp Arg Leu Pro Arg Val Gln Gly Val Tyr Asn Ser
            180                 185                 190

Asn Ala Ala Phe Thr Ser Asn Gly Ser Ser Ser Ser Asn Ser Thr
        195                 200                 205

Leu Pro Leu Leu Thr Arg Ser Gln Thr Gln Leu Ser Ser Gln Val Gly
    210                 215                 220

Gly Ser Ala Ala Gln Asn Arg Met Ser Ser Tyr Gly Tyr Gly Leu Ser
225                 230                 235                 240

Pro Asn Val Gln Asp His Val Ser Leu Asp Leu His Leu
                245                 250

<210> SEQ ID NO 251
<211> LENGTH: 774
<212> TYPE: DNA
<213> ORGANISM: Arabidopsis thaliana
<220> FEATURE:
<223> OTHER INFORMATION: G370

<400> SEQUENCE: 251
atggacgaaa ccaacggacg aagagaaact cacgatttca tgaacgtcaa cgttgaatcc      60
ttctctcagc ttcctttcat ccgccgtact cctcccaaag aaaaagccgc cattattcgt     120
ctcttcggcc aagagctcgt cggtgataac tccgacaact tatccgcaga accttctgat     180
catcaaacca ctaccaagaa cgatgagagc tctgagaata tcaaggacaa agacaaagaa     240
aaagataagg acaaagacaa agataacaac aacaacagga gattcgagtg tcactactgc     300
ttcagaaact cccaacttc tcaagcccta ggtggacatc aaaacgctca aaacgtgaa      360
cgtcaacacg ccaaacgcgg ttccatgaca tcataccttc atcatcatca gcctcatgac     420
cctcaccaca tctacggctt cctcaacaac caccaccacc gtcactatcc gtcttggacg     480
acggaagcta gatcatacta cggcggaggg ggacatcaaa cgccgtcgta ctactcaagg     540
aatactcttg ctcctccttc ttctaaccca ccgacaatca acggaagtcc tttaggtttg     600
tggcgtgtac cgccttccac gtcaacaaat actattcaag gcgtttactc atcttcacca     660
gcttcagcgt ttaggtcgca tgagcaagag actaataagg agcctaataa ctggccgtac     720
agattgatga acccaatgt gcaagatcat gtgagtctcg atcttcatct ctga            774

<210> SEQ ID NO 252
<211> LENGTH: 257
```

```
<212> TYPE: PRT
<213> ORGANISM: Arabidopsis thaliana
<220> FEATURE:
<223> OTHER INFORMATION: G370 polypeptide

<400> SEQUENCE: 252
```

Met Asp Glu Thr Asn Gly Arg Arg Glu Thr His Asp Phe Met Asn Val
1               5                   10                  15

Asn Val Glu Ser Phe Ser Gln Leu Pro Phe Ile Arg Arg Thr Pro Pro
            20                  25                  30

Lys Glu Lys Ala Ala Ile Ile Arg Leu Phe Gly Gln Glu Leu Val Gly
        35                  40                  45

Asp Asn Ser Asp Asn Leu Ser Ala Glu Pro Ser Asp His Gln Thr Thr
    50                  55                  60

Thr Lys Asn Asp Glu Ser Ser Glu Asn Ile Lys Asp Lys Asp Lys Glu
65                  70                  75                  80

Lys Asp Lys Asp Lys Asp Asn Asn Asn Arg Arg Phe Glu
                85                  90                  95

Cys His Tyr Cys Phe Arg Asn Phe Pro Thr Ser Gln Ala Leu Gly Gly
                100                 105                 110

His Gln Asn Ala His Lys Arg Glu Arg Gln His Ala Lys Arg Gly Ser
            115                 120                 125

Met Thr Ser Tyr Leu His His Gln Pro His Asp Pro His His Ile
    130                 135                 140

Tyr Gly Phe Leu Asn Asn His His Arg His Tyr Pro Ser Trp Thr
145                 150                 155                 160

Thr Glu Ala Arg Ser Tyr Tyr Gly Gly Gly Gly His Gln Thr Pro Ser
            165                 170                 175

Tyr Tyr Ser Arg Asn Thr Leu Ala Pro Pro Ser Ser Asn Pro Pro Thr
        180                 185                 190

Ile Asn Gly Ser Pro Leu Gly Leu Trp Arg Val Pro Pro Ser Thr Ser
    195                 200                 205

Thr Asn Thr Ile Gln Gly Val Tyr Ser Ser Ser Pro Ala Ser Ala Phe
210                 215                 220

Arg Ser His Glu Gln Glu Thr Asn Lys Glu Pro Asn Asn Trp Pro Tyr
225                 230                 235                 240

Arg Leu Met Lys Pro Asn Val Gln Asp His Val Ser Leu Asp Leu His
            245                 250                 255

Leu

```
<210> SEQ ID NO 253
<211> LENGTH: 2526
<212> TYPE: DNA
<213> ORGANISM: Arabidopsis thaliana
<220> FEATURE:
<223> OTHER INFORMATION: G680

<400> SEQUENCE: 253
cagttatctt cttccttctt ctctctgttt tttaaattta ttttagaga attttttttg        60 ttttgcttcc gatttgatta tttccgggaa cgatgacttc tccggggagt tcccggtgag      120
atgataagtc agattgcata cttgtctcct ccatggctac tctcaagggt tttggctgcg      180
gtggattcgt ttggtttctc tagaatctaa agaggttatc acaacggctt tgcaatttga      240
aaactttcat gtttgggag atcaaagatg gttctttttt tatactttac ttgttagaga       300
ggatttgaag cagcgaatag ctgcaaccgg tcctgttatg gatactaata catctggaga      360
```

```
agaattatta gctaaggcaa gaaagccata tacaataaca aagcagcgag agcgatggac    420
tgaggatgag catgagaggt ttctagaagc cttgaggctt tatggaagag cttggcaacg    480
aattgaagaa catattggga caaagactgc tgttcagatc agaagtcatg cacaaaagtt    540
cttcacaaag ttggagaaag aggctgaagt taaaggcatc cctgtttgcc aagctttgga    600
catagaaatt ccgcctcctc gtcctaaacg aaaacccaat actccttatc ctcgaaaacc    660
tgggaacaac ggtacatctt cctctcaagt atcatcagca aaagatgcaa aacttgtttc    720
atcggcctct tcttcacagt tgaatcaggc gttcttggat ttggaaaaaa tgccgttctc    780
tgagaaaaca tcaactggaa aagaaaatca agatgagaat tgctcgggtg tttctactgt    840
gaacaagtat cccttaccaa cgaaacaggt aagtggcgac attgaaacaa gtaagacctc    900
aactgtggac aacgcggttc aagatgttcc caagaagaac aaagacaaag atggtaacga    960
tggtactact gtgcacagca tgcaaaacta cccttggcat ttccacgcag atattgtgaa   1020
cgggaatata gcaaaatgcc ctcaaaatca tccctcaggt atggtatctc aagacttcat   1080
gtttcatcct atgagagaag aaactcacgg gcacgcaaat cttcaagcta aacagcatc   1140
tgctactact acagcttctc atcaagcgtt ccagcttgt cattcacagg atgattaccg   1200
ttcgtttctc cagatatcat ctactttctc caatcttatt atgtcaactc tcctacagaa   1260
tcctgcagct catgctgcag ctacattcgc tgcttcggtc tggccttatg cgagtgtcgg   1320
gaattctggt gattcatcaa ccccaatgag ctcttctcct ccaagtataa ctgccattgc   1380
cgctgctaca gtagcgctg caactgcttg gtgggcttct catggacttc ttcctgtatg   1440
cgctccagct ccaataacat gtgttccatt ctcaactgtt gcagttccaa ctccagcaat   1500
gactgaaatg gataccgttg aaaatactca accgtttgag aaacaaaaca cagctctgca   1560
agatcaaacc ttggcttcga aatctccagc ttcatcatct gatgattcag atgagactgg   1620
agtaaccaag ctaaatgccg actcaaaaac caatgatgat aaaattgagg aggttgttgt   1680
tactgccgct gtgcatgact caaacactgc ccagaagaaa aatcttgtgg accgctcatc   1740
gtgtggctca aatacacctt cagggagtga cgcagaaact gatgcattag ataaaatgga   1800
gaaagataaa gaggatgtga aggagacaga tgagaatcag ccagatgtta ttgagttaaa   1860
taaccgtaag attaaaatga gagacaacaa cagcaacaac aatgcaacta ctgattcgtg   1920
gaaggaagtc tccgaagagg gtcgtatagc gtttcaggct ctctttgcaa gagaaagatt   1980
gcctcaaagc ttttcgcctc tcaagtggc agagaatgtg aatagaaaac aaagtgacac   2040
gtcaatgcca ttggctccta atttcaaaag ccaggattct tgtgctgcag accaagaagg   2100
agtagtaatg atcggtgttg aacatgcaa gagtcttaaa acgagacaga caggatttaa   2160
gccatacaag agatgttcaa tggaagtgaa agagagccaa gttgggaaca taaacaatca   2220
aagtgatgaa aaagtctgca aaaggcttcg attggaagga gaagcttcta catgacagac   2280
ttggaggtaa aaaaaaaaca tccacatttt tatcaatatc tttaaatcta gtgttagtag   2340
tttgcttctc caatctttat gaaagagact tttaattttc cttccgaaca tttctttggt   2400
catgtcaggt tctgtaccat attacccccat gtccttgtctc ttgtctctgt ttgtgtatgc   2460
tacttgtggt ctatatgtca tctgctacta ctgttaatta accattaagc aatggatttg   2520
tcttta                                                              2526
```

<210> SEQ ID NO 254
<211> LENGTH: 645
<212> TYPE: PRT
<213> ORGANISM: Arabidopsis thaliana
<220> FEATURE:
<223> OTHER INFORMATION: G680 polypeptide

<400> SEQUENCE: 254

```
Met Asp Thr Asn Thr Ser Gly Glu Glu Leu Leu Ala Lys Ala Arg Lys
1               5                   10                  15

Pro Tyr Thr Ile Thr Lys Gln Arg Glu Arg Trp Thr Glu Asp Glu His
            20                  25                  30

Glu Arg Phe Leu Glu Ala Leu Arg Leu Tyr Gly Arg Ala Trp Gln Arg
        35                  40                  45

Ile Glu Glu His Ile Gly Thr Lys Thr Ala Val Gln Ile Arg Ser His
    50                  55                  60

Ala Gln Lys Phe Phe Thr Lys Leu Glu Lys Glu Ala Glu Val Lys Gly
65                  70                  75                  80

Ile Pro Val Cys Gln Ala Leu Asp Ile Glu Ile Pro Pro Arg Pro
                85                  90                  95

Lys Arg Lys Pro Asn Thr Pro Tyr Pro Arg Lys Pro Gly Asn Asn Gly
            100                 105                 110

Thr Ser Ser Ser Gln Val Ser Ser Ala Lys Asp Ala Lys Leu Val Ser
        115                 120                 125

Ser Ala Ser Ser Ser Gln Leu Asn Gln Ala Phe Leu Asp Leu Glu Lys
130                 135                 140

Met Pro Phe Ser Glu Lys Thr Ser Thr Gly Lys Glu Asn Gln Asp Glu
145                 150                 155                 160

Asn Cys Ser Gly Val Ser Thr Val Asn Lys Tyr Pro Leu Pro Thr Lys
                165                 170                 175

Gln Val Ser Gly Asp Ile Glu Thr Ser Lys Thr Ser Thr Val Asp Asn
            180                 185                 190

Ala Val Gln Asp Val Pro Lys Lys Asn Lys Asp Lys Asp Gly Asn Asp
        195                 200                 205

Gly Thr Thr Val His Ser Met Gln Asn Tyr Pro Trp His Phe His Ala
    210                 215                 220

Asp Ile Val Asn Gly Asn Ile Ala Lys Cys Pro Gln Asn His Pro Ser
225                 230                 235                 240

Gly Met Val Ser Gln Asp Phe Met Phe His Pro Met Arg Glu Glu Thr
                245                 250                 255

His Gly His Ala Asn Leu Gln Ala Thr Thr Ala Ser Ala Thr Thr Thr
            260                 265                 270

Ala Ser His Gln Ala Phe Pro Ala Cys His Ser Gln Asp Asp Tyr Arg
        275                 280                 285

Ser Phe Leu Gln Ile Ser Ser Thr Phe Ser Asn Leu Ile Met Ser Thr
    290                 295                 300

Leu Leu Gln Asn Pro Ala Ala His Ala Ala Thr Phe Ala Ala Ser
305                 310                 315                 320

Val Trp Pro Tyr Ala Ser Val Gly Asn Ser Gly Asp Ser Ser Thr Pro
                325                 330                 335

Met Ser Ser Ser Pro Ser Ile Thr Ala Ile Ala Ala Thr Val
            340                 345                 350

Ala Ala Ala Thr Ala Trp Trp Ala Ser His Gly Leu Leu Pro Val Cys
        355                 360                 365

Ala Pro Ala Pro Ile Thr Cys Val Pro Phe Ser Thr Val Ala Val Pro
    370                 375                 380

Thr Pro Ala Met Thr Glu Met Asp Thr Val Glu Asn Thr Gln Pro Phe
385                 390                 395                 400
```

Glu Lys Gln Asn Thr Ala Leu Gln Asp Gln Thr Leu Ala Ser Lys Ser
            405                 410                 415
Pro Ala Ser Ser Asp Asp Ser Asp Glu Thr Gly Val Thr Lys Leu
        420                 425                 430
Asn Ala Asp Ser Lys Thr Asn Asp Asp Lys Ile Glu Glu Val Val Val
        435                 440                 445
Thr Ala Ala Val His Asp Ser Asn Thr Ala Gln Lys Lys Asn Leu Val
    450                 455                 460
Asp Arg Ser Ser Cys Gly Ser Asn Thr Pro Ser Gly Ser Asp Ala Glu
465                 470                 475                 480
Thr Asp Ala Leu Asp Lys Met Glu Lys Asp Lys Glu Asp Val Lys Glu
            485                 490                 495
Thr Asp Glu Asn Gln Pro Asp Val Ile Glu Leu Asn Asn Arg Lys Ile
            500                 505                 510
Lys Met Arg Asp Asn Asn Ser Asn Asn Asn Ala Thr Thr Asp Ser Trp
        515                 520                 525
Lys Glu Val Ser Glu Glu Gly Arg Ile Ala Phe Gln Ala Leu Phe Ala
        530                 535                 540
Arg Glu Arg Leu Pro Gln Ser Phe Ser Pro Gln Val Ala Glu Asn
545                 550                 555                 560
Val Asn Arg Lys Gln Ser Asp Thr Ser Met Pro Leu Ala Pro Asn Phe
            565                 570                 575
Lys Ser Gln Asp Ser Cys Ala Ala Asp Gln Glu Gly Val Val Met Ile
            580                 585                 590
Gly Val Gly Thr Cys Lys Ser Leu Lys Thr Arg Gln Thr Gly Phe Lys
        595                 600                 605
Pro Tyr Lys Arg Cys Ser Met Glu Val Lys Glu Ser Gln Val Gly Asn
            610                 615                 620
Ile Asn Asn Gln Ser Asp Glu Lys Val Cys Lys Arg Leu Arg Leu Glu
625                 630                 635                 640
Gly Glu Ala Ser Thr
            645

<210> SEQ ID NO 255
<211> LENGTH: 1699
<212> TYPE: DNA
<213> ORGANISM: Arabidopsis thaliana
<220> FEATURE:
<223> OTHER INFORMATION: G5

<400> SEQUENCE: 255
tttttttttt gcaatctccc cctaatctgt tgtttctcgc ttcttcttct gttaatcatc      60
tgtctttcaa aagaaagaa aaagaaaaa ttcgatttct gggtttgttt ttgtcataca     120
gaaaaaatc aagcttatga atttgtgttt aattttttgt tttaatttga aaggcaggtt     180
ttttcagaac gagatcgttt tttcaaattt cttctgattt tacctctttt tttcttctta     240
gattttagtg aatcgagggt gaaattttg attccctctt tcggatcta cacagaggtt     300
gcttatttca aaccttttag atccattttt ttttaatttt ctcggaaaaa tccctgtttc     360
tttacttttt tataagtctc aggttcaatt ttttcggatt caaattttta ttttaaatgg     420
cagctgctat gaatttgtac acttgtagca gatcgtttca agactctggt ggtgaactca     480
tggacgcgct tgtaccttt atcaaaagcg tttccgattc tccttcttct tcttctgcag     540
cgtctgcgtc tgcgtttctt cacccctctg cgttttctct ccctcctctc cccggttatt     600

```
acccggattc aacgttcttg acccaaccgt tttcatacgg gtcggatctt caacaaaccg    660
ggtcattaat cggactcaac aacctctctt cttctcagat ccaccagatc cagtctcaga    720
tccatcatcc tcttcctccg acgcatcaca acaacaacaa ctctttctcg aatcttctca    780
gcccaaagcc gttactgatg aagcaatctg gagtcgctgg atcttgtttc gcttacggtt    840
caggtgttcc ttcgaagccg acgaagcttt acagaggtgt gaggcaacgt cactggggaa    900
aatgggtggc tgagatccgt ttgccgagaa atcggactcg tctctggctt gggacttttg    960
acacggcgga ggaagctgcg ttggcctatg ataaggcggc gtacaagctg cgcggcgatt   1020
tcgcccggct taacttccct aacctacgtc ataacggatt tcacatcgga ggcgatttcg   1080
gtgaatataa acctcttcac tcctcagtcg acgctaagct tgaagctatt tgtaaaagca   1140
tggcggagac tcagaaacag gacaaatcga cgaaatcatc gaagaaacgt gagaagaagg   1200
tttcgtcgcc agatctatcg gagaaagtga aggcggagga gaattcggtt tcgatcggtg   1260
gatctccacc ggtgacggag tttgaagagt ccaccgctgg atcttcgccg ttgtcggact   1320
tgacgttcgc tgacccggag gagccgccgc agtggaacga gacgttctcg ttggagaagt   1380
atccgtcgta cgagatcgat tgggattcga ttctagctta ggggcaaaat aggaaattca   1440
gccgcttgca atggagtttt tgtgaaattg catgactggc ccaagagtaa ttaattaaat   1500
atggattagt gttaaatttc gtatgttaat atttgtatta tggtttgtat tagtctctct   1560
gtgtcggtcc agcttgcggt tttttgtcag gctcgaccat gccacagttt tcattttatg   1620
taatcttttt ttcttttgtc ttatgtaatt tgtagcttca gtttcttcat ctataatgca   1680
attttattat gattatgtg                                                1699

<210> SEQ ID NO 256
<211> LENGTH: 334
<212> TYPE: PRT
<213> ORGANISM: Arabidopsis thaliana
<220> FEATURE:
<223> OTHER INFORMATION: G5 polypeptide

<400> SEQUENCE: 256

Met Ala Ala Met Asn Leu Tyr Thr Cys Ser Arg Ser Phe Gln Asp
1               5                   10                  15

Ser Gly Gly Glu Leu Met Asp Ala Leu Val Pro Phe Ile Lys Ser Val
            20                  25                  30

Ser Asp Ser Pro Ser Ser Ser Ala Ala Ser Ala Ser Ala Phe Leu
        35                  40                  45

His Pro Ser Ala Phe Ser Leu Pro Pro Leu Pro Gly Tyr Tyr Pro Asp
    50                  55                  60

Ser Thr Phe Leu Thr Gln Pro Phe Ser Tyr Gly Ser Asp Leu Gln Gln
65                  70                  75                  80

Thr Gly Ser Leu Ile Gly Leu Asn Asn Leu Ser Ser Gln Ile His
                85                  90                  95

Gln Ile Gln Ser Gln Ile His His Pro Leu Pro Pro Thr His His Asn
            100                 105                 110

Asn Asn Asn Ser Phe Ser Asn Leu Leu Ser Pro Lys Pro Leu Leu Met
        115                 120                 125

Lys Gln Ser Gly Val Ala Gly Ser Cys Phe Ala Tyr Gly Ser Gly Val
    130                 135                 140

Pro Ser Lys Pro Thr Lys Leu Tyr Arg Gly Val Arg Gln Arg His Trp
145                 150                 155                 160

Gly Lys Trp Val Ala Glu Ile Arg Leu Pro Arg Asn Arg Thr Arg Leu
```

-continued

```
                165                 170                 175
Trp Leu Gly Thr Phe Asp Thr Ala Glu Glu Ala Ala Leu Ala Tyr Asp
            180                 185                 190

Lys Ala Ala Tyr Lys Leu Arg Gly Asp Phe Ala Arg Leu Asn Phe Pro
            195                 200                 205

Asn Leu Arg His Asn Gly Phe His Ile Gly Gly Asp Phe Gly Glu Tyr
    210                 215                 220

Lys Pro Leu His Ser Ser Val Asp Ala Lys Leu Glu Ala Ile Cys Lys
225                 230                 235                 240

Ser Met Ala Glu Thr Gln Lys Gln Asp Lys Ser Thr Lys Ser Ser Lys
            245                 250                 255

Lys Arg Glu Lys Lys Val Ser Ser Pro Asp Leu Ser Glu Lys Val Lys
            260                 265                 270

Ala Glu Glu Asn Ser Val Ser Ile Gly Gly Ser Pro Pro Val Thr Glu
            275                 280                 285

Phe Glu Glu Ser Thr Ala Gly Ser Ser Pro Leu Ser Asp Leu Thr Phe
    290                 295                 300

Ala Asp Pro Glu Glu Pro Pro Gln Trp Asn Glu Thr Phe Ser Leu Glu
305                 310                 315                 320

Lys Tyr Pro Ser Tyr Glu Ile Asp Trp Asp Ser Ile Leu Ala
            325                 330
```

US 7,598,429 B2

TRANSCRIPTION FACTOR SEQUENCES FOR CONFERRING ADVANTAGEOUS PROPERTIES TO PLANTS

This application claims the benefit of U.S. Provisional Application No. 60/713,952, filed Aug. 31, 2005; and this application is a continuation-in-part of prior U.S. application Ser. No. 10/225,067, filed Aug. 9, 2002 which claims the benefit of U.S. Provisional Application No. 60/336,049, filed Nov. 19, 2001, U.S. Provisional Application No. 60/310,847, filed Aug. 9, 2001 and U.S. Provisional Application No. 60/338,692, filed Dec. 11, 2001; and, prior U.S. application Ser. No. 10/225,067, filed Aug. 9, 2002 is a continuation-in-part of U.S. Non-provisional application Ser. No. 09/837,944, filed Apr. 18, 2001 (now abandoned), and U.S. Non-provisional application Ser. No. 10/171,468, filed Jun. 14, 2002 (now abandoned); and, this application is a continuation-in-part of prior U.S. application Ser. No. 10/714,887, filed Nov. 13, 2003; and, this application is a continuation-in-part of prior U.S. application Ser. No. 10/666,642, filed Sep. 18, 2003 (pending) which claims the benefit of U.S. Provisional Application No. 60/465,809, filed Apr. 24, 2003, U.S. Provisional Application No. 60/434,166, filed Dec. 17, 2002 and U.S. Provisional Application No. 60/411,837, filed Sep. 18, 2002. Each of these applications is hereby incorporated by reference in their entirety.

The claimed invention, in the field of functional genomics and the characterization of plant genes for the improvement of plants, was made by or on behalf of Mendel Biotechnology, Inc. and Monsanto Company as a result of activities undertaken within the scope of a joint research agreement, in effect on or before the date the claimed invention was made.

FIELD OF THE INVENTION

This invention relates to the field of plant biology. More particularly, the present invention pertains to compositions and methods for phenotypically modifying a plant.

INTRODUCTION

Transgenic plants with improved traits, including enhanced yield, environmental stress tolerance, pest resistance, herbicide tolerance, improved seed compositions, and the like are desired by both farmers and consumers. Although considerable efforts in plant breeding have provided significant gains in desired traits, the ability to introduce specific DNA into plant genomes provides further opportunities for generation of plants with improved and/or unique traits. Fortunately, a plant's traits, such as its biochemical, developmental, or phenotypic characteristics, may be controlled through a number of cellular processes. One important way to manipulate that control is through transcription factors—proteins that influence the expression of a particular gene or sets of genes. Transformed and transgenic plants that comprise cells having altered levels of at least one selected transcription factor, for example, possess advantageous or desirable traits. Strategies for manipulating traits by altering a plant cell's transcription factor content can therefore result in plants and crops with commercially valuable properties. Polynucleotides encoding transcription factors have been identified, transformed into transgenic plants, and the plants have been analyzed for a variety of important improved traits. In so doing, important polynucleotide and polypeptide sequences for producing commercially valuable plants and crops as well as the methods for making and using them were identified. In some cases, because of epigenetic effects, positional effects, or the like, introducing recombinant DNA into a plant genome does not result in a transgenic plant having the desired phenotype with the enhanced agronomic trait. Therefore, methods to select individual transgenic events from a population may be required to identify those transgenic events that are characterized by the enhanced agronomic trait.

Other aspects and embodiments of the invention are described below and can be derived from the teachings of this disclosure as a whole.

BACKGROUND OF THE INVENTION

Transcription factors can modulate gene expression, either increasing or decreasing (inducing or repressing) the rate of transcription. This modulation results in differential levels of gene expression at various developmental stages, in different tissues and cell types, and in response to different exogenous (e.g., environmental) and endogenous stimuli throughout the life cycle of the organism.

Because transcription factors are key controlling elements of biological pathways, altering the expression levels of one or more transcription factors can change entire biological pathways in an organism. For example, manipulation of the levels of selected transcription factors may result in increased expression of economically useful proteins or metabolic chemicals in plants or to improve other agriculturally relevant characteristics. Conversely, blocked or reduced expression of a transcription factor may reduce biosynthesis of unwanted compounds or remove an undesirable trait. Therefore, manipulating transcription factor levels in a plant offers tremendous potential in agricultural biotechnology for modifying a plant's traits.

The present invention provides novel transcription factors useful for modifying a plant's phenotype in desirable ways.

SUMMARY OF THE INVENTION

The present invention pertains to transgenic plants, and methods for producing the transgenic plant, that have desirable characteristics relative to wild-type or control plants. The desirable characteristics in the transgenic plants, which have been transformed with a sequence that is closely or phylogenetically related to G47, polynucleotide SEQ ID NO: 65 and polypeptide SEQ ID NO: 66, include increased size and/or biomass, tolerance to osmotic stress or drought, and/or increased lignification. The transgenic plants may also be delayed in their flowering, relative to a control or wild-type plant of the same species. The transgenic plants are made by first producing an expression vector that comprises a nucleotide sequence encoding a polypeptide with a conserved domain, said domain having at least 69%, or at least 73%, or at least 80%, or at least 87% amino acid identity to the conserved domain of G47 (amino acid coordinates 11-80 of G47 or SEQ ID NO: 66). The expression vector is next introduced into a suitable target plant, and the polypeptide is overexpressed in this now transgenic plant. This results in the transgenic plant having increased size and/or biomass, tolerance to the osmotic stress or drought, delayed flowering, and/or increased lignification.

Methods for increasing plant size and/or biomass, increasing osmotic stress or drought tolerance of a plant, increasing lignin content, or causing a delay in development or flowering are also encompassed by the invention.

BRIEF DESCRIPTION OF THE SEQUENCE LISTING, TABLES, AND FIGURES

The Sequence Listing provides exemplary polynucleotide and polypeptide sequences of the invention. The traits associated with the use of the sequences are included in the Examples.

This application contains a Sequence Listing. CD-ROMs Copy 1 and Copy 2, and the CRF copy of the Sequence Listing under CFR Section 1.821(e), are read-only memory computer-readable compact discs. Each contains a copy of the Sequence Listing in ASCII text format. The Sequence Listing is named "MBI-0036-3CIP.ST25.txt", the electronic file of the Sequence Listing contained on each of these CD-ROMs was created on Mar. 13, 2006, and is 516 kilobytes in size. The copies of the Sequence Listing on the CD-ROM discs are hereby incorporated by reference in their entirety.

FIG. 1 shows a phylogenic tree of related plant families adapted from Daly et al. (2001 *Plant Physiology* 127: 1328-1333).

Figure 2:
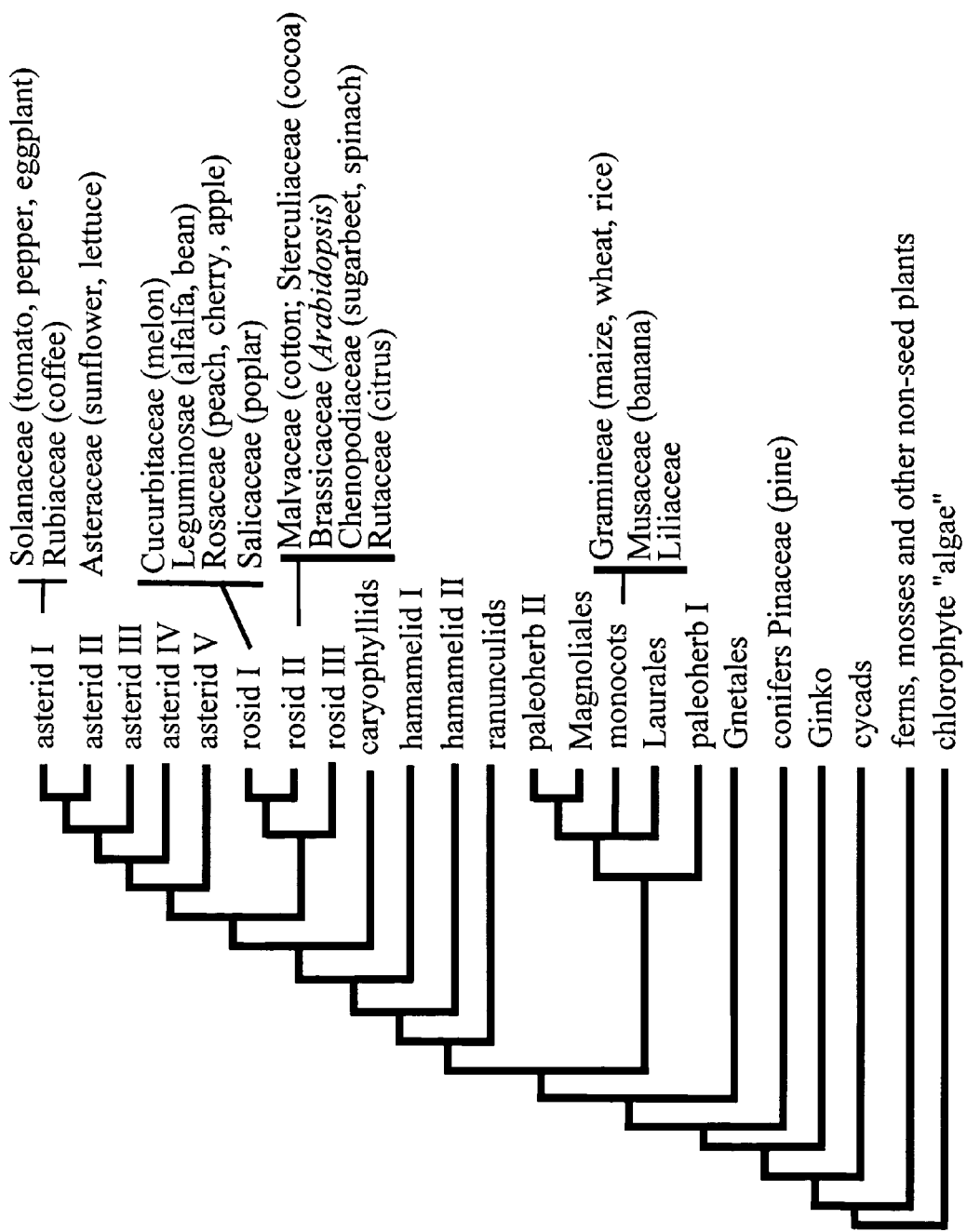

FIG. 2 shows a phylogenic dendogram depicting phylogenetic relationships of higher plant taxa, including clades containing tomato and *Arabidopsis*; adapted from Ku et al. (2000) *Proc. Natl. Acad. Sci. USA* 97: 9121-9126; and Chase et al. (1993) *Ann. Missouri Bot. Gard.* 80: 528-580.

Figure 3:
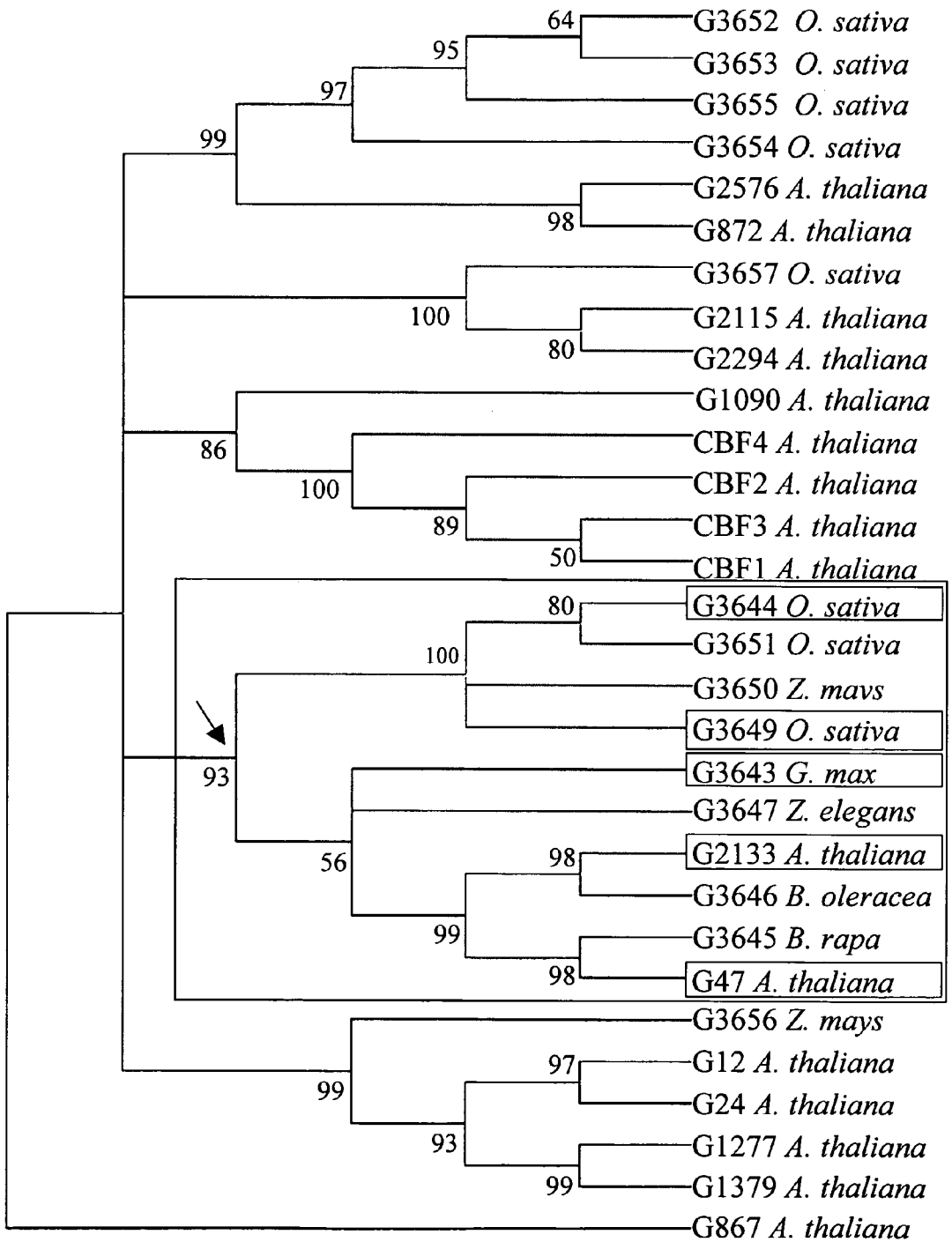

FIG. 3 shows a phylogenetic tree and multiple sequence alignments of G47 and related full length proteins were constructed using ClustalW (CLUSTAL W Multiple Sequence Alignment Program version 1.83, 2003) and MEGA2 (http://www.megasoftware.net) software. Sequences closely related to G47, SEQ ID NO: 66, fall within the G47 clade and descend from a common ancestral sequence represented by the arrow at an ancestral node of the tree. These phylogenetically-related sequences within the G47 clade that have thus far been shown to have a transcriptional regulatory activity of G47 by conferring similar morphological and physiological characteristics have conserved domains that are at least 69% identical to the conserved domain of G47 (amino acid coordinates 11-80). The percentage identity was determined by BLASTp analysis against a database containing G47 homologs, with default settings of a wordlength (W) of 3, an expectation (E) of 10, and the BLOSUM62 scoring matrix (see Henikoff & Henikoff (1989) *Proc. Natl. Acad. Sci. USA* 89: 10915-10919). ClustalW multiple alignment parameters for FIG. 3 were as follows:

Gap Opening Penalty: 10.00; Gap Extension Penalty: 0.20; Delay divergent sequences: 30%;

DNA Transitions Weight: 0.50; Protein weight matrix: Gonnet series; DNA weight matrix: IUB; Use negative matrix: OFF.

A FastA formatted alignment was then used to generate a phylogenetic tree in MEGA2 using the neighbor joining algorithm and a p-distance model. A test of phylogeny was done via bootstrap with 1000 replications and Random Seed set to default. Cut off values of the bootstrap tree were set to 50%. Orthologs of G47 are considered as being those proteins within the node of the tree below with a bootstrap value of 93, bounded by G3644 and G47, as indicated by the sequences within the box.

FIG. 4 shows a Clustal W alignment of the AP2 domains of the G47 clade and other representative AP2 proteins. The three residues indicated by the boxes define the G47 clade; clade members (indicated by the vertical line at left) have a two valines and a histidine residue at these positions, respectively. The SEQ ID NOs: of the subsequences appear within the parentheses in this Figure.

FIG. 5 shows the conserved domain of G47 (SEQ ID NO: 66) aligned against the conserved domains of *Arabidopsis* paralog sequence G2133 (SEQ ID NO: 152; 62 of 71 or 87% identical residues) and three orthologs, soy G3643 (SEQ ID NO: 158; 45 of 65 or 69% of residues are identical), rice G3649 (SEQ ID NO: 154; 35 of 44 or 80% of residues identical) and rice G3644 (SEQ ID NO: 156; 35 of 48 or 73% of residues identical). Alignments and percentage identity were determined from BLASTp analysis in which the conserved domain of G47, amino acid coordinates 11-80, were queried against a database containing the G47 homologs, with default settings of a wordlength (W) of 3, an expectation (E) of 10, and the BLOSUM62 scoring matrix (see Henikoff & Henikoff (1989) supra).

FIGS. 6A-6C show *Arabidopsis* G47, SEQ ID NO: 66 (FIG. 6A, plant at left), soy G3649, SEQ ID NO: 154 (FIG. 6B, plants at left and center), and rice G3643, SEQ ID NO: 158 (FIG. 6C, plants at left and center) overexpressors at 58, 44, and 33 days after planting, respectively. The overexpressors generally developed later, and some lines had larger rosettes and an increased amount of vegetative tissue compared to the control plants at the right of each photograph.

Figure 7A:
Figure 7B:
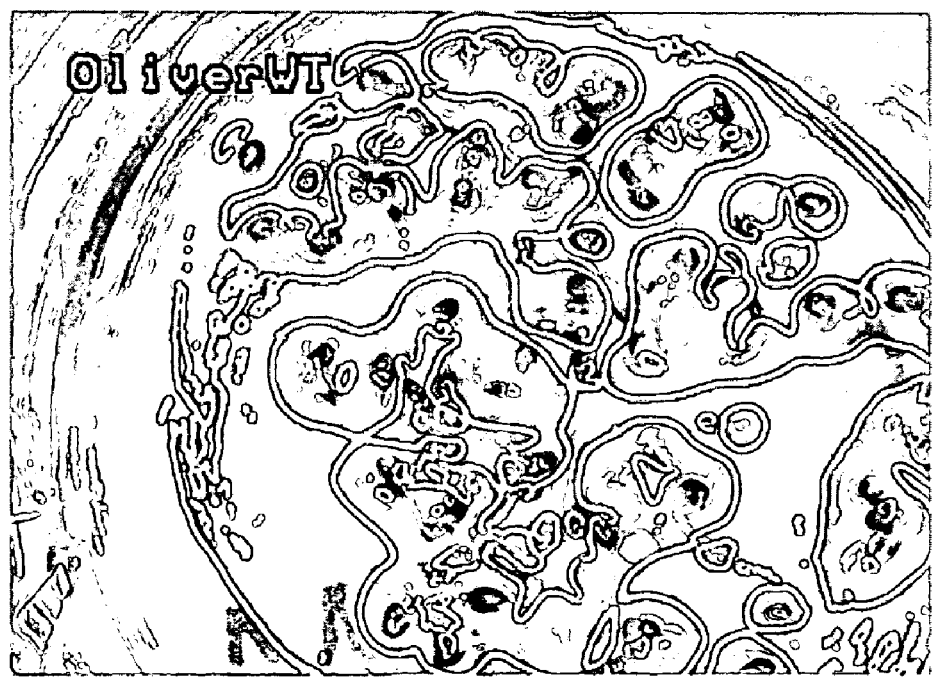

FIGS. 7A-7B compare seedlings ectopically expressing rice sequence G3644, SEQ ID NO: 156 (FIG. 7A) and wild-type seedling controls. The 35S::G3644 seedlings (FIG. 7A) were generally larger and greener after germination in a 150 mM NaCl than the wild-type control seedlings exposed to the same conditions (FIG. 7B). The small pale seedlings in FIG. 7A represent wild-type segregants, based on kanamycin resistance segregation data from the same population.

Figure 8A:
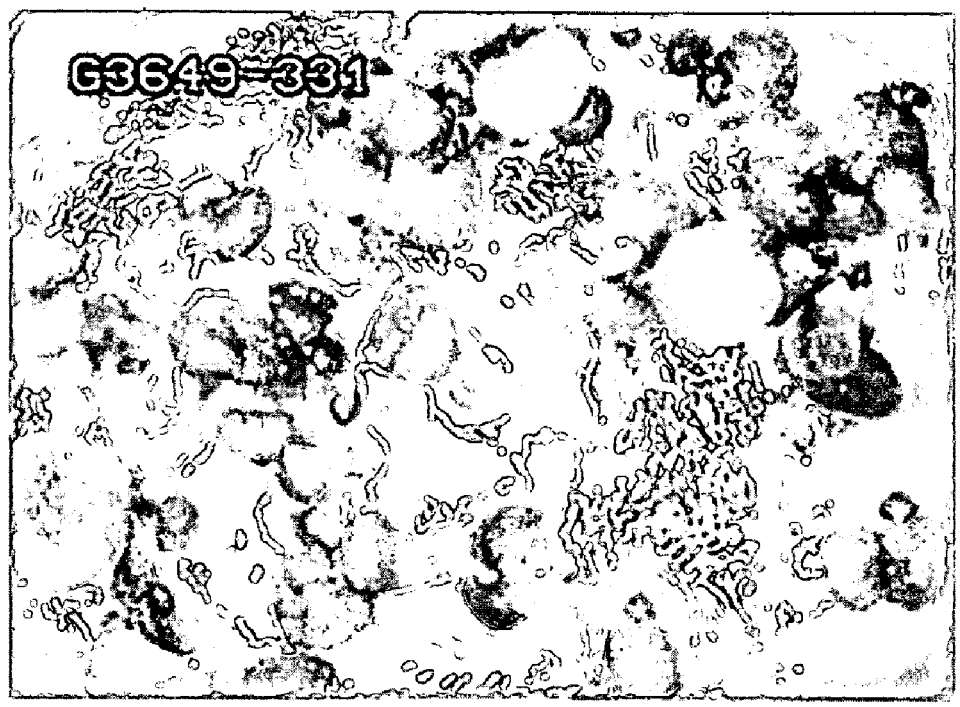
Figure 8B:
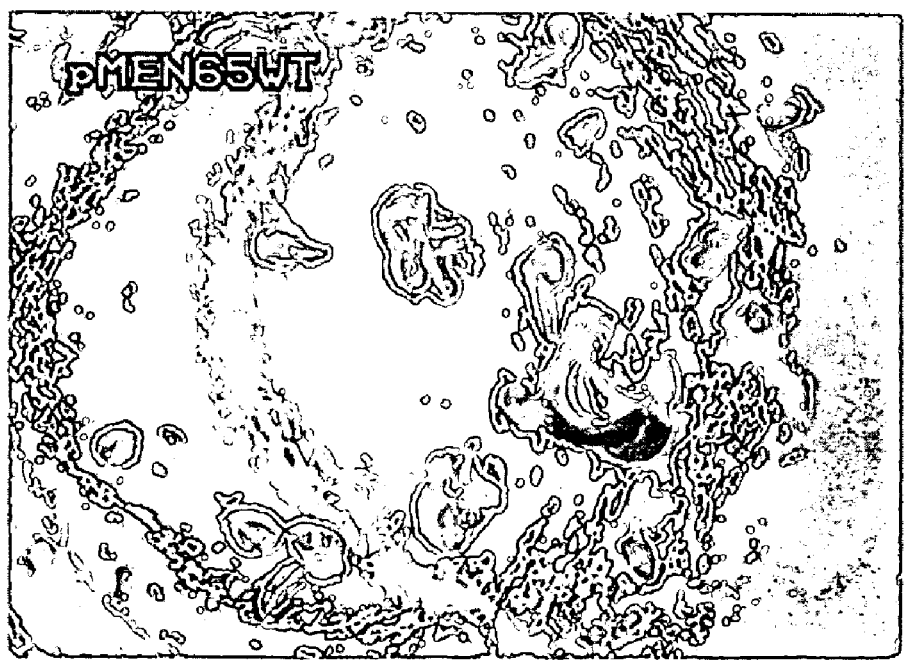

As shown in FIGS. 8A-8B, seedlings ectopically expressing rice sequence G3649, SEQ ID NO: 154 (FIG. 8A) were generally larger and greener after germination in a medium containing 0.3 µM abscisic acid than the wild-type control seedlings exposed to the same conditions (FIG. 8B).

Figure 9:
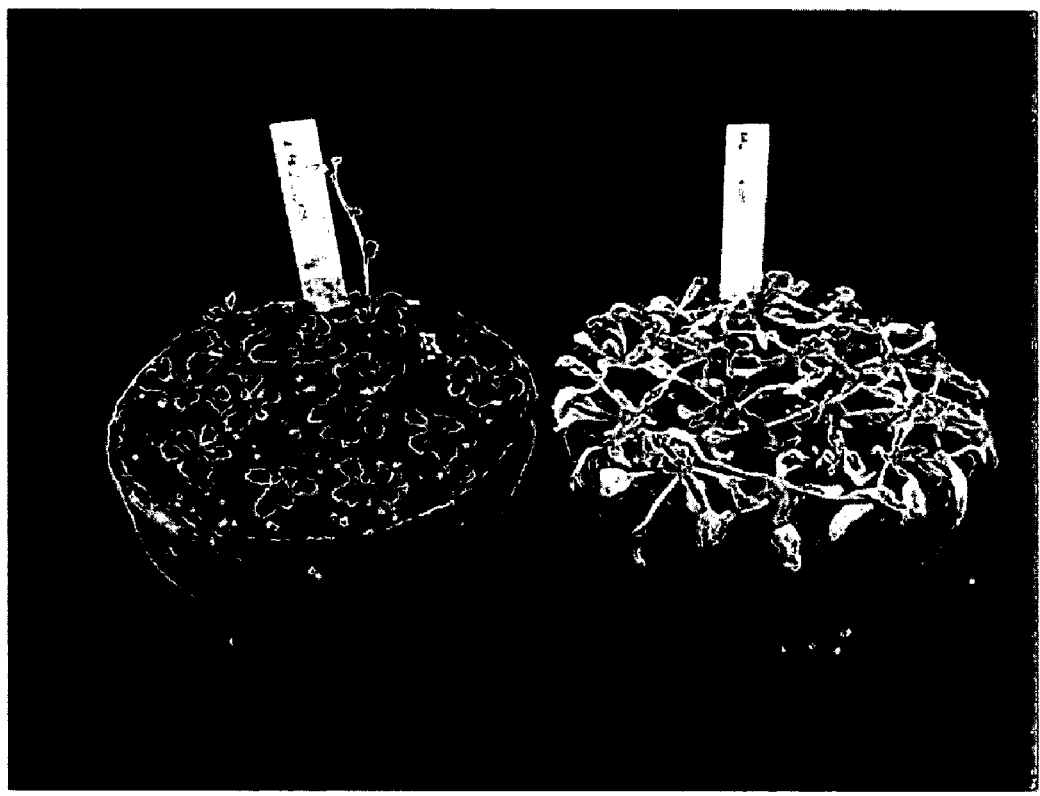

FIG. 9 illustrates a dramatic example of osmotic-stress tolerance. Seedlings overexpressing *Arabidopsis* G2133, SEQ ID NO: 152, in the pot at the left were significantly greener and more vigorous than the wild-type control seedlings, seen at right, after both sets of plants had been exposed to the same severe drought conditions and rewatered. The overexpressors readily recovered from the severe treatment after resumption of watering, whereas the few control plants at right that survived had been severely and adversely affected by the drought treatment.

DETAILED DESCRIPTION OF EXEMPLARY EMBODIMENTS

The present invention relates to polynucleotides and polypeptides for modifying phenotypes of plants, particularly those associated with increased biomass, increased disease resistance, and/or abiotic stress tolerance. Throughout this disclosure, various information sources are referred to and/or are specifically incorporated. The information sources include scientific journal articles, patent documents, textbooks, and World Wide Web browser-inactive page addresses. While the reference to these information sources clearly indicates that they can be used by one of skill in the art, each and every one of the information sources cited herein are specifically incorporated in their entirety, whether or not a specific mention of "incorporation by reference" is noted.

The contents and teachings of each and every one of the information sources can be relied on and used to make and use embodiments of the invention.

As used herein and in the appended claims, the singular forms "a", "an", and "the" include the plural reference unless the context clearly dictates otherwise. Thus, for example, a reference to "a host cell" includes a plurality of such host cells, and a reference to "a stress" is a reference to one or more stresses and equivalents thereof known to those skilled in the art, and so forth.

DEFINITIONS

"Nucleic acid molecule" refers to an oligonucleotide, polynucleotide or any fragment thereof. It may be DNA or RNA of genomic or synthetic origin, double-stranded or single-stranded, and combined with carbohydrate, lipids, protein, or other materials to perform a particular activity such as transformation or form a useful composition such as a peptide nucleic acid (PNA).

"Polynucleotide" is a nucleic acid molecule comprising a plurality of polymerized nucleotides, e.g., at least about 15 consecutive polymerized nucleotides. A polynucleotide may be a nucleic acid, oligonucleotide, nucleotide, or any fragment thereof. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single-stranded or double-stranded DNA or RNA. The polynucleotide optionally comprises modified bases or a modified backbone. The polynucleotide can be, e.g., genomic DNA or RNA, a transcript (such as an mRNA), a cDNA, a PCR product, a cloned DNA, a synthetic DNA or RNA, or the like. The polynucleotide can be combined with carbohydrate, lipids, protein, or other materials to perform a particular activity such as transformation or form a useful composition such as a peptide nucleic acid (PNA). The polynucleotide can comprise a sequence in either sense or antisense orientations. "Oligonucleotide" is substantially equivalent to the terms amplimer, primer, oligomer, element, target, and probe and is preferably single-stranded.

"Gene" or "gene sequence" refers to the partial or complete coding sequence of a gene, its complement, and its 5' or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter may be subjected to subsequent processing such as chemical modification or folding to obtain a functional protein or polypeptide. A gene may be isolated, partially isolated, or found with an organism's genome. By way of example, a transcription factor gene encodes a transcription factor polypeptide, which may be functional or require processing to function as an initiator of transcription.

Operationally, genes may be defined by the cis-trans test, a genetic test that determines whether two mutations occur in the same gene and that may be used to determine the limits of the genetically active unit (Rieger et al. (1976)). A gene generally includes regions preceding ("leaders"; upstream) and following ("trailers"; downstream) the coding region. A gene may also include intervening, non-coding sequences, referred to as "introns", located between individual coding segments, referred to as "exons". Most genes have an associated promoter region, a regulatory sequence 5' of the transcription initiation codon (there are some genes that do not have an identifiable promoter). The function of a gene may also be regulated by enhancers, operators, and other regulatory elements.

A "recombinant polynucleotide" is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acid.

An "isolated polynucleotide" is a polynucleotide, whether naturally occurring or recombinant, that is present outside the cell in which it is typically found in nature, whether purified or not. Optionally, an isolated polynucleotide is subject to one or more enrichment or purification procedures, e.g., cell lysis, extraction, centrifugation, precipitation, or the like.

A "polypeptide" is an amino acid sequence comprising a plurality of consecutive polymerized amino acid residues e.g., at least about 15 consecutive polymerized amino acid residues. In many instances, a polypeptide comprises a polymerized amino acid residue sequence that is a transcription factor or a domain or portion or fragment thereof. Additionally, the polypeptide may comprise: (i) a localization domain; (ii) an activation domain; (iii) a repression domain; (iv) an oligomerization domain; (v) a DNA-binding domain; or the like. The polypeptide optionally comprises modified amino acid residues, naturally occurring amino acid residues not encoded by a codon, non-naturally occurring amino acid residues.

"Protein" refers to an amino acid sequence, oligopeptide, peptide, polypeptide or portions thereof whether naturally occurring or synthetic.

"Portion", as used herein, refers to any part of a protein used for any purpose, but especially for the screening of a library of molecules which specifically bind to that portion or for the production of antibodies.

A "recombinant polypeptide" is a polypeptide produced by translation of a recombinant polynucleotide. A "synthetic polypeptide" is a polypeptide created by consecutive polymerization of isolated amino acid residues using methods well known in the art. An "isolated polypeptide," whether a naturally occurring or a recombinant polypeptide, is more enriched in (or out of) a cell than the polypeptide in its natural state in a wild-type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type standardized at 100%. Such an enrichment is not the result of a natural response of a wild-type plant. Alternatively, or additionally, the isolated polypeptide is separated from other cellular components with which it is typically associated, e.g., by any of the various protein purification methods herein.

"Homology" refers to sequence similarity between a reference sequence and at least a fragment of a newly sequenced clone insert or its encoded amino acid sequence.

"Identity" or "similarity" refers to sequence similarity between two polynucleotide sequences or between two polypeptide sequences, with identity being a more strict comparison. The phrases "percent identity" and "% identity" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value therebetween. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical, matching or corresponding nucleotides at positions shared by the polynucleotide sequences. A degree of identity of polypeptide sequences is a function of the number of identical amino acids at corresponding positions shared by the polypeptide sequences. A degree of homology or similarity of polypeptide sequences is a function of the number of amino acids at corresponding positions shared by the polypeptide sequences.

"Alignment" refers to a number of nucleotide bases or amino acid residue sequences aligned by lengthwise comparison so that components in common (i.e., nucleotide bases or amino acid residues at corresponding positions) may be visually and readily identified. The fraction or percentage of components in common is related to the homology or identity between the sequences. Alignments such as those of FIG. 4 or FIG. 5 may be used to identify conserved domains and relatedness within these domains. An alignment may suitably be determined by means of computer programs known in the art, such as MACVECTOR software (1999) (Accelrys, Inc., San Diego, Calif.).

A "conserved domain" or "conserved region" as used herein refers to a region in heterologous polynucleotide or polypeptide sequences where there is a relatively high degree of sequence identity between the distinct sequences. For example, an "AT-hook" domain", such as is found in a polypeptide member of AT-hook transcription factor family, is an example of a conserved domain. An "AP2" domain", such as is found in a polypeptide member of AP2 transcription factor family, is another example of a conserved domain. With respect to polynucleotides encoding presently disclosed transcription factors, a conserved domain is preferably at least nine base pairs (bp) in length. A conserved domain (for example, a DNA binding domain) with respect to presently disclosed polypeptides refers to a domain that exhibits at least about 38% sequence identity, or at least about 55% sequence identity, or at least about 62% sequence identity, or at least about 69%, or at least about 70%, or at least about 73%, or at least about 76%, or at least about 78%, or at least about 80%, or at least about 82%, or at least about 85%, or at least about 87%, or at least about 89%, or at least about 95%, amino acid residue sequence identity, to a conserved domain of a polypeptide of the invention. Sequences that possess or encode for conserved domains that meet these criteria of percentage identity, and may have comparable biological activity to the present transcription factor sequences. This is particularly true for sequences that derive from a common ancestral sequence that had the same or similar function, and for which the function has been retained. These sequences, which are closely and phylogenetically related, being members of a particular clade of transcription factor polypeptides, are encompassed by the invention. A fragment or domain can be referred to as outside a conserved domain, outside a consensus sequence, or outside a consensus DNA-binding site that is known to exist or that exists for a particular transcription factor class, family, or sub-family. In this case, the fragment or domain will not include the exact amino acids of a consensus sequence or consensus DNA-binding site of a transcription factor class, family or sub-family, or the exact amino acids of a particular transcription factor consensus sequence or consensus DNA-binding site. Furthermore, a particular fragment, region, or domain of a polypeptide, or a polynucleotide encoding a polypeptide, can be "outside a conserved domain" if all the amino acids of the fragment, region, or domain fall outside of a defined conserved domain(s) for a polypeptide or protein. Sequences having lesser degrees of identity but comparable biological activity are considered to be equivalents.

As one of ordinary skill in the art recognizes, conserved domains may be identified as regions or domains of identity to a specific consensus sequence (see, for example, Riechmann et al. (2000) *Science* 290: 2105-2110, Riechmann et al. (2000b) *Curr. Opin. Plant Biol.* 3: 423-434). Thus, by using alignment methods well known in the art, the conserved domains of the plant transcription factors, for example, for the AT-hook proteins (Reeves and Beckerbauer (2001) *Biochim. Biophys. Acta* 1519: 13-29; and Reeves (2001) *Gene* 277: 63-81), may be determined.

The conserved domains for many of the transcription factor sequences of the invention are listed in Table 4. A comparison of the regions of these polypeptides allows one of skill in the art (see, for example, Reeves and Nissen (1995) *Prog. Cell Cycle Res.* 1: 339-349) to identify domains or conserved domains for any of the polypeptides listed or referred to in this disclosure.

"Complementary" refers to the natural hydrogen bonding by base pairing between purines and pyrimidines. For example, the sequence A-C-G-T (5'->3') forms hydrogen bonds with its complements A-C-G-T (5'->3') or A-C-G-U (5'->3'). Two single-stranded molecules may be considered partially complementary, if only some of the nucleotides bond, or "completely complementary" if all of the nucleotides bond. The degree of complementarity between nucleic acid strands affects the efficiency and strength of hybridization and amplification reactions. "Fully complementary" refers to the case where bonding occurs between every base pair and its complement in a pair of sequences, and the two sequences have the same number of nucleotides.

The terms "highly stringent" or "highly stringent condition" refer to conditions that permit hybridization of DNA strands whose sequences are highly complementary, wherein these same conditions exclude hybridization of significantly mismatched DNAs. Polynucleotide sequences capable of hybridizing under stringent conditions with the polynucleotides of the present invention may be, for example, variants of the disclosed polynucleotide sequences, including allelic or splice variants, or sequences that encode orthologs or paralogs of presently disclosed polypeptides. Nucleic acid hybridization methods are disclosed in detail by Kashima et al. (1985) *Nature* 313: 402-404, Sambrook et al. (1989) *Molecular Cloning—A Laboratory Manual* (2nd Ed.), Vol. 1-3, Cold Spring Harbor Laboratory, Cold Spring Harbor, N.Y., 1989 ("Sambrook"), and by Haymes et al. (1985) *Nucleic Acid Hybridization: A Practical Approach*, IRL Press, Washington, D.C., which references are incorporated herein by reference.

In general, stringency is determined by the temperature, ionic strength, and concentration of denaturing agents (e.g., formamide) used in a hybridization and washing procedure (for a more detailed description of establishing and determining stringency, see the section "Identifying Polynucleotides or Nucleic Acids by Hybridization", below). The degree to which two nucleic acids hybridize under various conditions of stringency is correlated with the extent of their similarity. Thus, similar nucleic acid sequences from a variety of sources, such as within a plant's genome (as in the case of paralogs) or from another plant (as in the case of orthologs) that may perform similar functions can be isolated on the basis of their ability to hybridize with known transcription factor sequences. Numerous variations are possible in the conditions and means by which nucleic acid hybridization can be performed to isolate transcription factor sequences having similarity to transcription factor sequences known in the art and are not limited to those explicitly disclosed herein. Such an approach may be used to isolate polynucleotide sequences having various degrees of similarity with disclosed transcription factor sequences, such as, for example, encoded transcription factors having 38% or greater identity with the conserved domain of disclosed transcription factors.

The terms "paralog" and "ortholog" are defined below in the section entitled "Orthologs and Paralogs". In brief, orthologs and paralogs are evolutionarily related genes that have similar sequences and functions. Orthologs are structurally related genes in different species that are derived by a speciation event. Paralogs are structurally related genes within a single species that are derived by a duplication event.

The term "equivalog" describes members of a set of homologous proteins that are conserved with respect to function since their last common ancestor. Related proteins are grouped into equivalog families, and otherwise into protein families with other hierarchically defined homology types. This definition is provided at the Institute for Genomic Research (TIGR) World Wide Web (www) website, "tigr.org" under the heading "Terms associated with TIGRFAMs".

In general, the term "variant" refers to molecules with some differences, generated synthetically or naturally, in their base or amino acid sequences as compared to a reference (native) polynucleotide or polypeptide, respectively. These differences include substitutions, insertions, deletions or any desired combinations of such changes in a native polynucleotide of amino acid sequence.

With regard to polynucleotide variants, differences between presently disclosed polynucleotides and polynucleotide variants are limited so that the nucleotide sequences of the former and the latter are closely similar overall and, in many regions, identical. Due to the degeneracy of the genetic code, differences between the former and latter nucleotide sequences may be silent (i.e., the amino acids encoded by the polynucleotide are the same, and the variant polynucleotide sequence encodes the same amino acid sequence as the presently disclosed polynucleotide. Variant nucleotide sequences may encode different amino acid sequences, in which case such nucleotide differences will result in amino acid substitutions, additions, deletions, insertions, truncations or fusions with respect to the similar disclosed polynucleotide sequences. These variations may result in polynucleotide variants encoding polypeptides that share at least one functional characteristic. The degeneracy of the genetic code also dictates that many different variant polynucleotides can encode identical and/or substantially similar polypeptides in addition to those sequences illustrated in the Sequence Listing.

Also within the scope of the invention is a variant of a transcription factor nucleic acid listed in the Sequence Listing, that is, one having a sequence that differs from the one of the polynucleotide sequences in the Sequence Listing, or a complementary sequence, that encodes a functionally equivalent polypeptide (i.e., a polypeptide having some degree of equivalent or similar biological activity) but differs in sequence from the sequence in the Sequence Listing, due to degeneracy in the genetic code. Included within this definition are polymorphisms that may or may not be readily detectable using a particular oligonucleotide probe of the polynucleotide encoding polypeptide, and improper or unexpected hybridization to allelic variants, with a locus other than the normal chromosomal locus for the polynucleotide sequence encoding polypeptide.

"Allelic variant" or "polynucleotide allelic variant" refers to any of two or more alternative forms of a gene occupying the same chromosomal locus. Allelic variation arises naturally through mutation, and may result in phenotypic polymorphism within populations. Gene mutations may be "silent" or may encode polypeptides having altered amino acid sequence. "Allelic variant" and "polypeptide allelic variant" may also be used with respect to polypeptides, and in this case the terms refer to a polypeptide encoded by an allelic variant of a gene.

"Splice variant" or "polynucleotide splice variant" as used herein refers to alternative forms of RNA transcribed from a gene. Splice variation naturally occurs as a result of alternative sites being spliced within a single transcribed RNA molecule or between separately transcribed RNA molecules, and may result in several different forms of mRNA transcribed from the same gene. Thus, splice variants may encode polypeptides having different amino acid sequences, which may or may not have similar functions in the organism. "Splice variant" or "polypeptide splice variant" may also refer to a polypeptide encoded by a splice variant of a transcribed mRNA.

As used herein, "polynucleotide variants" may also refer to polynucleotide sequences that encode paralogs and orthologs of the presently disclosed polypeptide sequences. "Polypeptide variants" may refer to polypeptide sequences that are paralogs and orthologs of the presently disclosed polypeptide sequences.

Differences between presently disclosed polypeptides and polypeptide variants are limited so that the sequences of the former and the latter are closely similar overall and, in many regions, identical. Presently disclosed polypeptide sequences and similar polypeptide variants may differ in amino acid sequence by one or more substitutions, additions, deletions, fusions and truncations, which may be present in any combination. These differences may produce silent changes and result in a functionally equivalent transcription factor. Thus, it will be readily appreciated by those of skill in the art, that any of a variety of polynucleotide sequences is capable of encoding the transcription factors and transcription factor homolog polypeptides of the invention. A polypeptide sequence variant may have "conservative" changes, wherein a substituted amino acid has similar structural or chemical properties. Deliberate amino acid substitutions may thus be made on the basis of similarity in polarity, charge, solubility, hydrophobicity, hydrophilicity, and/or the amphipathic nature of the residues, as long as a significant amount of the functional or biological activity of the transcription factor is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine. More rarely, a variant may have "non-conservative" changes, e.g., replacement of a glycine with a tryptophan. Similar minor variations may also include amino acid deletions or insertions, or both. Related polypeptides may comprise, for example, additions and/or deletions of one or more N-linked or O-linked glycosylation sites, or an addition and/or a deletion of one or more cysteine residues. Guidance in determining which and how many amino acid residues may be substituted, inserted or deleted without abolishing functional or biological activity may be found using computer programs well known in the art, for example, DNASTAR software (see U.S. Pat. No. 5,840,544).

"Fragment", with respect to a polynucleotide, refers to a clone or any part of a polynucleotide molecule that retains a usable, functional characteristic. Useful fragments include oligonucleotides and polynucleotides that may be used in hybridization or amplification technologies or in the regulation of replication, transcription or translation. A "polynucleotide fragment" refers to any subsequence of a polynucleotide, typically, of at least about 9 consecutive nucleotides, preferably at least about 30 nucleotides, more preferably at least about 50 nucleotides, of any of the sequences provided herein. Exemplary polynucleotide fragments are the first sixty consecutive nucleotides of the transcription factor polynucleotides listed in the Sequence Listing. Exemplary fragments also include fragments that comprise a region that encodes an conserved domain of a transcription factor. Exemplary fragments also include fragments that comprise a conserved domain of a transcription factor. Exemplary fragments include fragments that comprise an conserved domain of a transcription factor, for example, amino acid residues 11-80 of G47 (SEQ ID NO: 66).

Fragments may also include subsequences of polypeptides and protein molecules, or a subsequence of the polypeptide. Fragments may have uses in that they may have antigenic potential. In some cases, the fragment or domain is a subsequence of the polypeptide which performs at least one biological function of the intact polypeptide in substantially the same manner, or to a similar extent, as does the intact polypeptide. For example, a polypeptide fragment can comprise a recognizable structural motif or functional domain such as a DNA-binding site or domain that binds to a DNA promoter region, an activation domain, or a domain for protein-protein interactions, and may initiate transcription. Fragments can vary in size from as few as 3 amino acid residues to the full length of the intact polypeptide, but are preferably at least about 30 amino acid residues in length and more preferably at least about 60 amino acid residues in length.

The invention also encompasses production of DNA sequences that encode transcription factors and transcription factor derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding transcription factors or any fragment thereof.

"Derivative" refers to the chemical modification of a nucleic acid molecule or amino acid sequence. Chemical modifications can include replacement of hydrogen by an alkyl, acyl, or amino group or glycosylation, pegylation, or any similar process that retains or enhances biological activity or lifespan of the molecule or sequence.

The term "plant" includes whole plants, shoot vegetative organs/structures (for example, leaves, stems and tubers), roots, flowers and floral organs/structures (for example, bracts, sepals, petals, stamens, carpels, anthers and ovules), seed (including embryo, endosperm, and seed coat) and fruit (the mature ovary), plant tissue (for example, vascular tissue, ground tissue, and the like) and cells (for example, guard cells, egg cells, and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, horsetails, psilophytes, lycophytes, bryophytes, and multicellular algae (see for example, FIG. 1, adapted from Daly et al. (2001) supra, FIG. 2, adapted from Ku et al. (2000) supra; and see also Tudge (2000) in *The Variety of Life*, Oxford University Press, New York, N.Y. pp. 547-606.

A "control plant" as used in the present invention refers to a plant cell, seed, plant component, plant tissue, plant organ or whole plant used to compare against transgenic or genetically modified plant for the purpose of identifying an enhanced phenotype in the transgenic or genetically modified plant. A control plant may in some cases be a transgenic plant line that comprises an empty vector or marker gene, but does not contain the recombinant polynucleotide of the present invention that is expressed in the transgenic or genetically modified plant being evaluated. In general, a control plant is a plant of the same line or variety as the transgenic or genetically modified plant being tested. A suitable control plant would include a genetically unaltered or non-transgenic plant of the parental line used to generate a transgenic plant herein.

A "transgenic plant" refers to a plant that contains genetic material not found in a wild-type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes.

A transgenic plant may contain an expression vector or cassette. The expression cassette typically comprises a polypeptide-encoding sequence operably linked (i.e., under regulatory control of) to appropriate inducible or constitutive regulatory sequences that allow for the controlled expression of polypeptide. The expression cassette can be introduced into a plant by transformation or by breeding after transformation of a parent plant. A plant refers to a whole plant as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

"Wild type" or "wild-type", as used herein, refers to a plant cell, seed, plant component, plant tissue, plant organ or whole plant that has not been genetically modified or treated in an experimental sense. Wild-type cells, seed, components, tissue, organs or whole plants may be used as controls to compare levels of expression and the extent and nature of trait modification with cells, tissue or plants of the same species in which a transcription factor expression is altered, e.g., in that it has been knocked out, overexpressed, or ectopically expressed.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, e.g., by employing Northern analysis, RT-PCR, microarray gene expression assays, or reporter gene expression systems, or by agricultural observations such as hyperosmotic stress tolerance or yield. Any technique can be used to measure the amount of, comparative level of, or difference in any selected chemical compound or macromolecule in the transgenic plants, however.

As used herein an "enhanced trait" means a characteristic of a transgenic plant that includes, but is not limited to, an enhance agronomic trait characterized by enhanced plant morphology, physiology, growth and development, yield, nutritional enhancement, disease or pest resistance, or environmental or chemical tolerance. In more specific aspects of this invention enhanced trait is selected from group of enhanced traits consisting of enhanced water use efficiency, enhanced cold tolerance, increased yield, enhanced nitrogen use efficiency, enhanced seed protein and enhanced seed oil. In an important aspect of the invention the enhanced trait is enhanced yield including increased yield under non-stress conditions and increased yield under environmental stress conditions. Stress conditions may include, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also affected by efficiency of germination (including germination in stressed conditions), growth rate (including growth rate in stressed conditions), ear number, seed number per ear, seed size, composition of seed (starch, oil, protein) and characteristics of seed fill.

Increased yield of a transgenic plant of the present invention can be measured in a number of ways, including plant volume, plant biomass, test weight, seed number per plant, seed weight, seed number per unit area (i.e. seeds, or weight of seeds, per acre), bushels per acre (bu/a), tonnes per acre, tons per acre, and/or kilo per hectare. For example, maize yield may be measured as production of shelled corn kernels per unit of production area, for example in bushels per acre or metric tons per hectare, often reported on a moisture adjusted basis, for example at 15.5 percent moisture. Increased yield may result from improved utilization of key biochemical compounds, such as nitrogen, phosphorous and carbohydrate, or from improved responses to environmental stresses, such as cold, heat, drought, salt, and attack by pests or pathogens. Recombinant DNA used in this invention can also be used to provide plants having improved growth and development, and ultimately increased yield, as the result of modified expression of plant growth regulators or modification of cell cycle or photosynthesis pathways. Also of interest is the generation of transgenic plants that demonstrate enhanced yield with respect to a seed component that may or may not correspond to an increase in overall plant yield. Such properties include enhancements in seed oil, seed molecules such as tocopherol, protein and starch, or oil particular oil components as may be manifest by an alteration in the ratios of seed components.

"Trait modification" refers to a detectable difference in a characteristic in a plant ectopically expressing a polynucleotide or polypeptide of the present invention relative to a plant not doing so, such as a wild-type plant. In some cases, the trait modification can be evaluated quantitatively. For example, the trait modification can entail at least about a 2% increase or decrease, or an even greater difference, in an observed trait as compared with a control or wild-type plant. It is known that there can be a natural variation in the modified trait. Therefore, the trait modification observed entails a change of the normal distribution and magnitude of the trait in the plants as compared to control or wild-type plants.

When two or more plants have "similar morphologies", "substantially similar morphologies", "a morphology that is substantially similar", or are "morphologically similar", the plants have comparable forms or appearances, including analogous features such as overall dimensions, height, width, mass, root mass, shape, glossiness, color, stem diameter, leaf size, leaf dimension, leaf density, internode distance, branching, root branching, number and form of inflorescences, and other macroscopic characteristics, and the individual plants are not readily distinguishable based on morphological characteristics alone.

"Modulates" refers to a change in activity (biological, chemical, or immunological) or lifespan resulting from specific binding between a molecule and either a nucleic acid molecule or a protein.

The term "transcript profile" refers to the expression levels of a set of genes in a cell in a particular state, particularly by comparison with the expression levels of that same set of genes in a cell of the same type in a reference state. For example, the transcript profile of a particular transcription factor in a suspension cell is the expression levels of a set of genes in a cell knocking out or overexpressing that transcription factor compared with the expression levels of that same set of genes in a suspension cell that has normal levels of that transcription factor. The transcript profile can be presented as a list of those genes whose expression level is significantly different between the two treatments, and the difference ratios. Differences and similarities between expression levels may also be evaluated and calculated using statistical and clustering methods.

With regard to transcription factor gene knockouts as used herein, the term "knockout" refers to a plant or plant cell having a disruption in at least one transcription factor gene in the plant or cell, where the disruption results in a reduced expression or activity of the transcription factor encoded by that gene compared to a control cell. The knockout can be the result of, for example, genomic disruptions, including transposons, tilling, and homologous recombination, antisense constructs, sense constructs, RNA silencing constructs, or RNA interference. A T-DNA insertion within a transcription factor gene is an example of a genotypic alteration that may abolish expression of that transcription factor gene.

"Ectopic expression or altered expression" in reference to a polynucleotide indicates that the pattern of expression in, e.g., a transgenic plant or plant tissue, is different from the expression pattern in a wild-type plant or a reference plant of the same species. The pattern of expression may also be compared with a reference expression pattern in a wild-type plant of the same species. For example, the polynucleotide or polypeptide is expressed in a cell or tissue type other than a cell or tissue type in which the sequence is expressed in the wild-type plant, or by expression at a time other than at the time the sequence is expressed in the wild-type plant, or by a response to different inducible agents, such as hormones or environmental signals, or at different expression levels (either higher or lower) compared with those found in a wild-type plant. The term also refers to altered expression patterns that are produced by lowering the levels of expression to below the detection level or completely abolishing expression. The resulting expression pattern can be transient or stable, constitutive or inducible. In reference to a polypeptide, the term "ectopic expression or altered expression" further may relate to altered activity levels resulting from the interactions of the polypeptides with exogenous or endogenous modulators or from interactions with factors or as a result of the chemical modification of the polypeptides.

The term "overexpression" as used herein refers to a greater expression level of a gene in a plant, plant cell or plant tissue, compared to expression in a wild-type plant, cell or tissue, at any developmental or temporal stage for the gene. Overexpression can occur when, for example, the genes encoding one or more transcription factors are under the control of a strong promoter (e.g., the cauliflower mosaic virus 35S transcription initiation region). Overexpression may also under the control of an inducible or tissue specific promoter. Thus, overexpression may occur throughout a plant, in specific tissues of the plant, or in the presence or absence of particular environmental signals, depending on the promoter used.

Overexpression may take place in plant cells normally lacking expression of polypeptides functionally equivalent or identical to the present transcription factors. Overexpression may also occur in plant cells where endogenous expression of the present transcription factors or functionally equivalent molecules normally occurs, but such normal expression is at a lower level. Overexpression thus results in a greater than normal production, or "overproduction" of the transcription factor in the plant, cell or tissue.

The term "transcription regulating region" refers to a DNA regulatory sequence that regulates expression of one or more genes in a plant when a transcription factor having one or more specific binding domains binds to the DNA regulatory sequence. Transcription factors of the present invention possess an conserved domain. The transcription factors of the invention also comprise an amino acid subsequence that forms a transcription activation domain that regulates expression of one or more abiotic stress tolerance genes in a plant when the transcription factor binds to the regulating region.

Traits which May be Modified

Trait modifications of particular interest include those to seed (such as embryo or endosperm), fruit, root, flower, leaf, stem, shoot, seedling or the like, including: enhanced tolerance to environmental conditions including freezing, chilling, heat, drought, water saturation, radiation and ozone; improved tolerance to microbial, fungal or viral diseases; improved tolerance to pest infestations, including nematodes, mollicutes, parasitic higher plants or the like; decreased herbicide sensitivity; improved tolerance of heavy metals or enhanced ability to take up heavy metals; improved growth under poor photoconditions (e.g., low light and/or short day length), or changes in expression levels of genes of interest. Other phenotype that can be modified relate to the production of plant metabolites, such as variations in the production of taxol, tocopherol, tocotrienol, sterols, phytosterols, vitamins, wax monomers, anti-oxidants, amino acids, lignins, cellulose, tannins, prenyllipids (such as chlorophylls and carotenoids), glucosinolates, and terpenoids, enhanced or compositionally altered protein or oil production (especially in seeds), or modified sugar (insoluble or soluble) and/or starch composition. Physical plant characteristics that can be modified include cell development (such as the number of trichomes), fruit and seed size and number, yields of plant parts such as stems, leaves, inflorescences, and roots, the stability of the seeds during storage, characteristics of the seed pod (e.g., susceptibility to shattering), root hair length and quantity, internode distances, or the quality of seed coat. Plant growth characteristics that can be modified include growth rate, germination rate of seeds, vigor of plants and seedlings, leaf and flower senescence, male sterility, apomixis, flowering time, flower abscission, rate of nitrogen uptake, osmotic sensitivity to soluble sugar concentrations, biomass or transpiration characteristics, as well as plant architecture characteristics such as apical dominance, branching patterns, number of organs, organ identity, organ shape or size.

Transcription Factors Modify Expression of Endogenous Genes

Expression of genes which encode transcription factors that modify expression of endogenous genes, polynucleotides, and proteins are well known in the art. In addition, transgenic plants comprising isolated polynucleotides encoding transcription factors may also modify expression of endogenous genes, polynucleotides, and proteins. Examples include Peng et al. (1997) *Genes Develop.* 11: 3194-3205) and Peng et al. (1999) *Nature* 400: 256-261). In addition, many others have demonstrated that an *Arabidopsis* transcription factor expressed in an exogenous plant species elicits the same or very similar phenotypic response. See, for example, Fu et al. (2001) *Plant Cell* 13: 1791-1802); Nandi et al. (2000) *Curr. Biol.* 10: 215-218); Coupland (1995) *Nature* 377: 482-483); and Weigel and Nilsson (1995) *Nature* 377: 482-500).

In another example, Mandel et al. (1992) Cell 71-133-143) and Suzuki et al. (2001) *Plant J.* 28: 409-418) teach that a transcription factor expressed in another plant species elicits the same or very similar phenotypic response of the endogenous sequence, as often predicted in earlier studies of *Arabidopsis* transcription factors in *Arabidopsis* (see Mandel et al. (1992) supra; Suzuki et al. (2001) supra).

Other examples include Müller et al. (2001) *Plant J.* 28: 169-179); Kim et al. (2001) *Plant J.* 25: 247-259); Kyozuka and Shimamoto (2002) *Plant Cell Physiol.* 43: 130-135); Boss and Thomas (2002, *Nature* 416: 847-850); He et al. (2000) *Transgenic Res.* 9: 223-227); and Robson et al. (2001) *Plant J.* 28: 619-631).

In yet another example, Gilmour et al. (1998) *Plant J.* 16: 433-442) teach an *Arabidopsis* AP2 transcription factor, CBF1, which, when overexpressed in transgenic plants, increases plant freezing tolerance. Jaglo et al (2001) *Plant Physiol.* 127: 910-017) further identified sequences in *Brassica napus* which encode CBF-like genes and that transcripts for these genes accumulated rapidly in response to low temperature. Transcripts encoding CBF-like proteins were also found to accumulate rapidly in response to low temperature in wheat, as well as in tomato. An alignment of the CBF proteins from *Arabidopsis, B. napus*, wheat, rye, and tomato revealed the presence of conserved amino acid sequences, PKK/RPAGRxKFxETRHP and DSAWR, which bracket the AP2/EREBP DNA binding domains of the proteins and distinguish them from other members of the AP2/EREBP protein family. (See Jaglo et al. (2001) supra.)

Polypeptides and Polynucleotides of the Invention

The present invention provides, among other things, transcription factors (TFs), and transcription factor homologue polypeptides, and isolated or recombinant polynucleotides encoding the polypeptides, or novel variant polypeptides or polynucleotides encoding novel variants of transcription factors derived from the specific sequences provided here. These polypeptides and polynucleotides may be employed to modify a plant's characteristic.

Exemplary polynucleotides encoding the polypeptides of the invention were identified in the *Arabidopsis thaliana* GenBank database using publicly available sequence analysis programs and parameters. Sequences initially identified were then further characterized to identify sequences comprising specified sequence strings corresponding to sequence motifs present in families of known transcription factors. In addition, further exemplary polynucleotides encoding the polypeptides of the invention were identified in the plant GenBank database using publicly available sequence analysis programs and parameters. Sequences initially identified were then further characterized to identify sequences comprising specified sequence strings corresponding to sequence motifs present in families of known transcription factors. Polynucleotide sequences meeting such criteria were confirmed as transcription factors.

Additional polynucleotides of the invention were identified by screening *Arabidopsis thaliana* and/or other plant cDNA libraries with probes corresponding to known transcription factors under low stringency hybridization conditions. Additional sequences, including full length coding sequences were subsequently recovered by the rapid amplification of cDNA ends (RACE) procedure, using a commercially available kit according to the manufacturer's instructions. Where necessary, multiple rounds of RACE are performed to isolate 5' and 3' ends. The full length cDNA was then recovered by a routine end-to-end polymerase chain reaction (PCR) using primers specific to the isolated 5' and 3' ends. Exemplary sequences are provided in the Sequence Listing.

The polynucleotides of the invention can be or were ectopically expressed in overexpressor or knockout plants and the changes in the characteristic(s) or trait(s) of the plants observed. Therefore, the polynucleotides and polypeptides can be employed to improve the characteristics of plants.

The polynucleotides of the invention can be or were ectopically expressed in overexpressor plant cells and the changes in the expression levels of a number of genes, polynucleotides, and/or proteins of the plant cells observed. Therefore, the polynucleotides and polypeptides can be employed to change expression levels of a genes, polynucleotides, and/or proteins of plants.

The polynucleotide sequences of the invention encode polypeptides that are members of well-known transcription factor families, including plant transcription factor families, as disclosed in Table 4. Generally, the transcription factors encoded by the present sequences are involved in cell differentiation and proliferation and the regulation of growth. Accordingly, one skilled in the art would recognize that by expressing the present sequences in a plant, one may change the expression of autologous genes or induce the expression of introduced genes. By affecting the expression of similar autologous sequences in a plant that have the biological activity of the present sequences, or by introducing the present sequences into a plant, one may alter a plant's phenotype to one with improved traits. The sequences of the invention may also be used to transform a plant and introduce desirable traits not found in the wild-type cultivar or strain. Plants may then be selected for those that produce the most desirable degree of over- or under-expression of target genes of interest and coincident trait improvement.

The sequences of the present invention may be from any species, particularly plant species, in a naturally occurring form or from any source whether natural, synthetic, semi-synthetic or recombinant. The sequences of the invention may also include fragments of the present amino acid sequences. In this context, a "fragment" refers to a fragment of a polypeptide sequence which is at least 5 to about 15 amino acids in length, most preferably at least 14 amino acids, and which retain some biological activity of a transcription factor. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

As one of ordinary skill in the art recognizes, transcription factors can be identified by the presence of a region or domain of structural similarity or identity to a specific consensus sequence or the presence of a specific consensus DNA-binding site or DNA-binding site motif (see, for example, Riechmann et al. (2000a) supra). The plant transcription factors may belong to one of the following transcription factor families: the AP2 (APETALA2) domain transcription factor family (Riechmann and Meyerowitz (1998) *Biol. Chem.* 379: 633-646); the MYB transcription factor family (ENBib; Martin and Paz-Ares (1997) *Trends Genet.* 13: 67-73); the MADS domain transcription factor family (Riechmann and Meyerowitz (1997) *Biol. Chem.* 378: 1079-1101); the WRKY protein family (Ishiguro and Nakamura (1994) *Mol. Gen. Genet.* 244: 563-571); the ankyrin-repeat protein family (Zhang et al. (1992) *Plant Cell* 4: 1575-1588); the zinc finger protein (Z) family (Klug and Schwabe (1995) *FASEB J.* 9: 597-604); Takatsuji (1998) *Cell. Mol. Life Sci.* 54: 582-596); the homeobox (HB) protein family (Buerglin (1994) in *Guidebook to the Homeobox Genes*, Duboule (ed.) Oxford University Press); the CAAT-element binding proteins (Forsburg and Guarente (1989) *Genes Dev.* 3: 1166-1178); the squamosa promoter binding proteins (SPB) (Klein et al. (1996) *Mol. Gen. Genet.* 1996 250: 7-16); the NAM protein family (Souer et al. (1996) *Cell* 85: 159-170); the IAA/AUX proteins (Abel et al. (1995) *J. Mol. Biol.* 251: 533-549); the HLH/MYC protein family (Littlewood et al. (1994) *Prot. Profile* 1: 639-709); the DNA-binding protein (DBP) family (Tucker et al. (1994) *EMBO J.* 13: 2994-3002); the bZIP family of transcription factors (Foster et al. (1994) *FASEB J* 8: 192-200); the Box P-binding protein (the BPF-1) family (da Costa e Silva et al. (1993) *Plant J.* 4: 125-135); the high mobility group (HMG) family (Bustin and Reeves (1996) *Prog. Nucl. Acids Res. Mol. Biol.* 54: 35-100); the scarecrow (SCR) family (Di Laurenzio et al. (1996) *Cell* 86: 423-433); the GF14 family (Wu et al. (1997) *Plant Physiol.* 114: 1421-1431); the polycomb (PCOMB) family (Goodrich et al. (1997) *Nature* 386: 44-51); the teosinte branched (TEO) family (Luo et al. (1996) *Nature* 383: 794-799); the AB13 family (Giraudat et al. (1992) *Plant Cell* 4: 1251-1261); the triple helix (TH) family (Dehesh et al. (1990) *Science* 250: 1397-1399); the EIL family (Chao et al. (1997) *Cell* 89: 1133-44); the AT-HOOK family (Reeves and Nissen (1990) *J. Biol. Chem.* 265: 8573-8582); the SIFA family (Zhou et al. (1995) *Nucleic Acids Res.* 23: 1165-1169); the bZIPT2 family (Lu and Ferl (1995) *Plant Physiol.* 109: 723); the YABBY family (Bowman et al. (1999) *Development* 126: 2387-96); the PAZ family (Bohmert et al. (1998) *EMBO J.* 17: 170-80); a family of miscellaneous (MISC) transcription factors including the DPBF family (Kim et al. (1997) *Plant J.* 11: 1237-1251) and the SPF1 family (Ishiguro and Nakamura (1994) *Mol. Gen. Genet.* 244: 563-571); the GARP family (Hall et al. (1998) *Plant Cell* 10: 925-936), the TUBBY family (Boggin et al (1999) *Science* 286: 2119-2125), the heat shock family (Wu (1995) *Annu. Rev. Cell Dev. Biol.* 11: 441-469), the ENBP family (Christiansen et al. (1996) *Plant Mol. Biol.* 32: 809-821), the RING-zinc family (Jensen et al. (1998) *FEBS Letters* 436: 283-287), the PDBP family (Janik et al. (1989) *Virology* 168: 320-329), the PCF family (Cubas et al. *Plant J.* (1999) 18: 215-22), the SRS (SHI-related) family (Fridborg et al. (1999) *Plant Cell* 11: 1019-1032), the CPP (cysteine-rich polycomb-like) family (Cvitanich et al. (2000) *Proc. Natl. Acad. Sci.* 97: 8163-8168), the ARF (auxin response factor) family (Ulmasov et al. (1999) *Proc. Natl. Acad. Sci.* 96: 5844-5849), the SWI/SNF family (Collingwood et al.

(1999) *J. Mol. Endocrinol.* 23: 255-275), the ACBF family (Seguin et al. (1997) *Plant Mol. Biol.* 35: 281-291), PCGL (CG-1 like) family (da Costa e Silva et al. (1994) *Plant Mol. Biol.* 25: 921-924) the ARID family (Vazquez et al. (1999) *Development* 126: 733-742), the Jumonji family (Balciunas et al. (2000), *Trends Biochem. Sci.* 25: 274-276), the bZIP-NIN family (Schauser et al. (1999) *Nature* 402: 191-195), the E2F family (Kaelin et al. (1992) *Cell* 70: 351-364) and the GRF-like family (Knaap et al. (2000) *Plant Physiol.* 122: 695-704). As indicated by any part of the list above and as known in the art, transcription factors have been sometimes categorized by class, family, and sub-family according to their structural content and consensus DNA-binding site motif, for example. Many of the classes and many of the families and sub-families are listed here. However, the inclusion of one sub-family and not another, or the inclusion of one family and not another, does not mean that the invention does not encompass polynucleotides or polypeptides of a certain family or sub-family. The list provided here is merely an example of the types of transcription factors and the knowledge available concerning the consensus sequences and consensus DNA-binding site motifs that help define them as known to those of skill in the art (each of the references noted above are specifically incorporated herein by reference). A transcription factor may include, but is not limited to, any polypeptide that can activate or repress transcription of a single gene or a number of genes. This polypeptide group includes, but is not limited to, DNA-binding proteins, DNA-binding protein binding proteins, protein kinases, protein phosphatases, protein methyltransferases, GTP-binding proteins, and receptors, and the like.

In addition to methods for modifying a plant phenotype by employing one or more polynucleotides and polypeptides of the invention described herein, the polynucleotides and polypeptides of the invention have a variety of additional uses. These uses include their use in the recombinant production (i.e., expression) of proteins; as regulators of plant gene expression, as diagnostic probes for the presence of complementary or partially complementary nucleic acids (including for detection of natural coding nucleic acids); as substrates for further reactions, e.g., mutation reactions, PCR reactions, or the like; as substrates for cloning e.g., including digestion or ligation reactions; and for identifying exogenous or endogenous modulators of the transcription factors.

Producing Polypeptides

The polynucleotides of the invention include sequences that encode transcription factors and transcription factor homologue polypeptides and sequences complementary thereto, as well as unique fragments of coding sequence, or sequence complementary thereto. Such polynucleotides can be, e.g., DNA or RNA, e.g., mRNA, cRNA, synthetic RNA, genomic DNA, cDNA synthetic DNA, oligonucleotides, etc. The polynucleotides are either double-stranded or single-stranded, and include either, or both sense (i.e., coding) sequences and antisense (i.e., non-coding, complementary) sequences. The polynucleotides include the coding sequence of a transcription factor, or transcription factor homologue polypeptide, in isolation, in combination with additional coding sequences (e.g., a purification tag, a localization signal, as a fusion-protein, as a pre-protein, or the like), in combination with non-coding sequences (e.g., introns or inteins, regulatory elements such as promoters, enhancers, terminators, and the like), and/or in a vector or host environment in which the polynucleotide encoding a transcription factor or transcription factor homologue polypeptide is an endogenous or exogenous gene.

A variety of methods exist for producing the polynucleotides of the invention. Procedures for identifying and isolating DNA clones are well known to those of skill in the art, and are described in, e.g., Berger and Kimmel, *Guide to Molecular Cloning Techniques, Methods in Enzymology* volume 152 Academic Press, Inc., San Diego, Calif. ("Berger"); Sambrook et al. supra, and *Current Protocols in Molecular Biology*, F. M. Ausubel et al., eds., Current Protocols, a joint venture between Greene Publishing Associates, Inc. and John Wiley & Sons, Inc., (supplemented through 2000) ("Ausubel").

Alternatively, polynucleotides of the invention, can be produced by a variety of in vitro amplification methods adapted to the present invention by appropriate selection of specific or degenerate primers. Examples of protocols sufficient to direct persons of skill through in vitro amplification methods, including the polymerase chain reaction (PCR) the ligase chain reaction (LCR), Qβ-replicase amplification and other RNA polymerase mediated techniques (e.g., NASBA), e.g., for the production of the homologous nucleic acids of the invention are found in Berger (supra), Sambrook (supra), and Ausubel (supra), as well as Mullis et al., (1987) *PCR Protocols A Guide to Methods and Applications* (Innis et al. eds) Academic Press Inc. San Diego, Calif. (1990) (Innis). Improved methods for cloning in vitro amplified nucleic acids are described in Wallace et al., U.S. Pat. No. 5,426,039. Improved methods for amplifying large nucleic acids by PCR are summarized in Cheng et al. (1994) *Nature* 369: 684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

Alternatively, polynucleotides and oligonucleotides of the invention can be assembled from fragments produced by solid-phase synthesis methods. Typically, fragments of up to approximately 100 bases are individually synthesized and then enzymatically or chemically ligated to produce a desired sequence, e.g., a polynucleotide encoding all or part of a transcription factor. For example, chemical synthesis using the phosphoramidite method is described, e.g., by Beaucage et al. (1981) *Tetrahedron Letters* 22: 1859-1869; and Matthes et al. (1984) *EMBO J.* 3: 801-805. According to such methods, oligonucleotides are synthesized, purified, annealed to their complementary strand, ligated and then optionally cloned into suitable vectors. And if so desired, the polynucleotides and polypeptides of the invention can be custom ordered from any of a number of commercial suppliers.

Homologous Sequences

Sequences homologous, i.e., that share significant sequence identity or similarity, to those provided in the Sequence Listing, derived from *Arabidopsis thaliana* or from other plants of choice are also an aspect of the invention. Homologous sequences can be derived from any plant including monocots and dicots and in particular agriculturally important plant species, including but not limited to, crops such as soybean, wheat, corn, potato, cotton, rice, rape, oilseed rape (including canola), sunflower, alfalfa, sugarcane and turf; or fruits and vegetables, such as banana, blackberry, blueberry, strawberry, and raspberry, cantaloupe, carrot, cauliflower, coffee, cucumber, eggplant, grapes, honeydew, lettuce, mango, melon, onion, papaya, peas, peppers, pineapple, pumpkin, spinach, squash, sweet corn, tobacco, tomato, watermelon, rosaceous fruits (such as apple, peach, pear, cherry and plum) and vegetable brassicas (such as broccoli, cabbage, cauliflower, Brussels sprouts, and kohlrabi). Other crops, fruits and vegetables whose phenotype can be changed include barley, rye, millet, sorghum, currant, avocado, citrus fruits such as oranges, lemons, grapefruit and tangerines, artichoke, cherries, nuts such as the walnut and peanut, endive, leek, roots, such as arrowroot, beet, cassava, turnip, radish, yam, and sweet potato, and beans. The homologous sequences may also be derived from woody species, such pine, poplar and eucalyptus, or mint or other labiates.

Orthologs and Paralogs

Several different methods are known by those of skill in the art for identifying and defining these functionally homologous sequences. Three general methods for defining paralogs and orthologs are described; a paralog or ortholog or homolog may be identified by one or more of the methods described below.

Orthologs and paralogs are evolutionarily related genes that have similar sequence and similar functions. Orthologs are structurally related genes in different species that are derived from a speciation event. Paralogs are structurally related genes within a single species that are derived by a duplication event.

Within a single plant species, gene duplication may cause two copies of a particular gene, giving rise to two or more genes with similar sequence and similar function known as paralogs. A paralog is therefore a similar gene with a similar function within the same species. Paralogs typically cluster together or in the same clade (a group of similar genes) when a gene family phylogeny is analyzed using programs such as CLUSTAL (Thompson et al. (1994) *Nucleic Acids Res.* 22: 4673-4680; Higgins et al. (1996) *Methods Enzymol.* 266: 383-402). Groups of similar genes can also be identified with pair-wise BLAST analysis (Feng and Doolittle (1987) *J. Mol. Evol.* 25: 351-360). For example, a clade of very similar MADS domain transcription factors from *Arabidopsis* all share a common function in flowering time (Ratcliffe et al. (2001) *Plant Physiol.* 126: 122-132), and a group of very similar AP2 domain transcription factors from *Arabidopsis* are involved in tolerance of plants to freezing (Gilmour et al. (1998) *Plant J.* 16: 433-442). Analysis of groups of similar genes with similar function that fall within one clade can yield sub-sequences that are particular to the clade. These subsequences, known as consensus sequences, can not only be used to define the sequences within each clade, but define the functions of these genes; genes within a clade may contain paralogous or orthologous sequences that share the same function. (See also, for example, Mount, D. W. (2001) *Bioinformatics: Sequence and Genome Analysis*, Cold Spring Harbor Laboratory Press, Cold Spring Harbor, N.Y. page 543.)

Speciation, the production of new species from a parental species, can also give rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Transcription factor gene sequences are thus conserved across diverse eukaryotic species lines (Goodrich et al. (1993) *Cell* 75: 519-530; Lin et al. (1991) *Nature* 353: 569-571; Sadowski et al. (1988) *Nature* 335: 563-564). Plants are no exception to this observation; diverse plant species possess transcription factors that have similar sequences and functions. It is well known in the art that protein function can be classified using phylogenetic analysis of gene trees combined with the corresponding species. Functional predictions can be greatly improved by focusing on how the genes became similar in sequence (i.e., evolution) rather than on the sequence similarity itself (Eisen, (1998) Genome Res. 8: 163-167): "[t]he first step in making functional predictions is the generation of a phylogenetic tree representing the evolutionary history of the gene of interest and its homologs. Such trees are distinct from clusters and other means of characterizing sequence similarity because they are inferred by techniques that help convert patterns of similarity into evolutionary relationships . . . . After the gene tree is inferred, biologically determined functions of the various homologs are overlaid onto the tree. Finally, the structure of the tree and the relative phylogenetic positions of genes of different functions are used to trace the history of functional changes, which is then used to predict functions of [as yet] uncharacterized genes" (Eisen, supra). Thus, once a phylogenic tree for a gene family of one species has been constructed using a program such as CLUSTAL (Thompson et al. (1994) *Nucleic Acids Res.* 22: 4673-4680; Higgins et al. (1996) *Methods Enzymol.* 266: 383-402), potential orthologous sequences can be placed into the phylogenetic tree and its relationship to genes from the species of interest can be determined. Once the ortholog pair has been identified, the function of the test ortholog can be determined by determining the function of the reference ortholog. It is then a matter of routine to align sequences that are most closely related by virtue of their presence in a related clade (e.g., a group of sequences descending from a strong node of a phylogenetic tree representing a common ancestral sequence) using BLAST or similar analysis, or compare similarity or identity of the amino acid residues of these sequences and/or their conserved domains or motifs that confer and correlate with conserved function.

Transcription factors that are homologous to the listed sequences will typically share at least about 30% amino acid sequence identity, or at least about 30% amino acid sequence identity outside of a known consensus sequence or consensus DNA-binding site. More closely related transcription factors can share at least about 50%, about 60%, about 65%, about 70%, about 75% or about 80% or about 90% or about 95% or about 98% or more sequence identity with the listed sequences, or with the listed sequences but excluding or outside a known consensus sequence or consensus DNA-binding site, or with the listed sequences excluding one or all conserved domain. Factors that are most closely related to the listed sequences share, e.g., at least about 85%, about 90% or about 95% or more % sequence identity to the listed sequences, or to the listed sequences but excluding or outside a known consensus sequence or consensus DNA-binding site or outside one or all conserved domain. At the nucleotide level, the sequences will typically share at least about 40% nucleotide sequence identity, preferably at least about 50%, about 60%, about 70% or about 80% sequence identity, and more preferably about 85%, about 90%, about 95% or about 97% or more sequence identity to one or more of the listed sequences, or to a listed sequence but excluding or outside a known consensus sequence or consensus DNA-binding site, or outside one or all conserved domain. The degeneracy of the genetic code enables major variations in the nucleotide sequence of a polynucleotide while maintaining the amino acid sequence of the encoded protein. Conserved domains (for example, a DNA binding domain) within a transcription factor family may exhibit a high degree of sequence homology, such as at least about at least about 65%, or at least about 69%, or at least about 70%, or at least about 73%, or at least about 76%, or at least about 78%, or at least about 80%, or at least about 82%, or at least about 85%, or at least about 87%, or at least about 89%, or at least about 95%, amino acid residue sequence identity, to a conserved domain of a transcription factor polypeptide of the invention listed in the Sequence Listing. Transcription factors that are homologous to the listed sequences should share at least 30%, or at least about 60%, or at least about 75%, or at least about 80%, or at least about 90%, or at least about 95% amino acid sequence identity over the entire length of the polypeptide or the homolog. In addition, transcription factors that are homologous to the listed sequences should share at least 30%, or at least about 60%, or at least about 75%, or at least about 80%, or at least about 90%, or at least about 95% amino acid sequence similarity over the entire length of the polypeptide or the homolog.

Percent identity can be determined electronically, e.g., by using the MEGALIGN program (DNASTAR, Inc. Madison, Wis.). The MEGALIGN program can create alignments between two or more sequences according to different methods, e.g., the clustal method. (See, e.g., Higgins and Sharp (1988) *Gene* 73: 237-244.) The clustal algorithm groups sequences into clusters by examining the distances between all pairs. The clusters are aligned pairwise and then in groups. Other alignment algorithms or programs may be used, including FASTA, BLAST, or ENTREZ, FASTA and BLAST. These are available as a part of the GCG sequence analysis package (University of Wisconsin, Madison, Wis.), and can be used with or without default settings. ENTREZ is available through the National Center for Biotechnology Information. In one embodiment, the percent identity of two sequences can be determined by the GCG program with a gap weight of 1, e.g., each amino acid gap is weighted as if it were a single amino acid or nucleotide mismatch between the two sequences (see U.S. Pat. No. 6,262,333).

Other techniques for alignment are described in Methods in Enzymology, vol. 266: *Computer Methods for Macromolecular Sequence Analysis* (1996), ed. Doolittle, Academic Press, Inc., San Diego, Calif., USA. Preferably, an alignment program that permits gaps in the sequence is utilized to align the sequences. The Smith-Waterman is one type of algorithm that permits gaps in sequence alignments (Shpaer (1997) *Methods Mol. Biol.* 70: 173-187). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

The percentage similarity between two polypeptide sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between polynucleotide sequences can also be counted or calculated by other methods known in the art, e.g., the Jotun Hein method. (See, e.g., Hein (1990) *Methods Enzymol.* 183: 626-645.) Identity between sequences can also be determined by other methods known in the art, e.g., by varying hybridization conditions (see US Patent Application No. 20010010913).

Thus, the invention provides methods for identifying a sequence similar or paralogous or orthologous or homologous to one or more polynucleotides as noted herein, or one or more target polypeptides encoded by the polynucleotides, or otherwise noted herein and may include linking or associating a given plant phenotype or gene function with a sequence. In the methods, a sequence database is provided (locally or across an inter or intra net) and a query is made against the sequence database using the relevant sequences herein and associated plant phenotypes or gene functions.

In addition, one or more polynucleotide sequences or one or more polypeptides encoded by the polynucleotide sequences may be used to search against a BLOCKS (Bairoch et al. (1997) *Nucleic Acids Res.* 25: 217-221), PFAM, and other databases which contain previously identified and annotated motifs, sequences and gene functions. Methods that search for primary sequence patterns with secondary structure gap penalties (Smith et al. (1992) *Protein Engineering* 5: 35-51) as well as algorithms such as Basic Local Alignment Search Tool (BLAST; Altschul (1993) *J. Mol. Evol.* 36: 290-300; Altschul et al. (1990) supra), BLOCKS (Henikoff and Henikoff (1991) *Nucl. Acids Res.* 19: 6565-6572), Hidden Markov Models (HMM; Eddy (1996) *Curr. Opin. Str. Biol.* 6: 361-365; Sonnhammer et al. (1997) *Proteins* 28: 405-420), and the like, can be used to manipulate and analyze polynucleotide and polypeptide sequences encoded by polynucleotides. These databases, algorithms and other methods are well known in the art and are described in Ausubel et al. (1997) *Short Protocols in Molecular Biology*, John Wiley & Sons, New York N.Y., unit 7.7) and in Meyers, R. A. (1995) *Molecular Biology and Biotechnology*, Wiley VCH, New York N.Y., p 856-853).

Furthermore, methods using manual alignment of sequences similar or homologous to one or more polynucleotide sequences or one or more polypeptides encoded by the polynucleotide sequences may be used to identify regions of similarity and conserved domains. Such manual methods are well-known of those of skill in the art and can include, for example, comparisons of tertiary structure between a polypeptide sequence encoded by a polynucleotide which comprises a known function, with a polypeptide sequence encoded by a polynucleotide sequence which has a function not yet determined. Such examples of tertiary structure may comprise predicted a helices, β-sheets, amphipathic helices, leucine zipper motifs, zinc finger motifs, proline-rich regions, cysteine repeat motifs, and the like.

VI. Identifying Polynucleotides or Nucleic Acids by Hybridization

Polynucleotides homologous to the sequences illustrated in the Sequence Listing and tables can be identified, e.g., by hybridization to each other under stringent or under highly stringent conditions. Single stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number thereof), as described in more detail in the references cited above. Encompassed by the invention are polynucleotide sequences that are capable of hybridizing to the polynucleotide sequences, listed in the Sequence Listing; and fragments, thereof under various conditions of stringency. (See, e.g., Wahl and Berger (1987) *Methods Enzymol.* 152: 399-

407; Kimmel, A. R. (1987) *Methods Enzymol.* 152: 507-511.) Estimates of homology are provided by either DNA-DNA or DNA-RNA hybridization under conditions of stringency as is well understood by those skilled in the art (Hames and Higgins, eds. (1985) *Nucleic Acid Hybridisation*, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

In addition to the nucleotide sequences listed in Table 4, full length cDNA, orthologs, paralogs and homologs of the present nucleotide sequences may be identified and isolated using well known methods. The cDNA libraries orthologs, paralogs and homologs of the present nucleotide sequences may be screened using hybridization methods to determine their utility as hybridization target or amplification probes.

An example of stringent hybridization conditions for hybridization of complementary nucleic acids which have more than 100 complementary residues on a filter in a Southern or northern blot is about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Nucleic acid molecules that hybridize under stringent conditions will typically hybridize to a probe based on either the entire cDNA or selected portions, e.g., to a unique subsequence, of the cDNA under wash conditions of 0.2×SSC to 2.0×SSC, 0.1% SDS at 50-65° C. For example, high stringency is about 0.2×SSC, 0.1% SDS at 65° C. Ultra-high stringency will be the same conditions except the wash temperature is raised about 3 to about 5° C., and ultra-ultra-high stringency will be the same conditions except the wash temperature is raised about 6 to about 9° C. For identification of less closely related homologues washes can be performed at a lower temperature, e.g., 50° C. In general, stringency is increased by raising the wash temperature and/or decreasing the concentration of SSC, as known in the art.

In another example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

The washing steps that follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C. Another preferred set of highly stringent conditions uses two final washes in 0.1×SSC, 0.1% SDS at 65° C. The most preferred high stringency washes are of at least about 68° C. For example, in a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, the wash steps will occur at 68° C. in 15 mM NaCl, 1.5 mM trisodium citrate, and 0.1% SDS. Additional variations on these conditions will be readily apparent to those skilled in the art (see U.S. Patent Application No. 20010010913).

As another example, stringent conditions can be selected such that an oligonucleotide that is perfectly complementary to the coding oligonucleotide hybridizes to the coding oligonucleotide with at least about a 5-10× higher signal to noise ratio than the ratio for hybridization of the perfectly complementary oligonucleotide to a nucleic acid encoding a transcription factor known as of the filing date of the application. Conditions can be selected such that a higher signal to noise ratio is observed in the particular assay which is used, e.g., about 15×, 25×, 35×, 50× or more. Accordingly, the subject nucleic acid hybridizes to the unique coding oligonucleotide with at least a 2× higher signal to noise ratio as compared to hybridization of the coding oligonucleotide to a nucleic acid encoding known polypeptide. Again, higher signal to noise ratios can be selected, e.g., about 5×, 10×, 25×, 35×, 50× or more. The particular signal will depend on the label used in the relevant assay, e.g., a fluorescent label, a colorimetric label, a radioactive label, or the like.

Alternatively, transcription factor homolog polypeptides can be obtained by screening an expression library using antibodies specific for one or more transcription factors. With the provision herein of the disclosed transcription factor, and transcription factor homologue nucleic acid sequences, the encoded polypeptide(s) can be expressed and purified in a heterologous expression system (e.g., *E. coli*) and used to raise antibodies (monoclonal or polyclonal) specific for the polypeptide(s) in question. Antibodies can also be raised against synthetic peptides derived from transcription factor, or transcription factor homologue, amino acid sequences. Methods of raising antibodies are well known in the art and are described in Harlow and Lane (1988) *Antibodies: A Laboratory Manual*, Cold Spring Harbor Laboratory, New York. Such antibodies can then be used to screen an expression library produced from the plant from which it is desired to clone additional transcription factor homologues, using the methods described above. The selected cDNAs can be confirmed by sequencing and enzymatic activity.

Sequence Variations

It will readily be appreciated by those of skill in the art, that any of a variety of polynucleotide sequences are capable of encoding the transcription factors and transcription factor homologue polypeptides of the invention. Due to the degeneracy of the genetic code, many different polynucleotides can encode identical and/or substantially similar polypeptides in addition to those sequences illustrated in the Sequence Listing. Nucleic acids having a sequence that differs from the sequences shown in the Sequence Listing, or complementary sequences, that encode functionally equivalent peptides (i.e., peptides having some degree of equivalent or similar biological activity) but differ in sequence from the sequence shown in the sequence listing due to degeneracy in the genetic code, are also within the scope of the invention.

Altered polynucleotide sequences encoding polypeptides include those sequences with deletions, insertions, or substitutions of different nucleotides, resulting in a polynucleotide encoding a polypeptide with at least one functional characteristic of the instant polypeptides. Included within this definition are polymorphisms which may or may not be readily detectable using a particular oligonucleotide probe of the polynucleotide encoding the instant polypeptides, and improper or unexpected hybridization to allelic variants, with a locus other than the normal chromosomal locus for the polynucleotide sequence encoding the instant polypeptides.

Allelic variant refers to any of two or more alternative forms of a gene occupying the same chromosomal locus. Allelic variation arises naturally through mutation, and may result in phenotypic polymorphism within populations. Gene mutations can be silent (i.e., no change in the encoded polypeptide) or may encode polypeptides having altered amino acid sequence. The term allelic variant is also used herein to denote a protein encoded by an allelic variant of a gene. Splice variant refers to alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Those skilled in the art would recognize that G47, SEQ ID NO: 66, represents a single transcription factor; allelic variation and alternative splicing may be expected to occur. Allelic variants of SEQ ID NO: 65 can be cloned by probing cDNA or genomic libraries from different individual organisms according to standard procedures. Allelic variants of the DNA sequence shown in SEQ ID NO: 65, including those containing silent mutations and those in which mutations result in amino acid sequence changes, are within the scope of the present invention, as are proteins which are allelic variants of SEQ ID NO: 66. cDNAs generated from alternatively spliced mRNAs, which retain the properties of the transcription factor are included within the scope of the present invention, as are polypeptides encoded by such cDNAs and mRNAs. Allelic variants and splice variants of these sequences can be cloned by probing cDNA or genomic libraries from different individual organisms or tissues according to standard procedures known in the art (see U.S. Pat. No. 6,388,064).

For example, Table 1 illustrates, e.g., that the codons AGC, AGT, TCA, TCC, TCG, and TCT all encode the same amino acid: serine. Accordingly, at each position in the sequence where there is a codon encoding serine, any of the above trinucleotide sequences can be used without altering the encoded polypeptide.

TABLE 1

| Amino acid | | | Possible Codons | | | |
|---|---|---|---|---|---|---|
| Alanine | Ala | A | GCA | GCC | GCG | GCU |
| Cysteine | Cys | C | TGC | TGT | | |
| Aspartic acid | Asp | D | GAC | GAT | | |
| Glutamic acid | Glu | E | GAA | GAG | | |
| Phenylalanine | Phe | F | TTC | TTT | | |
| Glycine | Gly | G | GGA | GGC | GGG | GGT |
| Histidine | His | H | CAC | CAT | | |
| Isoleucine | Ile | I | ATA | ATC | ATT | |
| Lysine | Lys | K | AAA | AAG | | |
| Leucine | Leu | L | TTA | TTG | CTA | CTC | CTG | CTT |
| Methionine | Met | M | ATG | | | |
| Asparagine | Asn | N | AAC | AAT | | |
| Proline | Pro | P | CCA | CCC | CCG | CCT |
| Glutamine | Gln | Q | CAA | CAG | | |
| Arginine | Arg | R | AGA | AGG | CGA | CGC | CGG | CGT |
| Serine | Ser | S | AGC | AGT | TCA | TCC | TCG | TCT |
| Threonine | Thr | T | ACA | ACC | ACG | ACT |
| Valine | Val | V | GTA | GTG | GTG | GTT |
| Tryptophan | Trp | W | TGG | | | |
| Tyrosine | Tyr | Y | TAC | TAT | | |

Sequence alterations that do not change the amino acid sequence encoded by the polynucleotide are termed "silent" variations. With the exception of the codons ATG and TGG, encoding methionine and tryptophan, respectively, any of the possible codons for the same amino acid can be substituted by a variety of techniques, e.g., site-directed mutagenesis, available in the art. Accordingly, any and all such variations of a sequence selected from the above table are a feature of the invention.

In addition to silent variations, other conservative variations that alter one, or a few amino acids in the encoded polypeptide, can be made without altering the function of the polypeptide, these conservative variants are, likewise, a feature of the invention.

For example, substitutions, deletions and insertions introduced into the sequences provided in the Sequence Listing are also envisioned by the invention. Such sequence modifications can be engineered into a sequence by site-directed mutagenesis (Wu (ed.) *Meth. Enzymol.* (1993) vol. 217, Academic Press) or the other methods noted below. Amino acid substitutions are typically of single residues; insertions usually will be on the order of about from 1 to 10 amino acid residues; and deletions will range about from 1 to 30 residues. In preferred embodiments, deletions or insertions are made in adjacent pairs, e.g., a deletion of two residues or insertion of two residues. Substitutions, deletions, insertions or any combination thereof can be combined to arrive at a sequence. The mutations that are made in the polynucleotide encoding the transcription factor should not place the sequence out of reading frame and should not create complementary regions that could produce secondary mRNA structure. Preferably, the polypeptide encoded by the DNA performs the desired function.

Conservative substitutions are those in which at least one residue in the amino acid sequence has been removed and a different residue inserted in its place. Such substitutions generally are made in accordance with the Table 2 when it is desired to maintain the activity of the protein. Table 2 shows amino acids which can be substituted for an amino acid in a protein and which are typically regarded as conservative substitutions.

TABLE 2

| Residue | Conservative Substitutions |
|---------|---------------------------|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Similar substitutions are those in which at least one residue in the amino acid sequence has been removed and a different residue inserted in its place. Such substitutions generally are made in accordance with the Table 3 when it is desired to maintain the activity of the protein. Table 3 shows amino acids which can be substituted for an amino acid in a protein and which are typically regarded as structural and functional substitutions. For example, a residue in column 1 of Table 3 may be substituted with residue in column 2; in addition, a residue in column 2 of Table 3 may be substituted with the residue of column 1.

TABLE 3

| Residue | Similar Substitutions |
|---------|----------------------|
| Ala | Ser; Thr; Gly; Val; Leu; Ile |
| Arg | Lys; His; Gly |
| Asn | Gln; His; Gly; Ser; Thr |
| Asp | Glu, Ser; Thr |
| Gln | Asn; Ala |
| Cys | Ser; Gly |
| Glu | Asp |
| Gly | Pro; Arg |
| His | Asn; Gln; Tyr; Phe; Lys; Arg |
| Ile | Ala; Leu; Val; Gly; Met |
| Leu | Ala; Ile; Val; Gly; Met |
| Lys | Arg; His; Gln; Gly; Pro |
| Met | Leu; Ile; Phe |
| Phe | Met; Leu; Tyr; Trp; His; Val; Ala |
| Ser | Thr; Gly; Asp; Ala; Val; Ile; His |
| Thr | Ser; Val; Ala; Gly |
| Trp | Tyr; Phe; His |
| Tyr | Trp; Phe; His |
| Val | Ala; Ile; Leu; Gly; Thr; Ser; Glu |

Substitutions that are less conservative than those in Table 2 can be selected by picking residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Further Modifying Sequences of the Invention—Mutation/Forced Evolution

In addition to generating silent or conservative substitutions as noted, above, the present invention optionally includes methods of modifying the sequences of the Sequence Listing. In the methods, nucleic acid or protein modification methods are used to alter the given sequences to produce new sequences and/or to chemically or enzymatically modify given sequences to change the properties of the nucleic acids or proteins.

Thus, in one embodiment, given nucleic acid sequences are modified, e.g., according to standard mutagenesis or artificial evolution methods to produce modified sequences. The modified sequences may be created using purified natural polynucleotides isolated from any organism or may be synthesized from purified compositions and chemicals using chemical means well know to those of skill in the art. For example, Ausubel, supra, provides additional details on mutagenesis methods. Artificial forced evolution methods are described, for example, by Stemmer (1994) Nature 370: 389-391, Stemmer (1994) Proc. Natl. Acad. Sci. USA 91: 10747-10751, and U.S. Pat. Nos. 5,811,238, 5,837,500, and 6,242,568. Methods for engineering synthetic transcription factors and other polypeptides are described, for example, by Zhang et al. (2000) J. Biol. Chem. 275: 33850-33860, Liu et al. (2001) J. Biol. Chem. 276: 11323-11334, and Isalan et al. (2001) Nature Biotechnol. 19: 656-660. Many other mutation and evolution methods are also available and expected to be within the skill of the practitioner.

Similarly, chemical or enzymatic alteration of expressed nucleic acids and polypeptides can be performed by standard methods. For example, sequence can be modified by addition of lipids, sugars, peptides, organic or inorganic compounds, by the inclusion of modified nucleotides or amino acids, or the like. For example, protein modification techniques are illustrated in Ausubel, supra. Further details on chemical and enzymatic modifications can be found herein. These modification methods can be used to modify any given sequence, or to modify any sequence produced by the various mutation and artificial evolution modification methods noted herein.

Accordingly, the invention provides for modification of any given nucleic acid by mutation, evolution, chemical or enzymatic modification, or other available methods, as well as for the products produced by practicing such methods, e.g., using the sequences herein as a starting substrate for the various modification approaches.

For example, optimized coding sequence containing codons preferred by a particular prokaryotic or eukaryotic host can be used e.g., to increase the rate of translation or to produce recombinant RNA transcripts having desirable properties, such as a longer half-life, as compared with transcripts produced using a non-optimized sequence. Translation stop codons can also be modified to reflect host preference. For example, preferred stop codons for *Saccharomyces cerevisiae* and mammals are TAA and TGA, respectively. The preferred stop codon for monocotyledonous plants is TGA, whereas insects and *E. coli* prefer to use TAA as the stop codon.

The polynucleotide sequences of the present invention can also be engineered in order to alter a coding sequence for a variety of reasons, including but not limited to, alterations which modify the sequence to facilitate cloning, processing and/or expression of the gene product. For example, alterations are optionally introduced using techniques which are well known in the art, e.g., site-directed mutagenesis, to insert new restriction sites, to alter glycosylation patterns, to change codon preference, to introduce splice sites, etc.

Furthermore, a fragment or domain derived from any of the polypeptides of the invention can be combined with domains derived from other transcription factors or synthetic domains to modify the biological activity of a transcription factor. For instance, a DNA-binding domain derived from a transcription factor of the invention can be combined with the activation domain of another transcription factor or with a synthetic activation domain. A transcription activation domain assists in initiating transcription from a DNA-binding site. Examples include the transcription activation region of VP16 or GAL4 (Moore et al. (1998) *Proc. Natl. Acad. Sci. USA* 95: 376-381; and Aoyama et al. (1995) *Plant Cell* 7: 1773-1785), peptides derived from bacterial sequences (Ma and Ptashne (1987) *Cell* 51; 113-119) and synthetic peptides (Giniger and Ptashne, (1987) *Nature* 330: 670-672).

Expression and Modification of Polypeptides

Typically, polynucleotide sequences of the invention are incorporated into recombinant DNA (or RNA) molecules that direct expression of polypeptides of the invention in appropriate host cells, transgenic plants, in vitro translation systems, or the like. Due to the inherent degeneracy of the genetic code, nucleic acid sequences which encode substantially the same or a functionally equivalent amino acid sequence can be substituted for any listed sequence to provide for cloning and expressing the relevant homologue.

Vectors, Promoters, and Expression Systems

The present invention includes recombinant constructs comprising one or more of the nucleic acid sequences herein. The constructs typically comprise a vector, such as a plasmid, a cosmid, a phage, a virus (e.g., a plant virus), a bacterial artificial chromosome (BAC), a yeast artificial chromosome (YAC), or the like, into which a nucleic acid sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available.

General texts that describe molecular biological techniques useful herein, including the use and production of vectors, promoters and many other relevant topics, include Berger, Sambrook and Ausubel, supra. Any of the identified sequences can be incorporated into a cassette or vector, e.g., for expression in plants. A number of expression vectors suitable for stable transformation of plant cells or for the establishment of transgenic plants have been described including those described in Weissbach and Weissbach, (1989) *Methods for Plant Molecular Biology*, Academic Press, and Gelvin et al., (1990) *Plant Molecular Biology Manual*, Kluwer Academic Publishers. Specific examples include those derived from a Ti plasmid of *Agrobacterium tumefaciens*, as well as those disclosed by Herrera-Estrella et al. (1983) *Nature* 303: 209, Bevan (1984) *Nucl Acid Res.* 12: 8711-8721, Klee (1985) *Bio/Technology* 3: 637-642, for dicotyledonous plants.

Alternatively, non-Ti vectors can be used to transfer the DNA into monocotyledonous plants and cells by using free DNA delivery techniques. Such methods can involve, for example, the use of liposomes, electroporation, microprojectile bombardment, silicon carbide whiskers, and viruses. By using these methods transgenic plants such as wheat, rice (Christou (1991) *Bio/Technology* 9: 957-962) and corn (Gordon-Kamm (1990) *Plant Cell* 2: 603-618) can be produced. An immature embryo can also be a good target tissue for monocots for direct DNA delivery techniques by using the particle gun (Weeks et al. (1993) *Plant Physiol.* 102: 1077-1084; Vasil (1993) *Bio/Technology* 10: 667-674; Wan and Lemeaux (1994) *Plant Physiol.* 104: 37-48, and for *Agrobacterium*-mediated DNA transfer (Ishida et al. (1996) *Nature Biotech.* 14: 745-750).

Typically, plant transformation vectors include one or more cloned plant coding sequence (genomic or cDNA) under the transcriptional control of 5' and 3' regulatory sequences and a dominant selectable marker. Such plant transformation vectors typically also contain a promoter (e.g., a regulatory region controlling inducible or constitutive, environmentally- or developmentally-regulated, or cell- or tissue-specific expression), a transcription initiation start site, an RNA processing signal (such as intron splice sites), a transcription termination site, and/or a polyadenylation signal.

Examples of constitutive plant promoters which can be useful for expressing the TF sequence include: the cauliflower mosaic virus (CaMV) 35S promoter, which confers constitutive, high-level expression in most plant tissues (see, e.g., Odell et al. (1985) *Nature* 313: 810-812); the nopaline synthase promoter (An et al. (1988) *Plant Physiol.* 88: 547-552); and the octopine synthase promoter (Fromm et al. (1989) *Plant Cell* 1: 977-984).

A variety of plant gene promoters that regulate gene expression in response to environmental, hormonal, chemical, developmental signals, and in a tissue-active manner can be used for expression of a TF sequence in plants. Choice of a promoter is based largely on the phenotype of interest and is determined by such factors as tissue (e.g., seed, fruit, root, pollen, vascular tissue, flower, carpel, etc.), inducibility (e.g., in response to wounding, heat, cold, drought, light, pathogens, etc.), timing, developmental stage, and the like. Numerous known promoters have been characterized and can favorably be employed to promote expression of a polynucleotide of the invention in a transgenic plant or cell of interest. For example, tissue specific promoters include: seed-specific promoters (such as the napin, phaseolin or DC3 promoter described in U.S. Pat. No. 5,773,697), fruit-specific promoters that are active during fruit ripening (such as the dru 1 promoter (U.S. Pat. No. 5,783,393), or the 2A11 promoter (U.S. Pat. No. 4,943,674) and the tomato polygalacturonase promoter (Bird et al. (1988) *Plant Mol. Biol.* 11: 651), root-specific promoters, such as those disclosed in U.S. Pat. Nos. 5,618,988, 5,837,848 and 5,905,186, pollen-active promoters such as PTA29, PTA26 and PTA13 (U.S. Pat. No. 5,792,929), promoters active in vascular tissue (Ringli and Keller (1998) *Plant Mol. Biol.* 37: 977-988), flower-specific (Kaiser et al, (1995) *Plant Mol. Biol.* 28: 231-243), pollen (Baerson et al. (1994) *Plant Mol. Biol.* 126: 1947-1959), carpels (Ohl et al. (1990) *Plant Cell* 2: 837-848), pollen and ovules (Baerson et al. (1993) *Plant Mol. Biol.* 22: 255-267), auxin-inducible promoters (such as that described in van der Kop et al. (1999)

*Plant Mol. Biol.* 39: 979-990 or Baumann et al. (1999) *Plant Cell* 11: 323-334), cytokinin-inducible promoter (Guevara-Garcia (1998) *Plant Mol. Biol.* 38: 743-753), promoters responsive to gibberellin (Shi et al. (1998) *Plant Mol. Biol.* 38: 1053-1060, Willmott et al. (1998) *Plant Mol. Biol.* 38: 817-825) and the like. Additional promoters are those that elicit expression in response to heat (Ainley et al. (1993) *Plant Mol. Biol.* 22: 13-23), light (e.g., the pea rbcS-3A promoter, Kuhlemeier et al. (1989) *Plant Cell* 1: 471, and the maize rbcS promoter, Schaffner and Sheen (1991) *Plant Cell* 3: 997); wounding (e.g., wunI, Siebertz et al. (1989) *Plant Cell* 1: 961); pathogens (such as the PR-1 promoter described in Buchel et al. (1999) *Plant Mol. Biol.* 40: 387-396, and the PDF1.2 promoter described in Manners et al. (1998) *Plant Mol. Biol.* 38: 1071-80), and chemicals such as methyl jasmonate or salicylic acid (Gatz et al. (1997) *Plant Mol. Biol.* 48: 89-108). In addition, the timing of the expression can be controlled by using promoters such as those acting at senescence (An and Amazon (1995) *Science* 270: 1986-1988); or late seed development (Odell et al. (1994) *Plant Physiol.* 106: 447-458).

Plant expression vectors can also include RNA processing signals that can be positioned within, upstream or downstream of the coding sequence. In addition, the expression vectors can include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

The following represent specific examples of expression constructs used to overexpress sequences of the invention. The choice of promoters may include, for example, the constitutive CaMV 35S promoter, the STM shoot apical meristem-specific promoter, the CUT1 epidermal-specific promoter, the LTP1 epidermal-specific promoter, the SUC2 vascular-specific promoter, the RBCS3 leaf-specific promoter, the ARSK1 root-specific promoter, the RD29A stress inducible promoter, the AP1 floral meristem-specific promoter (SEQ ID NO: 209-217, respectively). Many of these examples have been used to produce transgenic plants. These or other inducible or tissue-specific promoters may be incorporated into an expression vector comprising a transcription factor polynucleotide of the invention, where the promoter is operably linked to the transcription factor polynucleotide, can be envisioned and produced.

P894 (SEQ ID NO: 218) contained a 35S::G47 direct fusion and carries KanR. The construct contains a G47 cDNA clone.

An alternative means of overexpressing G47 makes use of the two constructs P6506 (SEQ ID NO: 233; 35S::LexA-GAL4TA) and P3853 (SEQ ID NO: 224; opLexA::G47), which together constituted a two-component system for expression of G47 from the 35S promoter. A kanamycin resistant transgenic line containing P6506 was established, and this was then supertransformed with the P3853 construct containing a cDNA clone of G47 and a sulfonamide resistance marker.

P1572 (SEQ ID NO: 219) comprised a 35S::G2133 direct promoter fusion and carries KanR. The construct contains a cDNA clone of G2133

P23456 (SEQ ID NO: 220) contained a 35S::G3649 direct promoter fusion and carries KanR. The construct contains a cDNA clone of G3649.

P23455 (SEQ ID NO: 221) contained a 35S::G3644 direct promoter fusion and carries KanR. The construct contains a cDNA clone of G3644.

P23465 (SEQ ID NO: 222) contained a 35S::G3643 direct fusion and carries KanR. The construct harbors a cDNA clone of G3643.

P25402 (SEQ ID NO: 223) contained a 35S::G3650 direct fusion and carries KanR. The construct contains a cDNA clone.

The two constructs P5318 (SEQ ID NO: 225; STM::LexA-GAL4TA) and P3853 (SEQ ID NO: 224; opLexA::G47) together constitute a two-component system for expression of G47 from the STM promoter. Kanamycin resistant transgenic lines containing P5318 were established (lines #5 and #10), and these were then supertransformed with the P3853 construct containing a cDNA clone of G47 and a sulfonamide resistance marker.

The two constructs P5288 (SEQ ID NO: 226; CUT1::LexA-GAL4TA) and P3853 (SEQ ID NO: 224; opLexA::G47) together constitute a two-component system for expression of G47 from the CUT1 promoter. A kanamycin resistant transgenic line containing P5288 was established, and this was then supertransformed with the P3853 construct containing a cDNA clone of G47 and a sulfonamide resistance marker.

The two constructs P5284 (SEQ ID NO: 235; RBCS3::LexA-GAL4TA) and P3853 (SEQ ID NO: 224; opLexA::G47) together constituted a two-component system for expression of G47 from the RBCS3 promoter. A kanamycin resistant transgenic line containing P5284 was established, and this was then supertransformed with the P3853 construct containing a cDNA clone of G47 and a sulfonamide resistance marker.

The two constructs P5290 (SEQ ID NO: 234; SUC2::LexA-GAL4TA) and P3853 (SEQ ID NO: 224; opLexA::G47) together constitute a two-component system for expression of G47 from the SUC2 promoter. A kanamycin resistant transgenic line containing P5290 was established, and this was then supertransformed with the P3853 construct containing a cDNA clone of G47 and a sulfonamide resistance marker.

The two constructs P5311 (SEQ ID NO: 236; ARSK1::LexA-GAL4TA) and P3853 (SEQ ID NO: 224; opLexA::G47) together constitute a two-component system for expression of G47 from the ARSK1 promoter. A kanamycin resistant transgenic line containing P5311 was established, and this was then supertransformed with the P3853 construct containing a cDNA clone of G47 and a sulfonamide resistance marker.

The two constructs P9002 (SEQ ID NO: 237; RD29A::LexA-GAL4TA) and P3853 (SEQ ID NO: 224; opLexA::G47) together constitute a two-component system for expression of G47 from the RD29A promoter. A kanamycin resistant transgenic line (#5) containing P9002 was established, and this was then supertransformed with the P3853 construct containing a cDNA clone of G47 and a sulfonamide resistance marker.

The two constructs P5326 (SEQ ID NO: 238; AP1::LexA-GAL4TA) and P3853 (SEQ ID NO: 224; opLexA::G47) together constitute a two-component system for expression of G47 from the AP1 promoter. A kanamycin resistant transgenic line containing P5326 was established, and this was then supertransformed with the P3853 construct containing a cDNA clone of G47 and a sulfonamide resistance marker.

P25186 (SEQ ID NO: 239) contains a 35S::GAL4-G47 fusion and carries KanR (addition to the G47 protein of a strong transcription activation domain from the yeast GAL4 gene). SEQ ID NO: 240 is the predicted polypeptide that results expression of the vector comprising SEQ ID NO: 239.

P25279 (SEQ ID NO: 241) carries a 35S::G47-GFP fusion directly fused to the 35S promoter and a KanR marker. SEQ ID NO: 242 is the predicted polypeptide that results expression of the vector comprising SEQ ID NO: 239.

Similar to constructs made with G47, other vectors may be produced that incorporate a promoter and other transcription factor polynucleotide combination. For example, the two constructs P9002 (SEQ ID NO: 237; RD29A::LexA-GAL4TA) and P4361 (SEQ ID NO: 227; opLexA::G2133) together constitute a two-component system for expression of G2133 from the RD29A promoter. A kanamycin resistant transgenic line containing P9002 was established, and this was then supertransformed with the P4361 construct containing a cDNA clone of G2133 and a sulfonamide resistance marker.

Additional Expression Elements

Specific initiation signals can aid in efficient translation of coding sequences. These signals can include, e.g., the ATG initiation codon and adjacent sequences. In cases where a coding sequence, its initiation codon and upstream sequences are inserted into the appropriate expression vector, no additional translational control signals may be needed. However, in cases where only coding sequence (e.g., a mature protein coding sequence), or a portion thereof, is inserted, exogenous transcriptional control signals including the ATG initiation codon can be separately provided. The initiation codon is provided in the correct reading frame to facilitate transcription. Exogenous transcriptional elements and initiation codons can be of various origins, both natural and synthetic. The efficiency of expression can be enhanced by the inclusion of enhancers appropriate to the cell system in use.

Expression Hosts

The present invention also relates to host cells which are transduced with vectors of the invention, and the production of polypeptides of the invention (including fragments thereof) by recombinant techniques. Host cells are genetically engineered (i.e., nucleic acids are introduced, e.g., transduced, transformed or transfected) with the vectors of this invention, which may be, for example, a cloning vector or an expression vector comprising the relevant nucleic acids herein. The vector is optionally a plasmid, a viral particle, a phage, a naked nucleic acid, etc. The engineered host cells can be cultured in conventional nutrient media modified as appropriate for activating promoters, selecting transformants, or amplifying the relevant gene. The culture conditions, such as temperature, pH and the like, are those previously used with the host cell selected for expression, and will be apparent to those skilled in the art and in the references cited herein, including, Sambrook and Ausubel.

The host cell can be a eukaryotic cell, such as a yeast cell, or a plant cell, or the host cell can be a prokaryotic cell, such as a bacterial cell. Plant protoplasts are also suitable for some applications. For example, the DNA fragments are introduced into plant tissues, cultured plant cells or plant protoplasts by standard methods including electroporation (Fromm et al. (1985) *Proc. Natl. Acad. Sci. USA* 82: 5824-5828, infection by viral vectors such as cauliflower mosaic virus (CaMV) (Hohn et al. (1982) *Molecular Biology of Plant Tumors*, (Academic Press, New York) pp. 549-560; U.S. Pat. No. 4,407, 956), high velocity ballistic penetration by small particles with the nucleic acid either within the matrix of small beads or particles, or on the surface (Klein et al., (1987) *Nature* 327: 70-73), use of pollen as vector (WO 85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch et al. (1984) *Science* 233: 496-498; Fraley et al. (1983) *Proc. Natl. Acad. Sci. USA* 80: 4803-4807).

The cell can include a nucleic acid of the invention which encodes a polypeptide, wherein the cells expresses a polypeptide of the invention. The cell can also include vector sequences, or the like. Furthermore, cells and transgenic plants that include any polypeptide or nucleic acid above or throughout this specification, e.g., produced by transduction of a vector of the invention, are an additional feature of the invention.

For long-term, high-yield production of recombinant proteins, stable expression can be used. Host cells transformed with a nucleotide sequence encoding a polypeptide of the invention are optionally cultured under conditions suitable for the expression and recovery of the encoded protein from cell culture. The protein or fragment thereof produced by a recombinant cell may be secreted, membrane-bound, or contained intracellularly, depending on the sequence and/or the vector used. As will be understood by those of skill in the art, expression vectors containing polynucleotides encoding mature proteins of the invention can be designed with signal sequences which direct secretion of the mature polypeptides through a prokaryotic or eukaryotic cell membrane.

Modified Amino Acid Residues

Polypeptides of the invention may contain one or more modified amino acid residues. The presence of modified amino acids may be advantageous in, for example, increasing polypeptide half-life, reducing polypeptide antigenicity or toxicity, increasing polypeptide storage stability, or the like. Amino acid residue(s) are modified, for example, co-translationally or post-translationally during recombinant production or modified by synthetic or chemical means.

Non-limiting examples of a modified amino acid residue include incorporation or other use of acetylated amino acids, glycosylated amino acids, sulfated amino acids, prenylated (e.g., farnesylated, geranylgeranylated) amino acids, PEG modified (e.g., "PEGylated") amino acids, biotinylated amino acids, carboxylated amino acids, phosphorylated amino acids, etc. References adequate to guide one of skill in the modification of amino acid residues are replete throughout the literature.

The modified amino acid residues may prevent or increase affinity of the polypeptide for another molecule, including, but not limited to, polynucleotide, proteins, carbohydrates, lipids and lipid derivatives, and other organic or synthetic compounds.

Identification of Additional Factors

A transcription factor provided by the present invention can also be used to identify additional endogenous or exogenous molecules that can affect a phenotype or trait of interest. On the one hand, such molecules include organic (small or large molecules) and/or inorganic compounds that affect expression of (i.e., regulate) a particular transcription factor. Alternatively, such molecules include endogenous molecules that are acted upon either at a transcriptional level by a transcription factor of the invention to modify a phenotype as desired. For example, the transcription factors can be employed to identify one or more downstream gene with which is subject to a regulatory effect of the transcription factor. In one approach, a transcription factor or transcription factor homologue of the invention is expressed in a host cell, e.g., a transgenic plant cell, tissue or explant, and expression products, either RNA or protein, of likely or random targets are monitored, e.g., by hybridization to a microarray of nucleic acid probes corresponding to genes expressed in a tissue or cell type of interest, by two-dimensional gel electrophoresis of protein products, or by any other method known in the art for assessing expression of gene products at the level of RNA or protein. Alternatively, a transcription factor of the invention can be used to identify promoter sequences (i.e., binding sites) involved in the regulation of a downstream target. After identifying a promoter sequence, interactions between the transcription factor and the promoter sequence can be modified by changing specific nucleotides in the promoter sequence or specific amino acids in the transcription factor that interact with the promoter sequence to alter a plant trait. Typically, transcription factor DNA-binding sites are identified by gel shift assays. After identifying the promoter regions, the promoter region sequences can be employed in double-stranded DNA arrays to identify molecules that affect the interactions of the transcription factors with their promoters (Bulyk et al. (1999) *Nature Biotechnol.* 17: 573-577).

The identified transcription factors are also useful to identify proteins that modify the activity of the transcription factor. Such modification can occur by covalent modification, such as by phosphorylation, or by protein-protein (homo or -heteropolymer) interactions. Any method suitable for detecting protein-protein interactions can be employed. Among the methods that can be employed are co-immunoprecipitation, cross-linking and co-purification through gradients or chromatographic columns, and the two-hybrid yeast system.

The two-hybrid system detects protein interactions in vivo and is described in Chien et al. ((1991), *Proc. Natl. Acad. Sci. USA* 88: 9578-9582) and is commercially available from Clontech (Palo Alto, Calif.). In such a system, plasmids are constructed that encode two hybrid proteins: one consists of the DNA-binding domain of a transcription activator protein fused to the TF polypeptide and the other consists of the transcription activator protein's activation domain fused to an unknown protein that is encoded by a cDNA that has been recombined into the plasmid as part of a cDNA library. The DNA-binding domain fusion plasmid and the cDNA library are transformed into a strain of the yeast *Saccharomyces cerevisiae* that contains a reporter gene (e.g., lacZ) whose regulatory region contains the transcription activator's binding site. Either hybrid protein alone cannot activate transcription of the reporter gene. Interaction of the two hybrid proteins reconstitutes the functional activator protein and results in expression of the reporter gene, which is detected by an assay for the reporter gene product. Then, the library plasmids responsible for reporter gene expression are isolated and sequenced to identify the proteins encoded by the library plasmids. After identifying proteins that interact with the transcription factors, assays for compounds that interfere with the TF protein-protein interactions can be preformed.

Identification of Modulators

In addition to the intracellular molecules described above, extracellular molecules that alter activity or expression of a transcription factor, either directly or indirectly, can be identified. For example, the methods can entail first placing a candidate molecule in contact with a plant or plant cell. The molecule can be introduced by topical administration, such as spraying or soaking of a plant, and then the molecule's effect on the expression or activity of the TF polypeptide or the expression of the polynucleotide monitored. Changes in the expression of the TF polypeptide can be monitored by use of polyclonal or monoclonal antibodies, gel electrophoresis or the like. Changes in the expression of the corresponding polynucleotide sequence can be detected by use of microarrays, Northerns, quantitative PCR, or any other technique for monitoring changes in mRNA expression. These techniques are exemplified in Ausubel et al. (eds) *Current Protocols in Molecular Biology*, John Wiley & Sons (1998, and supplements through 2001). Such changes in the expression levels can be correlated with modified plant traits and thus identified molecules can be useful for soaking or spraying on fruit, vegetable and grain crops to modify traits in plants.

Essentially any available composition can be tested for modulatory activity of expression or activity of any nucleic acid or polypeptide herein. Thus, available libraries of compounds such as chemicals, polypeptides, nucleic acids and the like can be tested for modulatory activity. Often, potential modulator compounds can be dissolved in aqueous or organic (e.g., DMSO-based) solutions for easy delivery to the cell or plant of interest in which the activity of the modulator is to be tested. Optionally, the assays are designed to screen large modulator composition libraries by automating the assay steps and providing compounds from any convenient source to assays, which are typically run in parallel (e.g., in microtiter formats on microtiter plates in robotic assays).

In one embodiment, high throughput screening methods involve providing a combinatorial library containing a large number of potential compounds (potential modulator compounds). Such "combinatorial chemical libraries" are then screened in one or more assays, as described herein, to identify those library members (particular chemical species or subclasses) that display a desired characteristic activity. The compounds thus identified can serve as target compounds.

A combinatorial chemical library can be, e.g., a collection of diverse chemical compounds generated by chemical synthesis or biological synthesis. For example, a combinatorial chemical library such as a polypeptide library is formed by combining a set of chemical building blocks (e.g., in one example, amino acids) in every possible way for a given compound length (i.e., the number of amino acids in a polypeptide compound of a set length). Exemplary libraries include peptide libraries, nucleic acid libraries, antibody libraries (see, e.g., Vaughn et al. (1996) *Nature Biotechnol.*, 14: 309-314 and PCT/US96/10287), carbohydrate libraries (see, e.g., Liang et al. *Science* (1996) 274: 1520-1522 and U.S. Pat. No. 5,593,853), peptide nucleic acid libraries (see, e.g., U.S. Pat. No. 5,539,083), and small organic molecule libraries (see, e.g., benzodiazepines, Baum *Chem. Eng. News* January 18, page 33 (1993); isoprenoids, U.S. Pat. No. 5,569, 588; thiazolidinones and metathiazanones, U.S. Pat. No. 5,549,974; pyrrolidines, U.S. Pat. Nos. 5,525,735 and 5,519, 134; morpholino compounds, U.S. Pat. No. 5,506,337) and the like.

Preparation and screening of combinatorial or other libraries is well known to those of skill in the art. Such combinatorial chemical libraries include, but are not limited to, peptide libraries (see, e.g., U.S. Pat. No. 5,010,175; Furka (1991) *Int. J. Pept. Prot. Res.* 37: 487-493; and Houghton et al. (1991) *Nature* 354: 84-88). Other chemistries for generating chemical diversity libraries can also be used.

In addition, as noted, compound screening equipment for high-throughput screening is generally available, e.g., using any of a number of well known robotic systems that have also been developed for solution phase chemistries useful in assay systems. These systems include automated workstations including an automated synthesis apparatus and robotic systems utilizing robotic arms. Any of the above devices are suitable for use with the present invention, e.g., for high-throughput screening of potential modulators. The nature and implementation of modifications to these devices (if any) so that they can operate as discussed herein will be apparent to persons skilled in the relevant art.

Indeed, entire high throughput screening systems are commercially available. These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. Similarly, microfluidic implementations of screening are also commercially available.

The manufacturers of such systems provide detailed protocols the various high throughput. Thus, for example, Zymark Corp. provides technical bulletins describing screening systems for detecting the modulation of gene transcription, ligand binding, and the like. The integrated systems herein, in addition to providing for sequence alignment and, optionally, synthesis of relevant nucleic acids, can include such screening apparatus to identify modulators that have an effect on one or more polynucleotides or polypeptides according to the present invention.

In some assays it is desirable to have positive controls to ensure that the components of the assays are working properly. At least two types of positive controls are appropriate. That is, known transcriptional activators or inhibitors can be incubated with cells/plants/etc. in one sample of the assay, and the resulting increase/decrease in transcription can be detected by measuring the resulting increase in RNA/protein expression, etc., according to the methods herein. It will be appreciated that modulators can also be combined with transcriptional activators or inhibitors to find modulators that inhibit transcriptional activation or transcriptional repression. Either expression of the nucleic acids and proteins herein or any additional nucleic acids or proteins activated by the nucleic acids or proteins herein, or both, can be monitored.

In an embodiment, the invention provides a method for identifying compositions that modulate the activity or expression of a polynucleotide or polypeptide of the invention. For example, a test compound, whether a small or large molecule, is placed in contact with a cell, plant (or plant tissue or explant), or composition comprising the polynucleotide or polypeptide of interest and a resulting effect on the cell, plant, (or tissue or explant) or composition is evaluated by monitoring, either directly or indirectly, one or more of: expression level of the polynucleotide or polypeptide, activity (or modulation of the activity) of the polynucleotide or polypeptide. In some cases, an alteration in a plant phenotype can be detected following contact of a plant (or plant cell, or tissue or explant) with the putative modulator, e.g., by modulation of expression or activity of a polynucleotide or polypeptide of the invention. Modulation of expression or activity of a polynucleotide or polypeptide of the invention may also be caused by molecular elements in a signal transduction second messenger pathway and such modulation can affect similar elements in the same or another signal transduction second messenger pathway.

Subsequences

Also contemplated are uses of polynucleotides, also referred to herein as oligonucleotides, typically having at least 12 bases, preferably at least 15, more preferably at least 20, 30, or 50 bases, which hybridize under at least highly stringent (or ultra-high stringent or ultra-ultra-high stringent conditions) conditions to a polynucleotide sequence described above. The polynucleotides may be used as probes, primers, sense and antisense agents, and the like, according to methods as noted supra.

Subsequences of the polynucleotides of the invention, including polynucleotide fragments and oligonucleotides are useful as nucleic acid probes and primers. An oligonucleotide suitable for use as a probe or primer is at least about 15 nucleotides in length, more often at least about 18 nucleotides, often at least about 21 nucleotides, frequently at least about 30 nucleotides, or about 40 nucleotides, or more in length. A nucleic acid probe is useful in hybridization protocols, e.g., to identify additional polypeptide homologues of the invention, including protocols for microarray experiments. Primers can be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods. See Sambrook and Ausubel, supra.

In addition, the invention includes an isolated or recombinant polypeptide including a subsequence of at least about 15 contiguous amino acids encoded by the recombinant or isolated polynucleotides of the invention. For example, such polypeptides, or domains or fragments thereof, can be used as immunogens, e.g., to produce antibodies specific for the polypeptide sequence, or as probes for detecting a sequence of interest. A subsequence can range in size from about 15 amino acids in length up to and including the full length of the polypeptide.

To be encompassed by the present invention, an expressed polypeptide which comprises such a polypeptide subsequence performs at least one biological function of the intact polypeptide in substantially the same manner, or to a similar extent, as does the intact polypeptide. For example, a polypeptide fragment can comprise a recognizable structural motif or functional domain such as a DNA binding domain that binds to a specific DNA promoter region, an activation domain or a domain for protein-protein interactions.

Production of Transgenic Plants

Modification of Traits

The polynucleotides of the invention are favorably employed to produce transgenic plants with various traits, or characteristics, that have been modified in a desirable manner, e.g., to improve the seed characteristics of a plant. For example, alteration of expression levels or patterns (e.g., spatial or temporal expression patterns) of one or more of the transcription factors (or transcription factor homologues) of the invention, as compared with the levels of the same protein found in a wild type plant, can be used to modify a plant's traits. An illustrative example of trait modification, improved characteristics, by altering expression levels of a particular transcription factor is described further in the Examples and the Sequence Listing.

*Arabidopsis* as a Model System

*Arabidopsis thaliana* is the object of rapidly growing attention as a model for genetics and metabolism in plants. *Arabidopsis* has a small genome, and well documented studies are available. It is easy to grow in large numbers and mutants defining important genetically controlled mechanisms are either available, or can readily be obtained. Various methods to introduce and express isolated homologous genes are available (see Koncz, et al., eds. *Methods in Arabidopsis Research*. et al. (1992), World Scientific, New Jersey, N. J., in "Preface"). Because of its small size, short life cycle, obligate autogamy and high fertility, *Arabidopsis* is also a choice organism for the isolation of mutants and studies in morphogenetic and development pathways, and control of these pathways by transcription factors (Koncz, supra, p. 72). A number of studies introducing transcription factors into *A. thaliana* have demonstrated the utility of this plant for understanding the mechanisms of gene regulation and trait alteration in plants. See, for example, Koncz, supra, and U.S. Pat. No. 6,417,428).

*Arabidopsis* Genes in Transgenic Plants.

Expression of genes which encode transcription factors modify expression of endogenous genes, polynucleotides, and proteins are well known in the art. In addition, transgenic plants comprising isolated polynucleotides encoding transcription factors may also modify expression of endogenous genes, polynucleotides, and proteins. Examples include Peng et al. (1997) *Genes Develop.* 11: 3194-3205) and Peng et al. (1999) *Nature* 400: 256-261). In addition, many others have demonstrated that an *Arabidopsis* transcription factor expressed in an exogenous plant species elicits the same or very similar phenotypic response. See, for example, Fu et al. (2001) *Plant Cell* 13: 1791-1802); Nandi et al. (2000) *Curr. Biol.* 10: 215-218); Coupland (1995) *Nature* 377: 482-483); and Weigel and Nilsson (1995, *Nature* 377: 482-500).

Homologous Genes Introduced into Transgenic Plants.

Homologous genes that may be derived from any plant, or from any source whether natural, synthetic, semi-synthetic or recombinant, and that share significant sequence identity or similarity to those provided by the present invention, may be introduced into plants, for example, crop plants, to confer desirable or improved traits. Consequently, transgenic plants may be produced that comprise a recombinant expression vector or cassette with a promoter operably linked to one or more sequences homologous to presently disclosed sequences. The promoter may be, for example, a plant or viral promoter.

The invention thus provides for methods for preparing transgenic plants, and for modifying plant traits. These methods include introducing into a plant a recombinant expression vector or cassette comprising a functional promoter operably linked to one or more sequences homologous to presently disclosed sequences. Plants and kits for producing these plants that result from the application of these methods are also encompassed by the present invention.

Traits of Interest

Examples of some of the traits that may be desirable in plants, and that may be provided by transforming the plants with the presently disclosed sequences, are listed in Tables 4 and 6.

The first column of Table 4 shows the polynucleotide SEQ ID NO; the second column shows the Mendel Gene ID No., GID; the third column shows the transcription factor family to which the polynucleotide belongs; the fourth column shows the category of the trait; the fifth column shows the trait(s) resulting from the knock out or overexpression of the polynucleotide in the transgenic plant; the sixth column ("Comment"), includes specific effects and utilities conferred by the polynucleotide of the first column; the seventh column shows the SEQ ID NO of the polypeptide encoded by the polynucleotide; and the eighth column shows the amino acid residue positions of the conserved domain in amino acid (AA) coordinates.

The first column (Col. 1) of Table 4 lists the SEQ ID NO: of presently disclosed polynucleotide sequences. The second column lists the corresponding GID number. The third column shows the transcription factor family in which each of the respective sequences is found. The fourth column lists the conserved domains in amino acid coordinates of the respective encoded polypeptide sequences. The fifth and sixth columns list the trait category and specific traits observed for plants overexpressing the respective sequences (except where noted as "KO" in Col. 2 for plants in which the respective sequence was knocked out).

TABLE 4

Sequences of the invention and the traits they confer in plants

| Col. 1 SEQ ID NO: | Col. 2 GID No. | Col. 3 Family | Col. 4 Conserved domains | Col. 5 Trait Category | Col. 6 Observed trait(s) |
|---|---|---|---|---|---|
| 1 | G1272 | PAZ | 800-837 | Seed glucosinolates | Decrease in seed glucosinolate M39497 |
| 3 | G1506 | GATA/Zn | 7-33 | Seed glucosinolates | Increase in glucosinolates M39502 and M39498 |
| 5 | G1897 | Z-Dof | 34-62 | Seed glucosinolates | Increase in seed glucosinolates M39491 and M39493 |
| 7 | G1946 | HS | 37-128 | Seed glucosinolates | Increase in seed glucosinolate M39501 Increased tolerance to phosphate-free media |
| 9 | G2113 | AP2 | 55-122 | Seed glucosinolates | Decrease in seed glucosinolate M39497, increase of glucosinolates M39501, M39494 and M39478 |
| 11 | G2117 | bZIP | 46-106 | Seed glucosinolates | Decrease in M39496 |
| 13 | G2155 | AT-hook | 18-38 | Seed glucosinolates Plant size | Increase in M39497 Large plant size |
| 15 | G2290 | WRKY | 147-205 | Seed glucosinolates | Increase in M39496 |
| 17 | G2340 | MYB-(R1)R2R3 | 14-120 | Seed glucosinolates | Altered glucosinolate profile |
| 21 | G353 | Z-C2H2 | 41-61, 84-104 | Seed glucosinolates | Increase in M39494 |
| 23 | G484 (KO) | CAAT | 11-104 | Seed glucosinolates | Altered glucosinolate profile |
| 25 | G674 | MYB-(R1)R2R3 | 20-120 | Seed glucosinolates | Increase in M39501 |

TABLE 4-continued

Sequences of the invention and the traits they confer in plants

| Col. 1 SEQ ID NO: | Col. 2 GID No. | Col. 3 Family | Col. 4 Conserved domains | Col. 5 Trait Category | Col. 6 Observed trait(s) |
|---|---|---|---|---|---|
| 27 | G1052 | bZIP | 201-261 | Seed prenyl lipids | Decrease in lutein and increase in xanthophyll 1 |
| 29 | G1328 | MYB-(R1)R2R3 | 14-119 | Seed prenyl lipids | Decreased seed lutein |
| 31 | G1930 | AP2 | 59-124, 179-273 | Seed prenyl lipids | Increased chlorophyll a and b content |
|  |  |  |  | C/N sensing | Increased tolerance to low nitrogen conditions in C/N sensing assay |
| 33 | G214 | MYB-related | 25-71 | Seed prenyl lipids; leaf fatty acids; prenyl lipids | Increased seed lutein; increased leaf fatty acids; increased chlorophyll, carotenoids |
|  |  |  |  | Plant size | Larger biomass (increased leaf number and size |
|  |  |  |  | Prenyl lipids | Darker green in vegetative and reproductive tissues due to a higher chlorophyll content in the later stages of development |
| 35 | G2509 | AP2 | 89-156 | Seed prenyl lipids | Increase in α-tocopherol |
| 37 | G2520 | HLH/MYC | 139-197 | Seed prenyl lipids; leaf glucosinolates | Increase in seed δ-tocopherol and decrease in seed γ-tocopherol.; increase in M39478 |
|  |  |  |  | C/N sensing | Increased tolerance to low nitrogen conditions in C/N sensing assay |
| 39 | G259 | HS | 40-131 | Seed prenyl lipids | Increase in α-tocopherol |
| 41 | G490 | CAAT | 48-143 | Seed prenyl lipids | Increase in seed δ-tocopherol |
| 43 | G652 | Z-CLDSH | 28-49, 137-151, 182-196 | Seed prenyl lipids; leaf glucosinolates | Increase in α-tocopherol; increase in M39480 |
| 45 | G748 | Z-Dof | 112-140 | Seed prenyl lipids | Increased lutein content |
| 47 | G883 | WRKY | 245-302 | Seed prenyl lipids | Decreased seed lutein |
| 49 | G20 | AP2 | 68-144 | Seed sterols | Increase in campesterol |
| 51 | G974 | AP2 | 80-147 | Seed oil content | Altered seed oil content |
| 53 | G2343 | MYB-(R1)R2R3 | 14-116 | Seed oil content | Increased seed oil content |
| 55 | G1777 | RING/C3HC4 | 124-247 | Seed oil and protein content | Increased seed oil content and decreased seed protein |
| 57 | G229 | MYB-(R1)R2R3 | 14-120 | Biochemistry: other | Up-regulation of genes involved in secondary metabolism; Genes coding for enzymes involved in alkaloid biosynthesis including indole-3-glycerol phosphatase and strictosidine synthase were induced; genes for enzymes involved in aromatic amino acid biosynthesis were also up-regulated including tryptophan synthase and tyrosine transaminase. Phenylalanine ammonia lyase, chalcone synthase and trans-cinnamate mono-oxygenase, involved in phenylpropenoid biosynthesis, were also induced |
| 59 | G663 | MYB-(R1)R2R3 | 9-111 | Biochemistry: other | Increased anthocyanins in leaf, root, seed |
| 61 | G362 | Z-C2H2 | 62-82 | Biochemistry: other | Increased trichome density and trichome products; increased |

TABLE 4-continued

Sequences of the invention and the traits they confer in plants

| Col. 1 SEQ ID NO: | Col. 2 GID No. | Col. 3 Family | Col. 4 Conserved domains | Col. 5 Trait Category | Col. 6 Observed trait(s) |
|---|---|---|---|---|---|
| | | | | | anthocyanins in various tissues |
| 63 | G2105 | TH | 100-153 | Biochemistry: other | Increased trichome density and trichome products |
| 65 | G47 | AP2 | 11-80 | Flowering Time Biochemistry: other Abiotic stress tolerance | Increased lignin content Increased cold tolerance Increased drought tolerance Increased desiccation tolerance Increased salt tolerance Late flowering Dark green Increased leaf size, larger rosettes and/or increased amount of vegetative tissue |
| 67 | G2123 | GF14 | 99-109 | Biochemistry: other | Putative 14-3-3 protein |
| 69 | G1266 | AP2 | 79-147 | Leaf fatty acids, insoluble sugars; | Changes in leaf fatty acids, insoluble sugars, decreased sensitivity to ABA |
| | | | | C/N sensing | Increased tolerance to low nitrogen conditions in C/N sensing assay |
| 71 | G1337 | Z-CO-like | 9-75 | Leaf fatty acids | Increase in the amount of oleic acid |
| | | | | Sugar sensing | Decreased tolerance to sucrose |
| 73 | G1399 | AT-hook | 86-93 | Leaf fatty acids | Increase of the percentage of the 16:0 fatty acid |
| 75 | G1465 | NAC | 242-306 | Leaf fatty acids | Increases in the percentages of 16:0, 16:1, 18:0 and 18:2 and decreases in 16:3 and 18:3 fatty acids |
| 77 | G1512 | RING/C3HC4 | 39-93 | Leaf fatty acids | Increase in 18:2 fatty acids |
| 79 | G1537 | HB | 14-74 | Leaf fatty acids | Altered leaf fatty acid composition |
| 81 | G2136 | MADS | 43-100 | Leaf fatty acids | Decrease in 18:3 fatty acid |
| 83 | G2147 | HLH/MYC | 163-220 | Leaf fatty acids | Increase in 16:0, increase in 18:2 fatty acids |
| 85 | G377 | RING/C3H2C3 | 85-128 | Leaf fatty acids | Increased 18:2 and decreased 18:3 leaf fatty acids |
| 87 | G962 | NAC | 53-175 | Leaf fatty acids | Increased 16:0 and decreased 18:3 leaf fatty acids |
| 89 | G975 | AP2 | 4-71 | Leaf fatty acids | Increased wax in leaves Increased C29, C31, and C33 alkanes increased up to 10-fold compared to control plants; More drought tolerant than controls |
| | | | | C/N sensing | Increased tolerance to low nitrogen conditions in C/N sensing assay |
| 91 | G987 | SCR | 395-462, 525-613, 1027-1102, 1162-1255 | Leaf fatty acids; leaf prenyl lipids | Reduction in 16:3 fatty acids; altered chlorophyll, tocopherol, carotenoid |
| 93 | G1069 | AT-hook | 67-74 | Leaf and seed glucosinolates | Altered leaf glucosinolate composition Increased seed glucosinolate M39497 |

TABLE 4-continued

Sequences of the invention and the traits they confer in plants

| Col. 1 SEQ ID NO: | Col. 2 GID No. | Col. 3 Family | Col. 4 Conserved domains | Col. 5 Trait Category | Col. 6 Observed trait(s) |
|---|---|---|---|---|---|
| | | | | | Increased 16:0 fatty acid, decreased 18:2 fatty acids, decreased sensitivity to ABA |
| | | | | C/N sensing | Increased tolerance to low nitrogen conditions in C/N sensing assay |
| 95 | G1198 | bZIP | 173-223 | Leaf glucosinolates | Increase in M39481 |
| 97 | G1322 | MYB-(R1)R2R3 | 26-130 | Leaf glucosinolates C/N sensing | Increase in M39480 Increased tolerance to low nitrogen conditions in C/N sensing assay |
| 99 | G1421 | AP2 | 74-151 | Leaf glucosinolates | Increased leaf content of glucosinolate M39482 |
| 101 | G1794 | AP2 | 182-249 | Leaf glucosinolates | Increased leaf content of glucosinolate M39480 |
| 103 | G2144 | HLH/MYC | 207-265 | Leaf glucosinolates | Increased leaf content of glucosinolate M39480 |
| | | | | C/N sensing | Increased tolerance to low nitrogen conditions in C/N sensing assay |
| 105 | G2512 | AP2 | 79-147 | Leaf glucosinolates | Increased leaf content of glucosinolate M39481 |
| | | | | C/N sensing | Increased tolerance to low nitrogen conditions in C/N sensing assay |
| 107 | G2552 | HLH/MYC | 124-181 | Leaf glucosinolates | Increased leaf content of glucosinolate M39480 |
| 109 | G264 | HS | 23-114 | Leaf glucosinolates | Increased leaf content of glucosinolate M39481 |
| 111 | G681 | MYB-(R1)R2R3 | 14-120 | Leaf glucosinolates | Increased leaf content of glucosinolate M39480 |
| 113 | G1012 | WRKY | 30-86 | Leaf insoluble sugars | Decreased rhamnose |
| 115 | G1309 | MYB-(R1)R2R3 | 9-114 | Leaf insoluble sugars | Increased mannose |
| 117 | G158 | MADS | 2-57 | Leaf insoluble sugars | Increased rhamnose |
| 119 | G1641 | MYB-related | 32-82, 141-189 | Leaf insoluble sugars | Increased rhamnose |
| 121 | G1865 | GRF-like | 45-162 | Leaf insoluble sugars | Increased galactose, decreased xylose |
| 123 | G2094 | GATA/Zn | 43-68 | Leaf insoluble sugars | Increase in arabinose |
| 125 | G211 | MYB-(R1)R2R3 | 24-137 | Leaf insoluble sugars | Increase in xylose |
| 127 | G242 | MYB-(R1)R2R3 | 6-105 | Leaf insoluble sugars | Increased arabinose |
| 129 | G2589 | MADS | 1-57 | Leaf insoluble sugars | Increase in arabinose |
| 131 | G274 | AKR | 94-600 | Leaf insoluble sugars | Increased leaf arabinose |
| 133 | G598 | DBP | 205-263 | Leaf insoluble sugars | Altered insoluble sugars; (increased galactose levels) |
| 135 | G1543 | HB | 135-195 | Leaf prenyl lipids | Increase in chlorophyll a and b Increased biomass |
| 137 | G280 | AT-hook | 97-104, 130-137-155-162, 185-192 | Leaf prenyl lipids | Increased δ- and γ-tocopherol |
| 139 | G2131 | AP2 | 50-121, 146-217 | Leaf sterols C/N sensing | Increase in campesterol Increased tolerance to low nitrogen conditions in C/N sensing assay |
| 141 | G2424 | MYB-(R1)R2R3 | 107-219 | Leaf sterols | Increase in stigmastanol |
| 143 | G2583 | AP2 | 4-71 | Leaf wax Flowering time | Glossy leaves, increased epicuticular wax content or altered composition Late developing, late flowering time |
| 147 | G977 | AP2 | 5-72 | Leaf wax | Altered epicuticular wax content or composition |

TABLE 4-continued

Sequences of the invention and the traits they confer in plants

| Col. 1 SEQ ID NO: | Col. 2 GID No. | Col. 3 Family | Col. 4 Conserved domains | Col. 5 Trait Category | Col. 6 Observed trait(s) |
|---|---|---|---|---|---|
| 151 | G2133 | AP2 | 11-82 | Flowering Time Biochemistry: other Abiotic stress tolerance | Increased cold tolerance Increased drought tolerance Increased desiccation tolerance Increased salt tolerance Late flowering Dark green Increased leaf size and/or larger rosette Increased seed size |
| 157 | G3643 | AP2 | 14-79 | Flowering Time Biochemistry: other Abiotic stress tolerance | Increased cold tolerance Increased drought tolerance Increased desiccation tolerance Increased heat tolerance Late flowering Dark green Larger plants |
| 155 | G3644 | AP2 | 55-102 | Flowering Time Biochemistry: other Abiotic stress tolerance | Increased salt tolerance Late flowering Dark green Large seedlings Large rosettes with long, broad leaves |
| 153 | G3649 | AP2 | 18-61 | Flowering Time Biochemistry: other Abiotic stress tolerance | Increased cold tolerance Increased drought tolerance Increased desiccation tolerance Decreased heat tolerance Late flowering Dark green Larger rosettes Large cauline leaves |
| 145 | G1387 | AP2 | 4-68 | | Few lines of overexpressors have been produced or examined |
| 149 | G4294 | AP2 | 5-72 | | Overexpressors not yet produced or examined |

Abbreviations:
KO—knockout

Table 5 lists a summary of orthologous and homologous sequences identified using BLAST (tblastx program). The first column shows the polynucleotide sequence identifier (SEQ ID NO), the second column shows the corresponding cDNA identifier (Gene ID), the third column shows the orthologous or homologous polynucleotide GenBank Accession Number (Test Sequence ID), the fourth column shows the calculated probability value that the sequence identity is due to chance (Smallest Sum Probability), the fifth column shows the plant species from which the test sequence was isolated (Test Sequence Species), and the sixth column shows the orthologous or homologous test sequence GenBank annotation (Test Sequence GenBank Annotation).

Of the identified sequences homologous to the *Arabidopsis* sequences provided in Table 5, the percent sequence identity among these sequences can be as low as 47%, or even lower sequence identity. The entire NCBI GenBank database was filtered for sequences from all plants except *Arabidopsis thaliana* by selecting all entries in the NCBI GenBank database associated with NCBI taxonomic ID 33090 (Viridiplantae; all plants) and excluding entries associated with taxonomic ID 3701 (*Arabidopsis thaliana*). These sequences are compared to those listed in the Sequence Listing, using the Washington University TBLASTX algorithm (version 2.0a19MP) at the default settings using gapped alignments with the filter "off". For each sequence listed in the Sequence Listing, individual comparisons were ordered by probability score (P-value), where the score reflects the probability that a particular alignment occurred by chance. For example, a score of 3.6e-40 is $3.6 \times 10^{-40}$. In addition to P-values, comparisons were also scored by percentage identity. Percentage identity reflects the degree to which two segments of DNA or protein are identical over a particular length. The identified homologous polynucleotide and polypeptide sequences and homologs of the *Arabidopsis* polynucleotides and polypeptides may be orthologs of the *Arabidopsis* polynucleotides and polypeptides and/or closely, phylogenetically-related sequences.

TABLE 5

Sequences phylogenetically related to *Arabidopsis* sequences shown to confer useful traits in plants

| Col. 1 SEQ ID NO | Col. 2 GID or Related Sequence Identifier (Accession No.) | Col. 3 Related to GID/SEQ ID NO | Col. 4 Smallest Sum Probability | Col. 5 Species from which Sequence is Derived | Col. 6 Test Sequence GenBank Annotation |
|---|---|---|---|---|---|
| 19 | G671 | G2340/17 | 1.0E−103 | *Arabidopsis thaliana* | |
| | BG269414 | G2340/17 | 1.60E−45 | *Mesembryanthemum crystallinum* | L0-3478T3 Ice plant Lambda Un |
| | BG448527 | G2340/17 | 5.30E−41 | *Medicago truncatula* | NF036F04RT1F1032 Developing root Medica |
| | AI730649 | G2340/17 | 1.10E−40 | *Gossypium hirsutum* | BNLGHi7595 Six-day Cotton fiber Gossypiu |
| | AW706006 | G2340/17 | 1.20E−39 | *Glycine max* | sk64f05.y1 Gm-c1016 *Glycine max* cDNA clone GENO |
| | PHMYBPH31 | G2340/17 | 1.60E−39 | *Petunia* x *hybrida* | *P. hybrida* myb.Ph3 gene encoding protein |
| | AI491024 | G2340/17 | 4.10E−39 | *Lycopersicon esculentum* | EST241733 tomato shoot, Cornell Lyc |
| | AMMIXTA | G2340/17 | 1.40E−38 | *Antirrhinum majus* | *A. majus* mixta mRNA. |
| | OSMYB1355 | G2340/17 | 2.40E−38 | *Oryza sativa* | *O. sativa* mRNA for myb factor, 1355 bp. |
| | BE495300 | G2340/17 | 2.80E−37 | *Secale cereale* | WHE1268_F02_K04ZS *Secale cereale* anther cDNA |
| | BG300704 | G2340/17 | 4.70E−36 | *Hordeum vulgare* | HVSMEb0018B03f *Hordeum vulgare* seedling sho |
| | gi2605617 | G2340/17 | 1.50E−44 | *Oryza sativa* | OSMYB1. |
| | gi20563 | G2340/17 | 7.30E−42 | *Petunia* x *hybrida* | protein 1. |
| | gi485867 | G2340/17 | 4.00E−41 | *Antirrhinum majus* | mixta. |
| | gi437327 | G2340/17 | 2.00E−39 | *Gossypium hirsutum* | MYB A; putative. |
| | gi19051 | G2340/17 | 3.10E−39 | *Hordeum vulgare* | MybHv1. |
| | gi227030 | G2340/17 | 3.10E−39 | *Hordeum vulgare* var. *distichum* | myb-related gene Hv1. |
| | gi1101770 | G2340/17 | 6.40E−38 | *Picea mariana* | MYB-like transcriptional factor MBF1. |
| | gi1430846 | G2340/17 | 6.30E−36 | *Lycopersicon esculentum* | myb-related transcription factor. |
| | gi5139814 | G2340/17 | 2.50E−35 | *Glycine max* | GmMYB29B2. |
| | gi6651292 | G2340/17 | 1.70E−34 | *Pimpinella brachycarpa* | myb-related transcription factor. |
| 145 | G1387 | G2583/143 | 6.00E−72 | *Arabidopsis thaliana* | |
| 89 | G975 | G2583/143 | 3.00E−56 | *Arabidopsis thaliana* | |
| 149 | G4294 | G2583/143 | 2.00E−49 | *Oryza sativa* | |
| | AW928465 | G2583/143 | 1.40E−43 | *Lycopersicon esculentum* | EST337253 tomato flower buds 8 mm tsm80e10.y1 |
| | BE023297 | G2583/143 | 2.40E−42 | *Glycine max* | Gm-c1015 *Glycine max* cDNA clone GENO |
| | AP003615 | G2583/143 | 1.60E−30 | *Oryza sativa* | chromosome 6 clone P0486H12, *** SEQUENCING IN |
| | AU088998 | G2583/143 | 2.90E−21 | *Lotus japonicus* | AU088998 *Lotus japonicus* flower bud cDNA Lo |
| | AT001828 | G2583/143 | 4.60E−20 | *Brassica rapa* subsp. *pekinensis* | AT001828 Flower bud cDNA Br |
| | BG415973 | G2583/143 | 2.40E−18 | *Hordeum vulgare* | HVSMEk0009E06f *Hordeum vulgare* testa/perica |
| | BF647090 | G2583/143 | 3.80E−17 | *Medicago truncatula* | NF007A06EC1F1038 Elicited cell culture |
| | BG560598 | G2583/143 | 2.90E−16 | *Sorghum propinquum* | RHIZ2_59_D07.b1_A003 Rhizome2 (RHIZ2) So |
| | AW011200 | G2583/143 | 6.60E−16 | *Pinus taeda* | ST17H08 Pine TriplEx shoot tip library *Pinus ta* |

TABLE 5-continued

Sequences phylogenetically related to *Arabidopsis* sequences shown to confer useful traits in plants

| Col. 1 SEQ ID NO | Col. 2 GID or Related Sequence Identifier (Accession No.) | Col. 3 Related to GID/SEQ ID NO | Col. 4 Smallest Sum Probability | Col. 5 Species from which Sequence is Derived | Col. 6 Test Sequence GenBank Annotation |
|---|---|---|---|---|---|
| | BF479478 | G2583/143 | 1.60E−15 | *Mesembryanthemum crystallinum* | L48-3155T3 Ice plant *Lambda* U |
| | gi19507 | G2583/143 | 1.40E−16 | *Lupinus polyphyllus* | put. pPLZ2 product (AA 1-164). |
| | gi10798644 | G2583/143 | 1.00E−12 | *Nicotiana tabacum* | AP2 domain-containing transcription fac |
| | gi8571476 | G2583/143 | 4.70E−12 | *Atriplex hortensis* | apetala2 domain-containing protein. |
| | gi2213783 | G2583/143 | 8.40E−12 | *Lycopersicon esculentum* | Pti5. |
| | gi8809573 | G2583/143 | 5.30E−11 | *Nicotiana sylvestris* | ethylene-responsive element binding |
| | gi4099914 | G2583/143 | 8.40E−11 | *Stylosanthes hamata* | ethylene-responsive element binding p |
| | gi6478845 | G2583/143 | 8.90E−11 | *Matricaria chamomilla* | ethylene-responsive element binding |
| | gi15290041 | G2583/143 | 9.40E−11 | *Oryza sativa* | hypothetical protein. |
| | gi12225884 | G2583/143 | 1.70E−10 | *Zea mays* | unnamed protein product. |
| | gi3264767 | G2583/143 | 3.40E−10 | *Prunus armeniaca* | AP2 domain containing protein. |
| 242 | G361 | G362/61 | 7.0Ee−17 | *Arabidopsis thaliana* | |
| 244 | G2826 | G362/61 | 5.0E−14 | *Arabidopsis thaliana* | |
| 246 | G2838 | G362/61 | 2.0E−12 | *Arabidopsis thaliana* | |
| 248 | G1995 | G362/61 | 5.0E−10 | *Arabidopsis thaliana* | |
| 250 | G370 | G362/61 | 5.0E−10 | *Arabidopsis thaliana* | |
| | BG581135 | G362/61 | 1.70E−19 | *Medicago truncatula* | EST482865 GVN *Medicago truncatula* cDNA |
| | BI206903 | G362/61 | 7.70E−18 | *Lycopersicon esculentum* | EST524943 cTOS *Lycopersicon esculen* |
| | BG047435 | G362/61 | 7.30E−17 | *Glycine max* | saa71c12.y1 Gm-c1060 *Glycine max* cDNA clone GEN |
| | AP003214 | G362/61 | 3.00E−12 | *Oryza sativa* | chromosome 1 clone OSJNBa0083M16, *** SEQUENCI |
| | BE366047 | G362/61 | 6.40E−12 | *Sorghum bicolor* | PI1_30_G05.b2_A002 Pathogen induced 1 (PI1) |
| | BF616974 | G362/61 | 1.90E−05 | *Hordeum vulgare* | HVSMEc0014C08f *Hordeum vulgare* seedling sho |
| | BG444243 | G362/61 | 3.70E−05 | *Gossypium arboreum* | GA__Ea0023L22f *Gossypium arboreum* 7-10 d |
| | BE500265 | G362/61 | 0.00015 | *Triticum aestivum* | WHE0981_F11_L20ZS Wheat pre-anthesis spik |
| | AB006604 | G362/61 | 0.00023 | *Petunia x hybrida* | mRNA for ZPT2-9, complete cds. |
| | AI163084 | G362/61 | 0.0004 | *Populus tremula x Populus tremuloides* | A031p65u Hybrid aspen |
| | gi15528588 | G362/61 | 4.20E−15 | *Oryza sativa* | hypothetical protein. |
| | gi2346984 | G362/61 | 3.80E−08 | *Petunia x hybrida* | ZPT2-9. |
| | gi7228329 | G362/61 | 0.012 | *Medicago sativa* | putative TFIIIA (or *kruppel*)-like zinc fi |
| | gi1763063 | G362/61 | 0.016 | *Glycine max* | SCOF-1. |
| | gi485814 | G362/61 | 0.026 | *Triticum aestivum* | WZF1. |
| | gi4666360 | G362/61 | 0.03 | *Datisca glomerata* | zinc-finger protein 1. |
| | gi2058504 | G362/61 | 0.079 | *Brassica rapa* | zinc-finger protein-1. |
| | gi861091 | G362/61 | 0.08 | *Pisum sativum* | putative zinc finger protein. |
| | gi2981169 | G362/61 | 0.42 | *Nicotiana tabacum* | osmotic stress-induced zinc-finger prot |
| | BM110736 | G2105/63 | 3.70E−45 | *Solanum tuberosum* | EST558272 potato roots *Solanum tuberosum* |

TABLE 5-continued

Sequences phylogenetically related to *Arabidopsis* sequences shown to confer useful traits in plants

| Col. 1 SEQ ID NO | Col. 2 GID or Related Sequence Identifier (Accession No.) | Col. 3 Related to GID/SEQ ID NO | Col. 4 Smallest Sum Probability | Col. 5 Species from which Sequence is Derived | Col. 6 Test Sequence GenBank Annotation |
|---|---|---|---|---|---|
| | BF646615 | G2105/63 | 6.60E−36 | *Medicago truncatula* | NF066C08EC1F1065 Elicited cell culture |
| | AB052729 | G2105/63 | 9.50E−30 | *Pisum sativum* | mRNA for DNA-binding protein DF1, complete cd |
| | OSJN00022 | G2105/63 | 1.10E−26 | *Oryza sativa* | chromosome 4 clone OSJNBa0011L07, *** SEQUENC |
| | AI777252 | G2105/63 | 4.20E−25 | *Lycopersicon esculentum* | EST258217 tomato resistant, Cornell |
| | BM500043 | G2105/63 | 6.70E−24 | *Zea mays* | 952036C09.y1 952 - BMS tissue from Walbot Lab (red |
| | AP004839 | G2105/63 | 1.90E−23 | *Oryza sativa* (*japonica* cultivar-group) | ( ) chromosome 2 clo |
| | AW596787 | G2105/63 | 2.30E−20 | *Glycine max* | sj16f10.y1 Gm-c1032 *Glycine max* cDNA clone GENO |
| | AV410715 | G2105/63 | 8.70E−20 | *Lotus japonicus* | AV410715 *Lotus japonicus* young plants (two- |
| | BM357046 | G2105/63 | 3.10E−14 | *Triphysaria versicolor* | 16I-G5 *Triphysaria versicolor* root-t |
| | gi13646986 | G2105/63 | 7.50E−32 | *Pisum sativum* | DNA-binding protein DF1. |
| | gi20249 | G2105/63 | 1.30E−27 | *Oryza sativa* | gt-2. |
| | gi18182311 | G2105/63 | 8.20E−22 | *Glycine max* | GT-2 factor. |
| | gi8096269 | G2105/63 | 0.24 | *Nicotiana tabacum* | KED. |
| 167 | G3645 | G47/65 | 9.0E−64 | *Brassica rapa subsp. Pekinensis* | |
| 151 | G2133 | G47/65 | 1.0E−47 | *Arabidopsis thaliana* | |
| 165 | G3646 | G47/65 | 2.0E−46 | *Brassica oleracea* | |
| 163 | G3647 | G47/65 | 2.0E−33 | *Zinnia elegans* | |
| 157 | G3643 | G47/65 | 1.0E−29 | *Glycine max* | |
| 155 | G3644 | G47/65 | 9.0Ee−26 | *Oryza sativa* (*japonica* cultivar-group) | |
| 159 | G3650 | G47/65 | 1.0E−23 | *Zea mays* | |
| 153 | G3649 | G47/65 | 1.0E−23 | *Oryza sativa* (*japonica* cultivar-group) | |
| 161 | G3651 | G47/65 | 9.0E−21 | *Oryza sativa* (*japonica* cultivar-group) | |
| | BE320193 | G47/65 | 5.90E−23 | *Medicago truncatula* | NF024B04RT1F1029 Developing root Medica |
| | AP003379 | G47/65 | 8.90E−20 | *Oryza sativa* | chromosome 1 clone P0408G07, *** SEQUENCING IN |
| | AW220454 | G47/65 | 7.90E−16 | *Lycopersicon esculentum* | EST302937 tomato root during/after |
| | BI434553 | G47/65 | 8.90E−16 | *Solanum tuberosum* | EST537314 P. infestans-challenged leaf So |
| | BF610198 | G47/65 | 1.30E−15 | *Pinus taeda* | NXSI_055_H04_F NXSI (Nsf Xylem Side wood Inclin |
| | BE659994 | G47/65 | 2.50E−15 | *Glycine max* | 4-G2 GmaxSC *Glycine max* cDNA, mRNA sequence. |
| | BG446456 | G47/65 | 5.00E−15 | *Gossypium arboreum* | GA__Eb0034M18f *Gossypium arboreum* 7-10 d |
| | BG321374 | G47/65 | 1.10E−14 | *Descurainia sophia* | Ds01_06d08_R Ds01_AAFC_ECORC_cold_stress |
| | AI728590 | G47/65 | 2.40E−14 | *Gossypium hirsutum* | BNLGHi11133 Six-day Cotton fiber Gossypi |

TABLE 5-continued

Sequences phylogenetically related to *Arabidopsis* sequences shown to confer useful traits in plants

| Col. 1 SEQ ID NO | Col. 2 GID or Related Sequence Identifier (Accession No.) | Col. 3 Related to GID/SEQ ID NO | Col. 4 Smallest Sum Probability | Col. 5 Species from which Sequence is Derived | Col. 6 Test Sequence GenBank Annotation |
|---|---|---|---|---|---|
| | gi14140155 | G47/65 | 2.90E−16 | *Oryza sativa* | putative AP2 domain transcription factor. |
| | gi5616086 | G47/65 | 7.90E−14 | *Brassica napus* | dehydration responsive element binding pro |
| | gi12225916 | G47/65 | 8.70E−14 | *Zea mays* | unnamed protein product. |
| | gi8571476 | G47/65 | 1.30E−13 | *Atriplex hortensis* | apetala2 domain-containing protein. |
| | gi8980313 | G47/65 | 9.00E−13 | *Catharanthus roseus* | AP2-domain DNA-binding protein. |
| | gi6478845 | G47/65 | 5.00E−12 | *Matricaria chamomilla* | ethylene-responsive element binding |
| | gi1208498 | G47/65 | 6.40E−12 | *Nicotiana tabacum* | EREBP-2. |
| | gi8809573 | G47/65 | 2.20E−11 | *Nicotiana sylvestris* | ethylene-responsive element binding |
| | gi7528276 | G47/65 | 3.40E−11 | *Mesembryanthemum crystallinum* | AP2-related transcription f |
| | gi3342211 | G47/65 | 4.50E−11 | *Lycopersicon esculentum* | Pti4. |
| 149 | G4294 | G975/89 | 2.0E−65 | *Oryza sativa* | |
| 143 | G2583 | G975/89 | 3.0E−56 | *Arabidopsis thaliana* | |
| 145 | G1387 | G975/89 | 5.0E−54 | *Arabidopsis thaliana* | |
| | AP003615 | G975/89 | 1.10E−51 | *Oryza sativa* | chromosome 6 clone P0486H12, *** SEQUENCING IN |
| | BG642554 | G975/89 | 1.10E−50 | *Lycopersicon esculentum* | EST356031 tomato flower buds, anthe |
| | AW705973 | G975/89 | 3.20E−45 | *Glycine max* | sk64c02.y1 Gm-c1016 *Glycine max* cDNA clone GENO |
| | AT001828 | G975/89 | 4.80E−34 | *Brassica rapa* subsp. *pekinensis* | AT001828 Flower bud cDNA Br |
| | BG415973 | G975/89 | 3.70E−29 | *Hordeum vulgare* | HVSMEk0009E06f *Hordeum vulgare* testa/perica |
| | AU088998 | G975/89 | 2.10E−27 | *Lotus japonicus* | AU088998 *Lotus japonicus* flower bud cDNA Lo |
| | AL377839 | G975/89 | 8.40E−21 | *Medicago truncatula* | MtBB34C04F1 MtBB *Medicago truncatula* cD |
| | BF479478 | G975/89 | 2.20E−18 | *Mesembryanthemum crystallinum* | L48-3155T3 Ice plant *Lambda* U |
| | BG560598 | G975/89 | 3.40E−18 | *Sorghum propinquum* | RHIZ2_59_D07.b1_A003 Rhizome2 (RHIZ2) So |
| | L46408 | G975/89 | 5.90E−18 | *Brassica rapa* | BNAF1258 Mustard flower buds *Brassica rapa* cD |
| | gi19507 | G975/89 | 2.10E−19 | *Lupinus polyphyllus* | put. pPLZ2 product (AA 1-164). |
| | gi2213783 | G975/89 | 1.80E−15 | *Lycopersicon esculentum* | Pti5. |
| | gi8571476 | G975/89 | 2.80E−14 | *Atriplex hortensis* | apetala2 domain-containing protein. |
| | gi4099914 | G975/89 | 7.90E−14 | *Stylosanthes hamata* | ethylene-responsive element binding p |
| | gi6478845 | G975/89 | 3.40E−13 | *Matricaria chamomilla* | ethylene-responsive element binding |
| | gi12225884 | G975/89 | 5.70E−13 | *Zea mays* | unnamed protein product. |
| | gi8809573 | G975/89 | 7.00E−13 | *Nicotiana sylvestris* | ethylene-responsive element binding |
| | gi15290041 | G975/89 | 1.20E−12 | *Oryza sativa* | hypothetical protein. |
| | gi8980313 | G975/89 | 1.20E−12 | *Catharanthus roseus* | AP2-domain DNA-binding protein. |
| | gi7528276 | G975/89 | 1.30E−12 | *Mesembryanthemum crystallinum* | AP2-related transcription f |

TABLE 5-continued

Sequences phylogenetically related to *Arabidopsis* sequences shown to confer useful traits in plants

| Col. 1 SEQ ID NO | Col. 2 GID or Related Sequence Identifier (Accession No.) | Col. 3 Related to GID/SEQ ID NO | Col. 4 Smallest Sum Probability | Col. 5 Species from which Sequence is Derived | Col. 6 Test Sequence GenBank Annotation |
|---|---|---|---|---|---|
| 252 | G680 | G214/33 | 1.0E−116 | *Arabidopsis thaliana* | |
| | AW979367 | G214/33 | 4.40E−35 | *Lycopersicon esculentum* | EST310415 tomato root deficiency, C |
| | BG156656 | G214/33 | 1.80E−33 | *Glycine max* | sab31d11.y1 Gm-c1026 *Glycine max* cDNA clone GEN |
| | BE597638 | G214/33 | 5.40E−28 | *Sorghum bicolor* | PI1__72__C05.b1__A002 Pathogen induced 1 (PI1) |
| | BI272895 | G214/33 | 5.70E−26 | *Medicago truncatula* | NF091A11FL1F1084 Developing flower Medi |
| | BE129981 | G214/33 | 3.90E−23 | *Zea mays* | 945034C05.X1 945 - Mixed adult tissues from Walbot |
| | BF889434 | G214/33 | 7.50E−14 | *Oryza sativa* | EST003 Magnaporthe grisea infected 16-day-old |
| | gi15528628 | G214/33 | 7.40E−14 | *Oryza sativa* | hypothetical protein~similar to *Oryza sativa* |
| | gi7677132 | G214/33 | 0.41 | *Secale cereale* | c-myb-like transcription factor. |
| | gi13676413 | G214/33 | 0.43 | *Glycine max* | hypothetical protein. |
| | gi12406993 | G214/33 | 0.57 | *Hordeum vulgare* | MCB1 protein. |
| | gi940288 | G214/33 | 0.85 | *Pisum sativum* | protein localized in the nucleoli of pea nu nuM1. |
| | gi1279563 | G214/33 | 0.92 | *Medicago sativa* | |
| | gi12005328 | G214/33 | 0.98 | *Hevea brasiliensis* | unknown. |
| | gi7688744 | G214/33 | 0.99 | *Lycopersicon esculentum* | asc1. |
| | gi1070004 | G214/33 | 0.99 | *Brassica napus* | Biotin carboxyl carrier protein. |
| | gi5326994 | G214/33 | 1 | *Daucus carota* | DNA topoisomerase I. |
| 254 | G5 | G974/51 | 1.0E−76 | *Arabidopsis thaliana* | |
| | BI421315 | G974/51 | 7.10E−54 | *Lycopersicon esculentum* | EST531981 tomato callus, TAMU Lycop |
| | AI966402 | G974/51 | 9.40E−47 | *Glycine max* | sc38e09.y1 Gm-c1014 *Glycine max* cDNA clone GENO |
| | AF274033 | G974/51 | 1.70E−43 | *Atriplex hortensis* | apetala2 domain-containing protein mRNA, |
| | BG592917 | G974/51 | 8.40E−43 | *Solanum tuberosum* | EST491595 cSTS *Solanum tuberosum* cDNA clo |
| | AI166481 | G974/51 | 6.20E−42 | *Populus balsamifera* subsp. *trichocarpa* | xylem.est.309 Poplar |
| | AW776927 | G974/51 | 2.10E−41 | *Medicago truncatula* | EST335992 DSIL *Medicago truncatula* cDNA |
| | AP004119 | G974/51 | 2.70E−41 | *Oryza sativa* | chromosome 2 clone OJ1288__G09, *** SEQUENCING |
| | BE918036 | G974/51 | 6.60E−38 | *Sorghum bicolor* | OV1__1__B03.b1__A002 Ovary 1 (OV1) Sorghum bic |
| | gi8571476 | G974/51 | 7.00E−45 | *Atriplex hortensis* | apetala2 domain-containing protein. |
| | gi14140155 | G974/51 | 4.40E−20 | *Oryza sativa* | putative AP2 domain transcription factor. |
| | gi3342211 | G974/51 | 9.10E−20 | *Lycopersicon esculentum* | Pti4. |
| | gi1208498 | G974/51 | 1.50E−19 | *Nicotiana tabacum* | EREBP-2. |
| | gi12225884 | G974/51 | 1.50E−19 | *Zea mays* | unnamed protein product. |
| | gi7528276 | G974/51 | 3.90E−19 | *Mesembryanthemum crystallinum* | AP2-related transcription f |

TABLE 5-continued

Sequences phylogenetically related to *Arabidopsis* sequences shown to confer useful traits in plants

| Col. 1 SEQ ID NO | Col. 2 GID or Related Sequence Identifier (Accession No.) | Col. 3 Related to GID/SEQ ID NO | Col. 4 Smallest Sum Probability | Col. 5 Species from which Sequence is Derived | Col. 6 Test Sequence GenBank Annotation |
|---|---|---|---|---|---|
| | gi8809571 | G974/51 | 3.90E−19 | *Nicotiana sylvestris* | ethylene-responsive element binding |
| | gi1688233 | G974/51 | 3.50E−18 | *Solanum tuberosum* | DNA binding protein homolog. |
| | gi3264767 | G974/51 | 9.40E−18 | *Prunus armeniaca* | AP2 domain containing protein. |
| | gi6478845 | G974/51 | 2.00E−17 | *Matricaria chamomilla* | ethylene-responsive element binding |
| | BI311137 | G2343/53 | 4.00E−45 | *Medicago truncatula* | EST5312887 GESD *Medicago truncatula* cDN |
| | BG130765 | G2343/53 | 5.10E−45 | *Lycopersicon esculentum* | EST463657 tomato crown gall Lycoper |
| | AW672062 | G2343/53 | 2.30E−44 | *Sorghum bicolor* | LG1__354__G05.b1__A002 Light Grown 1 (LG1) Sor |
| | AV421932 | G2343/53 | 2.70E−42 | *Lotus japonicus* | AV421932 *Lotus japonicus* young plants (two- |
| | BE611938 | G2343/53 | 9.10E−42 | *Glycine max* | sr01h04.y1 Gm-c1049 *Glycine max* cDNA clone GENO |
| | BF484214 | G2343/53 | 1.90E−37 | *Triticum aestivum* | WHE2309__F07__K13ZS Wheat pre-anthesis spik |
| | BG301022 | G2343/53 | 4.30E−35 | *Hordeum vulgare* | HVSMEb0019E16f *Hordeum vulgare* seedling sho |
| | AP003018 | G2343/53 | 3.20E−34 | *Oryza sativa* | genomic DNA, chromosome 1, BAC clone: OSJNBa000 |
| | BE495300 | G2343/53 | 3.30E−34 | *Secale cereale* | WHE1268__F02__K04ZS *Secale cereale* anther cDNA |
| | AI657290 | G2343/53 | 3.50E−34 | *Zea mays* | 486093A08.y1 486 - leaf primordia cDNA library fro |
| | gi1167486 | G2343/53 | 9.50E−53 | *Lycopersicon esculentum* | transcription factor. |
| | gi13366181 | G2343/53 | 1.30E−48 | *Oryza sativa* | putative transcription factor. |
| | gi2130045 | G2343/53 | 1.50E−37 | *Hordeum vulgare* | MybHv33 protein - barley. |
| | gi82310 | G2343/53 | 1.60E−34 | *Antirrhinum majus* | myb protein 330 - garden snapdragon. |
| | gi1732247 | G2343/53 | 4.20E−34 | *Nicotiana tabacum* | transcription factor Myb1. |
| | gi1841475 | G2343/53 | 7.80E−33 | *Pisum sativum* | Myb26. |
| | gi5139814 | G2343/53 | 2.80E−31 | *Glycine max* | GmMYB29B2. |
| | gi13346178 | G2343/53 | 4.90E−31 | *Gossypium hirsutum* | BNLGHi233. |
| | gi6651292 | G2343/53 | 2.70E−30 | *Pimpinella brachycarpa* | myb-related transcription factor. |
| | gi8247759 | G2343/53 | 1.10E−29 | *Triticum aestivum* | GAMyb protein. |
| | AF272573 | G2123/67 | 1.30E−50 | *Populus alba* x *Populus tremula* | clone INRA717-1-B4 14-3-3 pr |
| | BG581482 | G2123/67 | 3.70E−49 | *Medicago truncatula* | EST483216 GVN *Medicago truncatula* cDNA |
| | BG351501 | G2123/67 | 9.60E−49 | *Solanum tuberosum* | 109A12 Mature tuber lambda ZAP *Solanum* tu |
| | LETFT7 | G2123/67 | 1.20E−48 | *Lycopersicon esculentum* | mRNA for 14-3-3 protein, TFT7. |
| | AF228501 | G2123/67 | 4.50E−44 | *Glycine max* | 14-3-3-like protein mRNA, complete cds. |
| | BE643058 | G2123/67 | 5.30E−44 | *Ceratopteris richardii* | Cri2__7__M14__SP6 *Ceratopteris* Spore Li |
| | AF222805 | G2123/67 | 7.00E−43 | *Euphorbia esula* | 14-3-3-like protein mRNA, complete cds. |

TABLE 5-continued

Sequences phylogenetically related to *Arabidopsis* sequences shown to confer useful traits in plants

| Col. 1 SEQ ID NO | Col. 2 GID or Related Sequence Identifier (Accession No.) | Col. 3 Related to GID/SEQ ID NO | Col. 4 Smallest Sum Probability | Col. 5 Species from which Sequence is Derived | Col. 6 Test Sequence GenBank Annotation |
|---|---|---|---|---|---|
| | PSA238682 | G2123/67 | 1.30E−42 | *Pisum sativum* | mRNA for 14-3-3-like protein, sequence 2. |
| | BG443252 | G2123/67 | 1.80E−40 | *Gossypium arboreum* | GA__Ea0020A13f *Gossypium arboreum* 7-10 d |
| | AI727536 | G2123/67 | 9.70E−40 | *Gossypium hirsutum* | BNLGHi8338 Six-day Cotton fiber Gossypiu |
| | gi8515890 | G2123/67 | 1.80E−52 | *Populus alba* × *Populus tremula* | 14-3-3 protein. |
| | gi8099061 | G2123/67 | 3.70E−52 | *Populus* × *canescens* | 14-3-3 protein. |
| | gi7576887 | G2123/67 | 1.00E−50 | *Glycine max* | 14-3-3-like protein. |
| | gi3925703 | G2123/67 | 8.90E−50 | *Lycopersicon esculentum* | 14-3-3 protein. |
| | gi6752903 | G2123/67 | 8.90E−50 | *Euphorbia esula* | 14-3-3-like protein. |
| | gi913214 | G2123/67 | 2.10E−47 | *Nicotiana tabacum* | T14-3-3. |
| | gi11138322 | G2123/67 | 3.40E−47 | *Vicia faba* | vf14-3-3d protein. |
| | gi2879818 | G2123/67 | 8.50E−46 | *Solanum tuberosum* | 14-3-3 protein. |
| | gi1015462 | G2123/67 | 8.90E−46 | *Chlamydomonas reinhardtii* | 14-3-3 protein. |
| | gi2921512 | G2123/67 | 1.10E−45 | *Fritillaria agrestis* | GF14 protein. |
| | AC091246 | G1777/55 | 3.50E−96 | *Oryza sativa* | chromosome 3 clone OSJNBa0002I03, *** SEQUENCI |
| | BG136684 | G1777/55 | 1.10E−67 | *Lycopersicon pennellii* | EST477126 wild tomato pollen Lycoper |
| | AW703793 | G1777/55 | 2.50E−65 | *Glycine max* | sk12f08.y1 Gm-c1023 *Glycine max* cDNA clone GENO |
| | BE051040 | G1777/55 | 6.60E−59 | *Zea mays* | za71g01.b50 Maize Glume cDNAs Library *Zea mays* cDN |
| | AW933922 | G1777/55 | 2.90E−53 | *Lycopersicon esculentum* | EST359765 tomato fruit mature green |
| | BG600834 | G1777/55 | 3.40E−53 | *Solanum tuberosum* | EST505729 cSTS *Solanum tuberosum* cDNA clo |
| | BF440069 | G1777/55 | 3.20E−39 | *Thellungiella salsuginea* | Sc0136 *Thellungiella salsuginea* ZA |
| | BF587440 | G1777/55 | 4.20E−25 | *Sorghum propinquum* | FM1__36__D07.b1__A003 Floral-Induced Merist |
| | BI267961 | G1777/55 | 2.10E−23 | *Medicago truncatula* | NF118E09IN1F1071 Insect herbivory Medic |
| | BE415217 | G1777/55 | 2.50E−22 | *Triticum aestivum* | MWL025.F02F000208 ITEC MWL Wheat Root Lib |
| | gi1666171 | G1777/55 | 7.50E−24 | *Nicotiana plumbaginifolia* | unknown. |
| | gi643082 | G1777/55 | 1 | *Fragaria* × *ananassa* | unknown. |
| | AW928317 | G2520/37 | 4.60E−27 | *Lycopersicon esculentum* | EST307050 tomato flower buds 8 mm t |
| | BF271147 | G2520/37 | 2.60E−26 | *Gossypium arboreum* | GA__Eb0010K15f *Gossypium arboreum* 7-10 d |
| | BE329654 | G2520/37 | 2.60E−26 | *Glycine max* | so67c05.y1 Gm-c1040 *Glycine max* cDNA clone GENO |
| | BG103016 | G2520/37 | 4.40E−23 | *Sorghum propinquum* | RHIZ2__36__A10.b1__A003 Rhizome2 (RHIZ2) So |
| | BE606980 | G2520/37 | 1.00E−22 | *Triticum aestivum* | WHE0914__F04__K08ZS Wheat 5-15 DAP spike cD |
| | BG048756 | G2520/37 | 1.60E−22 | *Sorghum bicolor* | OV1__22__F05.b1__A002 Ovary 1 (OV1) *Sorghum bi* |

TABLE 5-continued

Sequences phylogenetically related to *Arabidopsis* sequences shown to confer useful traits in plants

| Col. 1 SEQ ID NO | Col. 2 GID or Related Sequence Identifier (Accession No.) | Col. 3 Related to GID/SEQ ID NO | Col. 4 Smallest Sum Probability | Col. 5 Species from which Sequence is Derived | Col. 6 Test Sequence GenBank Annotation |
|---|---|---|---|---|---|
| | AI162779 | G2520/37 | 2.10E−22 | *Populus tremula* x *Populus tremuloides* | A023P62U Hybrid aspen |
| | BI270049 | G2520/37 | 2.90E−22 | *Medicago truncatula* | NF004D04FL1F1042 Developing flower Medi |
| | BE921054 | G2520/37 | 3.90E−22 | *Solanum tuberosum* | EST424823 potato leaves and petioles Sola |
| | BF200249 | G2520/37 | 9.10E−22 | *Triticum monococcum* | WHE2254_F11_L22ZE *Triticum monococcum* s |
| | gi11862964 | G2520/37 | 4.50E−16 | *Oryza sativa* | hypothetical protein. |
| | gi5923912 | G2520/37 | 6.30E−16 | *Tulipa gesneriana* | bHLH transcription factor GBOF-1. |
| | gi6166283 | G2520/37 | 0.69 | *Pinus taeda* | helix-loop-helix protein 1A. |
| | gi1086538 | G2520/37 | 1 | *Oryza rufipogon* | transcriptional activator Rb homolog. |

For many of the traits listed in Table 6 that may be conferred to plants by ectopically expressing transcription factors of the invention, a single transcription factor gene may be used to increase or decrease, advance or delay, or improve or prove deleterious to a given trait. For example, overexpression of a transcription factor gene that naturally occurs in a plant may cause early flowering relative to non-transformed or wild-type plants. By knocking out the gene, or suppressing the gene (with, for example, antisense suppression) the plant may experience delayed flowering. Similarly, overexpressing or suppressing one or more genes can impart significant differences in production of plant products, such as different fatty acid ratios. Thus, suppressing a gene that causes a plant to be more sensitive to cold may improve a plant's tolerance of cold.

The first and second columns of Table 6 provide the Trait category and specific trait were generally observed in plants overexpressing the listed transcription factor sequence of the invention, or, where noted, in plants in which a specific transcription factor has been knocked out (KO). The third column lists the sequences for which a specific trait was observed when the expression of the sequence was altered, and the last column provides the utility and specific observations, relative to controls, for each of the sequences.

TABLE 6

Genes, traits and utilities that affect plant characteristics

| Trait Category | Traits | Transcription factor genes that impact traits | Utility/ Observations |
|---|---|---|---|
| Environmental stress resistance and tolerance | Increased osmotic stress tolerance | G353, G1069, G1930 | Enhanced germination rate, survivability, yield G47 (in a root growth assay on PEG-containing media, G47 overexpressing seedlings were larger and had more root growth compared to the wild-type) G353 (on PEG containing media, overexpressing seedlings were larger and greener than the wild-type) G1069 (overexpressing lines showed more tolerance to osmotic stress on high sucrose media) G1930 (with more seedling vigor on high sucrose than wild-type control plants) |
| | Altered C/N sensing and tolerance to low nitrogen conditions | G975, G1069, G1266, G1322, G1930, G2131, G2144, G2512, G2520 | Improved yield, less fertilizer required, improved stress tolerance and quality G975 (less anthocyanin accumulation on low nitrogen media, better |

TABLE 6-continued

Genes, traits and utilities that affect plant characteristics

| Trait Category | Traits | Transcription factor genes that impact traits | Utility/Observations |
|---|---|---|---|
| | | | tolerance to low nitrogen conditions than controls) G1069 (less anthocyanin accumulation on low nitrogen media, better tolerance to low nitrogen conditions than controls) G1266 (less anthocyanin accumulation on low nitrogen media, better tolerance to low nitrogen conditions than controls) G1322 (accumulation on low nitrogen media, better tolerance to low nitrogen conditions than controls) G1930 (less anthocyanin accumulation on low nitrogen media, better tolerance to low nitrogen conditions than controls) G2131 (less anthocyanin accumulation on low nitrogen media, better tolerance to low nitrogen conditions than controls) G2144 (less anthocyanin accumulation on low nitrogen media, better tolerance to low nitrogen conditions than controls) G2512 (less anthocyanin accumulation on low nitrogen media, better tolerance to low nitrogen conditions than controls) G2520 (less anthocyanin accumulation on low nitrogen media, better tolerance to low nitrogen conditions than controls) |
| | Increased tolerance to phosphate-limitation | G1946 | Improved yield, less fertilizer required, improved stress tolerance and quality G1946 (more secondary root growth on phosphate-free media than wild-type controls) |
| | Increased salt tolerance | G47, G1930, G3644 | G1930 (with more seedling vigor on high salt media than wild-type control plants) G47 and G3644 (homologs; more seedling vigor on high salt media than wild-type control plants) |
| | Increased cold stress resistance and/or improved germination in cold conditions | G47, G1322, G1930, G2133, G3643, G3649 | Enhanced germination, growth, earlier planting G1322 (at 8° C., overexpressor seedlings were slightly larger and had longer roots than wild type) G1930 (increased tolerance to 8° C. in a germination assay) G47 (with leaf RBCS3 or shoot apical meristem promoters) and closely-related homologs G2133, G3643 and G3649 (35S promoter) conferred increased tolerance to 8° C. in a germination assay relative to controls) |

TABLE 6-continued

Genes, traits and utilities that affect plant characteristics

| Trait Category | Traits | Transcription factor genes that impact traits | Utility/Observations |
|---|---|---|---|
| | Increased drought or desiccation tolerance | G47, G353, G975, G1069, G2133, G3643, G3644, G3649 | Improved survivability, yield, extended range<br>G353 (overexpressors had greater tolerance to drought than wild type in a soil-based assay)<br>G975 (overexpressors had greater tolerance to desiccation in plate-based assays, and greater tolerance to drought than wild type in a soil-based assay)<br>G1069 (overexpressors had greater tolerance to drought than wild type in a soil-based assay)<br>G47 and homologs G2133, G3643 and G3649 conferred increased water deprivation when overexpressed compared to controls (another homolog, G3644, was not tested in drought assays) |
| | Altered light response and shade tolerance | G377, G1069, G1322, G1794, G2144, G2520 | Enhanced germination, growth, development, flowering time, greater planting density and improved yield<br>G377 (overexpressors had altered leaf orientation)<br>G1322 (overexpressors exhibited constitutive photomorphogenesis)<br>G1069 (overexpressors exhibited altered leaf orientation)<br>G1794 (overexpressors exhibited constitutive photomorphogenesis)<br>G2144 overexpressors exhibited long hypocotyls<br>G2520 (overexpressors had long hypocotyls) |
| Sugar sensing | Altered plant response to sugars | G1337 | Photosynthetic rate, carbohydrate accumulation, biomass production, source-sink relationships, senescence<br>G1337 (G1337 overexpressors germinated poorly on high glucose compared to controls, thus G1337 may be involved in sugar sensing, transport, or metabolism) |
| Hormonal | Altered hormone sensitivity | G47, G1069, G1266 | Seed dormancy, drought tolerance; plant form, fruit ripening<br>G47 (overexpressors had decreased sensitivity to ABA)<br>G1069 (overexpressors had decreased sensitivity to ABA)<br>G1266 (overexpressors had decreased sensitivity to ABA) |
| Development, morphology | Altered overall plant architecture | G47, G353, G1543; G1794, G2509 | Altered vascular tissues, increased lignin content; altered cell wall content; and/or appearance<br>G47 (increased lignin content, stems were wider |

TABLE 6-continued

Genes, traits and utilities that affect plant characteristics

| Trait Category | Traits | Transcription factor genes that impact traits | Utility/Observations |
|---|---|---|---|
| | | | with a much greater number of xylem vessels than wild type)<br>G353 (overexpressors had short pedicels, downward pointing siliques, leaves had short petioles, were rather flat, rounded, and sometimes showed changes in coloration)<br>G1543 (some G1543 overexpressors exhibited contorted, stunted carpels; 35S::G1543 plants also exhibited altered branching pattern, and apical dominance was reduced)<br>G1794 (overexpressors exhibited decreased apical dominance)<br>G2509 (overexpressors exhibited decreased apical dominance) |
| | Increased size, stature and/or biomass | G47; G377, G1052, G1543, G2133, G2155, G3643, G3644, G3649 | Improved yield<br>G47 (stem sections were of wider diameter and vascular bundles were larger, sometimes multiple cauline leaves were present at each node; overexpression of G47 and its homologs G2133, G3643, G3644 and G3649, resulted in some lines that produced larger plants than controls with larger rosettes, seedlings and/or seeds)<br>G377 (some lines had broader, fuller rosette leaves than wild type)<br>G214 (larger biomass, increased leaf number and size compared to controls)<br>G1052 (larger leaves and were generally more sturdy than wild type)<br>G1543 (some overexpressors exhibited increased biomass, including tomato plants overexpressing this sequence)<br>G2155 (late in development, 35S::G2155 plants became very large relative to controls) |
| | Size: reduced stature or dwarfism | G280; G353; G362; G652; G674; G962; G977; G1198; G1266; G1309; G1322; G1421; G1537; G1641; G1794; G2094; G2144; G2147 | Ornamental utility (creation of dwarf varieties); small stature also provides wind resistance |
| | Flower structure, inflorescence | G47, G259, G353, G1543 | Ornamental horticulture; production of saffron or other edible flowers<br>G47 (thick and fleshy inflorescences)<br>G259 (rosette leaves were longer, narrower, darker green than controls, sepals were longer, narrower, and often fused at the tips)<br>G353 (35S::G353 plants had a reduction in flower |

TABLE 6-continued

Genes, traits and utilities that affect plant characteristics

| Trait Category | Traits | Transcription factor genes that impact traits | Utility/ Observations |
|---|---|---|---|
| | | | pedicel length and downward pointing siliques) G1543 (some lines showed contorted, stunted carpels) |
| | Number and development of trichomes | G362, G1930, G2105 | Improved resistance to pests and desiccation; essential oil production G362 (increased trichome density) G1930 (decreased trichome density) G2105 (adaxial leaf surfaces had a somewhat 'lumpy' appearance caused by trichomes being raised-up on small mounds of epidermal cells) |
| | Seed size, color, and number | G652; G2105 | Improved yield G652 (seeds produced by knockouts of G652 plants were somewhat wrinkled and misshapen) G2105 (pale, larger seeds than controls) |
| | Leaf shape, color, modifications | G377; G674; G977; G1198; G2094; G2105; G2113; G2117; G2144; G2155, G2583 | Appealing shape or shiny leaves for ornamental agriculture, increased biomass or photosynthesis G377 (during later rosette stage, leaves were rounder, darker green, and shorter than wild type. After flowering, 35S::G377 leaves had a greater blade area than wild-type) G674 (rounded, dark green leaves that sometimes pointed upward) G977 (dark green leaves that were generally wrinkled or curled) G1198 (smaller, narrower leaves) G2094 (leaves pf overexpressors were short, wide, and slightly yellowed compared to wild type., occasionally the leaves also showed mild serrations on their margins) G2105 (uneven leaf surface) G2113 (long petioles, vertical leaf orientation, leaves appeared narrow and were downward curling at the margins compared to controls) G2155 (slightly small, rounded, leaves that became dark green, very large and senesced later than wild type late in development) G2144 (pale, narrow, flat leaves that had long petioles and sometimes positioned in a vertical orientation) G2583 (narrow, curled leaves) |

TABLE 6-continued

Genes, traits and utilities that affect plant characteristics

| Trait Category | Traits | Transcription factor genes that impact traits | Utility/Observations |
|---|---|---|---|
| | Altered stem morphology | G47, G748 | Ornamental; digestibility<br>G47 (stems of wider diameter with large irregular vascular bundles containing greater number of xylem vessels than wild type; some xylem vessels within the bundles appeared narrow and more lignified)<br>G748 (thicker and more vascular bundles in stems than controls) |
| Pigment | Production of anthocyanin and prenyl lipids | G214; G259; G362, G490; G652, G748; G883; G977, G1052; G1328; G1930; G2509, G2520 | Antioxidant activity, vitamin E<br>G214 (darker green in vegetative and reproductive tissues due to a higher chlorophyll content in the later stages of development; increased seed lutein)<br>G259 (increase in seed α-tocopherol)<br>G362 (increased pigment production compared to controls, seeds developed patches of dark purple pigmentation, increased anthocyanin in seedling leaves; late flowering lines also became darkly pigmented.)<br>G490 (increased seed δ-tocopherol)<br>G652 (increase in seed α-tocopherol)<br>G748 overexpressors consistently produced greater root content than controls)<br>G883 (decreased seed lutein)<br>G1328 (decreased seed lutein)<br>G977 (darker green leaves than controls)<br>G1052 (overexpressors had decreased lutein and increased xanthophyll 1 relative to controls)<br>G1930 (increased chlorophyll content)<br>G2509 (increase in α-tocopherol)<br>G2520 (increase in seed δ-tocopherol and a decrease in seed γ-tocopherol) |
| Seed biochemistry | Production of seed sterols | G20 | Precursors for human steroid hormones; cholesterol modulators<br>G20 (increased campesterol) |
| | Production of seed glucosinolates | G353; G484; G674; G1069; G1272 (KO); G1506; G1897; G1946; G2113; G2117; G2155; G2290, G2340 | Defense against insects; putative anticancer activity; undesirable in animal feeds<br>G353 (increased M39494)<br>G484 (altered glucosinolate profile)<br>G674 (increased M39501)<br>G1069 (increased M39497)<br>G1272 (decreased M39497)<br>G1506 (increased M39502 and M39498)<br>G1897 (increased M39491 and M39493) |

TABLE 6-continued

Genes, traits and utilities that affect plant characteristics

| Trait Category | Traits | Transcription factor genes that impact traits | Utility/ Observations |
|---|---|---|---|
| | | | G1946 (increased M39501) G2113 (decreased M39497, increased M39501 and M39494) G2117 (increased M39497, decreased M39496) G2155 (increased M39497) G2290 (increased M39496) G2340 (extreme alteration in seed glucosinolate profile) |
| | Modified seed oil content | G229, G652, G663, G974; G1198; G1543; G1777; G1946; G2117, G2123; G2343 | Vegetable oil production; increased caloric value for animal feeds; lutein content G229 (increased seed oil) G652 (decreased seed oil) G663 (decreased seed oil) G1198 (increased seed oil) G1543 (decreased seed oil observed in Arabidopsis overexpressors, increased seed oil observed in soy) G1777 (increased seed oil) G1946 (increased seed oil) G2117 (decreased seed oil) G2123 (increased seed oil) |
| | Modified seed protein content | G229, G663, G1641; G1777; G1946; G2117; G2509 | Reduced caloric value for humans G229 (decreased seed protein) G663 (increased seed protein) G1641 (increased seed protein) G1777 (decreased seed protein) G1946 (decreased seed protein) G2117 (increased seed protein) G2509 (increased seed protein) |
| | Modified seed fatty acid content | G1069, G1421 | Altered nutritional value; increase in waxes for disease resistance G1069 (increased 16:0 fatty acids and decreased 18:2 fatty acids) G1421 (increased 18:1 and decreased 18:3 seed fatty acids) |
| Leaf biochemistry | Production of leaf glucosinolates | G264; G353; G652; G681; G1069; G1198; G1322; G1421; G1794; G2113,; G2144; G2512; G2520; G2552 | Defense against insects; putative anticancer activity; undesirable in animal feeds G264 (increased M39481) G353 (increased M39494) G652 (increased M39480) G681 (increased M39480) G1069 ( ) G1198 (increased M3948) G1322 (increased M39480) G1421 (increased M39482) G1794 (increased M39480) G2113 (increased M39478) G2144 (increased M39480) G2512 (increased M39481) G2520 (increased M39478) G2552 (increased M39480) |
| | Production of leaf phytosterols, inc. stigmastanol, campesterol | G2131; G2424 | Precursors for human steroid hormones; cholesterol modulators G2131 (Increase in leaf campesterol) |

TABLE 6-continued

Genes, traits and utilities that affect plant characteristics

| Trait Category | Traits | Transcription factor genes that impact traits | Utility/Observations |
|---|---|---|---|
| | Leaf fatty acid composition | G214; G377; G962; G975; G987 (KO); G1266; G1337; G1399, G1465; G1512; G2136; G2147, G2583 | G2424 (increase in stigmastanol) Altered nutritional value; increase in waxes for disease resistance G214 (increased leaf fatty acids) G377 (increase in leaf 18:2 fatty acids and decrease in leaf 18:3 fatty acids) G962 (increase in 16:0 leaf fatty acids, decrease in 18:3 leaf fatty acids) G987 KO (reduction in 16:3 fatty acids relative to controls) G975 (increased leaf fatty acids, glossy leaves) G1337 (increased leaf oleic acids) G1399 (increased leaf 16:0 fatty acid) G1465 (increased in 16:0, 16:1, 18:0 and 18:2 and decreased 16:3 and 18:3 leaf fatty acids) G1512 (increased 18:2 leaf fatty acids) G2136 (decreased 18:3 leaf fatty acids) G2147 increased 16:0 and 18:2 3 leaf fatty acids) G2583 (glossy leaves) |
| | Production of prenyl lipids, including tocopherol | G214; G259; G280; G362, G652; G987 (KO), G1543; G1930, G2509; G2520 | Antioxidant activity, vitamin E G214 (increased leaf chlorophyll and carotenoids) G259 (increased seed α-tocopherol) G280 (increased leaf δ and γ tocopherol) G362 (increased anthocyanin levels in various tissues at different stages of growth.; seedlings showed high levels of pigment in first true leaves, late flowering lines became darkly pigmented., seeds from developed patches of dark purple pigmentation) G652 (increased seed α-tocopherol) G987 (overexpressors had two xanthophylls not present in wild-type leaves, γ-tocopherol (which normally accumulate in seed tissue), and reduced levels of chlorophyll a and chlorophyll b in leaves) G1543 (dark green color, increased levels of carotenoids and chlorophylls a and b in leaves) G1930 (increased levels of chlorophyll a and chlorophyll b in seeds compared to controls) G2509 (increased seed α-tocopherol) |

TABLE 6-continued

Genes, traits and utilities that affect plant characteristics

| Trait Category | Traits | Transcription factor genes that impact traits | Utility/ Observations |
| --- | --- | --- | --- |
| | Sugar, starch, hemicellulose composition, | G158; G211; G242; G274; G1012; G1266; G1309; G1641; G1865; G2094; G2589 | G2520 (increase in seed δ-tocopherol and a decrease in seed γ-tocopherol) Improved food digestibility, increased hemicellulose & pectin content; increased fiber content; increased plant tensile strength, wood quality, pathogen resistance, pulp production and/or tuber starch content G158 (increased leaf rhamnose) G211 (increased leaf xylose) G242 (increased leaf arabinose) G274 (increased leaf arabinose) G1012 (decreased leaf rhamnose) G1266 (alterations in rhamnose, arabinose, xylose, and mannose, and galactose) G1309 (increased leaf mannose) G1641 (increased leaf rhamnose) G1865 (increased galactose, decreased xylose) G2094 (increased leaf arabinose) G2589 (increased leaf insoluble sugars - increased arabinose) |
| Growth, Reproduction | Plant growth rate and development | G1543 | Faster growth, increased biomass or yield, improved appearance; delay in bolting G1543 (faster growth of seedlings) |
| | Senescence; cell death | G652, G1897, G2155, G2340 | Altered yield, appearance; response to pathogens (potential protective response without the potentially detrimental consequences of a constitutive systemic acquired resistance) G652 (premature senescence of rosette leaves) G1897 (later senescence than controls) G2155 (senesced much later than controls) G2340 (overexpressors showed necrosis of blades of rosette and cauline leaves, necrotic lesions) |
| | Modified fertility | G652; G962; G977; G1266; G1421; G2094; G2113; G2147 | Prevents or minimizes escape of the pollen of genetically modified plants G652 (poor fertility) G962 (poor fertility) G977 (poor fertility) G1266 (poor fertility) G1421 (poor fertility) G2094 (poor fertility) G2113 (poor fertility) G2094 (poor fertility) G2147 (poor fertility) |

TABLE 6-continued

Genes, traits and utilities that affect plant characteristics

| Trait Category | Traits | Transcription factor genes that impact traits | Utility/ Observations |
|---|---|---|---|
| | Early flowering | G490; G1946; G2144; G2509 | Faster generation time; synchrony of flowering; potential for introducing new traits to single variety |
| | Delayed flowering | G47; G214; G362; G748; G1052; G1865; G1930, G2155, G2133, G3643, G3644, G3649 | Delayed time to pollen production of GMO plants; synchrony of flowering; increased yield |
| | Flower and leaf development | G259; G353; G377; G652; G1865; G1897; G2094 | Ornamental applications; decreased fertility G259 (rosette leaves were longer and narrow, dark green and curled compared to control plants, sepals were long, narrow, and often fused at the tips) G353 (reduction in flower pedicel length and downward pointing siliques) G377 (inflorescence stems were shorter than wild-type, during late rosette stage, leaves were rounder, darker green, and slightly shorter than those of wild type) G652 (reduced number of stamens: 4-5 of these organs rather than 6) G1865 (short, thick, inflorescence stems, greatly increased number of leaves; visible flower buds up to a month after wild type, continuous light conditions, by which time rosette leaves had become rather large and contorted) G1897 (narrow, dark-green rosette and cauline leaves, inflorescences had short internodes with various abnormalities, perianth organs were typically rather long and narrow., stamens were short, silique formation was poor) G2094 (inflorescence stems were often thin and carried short flowers, mild serrations on leaf margins) |
| | Flower abscission | G1897 | Ornamental: longer retention of flowers G1897 (delayed abscission of floral organs) |

* When co-expressed with G669 and G663

Significance of Modified Plant Traits

The sequences of the Sequence Listing, those in Tables 4-6, or those disclosed here can be used to prepare transgenic plants and plants with altered traits. The specific transgenic plants listed below are produced from the sequences of the Sequence Listing, as noted Tables 4-6 provides exemplary polynucleotide and polypeptide sequences of the invention.

Salt stress resistance. Soil salinity is one of the more important variables that determines where a plant may thrive. Salinity is especially important for the successful cultivation of crop plants, particular in many parts of the world that have naturally high soil salt concentrations, or where the soil has been over-utilized. Thus, presently disclosed transcription factor genes that provide increased salt tolerance during germination, the seedling stage, and throughout a plant's life cycle would find particular value for imparting survivability and yield in areas where a particular crop would not normally prosper.

Osmotic stress resistance. Presently disclosed transcription factor genes that confer resistance to osmotic stress may increase germination rate under adverse conditions, which could impact survivability and yield of seeds and plants.

Cold stress resistance. The potential utility of presently disclosed transcription factor genes that increase tolerance to cold is to confer better germination and growth in cold conditions. The germination of many crops is very sensitive to cold temperatures. Genes that would allow germination and seedling vigor in the cold would have highly significant utility in allowing seeds to be planted earlier in the season with a high rate of survivability. Transcription factor genes that confer better survivability in cooler climates allow a grower to move up planting time in the spring and extend the growing season further into autumn for higher crop yields.

Tolerance to freezing. The presently disclosed transcription factor genes that impart tolerance to freezing conditions are useful for enhancing the survivability and appearance of plants conditions or conditions that would otherwise cause extensive cellular damage. Thus, germination of seeds and survival may take place at temperatures significantly below that of the mean temperature required for germination of seeds and survival of non-transformed plants. As with salt tolerance, this has the added benefit of increasing the potential range of a crop plant into regions in which it would otherwise succumb. Cold tolerant transformed plants may also be planted earlier in the spring or later in autumn, with greater success than with non-transformed plants.

Heat stress tolerance. The germination of many crops is also sensitive to high temperatures. Presently disclosed transcription factor genes that provide increased heat tolerance are generally useful in producing plants that germinate and grow in hot conditions, may find particular use for crops that are planted late in the season, or extend the range of a plant by allowing growth in relatively hot climates.

Drought, low humidity tolerance. Strategies that allow plants to survive in low water conditions may include, for example, reduced surface area or surface oil or wax production. A number of presently disclosed transcription factor genes increase a plant's tolerance to low water conditions and provide the benefits of improved survivability, increased yield and an extended geographic and temporal planting range.

Radiation resistance. Presently disclosed transcription factor genes have been shown to increase lutein production. Lutein, like other xanthophylls such as zeaxanthin and violaxanthin, are important in the protection of plants against the damaging effects of excessive light. Lutein contributes, directly or indirectly, to the rapid rise of non-photochemical quenching in plants exposed to high light. Increased tolerance of field plants to visible and ultraviolet light impacts survivability and vigor, particularly for recent transplants. Also affected are the yield and appearance of harvested plants or plant parts. Crop plants engineered with presently disclosed transcription factor genes that cause the plant to produce higher levels of lutein therefore would have improved photoprotection, leading to less oxidative damage and increase vigor, survivability and higher yields under high light and ultraviolet light conditions.

Decreased herbicide sensitivity. Presently disclosed transcription factor genes that confer resistance or tolerance to herbicides (e.g., glyphosate) may find use in providing means to increase herbicide applications without detriment to desirable plants. This would allow for the increased use of a particular herbicide in a local environment, with the effect of increased detriment to undesirable species and less harm to transgenic, desirable cultivars.

Increased herbicide sensitivity. Knockouts of a number of the presently disclosed transcription factor genes have been shown to be lethal to developing embryos. Thus, these genes are potentially useful as herbicide targets.

Oxidative stress. In plants, as in all living things, abiotic and biotic stresses induce the formation of oxygen radicals, including superoxide and peroxide radicals. This has the effect of accelerating senescence, particularly in leaves, with the resulting loss of yield and adverse effect on appearance. Generally, plants that have the highest level of defense mechanisms, such as, for example, polyunsaturated moieties of membrane lipids, are most likely to thrive under conditions that introduce oxidative stress (e.g., high light, ozone, water deficit, particularly in combination). Introduction of the presently disclosed transcription factor genes that increase the level of oxidative stress defense mechanisms would provide beneficial effects on the yield and appearance of plants. One specific oxidizing agent, ozone, has been shown to cause significant foliar injury, which impacts yield and appearance of crop and ornamental plants. In addition to reduced foliar injury that would be found in ozone resistant plant created by transforming plants with some of the presently disclosed transcription factor genes, the latter have also been shown to have increased chlorophyll fluorescence (Yu-Sen Chang et al. *Bot. Bull. Acad. Sin.* (2001) 42: 265-272).

Heavy metal tolerance. Heavy metals such as lead, mercury, arsenic, chromium and others may have a significant adverse impact on plant respiration. Plants that have been transformed with presently disclosed transcription factor genes that confer improved resistance to heavy metals, through, for example, sequestering or reduced uptake of the metals will show improved vigor and yield in soils with relatively high concentrations of these elements. Conversely, transgenic transcription factors may also be introduced into plants to confer an increase in heavy metal uptake, which may benefit efforts to clean up contaminated soils.

Light response. Presently disclosed transcription factor genes that modify a plant's response to light may be useful for modifying a plant's growth or development, for example, photomorphogenesis in poor light, or accelerating flowering time in response to various light intensities, quality or duration to which a non-transformed plant would not similarly respond. Examples of such responses that have been demonstrated include leaf number and arrangement, and early flower bud appearances.

Overall plant architecture. Several presently disclosed transcription factor genes have been introduced into plants to alter numerous aspects of the plant's morphology. For example, it has been demonstrated that a number of transcription factors may be used to manipulate branching, such as the means to modify lateral branching, a possible application in the forestry industry. Transgenic plants have also been produced that have altered cell wall content, lignin production, flower organ number, or overall shape of the plants. Presently disclosed transcription factor genes transformed into plants may be used to affect plant morphology by increasing or decreasing internode distance, both of which may be advantageous under different circumstances. For example, for fast growth of woody plants to provide more biomass, or fewer knots, increased internode distances are generally desirable. For improved wind screening of shrubs or trees, or harvesting characteristics of, for example, members of the Gramineae family, decreased internode distance may be advantageous. These modifications would also prove useful in the ornamental horticulture industry for the creation of unique phenotypic characteristics of ornamental plants.

Increased stature. For some ornamental plants, the ability to provide larger varieties may be highly desirable. For many plants, including t fruit-bearing trees or trees and shrubs that serve as view or wind screens, increased stature provides obvious benefits. Crop species may also produce higher yields on larger cultivars Reduced stature or dwarfism. Presently disclosed transcription factor genes that decrease plant stature can be used to produce plants that are more resistant to damage by wind and rain, or more resistant to heat or low humidity or water deficit. Dwarf plants are also of significant interest to the ornamental horticulture industry, and particularly for home garden applications for which space availability may be limited.

Fruit size and number. Introduction of presently disclosed transcription factor genes that affect fruit size will have desirable impacts on fruit size and number, which may comprise increases in yield for fruit crops, or reduced fruit yield, such as when vegetative growth is preferred (e.g., with bushy ornamentals, or where fruit is undesirable, as with ornamental olive trees).

Flower structure, inflorescence, and development. Presently disclosed transgenic transcription factors have been used to create plants with larger flowers or arrangements of flowers that are distinct from wild-type or non-transformed cultivars. This would likely have the most value for the ornamental horticulture industry, where larger flowers or interesting presentations generally are preferred and command the highest prices. Flower structure may have advantageous effects on fertility, and could be used, for example, to decrease fertility by the absence, reduction or screening of reproductive components. One interesting application for manipulation of flower structure, for example, by introduced transcription factors could be in the increased production of edible flowers or flower parts, including saffron, which is derived from the stigmas of *Crocus sativus*.

Number and development of trichomes. Several presently disclosed transcription factor genes have been used to modify trichome number and amount of trichome products in plants. Trichome glands on the surface of many higher plants produce and secrete exudates that give protection from the elements and pests such as insects, microbes and herbivores. These exudates may physically immobilize insects and spores, may be insecticidal or ant-microbial or they may act as allergens or irritants to protect against herbivores. Trichomes have also been suggested to decrease transpiration by decreasing leaf surface air flow, and by exuding chemicals that protect the leaf from the sun.

Another potential utilities for sequences that increase trichome number is to increase the density of cotton fibers in cotton bolls. Cotton fibers are modified unicellular trichomes that are produced from the ovule epidermis. However, typically only 30% of the epidermal cells take on a trichome fate (Basra and Malik, 1984). Thus, cotton yields might be increased by inducing a greater proportion of the ovule epidermal cells to become fibers.

Seed size, color and number. The introduction of presently disclosed transcription factor genes into plants that alter the size or number of seeds may have a significant impact on yield, both when the product is the seed itself, or when biomass of the vegetative portion of the plant is increased by reducing seed production. In the case of fruit products, it is often advantageous to modify a plant to have reduced size or number of seeds relative to non-transformed plants to provide seedless or varieties with reduced numbers or smaller seeds. Presently disclosed transcription factor genes have also been shown to affect seed size, including the development of larger seeds. Seed size, in addition to seed coat integrity, thickness and permeability, seed water content and by a number of other components including antioxidants and oligosaccharides, may affect seed longevity in storage. This would be an important utility when the seed of a plant is the harvested crops, as with, for example, peas, beans, nuts, etc. Presently disclosed transcription factor genes have also been used to modify seed color, which could provide added appeal to a seed product.

Root development, modifications. By modifying the structure or development of roots by transforming into a plant one or more of the presently disclosed transcription factor genes, plants may be produced that have the capacity to thrive in otherwise unproductive soils. For example, grape roots that extend further into rocky soils, or that remain viable in water-logged soils, would increase the effective planting range of the crop. It may be advantageous to manipulate a plant to produce short roots, as when a soil in which the plant will be growing is occasionally flooded, or when pathogenic fungi or disease-causing nematodes are prevalent.

Modifications to root hairs. Presently disclosed transcription factor genes that increase root hair length or number potentially could be used to increase root growth or vigor, which might in turn allow better plant growth under adverse conditions such as limited nutrient or water availability.

Apical dominance. The modified expression of presently disclosed transcription factors that control apical dominance could be used in ornamental horticulture, for example, to modify plant architecture.

Branching patterns. Several presently disclosed transcription factor genes have been used to manipulate branching, which could provide benefits in the forestry industry. For example, reduction in the formation of lateral branches could reduce knot formation. Conversely, increasing the number of lateral branches could provide utility when a plant is used as a windscreen, or may also provide ornamental advantages.

Leaf shape, color and modifications. It has been demonstrated in laboratory experiments that overexpression of some of the presently disclosed transcription factors produced marked effects on leaf development. At early stages of growth, these transgenic seedlings developed narrow, upward pointing leaves with long petioles, possibly indicating a disruption in circadian-clock controlled processes or nyctinastic movements. Other transcription factor genes can be used to increase plant biomass; large size would be useful in crops where the vegetative portion of the plant is the marketable portion.

Siliques. Genes that later silique conformation in brassicates may be used to modify fruit ripening processes in brassicates and other plants, which may positively affect seed or fruit quality.

Stem morphology and shoot modifications. Laboratory studies have demonstrated that introducing several of the presently disclosed transcription factor genes into plants can cause stem bifurcations in shoots, in which the shoot meristems split to form two or three separate shoots. This unique appearance would be desirable in ornamental applications.

Diseases, pathogens and pests. A number of the presently disclosed transcription factor genes have been shown to or are likely to confer resistance to various plant diseases, pathogens and pests. The offending organisms include fungal pathogens *Fusarium oxysporum, Botrytis cinerea, Sclerotinia sclerotiorum*, and *Erysiphe orontii*. Bacterial pathogens to which resistance may be conferred include *Pseudomonas syringae*. Other problem organisms may potentially include nematodes, mollicutes, parasites, or herbivorous arthropods. In each case, one or more transformed transcription factor genes may provide some benefit to the plant to help prevent or overcome infestation. The mechanisms by which the transcription factors work could include increasing surface waxes or oils, surface thickness, local senescence, or the activation of signal transduction pathways that regulate plant defense in response to attacks by herbivorous pests (including, for example, protease inhibitors).

Increased tolerance of plants to nutrient-limited soils. Presently disclosed transcription factor genes introduced into plants may provide the means to improve uptake of essential nutrients, including nitrogenous compounds, phosphates, potassium, and trace minerals. The effect of these modifications is to increase the seedling germination and range of ornamental and crop plants. The utilities of presently disclosed transcription factor genes conferring tolerance to conditions of low nutrients also include cost savings to the grower by reducing the amounts of fertilizer needed, environmental benefits of reduced fertilizer runoff; and improved yield and stress tolerance. In addition, this gene could be used to alter seed protein amounts and/or composition that could impact yield as well as the nutritional value and production of various food products.

Hormone sensitivity. One or more of the presently disclosed transcription factor genes have been shown to affect plant abscisic acid (ABA) sensitivity. This plant hormone is likely the most important hormone in mediating the adaptation of a plant to stress. For example, ABA mediates conversion of apical meristems into dormant buds. In response to increasingly cold conditions, the newly developing leaves growing above the meristem become converted into stiff bud scales that closely wrap the meristem and protect it from mechanical damage during winter. ABA in the bud also enforces dormancy; during premature warm spells, the buds are inhibited from sprouting. Bud dormancy is eliminated after either a prolonged cold period of cold or a significant number of lengthening days. Thus, by affecting ABA sensitivity, introduced transcription factor genes may affect cold sensitivity and survivability. ABA is also important in protecting plants from drought tolerance.

Several other of the present transcription factor genes have been used to manipulate ethylene signal transduction and response pathways. These genes can thus be used to manipulate the processes influenced by ethylene, such as seed germination or fruit ripening, and to improve seed or fruit quality.

Production of seed and leaf prenyl lipids, including tocopherol. Prenyl lipids play a role in anchoring proteins in membranes or membranous organelles. Thus, modifying the prenyl lipid content of seeds and leaves could affect membrane integrity and function. A number of presently disclosed transcription factor genes have been shown to modify the tocopherol composition of plants. Tocopherols have both anti-oxidant and vitamin E activity.

Production of seed and leaf phytosterols: Presently disclosed transcription factor genes that modify levels of phytosterols in plants may have at least two utilities. First, phytosterols are an important source of precursors for the manufacture of human steroid hormones. Thus, regulation of transcription factor expression or activity could lead to elevated levels of important human steroid precursors for steroid semi-synthesis. For example, transcription factors that cause elevated levels of campesterol in leaves, or sitosterols and stigmasterols in seed crops, would be useful for this purpose. Phytosterols and their hydrogenated derivatives phytostanols also have proven cholesterol-lowering properties, and transcription factor genes that modify the expression of these compounds in plants would thus provide health benefits.

Production of seed and leaf glucosinolates. Some glucosinolates have anti-cancer activity; thus, increasing the levels or composition of these compounds by introducing several of the presently disclosed transcription factors might be of interest from a nutraceutical standpoint. (3) Glucosinolates form part of a plants natural defense against insects. Modification of glucosinolate composition or quantity could therefore afford increased protection from predators. Furthermore, in edible crops, tissue specific promoters might be used to ensure that these compounds accumulate specifically in tissues, such as the epidermis, which are not taken for consumption.

Modified seed oil content. The composition of seeds, particularly with respect to seed oil amounts and/or composition, is very important for the nutritional value and production of various food and feed products. Several of the presently disclosed transcription factor genes in seed lipid saturation that alter seed oil content could be used to improve the heat stability of oils or to improve the nutritional quality of seed oil, by, for example, reducing the number of calories in seed, increasing the number of calories in animal feeds, or altering the ratio of saturated to unsaturated lipids comprising the oils.

Seed and leaf fatty acid composition. A number of the presently disclosed transcription factor genes have been shown to alter the fatty acid composition in plants, and seeds in particular. This modification may find particular value for improving the nutritional value of, for example, seeds or whole plants. Dietary fatty acids ratios have been shown to have an effect on, for example, bone integrity and remodeling (see, for example, Weiler *Pediatr. Res.* (2000) 47: 5 692-697). The ratio of dietary fatty acids may alter the precursor pools of long-chain polyunsaturated fatty acids that serve as precursors for prostaglandin synthesis. In mammalian connective tissue, prostaglandins serve as important signals regulating the balance between resorption and formation in bone and cartilage. Thus dietary fatty acid ratios altered in seeds may affect the etiology and outcome of bone loss.

Modified seed protein content. As with seed oils, the composition of seeds, particularly with respect to protein amounts and/or composition, is very important for the nutritional value and production of various food and feed products. A number of the presently disclosed transcription factor genes modify the protein concentrations in seeds would provide nutritional benefits, and may be used to prolong storage, increase seed pest or disease resistance, or modify germination rates.

Production of flavonoids in leaves and other plant parts. Expression of presently disclosed transcription factor genes that increase flavonoid production in plants, including anthocyanins and condensed tannins, may be used to alter in pigment production for horticultural purposes, and possibly increasing stress resistance. Flavonoids have antimicrobial activity and could be used to engineer pathogen resistance. Several flavonoid compounds have health promoting effects such as the inhibition of tumor growth and cancer, prevention of bone loss and the prevention of the oxidation of lipids. Increasing levels of condensed tannins, whose biosynthetic pathway is shared with anthocyanin biosynthesis, in forage legumes is an important agronomic trait because they prevent pasture bloat by collapsing protein foams within the rumen. For a review on the utilities of flavonoids and their derivatives, refer to Dixon et al. (1999) *Trends Plant Sci.* 4: 394-400.

Production of diterpenes in leaves and other plant parts. Depending on the plant species, varying amounts of diverse secondary biochemicals (often lipophilic terpenes) are produced and exuded or volatilized by trichomes. These exotic secondary biochemicals, which are relatively easy to extract because they are on the surface of the leaf, have been widely used in such products as flavors and aromas, drugs, pesticides and cosmetics. Thus, the overexpression of genes that are used to produce diterpenes in plants may be accomplished by introducing transcription factor genes that induce said overexpression. One class of secondary metabolites, the diterpenes, can effect several biological systems such as tumor progression, prostaglandin synthesis and tissue inflammation. In addition, diterpenes can act as insect pheromones, termite allomones, and can exhibit neurotoxic, cytotoxic and antimitotic activities. As a result of this functional diversity, diterpenes have been the target of research several pharmaceutical ventures. In most cases where the metabolic pathways are impossible to engineer, increasing trichome density or size on leaves may be the only way to increase plant productivity.

Production of anthocyanin in leaves and other plant parts. Several presently disclosed transcription factor genes can be used to alter anthocyanin production in numerous plant species. The potential utilities of these genes include alterations in pigment production for horticultural purposes, and possibly increasing stress resistance in combination with another transcription factor.

Production of miscellaneous secondary metabolites. Microarray data suggests that flux through the aromatic amino acid biosynthetic pathways and primary and secondary metabolite biosynthetic pathways are up-regulated. Presently disclosed transcription factors have been shown to be involved in regulating alkaloid biosynthesis, in part by up-regulating the enzymes indole-3-glycerol phosphatase and strictosidine synthase. Phenylalanine ammonia lyase, chalcone synthase and trans-cinnamate mono-oxygenase are also induced, and are involved in phenylpropenoid biosynthesis.

Sugar, starch, hemicellulose composition. Overexpression of the presently disclosed transcription factors that affect sugar content resulted in plants with altered leaf insoluble sugar content. Transcription factors that alter plant cell wall composition have several potential applications including altering food digestibility, plant tensile strength, wood quality, pathogen resistance and in pulp production. The potential utilities of a gene involved in glucose-specific sugar sensing are to alter energy balance, photosynthetic rate, carbohydrate accumulation, biomass production, source-sink relationships, and senescence.

Hemicellulose is not desirable in paper pulps because of its lack of strength compared with cellulose. Thus modulating the amounts of cellulose vs. hemicellulose in the plant cell wall is desirable for the paper/lumber industry. Increasing the insoluble carbohydrate content in various fruits, vegetables, and other edible consumer products will result in enhanced fiber content. Increased fiber content would not only provide health benefits in food products, but might also increase digestibility of forage crops. In addition, the hemicellulose and pectin content of fruits and berries affects the quality of jam and catsup made from them. Changes in hemicellulose and pectin content could result in a superior consumer product.

Plant response to sugars and sugar composition. In addition to their important role as an energy source and structural component of the plant cell, sugars are central regulatory molecules that control several aspects of plant physiology, metabolism and development. It is thought that this control is achieved by regulating gene expression and, in higher plants, sugars have been shown to repress or activate plant genes involved in many essential processes such as photosynthesis, glyoxylate metabolism, respiration, starch and sucrose synthesis and degradation, pathogen response, wounding response, cell cycle regulation, pigmentation, flowering and senescence. The mechanisms by which sugars control gene expression are not understood.

Because sugars are important signaling molecules, the ability to control either the concentration of a signaling sugar or how the plant perceives or responds to a signaling sugar could be used to control plant development, physiology or metabolism. For example, the flux of sucrose (a disaccharide sugar used for systemically transporting carbon and energy in most plants) has been shown to affect gene expression and alter storage compound accumulation in seeds. Manipulation of the sucrose signaling pathway in seeds may therefore cause seeds to have more protein, oil or carbohydrate, depending on the type of manipulation. Similarly, in tubers, sucrose is converted to starch which is used as an energy store. It is thought that sugar signaling pathways may partially determine the levels of starch synthesized in the tubers. The manipulation of sugar signaling in tubers could lead to tubers with a higher starch content.

Thus, the presently disclosed transcription factor genes that manipulate the sugar signal transduction pathway may lead to altered gene expression to produce plants with desirable traits. In particular, manipulation of sugar signal transduction pathways could be used to alter source-sink relationships in seeds, tubers, roots and other storage organs leading to increase in yield.

Plant growth rate and development. A number of the presently disclosed transcription factor genes have been shown to have significant effects on plant growth rate and development. These observations have included, for example, more rapid or delayed growth and development of reproductive organs. This would provide utility for regions with short or long growing seasons, respectively. Accelerating plant growth would also improve early yield or increase biomass at an earlier stage, when such is desirable (for example, in producing forestry products).

Embryo development. Presently disclosed transcription factor genes that alter embryo development has been used to alter seed protein and oil amounts and/or composition which is very important for the nutritional value and production of various food products. Seed shape and seed coat may also be altered by these genes, which may provide for improved storage stability.

Seed germination rate. A number of the presently disclosed transcription factor genes have been shown to modify seed germination rate, including when the seeds are in conditions normally unfavorable for germination (e.g., cold, heat or salt stress, or in the presence of ABA), and may thus be used to modify and improve germination rates under adverse conditions.

Plant, seedling vigor. Seedlings transformed with presently disclosed transcription factors have been shown to possess larger cotyledons and appeared somewhat more advanced than control plants. This indicates that the seedlings developed more rapidly that the control plants. Rapid seedling development is likely to reduce loss due to diseases particularly prevalent at the seedling stage (e.g., damping off) and is thus important for survivability of plants germinating in the field or in controlled environments.

Senescence, cell death. Presently disclosed transcription factor genes may be used to alter senescence responses in plants. Although leaf senescence is thought to be an evolutionary adaptation to recycle nutrients, the ability to control senescence in an agricultural setting has significant value. For example, a delay in leaf senescence in some maize hybrids is associated with a significant increase in yields and a delay of a few days in the senescence of soybean plants can have a large impact on yield. Delayed flower senescence may also generate plants that retain their blossoms longer and this may be of potential interest to the ornamental horticulture industry.

Modified fertility. Plants that overexpress a number of the presently disclosed transcription factor genes have been shown to possess reduced fertility. This could be a desirable trait, as it could be exploited to prevent or minimize the escape of the pollen of genetically modified organisms (GMOs) into the environment.

Early and delayed flowering. Presently disclosed transcription factor genes that accelerate flowering could have valuable applications in such programs since they allow much faster generation times. In a number of species, for example, broccoli, cauliflower, where the reproductive parts of the plants constitute the crop and the vegetative tissues are discarded, it would be advantageous to accelerate time to flowering. Accelerating flowering could shorten crop and tree breeding programs. Additionally, in some instances, a faster generation time might allow additional harvests of a crop to be made within a given growing season. A number of *Arabidopsis* genes have already been shown to accelerate flowering when constitutively expressed. These include LEAFY, APETALA1 and CONSTANS (Mandel et al. (1995) Nature 377: 522-524; Weigel and Nilsson (1995) *Nature* 377: 495-500; and Simon et al. (1996) *Nature* 384: 59-62).

By regulating the expression of potential flowering using inducible promoters, flowering could be triggered by application of an inducer chemical. This would allow flowering to be synchronized across a crop and facilitate more efficient harvesting. Such inducible systems could also be used to tune the flowering of crop varieties to different latitudes. At present, species such as soybean and cotton are available as a series of maturity groups that are suitable for different latitudes on the basis of their flowering time (which is governed by day-length). A system in which flowering could be chemically controlled would allow a single high-yielding northern maturity group to be grown at any latitude. In southern regions such plants could be grown for longer, thereby increasing yields, before flowering was induced. In more northern areas, the induction would be used to ensure that the crop flowers prior to the first winter frosts.

In a sizeable number of species, for example, root crops, where the vegetative parts of the plants constitute the crop and the reproductive tissues are discarded, it would be advantageous to delay or prevent flowering. Extending vegetative development with presently disclosed transcription factor genes could thus bring about large increases in yields. Prevention of flowering might help maximize vegetative yields and prevent escape of genetically modified organism (GMO) pollen.

Extended flowering phase. Presently disclosed transcription factors that extend flowering time have utility in engineering plants with longer-lasting flowers for the horticulture industry, and for extending the time in which the plant is fertile.

Flower and leaf development. Presently disclosed transcription factor genes have been used to modify the development of flowers and leaves. This could be advantageous in the development of new ornamental cultivars that present unique configurations. In addition, some of these genes have been shown to reduce a plant's fertility, which is also useful for helping to prevent development of pollen of GMOs.

Flower abscission. Presently disclosed transcription factor genes introduced into plants have been used to retain flowers for longer periods. This would provide a significant benefit to the ornamental industry, for both cut flowers and woody plant varieties (of, for example, maize), as well as have the potential to lengthen the fertile period of a plant, which could positively impact yield and breeding programs.

A listing of specific effects and utilities that the presently disclosed transcription factor genes have on plants, as determined by direct observation and assay analysis, is provided in Tables 4 and 6.

Antisense and Co-suppression

In addition to expression of the nucleic acids of the invention as gene replacement or plant phenotype modification nucleic acids, the nucleic acids are also useful for sense and anti-sense suppression of expression, e.g., to down-regulate expression of a nucleic acid of the invention, e.g., as a further mechanism for modulating plant phenotype. That is, the nucleic acids of the invention, or subsequences or anti-sense sequences thereof, can be used to block expression of naturally occurring homologous nucleic acids. A variety of sense and anti-sense technologies are known in the art, e.g., as set forth in Lichtenstein and Nellen (1997) *Antisense Technology: A Practical Approach* IRL Press at Oxford University Press, Oxford, U.K. In general, sense or anti-sense sequences are introduced into a cell, where they are optionally amplified, e.g., by transcription. Such sequences include both simple oligonucleotide sequences and catalytic sequences such as ribozymes.

For example, a reduction or elimination of expression (i.e., a "knock-out") of a transcription factor or transcription factor homologue polypeptide in a transgenic plant, e.g., to modify a plant trait, can be obtained by introducing an antisense construct corresponding to the polypeptide of interest as a cDNA. For antisense suppression, the transcription factor or homologue cDNA is arranged in reverse orientation (with respect to the coding sequence) relative to the promoter sequence in the expression vector. The introduced sequence need not be the full length cDNA or gene, and need not be identical to the cDNA or gene found in the plant type to be transformed. Typically, the antisense sequence need only be capable of hybridizing to the target gene or RNA of interest. Thus, where the introduced sequence is of shorter length, a higher degree of homology to the endogenous transcription factor sequence will be needed for effective antisense suppression. While antisense sequences of various lengths can be utilized, preferably, the introduced antisense sequence in the vector will be at least 30 nucleotides in length, and improved antisense suppression will typically be observed as the length of the antisense sequence increases. Preferably, the length of the antisense sequence in the vector will be greater than 100 nucleotides. Transcription of an antisense construct as described results in the production of RNA molecules that are the reverse complement of mRNA molecules transcribed from the endogenous transcription factor gene in the plant cell.

Suppression of endogenous transcription factor gene expression can also be achieved using a ribozyme. Ribozymes are RNA molecules that possess highly specific endoribonuclease activity. The production and use of ribozymes are disclosed in U.S. Pat. No. 4,987,071 and U.S. Pat. No. 5,543,508. Synthetic ribozyme sequences including antisense RNAs can be used to confer RNA cleaving activity on the antisense RNA, such that endogenous mRNA molecules that hybridize to the antisense RNA are cleaved, which in turn leads to an enhanced antisense inhibition of endogenous gene expression.

Suppression of endogenous transcription factor gene expression can also be achieved using RNA interference, or RNAi. RNAi is a post-transcriptional, targeted gene-silencing technique that uses double-stranded RNA (dsRNA) to incite degradation of messenger RNA (mRNA) containing the same sequence as the dsRNA (Constans, (2002) *The Scientist* 16: 36). Small interfering RNAs, or siRNAs are produced in at least two steps: an endogenous ribonuclease cleaves longer dsRNA into shorter, 21-23 nucleotide-long RNAs. The siRNA segments then mediate the degradation of the target mRNA (Zamore, (2001) *Nature Struct. Biol.* 8:

746-50). RNAi has been used for gene function determination in a manner similar to antisense oligonucleotides (Constans, (2002) *The Scientist* 16: 36). Expression vectors that continually express siRNAs in transiently and stably transfected have been engineered to express small hairpin RNAs (shRNAs), which get processed in vivo into siRNAs-like molecules capable of carrying out gene-specific silencing (Brummelkamp et al. (2002) *Science* 296: 550-553, and Paddison et al. (2002) *Genes & Dev.* 16: 948-958). Post-transcriptional gene silencing by double-stranded RNA is discussed in further detail by Hammond et al. (2001) *Nature Rev Gen* 2: 110-119, Fire et al. (1998) *Nature* 391: 806-811 and Timmons and Fire (1998) *Nature* 395: 854.

Vectors in which RNA encoded by a transcription factor or transcription factor homologue cDNA is over-expressed can also be used to obtain co-suppression of a corresponding endogenous gene, e.g., in the manner described in U.S. Pat. No. 5,231,020 to Jorgensen. Such co-suppression (also termed sense suppression) does not require that the entire transcription factor cDNA be introduced into the plant cells, nor does it require that the introduced sequence be exactly identical to the endogenous transcription factor gene of interest. However, as with antisense suppression, the suppressive efficiency will be enhanced as specificity of hybridization is increased, e.g., as the introduced sequence is lengthened, and/or as the sequence similarity between the introduced sequence and the endogenous transcription factor gene is increased.

Vectors expressing an untranslatable form of the transcription factor mRNA, e.g., sequences comprising one or more stop codon, or nonsense mutation) can also be used to suppress expression of an endogenous transcription factor, thereby reducing or eliminating it's activity and modifying one or more traits. Methods for producing such constructs are described in U.S. Pat. No. 5,583,021. Preferably, such constructs are made by introducing a premature stop codon into the transcription factor gene. Alternatively, a plant trait can be modified by gene silencing using double-strand RNA (Sharp (1999) *Genes Devel.* 13: 139-141). Another method for abolishing the expression of a gene is by insertion mutagenesis using the T-DNA of *Agrobacterium tumefaciens*. After generating the insertion mutants, the mutants can be screened to identify those containing the insertion in a transcription factor or transcription factor homologue gene. Plants containing a single transgene insertion event at the desired gene can be crossed to generate homozygous plants for the mutation. Such methods are well known to those of skill in the art. (See for example Koncz et al. (1992) *Methods in Arabidopsis Research*, World Scientific.)

Alternatively, a plant phenotype can be altered by eliminating an endogenous gene, such as a transcription factor or transcription factor homologue, e.g., by homologous recombination (Kempin et al. (1997) *Nature* 389: 802-803).

A plant trait can also be modified by using the Cre-lox system (for example, as described in U.S. Pat. No. 5,658,772). A plant genome can be modified to include first and second lox sites that are then contacted with a Cre recombinase. If the lox sites are in the same orientation, the intervening DNA sequence between the two sites is excised. If the lox sites are in the opposite orientation, the intervening sequence is inverted.

The polynucleotides and polypeptides of this invention can also be expressed in a plant in the absence of an expression cassette by manipulating the activity or expression level of the endogenous gene by other means. For example, by ectopically expressing a gene by T-DNA activation tagging (Ichikawa et al. (1997) *Nature* 390 698-701; Kakimoto et al. (1996) *Science* 274: 982-985). This method entails transforming a plant with a gene tag containing multiple transcriptional enhancers and once the tag has inserted into the genome, expression of a flanking gene coding sequence becomes deregulated. In another example, the transcriptional machinery in a plant can be modified so as to increase transcription levels of a polynucleotide of the invention (See, e.g., PCT Publications WO 96/06166 and WO 98/53057 which describe the modification of the DNA-binding specificity of zinc finger proteins by changing particular amino acids in the DNA-binding motif).

The transgenic plant can also include the machinery necessary for expressing or altering the activity of a polypeptide encoded by an endogenous gene, for example by altering the phosphorylation state of the polypeptide to maintain it in an activated state.

Transgenic plants (or plant cells, or plant explants, or plant tissues) incorporating the polynucleotides of the invention and/or expressing the polypeptides of the invention can be produced by a variety of well established techniques as described above. Following construction of a vector, most typically an expression cassette, including a polynucleotide, e.g., encoding a transcription factor or transcription factor homologue, of the invention, standard techniques can be used to introduce the polynucleotide into a plant, a plant cell, a plant explant or a plant tissue of interest. Optionally, the plant cell, explant or tissue can be regenerated to produce a transgenic plant.

The plant can be any higher plant, including gymnosperms, monocotyledonous and dicotyledonous plants. Suitable protocols are available for Leguminosae (alfalfa, soybean, clover, etc.), Umbelliferae (carrot, celery, parsnip), Cruciferae (cabbage, radish, rapeseed, broccoli, etc.), Curcurbitaceae (melons and cucumber), Gramineae (wheat, corn, rice, barley, millet, etc.), Solanaceae (potato, tomato, tobacco, peppers, etc.), and various other crops. See protocols described in Ammirato et al. (1984) *Handbook of Plant Cell Culture-Crop Species*, Macmillan Publ. Co. Shimamoto et al. (1989) *Nature* 338: 274-276; Fromm et al. (1990) *Bio/Technology* 8: 833-839; and Vasil et al. (1990) *Bio/Technology* 8: 429-434.

Transformation and regeneration of both monocotyledonous and dicotyledonous plant cells is now routine, and the selection of the most appropriate transformation technique will be determined by the practitioner. The choice of method will vary with the type of plant to be transformed; those skilled in the art will recognize the suitability of particular methods for given plant types. Suitable methods can include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumefaciens* mediated transformation. Transformation means introducing a nucleotide sequence into a plant in a manner to cause stable or transient expression of the sequence.

Successful examples of the modification of plant characteristics by transformation with cloned sequences which serve to illustrate the current knowledge in this field of technology, and which are herein incorporated by reference, include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369 and 5,610,042.

Following transformation, plants are preferably selected using a dominant selectable marker incorporated into the transformation vector. Typically, such a marker will confer antibiotic or herbicide resistance on the transformed plants, and selection of transformants can be accomplished by exposing the plants to appropriate concentrations of the antibiotic or herbicide.

After transformed plants are selected and grown to maturity, those plants showing a modified trait are identified. The modified trait can be any of those traits described above. Additionally, to confirm that the modified trait is due to changes in expression levels or activity of the polypeptide or polynucleotide of the invention can be determined by analyzing mRNA expression using Northern blots, RT-PCR or microarrays, or protein expression using immunoblots or Western blots or gel shift assays.

Integrated Systems—Sequence Identity

Additionally, the present invention may be an integrated system, computer or computer readable medium that comprises an instruction set for determining the identity of one or more sequences in a database. In addition, the instruction set can be used to generate or identify sequences that meet any specified criteria. Furthermore, the instruction set may be used to associate or link certain functional benefits, such improved characteristics, with one or more identified sequence.

For example, the instruction set can include, e.g., a sequence comparison or other alignment program, e.g., an available program such as, for example, the Wisconsin Package Version 10.0, such as BLAST, FASTA, PILEUP, FINDPATTERNS or the like (GCG, Madison, Wis.). Public sequence databases such as GenBank, EMBL, Swiss-Prot and PIR or private sequence databases such as PHYTOSEQ sequence database (Incyte Genomics, Palo Alto, Calif.) can be searched.

Alignment of sequences for comparison can be conducted by the local homology algorithm of Smith and Waterman (1981) *Adv. Appl. Math.* 2: 482-489, by the homology alignment algorithm of Needleman and Wunsch (1970) *J. Mol. Biol.* 48: 443-453, by the search for similarity method of Pearson and Lipman (1988) *Proc. Natl. Acad. Sci. U.S.A.* 85: 2444-2448, by computerized implementations of these algorithms. After alignment, sequence comparisons between two (or more) polynucleotides or polypeptides are typically performed by comparing sequences of the two sequences over a comparison window to identify and compare local regions of sequence similarity. The comparison window can be a segment of at least about 20 contiguous positions, usually about 50 to about 200, more usually about 100 to about 150 contiguous positions. A description of the method is provided in Ausubel et al., supra.

A variety of methods for determining sequence relationships can be used, including manual alignment and computer assisted sequence alignment and analysis. This later approach is a preferred approach in the present invention, due to the increased throughput afforded by computer assisted methods. As noted above, a variety of computer programs for performing sequence alignment are available, or can be produced by one of skill.

One example algorithm that is suitable for determining percent sequence identity and sequence similarity is the BLAST algorithm, which is described in Altschul et al. *J. Mol. Biol.* 215: 403-410 (1990). Software for performing BLAST analyses is publicly available, e.g., through the National Center for Biotechnology Information (see internet website at ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89: 10915). Unless otherwise indicated, "sequence identity" here refers to the % sequence identity generated from a tblastx using the NCBI version of the algorithm at the default settings using gapped alignments with the filter "off" (see, for example, internet website at ncbi.nlm.nih.gov).

In addition to calculating percent sequence identity, the BLAST algorithm also performs a statistical analysis of the similarity between two sequences (see, e.g., Karlin & Altschul (1993) *Proc. Natl. Acad. Sci. USA* 90: 5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence (and, therefore, in this context, homologous) if the smallest sum probability in a comparison of the test nucleic acid to the reference nucleic acid is less than about 0.1, or less than about 0.01, and or even less than about 0.001. An additional example of a useful sequence alignment algorithm is PILEUP. PILEUP creates a multiple sequence alignment from a group of related sequences using progressive, pairwise alignments. The program can align, e.g., up to 300 sequences of a maximum length of 5,000 letters.

The integrated system, or computer typically includes a user input interface allowing a user to selectively view one or more sequence records corresponding to the one or more character strings, as well as an instruction set which aligns the one or more character strings with each other or with an additional character string to identify one or more region of sequence similarity. The system may include a link of one or more character strings with a particular phenotype or gene function. Typically, the system includes a user readable output element that displays an alignment produced by the alignment instruction set.

The methods of this invention can be implemented in a localized or distributed computing environment. In a distributed environment, the methods may be implemented on a single computer comprising multiple processors or on a multiplicity of computers. The computers can be linked, e.g. through a common bus, but more preferably the computer(s) are nodes on a network. The network can be a generalized or a dedicated local or wide-area network and, in certain preferred embodiments, the computers may be components of an intra-net or an internet.

Thus, the invention provides methods for identifying a sequence similar or homologous to one or more polynucleotides as noted herein, or one or more target polypeptides encoded by the polynucleotides, or otherwise noted herein and may include linking or associating a given plant phenotype or gene function with a sequence. In the methods, a sequence database is provided (locally or across an inter or intra net) and a query is made against the sequence database using the relevant sequences herein and associated plant phenotypes or gene functions.

Any sequence herein can be entered into the database, before or after querying the database. This provides for both expansion of the database and, if done before the querying step, for insertion of control sequences into the database. The control sequences can be detected by the query to ensure the general integrity of both the database and the query. As noted, the query can be performed using a web browser based interface. For example, the database can be a centralized public database such as those noted herein, and the querying can be done from a remote terminal or computer across an internet or intranet.

EXAMPLES

The following examples are intended to illustrate but not limit the present invention. The complete descriptions of the traits associated with each polynucleotide of the invention is fully disclosed in Table 4 and Table 6.

Example I

Full Length Gene Identification and Cloning

Putative transcription factor sequences (genomic or ESTs) related to known transcription factors were identified in the *Arabidopsis thaliana* GenBank database using the tblastn sequence analysis program using default parameters and a P-value cutoff threshold of −4 or −5 or lower, depending on the length of the query sequence. Putative transcription factor sequence hits were then screened to identify those containing particular sequence strings. If the sequence hits contained such sequence strings, the sequences were confirmed as transcription factors.

Alternatively, *Arabidopsis thaliana* cDNA libraries derived from different tissues or treatments, or genomic libraries were screened to identify novel members of a transcription family using a low stringency hybridization approach. Probes were synthesized using gene specific primers in a standard PCR reaction (annealing temperature 60° C.) and labeled with $^{32}$P dCTP using the High Prime DNA Labeling Kit (Boehringer Mannheim). Purified radiolabelled probes were added to filters immersed in Church hybridization medium (0.5 M NaPO$_4$ pH 7.0, 7% SDS, 1% w/v bovine serum albumin) and hybridized overnight at 60° C. with shaking. Filters were washed two times for 45 to 60 minutes with 1×SCC, 1% SDS at 60° C.

To identify additional sequence 5' or 3' of a partial cDNA sequence in a cDNA library, 5' and 3' rapid amplification of cDNA ends (RACE) was performed using the Marathon™ cDNA amplification kit (Clontech, Palo Alto, Calif.). Generally, the method entailed first isolating poly(A) mRNA, performing first and second strand cDNA synthesis to generate double stranded cDNA, blunting cDNA ends, followed by ligation of the Marathon™ Adaptor to the cDNA to form a library of adaptor-ligated ds cDNA.

Gene-specific primers were designed to be used along with adaptor specific primers for both 5' and 3' RACE reactions. Nested primers, rather than single primers, were used to increase PCR specificity. Using 5' and 3' RACE reactions, 5' and 3' RACE fragments were obtained, sequenced and cloned. The process can be repeated until 5' and 3' ends of the full-length gene were identified. Then the full-length cDNA was generated by PCR using primers specific to 5' and 3' ends of the gene by end-to-end PCR.

Example II

Construction of Expression Vectors

The sequence was amplified from a genomic or cDNA library using primers specific to sequences upstream and downstream of the coding region. The expression vector was pMEN20 or pMEN65, which are both derived from pMON316 (Sanders et al. (1987) *Nucleic Acids Res.* 15: 1543-1558) and contain the CaMV 35S promoter to express transgenes. To clone the sequence into the vector, both pMEN20 and the amplified DNA fragment were digested separately with SalI and NotI restriction enzymes at 37° C. for 2 hours. The digestion products were subject to electrophoresis in a 0.8% agarose gel and visualized by ethidium bromide staining. The DNA fragments containing the sequence and the linearized plasmid were excised and purified by using a Qiaquick gel extraction kit (Qiagen, Valencia Calif.). The fragments of interest were ligated at a ratio of 3:1 (vector to insert). Ligation reactions using T4 DNA ligase (New England Biolabs, Beverly Mass.) were carried out at 16° C. for 16 hours. The ligated DNAs were transformed into competent cells of the *E. coli* strain DH5α by using the heat shock method. The transformations were plated on LB plates containing 50 mg/l kanamycin (Sigma, St. Louis, Mo.). Individual colonies were grown overnight in five milliliters of LB broth containing 50 mg/l kanamycin at 37° C. Plasmid DNA was purified by using Qiaquick Mini Prep kits (Qiagen).

Example III

Transformation of *Agrobacterium* with the Expression Vector

After the plasmid vector containing the gene was constructed, the vector was used to transform *Agrobacterium tumefaciens* cells expressing the gene products. The stock of *Agrobacterium tumefaciens* cells for transformation were made as described by Nagel et al. (1990) *FEMS Microbiol Letts.* 67: 325-328. *Agrobacterium* strain ABI was grown in 250 ml LB medium (Sigma) overnight at 28° C. with shaking until an absorbance ($A_{600}$) of 0.5-1.0 was reached. Cells were harvested by centrifugation at 4,000×g for 15 min at 4° C. Cells were then resuspended in 250 µl chilled buffer (1 mM HEPES, pH adjusted to 7.0 with KOH). Cells were centrifuged again as described above and resuspended in 125 µl chilled buffer. Cells were then centrifuged and resuspended two more times in the same HEPES buffer as described above at a volume of 100 µl and 750 µl, respectively. Resuspended cells were then distributed into 40 µl aliquots, quickly frozen in liquid nitrogen, and stored at −80° C.

*Agrobacterium* cells were then transformed with plasmids prepared as described above following the protocol described by Nagel et al. For each DNA construct to be transformed, 50-100 ng DNA (generally resuspended in 10 mM Tris-HCl, 1 mM EDTA, pH 8.0) was mixed with 40 μl of *Agrobacterium* cells. The DNA/cell mixture was then transferred to a chilled cuvette with a 2 mm electrode gap and subject to a 2.5 kV charge dissipated at 25 μF and 200 μF using a Gene Pulser II apparatus (Bio-Rad, Hercules, Calif.). After electroporation, cells were immediately resuspended in 1.0 ml LB and allowed to recover without antibiotic selection for 2-4 hours at 28° C. in a shaking incubator. After recovery, cells were plated onto selective medium of LB broth containing 100 μg/ml spectinomycin (Sigma) and incubated for 24-48 hours at 28° C. Single colonies were then picked and inoculated in fresh medium. The presence of the plasmid construct was verified by PCR amplification and sequence analysis.

Example IV

Transformation of *Arabidopsis* Plants with *Agrobacterium tumefaciens* with Expression Vector After transformation of *Agrobacterium tumefaciens* with plasmid vectors containing the gene, single *Agrobacterium* colonies were identified, propagated, and used to transform *Arabidopsis* plants. Briefly, 500 ml cultures of LB medium containing 50 mg/l kanamycin were inoculated with the colonies and grown at 28° C. with shaking for 2 days until an optical absorbance at 600 nm wavelength over 1 cm ($A_{600}$) of >2.0 is reached. Cells were then harvested by centrifugation at 4,000×g for 10 min, and resuspended in infiltration medium (½× Murashige and Skoog salts (Sigma), 1× Gamborg's B-5 vitamins (Sigma), 5.0% (w/v) sucrose (Sigma), 0.044 μM benzylamino purine (Sigma), 200 μl/l Silwet L-77 (Lehle Seeds) until an $A_{600}$ of 0.8 was reached.

Prior to transformation, *Arabidopsis thaliana* seeds (ecotype Columbia) were sown at a density of ~10 plants per 4" pot onto Pro-Mix BX potting medium (Hummert International) covered with fiberglass mesh (18 mm×16 mm). Plants were grown under continuous illumination (50-75 $\mu E/m^2/sec$) at 22-23° C. with 65-70% relative humidity. After about 4 weeks, primary inflorescence stems (bolts) are cut off to encourage growth of multiple secondary bolts. After flowering of the mature secondary bolts, plants were prepared for transformation by removal of all siliques and opened flowers.

The pots were then immersed upside down in the mixture of *Agrobacterium* infiltration medium as described above for 30 sec, and placed on their sides to allow draining into a 1'×2' flat surface covered with plastic wrap. After 24 h, the plastic wrap was removed and pots are turned upright. The immersion procedure was repeated one week later, for a total of two immersions per pot. Seeds were then collected from each transformation pot and analyzed following the protocol described below.

Example V

Identification of *Arabidopsis* Primary Transformants

Seeds collected from the transformation pots were sterilized essentially as follows. Seeds were dispersed into in a solution containing 0.1% (v/v) Triton X-100 (Sigma) and sterile $H_2O$ and washed by shaking the suspension for 20 min. The wash solution was then drained and replaced with fresh wash solution to wash the seeds for 20 min with shaking. After removal of the second wash solution, a solution containing 0.1% (v/v) Triton X-100 and 70% ethanol (Equistar) was added to the seeds and the suspension was shaken for 5 min. After removal of the ethanol/detergent solution, a solution containing 0.1% (v/v) Triton X-100 and 30% (v/v) bleach (Clorox) was added to the seeds, and the suspension was shaken for 10 min. After removal of the bleach/detergent solution, seeds were then washed five times in sterile distilled $H_2O$. The seeds were stored in the last wash water at 4° C. for 2 days in the dark before being plated onto antibiotic selection medium (1× Murashige and Skoog salts (pH adjusted to 5.7 with 1M KOH), 1× Gamborg's B-5 vitamins, 0.9% phytagar (Life Technologies), and 50 mg/l kanamycin). Seeds were germinated under continuous illumination (50-75 $\mu E/m^2/sec$) at 22-23° C. After 7-10 days of growth under these conditions, kanamycin resistant primary transformants ($T_1$ generation) were visible and obtained. These seedlings were transferred first to fresh selection plates where the seedlings continued to grow for 3-5 more days, and then to soil (Pro-Mix BX potting medium).

Primary transformants were crossed and progeny seeds ($T_2$) collected; kanamycin resistant seedlings were selected and analyzed. The expression levels of the recombinant polynucleotides in the transformants varies from about a 5% expression level increase to a least a 100% expression level increase. Similar observations are made with respect to polypeptide level expression.

Example VI

Identification of *Arabidopsis* Plants with Transcription Factor Gene Knockouts

The screening of insertion mutagenized *Arabidopsis* collections for null mutants in a known target gene was essentially as described in Krysan et al (1999) *Plant Cell* 11: 2283-2290. Briefly, gene-specific primers, nested by 5-250 base pairs to each other, were designed from the 5' and 3' regions of a known target gene. Similarly, nested sets of primers were also created specific to each of the T-DNA or transposon ends (the "right" and "left" borders). All possible combinations of gene specific and T-DNA/transposon primers were used to detect by PCR an insertion event within or close to the target gene. The amplified DNA fragments were then sequenced which allows the precise determination of the T-DNA/transposon insertion point relative to the target gene. Insertion events within the coding or intervening sequence of the genes were deconvoluted from a pool comprising a plurality of insertion events to a single unique mutant plant for functional characterization. The method is described in more detail in Yu and Adam, U.S. application Ser. No. 09/177,733 filed Oct. 23, 1998.

Example VII

Morphological Analysis

Morphological analysis was performed to determine whether changes in transcription factor levels affect plant growth and development. This was primarily carried out on the T1 generation, when at least 10-20 independent lines were examined. However, in cases where a phenotype required confirmation or detailed characterization, plants from subsequent generations were also analyzed.

Primary transformants were selected on MS medium with 0.3% sucrose and 50 mg/l kanamycin. T2 and later generation plants were selected in the same manner, except that kanamycin was used at 35 mg/l. In cases where lines carry a sulfonamide marker (as in all lines generated by super-transformation), seeds were selected on MS medium with 0.3% sucrose and 1.5 mg/l sulfonamide. KO lines were usually germinated on plates without a selection. Seeds were cold-treated (stratified) on plates for 3 days in the dark (in order to increase germination efficiency) prior to transfer to growth cabinets. Initially, plates were incubated at 22° C. under a light intensity of approximately 100 microEinsteins for 7 days. At this stage, transformants were green, possessed the first two true leaves, and were easily distinguished from bleached kanamycin or sulfonamide-susceptible seedlings. Resistant seedlings were then transferred onto soil (Sunshine potting mix). Following transfer to soil, trays of seedlings were covered with plastic lids for 2-3 days to maintain humidity while they became established. Plants were grown on soil under fluorescent light at an intensity of 70-95 microEinsteins and a temperature of 18-23° C. Light conditions consisted of a 24-hour photoperiod unless otherwise stated. In instances where alterations in flowering time was apparent, flowering was re-examined under both 12-hour and 24-hour light to assess whether the phenotype was photoperiod dependent. Under 24-hour light growth conditions, the typical generation time (seed to seed) was approximately 14 weeks.

Because many aspects of *Arabidopsis* development are dependent on localized environmental conditions, in all cases plants were evaluated in comparison to controls in the same flat. Controls for transgenic lines were generally wild-type plants or, where specifically indicated, transgenic plants harboring an empty transformation vector selected on kanamycin or sulfonamide. Careful examination was made at the following stages: seedling (1 week), rosette (2-3 weeks), flowering (4-7 weeks), and late seed set (8-12 weeks). Seed was also inspected. Seedling morphology was assessed on selection plates. At all other stages, plants were macroscopically evaluated while growing on soil. All significant differences (including alterations in growth rate, size, leaf and flower morphology, coloration and flowering time) were recorded, but routine measurements were not be taken if no differences were apparent. In certain cases, stem sections were stained to reveal lignin distribution. In these instances, hand-sectioned stems were mounted in phloroglucinol saturated 2M HCl (which stains lignin pink) and viewed immediately under a dissection microscope.

Flowering time was measured by the number of rosette leaves present when a visible inflorescence of approximately 3 cm is apparent Rosette and total leaf number on the progeny stem are tightly correlated with the timing of flowering (Koornneef et al (1991) *Mol. Gen. Genet* 229: 57-66. The vernalization response was measured. For vernalization treatments, seeds were sown to MS agar plates, sealed with micropore tape, and placed in a 4° C. cold room with low light levels for 6-8 weeks. The plates were then transferred to the growth rooms alongside plates containing freshly sown non-vernalized controls. Rosette leaves were counted when a visible inflorescence of approximately 3 cm was apparent.

Example VIII

Biochemical Analysis

Experiments were also performed to identify those transformants or knockouts that exhibited modified biochemical characteristics. Among the biochemicals that were assayed were insoluble sugars, such as arabinose, fucose, galactose, mannose, rhamnose or xylose or the like; prenyl lipids, such as lutein, β-carotene, xanthophyll-1, xanthophyll-2, chlorophylls A or B, or α-, δ- or γ-tocopherol or the like; fatty acids, such as 16:0 (palmitic acid), 16:1 (palmitoleic acid), 18:0 (stearic acid), 18:1 (oleic acid), 18:2 (linoleic acid), 20:0, 18:3 (linolenic acid), 20:1 (eicosenoic acid), 20:2, 22:1 (erucic acid) or the like; waxes, such as by altering the levels of C29, C31, or C33 alkanes; sterols, such as brassicasterol, campesterol, stigmasterol, sitosterol or stigmastanol or the like, glucosinolates, protein or oil levels.

Fatty acids were measured using two methods depending on whether the tissue was from leaves or seeds. For leaves, lipids were extracted and esterified with hot methanolic $H_2SO_4$ and partitioned into hexane from methanolic brine. For seed fatty acids, seeds were pulverized and extracted in methanol:heptane:toluene:2,2-dimethoxypropane:$H_2SO_4$ (39:34:20:5:2) for 90 minutes at 80° C. After cooling to room temperature the upper phase, containing the seed fatty acid esters, was subjected to GC analysis. Fatty acid esters from both seed and leaf tissues were analyzed with a Supelco SP-2330 column.

Glucosinolates were purified from seeds or leaves by first heating the tissue at 95° C. for 10 minutes. Preheated ethanol:water (50:50) is and after heating at 95° C. for a further 10 minutes, the extraction solvent is applied to a DEAE Sephadex column which had been previously equilibrated with 0.5 M pyridine acetate. Desulfoglucosinolates were eluted with 300 μl water and analyzed by reverse phase HPLC monitoring at 226 nm.

For wax alkanes, samples were extracted using an identical method as fatty acids and extracts were analyzed on a HP 5890 GC coupled with a 5973 MSD. Samples were chromatographically isolated on a J&W DB35 mass spectrometer (J&W Scientific).

To measure prenyl lipids levels, seeds or leaves were pulverized with 1 to 2% pyrogallol as an antioxidant. For seeds, extracted samples were filtered and a portion removed for tocopherol and carotenoid/chlorophyll analysis by HPLC. The remaining material was saponified for sterol determination. For leaves, an aliquot was removed and diluted with methanol and chlorophyll A, chlorophyll B, and total carotenoids measured by spectrophotometry by determining optical absorbance at 665.2 nm, 652.5 nm, and 470 mm. An aliquot was removed for tocopherol and carotenoid/chlorophyll composition by HPLC using a Waters uBondapak C18 column (4.6 mm×150 mm). The remaining methanolic solution was saponified with 10% KOH at 80° C. for one hour. The samples were cooled and diluted with a mixture of methanol and water. A solution of 2% methylene chloride in hexane was mixed in and the samples were centrifuged. The aqueous methanol phase was again re-extracted 2% methylene chloride in hexane and, after centrifugation, the two upper phases were combined and evaporated. 2% methylene chloride in hexane was added to the tubes and the samples were then extracted with one ml of water. The upper phase was removed, dried, and resuspended in 400 μl of 2% methylene chloride in hexane and analyzed by gas chromatography using a 50 m DB-5 ms (0.25 mm ID, 0.25 um phase, J&W Scientific).

Insoluble sugar levels were measured by the method essentially described by Reiter et al., (1999) *Plant J.* 12: 335-345. This method analyzes the neutral sugar composition of cell wall polymers found in *Arabidopsis* leaves. Soluble sugars were separated from sugar polymers by extracting leaves with hot 70% ethanol. The remaining residue containing the insoluble polysaccharides was then acid hydrolyzed with allose added as an internal standard. Sugar monomers generated by the hydrolysis were then reduced to the corresponding alditols by treatment with NaBH4, then were acetylated to generate the volatile alditol acetates which were then analyzed by GC-FID. Identity of the peaks was determined by comparing the retention times of known sugars converted to the corresponding alditol acetates with the retention times of peaks from wild-type plant extracts. Alditol acetates were analyzed on a Supelco SP-2330 capillary column (30 m×250 um×0.2 um) using a temperature program beginning at 180° C. for 2 minutes followed by an increase to 220° C. in 4 minutes. After holding at 220° C. for 10 minutes, the oven temperature is increased to 240° C. in 2 minutes and held at this temperature for 10 minutes and brought back to room temperature.

To identify plants with alterations in total seed oil or protein content, 150 mg of seeds from T2 progeny plants were subjected to analysis by Near Infrared Reflectance Spectroscopy (NIRS) using a Foss NirSystems Model 6500 with a spinning cup transport system. NIRS is a non-destructive analytical method used to determine seed oil and protein composition. Infrared is the region of the electromagnetic spectrum located after the visible region in the direction of longer wavelengths. 'Near infrared' owns its name for being the infrared region near to the visible region of the electromagnetic spectrum. For practical purposes, near infrared comprises wavelengths between 800 and 2500 nm. NIRS is applied to organic compounds rich in O—H bonds (such as moisture, carbohydrates, and fats), C—H bonds (such as organic compounds and petroleum derivatives), and N—H bonds (such as proteins and amino acids). The NIRS analytical instruments operate by statistically correlating NIRS signals at several wavelengths with the characteristic or property intended to be measured. All biological substances contain thousands of C—H, O—H, and N—H bonds. Therefore, the exposure to near infrared radiation of a biological sample, such as a seed, results in a complex spectrum which contains qualitative and quantitative information about the physical and chemical composition of that sample.

The numerical value of a specific analyte in the sample, such as protein content or oil content, is mediated by a calibration approach known as chemometrics. Chemometrics applies statistical methods such as multiple linear regression (MLR), partial least squares (PLS), and principle component analysis (PCA) to the spectral data and correlates them with a physical property or other factor, that property or factor is directly determined rather than the analyte concentration itself. The method first provides "wet chemistry" data of the samples required to develop the calibration.

Calibration for *Arabidopsis* seed oil composition was performed using accelerated solvent extraction using 1 g seed sample size and was validated against certified canola seed. A similar wet chemistry approach was performed for seed protein composition calibration.

Data obtained from NIRS analysis was analyzed statistically using a nearest-neighbor (N—N) analysis. The N—N analysis allows removal of within-block spatial variability in a fairly flexible fashion which does not require prior knowledge of the pattern of variability in the chamber. Ideally, all hybrids are grown under identical experimental conditions within a block (rep). In reality, even in many block designs, significant within-block variability exists. Nearest-neighbor procedures are based on assumption that environmental effect of a plot is closely related to that of its neighbors. Nearest-neighbor methods use information from adjacent plots to adjust for within-block heterogeneity and so provide more precise estimates of treatment means and differences. If there is within-plot heterogeneity on a spatial scale that is larger than a single plot and smaller than the entire block, then yields from adjacent plots will be positively correlated. Information from neighboring plots can be used to reduce or remove the unwanted effect of the spatial heterogeneity, and hence improve the estimate of the treatment effect. Data from neighboring plots can also be used to reduce the influence of competition between adjacent plots. The Papadakis N—N analysis can be used with designs to remove within-block variability that would not be removed with the standard split plot analysis (Papadakis, 1973, Inst. d'Amelior. Plantes Thessaloniki (Greece) Bull. Scientif., No. 23; Papadakis, 1984, *Proc. Acad. Athens*, 59, 326-342).

Example IX

Plate-based Physiology Experimental Methods

Plate Assays. Twelve different plate-based physiological assays (shown below), representing a variety of drought-stress related conditions, are used as a pre-screen to identify top performing lines from each project (i.e. lines from transformation with a particular construct), that will be tested in subsequent soil based assays. Typically, ten lines are subjected to plate assays, from which the best three lines are selected for subsequent soil based assays. However, in projects where significant stress tolerance is not obtained in plate based assays, lines are not submitted for soil assays.

In addition, some projects are subjected to nutrient limitation studies. A nutrient limitation assay is intended to find genes that allow more plant growth upon deprivation of nitrogen. Nitrogen is a major nutrient affecting plant growth and development that ultimately impacts yield and stress tolerance. These assays monitor primarily root but also rosette growth on nitrogen deficient media. In all higher plants, inorganic nitrogen is first assimilated into glutamate, glutamine, aspartate and asparagine, the four amino acids used to transport assimilated nitrogen from sources (e.g. leaves) to sinks (e.g. developing seeds). This process is regulated by light, as well as by C/N metabolic status of the plant. We use a C/N sensing assay to look for alterations in the mechanisms plants use to sense internal levels of carbon and nitrogen metabolites which could activate signal transduction cascades that regulate the transcription of N-assimilatory genes. To determine whether these mechanisms are altered, we exploit the observation that wild-type plants grown on media containing high levels of sucrose (3%) without a nitrogen source accumulate high levels of anthocyanins. This sucrose induced anthocyanin accumulation can be relieved by the addition of either inorganic or organic nitrogen. We use glutamine as a nitrogen source since it also serves as a compound used to transport N in plants.

Germination assays. NaCl (150 mM), mannitol (300 mM), sucrose (9.4%), ABA (0.3 µM), Heat (32° C.), Cold (8° C.), −N is basal media minus nitrogen plus 3% sucrose and −N/+Gln is basal media minus nitrogen plus 3% sucrose and 1 mM glutamine.

Growth assays. Severe dehydration (drought), heat (32° C. for 5 days followed by recovery at 22° C.), chilling (8° C.), root development (visual assessment of lateral and primary roots, root hairs and overall growth). For the nitrogen limitation assay, all components of MS medium remain constant except N is reduced to 20 mg/L of $NH_4NO_3$. Note that 80% MS has 1.32 g/L $NH_4NO_3$ and 1.52 g/L $KNO_3$.

Unless otherwise stated, all experiments are performed with the *Arabidopsis thaliana* ecotype Columbia (col-0). Assays are usually performed on non-selected segregating T2 populations (in order to avoid the extra stress of selection). Control plants for assays on lines containing direct promoter-fusion constructs are Col-0 plants transformed an empty transformation vector (pMEN65). Controls for 2-component lines (generated by supertransformation) are the background promoter-driver lines (i.e. promoter::LexA-GAL4TA lines), into which the supertransformations were initially performed.

All assays are performed in tissue culture. Growing the plants under controlled temperature and humidity on sterile medium produces uniform plant material that has not been exposed to additional stresses (such as water stress) which could cause variability in the results obtained. All assays were designed to detect plants that are more tolerant or less tolerant to the particular stress condition and were developed with reference to the following publications: Jang et al. (1997) *Plant Cell* 9: 5-19; Smeekens (1998) *Curr. Opin. Plant Biol.* 1: 230-234; Liu and Zhu (1997) *Proc. Natl. Acad. Sci. U.S.A.* 94: 14960-14964; Saleki et al. (1993) *Plant Physiol.* 101: 839-845; Wu et al. (1996) *Plant Cell* 8: 617-627; Zhu et al. (1998) *Plant Cell* 10: 1181-1191; Alia et al. (1998) *Plant J.* 16: 155-161; Xin and Browse, (1998) *Proc. Natl. Acad. Sci. U.S.A.* 95: 7799-7804; Leon-Kloosterziel et al. (1996) *Plant Physiol.* 110: 233-240. Where possible, assay conditions were originally tested in a blind experiment with controls that had phenotypes related to the condition tested.

Procedures

Prior to plating, seed for all experiments are surface sterilized in the following manner: (1) 5 minute incubation with mixing in 70% ethanol, (2) 20 minute incubation with mixing in 30% bleach, 0.01% triton-X 100, (3) 5× rinses with sterile water, (4) Seeds are re-suspended in 0.1% sterile agarose and stratified at 4° C. for 3-4 days.

All germination assays follow modifications of the same basic protocol. Sterile seeds are sown on the conditional media that has a basal composition of 80% MS+Vitamins. Plates are incubated at 22° C. under 24-hour light (120-130 $\mu E\ m^{-2}\ s^{-1}$) in a growth chamber. Evaluation of germination and seedling vigor is done 5 days after planting. For assessment of root development, seedlings germinated on 80% MS+Vitamins+1% sucrose are transferred to square plates at 7 days. Evaluation is done 5 days after transfer following growth in a vertical position. Qualitative differences are recorded including lateral and primary root length, root hair number and length, and overall growth.

For chilling (8° C.) and heat sensitivity (32° C.) growth assays, seeds are germinated and grown for 7 days on MS+Vitamins+1% sucrose at 22° C. and then are transferred to chilling or heat stress conditions. Heat stress is applied for 5 days, after which the plants are transferred back to 22° C. for recovery and evaluated after a further 5 days. Plants are subjected to chilling conditions (8° C.) and evaluated at 10 days and 17 days.

For severe dehydration (drought) assays, seedlings are grown for 14 days on MS+Vitamins+1% Sucrose at 22° C. Plates are opened in the sterile hood for 3 hr for hardening and then seedlings are removed from the media and let dry for 2 h in the hood. After this time they are transferred back to plates and incubated at 22° C. for recovery. Plants are evaluated after 5 days.

Experiments were also performed to identify those transformants or knockouts that exhibited modified sugar-sensing. For such studies, seeds from transformants were germinated on media containing 5% glucose or 9.4% sucrose which normally partially restrict hypocotyl elongation. Plants with altered sugar sensing may have either longer or shorter hypocotyls than normal plants when grown on this media. Additionally, other plant traits may be varied such as root mass.

Example X

Soil Drought Experimental Methods

The soil drought assay (performed in clay pots) is based on that described by Haake et al. (2002). In the current procedure, seedlings were first germinated on selection plates containing either kanamycin or sulfonamide. Seeds were sterilized by a 2 minute ethanol treatment followed by 20 minutes in 30% bleach/0.01% Tween and five washes in distilled water. Seeds are sown to MS agar in 0.1% agarose and stratified for 3 days at 4° C., before transfer to growth cabinets with a temperature of 22° C. After 7 days of growth on selection plates, seedlings are transplanted to 3.5 inch diameter clay pots containing 80 g of a 50:50 mix of vermiculite:perlite topped with 80 g of ProMix. Typically, each pot contains 14 seedlings, and plants of the transgenic line being tested are in separate pots to the wild-type controls. Pots containing the transgenic line versus control pots were interspersed in the growth room, maintained under 24-hour light conditions (18-23° C., and 90-100 $\mu E\ m^{-2}\ s^{-1}$) and watered for a period of 14 days. Water was then withheld and pots were placed on absorbent diaper paper for a period of 8-10 days to apply a drought treatment. After this period, a visual qualitative "drought score" from 0-6 is assigned to record the extent of visible drought stress symptoms. A score of "6" corresponds to no visible symptoms whereas a score of "0" corresponds to extreme wilting and the leaves having a "crispy" texture. At the end of the drought period, pots are re-watered and scored after 5-6 days; the number of surviving plants in each pot is counted, and the proportion of the total plants in the pot that survived is calculated.

Slit-pot method. A variation of the above method was sometimes used, whereby plants for a given transgenic line were compared to wild-type controls in the same pot. For those studies, 7 wild-type seedlings were transplanted into one half of a 3.5 inch pot and 7 seedlings of the line being tested were transplanted into the other half of the pot.

Analysis of results. In a given experiment, we typically compare 6 or more pots of a transgenic line with 6 or more pots of the appropriate control. (In the split pot method, 12 or more pots are used.) The mean drought score and mean proportion of plants surviving (survival rate) are calculated for both the transgenic line and the wild-type pots. In each case a p-value* is calculated, which indicates the significance of the difference between the two mean values. The results for each transgenic line across each planting for a particular project are then presented in a results table. Results where the lines show a significantly better or worse performance versus the control are highlighted.

Calculation of p-values. For the assays where control and experimental plants are in separate pots, survival is analyzed with a logistic regression to account for the fact that the random variable is a proportion between 0 and 1. The reported p-value is the significance of the experimental proportion contrasted to the control, based upon regressing the logit-transformed data.

Drought score, being an ordered factor with no real numeric meaning, is analyzed with a non-parametric test between the experimental and control groups. The p-value is calculated with a Mann-Whitney rank-sum test.

For the split-pot assays, matched control and experimental measurements are available for both variables. In lieu of a direct transformed regression technique for this data, the logit-transformed proportions are analyzed by parametric methods. The p-value is derived from a paired-t-test on the transformed data. For the paired score data, the p-value from a Wilcoxon test is reported.

Measurement of Photosynthesis. Photosynthesis was measured using a LICOR LI-6400. The LI-6400 uses infrared gas analyzers to measure carbon dioxide to generate a photosynthesis measurement. It is based upon the difference of the $CO_2$ reference (the amount put into the chamber) and the $CO_2$ sample (the amount that leaves the chamber). Since photosynthesis is the process of converting $CO_2$ to carbohydrates, we expect to see a decrease in the amount of $CO_2$ sample. From this difference, a photosynthesis rate can be generated. In some cases, respiration may occur and an increase in $CO_2$ detected. To perform measurements, the LI-6400 is set-up and calibrated as per LI-6400 standard directions. Photosynthesis is measured in the youngest most fully expanded leaf at 300 and 1000 ppm $CO_2$ using a metal halide light source. This light source provides about 700 $\mu E$ $m^{-2}$ $s^{-1}$.

Fluorescence was measured in dark and light adapted leaves using either a LI-6400 (LICOR) with a leaf chamber fluorometer attachment or an OS-1 (Opti-Sciences) as described in the manufacturer's literature. When the LI-6400 was used, all manipulations were performed under a dark shade cloth. Plants were dark adapted by placing in a box under this shade cloth until used. The OS-30 utilized small clips to create dark adapted leaves.

Chlorophyll/carotenoid determination. For some experiments, chlorophyll was estimated in methanolic extracts using the method of Porra et al. (1989) *Biochim. et Biophys. Acta* 975: 384-394. Carotenoids were estimated in the same extract at 450 nm using an A(1%) of 2500. We currently are measuring chlorophyll using a SPAD-502 (Minolata). When the SPAD-502 is being used to measure chlorophyll, both carotenoid and chlorophyll content and amount can also be determined via HPLC. Pigments are extracted from leave tissue by homogenizing leaves in acetone:ethyl acetate (3:2). Water was added, the mixture centrifuged, and the upper phase removed for HPLC analysis. Samples are analyzed using a Zorbax C18 (non-endcapped) column (250×4.6) with a gradient of acetonitrile:water (85:15) to acetonitrile:methanol (85:15) in 12.5 minutes. After holding at these conditions for two minutes, solvent conditions were changed to methanol:ethyl acetate (68:32) in two minutes. Carotenoids and chlorophylls are quantified using peak areas and response factors calculated using lutein and β-carotene as standards.

Example XI

Experimental Results

G2340: (SEQ ID NOs. 17 and 18)

G2340 was analyzed using transgenic plants in which the gene was expressed under the control of the 35S promoter. Overexpression of G2340 produced a spectrum of deleterious effects on *Arabidopsis* growth and development. 35S::G2340 primary transformants were generally smaller than controls, and at early stages some displayed leaves that were held in a vertical orientation. The most severely affected lines died at early stages. Others survived, but displayed necrosis of the blades in later rosette leaves and cauline leaves. Inflorescence development was also highly abnormal; stems were typically shorter than wild type, often 'kinked' at nodes, and the tissue had a rather fleshy succulent appearance. Flower buds were frequently poorly formed, failed to open and withered away without siliques developing. Additionally, secondary shoot growth frequently failed the tips of such structures sometimes senesced. Due to these abnormalities, many of the primary transformants were completely infertile. Three T1 lines (#1, 5,20) with a relatively weak phenotype, which did set some seed, were selected for further study. Plants from the T2-20 population displayed a strong phenotype, and died early in development. The other two T2 populations were slightly small, but the effects were much weaker than those seen in the parental plants, suggesting that activity of the transgene might have become reduced between the generations. It should be noted that G2340 and G671 (SEQ ID NO: 19) are part of the same clade and that they had very similar morphological phenotypes and a similar expression pattern. These two genes may have overlapping or redundant phenotypes in the plant. Small, pale seedlings with strap-like leaves that held a vertical orientation were found in the mixed line populations of 35S::G2340 transgenic seedlings when grown under sterile conditions, similar to those observed in soil grown plants in the T1 generation. The necrotic lesions observed on the T1 plants grown in soil were not observed on the plants grown in culture leaving uncertainty as to whether the necrotic lesion phenotype is a classic lesion mimic phenotype that would suggest that G2340 is involved in cell death responses or if the G2340 overexpressor plants are simply hyper-sensitive to stresses. One class of lesion mimic forms progressive lesions following an inductive stress. Lesion formation may be induced in G2340 overexpressing plants grown in culture. In addition to the morphological changes, overexpression of G2340 resulted in an extreme alteration in seed glucosinolate profile. This phenotype was observed in one line, line 1, in seed from two independent plantings. According to RT-PCR analysis, G2340 was expressed primarily in roots and was slightly induced in leaf tissue in response to auxin and heat treatments. G2340 can be used to engineer plants with an inducible cell death response. A gene that regulates cell death in plants can be used to induce a pathogen protective hyper-response (HR) in plants without the potentially detrimental consequences of a constitutive systemic acquired resistance (SAR). Other potential utilities include the creation of novel abscission zones or inducing death in reproductive organs to prevent the spread of pollen, transgenic or otherwise. In the case of necrotrophic pathogens that rely on dead plant tissue as a source of nutrients, prevention of cell death could confer tolerance to these diseases. Overexpression of G2340 in *Arabidopsis* also resulted in an extreme alteration in seed glucosinolate profile. Therefore, the gene can be used to alter glucosinolate composition in plants. Increases or decreases in specific glucosinolates or total glucosinolate content are desirable depending upon the particular application. For example: (1) Glucosinolates are undesirable components of the oilseeds used in animal feed, since they produce toxic effects. Low-glucosinolate varieties of canola have been developed to combat this problem. (2) Some glucosinolates have anti-cancer activity; thus, increasing the levels or composition of these compounds might be of interest from a nutraceutical standpoint. (3) Glucosinolates form part of a plants natural defense against insects. Modification of glucosinolate composition or quantity can therefore afford increased protection from predators. Furthermore, in edible crops, tissue specific promoters can be used to ensure that these compounds accumulate specifically in tissues, such as the epidermis, which are not taken for consumption.

G2583: (SEQ ID NOs. 143 and 144)

G2583 was studied using transgenic plants in which the gene was expressed under the control of the 35S promoter. Most notably, 35S::G2583 plants exhibited extremely glossy leaves. At early stages, 35S::G2583 seedlings appeared normal, but by about two weeks after sowing, the plants exhibited very striking shiny leaves, which were apparent until very late in development. In addition to this phenotype, it should be noted that many lines displayed a variety of other effects such as a reduction in overall size, narrow curled leaves, or various non-specific floral abnormalities, which reduced fertility. These effects on leaf appearance were observed in 18/20 primary transformants, and in all the plants from 4/6 of the T2 lines (#2,4,9 and 15) examined. The glossy nature of the leaves from 35S::G2583 plants can be a consequence of changes in epicuticular wax content or composition. G2583 belongs to a small clade within the large AP2/EREBP *Arabidopsis* family that also contains G975 (SEQ ID NO: 89), G1387 (SEQ ID NO: 145), and G977 (SEQ ID NO: 147). Overexpression of G975 (SEQ ID NO: 89) caused a substantial increase in leaf wax components, as well as morphological phenotypes resembling those observed in 35S::G2583 plants. G2583 was ubiquitously expressed (at higher levels in root, flower, embryo, and silique tissues). G2583 can be used to modify plant appearance (shiny leaves). In addition, it can be used to manipulate wax composition, amount, or distribution, which in turn can modify plant tolerance to drought and/or low humidity or resistance to insects.

G362: (SEQ ID NOs. 61 and 62)

G362 was analyzed using transgenic plants in which G362 was expressed under the control of the 35S promoter. 35S::G362 had a number of developmental effects with the most prominent result being an increase in trichome number as well as the ectopic formation of trichomes. Overexpression of G362 also increased anthocyanin levels in various tissues at different stages of growth. Seedlings sometimes showed high levels of pigment in the first true leaves. Late flowering lines also became darkly pigmented. Seeds from a number of lines were observed to develop patches of dark purple pigmentation. Inflorescences from 35S::G362 plants were thin, and flowers sometimes displayed poorly developed organs. The seed yield from many lines was somewhat poor. As determined by RT-PCR, G362 is expressed in roots, and is expressed at significantly lower levels in siliques, seedlings and shoots. No expression of G362 was detected in the other tissues tested. G362 expression was induced in rosette leaves by heat stress. G362 can be used to alter trichome number and distribution in plants. Trichome glands on the surface of many higher plants produce and secrete exudates which give protection from the elements and pests such as insects, microbes and herbivores. These exudates may physically immobilize insects and spores, may be insecticidal or ant-microbial or they may allergens or irritants to protect against herbivores. Trichomes have also been suggested to decrease transpiration by decreasing leaf surface air flow, and by exuding chemicals that protect the leaf from the sun. Another use for G362 is to increase the density of cotton fibers in cotton bolls. Cotton fibers are modified unicellular trichomes that are produced from the ovule epidermis. However, typically only 30% of the epidermal cells take on a trichome fate (Basra and Malik (1984) *Int. Rev. Cytol.* 89: 65-113). Thus, cotton yields can be increased by inducing a greater proportion of the ovule epidermal cells to become fibers. Depending on the plant species, varying amounts of diverse secondary biochemicals (often lipophilic terpenes) are produced and exuded or volatilized by trichomes. These exotic secondary biochemicals, which are relatively easy to extract because they are on the surface of the leaf, have been widely used in such products as flavors and aromas, drugs, pesticides and cosmetics. One class of secondary metabolites, the diterpenes, can effect several biological systems such as tumor progression, prostaglandin synthesis and tissue inflammation. In addition, diterpenes can act as insect pheromones, termite allomones, and can exhibit neurotoxic, cytotoxic and antimitotic activities. As a result of this functional diversity, diterpenes have been the target of research several pharmaceutical ventures. In most cases where the metabolic pathways are impossible to engineer, increasing trichome density or size on leaves may be the only way to increase plant productivity. Thus, the use of G362 and its homologs to increase trichome density, size or type can have profound utilities in molecular farming practices (for example, the use of trichomes as a manufacturing system for complex secondary metabolites), and in producing insect resistant and herbivore resistant plants. In addition, G362 can be used to alter a plant's time to flowering.

G2105: (SEQ ID NOs. 63 and 64)

The ORF boundary of G2105 was determined and G2105 was analyzed using transgenic plants in which G2105 was expressed under the control of the 35S promoter. Two of four T2 lines examined appeared dark green and were smaller than wild type at all stages of development. Additionally, the adaxial leaf surfaces from these plants had a somewhat 'lumpy' appearance caused by trichomes being raised-up on small mounds of epidermal cells. Two lines of G2105 overexpressing plants had larger seed. G2105 expression was root specific and induced in leaves by auxin, abscisic acid, high temperature, salt and osmotic stress treatments. On the basis of the analyses, G2105 can be used to manipulate some aspect of plant growth or development, particularly in trichome development. In addition, G2105 can be used to modify seed size and/or morphology, which can have an impact on yield. The promoter of G2105 can have some utility as a root specific promoter.

G47 (SEQ ID NOs. 65 and 66)

G47 was studied using transgenic plants in which the gene was expressed under the control of the 35S promoter. Overexpression of G47 resulted in a variety of morphological and physiological phenotypic alterations. 35S::G47 plants showed enhanced tolerance to osmotic stress. In a root growth assay on PEG-containing media, G47 overexpressing transgenic seedlings were larger and had more root growth compared with wild-type controls. G47 expression levels may be altered by environmental conditions, in particular reduced by salt and osmotic stresses. In addition to the phenotype observed in the osmotic stress assay, germination efficiency for the seeds from G47 overexpressor plants was low. Overexpression of G47 also produced a substantial delay in flowering time and caused a marked change in shoot architecture. 35S::G47 transformants were small at early stages and switched to flowering more than a week later than wild-type controls (continuous light conditions). The inflorescences from these plants appeared thick and fleshy, had reduced apical dominance, and exhibited reduced internode elongation leading to a short compact stature. The branching pattern of the stems also appeared abnormal, with the primary shoot becoming 'kinked' at each coflorescence node. Additionally, the plants showed slightly reduced fertility and formed rather small siliques that were borne on short pedicels and held vertically, close against the stem. Additional alterations were detected in the inflorescence stems of 35S::G47 plants. Stem sections from T2-21 and T2-24 plants were of wider diameter, and had large irregular vascular bundles containing a much greater number of xylem vessels than wild type. Furthermore, some of the xylem vessels within the bundles appeared narrow and were possibly more lignified than were those of controls. G47 was expressed at higher levels in rosette leaves, and transcripts were detected in other tissues (flower, embryo, silique, and germinating seedling). G47 can be used to manipulate flowering time, to modify plant architecture and stem structure (including development of vascular tissues and lignin content) and to improve plant performance under osmotic stress. The use of G47 or of G47 orthologs from tree species can be used to modulate lignin content of a plant. This allows the quality of wood used for furniture or construction to be improved. Lignin is energy rich; increasing lignin composition could therefore be valuable in raising the energy content of wood used for fuel. Conversely, the pulp and paper industries seek wood with a reduced lignin content. Currently, lignin must be removed in a costly process that involves the use of many polluting chemicals. Consequently, lignin is a serious barrier to efficient pulp and paper production. In addition to forest biotechnology applications, changing lignin content might increase the palatability of various fruits and vegetables. A wide variety of applications exist for systems that either lengthen or shorten the time to flowering.

Closely-related homologs of G47, determined by BLAST, alignment and phylogeneitc analysis, include G2133 (SEQ ID NO: 152), G3643 (SEQ ID NO: 158), G3644 (SEQ ID NO: 156), and G3649 (SEQ ID NO: 154). Each of these sequences has conferred a transcriptional regulatory activity of G47 in that when any of these sequences were overexpressed in plants, they have each produced some lines that were larger, later in their development and flowering, and more tolerant to water-deprivation, cold or salt, similar to plants overexpressing G47 (Table 4), as compared to controls.

G975: (SEQ ID NOs. 89 and 90)

G975 was identified as a new member of the AP2/EREBP family (EREBP subfamily) of transcription factors. G975 was expressed in flowers and, at lower levels, in shoots, leaves, and siliques. GC-FID and GC-MS analyses of leaves from G975 overexpressing plants showed that the levels of C29, C31, and C33 alkanes were substantially increased (up to 10-fold) compared with control plants. A number of additional compounds of similar molecular weight, presumably also wax components, also accumulated to significantly higher levels in G975 overexpressing plants. C29 alkanes constituted close to 50% of the wax content in wild-type plants (Millar et al. (1998) *Plant Cell* 11: 1889-1902), suggesting that a major increase in total wax content occurred in the G975 transgenic plants. However, the transgenic plants had an almost normal phenotype (although small morphological differences are detected in leaf appearance), indicating that overexpression of G975 was not deleterious to the plant. Overexpression of G975 did not cause the dramatic alterations in plant morphology that had been reported for *Arabidopsis* plants in which the FATTY ACID ELONGATION1 gene was overexpressed (Millar et al. (1998) supra). G975 may regulate the expression of some of the genes involved in wax metabolism. One *Arabidopsis* AP2 sequence (G1387; SEQ ID NO: 145) that is significantly more closely related to G975 than the rest of the members of the AP2/EREBP family is predicted to have a function and a use related to that of G975. G975 can be used to manipulate wax composition, amount, or distribution, which in turn can modify plant tolerance to drought and/or low humidity or resistance to insects, as well as plant appearance (shiny leaves). G975 can also be used to specifically alter wax composition, amount, or distribution in those plants and crops from which wax is a valuable product.

A non-*Arabidopsis* gene that is related to G975 is LA6408 BNAF1258 Mustard flower buds *Brassica rapa* cDNA clone F1258. The similarity between G975 and the *Brassica rapa* gene represented by EST LA6408 extends beyond the conserved AP2 domain that characterizes the AP2/EREBP family. This *Brassica rapa* gene appeared to be more closely related to G975 than *Arabidopsis* G1387, indicating that EST LA6408 may represent a true G975 ortholog. The similarity between G975 and *Arabidopsis* G1387 (SEQ ID NO: 145) also extends beyond the conserved AP2 domain.

G2583 (SEQ ID NO: 143 and 144), a closely-related homolog of G975 determined by BLAST, alignment and phylogeneitc analysis, has been shown to confer a transcriptional regulatory activity of G975 in that when the polypeptide sequences were overexpressed in plants and produced some lines that were later in their development and flowering, and produced shiny leaves, indicating more wax production, similar to plants overexpressing G975 (Table 4), as compared to controls. Other closely related sequences include G1387 (SEQ ID NO: 145 and 146), and G4294 (SEQ ID NO: 149 and 150). Although detailed analyses with plants overexpressing these sequence have not yet been performed, plants overexpressing these related sequences are likely to confer some similar transcriptional regulatory activity and traits as G975.

G214: (SEQ ID NOs. 33 and 34)

G214 overexpressing lines were late bolting, showed larger biomass (increased leaf number and size), and were darker green in vegetative and reproductive tissues due to a higher chlorophyll content in the later stages of development. In these later stages, the overexpressor plants also had higher insoluble sugar, leaf fatty acid, and carotenoid content per unit area. Line 11 also showed a significant, repeatable increase in lutein levels in seeds. Micro-array data was consistent with the morphological and biochemical data in that the genes that were highly induced included chloroplast localized enzymes, and light regulated genes such as Rubisco, carbonic anhydrase, and the photosystem 1 reaction center subunit precursor. A chlorophyll biosynthetic enzyme was also highly induced, consistent with the dark green color of the adult leaves and perhaps a higher photosynthetic rate. A measurement of leaf fatty acid in the older overexpressors suggested that the overall levels were higher than wild-type levels (except for the percent composition of 16:3 in line 11). Percent composition of 16:1 and 16:3 (fatty acids found primarily in plastids) is similar to wild-type arguing against an increase in chloroplast number as an explanation for increase chlorophyll content in the leaves. G214 overexpressing lines 3, 11, and 15 were sensitive to germination on high glucose showing less cotyledon expansion and hypocotyl elongation suggesting the late bolting and dark green phenotype could be tied into carbon sensing which has been shown to regulate phytochrome A signaling. Sugars are key regulatory molecules that affect diverse processes in higher plants including germination, growth, flowering, senescence, sugar metabolism and photosynthesis. Glucose-specific hexose-sensing has also been described in plants and implicated in cell division and the repression of famine genes (photosynthetic or glyoxylate cycles). Potential utilities of G214 include increasing chlorophyll content allowing more growth and productivity in conditions of low light. With a potentially higher photosynthetic rate, fruits can have higher sugar content. Increased carotenoid content can be used as a nutraceutical to produce foods with greater antioxidant capability. Also G214 can be used to manipulate seed composition which is very important for the nutritional value and production of various food products.

G214 is homologous to a tomato (Cornell *Lycopersicon esculentum*) EST (cLER12A11) generated from a *Pseudomonas* resistant line.

G974: (SEQ ID NOs. 51 and 52)

The complete sequence of G974 was obtained and G974 was studied using transgenic plants in which G974 was expressed under the control of the 35S promoter. Constitutive expression of G974 produced deleterious effects: the majority of 35S::G974 primary transformants showed a reduction in overall size and developed rather slowly compared to wild type controls. These phenotypic alterations were not observed in the T2 generation, perhaps indicating silencing of the transgene. The T2 plants were wild-type in the physiological and biochemical analyses performed. G974 was ubiquitously expressed. 35S::G974 had altered seed oil content Several AP2 proteins from a variety of species (*Atriplex hortensis, Lycopersicon esculentum, Glycine max, Populus balsamifera, Medicago truncatula*) exhibited some sequence similarity with G974 outside of the signature AP2 domain sequence, and bear nearly identical AP2 domains. These proteins may be related.

G2343: (SEQ ID NOs. 53 and 54)

The complete sequence of G2343 was determined and G2343 was analyzed using transgenic plants in which G2343 was expressed under the control of the 35S promoter. The phenotype of these transgenic plants was wild-type in all assays performed. As determined by RT-PCR, G2343 is expressed in shoots, embryos and siliques. G2343 expression is induced in rosette leaves by auxin, heat stress, and infection by *Fusarium oxysporum*. 35S::G2343 had an altered seed oil content G2343 is a related tomato gene LETHM1 (CAA64615). Similarity between G2343 and LETHM1 extends beyond the signature motif of the family to a level that would suggest the genes are orthologs.

G2123: (SEQ ID NOs. 67 and 68)

G2123 was analyzed using transgenic plants in which G2123 was expressed under the control of the 35S promoter. The phenotype of these transgenic plants was wild-type in all assays performed. G2123 was expressed primarily in developing seeds and silique tissue in wild-type plants. G2123 corresponds to a predicted putative 14-3-3 protein in annotated BAC clone T11I11 (AC012680), from chromosome 1 of *Arabidopsis*.

G1777: (SEQ ID NOs. 55 and 56)

G1777 (SEQ ID NO: 55) was analyzed using transgenic plants in which G1777 was expressed under the control of the 35S promoter. Overexpression of G1777 in *Arabidopsis* resulted in an increase in seed oil content and a decrease in seed protein content in T2 lines 1 and 13. The change in seed oil in line 1 was just below the significance cutoff, but the seed protein change was significant. G1777 was expressed in all examined tissue of *Arabidopsis*. G1777 was induced by auxin and ABA treatment, and by heat stress. G1777 has utility in manipulating seed oil and protein content.

G2520: (SEQ ID NOs. 37 and 38)

G2520 was analyzed using transgenic plants in which G2520 was expressed under the control of the 35S promoter. At early stages, 35S::G2520 transformants displayed abnormal curled cotyledons, long hypocotyls, and rather short roots. During the vegetative phase, these plants formed somewhat small flat leaves. Following the switch to reproductive growth, 35S::G2520 inflorescences were typically very spindly, slightly pale colored, and stems often split open at late stages. Flowers were frequently small with narrow organs and showed poor pollen production. As a result, the seed yield from 35S::G2520 plants was low compared to wild-type controls. These effects were observed in the majority of primary transformants, and to varying extents, in all three of the T2 populations. Overexpression of G2520 also resulted in an increase in the leaf glucosinolate M39478 in lines 11 and 14. In addition, these lines showed an increase in seed δ-tocopherol and a decrease in seed γ-tocopherol. No altered phenotypes were detected in any of the physiological assays. G2520 was expressed throughout the plant and was induced by ABA, heat, salt, drought and osmotic stress. G2520 is useful for manipulating plant development and altering leaf glucosinolate composition. Increases or decreases in specific glucosinolates or total glucosinolate content are be desirable depending upon the particular application. For example: (1) Glucosinolates are undesirable components of the oilseeds used in animal feed, since they produce toxic effects. Low-glucosinolate varieties of canola have been developed to combat this problem. (2) Some glucosinolates have anti-cancer activity; thus, increasing the levels or composition of these compounds might be of interest from a nutraceutical standpoint. (3) Glucosinolates form part of a plant's natural defense against insects. Modification of glucosinolate composition or quantity can therefore afford increased protection from predators. Furthermore, in edible crops, tissue specific promoters can be used to ensure that these compounds accumulate specifically in tissues, such as the epidermis, which are not taken for consumption. G2520 can also be used to modify seed tocopherol composition. Tocopherols have antioxidant and vitamin E activity.

Example XII

Identification of Homologous Sequences

Homologous sequences from *Arabidopsis* and plant species other than *Arabidopsis* were identified using database sequence search tools, such as the Basic Local Alignment Search Tool (BLAST) (Altschul et al. (1990) *J. Mol. Biol.* 215: 403-410; and Altschul et al. (1997) *Nucl. Acid Res.* 25: 3389-3402). The tblastx sequence analysis programs were employed using the BLOSUM-62 scoring matrix (Henikoff and Henikoff (1992) *Proc. Natl. Acad. Sci. USA* 89: 10915-10919).

The polynucleotide and polypeptide sequences derived from monocots (e.g., the rice or maize sequences) may be used to transform both monocot and dicot plants, and those derived from dicots (e.g., the *Arabidopsis* and soy sequences) may be used to transform either group, although it is expected that some of these sequences will function best if the gene is transformed into a plant from the same class as that from which the sequence is derived.

Example XIII

Transformation of Dicots to Produce Improved Biochemical and Other Traits

Homologous sequences from *Arabidopsis* and plant species other than *Arabidopsis* were identified using database sequence search tools, such as the Basic Local Alignment Search Tool (BLAST) (Altschul et al. (1990) supra; and Altschul et al. (1997) supra). The tblastx sequence analysis programs were employed using the BLOSUM-62 scoring matrix (Henikoff and Henikoff (1992) supra).

Crop species including tomato and soybean plants that overexpress any of a considerable number of the transcription factor polypeptides of the invention have been shown experimentally to produce plants with increased drought tolerance and/or biomass in field trials. For example, tomato plants overexpressing the G2153 polypeptide have been found to be larger than wild-type control tomato plants. For example, soy plants overexpressing a number of G481, G682, G867 and G 1073 orthologs have been shown to be more drought tolerant than control plants. These observations indicate that these genes, when overexpressed, will result in larger yields than non-transformed plants in both stressed and non-stressed conditions.

Thus, transcription factor polynucleotide sequences listed in the Sequence Listing recombined into, for example, one of the expression vectors of the invention, or another suitable expression vector, may be transformed into a plant for the purpose of modifying plant traits for the purpose of improving yield and/or quality. The expression vector may contain a constitutive, tissue-specific or inducible promoter operably linked to the transcription factor polynucleotide. The cloning vector may be introduced into a variety of plants by means well known in the art such as, for example, direct DNA transfer or *Agrobacterium tumefaciens*-mediated transformation. It is now routine to produce transgenic plants using most dicot plants (see Weissbach and Weissbach, (1989) supra; Gelvin et al. (1990) supra; Herrera-Estrella et al. (1983) supra; Bevan (1984) supra; and Klee (1985) supra). Methods for analysis of traits are routine in the art and examples are disclosed above.

Numerous protocols for the transformation of tomato and soy plants have been previously described, and are well known in the art. Gruber et al. (1993) in *Methods in Plant Molecular Biology and Biotechnology*, p. 89-119, and Glick and Thompson (1993) *Methods in Plant Molecular Biology and Biotechnology*, eds., CRC Press, Inc., Boca Raton, describe several expression vectors and culture methods that may be used for cell or tissue transformation and subsequent regeneration. For soybean transformation, methods are described by Miki et al. (1993) in *Methods in Plant Molecular Biology and Biotechnology*, p. 67-88, Glick and Thompson, eds., CRC Press, Inc., Boca Raton; and U.S. Pat. No. 5,563,055, (Townsend and Thomas), issued Oct. 8, 1996.

There are a substantial number of alternatives to *Agrobacterium*-mediated transformation protocols, other methods for the purpose of transferring exogenous genes into soybeans or tomatoes. One such method is microprojectile-mediated transformation, in which DNA on the surface of microprojectile particles is driven into plant tissues with a biolistic device (see, for example, Sanford et al. (1987) *Part. Sci. Technol.* 5: 27-37; Christou et al. (1992) *Plant. J.* 2: 275-281; Sanford (1993) *Methods Enzymol.* 217: 483-509; Klein et al. (1987) *Nature* 327: 70-73; U.S. Pat. No. 5,015,580 (Christou et al), issued May 14, 1991; and U.S. Pat. No. 5,322,783 (Tomes et al.), issued Jun. 21, 1994).

Alternatively, sonication methods (see, for example, Zhang et al. (1991) *Bio/Technology* 9: 996-997); direct uptake of DNA into protoplasts using $CaCl_2$ precipitation, polyvinyl alcohol or poly-L-ornithine (see, for example, Hain et al. (1985) *Mol. Gen. Genet.* 199: 161-168; Draper et al. (1982) *Plant Cell Physiol.* 23: 451-458); liposome or spheroplast fusion (see, for example, Deshayes et al. (1985) *EMBO J*, 4: 2731-2737; Christou et al. (1987) *Proc. Natl. Acad. Sci. USA* 84: 3962-3966); and electroporation of protoplasts and whole cells and tissues (see, for example, Donn et al. (1990) in *Abstracts of VIIth International Congress on Plant Cell and Tissue Culture IAPTC*, A2-38: 53; D'Halluin et al. (1992); and Spencer et al. (1994) *Plant Mol. Biol.* 24: 51-61) have been used to introduce foreign DNA and expression vectors into plants.

After a plant or plant cell is transformed (and the latter regenerated into a plant), the transformed plant may be crossed with itself or a plant from the same line, a non-transformed or wild-type plant, or another transformed plant from a different transgenic line of plants. Crossing provides the advantages of producing new and often stable transgenic varieties. Genes and the traits they confer that have been introduced into a tomato or soybean line may be moved into distinct line of plants using traditional backcrossing techniques well known in the art. Transformation of tomato plants may be conducted using the protocols of Koornneef et al (1986) In *Tomato Biotechnology*: Alan R. Liss, Inc., 169-178, and in U.S. Pat. No. 6,613,962, the latter method described in brief here. Eight day old cotyledon explants are precultured for 24 hours in Petri dishes containing a feeder layer of Petunia hybrida suspension cells plated on MS medium with 2% (w/v) sucrose and 0.8% agar supplemented with 10 µM α-naphthalene acetic acid and 4.4 µM 6-benzylaminopurine. The explants are then infected with a diluted overnight culture of *Agrobacterium tumefaciens* containing an expression vector comprising a polynucleotide of the invention for 5-10 minutes, blotted dry on sterile filter paper and cocultured for 48 hours on the original feeder layer plates. Culture conditions are as described above. Overnight cultures of *Agrobacterium tumefaciens* are diluted in liquid MS medium with 2% (w/v/) sucrose, pH 5.7) to an $OD_{600}$ of 0.8.

Following cocultivation, the cotyledon explants are transferred to Petri dishes with selective medium comprising MS medium with 4.56 µM zeatin, 67.3 µM vancomycin, 418.9 µM cefotaxime and 171.6 µM kanamycin sulfate, and cultured under the culture conditions described above. The explants are subcultured every three weeks onto fresh medium. Emerging shoots are dissected from the underlying callus and transferred to glass jars with selective medium without zeatin to form roots. The formation of roots in a kanamycin sulfate-containing medium is a positive indication of a successful transformation.

Transformation of soybean plants may be conducted using the methods found in, for example, U.S. Pat. No. 5,563,055 (Townsend et al., issued Oct. 8, 1996), described in brief here. In this method soybean seed is surface sterilized by exposure to chlorine gas evolved in a glass bell jar. Seeds are germinated by plating on 1/10 strength agar solidified medium without plant growth regulators and culturing at 28° C. with a 16 hour day length. After three or four days, seed may be prepared for cocultivation. The seedcoat is removed and the elongating radicle removed 3-4 mm below the cotyledons.

Overnight cultures of *Agrobacterium tumefaciens* harboring the expression vector comprising a polynucleotide of the invention are grown to log phase, pooled, and concentrated by centrifugation. Inoculations are conducted in batches such that each plate of seed was treated with a newly resuspended pellet of *Agrobacterium*. The pellets are resuspended in 20 ml inoculation medium. The inoculum is poured into a Petri dish containing prepared seed and the cotyledonary nodes are macerated with a surgical blade. After 30 minutes the explants are transferred to plates of the same medium that has been solidified. Explants are embedded with the adaxial side up and level with the surface of the medium and cultured at 22° C. for three days under white fluorescent light. These plants may then be regenerated according to methods well established in the art, such as by moving the explants after three days to a liquid counter-selection medium (see U.S. Pat. No. 5,563,055).

The explants may then be picked, embedded and cultured in solidified selection medium. After one month on selective media transformed tissue becomes visible as green sectors of regenerating tissue against a background of bleached, less healthy tissue. Explants with green sectors are transferred to an elongation medium. Culture is continued on this medium with transfers to fresh plates every two weeks. When shoots are 0.5 cm in length they may be excised at the base and placed in a rooting medium.

Example XIV

Transformation of Cereal Plants with an Expression Vector

Cereal plants such as, but not limited to, corn, wheat, rice, sorghum, or barley, may be transformed with the present polynucleotide sequences, including monocot or dicot-derived sequences such as those presented in Tables 4-6, cloned into a vector such as pGA643 and containing a kanamycin-resistance marker, and expressed constitutively under, for example, the CaMV 35S or COR15 promoters, or with tissue-specific or inducible promoters. The expression vectors may be one found in the Sequence Listing, or any other suitable expression vector may be similarly used. For example, pMEN020 may be modified to replace the NptII coding region with the BAR gene of *Streptomyces hygroscopicus* that confers resistance to phosphinothricin. The KpnI and BglII sites of the Bar gene are removed by site-directed mutagenesis with silent codon changes.

The cloning vector may be introduced into a variety of cereal plants by means well known in the art including direct DNA transfer or *Agrobacterium tumefaciens*-mediated transformation. The latter approach may be accomplished by a variety of means, including, for example, that of U.S. Pat. No. 5,591,616, in which monocotyledon callus is transformed by contacting dedifferentiating tissue with the *Agrobacterium* containing the cloning vector.

The sample tissues are immersed in a suspension of $3\times10^{-9}$ cells of *Agrobacterium* containing the cloning vector for 3-10 minutes. The callus material is cultured on solid medium at 25° C. in the dark for several days. The calli grown on this medium are transferred to Regeneration medium. Transfers are continued every 2-3 weeks (2 or 3 times) until shoots develop. Shoots are then transferred to Shoot-Elongation medium every 2-3 weeks. Healthy looking shoots are transferred to rooting medium and after roots have developed, the plants are placed into moist potting soil.

The transformed plants are then analyzed for the presence of the NPTII gene/kanamycin resistance by ELISA, using the ELISA NPTII kit from 5Prime-3Prime Inc. (Boulder, Colo.).

It is also routine to use other methods to produce transgenic plants of most cereal crops (Vasil (1994) *Plant Mol. Biol.* 25: 925-937) such as corn, wheat, rice, sorghum (Cassas et al. (1993) *Proc. Natl. Acad. Sci.* 90: 11212-1121), and barley (Wan and Lemeaux (1994) *Plant Physiol.* 104: 37-48). DNA transfer methods such as the microprojectile method can be used for corn (Fromm et al. (1990) supra; Gordon-Kamm et al. (1990) supra; Ishida (1990) *Nature Biotechnol.* 14: 745-750), wheat (Vasil et al. (1992) *Bio/Technol.* 10: 667-674; Vasil et al. (1993a) *Bio/Technology* 10: 667-674; Vasil et al. (1993b) *Bio/Technol.* 11: 1553-1558; Weeks et al. (1993) supra), and rice (Christou (1991) *Bio/Technology* 9: 957-962; Hiei et al. (1994) *Plant J.* 6: 271-282; Aldemita and Hodges (1996) *Planta* 199: 612-617; and Hiei et al. (1997) *Plant Mol. Biol.* 35: 205-218). For most cereal plants, embryogenic cells derived from immature scutellum tissues are the preferred cellular targets for transformation (Hiei et al. (1997) supra; Vasil (1994) supra). For transforming corn embryogenic cells derived from immature scutellar tissue using microprojectile bombardment, the A188XB73 genotype is the preferred genotype (Fromm et al. (1990) supra; Gordon-Kamm et al. (1990) supra). After microprojectile bombardment the tissues are selected on phosphinothricin to identify the transgenic embryogenic cells (Gordon-Kamm (1990) *Plant Cell* 2: 603-618). Transgenic plants are regenerated by standard corn regeneration techniques (Fromm et al. (1990) supra; Gordon-Kamm et al. (1990) supra).

Example XV

Transcription Factor Expression and Analysis of Improved Traits

Biochemical assays such as those disclosed above may be used to identify improved characteristics in any of the transgenic or knock plants produced with sequences of the invention, such as polynucleotides SEQ ID NO: 2n−1, wherein n=1-84, or SEQ ID NO: 2n, wherein n=121-127.

Northern blot analysis, RT-PCR or microarray analysis of the regenerated, transformed plants may also be used to show expression of a transcription factor polypeptide or the invention and related genes that are capable of inducing improved biochemical characteristics, abiotic stress tolerance, and/or larger size.

To verify the ability to confer stress resistance, mature plants overexpressing a transcription factor of the invention, or alternatively, seedling progeny of these plants, may be challenged by a stress such as drought, heat, cold, high salt, or desiccation. Alternatively, these plants may challenged in a hyperosmotic stress condition that may also measure altered sugar sensing, such as a high sugar condition. By comparing control plants (for example, wild type) and transgenic plants similarly treated, the transgenic plants may be shown to have greater tolerance to the particular stress.

After a dicot plant, monocot plant or plant cell has been transformed (and the latter regenerated into a plant) and shown to have improved biochemical characteristics, greater size or tolerance to abiotic stress, or produce greater yield relative to a control plant under the stress conditions, the transformed monocot plant may be crossed with itself or a plant from the same line, a non-transformed or wild-type monocot plant, or another transformed monocot plant from a different transgenic line of plants.

These experiments would demonstrate that transcription factor polypeptides of the invention can be identified and shown to confer improved biochemical characteristics, larger size, greater yield, and/or abiotic stress tolerance in dicots or monocots, including multiple improved biochemical characteristics and/or tolerance to multiple stresses.

It is expected that the same methods may be applied to identify other useful and valuable sequences of the present transcription factor clades, and the sequences may be derived from a diverse range of species.

All references, publications, patent documents, web pages, and other documents cited or mentioned herein are hereby incorporated by reference in their entirety for all purposes. Although the invention has been described with reference to specific embodiments and examples, it should be understood that one of ordinary skill can make various modifications without departing from the spirit of the invention. The scope of the invention is not limited to the specific embodiments and examples provided.

What is claimed is:

1. A method for producing a transgenic plant having a larger size than a wild-type plant of the same species, the method steps comprising:
   (a) producing a nucleic acid construct encoding a polypeptide comprising a conserved domain with at least 69% sequence identity to the conserved domain of amino acid coordinates 11-80 of SEQ ID NO: 66, wherein the polypeptide has a property of SEQ ID NO: 66 of increasing size in a plant relative to a wild-type plant, wherein percent sequence identity is determined with a BLASTp algorithm with default settings of a wordlength (W) of 3, an expectation (E) of 10, and the BLOSUM62 scoring matrix; and
   (b) introducing the nucleic acid construct into a target plant to produce a transgenic plant; wherein the polypeptide is overexpressed in the transgenic plant and said overexpression results in the transgenic plant having larger size than the wild-type plant.

2. The method of claim 1, wherein the polypeptide comprises a conserved domain with at least 73% sequence identity to the conserved domain of amino acid coordinates 11-80 of SEQ ID NO: 66.

3. The method of claim 1, wherein the transgenic plant produces a transgenic seed, and a transgenic progeny plant grown from the transgenic seed has a larger size than the control plant.

4. The method of claim 1, wherein the polypeptide is selected from the group consisting of SEQ ID NOs: 66, 152, 154, 156, and 158.

5. The method of claim 1, wherein the nucleic acid construct comprises a constitutive, inducible, or tissue-specific promoter operably linked to a nucleotide sequence encoding the polypeptide.

6. A method for delaying flowering time of a plant relative to a wild-type plant of the same species, the method steps comprising:
   (a) producing a nucleic acid construct encoding a polypeptide comprising a conserved domain with at least 69% sequence identity to the conserved domain of amino acid coordinates 11-80 of SEQ ID NO: 66, wherein the polypeptide has a property of SEQ ID NO: 66 of increasing size and/or delaying flowering in a plant relative to a wild-type plant, wherein percent sequence identity is determined with a BLASTp algorithm with default settings of a wordlength (W) of 3, an expectation (E) of 10, and the BLOSUM62 scoring matrix;
   (b) introducing the nucleic acid construct into a target plant to produce a transgenic plant, wherein the polypeptide is overexpressed in the transgenic plant; and
   (c) selecting the tranagenic plant by identifying its larger size and/or delayed flowering relative to the wild-type plant.

7. The method of claim 6, wherein the polypeptide comprises a conserved domain with at least 73% sequence identity to the conserved domain of amino acid coordinates 11-80 of SEQ ID NO: 66.

8. The method of claim 6, wherein the transgenic plant produces a transgenic seed, and a transgenic progeny plant grown from the transgenic seed has a larger size than the control plant.

9. The method of claim 6, wherein the polypeptide is selected from the group consisting of SEQ ID NOs: 66, 152, 154, 156, and 158.

10. The method of claim 6, wherein the nucleic acid construct comprises a constitutive, inducible, or tissue-specific promoter operably linked to a nucleotide sequence encoding the polypeptide.

11. A method for producing a plant having greater tolerance to hyperosmotic stress and/or water deprivation relative to a wild-type plant of the same species, the method steps comprising:
   (a) producing a nucleic acid construct encoding a polypeptide comprising a conserved domain with at least 69% sequence identity to the conserved domain of amino acid coordinates 11-80 of SEQ ID NO: 66, wherein the polypeptide has a property of SEQ ID NO: 66 of increasing tolerance to hyperosmotic stress and/or water deprivation in a plant relative to the wild-type plant, wherein percent sequence identity is determined with a BLASTp algorithm with default settings of a wordlength (W) of 3, an expectation (E) of 10, and the BLOSUM62 scoring matrix; and (b) introducing the nucleic acid construct into a target plant to produce a transgenic plant;

wherein the polypeptide is overexpressed in the transgenic plant and said overexpression results in the transgenic plant having greater tolerance than the wild-type plant to the hyperosmotic stress and/or the water deprivation.

12. The method of claim 11, wherein during the hyperosmotic stress and/or the water deprivation the plant has larger size, more root growth, or greener color relative to the wild-type plant subjected to the hyperosmotic stress and/or the water deprivation.

13. The method of claim 11, wherein the transgenic plant has greater tolerance than the wild-type plant to 150 mM NaCl.

14. The method of claim 11, wherein the polypeptide comprises a conserved domain with at least 73% sequence identity to the conserved domain of amino acid coordinates 11-80 of SEQ ID NO: 66.

15. The method of claim 11, wherein the transgenic plant produces a transgenic seed, and a tranagenic progeny plant grown from the transgenic seed has a larger size than the control plant.

16. The method of claim 11, wherein the polypeptide is selected from the group consisting of SEQ ID NOs: 66, 152, 154, 156, and 158.

17. The method of claim 11, wherein the nucleic acid comprises a constitutive, inducible, or tissue-specific promoter operably linked to a nucleotide sequence encoding the polypeptide.

18. A method for increasing a plant's tolerance to hyperosmotic stress and/or water deprivation relative to a wild-type plant of the same species, the method steps comprising:

(a) producing a nucleic acid construct encoding a polypeptide comprising a conserved domain with at least 69% sequence identity to the conserved domain of amino acid coordinates 11-80 of SEQ ID NO: 66, wherein the polypeptide has a property of SEQ ID NO: 66 of increasing tolerance to hyperosmotic stress and/or water deprivation in a plant relative to tolerance of the wild-type plant to hyperosmotie stress and/or water deprivation, and wherein percent sequence identity is determined with a BLASTp algorithm with default settings of a wordlength (W) of 3, an expectation (E) of 10, and the BLOSUM62 scoring matrix; and (b) introducing the nucleic acid construct into a target plant to produce a transgenic plant, wherein the polypeptide is overexpressed in the transgenic plant; and (c) selecting the transgenic plant by identifying its greater tolerance than the wild-type plant to the hyperosmotic stress and/or the water deprivation.

19. The method of claim 18, wherein the polypeptide comprises a conserved domain with at least 73% sequence identity to the conserved domain of amino acid coordinates 11-80 of SEQ ID NO: 66.

20. The method of claim 18, wherein the polypeptide is selected from the group consisting of SEQ ID NOs: 66, 152, 154, 156, and 158.

21. The method of claim 18, wherein the nucleic acid construct comprises a constitutive, inducible, or tissue-specific promoter operably linked to a nucleotide sequence encoding the polypeptide.

* * * * *